United States Patent
Kai et al.

(10) Patent No.: US 9,550,763 B2
(45) Date of Patent: Jan. 24, 2017

(54) HETEROCYCLIC RING AND CARBOCYCLIC DERIVATIVE

(71) Applicant: Shionogi & Co., Ltd., Osaka (JP)

(72) Inventors: Hiroyuki Kai, Osaka (JP); Satoru Tanaka, Osaka (JP); Yoshiharu Hiramatsu, Osaka (JP); Azusa Nozu, Osaka (JP); Ken'ichioh Nakamura, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 82 days.

(21) Appl. No.: 14/377,331

(22) PCT Filed: Feb. 8, 2013

(86) PCT No.: PCT/JP2013/052991
§ 371 (c)(1),
(2) Date: Aug. 7, 2014

(87) PCT Pub. No.: WO2013/118855
PCT Pub. Date: Aug. 15, 2013

(65) Prior Publication Data
US 2016/0024072 A1 Jan. 28, 2016

(30) Foreign Application Priority Data

Feb. 9, 2012 (JP) ................ 2012-025726
Jul. 2, 2012 (JP) ................ 2012-148613

(51) Int. Cl.
A61K 31/506 (2006.01)
C07D 417/14 (2006.01)
(Continued)

(52) U.S. Cl.
CPC ........... C07D 417/14 (2013.01); C07D 239/54 (2013.01); C07D 239/545 (2013.01);
(Continued)

(58) Field of Classification Search
CPC ... C07D 405/14; C07D 401/12; C07D 405/12; C07D 239/54; C07D 417/12; C07D 417/14; C07D 239/545; C07D 413/14; C07D 413/12; C07D 403/12; C07D 401/14
See application file for complete search history.

(56) References Cited

U.S. PATENT DOCUMENTS 3,598,815 A  8/1971 Gilles et al.
4,021,249 A  5/1977 Noguchi et al.
(Continued)

FOREIGN PATENT DOCUMENTS

EP  0 005 911   12/1979
EP  0 547 461    6/1993
(Continued)

OTHER PUBLICATIONS

Cantin et al., Bioorg. Med. Chem. Lett. (2012), vol. 22 (7), p. 2565-2571.
Jahangir et al., Bioorg. Med. Chem. Lett. (2009), vol. 19, p. 1632-1635.
Kong et al., Chemistry A. European Journal (2012), vol. 18(5), p. 1476-1486.
Notification of Transmittal of Translation of the International Preliminary Report on Patentability (PCT/IB/338); English-language translation of International Preliminary Report on Patentability (PCT/IB/373) issued Aug. 12, 2014, and Written Opinion from the International Searching Authority (PCT/ISA/237) mailed Mar. 12, 2013, for International Application No. PCT/JP2013/052991.
C. Kennedy, "P2X Receptors. Targets for Novel Analgesics?", The Neuroscientist, vol. 11, No. 4, pp. 345-356 (2005).
D. A. Cockayne, et al., "$P2X_2$, knockout mice and $P2X_2/P2X_3$ double knockout mice reveal a role for the $P2X_2$ receptor subunit in mediating multiple sensory effects of ATP", J. Physiol., vol. 567, No. 2, pp. 621-639 (2005).
C. Shieh et al., "P2X receptor ligands and pain", Expert Opinion Ther. Patents, vol. 16, No. 8, pp. 1113-1127 (2006).
R. A. North, "$P2X_3$ receptors and peripheral pain mechanisms", J. Physiology, vol. 554, No. 2, pp. 301-308 (2003).
(Continued)

*Primary Examiner* — Alexander R Pagano
(74) *Attorney, Agent, or Firm* — Finnegan, Henderson, Farabow, Garrett & Dunner, L.L.P.

(57) ABSTRACT

The present invention provides novel compounds having a $P2X_3$ and/or $P2X_{2/3}$ receptor antagonistic effect, e.g. a compound of Formula (I):

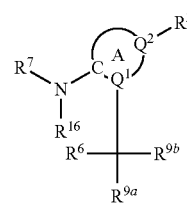

(I)

wherein
$R^2$ is a hydrogen atom or the like;
ring A is five- to seven-cycloalkane or the like;
C is a carbon atom;
$Q^1$ and $Q^2$ are carbon atoms or the like;
$R^{9a}$ and $R^{9b}$ are carbon atoms or the like;
$R^6$ is cycloalkyl or the like;
$R^7$ is a group represented by the formula:

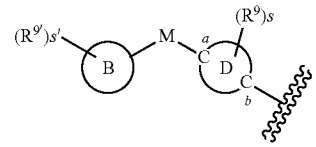

wherein
ring D is benzene or the like;
carbon atom a and b are carbon atoms;
ring B is an aromatic carbocyclic ring or the like;
s and s' are 0 or the like;
$R^9$ and $R^{9'}$ are halogen or the like,
or the like,
or its pharmaceutically acceptable salt.

29 Claims, No Drawings

(51) Int. Cl.

| | | |
|---|---|---|
| C07D 405/14 | (2006.01) | |
| C07D 401/12 | (2006.01) | |
| C07D 405/12 | (2006.01) | |
| C07D 239/54 | (2006.01) | |
| C07D 417/12 | (2006.01) | |
| C07D 239/545 | (2006.01) | |
| C07D 401/14 | (2006.01) | |
| C07D 403/12 | (2006.01) | |
| C07D 413/12 | (2006.01) | |
| C07D 413/14 | (2006.01) | |

(52) U.S. Cl.
CPC ......... *C07D 401/12* (2013.01); *C07D 401/14* (2013.01); *C07D 403/12* (2013.01); *C07D 405/12* (2013.01); *C07D 405/14* (2013.01); *C07D 413/12* (2013.01); *C07D 413/14* (2013.01); *C07D 417/12* (2013.01); *A61K 31/506* (2013.01)

(56) References Cited

U.S. PATENT DOCUMENTS

| | | | |
|---|---|---|---|
| 4,127,718 | A | 11/1978 | Illy et al. |
| 4,156,002 | A | 5/1979 | Brown et al. |
| 4,158,724 | A | 6/1979 | Illy et al. |
| 4,254,122 | A | 3/1981 | Brown |
| 4,317,911 | A | 3/1982 | Rasberger et al. |
| 4,518,688 | A | 5/1985 | Leppard et al. |
| 5,232,924 | A | 8/1993 | Watanabe et al. |
| 5,389,599 | A | 2/1995 | Schallner et al. |
| 6,177,437 | B1 | 1/2001 | Wright |
| 7,745,451 | B2 | 6/2010 | Kelly et al. |
| 7,858,632 | B2 | 12/2010 | Broka et al. |
| 8,101,644 | B2 * | 1/2012 | Kai .......... A61K 31/40 514/405 |
| 8,497,263 | B2 * | 7/2013 | Kai .......... A61K 31/40 514/221 |
| 8,575,197 | B2 * | 11/2013 | Kai .......... C07D 207/38 514/333 |
| 9,150,546 | B2 * | 10/2015 | Kai .......... C07D 251/46 |
| 9,212,130 | B2 * | 12/2015 | Kai .......... C07C 217/92 |
| 2002/0049320 | A1 | 4/2002 | Gopalsamy et al. |
| 2007/0037974 | A1 | 2/2007 | Brotherton-Pleiss et al. |
| 2007/0049534 | A1 | 3/2007 | Dillon et al. |
| 2007/0049609 | A1 | 3/2007 | Broka et al. |
| 2007/0049610 | A1 | 3/2007 | Dillon et al. |
| 2007/0049758 | A1 | 3/2007 | Dillon et al. |
| 2009/0099195 | A1 | 4/2009 | Bayrakdarian et al. |
| 2009/0270369 | A1 | 10/2009 | Ozaki et al. |
| 2010/0317676 | A1 | 12/2010 | Kelly et al. |
| 2011/0077242 | A1 | 3/2011 | Broka et al. |
| 2011/0183939 | A1 * | 7/2011 | Kai .......... C07D 207/38 514/63 |
| 2011/0237578 | A1 | 9/2011 | Wei et al. |
| 2013/0225596 | A1 | 8/2013 | Kai et al. |
| 2016/0052892 | A1 * | 2/2016 | Kai .......... C07C 217/92 514/235.8 |
| 2016/0185736 | A1 * | 6/2016 | Kai .......... C07D 251/46 514/157 |

FOREIGN PATENT DOCUMENTS

| | | | |
|---|---|---|---|
| EP | 2 399 910 A1 | 12/2011 | |
| EP | 2604595 | 6/2013 | |
| JP | 57-144269 | 9/1982 | |
| JP | 62-156110 | 7/1987 | |
| JP | 11-189577 | 7/1999 | |
| JP | WO 9952881 A1 * | 10/1999 | ............ A01N 43/54 |
| JP | 2000-72757 | 3/2000 | |
| JP | 2001-131156 | 5/2001 | |
| JP | 2006528640 | 2/2005 | |
| JP | 2007-526268 | 9/2007 | |
| JP | 2008-546639 | 12/2008 | |
| JP | 2009-7258 | 1/2009 | |
| JP | 2010-526138 | 7/2010 | |
| JP | 2010523667 | 7/2010 | |
| JP | WO 2012020742 A1 * | 2/2012 | ............ C07C 217/92 |
| RU | 2057754 | 4/1996 | |
| SU | 867303 | 9/1981 | |
| WO | WO 99/52881 | 10/1999 | |
| WO | WO 00/39101 | 7/2000 | |
| WO | WO-00/51990 | 9/2000 | |
| WO | WO 01/55093 A1 | 8/2001 | |
| WO | WO 02/074726 A2 | 9/2002 | |
| WO | WO 02/074726 A3 | 9/2002 | |
| WO | WO 02/094767 A2 | 11/2002 | |
| WO | WO 2004/054617 A1 | 7/2004 | |
| WO | WO-2005/009980 | 2/2005 | |
| WO | WO 2005/009980 A1 | 2/2005 | |
| WO | WO 2005/095359 A1 | 10/2005 | |
| WO | WO 2006/012639 | 2/2006 | |
| WO | WO 2008/016522 | 2/2006 | |
| WO | WO 2006/074057 A2 | 7/2006 | |
| WO | WO 2006/074057 A3 | 7/2006 | |
| WO | WO 2006/102112 A2 | 9/2006 | |
| WO | WO 2006/104713 A1 | 10/2006 | |
| WO | WO 2006/104715 A1 | 10/2006 | |
| WO | WO 2006/119502 A2 | 11/2006 | |
| WO | WO 2006/119504 A2 | 11/2006 | |
| WO | WO 2006/119504 A3 | 11/2006 | |
| WO | WO 2007/079163 | 7/2007 | |
| WO | WO-2007/079214 | 7/2007 | |
| WO | WO 2008/005538 A2 | 1/2008 | |
| WO | WO 2008/005538 A3 | 1/2008 | |
| WO | WO 2008/089051 | 7/2008 | |
| WO | WO 2008/089051 A1 | 7/2008 | |
| WO | WO 2008/136756 A1 | 11/2008 | |
| WO | WO 2009/058853 | 5/2009 | |
| WO | WO 2010/020742 A1 | 2/2010 | |
| WO | WO 2010/051188 A1 | 5/2010 | |
| WO | WO 2008/127591 A2 | 7/2010 | |
| WO | WO 2010/092966 A1 | 8/2010 | |
| WO | WO 2010/149578 | 12/2010 | |
| WO | WO 2011/017347 | 2/2011 | |
| WO | WO 2012/016182 A1 | 2/2012 | |
| WO | WO 2012/020742 A1 | 2/2012 | |
| WO | WO 2012/020749 A1 | 2/2012 | |
| WO | WO 2012/135800 A1 | 10/2012 | |
| WO | WO 2013/089212 | 6/2013 | |

OTHER PUBLICATIONS

C. Kennedy et al., "Crossing the pain barrier: P2 receptors as targets for novel analgesics", J. Physiology, vol. 553, No. 3, pp. 683-694 (2003).

J. R. Gever et al., "Pharmacology of P2X channels", Pflugers Arch—Eur J Physiol, vol. 452, pp. 513-537 (2006).

M. F. Jarvis et al., "A-317491, a novel potent and selective non-nucleotide antagonist of P2X$_3$ and P2X$_{2/3}$ receptors, reduces chronic inflammatory and neuropathic pain in the rat", PNAS, vol. 99, No. 26, pp. 17179-17184 (2002).

I. Brouns et al., "Intraepithellal Vagal Sensory Nerve Terminals in Rat Pulmonary Neuroepithelial Bodies Express P2X$_3$ Receptors", Am. J. Respir. Cell Mol. Biol., vol. 23, pp. 52-61 (2000).

O. K. Basoglu, MD, et al., "Effects of Aerosolized Adenosine 5'—Triphosphate vs Adenosine 5'—Monophosphate on Dyspnea and Airway Caliber in Healthy Nonsmokers and Patients with Asthma", Chest, vol. 128. No. 4, pp. 1905-1909 (2005).

D. Adriaensen et al., "Functional Morphology of Pulmonary Neuroepithelial Bodies: Extremely Complex Airway Receptors", The Anatomical Record Part A, vol. 270A, pp. 25-40 (2003).

D. S. Carter et al., "Identification and SAR of novel diaminopyrimidines. Part 1: The discovery of RO-4, a dual P2X$_3$/P2X$_{2/3}$ antagonist for the treatment of pain", Bioorganic & Medicinal Chemistry Letters, vol. 19, pp. 1825-1631 (2009).

G. Balboni et al., "Triazine Compounds as Antagonists at Bv8-Prokineticin Receptors", Journal of Medicinal Chemistry, vol. 51, No. 23, pp. 7635-7639 (2008).

International Search Report from the Japanese Patent Office for International Application No. PCT/JP2013/052991 mailed Mar. 12, 2013.

(56) References Cited

OTHER PUBLICATIONS

Akteries et al., "Reactions of Carbonyl Diisocyanate With Amides and Acids," Chem. Ser., vol. 119, pp. 669-682 (1986).
Bernatowicz, et al., 1H-Pyrazole-1-carboxamidine Hydrochloride: An Attractive Reagent for Guanylation of Amines and Its Application to Peptide Synthesis, J. Org. Chem., vol. 57, pp. 2497-2502, (1992).
CAS RN 857972-98-6 (entered into STN Aug. 3, 2005).
Dråger, et al., "A new reagent and its polymer-supported variant for the amidination of amines", Tetrahedron Letters, vol. 43, pp. 1401-1403, (2002).
English-language International Search Report from the Japanese Patent Office for International Application No. PCT/JP2010/051920 mailed Mar. 30, 2010.
English-language International Search Report for International Application No. PCT/JP2011/068113 from The Japanese Patent Office mailed Nov. 1, 2011.
English-language International Search Report for International Application No. PCT/JP2011/068097 from the Japanese Patent Office mailed Nov. 15, 2011.
English-language Abstract of Okano, Natsuko et al., "Preparation of 2-phenylaminopyrimidinones, intermediates as pesticides and herbicides in agriculture", Chem. Abstracts Service, Columbus, OH (1999); STN Accession No. 1999-672770.
English-language Abstract of Fukuchi, T et al., "Novel 2-aminopyrimidinone derivatives, useful as insecticide and acaricide", Thomson Scientific, London, GB (May 15, 2001); STN Accession No. 2001-468100.
English-language Abstract of Fukuchi, T et al., "2-anlllno-4(3H)-pyrimidinone derivatives, pesticidally/herbicidally active, useful in agriculture/horticulture and their preparation", Thomson Scientific, London, GB (2003); STN Accession No. 2003-318151.
English-language Abstract of Fukuchi, T et al., "A novel 2-substituted amoni-5,6-dihydro-4(3H)-pyrimidinone derivative", Thomson Scientific, London, GB (2001); STN Accession No. 2001-491646.
Esayan, et al., Synthesis and sulfuric acid hydrolysis γ-chlorocrotylbenzyl (alkyl) isocyanurates, Armyanskii Khimicheskii Zhurnal, vol. 28, No. 4, pp. 332-337, (1975).
Gopalsamy et al., "Combinatorial Synthesis of Heterocycles: Solid-Phase Synthesis of 6-Amino-2,4-Dioxo-3,4-Dihydro-1,3 5-Triazine Derivatives," J. Comb. Chem., vol. 3, pp. 278-283 (2001).
Han, Jun, "Advances in Characterization of Pharmaceutical Hydrates," Trends in Bio/Pharmaceutical industry, pp. 25-29, Mar. 2006.
Ji-Zhen, Li et al., "Polymer Supported Synthesis of Multi-substituted Pyrimidine-4-one Derivatives via Pbf-activated Thiourea", Chem. Research in Chinese Universities, vol. 27, No. 2, (2011) pp. 221-223.
Kennedy et al., "Topical Review, Crossing the pain barrier: P2 receptors as targets for novel analgesics", J. Physiol., vol. 553, No. 3, pp. 663-694, (2003).
Knotz, "1-Chloromethylisatin, an excellent reagent for the identification of carboxylic acids and NH-acid compounds", Scientia Pharmaceutica, vol. 38, No. 4, pp. 227-233, (1970).
Lerchova, et al., "Antioxidants and Stabilizers, L. Transformation of the 1,3,5-Tris(4-hydrosy-3,5-di-tert-butylbenzyl)cyanuric acid into Alkylperoxycyclohexadienones, their Properties and Effects on the Oxidation of Tetralin and Polypropylene", Angewandte Makromolekulare Chemie, vol. 39, No. 1, pp. 107-118, (1974).
Notification of Transmittal of Translation of the International Preliminary Report on Patentability, International Preliminary Report on Patentability, and Translation of the Written Opinion of the International Searching Authority, for International Patent Application No. PCT/JP2010/051920, mailed Sep. 22, 2011 (14 pages).
Notification of Transmittal of Translation of the International Preliminary Report on Patentability, International Preliminary Report on Patentability, and Translation of the Written Opinion of the International Searching Authority, for International Patent Application No. PCT/JP2011/068097, mailed Mar. 21, 2013 (10 pages).
Notification of Transmittal of Translation of the International Preliminary Report on Patentability, International Preliminary Report on Patentability, and Translation of the Written Opinion of the International Searching Authority, for International Patent Application No. PCT/JP2011/068113, mailed Mar. 21, 2013 (15 pages).
Office Action dated Nov. 7, 2014 in U.S. Appl. No. 13/201,209.
Office Action dated Apr. 2, 2013 in U.S. Appl. No. 13/201,209.
Office Action dated Dec. 4, 2012 in U.S. Appl. No. 13/201,209.
Office Action dated Jan. 28, 2015 in U.S. Appl. No. 13/816,085.
Office Action dated Feb. 26, 2015 in U.S. Appl. No. 13/814,346.
Pecchi, et al., "Identification and structure-activity relationship of 2-morpholino 6-(3-hydroxyphenyl) pyrimidines, a class of potent and selective P13 kinase inhibitors", Bioorganic & Medicinal Chemistry Letters, vol. 20, No. 23, pp. 6895-6898, (2010).
Schriof-Gregoire, et al., "Preparation of N-alkyl-N-carboalkoxy guanidines: unexpected effective trans-alkoxylation transforming the 2,2,2-trichioroethoxycarbonyl into various carbamates", Tetrahedron Letters, vol. 48, pp. 2357-2359, (2007).
Shao, et al., "Strapped porphyrin rosettes based on the melarnine-cyanuric acid motif. Self-assembly and supramolecular recognition", Tetrahedron, vol. 60, No. 41, pp. 9155-9162, (2004).
Simov et al., "Triazines and Other 6-Membered Rings," Chemical Abstracts, Heterocyclic Compounds, vol. 67, pp. 10245 (1967).
Somogyi, L. et al., "Cyclisierungsreaktionen von mono—und disubstituierten Biguaniden mit Phenylisothiocyanat," Chem. Bar., vol. 100; pp. 1975-1982 (1967).
Supplementary European Search Report for European Application No. 10741243, mailed Sep. 13, 2012.
Supplementary European Search Report for European Application No. 11816406, mailed Oct. 20, 2014.
Suyama et al., "The Reaction of 3-Cyano-2-Methyl-1-Phenylisothiourea With Isocyanate, Isothiocyanate and Carbodimide," Nippon Kagaku Kaishi, No. 9, pp. 845-848 (1996).
Vippagunta, Sudha R., "Crystalline Solids," Advanced Drug Delivery Reviews 48 (2001) pp. 3-26.
Zuen, et al., "Crystalline furanic polyisocyanates", Polymer Bulletin 26, vol. 26, No. 4, pp. 383-390, (1991).

\* cited by examiner

HETEROCYCLIC RING AND CARBOCYCLIC DERIVATIVE

This is a National Phase Application under 35 U.S.C. §371 of International Application No. PCT/JP2013/052991, filed Feb. 8, 2013, and claims priority to Japanese Patent Application No. 2012-025726, filed Feb. 9, 2012, and Japanese Patent Application No. 2012-148613, filed Jul. 2, 2012, the content of each of which is incorporated herein by reference.

TECHNICAL FIELD

The invention relates to a compound useful for the treatment of diseases or conditions associated with P2X receptor, specifically to $P2X_3$ and/or $P2X_{2/3}$ receptor, and a pharmaceutical composition comprising such compound.

BACKGROUND ART

Adenosine triphosphate (ATP) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. ATP thus released mediates various extracellular signal transductions through an ATP receptor (Non-Patent Document 4, Non-Patent Document 5).

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel (Non-Patent Document 6).

ATP is known to cause pain, and studies with $P2X_3$ knockout and knockdown methodologies have shown that $P2X_3$ receptor mediates transmission of chronic pain. $P2X_3$ receptors are expressed in a specific manner on peripheral sensory nerve to form a homo-complex or hetero-complex with $P2X_2$ ($P2X_{2/3}$) (Non-Patent Document 1).

Later, the compound A-317491 was reported as a specific antagonist to $P2X_3$ and $P2X_{2/3}$ receptors. A-317491 is tri-substituted-N-[(1S)-1,2,3,4-tetrahydro-1-naphthalenyl]benzamide derivative represented by the formula:

[Chemical Formula 1]

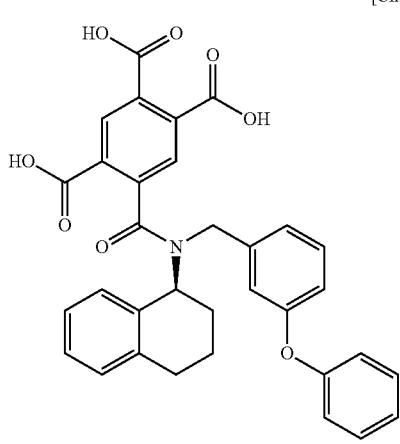

(Patent Document 1). It was reported to exhibit an antagonist activity to $P2X_3$ and $P2X_{2/3}$ receptors and analgesic action in neuropathic pain model and inflammatory pain model (Non-Patent Document 7). This indicates that pain sensation is transmitted via $P2X_3$ or $P2X_{2/3}$ receptor and that a compound having a $P2X_3$ or $P2X_{2/3}$ receptor antagonistic activity is useful as an analgesic. Also, compounds that exhibit $P2X_3$ or $P2X_{2/3}$ receptor antagonistic activity are described in Patent Documents 2-7.

Additionally, it was recently reported that vesical reflex was strongly reduced in $P2X_3$ knockout mouse (Non-Patent Document 2), suggesting that a compound having $P2X_3$ antagonistic activity is useful in the treatment of diseases caused by overactive bladder. Also, compounds that exhibit $P2X_3$ or $P2X_{2/3}$ receptor antagonistic activity are described in Patent Documents 2-7.

In addition, $P2X_3$ receptor is expressed in neuroepithelial bodies (NEB) of the lung (Non-Patent Document 9), ATP induces cough (Non-Patent Document 10), and the like, therefore it is suggested that $P2X_3$ receptor participates in signal transduction in the respiratory system (Non-Patent Document 11). These reports suggest the possibility that compounds that exhibit $P2X_3$ receptor antagonistic activity are useful in the treatment of respiratory diseases.

Later, the compound A-317491 known as a specific antagonist to $P2X_3$ and $P2X_{2/3}$ is receptors was reported inhibiting an activity of afferent vagal A fiber in pulmonary diseases (Patent Document WO2006/012639). Additionally, biphenyl and phenyl-pyridine derivatives were reported as a specific antagonist to $P2X_3$ and $P2X_{2/3}$ receptors, and it is suggested that the biphenyl and phenyl-pyridine derivatives exhibit improving effect on respiratory diseases in asthma and lung model (Patent Document WO2010/149578). Also, compounds that exhibit $P2X_3$ or $P2X_{2/3}$ receptor antagonistic activity are described in Patent Documents 2-7.

Patent Documents 8-17, and 23 disclose compounds having similar structure to the compounds of the present invention but they do not disclose analgesic effect and $P2X_3$ or $P2X_{2/3}$ receptor antagonistic activity. Patent Document 18-22 and Non-Patent Document 11 disclose compounds having $P2X_3$ receptor antagonistic activity but the structures are different with those of the compounds of the present invention.

PRIOR ART

Patent Document

[Patent Document 1] WO02/094767
[Patent Document 2] WO2005/095359
[Patent Document 3] US2007/0037974
[Patent Document 4] US2007/0049758
[Patent Document 5] US2007/0049610
[Patent Document 6] US2007/0049609
[Patent Document 7] US2007/0049534
[Patent Document 8] JP2009-007258
[Patent Document 9] JP11-189577
[Patent Document 10] WO2001/055098
[Patent Document 11] WO2008/005538
[Patent Document 12] WO2006/074057
[Patent Document 13] WO2004/054617
[Patent Document 14] WO2000/039101
[Patent Document 15] WO2002/074726
[Patent Document 16] WO2012/135800
[Patent Document 17] WO2012/016182
[Patent Document 18] WO2010/092966
[Patent Document 19] WO2010/020742

[Patent Document 20] WO2010/020749
[Patent Document 21] WO2008/136756
[Patent Document 22] WO2006/119504
[Patent Document 23] WO2008/089051

Non-Patent Document

[Non-Patent Document 1] Neuroscientist (2005), 11, pp. 345-356
[Non-Patent Document 2] J. Physiol. 567.2 (2005), pp. 621-639
[Non-Patent Document 3] Expert Opin. Ther. Patens (2006), 16(8), pp. 113-1127
[Non-Patent Document 4] J. Physiology (2003), 554(2), pp. 301-308
[Non-Patent Document 5] J. Physiology (2003), 553(3), pp. 683-694
[Non-Patent Document 6] Pflungers Arch Eur J physiol (2006), pp. 452, 513-537
[Non-Patent Document 7] PNAS (2002), 99(26), pp. 17179-17184
[Non-Patent Document 8] Brouns et al. Am J Respir Cell Mol Biol (2000), 23, pp. 52-61
[Non-Patent Document 9] Baeoglu et al. Chest. (2005), 128(4), pp. 1905-9
[Non-Patent Document 10] Adriaensen et al. THE ANATOMICAL RECORD PART A (2003), 270A, pp. 25-40
[Non-Patent Document 11] Bioorganic & Medicinal Chemistry Letters, (2009), vol. 19, pp. 1628-1631

SUMMARY OF THE INVENTION

Problems to be Solved by the Invention

The present invention provides a novel compound having a P2X$_3$ and/or P2X$_{2/3}$ receptor antagonistic activity. It also provides a pharmaceutical composition having a P2X$_3$ and/or P2X$_{2/3}$ receptor antagonistic activity.

Means for Solving the Problem

Through their extensive research to solve the aforementioned problems, the inventors have found novel compounds that bind specifically to P2X$_3$ and/or P2X$_{2/8}$ receptor and exhibit an antagonistic activity, and novel compounds that bind specifically to P2X$_3$ and/or P2X$_{2/3}$ receptor. Additionally, they have discovered pharmaceutical compositions that have P2X$_3$ and/or P2X$_{2/3}$ antagonistic activity.

The compounds and pharmaceutical compositions encompassed by the present invention produced excellent results of P2X$_3$ receptor inhibitory effect, P2X$_3$ receptor inhibitory effect in the presence of rat serum albumin (hereinafter referred to as RSA) and the like. The compounds encompassed by the present invention or the pharmaceutical compositions encompassed by the present invention also produced excellent results in CYP enzyme inhibition assay, FAT assay, solubility assay, metabolic stability assay, hERG inhibitory activity assay, bioavailability assay, and/or protein binding assay and the like.

This invention relates to the following:
(1) A compound of Formula (I):

[Chemical Formula 2]

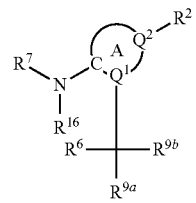

(I)

wherein
R$^2$ is a hydrogen atom, hydroxy, carboxy, halogen, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, substituted sulfonyl, substituted sulfinyl, substituted or unsubstituted imino, substituted or unsubstituted amino or substituted or unsubstituted guanidyl;
ring A is substituted or unsubstituted five- to seven-membered cycloalkane, substituted or unsubstituted five- to seven-membered cycloalkene, a substituted or unsubstituted five- to seven-membered nitrogen containing non-aromatic heterocyclic ring, substituted or unsubstituted benzene, or a substituted or unsubstituted five- or six-membered aromatic heterocyclic ring, or,
a fused ring consisting of same or different two rings selected from substituted or unsubstituted five- to seven-membered cycloalkane, substituted or unsubstituted five- to seven-membered cycloalkene, a substituted or unsubstituted five- to seven-membered nitrogen containing non-aromatic heterocyclic ring, substituted or unsubstituted benzene, and a substituted or unsubstituted five- or six-membered aromatic heterocyclic ring, provided that ring A is not substituted or unsubstituted triazine;
C is a carbon atom;
$Q^1$ and $Q^2$ are each independently a carbon atom or a nitrogen atom;
$R^{9a}$ and $R^{9b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy;
$R^6$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^{16}$ is a hydrogen atom, substituted or unsubstituted alkyl, substituted or unsubstituted alkenyl, substituted or unsubstituted alkynyl or substituted or unsubstituted acyl;
$R^7$ is a group represented by the formula:

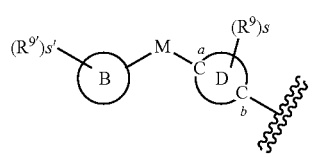

[Chemical Formula 3]

wherein
ring D is benzene, pyridine, pyrimidine, pyrazine or pyridazine;
carbon atom a and carbon atom b are carbon atoms which constitute ring D;
-M- is —O—, —S—, —N($R^{10}$)—, or —C($R^{10a}$)($R^{10b}$)—;
$R^{10}$ is a hydrogen atom, substituted or unsubstituted alkyl, substituted or unsubstituted alkenyl, substituted or unsubstituted alkynyl or substituted or unsubstituted acyl;
$R^{10a}$ and $R^{10b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy;
ring B is an aromatic carbocyclic ring, a non-aromatic carbocyclic ring, an aromatic heterocyclic ring or a non-aromatic heterocyclic ring;
s and s' are each independently integers of 0 to 3;
$R^9$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy;
$R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy,
or
a group represented by the formula:

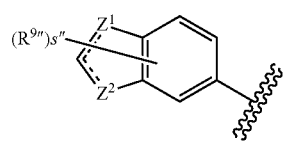

[Chemical Formula 4]

wherein a group represented by the formula:

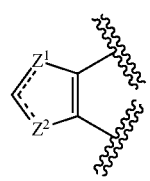

[Chemical Formula 5]

is a group represented by the formula:

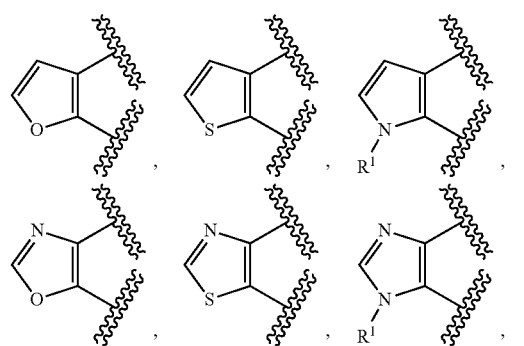

[Chemical Formula 6]

-continued

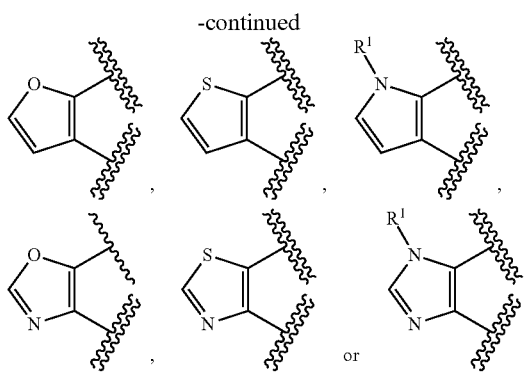

wherein
R[1] is a hydrogen atom, substituted or unsubstituted alkyl, substituted or unsubstituted alkenyl, substituted or unsubstituted alkynyl, or substituted or unsubstituted acyl;
s" is an integer of 0 to 3;
R[9'''] are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; provided that
(i) a compound represented by Formula (I)
wherein a group represented by the formula:

[Chemical Formula 7]

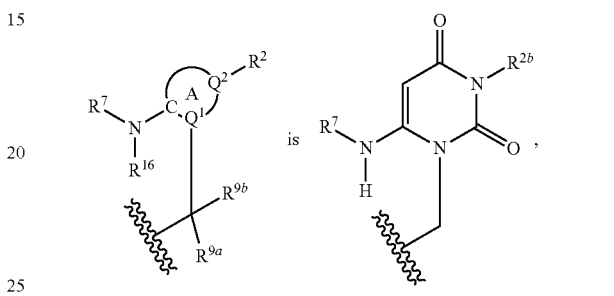

R[7] is 4-(6-methyl-3-pyridyl)oxy-phenyl, 4-(5-fluoro-3-pyridyl)oxy-phenyl or 4-(5-fluoro-6-methyl-3-pyridyl)oxy-phenyl, and R[2b] is substituted or unsubstituted amino;
(ii) a compound represented by Formula (I) wherein ring A is substituted or unsubstituted benzene, ring D is substituted or unsubstituted pyrimidine, and R[6] is unsubstituted phenyl;
(iii) a compound represented by Formula (I) wherein ring A is substituted or unsubstituted cycloalkene, and ring D is substituted or unsubstituted benzene;

(iv) a compound represented by Formula (I) wherein ring A is substituted or unsubstituted benzene or substituted or unsubstituted naphthalene, ring D is substituted or unsubstituted benzene, and R[6] is unsubstituted phenyl;
(v) a compound represented by Formula (I) wherein ring A is, substituted or unsubstituted benzene, and R[6] is 2,6-di-tert-butyl-4-hydroxyphenyl,
(vi) a compound represented by Formula (I)
wherein a group represented by the formula:

[Chemical Formula 8]

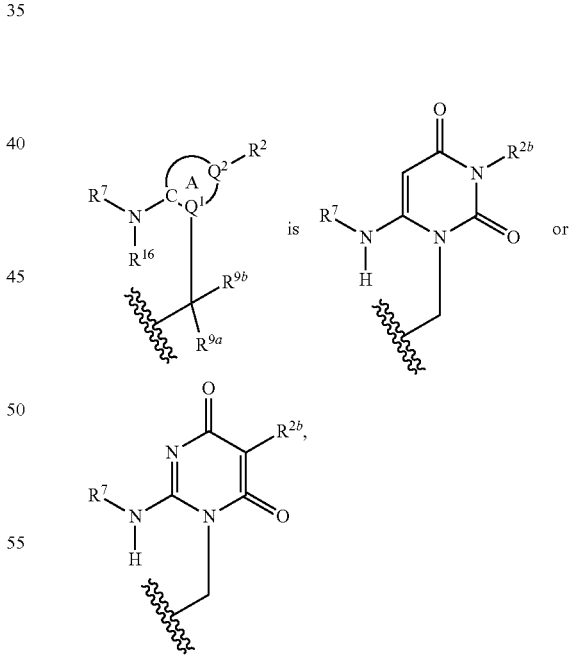

R[7] is 2-methyl-benzothiazol-6-yl, and R[2a] is substituted alkyl;
(vii) a compound represented by Formula (I)
wherein a group represented by the formula:

[Chemical Formula 9]

R[7] is 2-methyl-benzothiazol-6-yl, R[1b] is a hydrogen atom or unsubstituted alkyl, and R[2b] is a hydrogen atom, carboxy, halogen, unsubstituted alkyl, unsubstituted alkenyl, substituted or unsubstituted alkyloxycarbonyl, substituted or unsubstituted amino, or substituted or unsubstituted carbamoyl, and (viii) the following compounds:
[Chemical Formula 10]
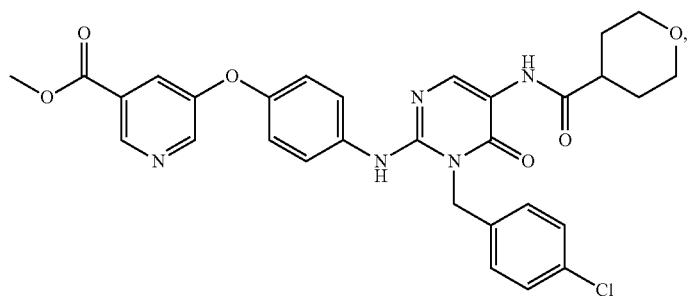
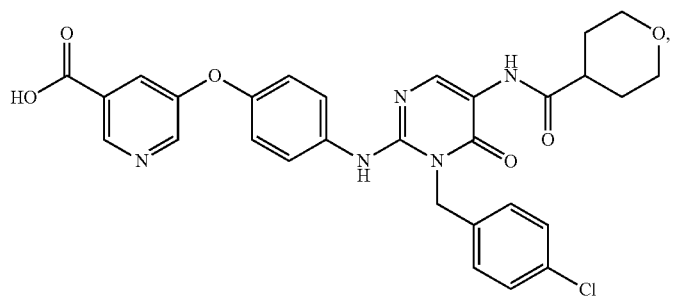
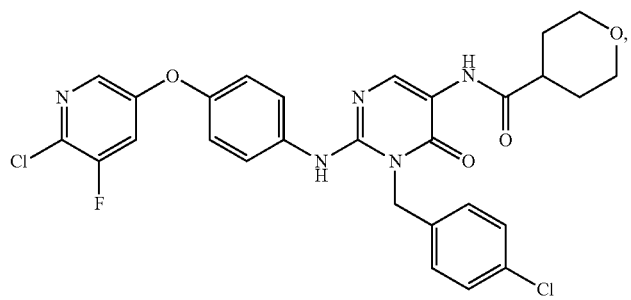
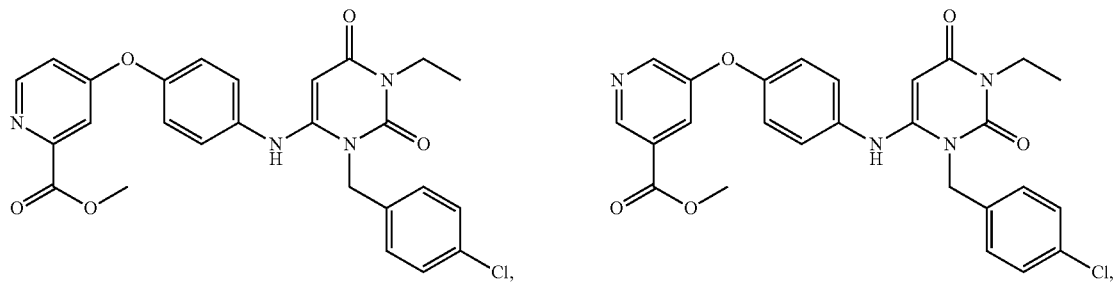
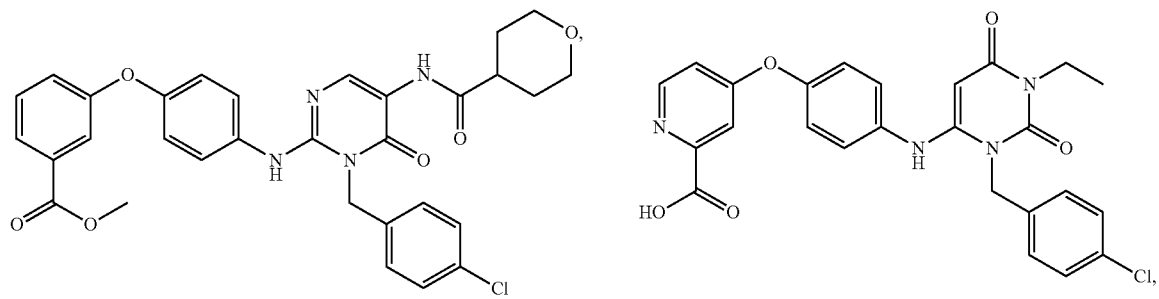

-continued
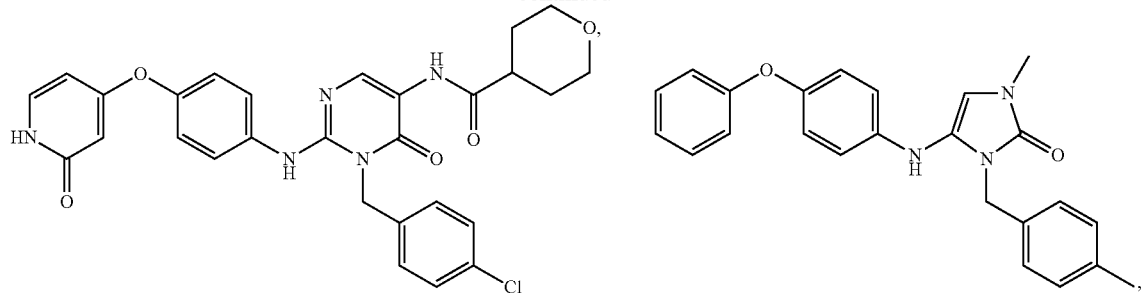
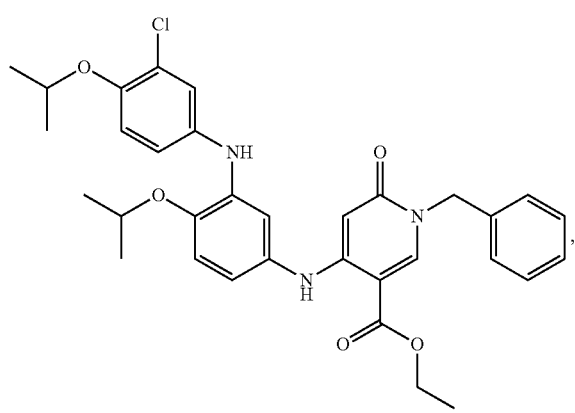
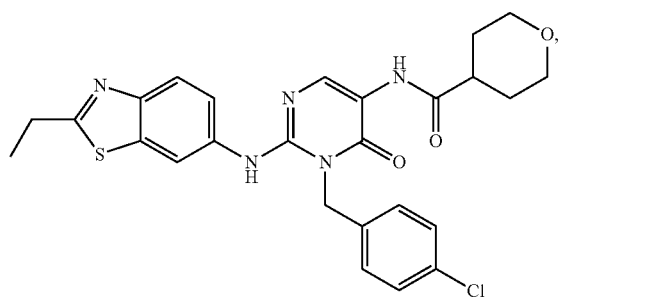
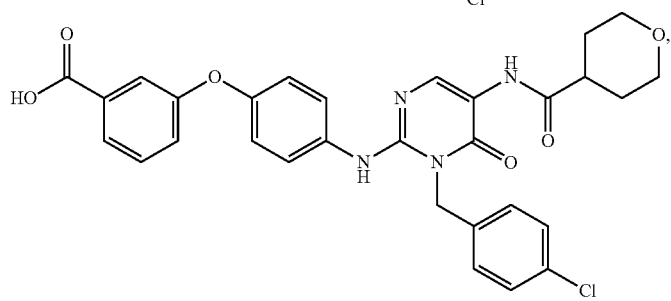
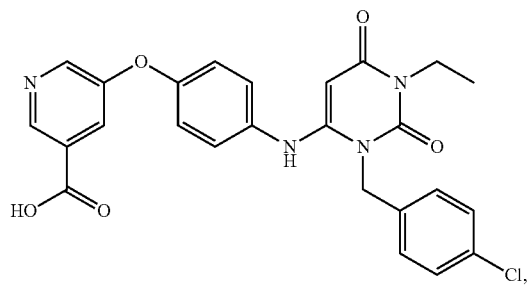

-continued
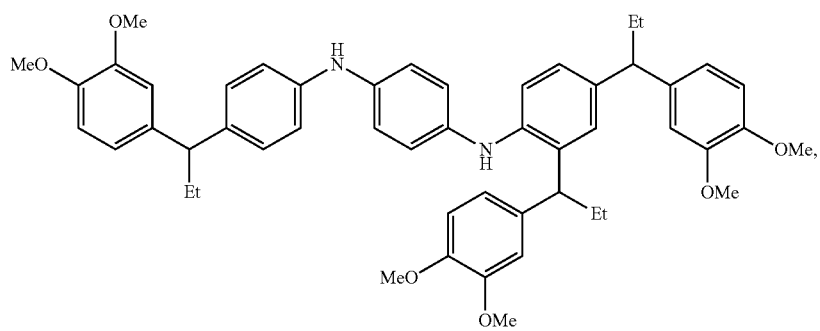
[Chemical Formula 11]
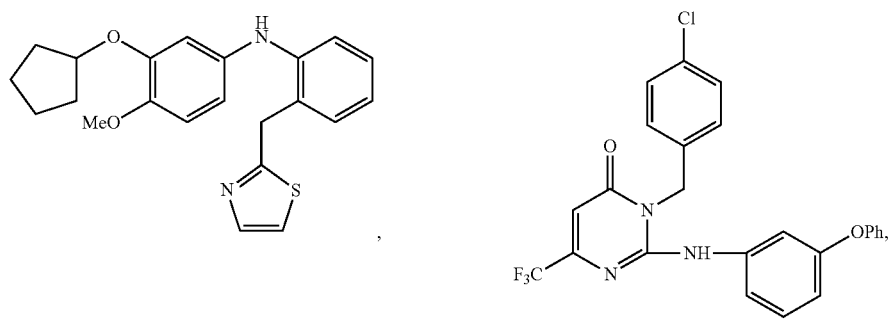
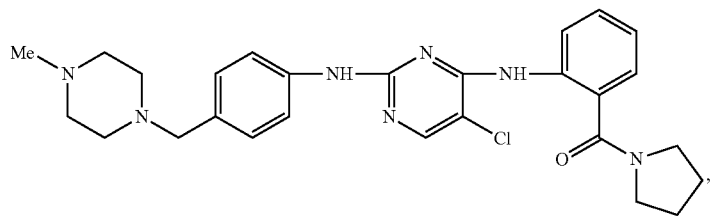
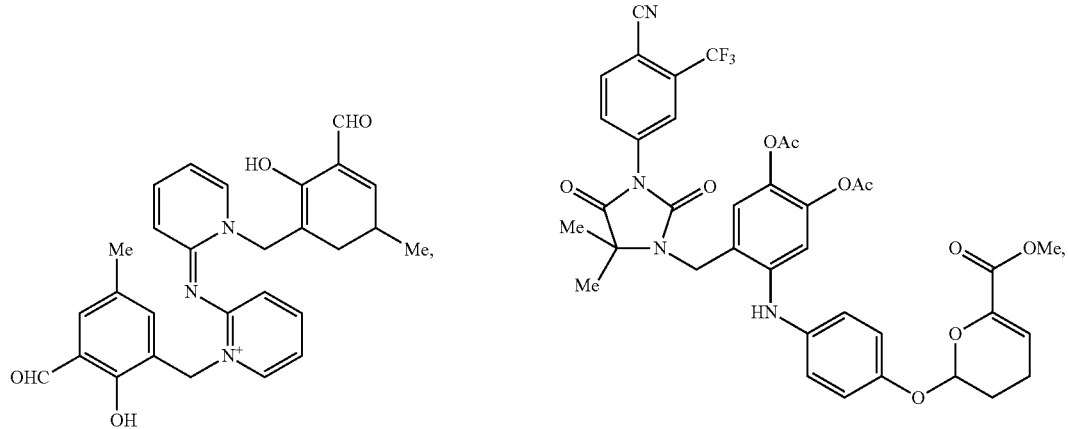

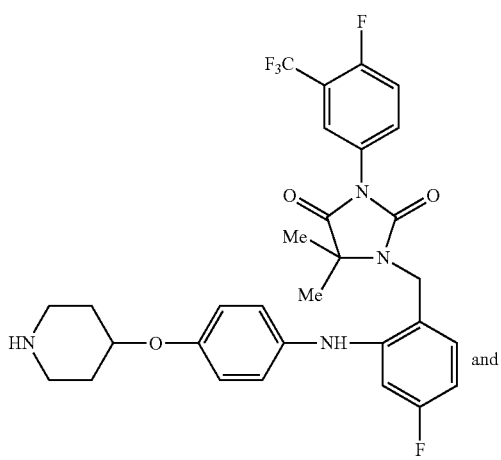
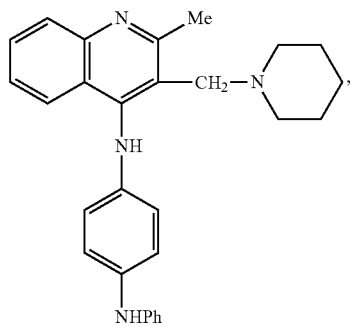

wherein "Me" is methyl, "Et" is ethyl, "Ph" is phenyl, and "Ac" is acetyl, are excluded,
or its pharmaceutically acceptable salt.
(1A) The compound according to the above (1), provided that the following compound:

[Chemical Formula 12]

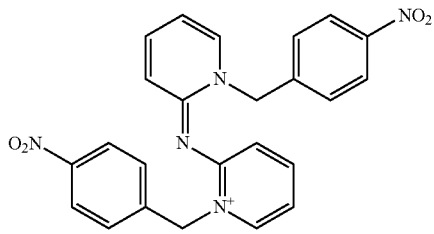

is excluded, or its pharmaceutically acceptable salt.
(1B) A compound of Formula (I):

[Chemcial Formula 13]

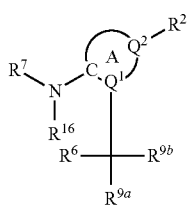

(I)

wherein
$R^2$ is a hydrogen atom, hydroxy, carboxy, halogen, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, substituted or unsubstituted imino or substituted or unsubstituted amino;
ring A is substituted or unsubstituted five- to seven-membered cycloalkane, substituted or unsubstituted five- to seven-membered cycloalkene, a substituted or unsubstituted five- to seven-membered nitrogen containing non-aromatic heterocyclic ring, substituted or unsubstituted benzene, or a substituted or unsubstituted five- or six-membered aromatic heterocyclic ring, or
a fused ring consisting of same or different two rings selected from substituted or unsubstituted five- to seven-membered cycloalkane, substituted or unsubstituted five- to seven-membered cycloalkene, a substituted or unsubstituted five- to seven-membered nitrogen containing non-aromatic heterocyclic group, substituted or unsubstituted benzene, and a substituted or unsubstituted five- or six-membered aromatic heterocyclic ring,
provided that ring A is not substituted or unsubstituted triazine;
C is a carbon atom;
$Q^1$ and $Q^2$ are each independently a carbon atom or a nitrogen atom;
$R^{9a}$ and $R^{9b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;
$R^6$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^{16}$ is a hydrogen atom, substituted or unsubstituted alkyl, substituted or unsubstituted alkenyl, substituted or unsubstituted alkynyl or substituted or unsubstituted acyl;

$R^7$ is a group represented by the formula:

[Chemical Formula 14]

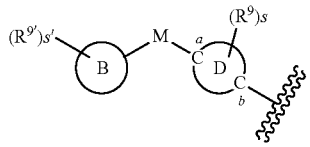

wherein
ring D is benzene, pyridine, pyrimidine, pyrazine or pyridazine; carbon atom a and carbon atom b are carbon atoms which constitute ring D;

-M- is —O—, —S—, —N($R^{10}$)—, or —C($R^{10a}$)($R^{10b}$)—;

$R^{10}$ is a hydrogen atom, substituted or unsubstituted alkyl, substituted or unsubstituted alkenyl, substituted or unsubstituted alkynyl or substituted or unsubstituted acyl;

$R^{10a}$ and $R^{10b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy;

ring B is an aromatic carbocyclic ring, a non-aromatic carbocyclic ring, an aromatic heterocyclic ring or a non-aromatic heterocyclic ring, s and s' are each independently integers of 0 to 3;

$R^9$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;

$R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or a group represented by the formula:

[Chemical Formula 15]

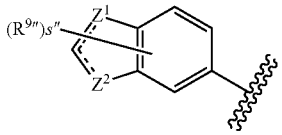

wherein a group represented by the formula:

[Chemical Formula 16]

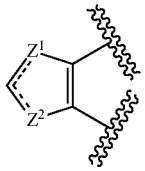

is a group represented by the formula:

[Chemical Formula 17]

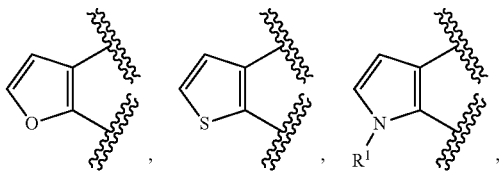

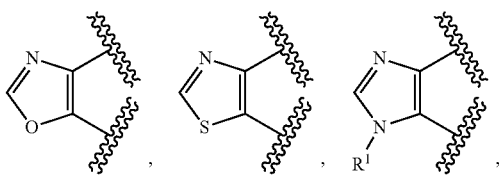

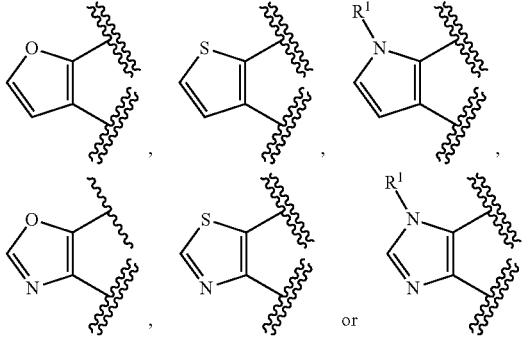

or wherein
R¹ is a hydrogen atom, substituted or unsubstituted alkyl, substituted or unsubstituted alkenyl, substituted or unsubstituted alkynyl, or substituted or unsubstituted acyl;
s" is an integer of 0 to 3;
$R^{9'''}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, provided that
(i) a compound represented by Formula (I)
wherein a group represented by the formula:

[Chemical Formula 18]

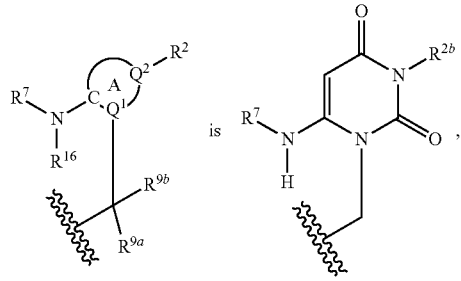 is 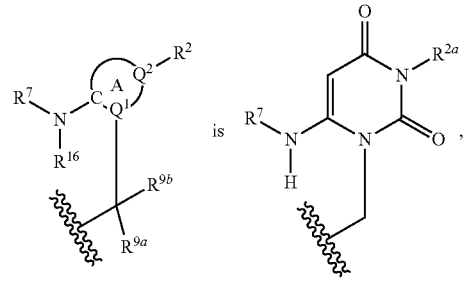,

R⁷ is 4-(6-methyl-3-pyridyl)oxy-phenyl, 4-(5-fluoro-3-pyridyl)oxy-phenyl or 4-(5-fluoro-6-methyl-3-pyridyl)oxy-phenyl, and $R^{2b}$ is substituted or unsubstituted amino;
(ii) a compound represented by Formula (I) wherein ring A is substituted or unsubstituted benzene, ring D is substituted or unsubstituted pyrimidine, and R⁶ is unsubstituted phenyl;
(iii) a compound represented by Formula (I) wherein ring A is substituted or unsubstituted cycloalkene, and ring D is substituted or unsubstituted benzene;
(iv) a compound represented by Formula (I) wherein ring A is substituted or unsubstituted benzene or substituted or unsubstituted naphthalene, ring D is substituted or unsubstituted benzene, and R⁶ is unsubstituted phenyl;
(v) a compound represented by Formula (I) wherein ring A is, substituted or unsubstituted benzene, and R⁶ is 2,6-di-tert-butyl-4-hydroxyphenyl;
(vi) a compound represented by Formula (I)

[Chemical Formula 19]

R⁷ is 2-methyl-benzothiazol-6-yl, and $R^{2a}$ is substituted alkyl,
(vii) a compound represented by Formula (I)
wherein a group represented by the formula:

[Chemical Formula 20]

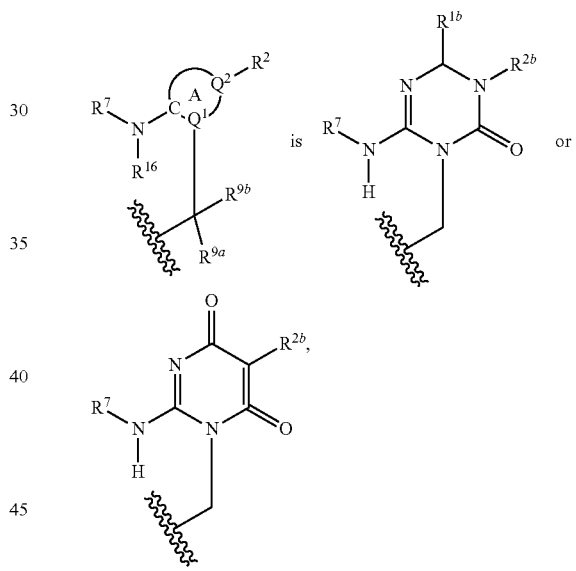

R⁷ is 2-methyl-benzothiazol-6-yl, $R^{1b}$ is a hydrogen atom or unsubstituted alkyl, and $R^{2b}$ is a hydrogen atom, carboxy, halogen, unsubstituted alkyl, unsubstituted alkenyl, substituted or unsubstituted alkyloxycarbonyl, substituted or unsubstituted amino, or substituted or unsubstituted carbamoyl; and
(viii) the following compounds:

[Chemical Formula 21]

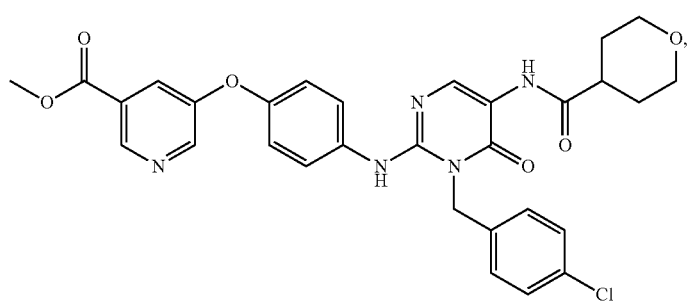

-continued
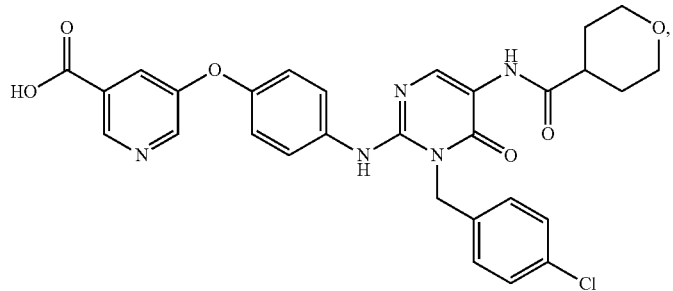
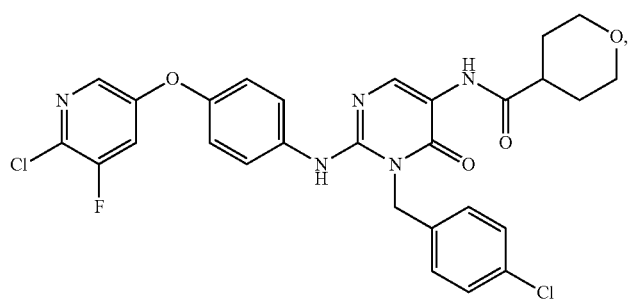
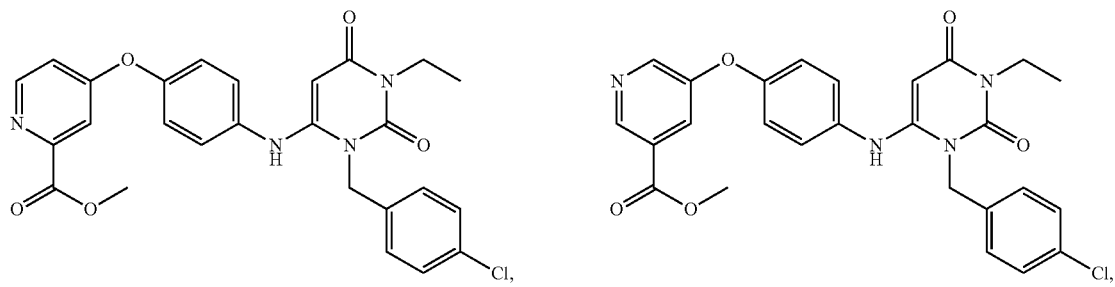
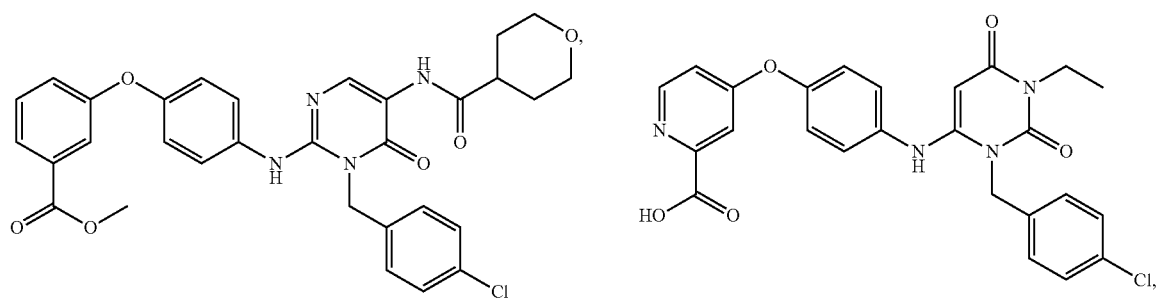
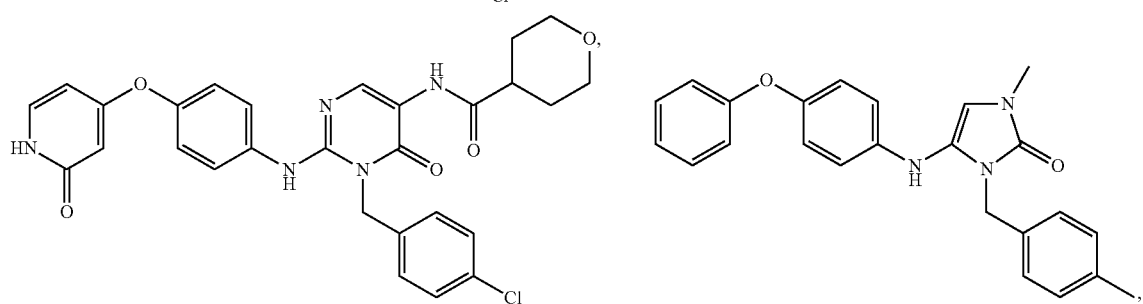

-continued
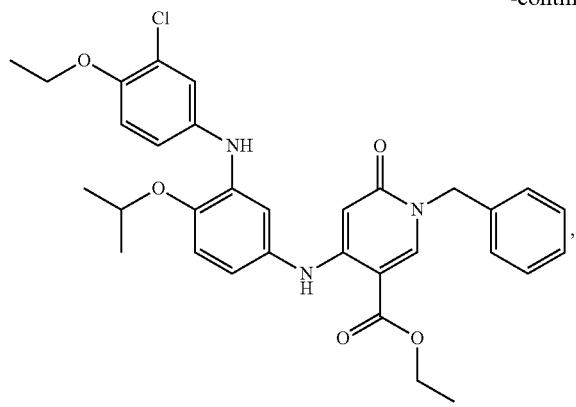
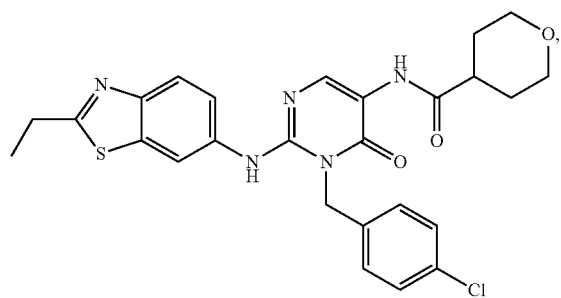
[Chemical Formula 22]
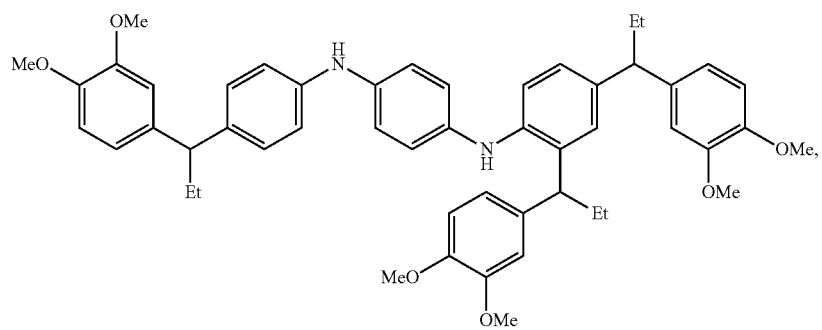
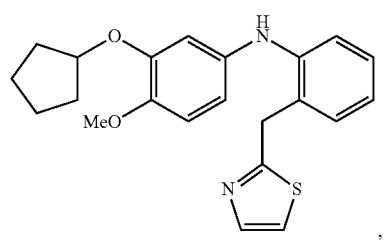
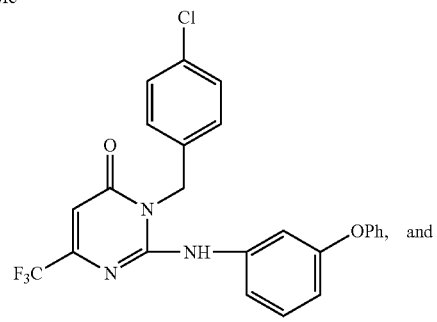
and
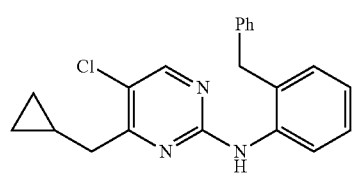 [SMILES: Clc1cnc(Nc2ccccc2Cc2ccccc2)nc1CC1CC1]

wherein "Me" is methyl, "Et" is ethyl, and "Ph" is phenyl, are excluded,
or its pharmaceutically acceptable salt.
(2) The compound according to the above (1), wherein $R^7$ is a group represented by the formula:

[Chemical Formula 23]

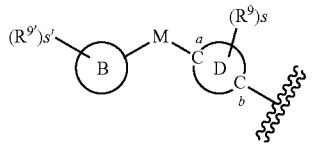

wherein ring D, carbon atom a, carbon atom b, -M-, ring B, s, s', $R^9$, and $R^{9'}$ are as defined in the above (1),
or its pharmaceutically acceptable salt.
(3A) A compound of Formula (II):

[Chemcial Formula 24]

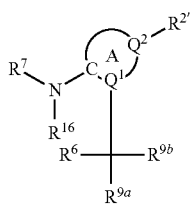

(II)

wherein
$R^{2'}$ is C3-C6 alkyl substituted with 3 to 5 hydroxy groups and optionally with one or more substituents selected from the Substituent Group A (Substituent Group A: halogen, cyano, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo);
C3-C6 alkenyl substituted with 3 to 5 hydroxy groups and optionally with one or more substituents selected from the Substituent Group A; or
C3-C6 alkynyl substituted with 3 to 5 hydroxy groups and optionally with one or more substituents selected from the Substituent Group A;
ring A is substituted or unsubstituted five- to seven-membered cycloalkane, substituted or unsubstituted five- to seven-membered cycloalkene, a substituted or unsubstituted five- to seven-membered nitrogen containing non-aromatic heterocyclic ring, a substituted or unsubstituted benzene ring, or a substituted or unsubstituted five- or six-membered aromatic heterocyclic ring, or
a fused ring consisting of same or different two rings selected from substituted or unsubstituted five- to seven-membered cycloalkane, substituted or unsubstituted five- to seven-membered cycloalkene, a substituted or unsubstituted five- to seven-membered nitrogen containing non-aromatic heterocyclic group, substituted or unsubstituted benzene, and a substituted or unsubstituted five- or six-membered aromatic heterocyclic ring,
provided that ring A is not substituted or unsubstituted triazine;
C is a carbon atom;
$Q^1$ and $Q^2$ are each independently a carbon atom or a nitrogen atom;
$R^{9a}$ and $R^{9b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy;
$R^6$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^{16}$ is a hydrogen atom, substituted or unsubstituted alkyl, substituted or unsubstituted alkenyl, substituted or unsubstituted alkynyl or substituted or unsubstituted acyl;
$R^7$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl,
or its pharmaceutically acceptable salt.
(3) The compound according to any one of the above (1), (1A), (1B), (2) and (3A), wherein ring A is substituted or unsubstituted six-membered cycloalkane, substituted or unsubstituted six-membered cycloalkene, a substituted or unsubstituted six-membered nitrogen containing non-aromatic heterocyclic ring, substituted or unsubstituted benzene, or a substituted or unsubstituted six-membered aromatic heterocyclic ring, provided that ring A is not substituted or unsubstituted triazine;
C is attached to $Q^1$ and both of C and $Q^1$ are ring atoms,
$R^6$ is a group represented by the formula:

[Chemical Formula 25]

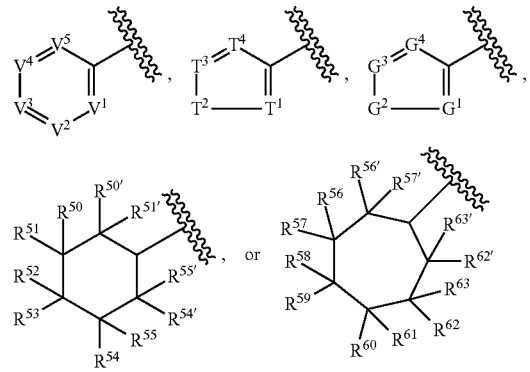

wherein $=V^1-V^2=V^3-V^4=V-$ is a group selected from the following (i)-(p) and (p'):

(i): =C(R^{A'})—C(R^A)=C(R^B)—C(R^C)=C(R^{C'})—;
(j): =N—C(R^A)=C(R^B)—C(R^C)=C(R^{C'})—;
(k): =C(R^{A'})—N=C(R^B)—C(R^C)=C(R^{C'})—;
(l): =C(R^{A'})—C(R^A)=N—C(R^C)=C(R^{C'})—;
(m): =C(R^{A'})—N=N—C(R^C)=C(R^{C'})—;
(n): =N—C(R^A)=C(R^B)—C(R^C)=N—;
(o): =N—N=C(R^B)—C(R^C)=C(R^{C'})—;
(p): =C(R^{A'})—N=C(R^B)—N=C(R^{C'})—; and
(p'): =N—C(R^A)=C(R^B)—N=C(R^{C'})—;
$R^A$, $R^{A'}$, $R^B$, $R^C$ and $R^{C'}$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;
=$T^1$-$T^2$=$T^3$-$T^4$- is a group selected from the following (q)-(t):
(q): =C(R^{D'})—C(R^D)=C(R^E)—S—;
(r): =C(R^{D'})—C(R^D)=C(R^E)—O—;
(s): =N—C(R^D)=C(R^E)—S—; and
(t): =N—C(R^D)=C(R^E)—O—;
$R^D$, $R^{D'}$ and $R^E$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;
=$G^1$-$G^2$=$G^3$-$G^4$- is a group selected from the following (u)-(x):
(u): =C(R^{F'})—S—C(R^F)=C(R^{F''})—;
(v): =C(R^{F'})—O—C(R^F)=C(R^{F''})—;
(w): =C(R^{F'})—S—C(R^F)=N—; and
(x): =C(R^{F'})—O—C(R^F)=N—;
$R^F$, $R^{F'}$ and $R^{F''}$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;
$R^{50}$, $R^{50'}$, $R^{51}$, $R^{51'}$, $R^{52}$, $R^{53}$, $R^{54}$, $R^{54'}$, $R^{55}$, $R^{55'}$, $R^{56}$, $R^{56'}$, $R^{57}$, $R^{57'}$, $R^{58}$, $R^{59}$, $R^{60}$, $R^{61}$, $R^{62}$, $R^{62'}$, $R^{63}$ and $R^{63'}$ are each independently a hydrogen atom, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or its pharmaceutically acceptable salt.

(3B) The compound according to any one of the above (1), (1A), (1B), and (2), wherein ring A is substituted or unsubstituted six-membered cycloalkane, substituted or unsubstituted six-membered cycloalkene, a substituted or unsubstituted six-membered nitrogen containing non-aromatic heterocyclic ring, substituted or unsubstituted benzene, or a substituted or unsubstituted six-membered aromatic heterocyclic ring, provided that ring A is not substituted or unsubstituted triazine;

C is attached to $Q^1$ and both of C and $Q^1$ are ring atoms, $R^6$ is a group represented by the formula:

[Chemical Formula 26]

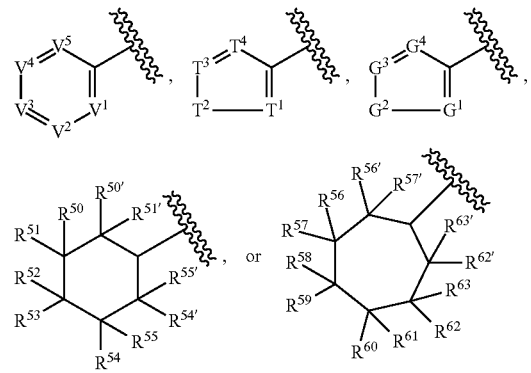

wherein =$V^1$—$V^2$=$V^3$—$V^4$=V— is a group selected from the following (i)-(p) and (p'):
(i): =C(H)—C(R^A)=C(R^B)—C(R^C)=C(H)—;
(j): =N—C(R^A)=C(R^B)—C(R^C)=C(H)—;
(k): =C(H)—N=C(R^B)—C(R^C)=C(H)—;
(l): =C(H)—C(R^A)=N—C(R^C)=C(H)—;
(m): =C(H)—N=N—C(R^C)=C(H)—;
(n): =N—C(R^A)=C(R^B)—C(R^C)=N—;
(o): =N—N=C(R^B)—C(R^C)=C(H)—;
(p): =C(H)—N=C(R^B)—N=C(H)—; and
(p'): =N—C(R^A)=C(R^B)—N=C(H)—;

$R^A$, $R^B$, and $R^C$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;

$=T^1-T^2=T^3-T^4-$ is a group selected from the following (q)-(t):

(q): $=C(R^{D'})—C(R^D)=C(R^E)—S—$;
(r): $=C(R^{D'})—C(R^D)=C(R^E)—O—$;
(s): $=N—C(R^D)=C(R^E)—S—$; and
(t): $=N—C(R^D)=C(R^E)—O—$;

$R^D$ and $R^E$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;

$=G^1-G^2-G^3=G^4-$ is a group selected from the following (u)-(x):

(u): $=C(H)—S—C(R^F)—C(H)—$;
(v): $=C(H)—O—C(R^F)—C(H)—$;
(w): $=C(H)—S—C(R^F)=N—$; and
(x): $=C(H)—O—C(R^F)=N—$;

$R^F$ is a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;

$R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently a hydrogen atom, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy or substituted or unsubstituted alkynyloxy, or its pharmaceutically acceptable salt.

(4) The compound according to any one of the above (1), (1A), (1B), and (2), wherein ring A is (i) a substituted or unsubstituted six-membered nitrogen containing non-aromatic heterocyclic ring,
(ii) substituted or unsubstituted pyrimidine,
(iii) substituted or unsubstituted benzene,
(iv) substituted or unsubstituted pyrazole, or
(v) a fused ring consisting of same or different two rings selected from a substituted or unsubstituted five- to seven-membered nitrogen containing non-aromatic heterocyclic ring, substituted or unsubstituted benzene, and a substituted or unsubstituted five- or six-membered aromatic heterocyclic ring, or its pharmaceutically acceptable salt.

(4A) The compound according to any one of the above (1), (1A), (1B), (2), (3A), (3) and (3B), wherein ring A is substituted or unsubstituted six-membered non-aromatic heterocyclyl containing two nitrogen atoms or substituted or unsubstituted pyrimidine, or its pharmaceutically acceptable salt.

(5) The compound according to the above (4) or (3A), wherein the group represented by the formula:

[Chemcial Formula 27]

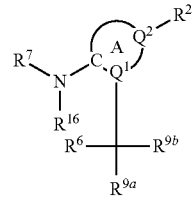

is a group represented by the formula:

[Chemical Formula 28]

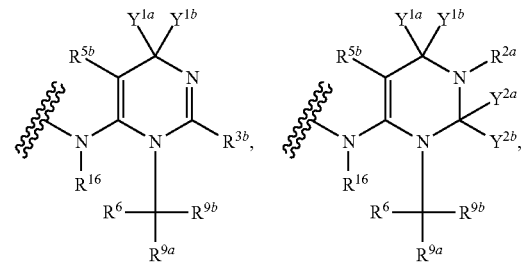

-continued

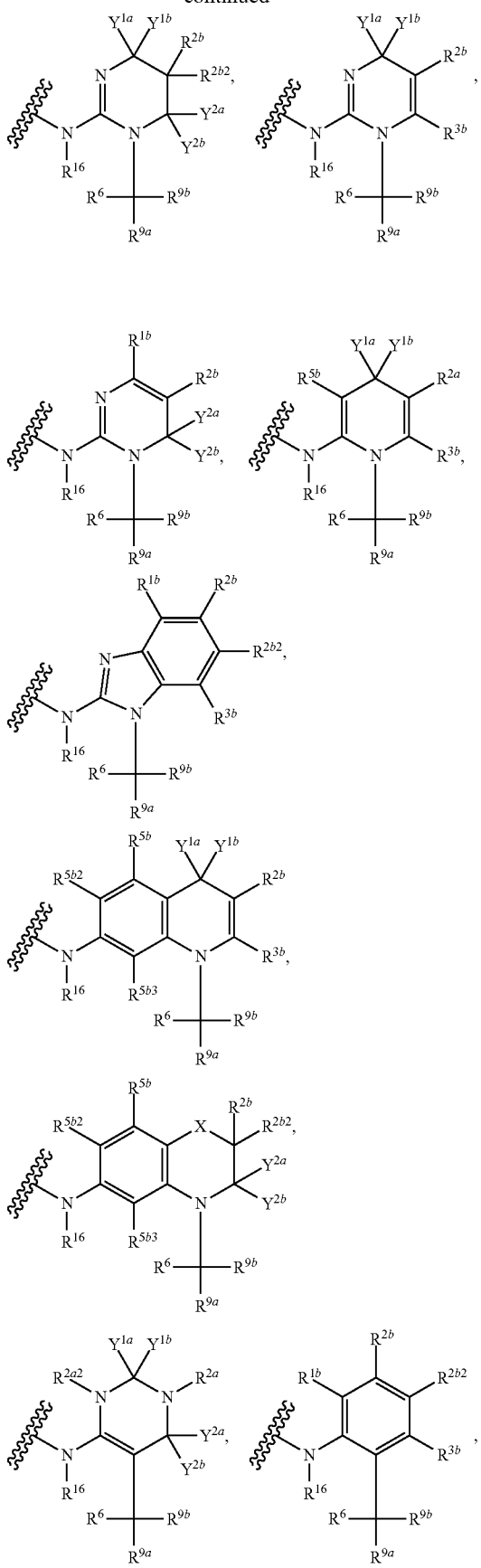
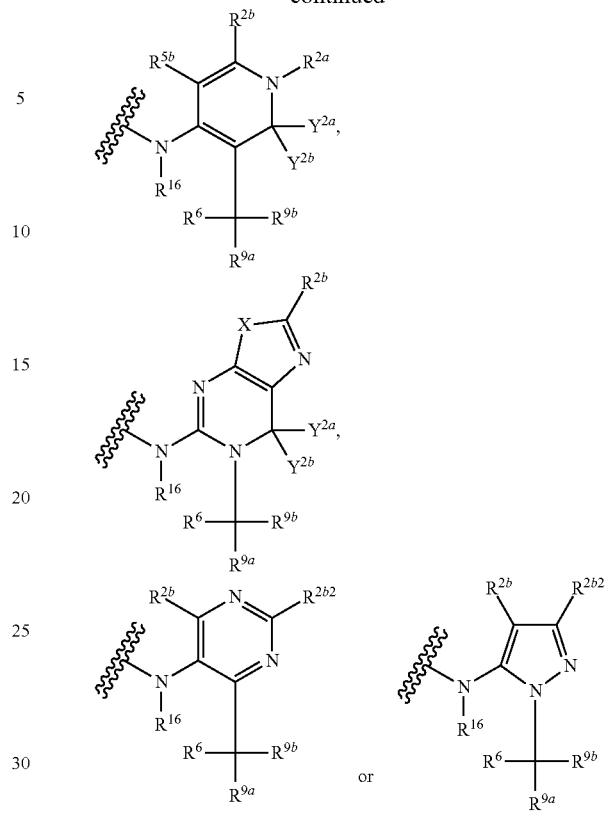

wherein $Y^{1a}$, $Y^{1b}$, $Y^{2a}$, $Y^{2b}$, $R^{1b}$, $R^{2b}$, $R^{2b2}$, $R^{3b}$, $R^{5b}$, $R^{5b2}$, and $R^{5b3}$ are each independently a hydrogen atom, carboxy, hydroxy, halogen, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, substituted or unsubstituted imino, or substituted or unsubstituted amino, or $Y^{1a}$ and $Y^{1b}$, and/or $Y^{2a}$ and $Y^{2b}$ may be taken together to form oxo or thioxo; —X— is —O—, —S—, or —N($R^{2a}$)—;

$R^{2a}$ and $R^{2a2}$ are each independently a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, or substituted or unsubstituted sulfamoyl;

$R^{9a}$, $R^{9b}$, and $R^{16}$ are as defined in the above (1);

$R^6$ is as defined in the above (3);

or its pharmaceutically acceptable salt.

Preferably, —X— is —O—, s' is an integer of 1 to 3, and $R^{9'}$ is a group except a substituted or unsubstituted non-aromatic heterocyclic group in (5).

(5A) The compound according to any one of the above (1), (1A), (1B), (2), (3A), (3), (3B), (4), and (4A), wherein the group represented by the formula:

[Chemical Formula 29]

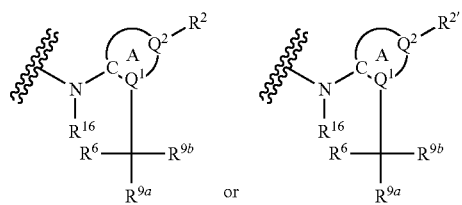

is a group represented by the formula:

[Chemical Formula 30]

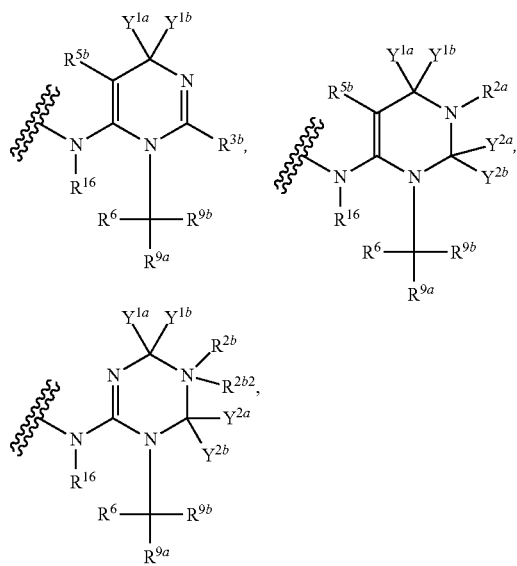

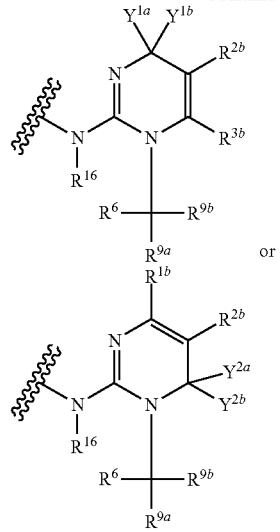

wherein $Y^{1a}$, $Y^{1b}$, $Y^{2a}$, $Y^{2b}$, $R^{1b}$, $R^{2b}$, $R^{2b2}$, $R^{3b}$, and $R^{5b}$ are each independently a hydrogen atom, carboxy, hydroxy, halogen, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, substituted or unsubstituted imino or substituted or unsubstituted amino, or, $Y^{1a}$ and $Y^{1b}$, and/or, $Y^{2a}$ and $Y^{2b}$ are taken together to form oxo or thioxo;

$R^{2a}$ is a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, or substituted or unsubstituted sulfamoyl;

$R^{9a}$, $R^{9b}$ and $R^{16}$ are as defined in the above (1);

$R^6$ is as defined in the above (4), or its pharmaceutically acceptable salt.

(5B) The compound according to any one of the above (1), (1A), (1B), (2), (3A), (3), (3B), (4), and (4A), wherein.

the group represented by the formula:

[Chemical Formula 31]

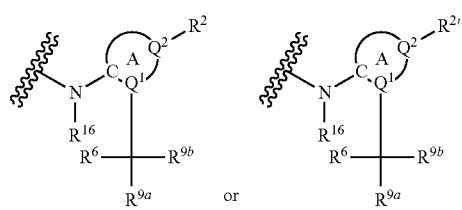

is a group represented by the formula

[Chemical Formula 32]

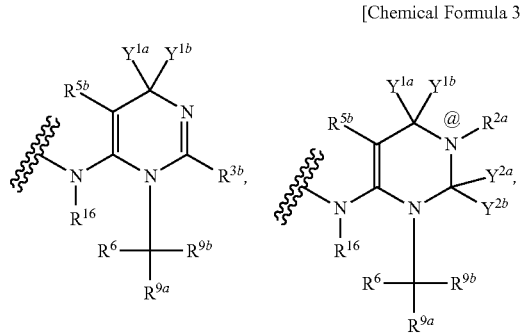

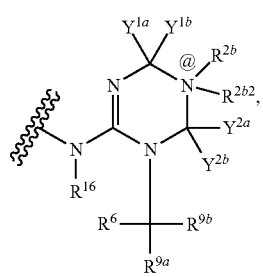

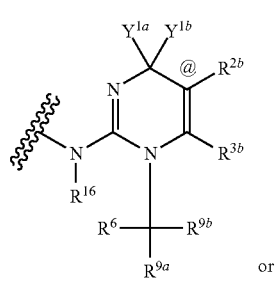

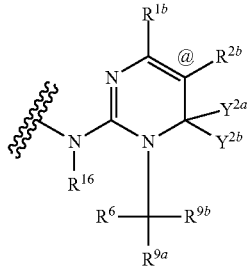

wherein $Y^{1a}$, $Y^{1b}$, $Y^{2a}$, $Y^{2b}$, $R^{1b}$, $R^{2b}$, $R^{2b2}$, $R^{3b}$, $R^{5b}$, and $R^{2a}$ are as defined in the above (6);

$R^{9a}$, $R^{9b}$ and $R^{16}$ are as defined in the above (1);

$R^6$ are as defined in the above (4), or its pharmaceutically acceptable salt.

wherein a ring atom represented by $Q^2$ in ring A corresponds to the ring atoms with "@", to which $R^{2a}$, $R^{2b}$, $R^{2b2}$, and the like bond in the above formula.

(6) The compound according to any one of the above (5), (5A), and (5B), wherein the group represented by the formula:

[Chemical Formula 33]

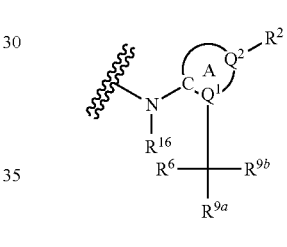

is a group represented by the formula:

[Chemical Formula 34]

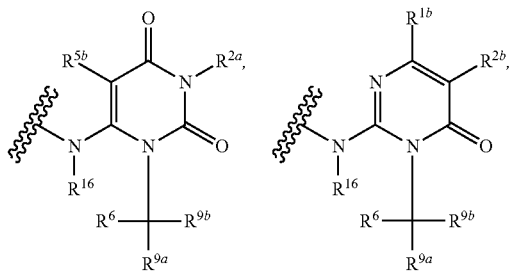

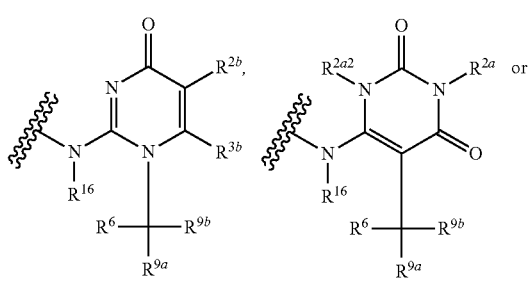

-continued

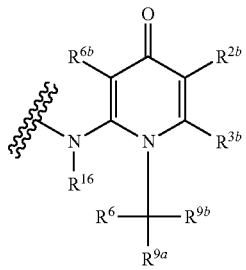

wherein $R^{2a}$, $R^{2a2}$, $R^{1b}$, $R^{2b}$, $R^{3b}$, and $R^{5b}$ are as defined in the above (5);
$R^{9a}$, $R^{9b}$, and $R^{16}$ are as defined in the above (1);
$R^6$ is as defined in the above (3),
or its pharmaceutically acceptable salt.

(6A) The compound according to the above (5), (5A), and (5B), wherein the group represented by the formula:

[Chemical Formula 35]

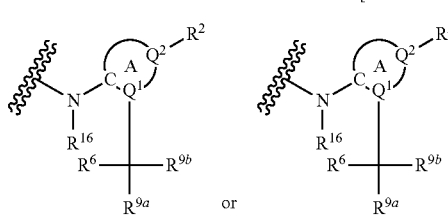

is a group represented by the formula:

[Chemical Formula 36]

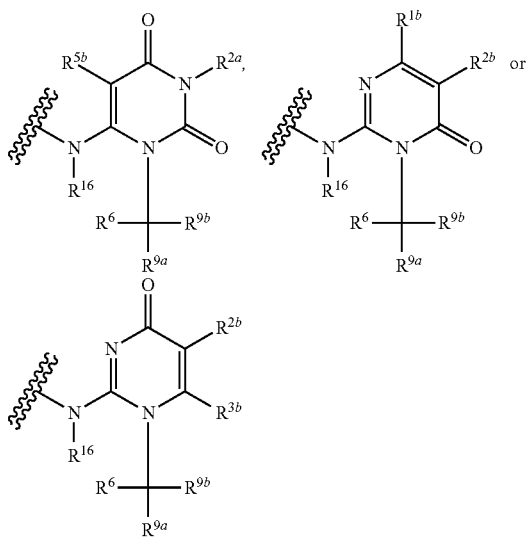

wherein $R^{2a}$, $R^{1b}$, $R^{2b}$, $R^{3b}$, and $R^{5b}$ are as defined in the above (5A);
$R^{9a}$, $R^{9b}$, and $R^{16}$ are as defined in the above (1);
$R^6$ is as defined in the above (3),
or its pharmaceutically acceptable salt.

(6B) The compound according to any one of the above (5B), wherein the group represented by the formula:

[Chemical Formula 37]

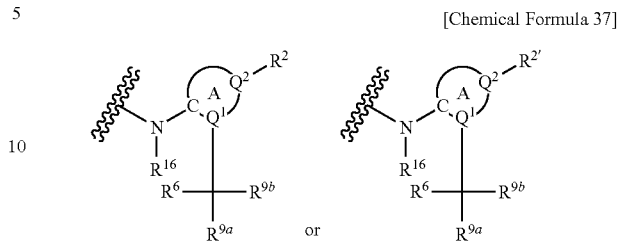

is a group represented by the formula

[Chemical Formula 38]

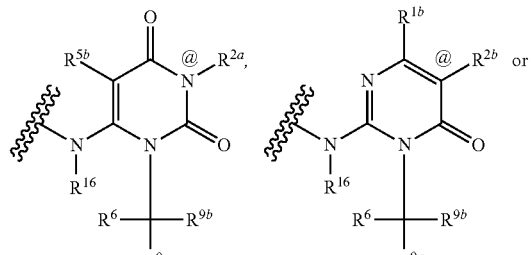

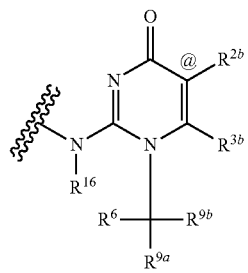

wherein $R^{1b}$, $R^{2a}$, $R^{2b}$, $R^{3b}$, $R^{9a}$, $R^{9b}$, $R^6$, and $R^{16}$ are as defined in the above (5B), or its pharmaceutically acceptable salt.
wherein a ring atom represented by $Q^2$ in ring A corresponds to the ring atoms with "@", to which $R^{2a}$, $R^{2b}$, and the like bond in the above formula.

(7) The compound according to the above (5), wherein the group represented by the formula:

[Chemical Formula 39]

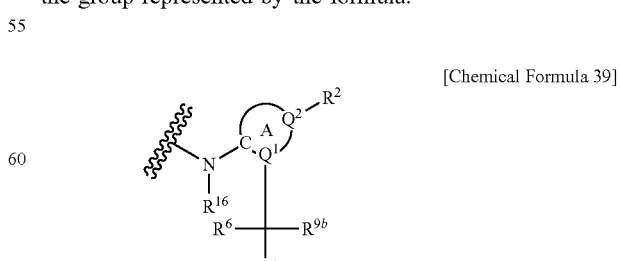

is a group represented by the formula.

[Chemical Formula 40]

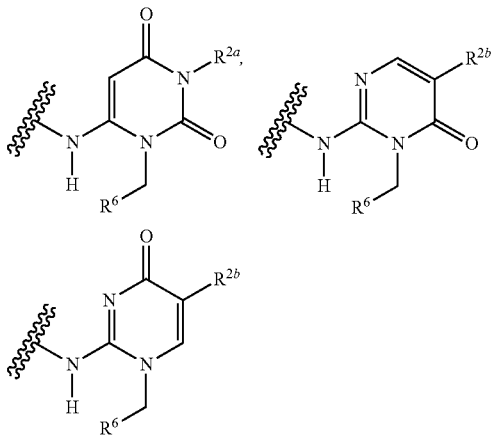

wherein $R^{2a}$ and $R^{2b}$ are as defined in the above (5);
$R^6$ is as defined in the above (3),
or its pharmaceutically acceptable salt.

(7A) The compound according to the above (5A) wherein the group represented by the formula:

[Chemical Formula 41]

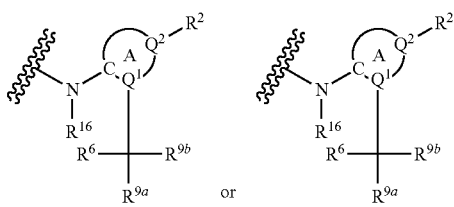

is a group represented by the formula:

[Chemical Formula 42]

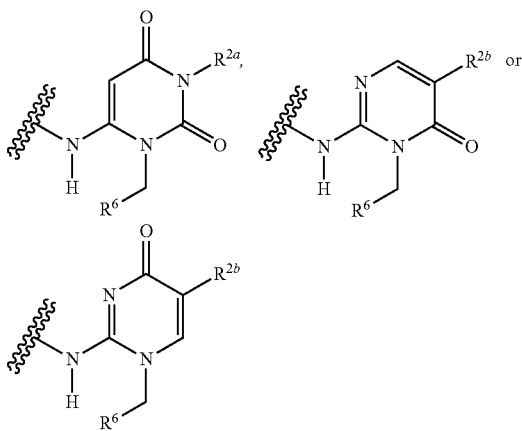

wherein $R^{2a}$ and $R^{2b}$ are as defined in the above (5A);
$R^6$ is as defined in the above (3),
or its pharmaceutically acceptable salt.

(7B) The compound according to the above (5B), wherein the group represented by the formula:

[Chemical Formula 43]

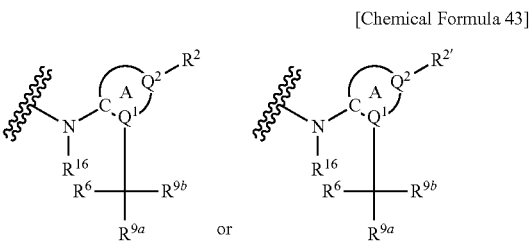

is a group represented by the formula:

[Chemical Formula 44]

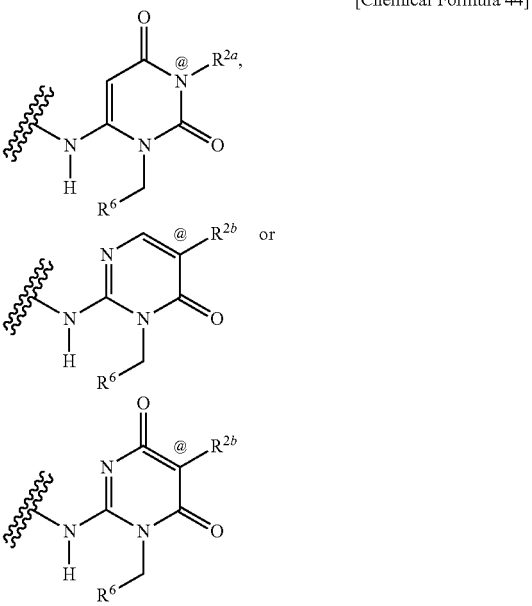

wherein $R^{2a}$, $R^{2b}$ and $R^6$ are as defined in the above (5B), or its pharmaceutically acceptable salt.
wherein a ring atom represented by $Q^2$ in ring A corresponds to the ring atoms with "@", to which $R^{2a}$, $R^{2b}$, and the like bond in the above formula.

(8A) The compound according to any one of the above (1), (1A), (1B), (2), (3), (3B), (4), (4A), (5), (5A), (5B), (6), (6A), (6B), (7), (7A), and (7B),
wherein $R^2$, $R^{2a}$ or $R^{2b}$ are C3-C6 alkyl substituted with 3 to 5 hydroxy groups and optionally with one or more substituents selected from the Substituent Group A (Substituent Group A: halogen, cyano, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo);
C3-C6 alkenyl substituted with 3 to 5 hydroxy groups and optionally with one or more substituents selected from the Substituent Group A; or
C3-C6 alkynyl substituted with 3 to 5 hydroxy groups and optionally with one or more substituents selected from the Substituent Group A,
or its pharmaceutically acceptable salt.

(8B) The compound according to any one of the above (1), (1A), (1B), (2), (3), (3B), (4), (4A), (5), (5A), (5B), (6), (6A), (6B), (7), (7A), and (7B), wherein $Q^2$ is a nitrogen atom, and $R^{2a}$ C3-C6 alkyl substituted with 3 to 5 hydroxy groups and optionally with one or more substituents selected from the Substituent Group A; C3-C6 alkenyl substituted with 3 to 5 hydroxy groups and optionally with one or more substituents selected from the Substituent Group A; or C3-C6 alkynyl substituted with 3 to 5 hydroxy groups and optionally with one or more substituents selected from the Substituent Group A, or its pharmaceutically acceptable salt.

(8) The compound according to any one of the above (1), (1A), (1B), (2), (3), (3B), (4), (4A), (5), (5A), (5B), (6), (6A), (6B), (7), (7A), and (7B), wherein —$R^2$, —$R^{2a}$, —$R^{2b}$ or —$R^{2b2}$ is the formula: —$(C(R^{11c})(R^{11d}))$m'-COOR
wherein $R^{11c}$ are each independently a hydrogen atom, substituted or unsubstituted alkyl, substituted or unsubstituted alkenyl, or substituted or unsubstituted alkynyl;
$R^{11d}$ are each independently a hydrogen atom, substituted or unsubstituted alkyl, substituted or unsubstituted alkenyl, or substituted or unsubstituted alkynyl; or
$R^{11c}$ and $R^{11d}$ attached to the same carbon atom are taken together to form substituted or unsubstituted cycloalkane, substituted or unsubstituted cycloalkane or a substituted or unsubstituted non-aromatic heterocyclic ring;
R is hydrogen or substituted or unsubstituted alkyl;
m' is an integer of 1 to 4,
or its pharmaceutically acceptable salt.

(8C) The compound according to any one of the above (1), (1A), (1B), (2), (3), (3B), (4), (4A), (5), (5A), (5B), (6), (6A), (6B), (7), (7A), and (7B), wherein —$R^2$, —$R^{2a}$ or —$R^{2b}$ is the formula: —$(C(R^{11c})(R^{11d}))$m'-COOH
wherein $R^{11c}$ are each independently a hydrogen atom, substituted or unsubstituted alkyl, substituted or unsubstituted alkenyl, or substituted or unsubstituted alkynyl;
$R^{11d}$ are each independently a hydrogen atom, substituted or unsubstituted alkyl, substituted or unsubstituted alkenyl, or substituted or unsubstituted alkynyl; or
$R^{11c}$ and $R^{11d}$ attached to the same carbon atom are taken together to form substituted or unsubstituted cycloalkane, substituted or unsubstituted cycloalkane or a substituted or unsubstituted non-aromatic heterocyclic ring;
m' is an integer of 1 to 4,
or its pharmaceutically acceptable salt.

(9) The compound according to any one of the above (1), (1A), (1B), (2), (3), (3B), (4), (4A), (5), (5A), (5B), (6), (6A), (6B), (7), (7A), and (7B), wherein $R^2$, $R^{2a}$, $R^{2b}$ or $R^{2b2}$ is unsubstituted alkyl, or its pharmaceutically acceptable salt.

(9A) The compound according to any one of the above (1), (A), (B), (2), (2), (3), (3B), (4), (4A), (5), (5A), (5B), (6), (6A), (6B), (7), (7A), and (7B), wherein $R^2$, $R^{2a}$, and $R^{2b}$ is unsubstituted alkyl, or its pharmaceutically acceptable salt.

(10) The compound according to any one of the above (1), (1A), (1B), (2), (3), (5B), (4), (4A), (5), (5A), (5B), (6), (6A), (6B), (7), (7A), and (7B),
wherein
—$R^2$, —$R^{2b}$ or —$R^{2b2}$ is the formula: —NH—C(=O)—(C($R^{8a}$)($R^{8b}$))n-$R^{13}$
wherein n is an integer of 0 to 4;
$R^{8a}$ are each independently a hydrogen atom, halogen, hydroxy, or substituted or unsubstituted alkyl;
$R^{8b}$ are each independently a hydrogen atom, halogen, hydroxy, or substituted or unsubstituted alkyl;
$R^{18}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl;
the formula: —C(=O)—NH—(C($R^{8a'}$)($R^{8b'}$))n'—$R^{13'}$
wherein n' is an integer of 0 to 4;
$R^{8a'}$ are each independently a hydrogen atom, halogen, hydroxy, or substituted or unsubstituted alkyl;
$R^{8b'}$ are each independently a hydrogen atom, halogen, hydroxy, or substituted or unsubstituted alkyl;
$R^{18'}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl; or
the formula: —(C($R^{8a''}$)($R^{8b''}$))n"—$R^{13''}$
wherein n" is an integer of 0 to 4;
$R^{8a''}$ are each independently a hydrogen atom, halogen, hydroxy, or substituted or unsubstituted alkyl;
$R^{8b''}$ are each independently a hydrogen atom, halogen, hydroxy, or substituted or unsubstituted alkyl
$R^{13''}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or its pharmaceutically acceptable salt.

(10A) The compound according to any one of the above (1), (1A), (1B), (2), (3), (3B), (4), (4A), (5), (5A), (5B), (6), (6A), (6B), (7), (7A), and (7B), wherein $Q^2$ is a nitrogen atom, and $R^{2a}$ is unsubstituted alkyl, or its pharmaceutically acceptable salt.

(10B) The compound according to any one of the above (1), (1A), (1B), (2), (3), (3B), (4), (4A), (5), (5A), (5B), (6), (6A), (6B), (7), (7A), and (7B), wherein —$R^{2b}$ or —$R^{2b2}$ is the formula: —NH—C(=O)—(C($R^{8a}$)($R^{8b}$))n-$R^{13}$ wherein n is an integer of 0 to 4;

$R^{8a}$ are each independently a hydrogen atom, halogen, hydroxy, or substituted or unsubstituted alkyl;

$R^{8b}$ are each independently a hydrogen atom, halogen, hydroxy, or substituted or unsubstituted alkyl;

$R^{18}$ is a hydrogen atom, substituted or unsubstituted alkyl, substituted or unsubstituted alkenyl, substituted or unsubstituted alkynyl, hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl;

the formula: —C(=O)—NH—(C($R^{8a'}$)($R^{8b'}$))n'—$R^{13'}$ wherein n' is an integer of 0 to 4;

$R^{8a'}$ are each independently a hydrogen atom, halogen, hydroxy, or substituted or unsubstituted alkyl;

$R^{8b'}$ are each independently a hydrogen atom, halogen, hydroxy, or substituted or unsubstituted alkyl;

$R^{13'}$ is a hydrogen atom, substituted or unsubstituted alkyl, substituted or unsubstituted alkenyl, substituted or unsubstituted alkynyl, hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl; or, the formula: —(C($R^{8a''}$)($R^{8b''}$))n''—$R^{13''}$ wherein n'' is an integer of 0 to 4;

$R^{8a''}$ are each independently a hydrogen atom, halogen, hydroxy, or substituted or unsubstituted alkyl;

$R^{8b''}$ are each independently a hydrogen atom, halogen, hydroxy, or substituted or unsubstituted alkyl;

$R^{13''}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or its pharmaceutically acceptable salt.

(10C) The compound according to the above (10B), wherein

—$R^{2b}$ or —$R^{2b2}$ is the formula: —NH—C(=O)—(C($R^{8a}$)($R^{8b}$))n-$R^{18}$ wherein n is 0;

$R^{13}$ is substituted or unsubstituted alkyl, substituted or unsubstituted alkenyl, substituted or unsubstituted alkynyl, a substituted or unsubstituted non-aromatic heterocyclic group, substituted or unsubstituted heteroaryl, substituted or unsubstituted alkyloxy, substituted or unsubstituted alkenyloxy or substituted or unsubstituted alkynyloxy;

other symbols are as defined in the above (10B), or its pharmaceutically acceptable salt.

(11) The compound according to any one of the above (1), (1A), (1B), (2), (3A), (3), (3B), (4), (4A), (5), (5A), (5B), (6), (6A), (6B), (8A), (8B), (8), (8C), (9), (9A), (10), (10A) and (10B), wherein $R^{9a}$ and $R^{9b}$ are both hydrogen atoms, or its pharmaceutically acceptable salt.

(12) The compound according to any one of the above (1), (1A), (1B), (2), (3A), (3), (3B), (4), (4A), (5), (5A), (5B), (6), (6A), (6B), (7), (7A), (7B), (8A), (8B), (8), (8C), (9), (9A), (10), (10A), (10B), (10C) and (11), wherein $R^6$ is a group represented by the formula:

[Chemical Formula 45]

wherein =$V^1$—$V^2$=$V^3$—$V^4$=$V^5$— is as defined in the above (3), or its pharmaceutically acceptable salt.

(13) The compound according to any one of the above (1), (1A), (1B), (2), (3A), (3), (3B), (4), (4A), (5), (5A), (5B), (6), (6A), (6B), (7), (7A), (7B), (8A), (8B), (8), (8C), (9), (9A), (10), (10A), (10B), (10C), (11) and (12), wherein $R^6$ is a group represented by the formula:

[Chemical Formula 46]

wherein =$V^1$—$V^2$=$V^3$—$V^4$=$V^5$— is (i): =C($R^{A'}$)—C($R^A$)=C($R^B$)—C($R^C$)=C($R^{C'}$)—, wherein $R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl, or its pharmaceutically acceptable salt.

(13A) The compound according to any one of the above (1), (1A), (1B), (2), (3A), (3), (3B), (4), (4A), (5), (5A), (5B), (6), (6A), (6B), (7), (7A), (7B), (5A), (8B), (8), (8C), (9), (9A), (10), (10A), (10B), (10C), (11) and (12), wherein $R^6$ is a group represented by the formula:

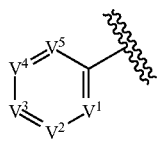

[Chemical Formula 47]

wherein =$V^1$—$V^2$=$V^3$—$V^4$=$V^1$— is (i): =C(H)—C($R^A$)=C($R^B$)—C($R^C$)=C(H)—,
wherein $R^A$, $R^B$ and $R^C$ are each independently halogen, alkyl, alkenyl, alkynyl, alkyloxy, alkenyloxy, alkynyloxy, cycloalkyl, cycloalkenyl, cycloalkynyl, or alkylsilylalkynyl, or its pharmaceutically acceptable salt.

(14) The compound according to any one of the above (1), (1A), (1B), (2), (3A), (3), (5B), (4), (4A), (5), (5A), (5B), (6), (6A), (6B), (8A), (8B), (8), (8C), (9), (9A), (10), (10A), (10B), (10C), (11), (12), (13) and (13A), wherein $R^{16}$ is a hydrogen atom, or its pharmaceutically acceptable salt.

(15) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A) and (14), wherein s' is an integer of 1 to 2, and at least one of $R^{9'}$ is halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl, or its pharmaceutically acceptable salt.

(15A) The compound according to any one of the above (1), (1A), (1B), (2), (3), (3B), (4), (4A), (5), (A), (5B), (6), (6A), (6B), (7), (7A), (7B), (5A), (5B), (8), (8C), (9), (9A), (10), (10A), (10B), (10C), (11), (12), (13), (13A) and (14), wherein s' is an integer of 1 to 2, and at least one of $R^{9'}$ is hydroxy, carboxy, cyano, substituted alkyl, substituted or unsubstituted carbamoyl, substituted or unsubstituted amino, substituted or unsubstituted sulfamoyl, substituted sulfonyl or substituted sulfinyl, or its pharmaceutically acceptable salt.

(16) The compound according to any one of the above (1), (1A), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15) and (15A), wherein s' is 1, and $R^{9'}$ is halogen, carboxy, substituted or unsubstituted alkyl or substituted or unsubstituted carbamoyl, or its pharmaceutically acceptable salt.

(16A) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (18A), (14), (15) and (15A), wherein s' is 1, and $R^{9'}$ is carboxy or substituted or unsubstituted carbamoyl, or its pharmaceutically acceptable salt.

(16B) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15) and (15A), wherein s' is 1, and $R^{9'}$ is substituted or unsubstituted carbamoyl, or its pharmaceutically acceptable salt.

(17) The compound according to any one of the above (1), (1A), (1B), (2), (3), (3B), (4), (4A), (5), (5A), (5B), (6), (6A), (6B), (7), (7A), (7B), (5A), (8B), (8), (8C), (9), (9A), (10), (10A), (10B), (10C), (11), (12), (13), (13A) and (14), wherein s' is 0, or its pharmaceutically acceptable salt.

(18) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B) and (17), wherein ring B is an aromatic heterocyclic ring, or its pharmaceutically acceptable salt.

(19) The compound according to any one of the above (1), (1A), (1B), (2), (3), (5B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17) and (18), wherein ring B is thiazole, isothiazole, oxazole, isoxazole, pyrazole, imidazole, triazole, furan, thiophene, thiadiazole, oxadiazole, pyridine, pyrimidine, pyrazine, pyridazine, triazine or benzoxazole, or its pharmaceutically acceptable salt.

(19A) The compound according to any one of the above (1), (1A), (1B), (2), (3), (5B), (4), (4A), (5), (5A), (5B), (6), (6A), (6B), (7), (7A), (7B), (8A), (5B), (8), (8C), (9), (9A), (10), (10A), (10B), (10C), (11), (12), (13), (13A), (14), (15), (15A), (16), (16A), (16B), (17) and (18), wherein ring B is thiazole, isothiazole, oxazole, isoxazole, pyrazole, imidazole, triazole, furan, thiophen, thiadiazole, oxadiazole, pyrimidine, pyrazine, pyridazine, triazine or benzoxazole, or its pharmaceutically acceptable salt.

(20) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17) and (18), wherein ring B is thiazole, isothiazole, oxazole, isoxazole, thiadiazole, oxadiazole, pyridine, pyrimidine, pyrazine or pyridazine, or its pharmaceutically acceptable salt.

(20A) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17) and (18), wherein ring B is thiazole, isothiazole, oxazole, isoxazole, thiadiazole, oxadiazole, pyrimidine, pyrazine or pyridazine, or its pharmaceutically acceptable salt.

(21) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (100), (11), (12), (13), (13A), (14), (15), (15A), (16), (16A), (16B), (17), (18), (19), (19A), (20) and (20A), wherein -M- is —O—, or its pharmaceutically acceptable salt.

(22) The compound according to any one of the above (1), (1A), (1B), (2), (3), (3B), (4), (4A), (5), (5A), (5B), (6), (6A), (6B), (7), (7A), (B), (8A), (8B), (8), (8C), (9), (9A), (10), (10A), (10B), (10C), (11), (12), (13), (13A), (14), (15), (15A), (16), (16A), (16B), (17), (18), (19), (19A), (20), (20A) and (21), wherein ring D is benzene, or its pharmaceutically acceptable salt.

(23) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21) and (22), wherein carbon atom a is positioned on ring D in a (1,4) relationship with respect to carbon atom b, or its pharmaceutically acceptable salt.

(24) The compound according to any one of the above (1), (1A), (1B), (2), (3), (3B), (4), (4A), (5), (5A), (5B), (6), (5A), (6B), (7), (7A), (7B), (BA), (8B), (8), (SC), (9), (9A), (10), (10A), (10B), (10C), (11), (12), (13), (13A), (14), (15), (15A), (16), (16A), (16B), (17), (18), (19), (19A), (20), (20A), (21), (22), (23) and (24), wherein a is 1 or 2, and at least one of $R^9$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyl or substituted or unsubstituted cycloalkenyl, or its pharmaceutically acceptable salt.

(25) The compound according to any one of the above (1), (1A), (1B), (2), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21), (22), (23) and (24), wherein a is 0, or its pharmaceutically acceptable salt.

(26) The compound according to any one of the above (1), (1A), (1B), (2), (3), (3B), (4), (4A), (5), (5A), (5B), (6), (6A), (6B), (7), (7A), (7B), (5A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21), (22), (23), (24) and (25), wherein a group represented by the formula:

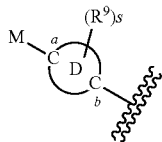

[Chemical Formula 48]

wherein ring D, a carbon atom a, a carbon atom b, -M-, s, and $R^9$ are as defined in the above (1), is a group represented by the formula:

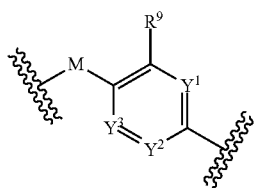

[Chemical Formula 49]

wherein -M- is as defined in the above (1);

R is halogen or substituted or unsubstituted alkyl;

$Y^1$, $Y^2$ and $Y^3$ are each independently CH or N;

provided that $Y^1$, $Y^2$ and $Y^3$ are not N at the same time, or its pharmaceutically acceptable salt.

(27) The compound according to any one of the above (1), (1A), (1B), (3), (3B), (4), (4A), (5), (5A), (5B), (6), (6A), (6B), (7), (7A), (7B), (8A), (5B), (8), (8C), (9), (9A), (10), (10A), (10B), (10C), (11), (12), (13), (13A), (14), (15), (15A), (16), (16A), (16B), (17), (18), (19), (19A), (20), (20A), (21), (24) and (25), wherein $R^7$ is a group represented by the formula:

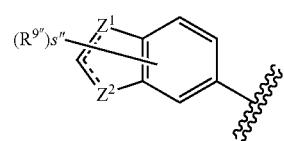

[Chemical Formula 50]

wherein a group represented by the formula:

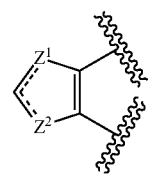

[Chemical Formula 51]

is a group represented by the formula:

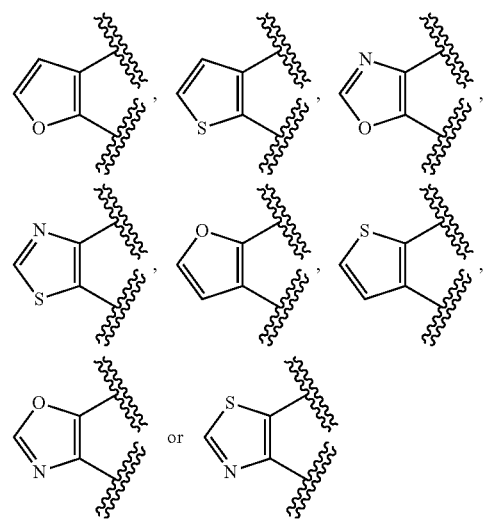

[Chemical Formula 52]

s" is an integer 0 to 2;

$R^{9''}$ are each independently substituted or unsubstituted alkyl, substituted or unsubstituted alkenyl or substituted or unsubstituted alkynyl, or its pharmaceutically acceptable salt.

(27A) The compound according to any one of the above (1), (1A), (1B), (3A), (3), (3B), (4), (4A), (5), (5A), (5B), (6), (6A), (6B), (7), (7A), (7B), (5A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21), (22), (23), (24), (25) and (26), wherein $R^7$ or $R^{7'}$ is a group represented by the formula:

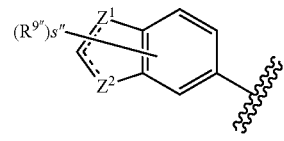

[Chemical Formula 53]

wherein a group represented by the formula:

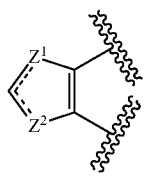

is a group represented by the formula:

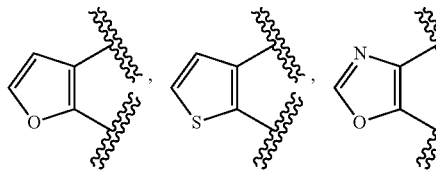

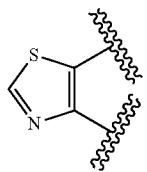

s" and $R^{9'}$ are as defined in the above (27),
or its pharmaceutically acceptable salt.

(27B) The compound according to any one of the above (1), (1A), (1B), (2), (3A), (8A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21), (22), (23), (24), (25), (26), (27) and (27A), wherein
a group represented by the formula:

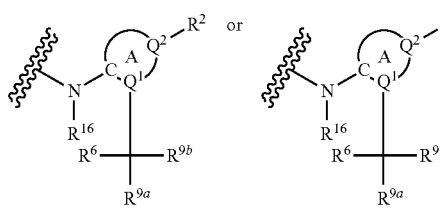

is a group represented by the formula:

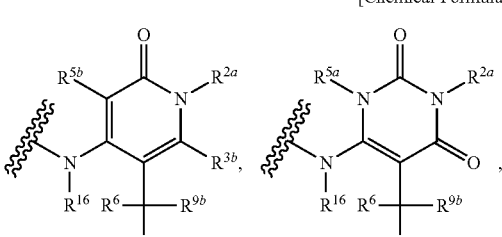

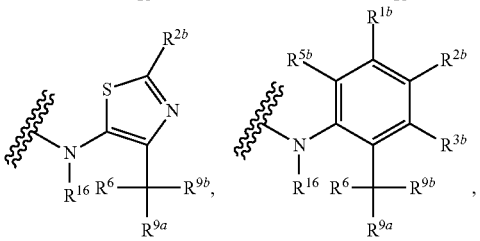

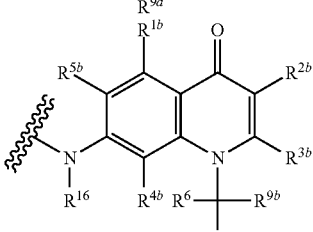

wherein $R^{4b}$ is a hydrogen atom, carboxy, hydroxy, halogen, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino;

$R^{5a}$ is a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl or substituted or unsubstituted sulfamoyl;

$R^{1b}$, $R^{2b}$, $R^{3b}$, $R^{5b}$, $R^{2a}$, $R^{9a}$, $R^{9b}$, $R^6$, and $R^{16}$ are as defined in the above (1), or its pharmaceutically acceptable salt.

(28) The compound according to any one of the above (1), (1A), (1B), (2), (3A), (3), (3B), (4), (4A), (5), (5A), (5B), (6), (6A), (6B), (7), (7A), (7B), (8), (8C), (9) and (9A), represented by the formula:

[Chemical Formula 58]

wherein $R^{2b}$ is substituted or unsubstituted alkyl, substituted or unsubstituted alkyloxy, substituted or unsubstituted cycloalkyl, a substituted or unsubstituted non-aromatic heterocyclic group, substituted or unsubstituted aryl, substituted or unsubstituted heteroaryl, substituted or unsubstituted amino or substituted or unsubstituted carbamoyl;

$R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;

ring B is thiazole, isothiazole, oxazole, isoxazole, thiadiazole, oxadiazole, pyridine, pyrimidine, pyrazine or pyridazine;

s and s' are each independently integers of 0 to 3;

$R^9$ are each independently halogen, hydroxy, cyano, substituted or unsubstituted alkyl or substituted or unsubstituted alkyloxy;

$R^{9'}$ are each independently halogen, hydroxy, carboxy cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl, or its pharmaceutically acceptable salt.

(29) The compound according to any one of the above (1), (1A), (1B), (2), (3A), (3), (3B), (4), (4A), (5), (5A), (5B), (6), (6A), (6B), (7), (7A), (7B), (8), (8C), (9) and (9A), represented by the formula:

[Chemical Formula 59]

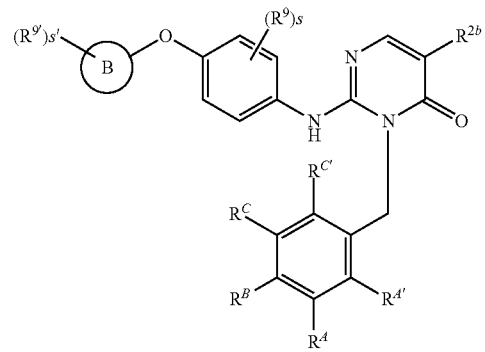

wherein $R^{2b}$ is substituted or unsubstituted alkyl, substituted or unsubstituted alkyloxy, substituted or unsubstituted cycloalkyl, a substituted or unsubstituted non-aromatic heterocyclic group, substituted or unsubstituted aryl, substituted or unsubstituted heteroaryl, substituted or unsubstituted amino or substituted or unsubstituted carbamoyl;

$R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;

ring B is thiazole, isothiazole, oxazole, isoxazole, thiadiazole, oxadiazole, pyridine, pyrimidine, pyrazine or pyridazine;

provided that ring B is not pyridine when $R^{2b}$ is amino or amino substituted with optionally substituted acyl;

s and s' are each independently integers of 0 to 3;

$R^9$ are each independently halogen, hydroxy, cyano, substituted or unsubstituted alkyl or substituted or unsubstituted alkyloxy;

$R^{9'}$ are each independently halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl, or its pharmaceutically acceptable salt.

(30) The compound according to any one of the above (1), (1A), (1B), (2), (3A), (3), (3B), (4), (4A), (5), (5A), (5B), (6), (6A), (6B), (7), (7A), (7B), (8), (8C), (9) and (9A), represented by the formula:

[Chemical Formula 60]

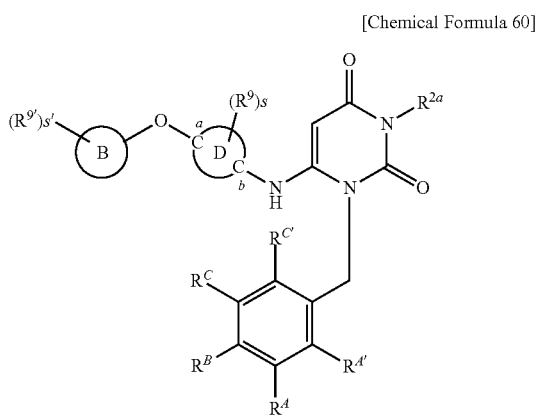

wherein
ring D is benzene or pyridine;
carbon atom a and carbon atom b are carbon atoms which constitute ring D;
$R^{2a}$ is substituted or unsubstituted alkyl, substituted or unsubstituted cycloalkyl, a substituted or unsubstituted non-aromatic heterocyclic group, substituted or unsubstituted aryl, substituted or unsubstituted heteroaryl or substituted or unsubstituted carbamoyl;
$R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;
ring B is thiazole, isothiazole, oxazole, isoxazole, thiadiazole, oxadiazole, pyridine, pyrimidine, pyrazine or pyridazine;
provided that

[Chemical Formula 61]

is not or when $R^{2a}$ is unsubstituted alkyl;
s and s' are each independently integers of 0 to 3;
$R^9$ are each independently halogen, hydroxy, cyano, substituted or unsubstituted alkyl or substituted or unsubstituted alkyloxy;
$R^{9'}$ are each independently halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl, or its pharmaceutically acceptable salt.

(31) A pharmaceutical composition comprising the compound according to any one of the above (1), (1A), (1B), (2), (3A), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21), (22), (23), (24), (25), (26), (27), (27A), (27B), (28), (29) and (30), or its pharmaceutically acceptable salt.

(32) The pharmaceutical composition according to the above (31), wherein the composition has a $P2X_3$ and/or $P2X_{2/3}$ receptor antagonistic activity.

(33) A compound according to any one of the above (1), (1A), (1B), (2), (3B), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21), (22), (23), (24), (25), (26), (27), (27A), (27B), (28), (29) and (30), or its pharmaceutically acceptable salt, for use in a method for treating and/or preventing a disease related to $P2X_3$ and/or $P2X_{2/3}$ receptor.

(34) A method for treating and/or preventing a disease related to $P2X_3$ and/or $P2X_{2/3}$ receptor comprising administering the compound according to any one of the above (1), (1A), (1B), (2), (5A), (3), (3B), (4), (4A), (5), (5A), (5B), (6), (6A), (6B), (7), (7A), (7B), (8A), (8B), (8), (8C), (9), (9A), (10), (10A), (10B), (100), (11), (12), (13), (13A), (14), (15), (15A), (16), (16A), (16B), (17), (18), (19), (19A), (20), (20A), (21), (22), (23), (24), (25), (26), (27), (27A), (27B), (28), (29) and (30), or its pharmaceutically acceptable salt.

(35) Use of the compound of any one of the above (1), (1A), (1B), (2), (3A), (3), (3B), (4), (4A), (5), (5A), (5B), (6), (6A), (6B), (7), (7A), (7B), (8A), (8B), (8), (8C), (9), (9A), (10), (10A), (10B), (10C), (11), (12), (13), (13A), (14), (15), (15A), (16), (16A), (16B), (17), (18), (19), (19A), (20), (20A), (21), (22), (23), (24), (25), (26), (27), (27A), (27B), (28), (29) and (30), or its pharmaceutically acceptable salt, in the manufacturing of an agent for treating and/or preventing a disease related to $P2X_3$ and/or $P2X_{2/3}$ receptor.

Effect of the Invention

The compound of the invention has an antagonistic activity on $P2X_3$ and/or $P2X_{2/3}$ receptor and is useful in the treatment of diseases or conditions associated with a $P2X_3$ and/or $P2X_{2/3}$ receptor, particularly chronic pain, urination disorder, and chronic cough.

MODE FOR CARRYING OUT THE INVENTION

As used throughout the specification, the following terms have the following meaning unless specifically indicated.

The term "halogen" means fluoro, chloro, bromo and iodo.

The halogen moiety in said "haloalkyl", "haloalkylcarbamoyl" and "haloalkyloxy" is as defined above for "halogen".

The term "alkyl" includes a straight or branched chain monovalent hydrocarbon group of a carbon number of 1 to 15, as one embodiment a carbon number of 1 to 10, and as another embodiment a carbon number of 1 to 6. Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl, n-undecanyl, dodecanyl, tridecanyl, and the like.

In the present specification, the carbon number in the term "alkyl" may be limited. For example, C3-C6 alkyl means "alkyl" of a carbon number of 3 to 6.

Examples of "alkyl" for $R^c$ are n-propyl and the like.

The alkyl moiety in said "haloalkyl", "hydroxyalkyl", "carboxyalkyl", "aminoalkyl", "alkylaminoalkyl", "alkylamino", "alkylimino", "alkylsulfonyl", "alkylsulfamoyl", "alkylcarbamoyl", "carbamoylalkylcarbamoyl", "cycloalkylalkyl", "arylalkyl", "heteroarylalkyl", "alkylsilylalkynyl", "alkylsulfonyl", "alkylsulfinyl", "alkylcarbamoyl", "alkylcarbamoylalky", "alkylcarbamoylalkyloxy", "alkylsulfamoyl", "alkylsulfamoylalkyl", "haloalkylcarbamoyl", "hydroxyalkylcarbamoyl", "alkyloxycarbonylalkyl", "alkylcarbamoylamino", "alkyloxycarbonylamino", "alkylsulfonylcarbamoyl", "arylalkylamino", and "non-aromatic heterocyclylalkyl" is as defined above for "alkyl".

The term "alkyloxy" includes an alkyloxy group of which alkyl moiety is as defined above for "alkyl". For example, methoxy, ethoxy, propoxy, isopropoxy, butoxy, isobutoxy, sec-butoxy, tert-butoxy, pentyloxy, isopentyloxy, neopentyloxy, hexyloxy, etc are exemplified as alkyloxy.

The alkyloxy moiety in said "haloalkyloxy", "arylalkyloxy", "alkyloxycarbonyl", "alkyloxycarbonylalkyl", "alkyloxyalkyloxy", "alkyloxycarbonylacyl", "alkylcarbamoylalkyloxy", "carbamoylalkyloxy", "carboxyalkyloxy", "alkyloxyimino", "alkyloxycarbonylcarbonylamino", "non-aromatic heterocyclylalkyloxy", "heteroarylalkyloxy", "non-aromatic carbocyclylalkyloxy" is as defined above for "alkyloxy".

For example, methylthio, ethylthio, propylthio, isopropylthio, butylthio, isobutylthio, sec-butylthio, tert-butylthio, pentylthio, isopentylthio, neopentylthio, hexylthio, and the like are exemplified as "alkylthio".

For example, methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, and the like are exemplified as "alkyloxycarbonyl".

For example, mono- or di-alkylcarbamoyl, such as methylcarbamoyl, ethylcarbamoyl, n-propylcarbamoyl, isopropylcarbamoyl, cyclopropylcarbamoyl, n-butylcarbamoyl, dimethylcarbamoyl, diethylcarbamoyl, dipropylcarbamoyl, and the like are exemplified as "alkylcarbamoyl".

The term "alkenyl" includes linear or branched alkenyl of a carbon number of 2 to 15, as one embodiment a carbon number of 2 to 10, and as another embodiment a carbon number of 2 to 6 having one or more double bonds at any available position. Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl and the like.

In the present specification, the carbon number in the term "alkenyl" may be limited. For example, C3-C6 alkenyl means "alkenyl" of a carbon number of 3 to 6.

The alkenyl moiety in said "alkenyloxy", "alkenylthio", "alkenylcarbamoyl", "alkenylsulfamoyl" and "alkenyloxycarbonyl" is as defined above for "alkenyl".

The term "alkynyl" includes a linear or branched alkynyl of a carbon number of 2 to 15, as one embodiment a carbon number of 2 to 10, as another embodiment a carbon number 2 to 6. Examples include ethynyl, propynyl, butynyl, pentynyl, hexynyl, heptynyl, octynyl, nonynyl and decynyl. These have one or more triple bonds at any available position and may further a double bond.

In the present specification, the carbon number in the term "alkynyl" may be limited. For example, C3-C6 alkynyl means "alkynyl" of a carbon number of 3 to 6.

The alkynyl moiety in said "alkynyloxy", "alkynylthio", "alkynyloxycarbonyl", and "alkylsilylalkynyl" is as defined above for "alkynyl".

The term "acyl" includes a group of the formula R—C(=O)—, wherein R is, for example, "hydrogen", "alkyl", "alkenyl" or "alkynyl" as defined above and "cycloalkyl", "cycloalkenyl", "non-aromatic heterocyclic group", "aryl" or "heteroaryl" as defined below.

The acyl moiety in "acyloxy", "acyloxyacyl", "acylamino", "acylimino", and "alkyloxycarbonylacyl" is as defined above for "acyl".

The term "cycloalkane" includes a monocyclic or polycyclic saturated cyclic carbocyclic ring containing from 3 to 10 carbons. Monocyclic cycloalkane includes, for example, cyclopropane, cyclobutane, cyclopentane, cyclohexane, cycloheptane, cyclooctane, cyclononane, cyclodecane, etc. Polycyclic cycloalkane includes norbornanane, tetrahydronaphthalene, etc.

The term "cycloalkyl" includes a monovalent group derived from "cycloalkane" as defined above. Monocyclic cycloalkyl includes, for example, cyclopropyl, cyclobutyl, cyclopentyl, cyclohexyl, cycloheptyl, cyclooctyl, cyclononyl, cyclodecyl, etc. As one embodiment, C3-C8 cycloalkane is exemplified. As another embodiment, C3-C7 cycloalkane is exemplified. Polycyclic cycloalkyl includes norbornyl, tetrahydronaphthalene-5-yl, tetrahydronaphthalene-6-yl, etc.

Examples of "cycloalkyl" for $R^6$ are cyclopentyl, cyclohexyl, cycloheptyl, cyclooctyl and the like.

Examples of "cycloalkyl" for $R^7$ are cyclopentyl, cyclohexyl, cycloheptyl, cyclooctyl and the like.

The cycloalkyl moiety in said "cycloalkylcarbonyl", "cycloalkyloxycarbonyl", "cycloalkylalkyl" and "cycloalkyloxy" is as defined above for "cycloalkyl".

The term "cycloalkene" includes a non-aromatic monocyclic or polycyclic ring of 3 to 10 carbons containing at least one carbon-carbon double bond. As one embodiment C3-C8 cycloalkene is exemplified. As another embodiment C3-C7 cycloalkene is exemplified. Monocyclic cycloalkene includes, for example, cyclopentene, cyclohexene, etc. Polycyclic cycloalkene includes norbornene, indene, etc.

The term "cycloalkenyl" includes a monovalent group derived from "cycloalkene" as defined above. Monocyclic cycloalkenyl includes cyclopentenyl, cyclohexenyl, etc. As one embodiment, C3-C8 cycloalkane is exemplified. As another embodiment, C3-C7 cycloalkane is exemplified. Polycyclic cycloalkenyl includes norbornenyl, indene-1-yl, indene-2-yl, indene-3-yl, etc.

The cycloalkenyl moiety in said "cycloalkenyloxycarbonyl" and "cyclolalkenyloxy" is as defined above for "cycloalkenyl".

The term "aromatic carbocyclic ring" includes an aromatic hydrocarbocyclic ring which is monocyclic or fused-cyclic, such as benzene ring, naphthalene ring, anthracene ring, phenanthrene ring, etc.

The term "aryl" includes a monovalent group derived from "aromatic carbocyclic ring" as defined above. For example, phenyl, 1-naphthyl, 2-naphthyl, anthryl, phenanthryl, etc. are exemplified.

Preferable "aryl" for $R^6$ is phenyl.

Preferable "aryl" for $R^7$ is phenyl.

The aryl moiety in said. "arylalkyl", "aryloxy", "arylthio", "arylcarbonyl", "arylalkyloxy", and "aryloxycarbonyl" is as defined above for "aryl".

The term "heterocyclic ring" includes an aromatic or a non-aromatic monocyclic or fused-cyclic ring, which includes a five- to seven-membered ring having at least one nitrogen atom, oxygen atom, and/or sulfur atom in the ring; a fused ring consisting of two or more said five- to seven-membered rings; or a fused ring consisting of said five- to seven-membered ring having at least one nitrogen atom, oxygen atom, and/or sulfur atom in the ring fused to one or more "aromatic carbocyclic ring", "cycloalkane" or "cycloalkene" as defined above.

For example, a monocyclic non-aromatic heterocyclic ring such as pyrroline, pyrrolidine, piperidine, piperazine, morpholine, thiomorpholine, tetrahydropyrane, dihydropyridine, dihydropyridazine, dioxane, oxathiolane, thiane, tetrahydrofuran, tetrahydropyran, tetrahydrothiazole, tetrahydroisothiazole, etc.;

a monocyclic aromatic heterocyclic ring such as pyrrole, pyrazine, pyrazole, tetrazole, furan, thiophene, pyridine, imidazole, triazole, tetrazole, triazine, pyridazine, pyrimidine, isoxazole, thiazole, isothiazole, thiadiazole, oxazole, oxadiazole, etc; and a fused heterocyclic ring such as indole, isoindole, indazole, indolizine, indoline, isoindoline, quinoline, isoquinoline, cinnoline, phthalazine, quinazoline, naphthyridine, quinoxaline, purine, pteridine, benzopyrane, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazole, benzodioxane, tetrahydroquinoline, tetrahydrobenzothiophene, etc. are exemplified.

The term "heterocyclic group" includes a monovalent group derived from "heterocyclic ring" as defined above.

For example, monocyclic non-aromatic heterocyclic groups such as pyrrolinyl, pyrrolidino, pyrrolidinyl, imidazolinyl, imidazolidinyl, pyrazolinyl, pyrazolidinyl, piperidino, piperidyl, piperazino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl, etc.;

monocyclic aromatic heterocyclic groups such as pyrrolyl, pyrazinyl, pyrazolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, oxadiazolyl, etc; and fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolinyl, benzodioxanyl, tetrahydroquinoline, tetrahydrobenzothienyl, etc. are exemplified.

The term "non-aromatic carbocyclic ring" includes "cycloalkane" as defined above, "cycloalkene" as defined above, a fused ring consisting of "aromatic carbocyclic ring" as defined above fused to "cycloalkane" or "cycloalkene" as defined above. As a fused ring, indene and the like are exemplified.

The term "non-aromatic carbocyclic group" includes a monovalent group derived from "non-aromatic carbocyclic ring" as defined above. For example, cyclopropyl, cyclobutyl, cyclopentyl, cyclohexyl, cycloheptyl, cyclooctyl, cyclononyl, cyclodecyl, cyclopentenyl, cyclohexenyl, norbornyl, tetrahydronaphthalene-5-yl, tetrahydronaphthalene-6-yl, norbornenyl, inden-1-yl, inden-2-yl, inden-3-yl and the like are exemplified.

The non-aromatic carbocyclyl moiety in said "non-aromatic carbocyclyloxy", "non-aromatic carbocyclylalkyl", and "non-aromatic carbocyclylalkyloxy" is as defined above for "non-aromatic carbocyclic ring".

The term "aromatic heterocyclic ring" includes aromatic rings of "heterocyclic ring" as defined above.

"Aromatic heterocyclic ring" includes a five- to seven-membered aromatic ring having at least one nitrogen atom, oxygen atom, and/or sulfur atom in the ring; a fused aromatic ring consisting of two or more said rings; and a fused ring consisting of a five- to seven-membered aromatic ring having at least one nitrogen atom, oxygen atom, and/or sulfur atom in the ring fused to one or more "aromatic carbocyclic ring" as defined above.

For example, a monocyclic aromatic heterocyclic ring such as pyrazine, pyrazole, tetrazole, furan, thiophene, pyridine, imidazole, triazole, triazine, pyridazine, pyrimidine, pyrazine, isoxazole, thiazole, isothiazole, thiadiazole, oxazole, oxadiazole, etc; and a fused aromatic heterocyclic ring such as indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazoline, etc. are exemplified.

The term "heteroaryl" includes a monovalent group derived from "aromatic heterocyclic ring" as defined above. "Heteroaryl" includes a five- to seven-membered aromatic group having at least one nitrogen atom, oxygen atom, and/or sulfur atom in the ring;

a fused aromatic group consisting of two or more said rings; and a fused ring consisting of a five- to seven-membered aromatic group having at least one nitrogen atom, oxygen atom, and/or sulfur atom in the ring fused to one or more "aromatic carbocyclic ring" as defined above.

For example, monocyclic heteroaryl such as pyrrolyl, pyrazinyl, pyrazolyl, indolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, oxadiazolyl, etc; and fused heteroaryl such as isoindolyl, indazolyl, indolizinyl, isoindolinyl, quinolyl, isoquinolyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolinyl, etc. are exemplified.

One of examples of "heteroaryl" for $R^2$ is pyridyl.

One of examples of "heteroaryl" for $R^{7'}$ is pyridyl, pyrimidinyl, benzofuryl, benzothienyl, indolyl, benzisoxazolyl, benzothiazolyl, etc.

One of examples of "heteroaryl" for $R^{7'}$ is pyridyl.

The heteroaryl moiety in said "heteroarylalkyl", "heteroarylalkyloxy", "heteroaryloxy", "heteroarylcarbonyl", and "heteroaryloxycarbonyl" is as defined above for "heteroaryl".

The term "non-aromatic heterocyclic ring" includes non-aromatic rings of "heterocyclic ring" as defined above.

"Non-aromatic heterocyclic ring" includes, a four- to seven-membered non-aromatic ring having at least one nitrogen atom, oxygen atom, and/or sulfur atom in the ring;

a fused non-aromatic ring consisting of two or more said rings;

a fused ring consisting of a five- to seven-membered aromatic ring having at least one nitrogen atom, oxygen atom, and/or sulfur atom in the ring fused to one or more "cycloalkane" or "cycloalkene" as defined above; and a fused ring consisting of a five- to seven-membered non-aromatic heterocyclic ring having at least one nitrogen atom, oxygen atom, and/or sulfur atom in the ring fused to one or more "aromatic carbocyclic ring" or "non-aromatic carbocyclic ring" as defined above.

For example, monocyclic non-aromatic heterocyclic ring such as oxetane, thietane, azetidine, pyrroline, pyrrolidine, imidazoline, imidazolidine, pyrazoline, pyrazolidine, piperidine, piperazine, morpholine, thiomorpholine, thiomorpholine, tetrahydropyran, dihydropyridine, dihydropyridazine, dihydropyrazine, dioxane, oxathiolane, thiane, tetrahydrofuran, tetrahydropyran, tetrahydrothiazoline, tetrahydroisothiazoline etc.;

a fused non-aromatic heterocyclic ring such as indoline, isoindoline, benzopyrane, benzodioxane, tetrahydroquinoline, benzo[d]oxazole-2(3H)-one, tetrahydrobenzothiophene etc. are exemplified.

"Non-aromatic heterocyclic group" includes a monovalent group derived from "non-aromatic heterocyclic ring" as defined above.

Examples are monocyclic non-aromatic heterocyclic group such as pyrrolinyl, pyrrolidine, pyrrolidinyl, imidazolinyl, imidazolidinyl, pyrazolinyl, pyrazolidinyl, piperidino, piperidyl, piperazine, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydrlisothiazolinyl etc. and a fused heterocyclic group such as benzodioxane, tetrahydroquinoline, benzo[d]oxazole-2(3H)-one, tetrahydfobenzothiophene etc.

The non-aromatic heterocyclyl moiety in said "non-aromatic heterocyclyloxy", "non-aromatic heterocyclyloxycarbonyl", "non-aromatic heterocyclylimino", "non-aromatic heterocyclylalkyl", "non-aromatic heterocyclylalkyloxy", and "non-aromatic heterocyclylcarbonyl" is as defined above for "non-aromatic heterocyclic ring".

The term "nitrogen-containing non-aromatic heterocyclic group" includes a group derived from a four- to seven-membered non-aromatic ring which contains at least one nitrogen atom in the ring and may contain one or more atoms arbitrarily selected from an oxygen atom and an sulfur atom in the ring and a fused ring consisting of two or more said rings. Examples are pyrrolinyl, pyrrolidino, pyrrolidinyl, piperidino, piperidyl, piperazino, piperazinyl, morpholinyl, morpholino, thiomorpholino etc.

Substituents for "substituted alkyl", "substituted alkenyl", "substituted alkynyl", "substituted alkyloxy", "substituted alkenyloxy", "substituted alkynyloxy", "substituted alkylthio", "substituted alkenylthio", "substituted alkynylthio", "substituted alkyloxycarbonyl", "substituted alkenyloxycarbonyl", "substituted alkynyloxycarbonyl" and "substituted alkylcarbamoyl" include but are not limited to one or more same or different substituents selected from the group consisting of: hydroxy, carboxy, halogen (F, Cl, Br, I), haloalkyloxy (e.g., $CF_3O$), cycloalkyl (e.g., cyclopropyl), cycloalkenyl (e.g., cyclopropenyl), lower alkyloxy (e.g., methoxy, ethoxy, propoxy, butoxy, etc.), alkenyloxy (e.g., vinyloxy, allyloxy, etc.), alkyloxycarbonyl (e.g., methoxycarbonyl, ethoxycarbonyl, tert-butoxycarbonyl, etc.), nitro, nitroso, amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, alkylsulfonylamino (e.g., methanesulfonylamino), alkylsulfinylamino (e.g., methanesulfinylamino), non-aromatic heterocyclylamino (e.g. 4-tetrahydropyranylamino etc.) imino, hydroxyimino, alkylimino (e.g., methylimino, ethylimino, dimethylimino, etc.), alkyloxyimino (e.g., methoxyimino, ethoxyimino, etc.) acylimino (e.g., acetylimino, benzoylimino, etc.), azido, aryl (e.g., phenyl, etc.), arylalkyl (e.g., benzyl, phenylethyl etc.), arylalkyloxy (e.g., benzyloxy), a non-aromatic heterocyclic group (e.g., pyrrolinyl, piperidyl, piperazinopyrrolidino, pyrrolidinyl, morpholinyl, morpholino, 2,2-dimethyl-1,3-dioxopyranyl etc.), heteroaryl (e.g., furyl, thienyl, pyridyl, isoxazolyl, thiazolyl, thiadiazolyl, oxazolyl, oxadiazolyl, tetrazolyl, indolyl, benzofuryl etc.), heteroarylalkyl (e.g., pyridylmethyl, pyridylethyl etc.), cyano, isocyano, isocyanato, thiocyanato, isothiocyanato, mercapto, alkylthio (e.g., methylthio, etc.), alkylsulfonyl (e.g., methanesulfonyl, ethanesulfonyl), carbamoyl, alkylcarbamoyl (e.g., methylcarbamoyl, ethylcarbamoyl, dimethylcarbamoyl, etc.), sulfamoyl, alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, phthalimido, tri-alkylsilyl (e.g., trimethylsilyl, etc.), hydroxyalkylcarbamoyl (hydroxyethylcarbamoyl, etc.), tetrahydropyranyloxy, carbamoylamino, alkylcarbamoylamino (e.g., methylcarbamoylamino, etc.), haloalkylcarbamoyl (e.g., trifluoroethylcarbamoyl, etc.), alkyloxyalkyloxy (e.g., methyloxymethyloxy, etc.), carbamoylcarbamoyl, alkylsulfonylcarbamoyl (e.g., methanesulfonylcarbamoyl) and oxo.

Substituents for "substituted acyl" are selected from the substituents as defined above for "substituted alkyl", the above "alkyl", the above "alkenyl" and the above "alkynyl". If R in acyl (R—C(═O)—) is "cycloalkyl", "cycloalkenyl", "non-aromatic heterocyclic group", "aryl", or "heteroaryl", then each ring may be substituted with alkyl (e.g., methyl, ethyl, isopropyl, tert-butyl, etc.), haloalkyl (e.g., $CF_3$, $CH_2CF_3$, $CH_2CCl_3$, etc.), alkenyl, alkynyl (e.g., ethynyl), alkyloxy (e.g., methoxy, ethoxy, isopropyloxy), halogen (e.g., fluoro, chloro etc.) or the like.

Substituents for "substituted carbamoyl", "substituted thiocarbamoyl" and "substituted sulfamoyl" are one or more same or different groups selected from, but are not limited to, the group consisting of:

hydroxy, carboxy, halogen (F, Cl, Br, I), alkyl (e.g., methyl, ethyl), substituted alkyl (wherein substituents are one or more same or different groups selected from hydroxyl, carboxy, halogen, alkyloxycarbonyl, alkyloxy, carbamoyl, alkylcarbamoyl, acyl, acylamino, acyloxy, cyano, cyanoimino, and aryloxy), alkenyl (e.g., vinyl), substituted alkenyl (wherein substituents are one or more same or different groups selected from hydroxyl, carboxy, halogen, alkyloxycarbonyl, alkyloxy, carbamoyl, alkylcarbamoyl, acyl, acylamino, acyloxy, cyano, cyanoimino, and aryloxy), alkynyl (e.g., ethynyl), substituted alkynyl (wherein substituents are one or more same or different groups selected from hydroxyl, carboxy, halogen, alkyloxycarbonyl, alkyloxy, carbamoyl, alkylcarbamoyl, acyl, acylamino, acyloxy, cyano, cyanoimino, and aryloxy), cycloalkylalkyl,
cycloalkylalkyl substituted with one or more same or different substituents selected from the after-mentioned Group Z,
arylalkyl,
arylalkyl substituted with one or more same or different substituents selected from the after-mentioned Group Z,
non-aromatic heterocyclylalkyl,
non-aromatic heterocyclylalkyl substituted with one or more same or different substituents selected from the after-mentioned Group Z,
heteroarylalkyl,
heteroarylalkyl substituted with one or more same or different substituents selected from the after-mentioned Group Z,
alkyloxycarbonyl (e.g., methoxycarbonyl, ethoxycarbonyl, tert-butoxycarbonyl, etc.), amino,
substituted amino (wherein substituents are one or more same or different groups selected from alkyl, acyl (e.g., acetyl, benzoyl etc.), acyloxyacyl, alkyloxycarbonylacyl, alkyloxycarbonylcarbonyl, arylalkyl (e.g., benzyl, trityl etc.), and hydroxyl), cycloalkyl (e.g., cyclopropyl),
cycloalkyl substituted with one or more same or different substituents selected from the after-mentioned Group Z,
cycloalkenyl (e.g., cyclopropenyl),
cycloalkenyl substituted with one or more same or different substituents selected from the after-mentioned Group Z,
aryl (e.g., phenyl, etc.),
aryl substituted with one or more same or different substituents selected from the after-mentioned Group Z,
a non-aromatic heterocyclic group (e.g., 4-tetrahydropyranyl etc.),
a non-aromatic heterocyclic group substituted with one or more same or different substituents selected from the after-mentioned Group Z,
heteroaryl (e.g., pyridyl etc.),
heteroaryl substituted with one or more same or different substituents selected from the after-mentioned Group Z,
cyano, isocyano, isocyanato, thiocyanato, isothiocyanato and acyl (e.g., formyl, acetyl, etc.).

Substituents for "substituted sulfonyl" or "substituted sulfinyl" are selected from the above "substituted or unsubstituted alkyl", the above "substituted or unsubstituted alkenyl", the above "substituted or unsubstituted alkynyl", the after-mentioned "substituted or unsubstituted cycloalkyl", the after-mentioned "substituted or unsubstituted cycloalkenyl", the after-mentioned "a substituted or unsubstituted non-aromatic heterocyclic group", the after-mentioned "substituted or unsubstituted aryl", and the after-mentioned "substituted or unsubstituted heteroaryl". If R in R—S(=O)$_2$— or R—S(=O)— is "cycloalkyl", "cycloalkenyl", "non-aromatic heterocyclic group", "aryl", "heteroaryl" or the like, then each ring may be substituted with alkyl (e.g., methyl, ethyl, isopropyl, tert-butyl, etc.), haloalkyl (e.g., CF$_3$, CH$_2$CF$_3$, CH$_2$CCl$_3$, etc.), alkenyl, alkynyl (e.g., ethynyl), alkyloxy (e.g., methoxy, ethoxy, isopropyloxy), halogen (e.g., fluoro, chloro etc.) or the like.

Substituents for "substituted amino", "substituted imino" and "substituted guanidyl" are one or more same or different groups selected from, but are not limited to, the group consisting of:
alkyl (e.g., methyl, ethyl, isopropyl, tert-butyl etc.),
substituted alkyl (wherein substituents are one or more same or different groups selected from hydroxyl, carboxy, halogen, alkyloxycarbonyl, alkyloxy, carbamoyl, alkylcarbamoyl, acyl, acylamino, acyloxy, cyano, amino, imino, cyanoimino, and aryloxy),
alkenyl (e.g., vinyl), alkynyl (e.g., ethynyl), cycloalkyl (e.g., cyclopropyl), cycloalkenyl (e.g., cyclopropenyl), alkyloxy (e.g., methoxy, ethoxy, propoxy, butoxy, etc.), haloalkyloxy (e.g., CF$_3$O), alkenyloxy (e.g., vinyloxy, allyloxy, etc.), alkyloxycarbonyl (methoxycarbonyl, tert-butyloxycarbonyl, etc.), amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, imino, hydroxyimino, alkylimino (e.g., methylimino, ethylimino, dimethylimino, etc.), alkyloxyimino (e.g., methoxyimino, ethoxyimino, etc.), acylimino (e.g., acetylimino, benzoylimino, etc.), aryl (e.g., phenyl, etc.), arylalkyl (e.g., benzyl, etc.), aryloxy (e.g., phenoxy etc.), a non-aromatic heterocyclic group (e.g., pyrrolinyl, pyrrolidino, piperidino, piperidyl, piperazino, piperazinyl, morpholinyl, morpholino etc.), non-aromatic heterocyclylalkyl, heteroaryl (e.g., pyridyl, thienyl, thiazolyl, furyl etc.), heteroarylalkyl (e.g., pyridylmethyl, thienylmethyl, thiazolylmethyl, furylmethyl etc.), non-aromatic heterocyclyloxy (pipierazinooxy, piperidinooxy etc.), heteroaryloxy (pyridyloxy etc.), hydroxy, halogen, (F, Cl, Br, I), cyano, acyl (e.g., formyl, acetyl, 4-tetrahydropyranylcarbonyl, isoxazoicarbonyl etc.), substituted acyl (wherein substituents are one or more same or different groups selected from hydroxyl, halogen, amino, alkylamino, and cyano),
cycloalkylcarbonyl substituted with one or more same or different substituents selected from the after-mentioned Substituent Group Z,
non-aromatic heterocyclylcarbonyl substituted with one or more same or different substituents selected from the after-mentioned Substituent Group Z,
arylcarbonyl substituted with, one or more same or different substituents selected from the after-mentioned Substituent Group Z,
heteroarylcarbonyl substituted with one or more same or different substituents selected from the after-mentioned Substituent Group Z,
alkylsulfonyl (e.g., methanesulfonyl etc.), non-aromatic heterocyclicylsulfonyl (e.g., 4-tetrahydropyranylsulfonyl etc.), alkylsulfinyl (e.g., methansulfinyl), carbamoyl, alkylcarbamoyl (e.g., methylcarbamoyl etc.), alkylcarbamoylalkyl (e.g., methylcarbamoylmethyl etc.), carbamoylalkyl (e.g., carbamoylmethyl etc.), carboxyalkyl (e.g., carboxymethyl etc.), sulfamoyl, alkylsulfamoyl (e.g., methylsulfamoyl etc.), alkylsulfamoylalkyl (e.g., methylsulfamoylmethyl etc.), and sulfamoylalkyl (e.g, sulfamoylmethyl etc.).

Particularly, substituents for "substituted imino" and "substituted guanidyl" are one or more same or different groups selected the group consisting of: alkyl, cyano, and alkyloxycarbonyl.

Substituents for "substituted cycloalkyl", "substituted cycloalkenyl", "substituted aryl", "substituted phenyl", "substituted heterocyclic group", "substituted heteroaryl", "a substituted non-aromatic carbocyclic group", "a substituted non-aromatic heterocyclic group", "a substituted nitrogen-containing non-aromatic heterocyclic group", "substituted cycloalkyloxy", "substituted cycloalkyenyloxy", "substituted aryloxy", "substituted heteroaryloxy", "substituted non-aromatic heterocyclyloxy", "substituted cycloalkylthio", "substituted cycloalkyenylthio", "substituted arylthio", "substituted heteroarylthio", "substituted non-aromatic heterocyclylthio", "substituted cycloalkyloxycarbonyl", "substituted cycloalkyenyloxycarbonyl", "substituted non-aromatic heterocyclyloxycarbonyl", "substituted aryloxycarbonyl", "substituted heteroaryloxycarbonyl", "substituted five- to seven-membered cycloalkane", "substituted five- to seven-membered cycloalkane", "a substituted five- to seven-membered nitrogen-containing non-aromatic heterocyclic ring", "substituted benzene", "a substituted five- or six-membered aromatic heterocyclic ring", "substituted triazine", "substituted pyrimidine", "substituted pyrazole", "substituted cycloalkane", "substituted naphthalene", "substituted tetrahydropyranyl", and "substituted tetrahydrothiopyranyl" are one or more same or different groups selected from, but are not limited to, the group consisting of:

(I) alkyl (e.g., methyl, ethyl, isopropyl, tert-butyl etc.),
(II) substituted alkyl (wherein substituents are one or more same or different groups selected from hydroxyl, carboxy, halogen, alkyloxycarbonyl, alkyloxy, carbamoyl, alkylcarbamoyl, acyl, acylamino, acyloxy and cyano),
(III) alkyloxy (e.g., methoxy, ethoxy, propoxy, butoxy, etc.),
(IV) substituted alkyloxy (wherein substituents are one or more same or different groups selected from hydroxyl, carboxy, halogen, alkyloxycarbonyl, alkyloxy, carbamoyl, alkylcarbamoyl, acyl, acylamino, acyloxy and, cyano. e.g., $CF_3O$, $CHCF_3O$, etc.),
(V) alkenyl (e.g., vinyl),
(VI) substituted alkenyl (wherein substituents are one or more same or different groups selected from hydroxyl, carboxy, halogen, alkyloxycarbonyl, alkyloxy, carbamoyl, alkylcarbamoyl, acyl, acylamino, acyloxy and cyano),
(VII) alkynyl (e.g., ethynyl),
(VIII) substituted alkynyl (wherein substituents are one or more same or different groups selected from hydroxyl, carboxy, halogen, alkyloxycarbonyl, alkyloxy, carbamoyl, alkylcarbamoyl, acyl, acylamino, acyloxy and cyano),
(IX) alkenyloxy (e.g., vinyloxy, allyloxy, etc.),
(X) substituted alkenylozy (wherein substituents are one or more same or different groups selected from hydroxyl, carboxy, halogen, alkyloxycarbonyl, alkyloxy, carbamoyl, alkylcarbamoyl, acyl, acylamino, acyloxy and cyano),
(XI) alkyloxycarbonyl (e.g., methoxycarbonyl, ethoxycarbonyl, tert-butoxycarbonyl, etc.),
(XII) nitro,
(XIII) nitroso,
(XIV) amino,
(XV) alkylamino (e.g., methylamino, ethylamino, dimethylamino, etc.),
(XVI) acylamino (e.g., acetylamino, benzoylamino, etc.),
(XVII) hydroxyamino,
(XVIII) amino substituted with one or two same or different substituents selected from the after-mentioned Substituent Group Y,
(XIX) imino,
(XX) hydroxyimino,
(XXI) alkylimino (e.g., methylimino, ethylimino, dimethylimino etc.),
(XXII) alkyloxyimino (e.g., methoxyimino, ethoxyimino etc.),
(XXIII) acylimino (e.g., acetylimino, benzoylimino etc.),
(XXIV) azido,
(XV) aryl (e.g., phenyl etc.),
(XVI) aryl substituted with one or more same or different substituents selected from the after-mentioned Substituent Group Z,
(XVII) arylalkyl (e.g., benzyl etc.),
(XVIII) arylalkyl substituted with one or more same or different substituents selected from the after-mentioned Substituent Group Z,
(XXIX) aryloxy (e.g., phenyloxy etc.),
(XXX) aryloxy substituted with one or more same or different substituents selected from the after-mentioned Substituent Group Z,
(XXXI) arylalkyloxy (e.g., benzyloxy etc.),
(XXXII) arylalkyloxy substituted with one or more same or different substituents selected from the after-mentioned Substituent Group Z,
(XXXIII) arylalkylamino (e.g., benzylamino, tritylamino, etc.),
(XXXIV) arylalkylamino substituted with one or more same or different substituents selected from the after-mentioned Substituent Group Z,
(XXXV) a non-aromatic heterocyclic group (e.g., pyrrolinyl, pyrrolidino, piperidino, piperidyl, piperazino, piperazinyl, morpholinyl, morpholino etc.),
(XXXVI) a non-aromatic heterocyclic group substituted with one or more same or different substituents selected from the after-mentioned Substituent Group Z,
(XXXVII) non-aromatic heterocyclylalkyl,
(XXXVIII) non-aromatic heterocyclylalkyl substituted with one or more same or different substituents selected from the after-mentioned Substituent Group Z,
(XXXIX) non-aromatic heterocyclyloxy (e.g., piperazinooxy, piperizinooxy etc.),
(XXXX) non-aromatic heterocyclyloxy substituted with one or more same or different substituents selected from the after-mentioned Substituent Group Z,
(XXXXI) non-aromatic heterocyclylalkyloxy,
(XXXXII) non-aromatic heterocyclylalkyloxy substituted with one or more same or different substituents selected from the after-mentioned Substituent Group Z,
(XXXXIII) non-aromatic heterocyclylalkylamino,
(XXXXIV) non-aromatic heterocyclylalkylamino substituted with one or more same or different substituents selected from the after-mentioned Substituent Group Z,
(XXXXV) a non-aromatic carbocyclic group (e.g., cycloalkyl, cycloalkenyl, etc.),
(XXXXVI) a non-aromatic carbocyclic group substituted with one or more same or different substituents selected from the after-mentioned Substituent Group Z,
(XXXXVII) non-aromatic carbocyclylalkyl,
(XXXXVIII) non-aromatic carbocyclylalkyl substituted with one or more same or different substituents selected from the after-mentioned Substituent Group Z,
(XXXXIX) non-aromatic carbocyclyloxy (e.g., cyclopropyloxy etc.),
(L) non-aromatic carbocyclyloxy substituted with one or more same or different substituents selected from the after-mentioned Substituent Group Z,
(LI) non-aromatic carbocyclylalkyloxy (e.g., cyclopropylmethyloxy etc.),
(LII) non-aromatic carbocyclylalkyloxy substituted with one or more same or different substituents selected from the after-mentioned Substituent Group Z,
(LIII) non-aromatic carbocyclylalkylamino,
(LIV) non-aromatic carbocyclylalkylamino substituted with one or more same or different substituents selected from the after-mentioned Substituent Group Z,
(LV) heteroaryl (e.g., pyridyl, thienyl, thiazolyl, furyl etc.),
(LVI) heteroaryl substituted with one or more same or different substituents selected from the after-mentioned Substituent Group Z,
(LVII) heteroarylalkyl (e.g., pyridylmethyl, thienylmethyl, thiazolylmethyl, furylmethyl etc.),
(LVIII) heteroarylalkyl substituted with one or more same or different substituents selected from the after-mentioned Substituent Group Z, (LIX) heteroaryloxy (e.g., pyridyloxy, pyridazinyloxy, pyrimidinyloxy, pyrazinyloxy, oxazolyloxy, isoxazolyloxy, oxadiazolyloxy, thiazolyloxy, isothiazolyloxy, thiadiazolyloxy, furyloxy, thienyloxy etc.), (LX) heteroaryloxy substituted with one or more same or different substituents selected from the after-mentioned Substituent Group Z, (LXI) heteroarylalkyloxy, (LXII) heteroarylalkyloxy substituted with one or more same or different substituents selected from the after-mentioned Substituent Group Z, (LXIII) heteroarylalkylamino, (LXIV) heteroarylalkylamino substituted with one or more same or different substituents selected from the after-mentioned Substituent Group Z, (LXV) cyano, (LXVI) isocyano, (LXVII) isocyanato, (LXVIII) thiocyanato, (LXIX) isothiocyanato, (LXX) mercapto, (LXXI) alkylthio (e.g., methylthio etc.), (LXXII) alkylsulfonyl (e.g., methanesulfonyl, ethanesulfonyl), (LXXIII) substituted or unsubstituted carbamoyl (e.g., carbamoyl, N-methyl-N-methoxycarbamoyl etc.), (LXXIV) substituted or unsubstituted alkylcarbamoyl (e.g., methylcarbamoyl, ethylcarbamoyl, dimethylcarbamoyl, hydroxyethylcarbamoyl, trifluoromethylcarbamoyl, trifluoroethylcarbamoyl etc.), (LXXV) sulfamoyl, (LXXVI) alkylsulfamoyl, (LXXVII) hydroxyl, (LXXVIII) carboxy, (LXXIX) halogen (F, Cl, Br, I), (LXXX) acyl (e.g., formyl, acetyl etc.), (LXXXI) formyloxy, (LXXXII) thioformyl, (LXXXIII) thiocarboxy, (LXXXIV) dithiocarboxy, (LXXXV) thiocarbamoyl, (LXXXVI)sulfino, (LXXXVII) sulfo, (LXXXVIII) hydrazino, (LXXXIX) azido, (LXXXX) ureido, (LXXXXI) amidino, (LXXXXII) guanidine, (LXXXXIII) phthalimido, and (LXXXXIV) oxo.

A substituent Group Y includes hydroxy alkyl (e.g., hydroxyethyl, —C(CH$_3$)$_2$CH$_2$OH etc.), alkyloxycarbonyl (methoxycarbonyl, tert-butyloxycarbonyl etc.), alkyloxycarbonylalkyl, alkylsulfonyl (e.g., methanesulfonyl etc.), alkylsulfinyl (e.g., methanesulfinyl etc.), carbamoyl, alkylcarbamoyl (e.g., methylcarbamoyl etc.), alkylcarbamoylalkyl (e.g., methylcarbamoylmethyl etc.), carbamoylalkyl (e.g., carbamoylmethyl etc.), carboxyalkyl (e.g., carboxymethyl etc.), sulfamoyl, alkylsulfamoyl (e.g., methylsulfamoyl etc.), alkylsulfamoylalkyl (e.g., methylsulfamoylmethyl etc.) and sulfamoylalkyl (e.g., sulfamoylmethyl etc.).

A substituent Group Z includes halogen (e.g., F, Cl etc.), hydroxy, carboxy, carboxyalkyloxy (e.g., carboxymethyloxy etc.), cyano, nitro, alkyl (e.g., methyl etc.), hydroxyalkyl (e.g., hydroxymethyl etc.), aminoalkyl, alkylaminoalkyl, alkenyl, alkynyl, alkyloxy, alkenyloxy, alkynyloxy, alkylthio, alkenylthio, alkynylthio, acyl, alkyloxycarbonyl (e.g., methyloxycarbonyl, ethyloxycarbonyl etc.), alkenyloxycarbonyl, alkynyloxycarbonyl, carbamoyl, carbamoylalkyloxy (e.g., carbamoylmethyloxy etc.), alkylcarbamoyl (e.g., methylcarbamoyl, ethylcarbamoyl etc.), haloalkylcarbamoyl, cycloalkylcarbamoyl (e.g., cyclopropylcarbamoyl etc), alkylcarbamoylalkyloxy (e.g., methylcarbamoylmethyloxy etc), hydroxyalkylcarbamoyl (e.g., hydroxyethylcarbamoyl etc), cyanocarbamoyl, amino, acylamino, amino substituted with one or two same or different substituent selected from the above substituent Group Y, sulfamoyl, methylsulfonyl, methylsulfinyl, cycloalkyl, cycloalkenyl, a non-aromatic heterocyclic group, aryl, heteroaryl (e.g., tetrazolyl etc), cycloalkyloxy, cycloalkenyloxy, non-aromatic heterocyclyloxy, aryloxy heteroaryloxy and oxo.

As substituents for "substituted aryl" and "substituted heteroaryl" for $R^6$, halogen, alkyl, alkenyl, alkynyl, alkyloxy, cycloalkyl, alkylsilylalkynyl and the like are exemplified.

As substituents for "substituted aryl" and "substituted heteroaryl" for $R^6$, fluoro, chloro, bromo, iodo, methyl, ethyl, propyl, isopropyl, propenyl, vinyl, ethynyl, methyloxy, cyclopropyl, trimethylsilylethynyl and the like are exemplified.

As "heteroaryloxy" as substituents for "substituted aryl" and "substituted heteroaryl" for $R^{7'}$, pyrrolyloxy, pyrazinyloxy, pyrazolyloxy, indolyloxy, tetrazolyloxy, furyloxy, thienyloxy, pyridyloxy, imidazolyloxy, triazolyloxy, tetrazolyloxy, triazinyloxy, pyridazinyloxy, pyrimidinyloxy, pyrazinyloxy, isoxazolyloxy, thiazolyloxy, isothiazolyloxy, thiadiazolyloxy, oxazolyloxy, oxadiazolyloxy, and the like are exemplified.

As substituents for "substituted aryl" and "substituted heteroaryl" for $R^{7'}$, unsubstituted heteroaryloxy, heteroaryloxy substituted with one or more same or different substituents selected from the above-mentioned Substituent Group Z, and the like are exemplified. Furthermore, in addition to the above substituents, halogen, hydroxy, carboxy, cyano, nitro, alkyl, haloalkyl, haloalkyloxy, alkyloxy, amino, and the like are exemplified. The above "heteroaryloxy" is unsubstituted groups or groups substituted with one or more same or different substituents selected from the above-mentioned Substituent Group Z. "Heteroaryloxy" is selected from the following groups: pyrrolyloxy, pyrazinyloxy, pyrazolyloxy, indolyloxy, tetrazolyloxy, furyloxy, thienyloxy, pyridyloxy, imidazolyloxy, triazolyloxy, tetrazolyloxy, triazinyloxy, pyridazinyloxy, pyrimidinyloxy, pyrazinyloxy, isoxazolyloxy, thiazolyloxy, isothiazolyloxy, thiadiazolyloxy, oxazolyloxy, and oxadiazolyloxy.

As substituents for "substituted amino" for $R^{9'}$ or $R^{9'''}$, carbamoyl, alkylcarbamoyl (e.g., methylcarbamoyl etc.), alkylcarbamoylalkyl (e.g., methylcarbamoylmethyl etc), carbamoylalkyl (e.g., carbamoylmethyl etc), or carboxyalkyl (e.g., carboxymethyl ect) are exemplified.

Examples of $R^{9'}$ or $R^{9'''}$ are halogen, hydroxy, carboxy, cyano, nitro, alkyl, hydrozyalkyl, haloalkyl, aminoalkyl, alkylaminoalkyl, carboxyalkyl, alkyloxycarbonylalkyl, alkenyl, alkynyl, alkyloxy, alkenyloxy, alkynyloxy, alkylthio, alkenylthio, alkynylthio, acyl, alkyloxycarbonyl, alkenyloxycarbonyl, alkynyloxycarbonyl, carbamoyl, alkylcarbamoyl, haloalkylcarbamoyl, hydroxyalkylcarbamoyl, cyanocarbamoyl, amino, acylamino, amino substituted with one or more same or different substituents selected from the above-mentioned Substituent Group Y, sulfamoyl, methylsulfonyl, methyl, and the like.

In the formula: —(C($R^{8a''}$)($R^{8b''}$))n"—$R^{13''}$ in —$R^{2b}$ or —$R^{2b2}$, example of n" is an integer of 1 to 8.

In the formula: —(C($R^{11c}$)($R^{11d}$))m'-COOR in —$R^2$, —$R^{2a}$, —$R^{2b}$, or —$R^{2b2}$, example of m" is an integer of 1 to 3.

In $R^7$, the positions of carbon atom a, $Q^a$ atom, $Q^b$ atom, carbon atom b, $Q^c$ atom and $Q^d$ atom which constitute a benzene ring, a pyridine ring, a pyrimidine ring, a pyrazine ring or a pyridazine ring as ring D is defined as 1-position, 2-position, 3-position, 4-position, 5-position and 6-position, respectively. Each of the position numbers of these atoms is different from position number based on IUPAC nomenclature. That is, "carbon atom a is positioned on ring D in a (1,4) relationship with respect to carbon atom b" includes the followings:

[Chemical Formula 62]

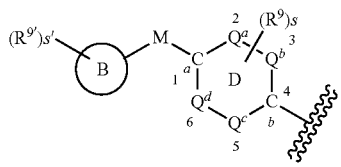

wherein $Q^a$ atom, $Q^b$ atom, $Q^c$ atom and $Q^d$ atom are each independently a carbon atom or a nitrogen atom, -M-, ring D, ring B, s, s', $R^9$ and $R^{9'}$ are as defined in the above (1).

When ring A is six-membered ring, "C is attached to $Q^1$ and both of C and $Q^1$ are ring atoms" in ring A includes the followings:

[Chemical Formula 63]

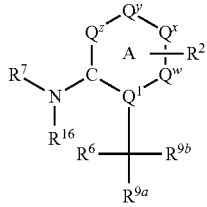

wherein $Q^w$ atom, $Q^x$ atom, $Q^y$ atom and $Q^z$ atom are each independently a carbon atom or a nitrogen atom, $R^2$, $R^{9a}$, $R^{9b}$, $R^6$, $R^{16}$, and, $R^{17}$ are as defined in the above (1); $R^6$ is as defined in the above (3).

In Formula (I), "$R^{11c}$ and $R^{11d}$ attached to the same carbon atom are taken together to form substituted or unsubstituted cycloalkane, substituted or unsubstituted cycloalkene, or a substituted or unsubstituted non-aromatic heterocyclic ring" includes the followings:

[Chemical Formula 64]

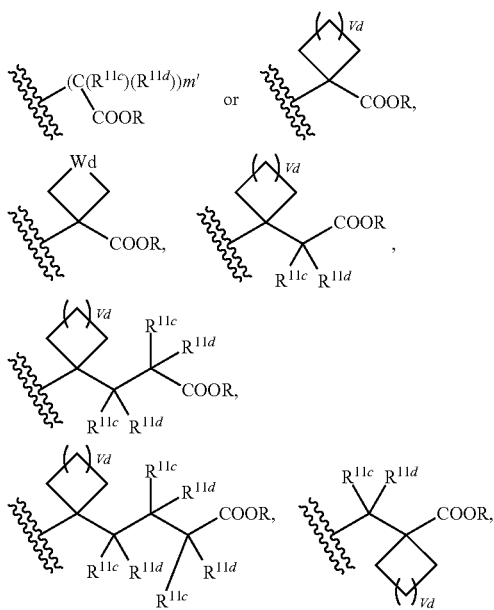

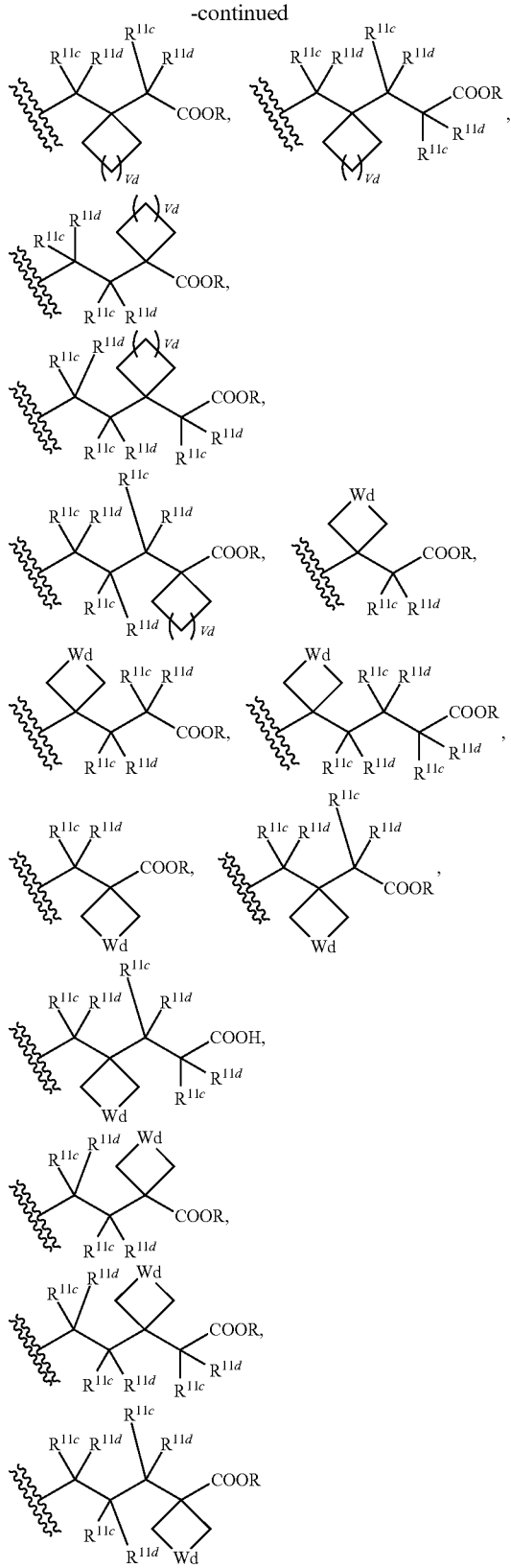

etc wherein m', $R^{11c}$ and $R^{11d}$ are as defined in the above (8); Vd is an integer of 0 to 3 (e.g., 0 or 1, and e.g., 0); -Wd- is —O—, —S— or —N($R^{17d}$)— (e.g., —O—);

$R^{17d}$ is a hydrogen atom, substituted or unsubstituted alkyl, substituted or unsubstituted alkenyl, substituted or unsubstituted alkynyl, substituted or unsubstituted acyl or the like.

In Formula (I) and (II), when ring A is "a six-membered nitrogen-containing non-aromatic heterocyclic group", ring A includes the above-menthioned six-membered "non-aromatic heterocyclic group" having at least one nitrogen atom. For example, piperidine, 1,4-dihydropyridine, 1,2,3,4-tetrahydropyridine, piperazine, 1,2,3,4-tetrahydropyrazine, 1,4-dihydropyrazine, hexahydropyrimridine, 1,2,3,4-tetrahydropyrimidine and the like are exemplified.

In Formula (I) and (II), when ring A is "a six-membered non-aromatic heterocyclic group containing two nitrogen atoms", ring A includes the above-menthioned six-membered "non-aromatic heterocyclic group" having two nitrogen atoms. For example, piperazine, 1,2,3,4-tetrahydropyrazine, 1,4-dihydropyrazine, hexahydropyrimidine, 1,2,3,4-tetrahydropyrimidine and the like are exemplified.

In Formula (I) or (II), when $R^2$, $R^{2a}$, $R^{2b}$, or $R^{2'}$ is "C3-C6 alkyl substituted with three to five hydroxy groups and optionally substituted with one or more substituents selected from the Substituent Group A (Substituent Group A: halogen, cyano, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, or thioxo), C3-C6 alkyl is always substituted with three to five hydroxy groups and optionally substituted with one or more substituents selected from the Substituent Group A. For example, $R^2$, $R^{2a}$, $R^{2b}$, or $R^{2'}$ includes the followings:

[Chemical Formula 65]

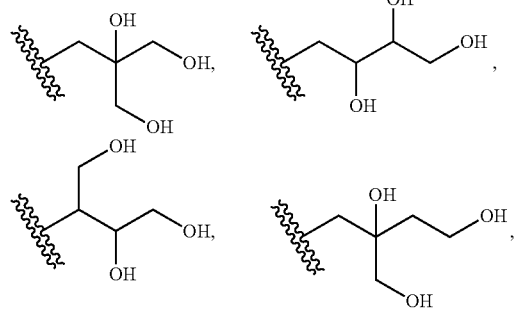

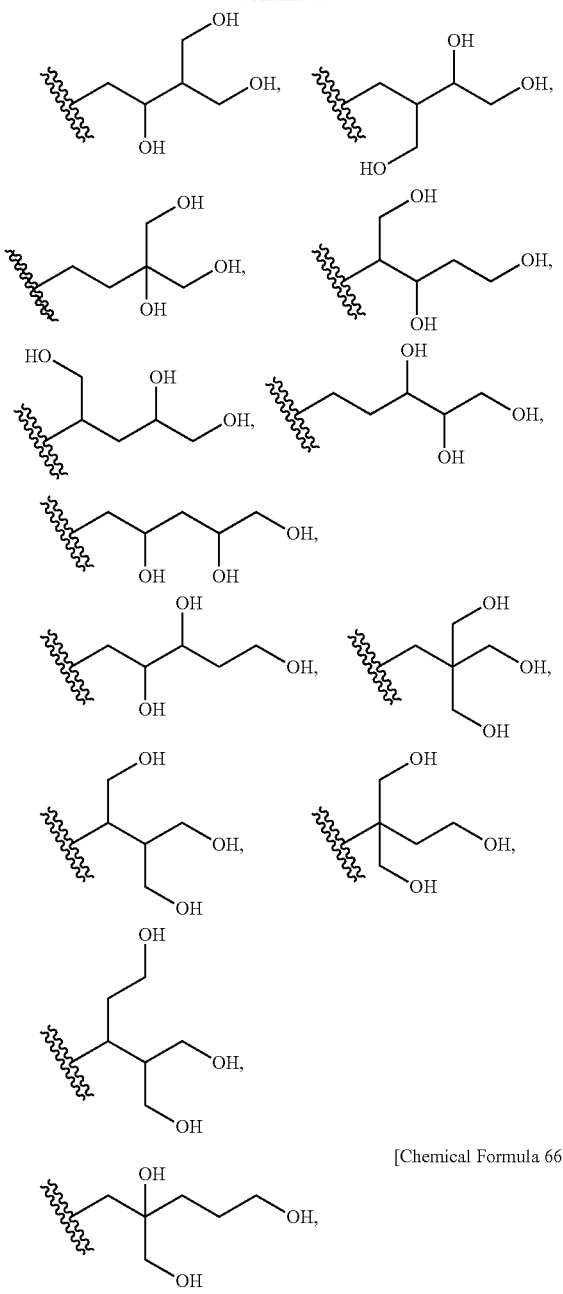

[Chemical Formula 66]

71
-continued
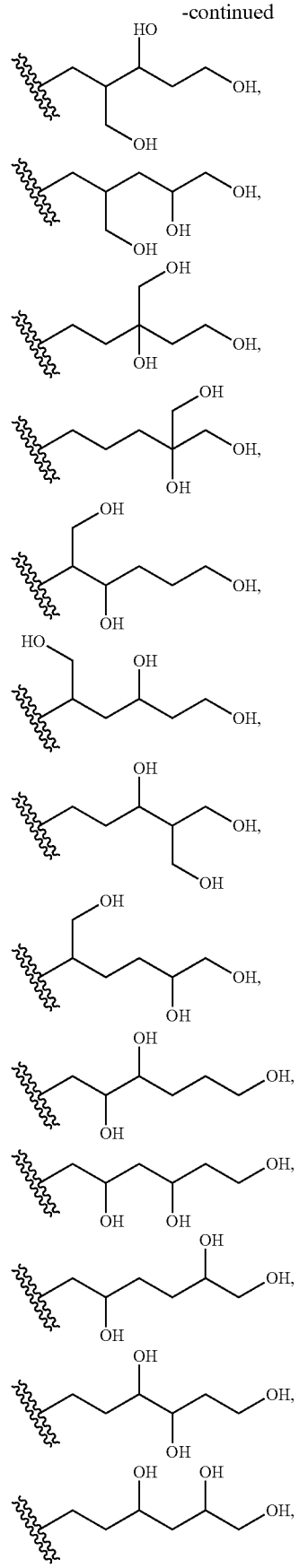
72
-continued
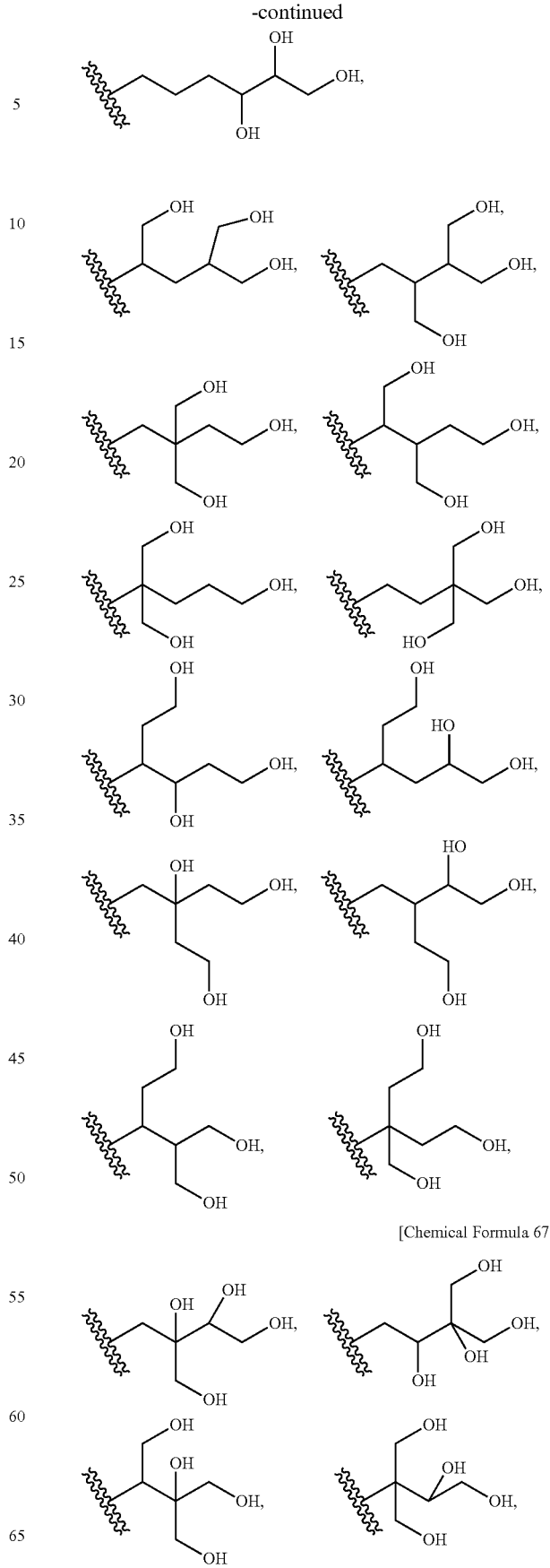
[Chemical Formula 67]

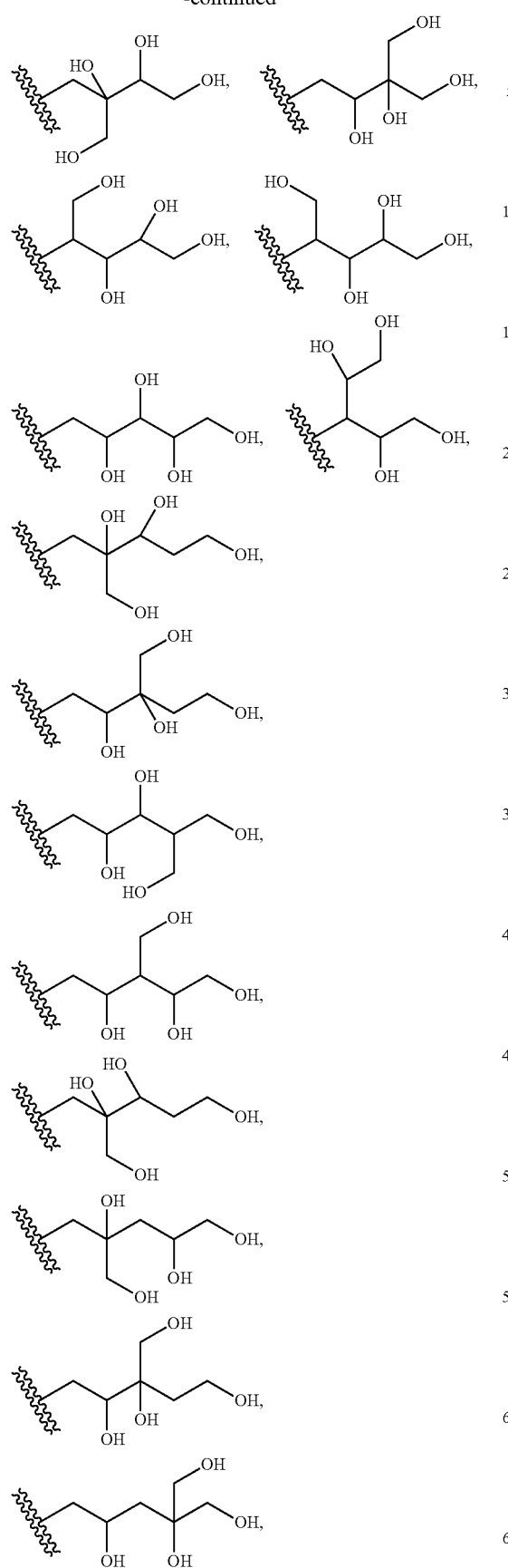
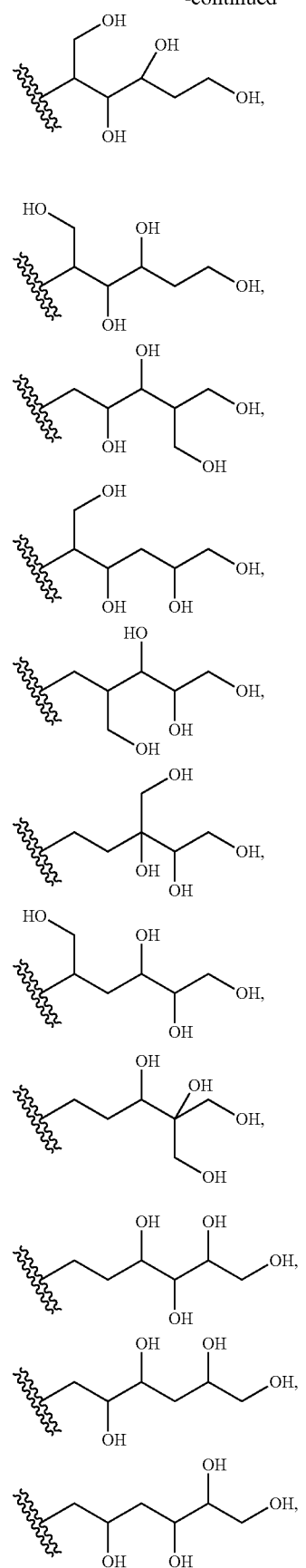

-continued
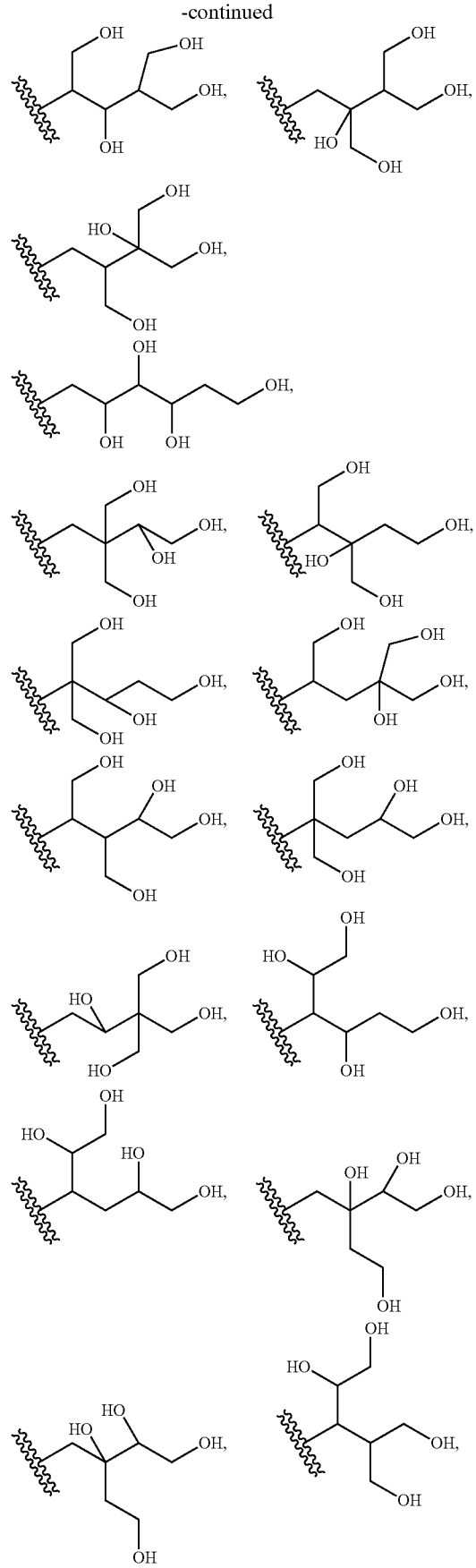
-continued
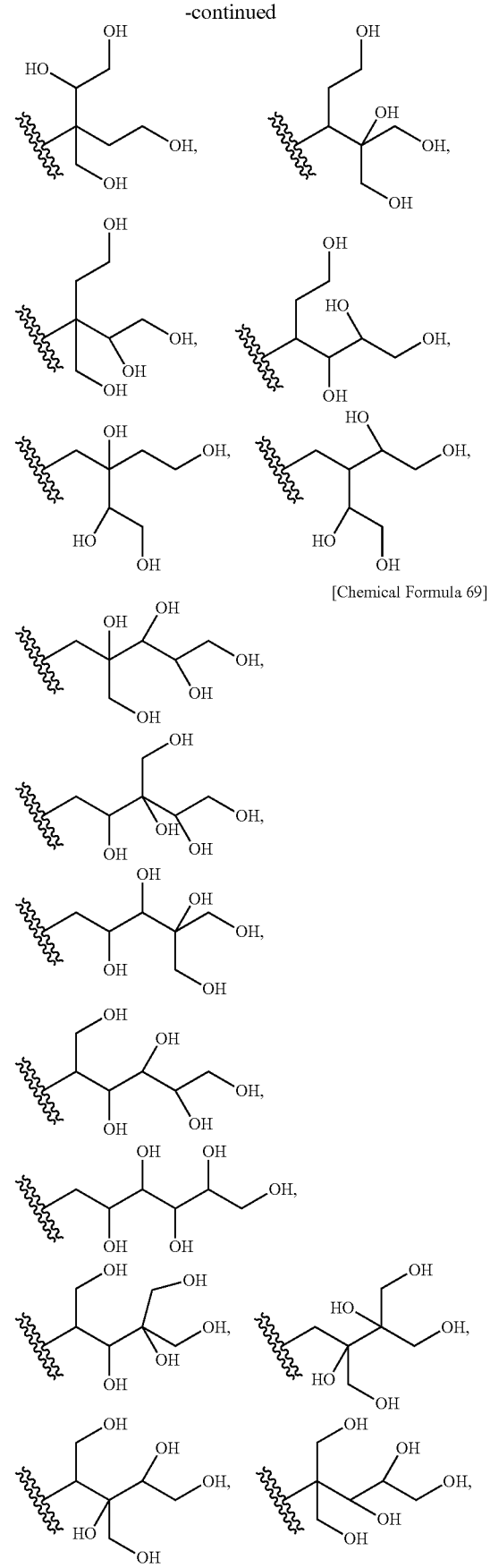
[Chemical Formula 69]

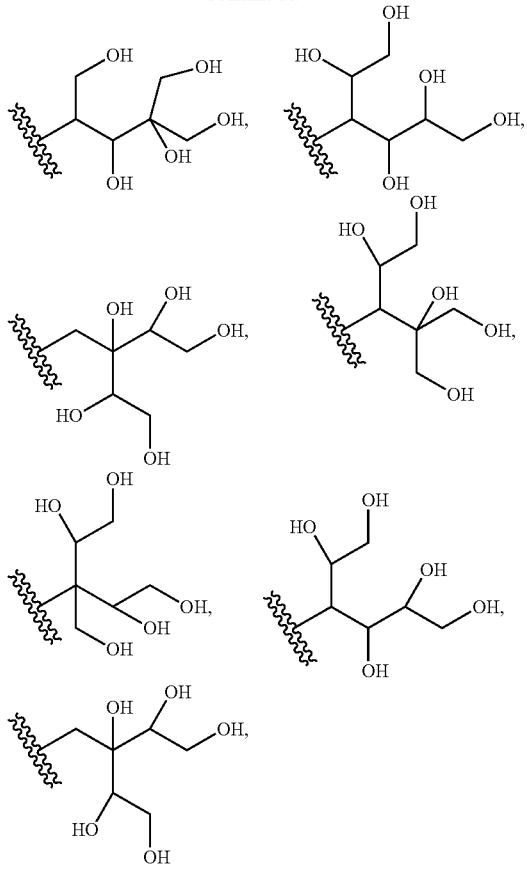

As the compound represented by Formula (I) of the invention, the following compounds are exemplified.
A compound of Formula (I-a):

[Chemical Formula 70]

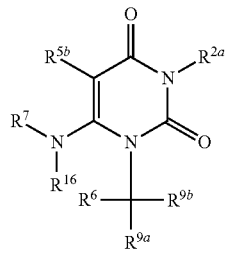

wherein
$R^{5b}$ is:
(a1) a hydrogen atom or halogen; or
(a2) a hydrogen atom;
$R^{2a}$ is:
(b1) C3-C6 alkyl substituted with three to five hydroxy groups; C3-C6 alkenyl substituted with three to five hydroxyl groups; or C3-C6 alkynyl substituted with three to five hydroxyl groups;
(b2) C3-C6 alkyl substituted with three to five hydroxy groups;
(b3) C4 alkyl substituted with three hydroxy groups, C4 alkenyl substituted with three hydroxyl groups, or C4 alkynyl substituted with three hydroxy groups;
(b4) C4 alkyl substituted with three hydroxy groups;

(b5) a group represented by the formula: —(C($R^{11c}$)($R^{11d}$))m'-COOR
wherein $R^{11c}$ are each independently a hydrogen atom, substituted or unsubstituted alkyl, substituted or unsubstituted alkenyl, or substituted or unsubstituted alkynyl;
$R^{11d}$ are each independently a hydrogen atom, substituted or unsubstituted alkyl, substituted or unsubstituted alkenyl, or substituted or unsubstituted alkynyl;
R is hydrogen or substituted or unsubstituted alkyl;
m' is an integer of 1 to 4;
(b6) a group represented by the formula: —(CH$_2$)m'-COOH;
wherein m' is an integer of 1 to 4;
(b7) unsubstituted alkyl, unsubstituted alkenyl or unsubstituted alkynyl
(b8) unsubstituted alkyl
(b9) substituted or unsubstituted alkyl, substituted or unsubstituted alkenyl, or substituted or unsubstituted alkynyl; or
(b10) substituted or unsubstituted alkyl;
$R^{9a}$ and $R^{9b}$ are each independently a hydrogen atom or halogen;
$R^6$ is a group represented by the formula:

[Chemical Formula 71]

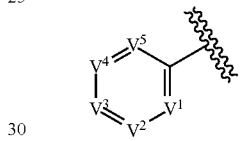

wherein =$V^1$—$V^2$=$V^3$—$V^4$=$V^5$— is (i): =C($R^{A'}$)—C($R^A$)=C($R^B$)—C($R^{C'}$)=C(H)—;
$R^A$, $R^{A'}$, $R^B$, $R^C$ and $R^{C'}$ are each independently:
(c1) a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl; or
(c2) a hydrogen atom or halogen;
$R^{16}$ is a hydrogen atom;
$R^7$ is a group represented by the formula:

[Chemical Formula 72]

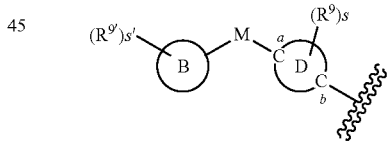

wherein
ring D is benzene;
carbon atom a and carbon atom b are carbon atoms which constitute ring D;
-M- is —O—;
ring B is:
(d1) an aromatic carbocyclic ring or an aromatic heterocyclic ring;
(d2) benzene, thiazole, isothiazole, oxazole, isoxazole, furan, thiophen, thiadiazole, oxadiazole, pyridine, pyrimidine, pyrazine or pyridazine; or
(d3) benzene, thiazole, thiadiazole, oxadiazole or pyridine;
s is 0 or 1;
$R^9$ is:
(e1) halogen, substituted or unsubstituted alkyl, substituted or unsubstituted alkenyl, substituted or unsubstituted alkynyl, substituted or unsubstituted alkyloxy, substituted or unsubstituted alkenyloxy or substituted or unsubstituted alkynyloxy; or (e2) halogen or substituted or unsubstituted alkyl;

s' is an integer 0 to 2;

$R^{9'}$ are each independently:

(f1) halogen, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl or substituted or unsubstituted carbamoyl; or (f2) halogen, carboxy, cyano, substituted or unsubstituted alkyl, substituted or unsubstituted alkyloxy, substituted or unsubstituted alkyloxycarbonyl or substituted or unsubstituted carbamoyl provided that the following compounds:

[Chemical Formula 73]

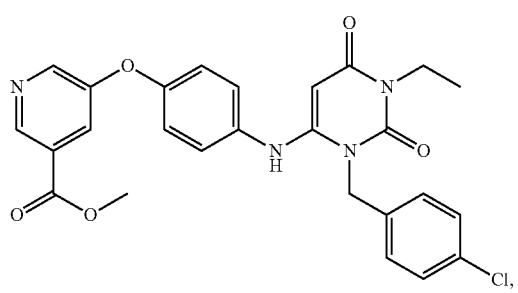

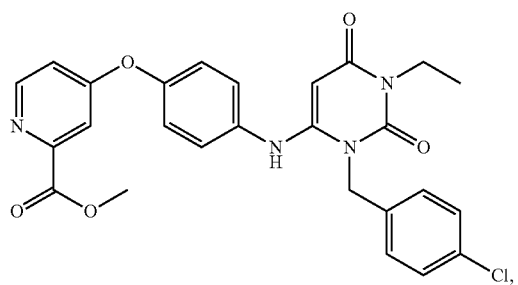

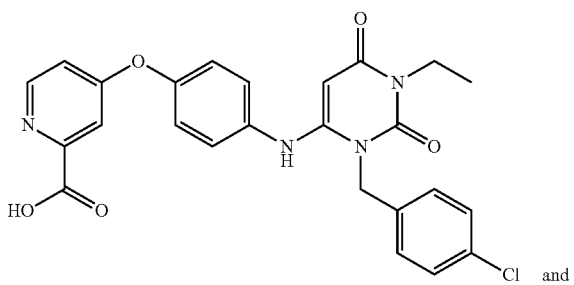 and

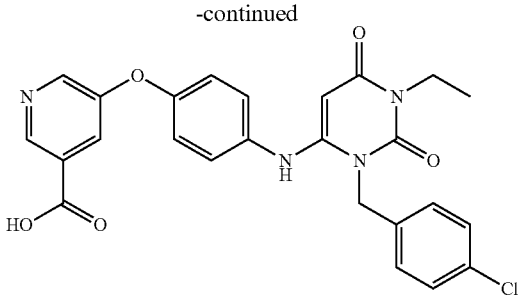

are excluded.

or its pharmaceutically acceptable salt.

The compound represented by the formula (I-a) includes the compounds comprising the combination of some or all of options of the above. Specifically, the following combinations are included.

(a1,b1,c1,d1,e1,f1),(a1,b1,c1,d1,e1,f2),(a1,b1,c1,d1,e2,f1),
(a1,b1,c1,d1,e2,f2),(a1,b1,c1,d2,e1,f1),(a1,b1,c1,d2,e1,f2),
(a1,b1,c1,d2,e2,f1),(a1,b1,c1,d2,e2,f2),(a1,b1,c1,d3,e1,f1),
(a1,b1,c1,d3,e1,f2),(a1,b1,c1,d3,e2,f1),(a1,b1,c1,d3,e2,f2),
(a1,b1,c2,d1,e1,f1),(a1,b1,c2,d1,e1,f2),(a1,b1,c2,d1,e2,f1),
(a1,b1,c2,d1,e2,f2),(a1,b1,c2,d2,e1,f1),(a1,b1,c2,d2,e1,f2),
(a1,b1,c2,d2,e2,f1),(a1,b1,c2,d2,e2,f2),(a1,b1,c2,d3,e1,f1),
(a1,b1,c2,d3,e1,f2),(a1,b1,c2,d3,e2,f1),(a1,b1,c2,d3,e2,f2),
(a1,b2,c1,d1,e1,f1),(a1,b2,c1,d1,e1,f2),
(a1,b2,c1,d1,e2,f1),(a1,b2,c1,d1,e2,f2),(a1,b2,c1,d2,e1,f1),
(a1,b2,c1,d2,e1,f2),(a1,b2,c1,d2,e2,f1),(a1,b2,c1,d2,e2,f2),
(a1,b2,c1,d3,e1,f1),(a1,b2,c1,d3,e1,f2),(a1,b2,c1,d3,e2,f1),
(a1,b2,c1,d3,e2,f2),(a1,b2,c2,d1,e1,f1),(a1,b2,c2,d1,e1,f2),
(a1,b2,c2,d1,e2,f1),(a1,b2,c2,d1,e2,f2),(a1,b2,c2,d2,e1,f1),
(a1,b2,c2,d2,e1,f2),(a1,b2,c2,d2,e2,f1),(a1,b2,c2,d2,e2,f2),
(a1,b2,c2,d3,e1,f1),(a1,b2,c2,d3,e1,f2),(a1,b2,c2,d3,e2,f1),
(a1,b2,c2,d3,e2,f2),(a1,b3,c1,d1,e1,f1),(a1,b3,c1,d1,e1,f2),
(a1,b3,c1,d1,e2,f1),(a1,b3,c1,d1,e2,f2),(a1,b3,c1,d2,e1,f1),
(a1,b3,c1,d2,e1,f2),(a1,b3,c1,d2,e2,f1),(a1,b3,c1,d2,e2,f2),
(a1,b3,c1,d3,e1,f1),(a1,b3,c1,d3,e1,f2),(a1,b3,c1,d3,e2,f1),
(a1,b3,c1,d3,e2,f2),(a1,b3,c2,d1,e1,f1),(a1,b1,c2,d1,e1,f2),
(a1,b3,c2,d1,e2,f1),(a1,b3,c2,d2,e2,f2),(a1,b3,c2,d2,e1,f1),
(a1,b3,c2,d2,e1,f2),(a1,b3,c2,d2,e2,f1),(a1,b3,c2,d2,e2,f2),
(a1,b3,c2,d3,e1,f1),(a1,b3,c2,d3,e1,f2),(a1,b3,c2,d3,e2,f1),
(a1,b3,c2,d3,e2,f2),(a1,b4,c1,d1,e1,f1),(a1,b4,c1,d1,e1,f2),
(a1,b4,c1,d1,e2,f1),(a1,b4,c1,d1,e2,f2),(a1,b4,c1,d2,e1,f1),
(a1,b4,c1,d2,e1,f2),(a1,b4,c1,d2,e2,f1),(a1,b4,c1,d2,e2,f2),
(a1,b4,c1,d3,e1,f1),(a1,b4,c1,d3,e1,f2),(a1,b4,c1,d3,e2,f1),
(a1,b4,c1,d3,e2,f2),(a1,b4,c2,d1,e1,f1),(a1,b4,c2,d1,e1,f2),
(a1,b4,c2,d1,e2,f1),(a1,b4,c2,d1,e2,f2),(a1,b4,c2,d2,e1,f1),
(a1,b4,c2,d2,e1,f2),(a1,b4,c2,d2,e2,f1),(a1,b4,c2,d2,e2,f2),
(a1,b4,c2,d3,e1,f1),(a1,b4,c2,d3,e1,f2),(a1,b4,c2,d3,e2,f1),
(a1,b4,c2,d3,e2,f2),(a1,b5,c1,d1,e1,f1),(a1,b5,c1,d1,e1,f2),
(a1,b5,c1,d1,e2,f1),(a1,b5,c1,d1,e2,f2),(a1,b5,c1,d2,e1,f1),
(a1,b5,c1,d2,e1,f2),(a1,b5,c1,d2,e2,f1),(a1,b5,c1,d2,e2,f2),
(a1,b5,c1,d3,e1,f1),(a1,b5,c1,d3,e1,f2),(a1,b5,c1,d3,e2,f1),
(a1,b5,c1,d3,e2,f2),(a1,b5,c2,d1,e1,f1),(a1,b5,c2,d1,e1,f2),
(a1,b5,c2,d1,e2,f1),(a1,b5,c2,d1,e2,f2),(a1,b5,c2,d2,e1,f1),
(a1,b5,c2,d2,e1,f2),(a1,b5,c2,d2,e2,f1),(a1,b5,c2,d2,e2,f2),
(a1,b5,c2,d3,e1,f1),(a1,b5,c2,d3,e1,f2),(a1,b5,c2,d3,e2,f1),
(a1,b5,c2,d3,e2,f2),(a1,b6,c1,d1,e1,f1),(a1,b6,c1,d1,e1,f2),
(a1,b6,c1,d1,e2,f1),(a1,b6,c1,d1,e2,f2),(a1,b6,c1,d2,e1,f1),
(a1,b6,c1,d2,e1,f2),(a1,b6,c1,d2,e2,f1),(a1,b6,c1,d2,e2,f2),
(a1,b6,c1,d3,e1,f1),(a1,b6,c1,d3,e1,f2),(a1,b6,c1,d3,e2,f1),
(a1,b6,c1,d3,e2,f2),(a1,b6,c2,d1,e1,f1),(a1,b6,c2,d1,e1,f2),
(a1,b6,c2,d1,e2,f1),(a1,b6,c2,d1,e2,f2),(a1,b6,c2,d2,e1,f1),
(a1,b6,c2,d2,e1,f2),(a1,b6,c2,d2,e2,f1),(a1,b6,c2,d2,e2,f2),
(a1,b6,c2,d3,e1,f1),(a1,b6,c2,d3,e1,f2),(a1,b6,c2,d3,e2,f1), (a1,b6,c2,d3,e2,f2),(a1,b7,c1,d1,e1,f1),(a1,b7,c1,d1,e1,f2), (a1,b7,c1,d1,e2,f1),(a1,b7,c1,d1,e2,f2),(a1,b7,c1,d2,e1,f1), (a1,b7,c1,d2,e1,f2),(a1,b7,c1,d2,e2,f1),(a1,b7,c1,d2,e2,f2), (a1,b7,c1,d3,e1,f1),(a1,b7,c1,d3,e1,f2),(a1,b7,c1,d3,e2,f1), (a1,b7,c1,d3,e2,f2),(a1,b7,c2,d1,e1,f1),(a1,b7,c2,d1,e1,f2), (a1,b7,c2,d1,e2,f1),(a1,b7,c2,d1,e2,f2),(a1,b7,c2,d2,e1,f1), (a1,b7,c2,d2,e1,f2),(a1,b7,c2,d2,e2,f1),(a1,b7,c2,d2,e2,f2), (a1,b7,c2,d3,e1,f1),(a1,b7,c2,d3,e1,f2),(a1,b7,c2,d3,e2,f1), (a1,b7,c2,d2,e2,f2),(a1,b8,c1,d1,e1,f1),(a1,b8,c1,d1,e1,f2), (a1,b8,c1,d1,e2,f1),(a1,b8,c1,d1,e2,f2),(a1,b8,c1,d2,e1,f1), (a1,b8,c1,d2,e1,f2),(a1,b8,c1,d2,e2,f1),(a1,b8,c1,d2,e2,f2), (a1,b8,c1,d3,e1,f1),(a1,b8,c2,d1,e2,f2),(a1,b8,c1,d3,e2,f1), (a1,b8,c1,d3,e2,f2),(a1,b8,c2,d1,e1,f1),(a1,b8,c2,d1,e1,f2), (a1,b8,c2,d1,e2,f1),(a1,b8,c2,d1,e2,f2),(a1,b8,c2,d2,e1,f1), (a1,b8,c2,d2,e1,f2),(a1,b8,c2,d2,e2,f1),(a1,b8,c2,d2,e2,f2), (a1,b8,c2,d3,e1,f1),(a1,b8,c2,d3,e1,f2),(a1,b8,c2,d3,e2,f1), (a1,b8,c2,d3,e2,f2),(a1,b9,c1,d1,e1,f1),(a1,b9,c1,d1,e1,f2), (a1,b9,c1,d1,e2,f1),(a1,b9,c1,d1,e2,f2),(a1,b9,c1,d2,e1,f1), (a1,b9,c1,d2,e1,f2),(a1,b9,c1,d2,e2,f1),(a1,b9,c1,d2,e2,f2), (a1,b9,c1,d3,e1,f1),(a1,b9,c1,d3,e1,f2),(a1,b9,c1,d3,e2,f1), (a1,b9,c1,d3,e2,f2),(a1,b9,c2,d1,e1,f1),(a1,b9,c2,d1,e1,f2), (a1,b9,c2,d1,e2,f1),(a1,b9,c2,d1,e2,f2),(a1,b9,c2,d2,e1,f1), (a1,b9,c2,d2,e1,f2),(a1,b9,c2,d2,e2,f1),(a1,b9,c2,d2,e2,f2), (a1,b9,c2,d3,e1,f1),(a1,b9,c2,d3,e1,f2),(a1,b9,c2,d3,e2,f1), (a1,b9,c2,d3,e2,f2),(a1,b10,c1,d1,e1,f1),(a1,b10,c1,d1,e1, f2),(a1,b10,c1,d1,e2,f1),(a1,b10,c1,d1,e2,f2),(a1,b10,c1,d2, e1,f1),(a1,b10,c1,d2,e1,f2),(a1,b10,c1,d2,e2,f1),(a1,b10,c1, d2,e2,f2),(a1,b10,c1,d3,e1,f1),(a1,b10,c1,d3,e1,f2),(a1,b10, c1,d3,e2,f1),(a1,b10,c1,d3,e2,f2),(a1,b10,c2,d1,e1,f1),(a1, b10,c2,d1,e1,f2),(a1,b10,c2,d1,e2,f1),(a1,b10,c2,d1,e2,f2), (a1,b10,c2,d2,e1,f1),(a1,b10,c2,d2,e1,f2),(a1,b10,c2,d2,e2, f1),(a1,b10,c2,d2,e2,f2),(a1,b10,c2,d3,e1,f1),(a1,b10,c2,d3, e1,f2),(a1,b10,c2,d3,e2,f1),(a1,b10,c2,d3,e2,f2),(a2,b1,c1, d1,e1,f1),(a2,b1,c1,d1,e1,f2),(a2,b1,c1,d1,e2,f1),(a2,b1,c1, d1,e2,f2),(a2,b1,c1,d2,e1,f1),(a2,b1,c1,d2,e2,f2),(a2,b1,c1, d2,e2,f1),(a2,b1,c1,d2,e2,f2),(a2,b1,c1,d3,e1,f1),(a2,b1,c1, d3,e1,f2),(a2,b1,c1,d3,e2,f1),(a2,b1,c1,d3,e2,f2),(a2,b1,c2, d1,e1,f1),(a2,b1,c2,d1,e1,f2),(a2,b1,c2,d1,e2,f1),(a2,b1,c2, d1,e2,f2),(a2,b1,c2,d2,e1,f1),(a2,b1,c2,d2,e1,f2),(a2,b1,c2, d2,e2,f1),(a2,b1,c2,d2,e2,f2),(a2,b1,c2,d3,e1,f1),(a2,b1,c2, d3,e1,f2), (a2,b1,c2,d3,e2,f1),(a2,b1,c2,d3,e2,f2),(a2,b2,c1,d1,e1,f1), (a2,b2,c1,d1,e1,f2),(a2,b2,c1,d1,e2,f1),(a2,b2,c1,d1,e2,f2), (a2,b2,c1,d2,e1,f1),(a2,b2,c1,d2,e1,f2),(a2,b2,c1,d2,e2,f1), (a2,b2,c1,d2,e2,f2),(a2,b2,c1,d3,e1,f1),(a2,b2,c1,d3,e1,f2), (a2,b2,c1,d3,e2,f1),(a2,b2,c1,d3,e2,f2),(a2,b2,c2,d1,e1,f1), (a2,b2,c2,d1,e1,f2),(a2,b2,c2,d1,e2,f1),(a2,b2,c2,d1,e2,f2), (a2,b2,c2,d2,e1,f1),(a2,b2,c2,d2,e1,f2),(a2,b2,c2,d2,e2,f1), (a2,b2,c2,d2,e2,f2),(a2,b2,c2,d3,e1,f1),(a2,b2,c2,d3,e1,f2), (a2,b2,c2,d3,e2,f1),(a2,b2,c2,d3,e2,f2),(a2,b3,c1,d1,e1,f1), (a2,b3,c1,d1,e1,f2),(a2,b3,c1,d1,e2,f1),(a2,b3,c1,d1,e2,f2), (a2,b3,c1,d2,e1,f1),(a2,b3,c1,d2,e1,f2),(a2,b3,c1,d2,e2,f1), (a2,b3,c1,d2,e2,f2),(a2,b3,c1,d3,e1,f1),(a2,b3,c1,d3,e1,f2), (a2,b3,c1,d3,e2,f1),(a2,b3,c1,d3,e2,f2),(a2,b3,c2,d1,e1,f1), (a2,b3,c2,d1,e1,f2),(a2,b3,c2,d1,e2,f1),(a2,b3,c2,d1,e2,f2), (a2,b3,c2,d2,e1,f1),(a2,b3,c2,d2,e1,f2),(a2,b3,c2,d2,e2,f1), (a2,b3,c2,d2,e2,f2),(a2,b3,c2,d3,e1,f1),(a2,b3,c2,d3,e1,f2), (a2,b3,c2,d3,e2,f1),(a2,b3,c2,d3,e2,f2),(a2,b4,c1,d1,e1,f1), (a2,b4,c1,d1,e1,f2),(a2,b4,c1,d1,e2,f1),(a2,b4,c1,d1,e2,f2), (a2,b4,c1,d2,e1,f1),(a2,b4,c1,d2,e1,f2),(a2,b4,c1,d2,e2,f1), (a2,b4,c1,d2,e2,f2),(a2,b4,c1,d3,e1,f1),(a2,b4,c1,d3,e1,f2), (a2,b4,c1,d3,e2,f1),(a2,b4,c1,d3,e2,f2),(a2,b4,c2,d1,e1,f1), (a2,b4,c2,d1,e1,f2),(a2,b4,c2,d1,e2,f1),(a2,b4,c2,d1,e2,f2), (a2,b4,c2,d2,e1,f1),(a2,b4,c2,d2,e1,f2),(a2,b4,c2,d2,e2,f1), (a2,b4,c2,d2,e2,f2),(a2,b4,c2,d3,e1,f1),(a2,b4,c2,d3,e1,f2), (a2,b4,c2,d3,e2,f1),(a2,b4,c2,d3,e2,f2),(a2,b5,c1,d1,e1,f1), (a2,b5,c1,d1,e1,f2),(a2,b5,c1,d1,e2,f1),(a2,b5,c1,d1,e2,f2), (a2,b5,c1,d2,e1,f1),(a2,b5,c1,d2,e1,f2),(a2,b5,c1,d2,e2,f1), (a2,b5,c1,d2,e2,f2),(a2,b5,c1,d3,e1,f1),(a2,b5,c1,d3,e1,f2), (a2,b5,c1,d3,e2,f1),(a2,b5,c1,d3,e2,f2),(a2,b5,c2,d1,e1,f1), (a2,b5,c2,d1,e1,f2),(a2,b5,c2,d1,e2,f1),(a2,b5,c2,d1,e2,f2), (a2,b5,c2,d2,e1,f1),(a2,b5,c2,d2,e1,f2),(a2,b5,c2,d2,e2,f1), (a2,b5,c2,d2,e2,f2),(a2,b5,c2,d3,e1,f1),(a2,b5,c2,d3,e1,f2), (a2,b5,c2,d3,e2,f1),(a2,b5,c2,d3,e2,f2),(a2,b6,c1,d1,e1,f1), (a2,b6,c1,d1,e1,f2),(a2,b6,c1,d1,e2,f1),(a2,b6,c1,d1,e2,f2), (a2,b6,c1,d2,e1,f1),(a2,b6,c1,d2,e1,f2),(a2,b6,c1,d2,e2,f1), (a2,b6,c1,d2,e2,f2),(a2,b6,c1,d3,e1,f1),(a2,b6,c1,d3,e1,f2), (a2,b6,c1,d3,e2,f1),(a2,b6,c1,d3,e2,f2),(a2,b6,c2,d1,e1,f1), (a2,b6,c2,d1,e1,f2),(a2,b6,c2,d1,e2,f1),(a2,b6,c2,d1,e2,f2), (a2,b6,c2,d2,e1,f1),(a2,b6,c2,d2,e1,f2),(a2,b6,c2,d2,e2,f1), (a2,b6,c2,d2,e2,f2),(a2,b6,c2,d3,e1,f1),(a2,b6,c2,d3,e1,f2), (a2,b6,c2,d3,e2,f1),(a2,b6,c2,d3,e2,f2),(a2,b7,c1,d1,e1,f1), (a2,b7,c1,d1,e1,f2),(a2,b7,c1,d1,e2,f1),(a2,b7,c1,d1,e2,f2), (a2,b7,c1,d2,e1,f1),(a2,b7,c1,d2,e1,f2),(a2,b7,c1,d2,e2,f1), (a2,b7,c1,d2,e2,f2),(a2,b7,c1,d3,e1,f1),(a2,b7,c1,d3,e1,f2), (a2,b7,c1,d3,e2,f1),(a2,b7,c1,d3,e2,f2),(a2,b7,c2,d1,e1,f1), (a2,b7,c2,d1,e1,f2),(a2,b7,c2,d1,e2,f1),(a2,b7,c2,d1,e2,f2), (a2,b7,c2,d2,e1,f1),(a2,b7,c2,d2,e1,f2),(a2,b7,c2,d2,e2,f1), (a2,b7,c2,d2,e2,f2),(a2,b7,c2,d3,e1,f1),(a2,b7,c2,d3,e1,f2), (a2,b7,c2,d3,e2,f1),(a2,b7,c2,d3,e2,f2),(a2,b8,c1,d1,e1,f1), (a2,b8,c1,d1,e1,f2),(a2,b8,c1,d1,e2,f1),(a2,b8,c1,d1,e2,f2), (a2,b8,c1,d2,e1,f1),(a2,b8,c1,d2,e1,f2),(a2,b8,c1,d2,e2,f1), (a2,b8,c1,d2,e2,f2),(a2,b8,c1,d3,e1,f1),(a2,b8,c1,d3,e1,f2), (a2,b8,c1,d3,e2,f1),(a2,b8,c1,d3,e2,f2),(a2,b8,c2,d1,e1,f1), (a2,b8,c2,d1,e1,f2),(a2,b8,c2,d1,e2,f1),(a2,b8,c2,d1,e2,f2), (a2,b8,c2,d2,e1,f1),(a2,b8,c2,d2,e1,f2),(a2,b8,c2,d2,e2,f1), (a2,b8,c2,d2,e2,f2),(a2,b8,c2,d3,e1,f1),(a2,b8,c2,d3,e1,f2), (a2,b8,c2,d3,e2,f1),(a2,b8,c2,d3,e2,f2),(a2,b9,c1,d1,e1,f1), (a2,b9,c1,d1,e1,f2),(a2,b9,c1,d1,e2,f1),(a2,b9,c1,d1,e2,f2), (a2,b9,c1,d2,e1,f1),(a2,b9,c1,d2,e1,f2),(a2,b9,c1,d2,e2,f1), (a2,b9,c1,d2,e2,f2),(a2,b9,c1,d3,e1,f1),(a2,b9,c1,d3,e1,f2), (a2,b9,c1,d3,e2,f1),(a2,b9,c1,d3,e2,f2),(a2,b9,c2,d1,e1,f1), (a2,b9,c2,d1,e1,f2),(a2,b9,c2,d1,e2,f1),(a2,b9,c2,d1,e2,f2), (a2,b9,c2,d2,e1,f1),(a2,b9,c2,d2,e1,f2),(a2,b9,c2,d2,e2,f1), (a2,b9,c2,d2,e2,f2),(a2,b9,c2,d3,e1,f1),(a2,b9,c2,d3,e1,f2), (a2,b9,c2,d3,e2,f1),(a2,b9,c2,d3,e2,f2),(a2,b10,c1,d1,e1,f1), (a2,b10,c1,d1,e1,f2),(a2,b10,c1,d1,e2,f1),(a2,b10,c1,d1,e2, f2),(a2,b10,c1,d2,e1,f1),(a2,b10,c1,d2,e1,f2),(a2,b10,c1,d2, e2,f1),(a2,b10,c1,d2,e2,f2),(a2,b10,c1,d3,e1,f1),(a2,b10,c1, d3,e1,f2),(a2,b10,c1,d3,e2,f1),(a2,b10,c1,d3,e2,f2),(a2,b10, c2,d1,e1,f1),(a2,b10,c2,d1,e1,f2),(a2,b10,c2,d1,e2,f1),(a2, b10,c2,d1,e2,f2),(a2,b10,c2,d2,e1,f1),(a2,b10,c2,d2,e1,f2), (a2,b10,c2,d2,e2,f1),(a2,b10,c2,d2,e2,f2),(a2,b10,c2,d3,e1, f1),(a2,b10,c2,d3,e1,f2),(a2,b10,c2,d3,e2,f1),(a2,b10,c2,d3, e2,f2)

As the compound represented by Formula (I) of the invention, the following compounds are exemplified.

A compound of Formula (I-b):

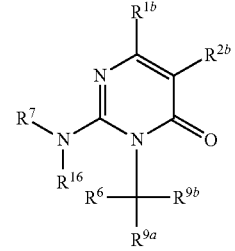

[Chemical Formula 74]

wherein
R$^{1b}$ is:
(aa1) a hydrogen atom or halogen; or
(aa2) a hydrogen atom;
R$^{2b}$ is:
(ab1) a group represented by the formula: —NH—C(=O)—(C(R$^{8a}$)(R$^{8b}$))n-R$^{13}$
wherein n is 0 or 1;
R$^{8a}$ and R$^{8b}$ are each independently a hydrogen atom or halogen;
R$^{13}$ is a hydrogen atom, substituted or unsubstituted alkyl, substituted or unsubstituted alkenyl, substituted or unsubstituted alkynyl, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy; or
—C(=O)—NH—(C(R$^{8a'}$)(R$^{8b'}$))n'—R$^{13'}$
wherein n' is 0 or 1;
R$^{8a'}$ and R$^{8b'}$ are each independently a hydrogen atom or halogen;
R$^{13'}$ is a hydrogen atom, substituted or unsubstituted alkyl, substituted or unsubstituted alkenyl, substituted or unsubstituted alkynyl, substituted or unsubstituted cycloalkyl, a substituted or unsubstituted non-aromatic heterocyclic group, substituted or unsubstituted aryl, substituted or unsubstituted heteroaryl, substituted or unsubstituted amino, substituted or unsubstituted carbamoyl, substituted or unsubstituted alkyloxy, substituted or unsubstituted alkenyloxy, substituted or unsubstituted alkynyloxy;
(ab2) a group represented by the formula: —NH—C(=O)—(C(R$^{8a}$)(R$^{8b}$))n-R$^{18}$
wherein n is 0 or 1;
R$^{8a}$ and R$^{8b}$ are each independently a hydrogen atom or halogen;
R$^{13}$ is a hydrogen atom, substituted or unsubstituted alkyl, substituted or unsubstituted alkenyl, substituted or unsubstituted alkynyl, substituted or unsubstituted non-aromatic heterocyclic group, substituted or unsubstituted alkyloxy, substituted or unsubstituted alkenyloxy, substituted or unsubstituted alkynyloxy; or
—C(=O)—NH—(C(R$^{8a'}$)(R$^{8b'}$))n'—R$^{13'}$
wherein n' is 0 or 1;
R$^{8a'}$ and R$^{8b'}$ are each independently a hydrogen atom or halogen;
R$^{13'}$ is a hydrogen atom, substituted or unsubstituted alkyl, substituted or unsubstituted alkenyl, substituted or unsubstituted alkynyl, substituted or a unsubstituted non-aromatic heterocyclic group, substituted or unsubstituted alkyloxy, substituted or unsubstituted alkenyloxy, substituted or unsubstituted alkynyloxy;
(ab3) a group represented by the formula: —NH—C(=O)—R$^{13}$
wherein R$^{13}$ is a hydrogen atom, substituted or unsubstituted alkyl, substituted or unsubstituted alkenyl, substituted or unsubstituted alkynyl, substituted or unsubstituted tetrahydropyranyl, substituted or unsubstituted tetrahydrothiopyranyl, substituted or unsubstituted alkyloxy, substituted or unsubstituted alkenyloxy, substituted or unsubstituted alkynyloxy; or
—C(=O)—NH—R$^{13'}$ wherein R$^{13'}$ is a hydrogen atom, substituted or unsubstituted alkyl, substituted or unsubstituted alkenyl, substituted or unsubstituted alkynyl, substituted or unsubstituted tetrahydropyranyl, substituted or unsubstituted tetrahydrothiopyranyl, substituted or unsubstituted alkyloxy, substituted or unsubstituted alkenyloxy, substituted or unsubstituted alkynyloxy;
(ab4) a group represented by the formula: —NH—C(=O)—R$^{13}$
wherein R$^{13}$ is a hydrogen atom, substituted or unsubstituted alkyl, substituted or unsubstituted tetrahydropyranyl, substituted or unsubstituted alkyloxy; or
—C(=O)—NH—R$^{13'}$
wherein R$^{13'}$ is a hydrogen atom, substituted or unsubstituted alkyl, substituted or unsubstituted tetrahydropyranyl, substituted or unsubstituted alkyloxy;
(ab5) a group represented by the formula: —NH—C(=O)—R$^{13}$
wherein R$^{13}$ is substituted or unsubstituted alkyl, or substituted or unsubstituted; or
—C(=O)—NH—R$^{13'}$
wherein R$^{13'}$ is substituted or unsubstituted alkyl, or substituted or unsubstituted alkyloxy; or
(ab6) nitro, substituted or unsubstituted carbamoyl, substituted or unsubstituted sulfamoyl, or substituted or unsubstituted amino;
(ab7) substituted or unsubstituted alkyl, substituted or unsubstituted alkyloxy, substituted or unsubstituted cycloalkyl, a substituted or unsubstituted non-aromatic heterocyclic group, substituted or unsubstituted aryl, substituted or unsubstituted heteroaryl, substituted or unsubstituted amino, or substituted or unsubstituted carbamoyl; or
(ab8) substituted or unsubstituted alkyl (preferably substituted C1~C6 alkyl and C3~C6 unsubstituted alkyl), substituted or unsubstituted cycloalkyl, a substituted or unsubstituted non-aromatic heterocyclic group, substituted or unsubstituted aryl or substituted or unsubstituted heteroaryl;
R$^{9a}$ and R$^{9b}$ are each independently a hydrogen atom or halogen;
R$^{6}$ is a group represented by the formula:

[Chemical Formula 75]

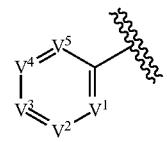

wherein =V$^{1}$—V$^{2}$=V$^{3}$—V$^{4}$=V$^{5}$- is (i): =C(R$^{A'}$)—C(R$^{A}$)=C(R$^{B}$)—C(R$^{C'}$)=C(H)—,
each symbol is as defined in the above (3);
(ac1) R$^{6}$ is a group represented by the formula:

[Chemical Formula 76]

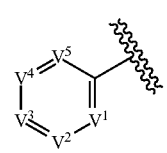

wherein =V$^{1}$—V$^{2}$=V$^{3}$—V$^{4}$=V$^{5}$— is (i): =C(R$^{A'}$)—C(R$^{A}$)=C(R$^{B}$)—C(R$^{C}$)=C(R$^{C'}$)—, $R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl or alkylsilylalkynyl; or (ac2) $R^6$ is a group represented by the formula:

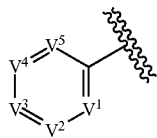

[Chemical Formula 77]

wherein $=V^1-V^2=V^3-V^4=V^5-$ is (i): $=C(R^{A'})-C(R^A)=C(R^B)-C(R^C)=C(R^{C'})-$, $R^A$, $R^{A'}$, $R^B$, $R^C$ and $R^{C'}$ are each independently a hydrogen atom or halogen;

$R^{16}$ is a hydrogen atom;

$R^7$ is a group represented by the formula:

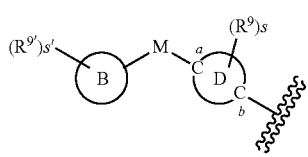

[Chemical Formula 78]

wherein ring D is benzene;

carbon atom a and carbon atom b are carbon atoms which constitute ring D;

-M- is —O—;

ring B is:

(ad1) an aromatic carbocyclic ring or an aromatic heterocyclic ring;

(ad2) benzene, thiazole, isothiazole, oxazole, isoxazole, furan, thiophen, thiadiazole, oxadiazole, pyridine, pyrimidine, pyrazine or pyridazine; or (ad3) benzene, thiazole, thiadiazole, oxadiazole or pyridine;

(ad4) thiazole, isothiazole, oxazole, isoxazole, thiadiazole, oxadiazole, pyridine, pyrimidine, pyrazine or pyridazine;

s is 0 or 1;

$R^9$ are each independently:

(ae1) halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

(ae2) halogen, or substituted or unsubstituted alkyl; or (ae3) halogen, hydroxy, cyano, substituted or unsubstituted alkyl, or substituted or unsubstituted alkyloxy;

s' is an integer of 0 to 2;

$R^{9'}$ are each independently:

(af1) halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, or substituted sulfinyl;

(af2) halogen, hydroxy, carboxy, cyano, substituted or unsubstituted alkyl, substituted or unsubstituted alkyloxy, substituted or unsubstituted alkyloxycarbonyl, substituted or unsubstituted carbamoyl, substituted or unsubstituted amino, substituted or unsubstituted sulfamoyl, substituted sulfonyl, or substituted sulfinyl;

(af3) halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl, or substituted or unsubstituted alkyloxycarbonyl; or (af4) carboxy or unsubstituted alkyloxycarbonyl;

provided that (i) a compound represented by Formula (I)

wherein a group represented by the formula:

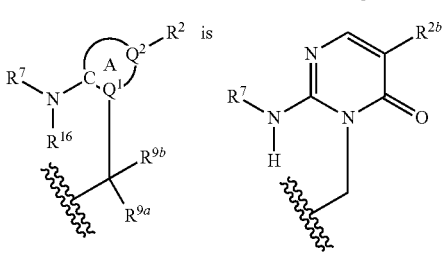

[Chemical Formula 79]

$R^7$ is 4-(6-methyl-3-pyridyl)oxy-phenyl, 4-(5-fluoro-3-pyridyl)oxy-phenyl or 4-(5-fluoro-6-methyl-3-pyridyl)oxy-phenyl, $R^{2b}$ is substituted or unsubstituted amino, and (ii) the following compounds:

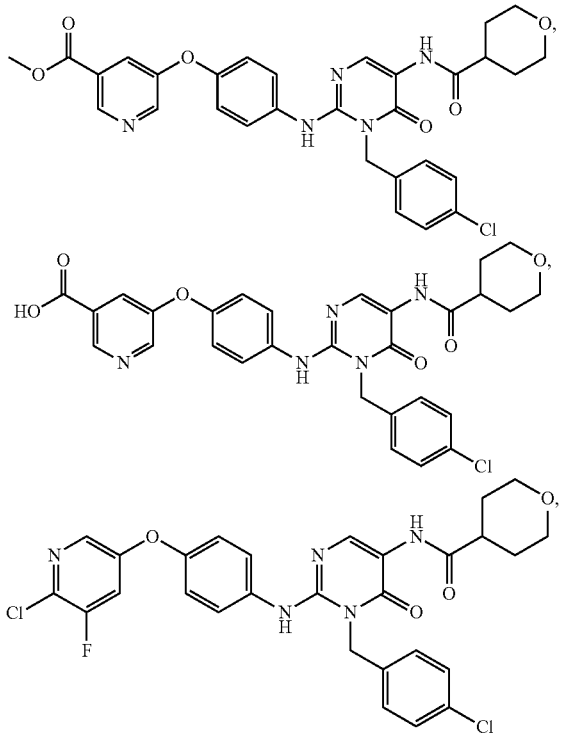

[Chemical Formula 80]

-continued

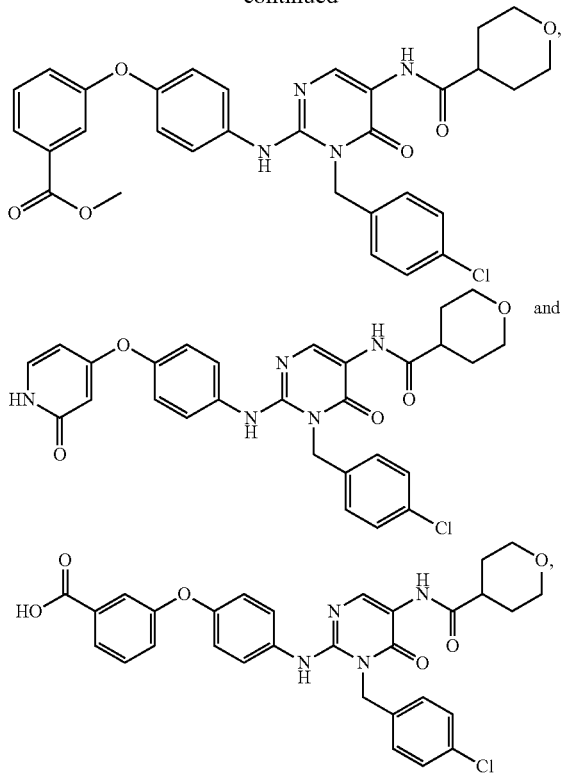

are excluded,
or its pharmaceutically acceptable salt.

The compound represented by the formula (I-b) includes the compounds comprising the combination of some or all of options of the above. Specifically, the following combinations are included.

(aa1,ab1,ac1,ad1,ae1,af1),(aa1,ab1,ac1,ad1,ae1,af2),(aa1,ab1,ac1,ad1,ae1,af3),(aa1,ab1,ac1,ad1,ae1,af4),(aa1,ab1,ac1,ad1,ae2,af1),(aa1,ab1,ac1,ad1,ae2,af2),(aa1,ab1,ac1,ad1,ae2,af3),(aa1,ab1,ac1,ad1,ae2,af4),(aa1,ab1,ac1,ad1,ae3,af1),(aa1,ab1,ac1,ad1,ae3,af2),(aa1,ab1,ac1,ad1,ae3,af3),(aa1,ab1,ac1,ad1,ae3,af4),(aa1,ab1,ac1,ad2,ae1,af1),(aa1,ab1,ac1,ad2,ae1,af2),(aa1,ab1,ac1,ad2,ae1,af3),(aa1,ab1,ac1,ad2,ae1,af4),(aa1,ab1,ac1,ad2,ae2,af1),(aa1,ab1,ac1,ad2,ae2,af2),(aa1,ab1,ac1,ad2,ae2,af3),(aa1,ab1,ac1,ad2,ae2,af4),(aa1,ab1,ac1,ad2,ae3,af1),(aa1,ab1,ac1,ad2,ae3,af2),(aa1,ab1,ac1,ad2,ae3,af3),(aa1,ab1,ac1,ad2,ae3,af4),(aa1,ab1,ac1,ad8,ae1,af1),(aa1,ab1,ac1,ad3,ae1,af2),(aa1,ab1,ac1,ad3,ae1,af3),(aa1,ab1,ac1,ad3,ae1,af4),(aa1,ab1,ac1,ad3,ae2,af1),(aa1,ab1,ac1,ad3,ae2,af2),(aa1,ab1,ac1,ad3,ae2,af3),(aa1,ab1,ac1,ad3,ae2,af4),(aa1,ab1,ac1,ad3,ae3,af1),(aa1,ab1,ac1,ad3,ae3,af2),(aa1,ab1,ac1,ad3,ae3,af3),(aa1,ab1,ac1,ad3,ae3,af4),(aa1,ab1,ac1,ad4,ae1,af1),(aa1,ab1,ac1,ad4,ae1,af2),(aa1,ab1,ac1,ad4,ae1,af3),(aa1,ab1,ac1,ad4,ae1,af4),(aa1,ab1,ac1,ad4,ae2,af1),(aa1,ab1,ac1,ad4,ae2,af2),(aa1,ab1,ac1,ad4,ae2,af3),(aa1,ab1,ac1,ad4,ae2,af4),(aa1,ab1,ac1,ad4,ae3,af1),(aa1,ab1,ac1,ad4,ae3,af2),(aa1,ab1,ac1,ad4,ae3,af3),(aa1,ab1,ac1,ad4,ae3,af4),(aa1,ab1,ac2,ad1,ae1,af1),(aa1,ab1,ac2,ad1,ae1,af2),(aa1,ab1,ac2,ad1,ae1,af3),(aa1,ab1,ac2,ad1,ae1,af4),(aa1,ab1,ac2,ad1,ae2,af1),(aa1,ab1,ac2,ad1,ae2,af2),(aa1,ab1,ac2,ad1,ae2,af3),(aa1,ab1,ac2,ad1,ae2,af4),(aa1,ab1,ac2,ad1,ae3,af1),(aa1,ab1,ac2,ad1,ae3,af2),(aa1,ab1,ac2,ad1,ae3,af3),(aa1,ab1,ac2,ad1,ae3,af4),(aa1,ab1,ac2,ad2,ae1,af1),(aa1,ab1,ac2,ad2,ae1,af2),(aa1,ab1,ac2,ad2,ae1,af3),(aa1,ab1,ac2,ad2,ae1,af4),(aa1,ab1,ac2,ad2,ae2,af1),(aa1,ab1,ac2,ad2,ae2,af2),(aa1,ab1,ac2,ad2,ae2,af3),(aa1,ab1,ac2,ad2,ae3,af1),(aa1,ab1,ac2,ad2,ae3,af2),(aa1,ab1,ac2,ad2,ae3,af3),(aa1,ab1,ac2,ad2,ae3,af4),(aa1,ab1,ac2,ad3,ae1,af1),(aa1,ab1,ac2,ad3,ae1,af2),(aa1,ab1,ac2,ad3,ae1,af3),(aa1,ab1,ac2,ad3,ae1,af4),(aa1,ab1,ac2,ad3,ae2,af1),(aa1,ab1,ac2,ad3,ae2,af2),(aa1,ab1,ac2,ad3,ae2,af3),(aa1,ab1,ac2,ad3,ae2,af4),(aa1,ab1,ac2,ad3,ae3,af1),(aa1,ab1,ac2,ad3,ae3,af2),(aa1,ab1,ac2,ad3,ae3,af3),(aa1,ab1,ac2,ad3,ae3,af4),(aa1,ab1,ac2,ad4,ae1,af1),(aa1,ab1,ac2,ad4,ae1,af2),(aa1,ab1,ac2,ad4,ae1,af3),(aa1,ab1,ac2,ad4,ae1,af4),(aa1,ab1,ac2,ad4,ae2,af1),(aa1,ab1,ac2,ad4,ae2,af2),(aa1,ab1,ac2,ad4,ae2,af3),(aa1,ab1,ac2,ad4,ae2,af4),(aa1,ab1,ac2,ad4,ae3,af1),(aa1,ab1,ac2,ad4,ae3,af2),(aa1,ab1,ac2,ad4,ae3,af3),(aa1,ab1,ac2,ad4,ae3,af4),(aa1,ab2,ac1,ad1,ae1,af1),(aa1,ab2,ac1,ad1,ae1,af2),(aa1,ab2,ac1,ad1,ae1,af3),(aa1,ab2,ac1,ad1,ae1,af4),(aa1,ab2,ac1,ad1,ae2,af1),(aa1,ab2,ac1,ad1,ae2,af2),(aa1,ab2,ac1,ad1,ae2,af3),(aa1,ab2,ac1,ad1,ae2,af4),(aa1,ab2,ac1,ad1,ae3,af1),(aa1,ab2,ac1,ad1,ae3,af2),(aa1,ab2,ac1,ad1,ae3,af3),(aa1,ab2,ac1,ad1,ae3,af4),(aa1,ab2,ac1,ad2,ae1,af1),(aa1,ab2,ac1,ad2,ae1,af2),(aa1,ab2,ac1,ad2,ae1,af3),(aa1,ab2,ac1,ad2,ae1,af4),(aa1,ab2,ac1,ad2,ae2,af1),(aa1,ab2,ac1,ad2,ae2,af2),(aa1,ab2,ac1,ad2,ae2,af3),(aa1,ab2,ac1,ad2,ae2,af4),(aa1,ab2,ac1,ad2,ae3,af1),(aa1,ab2,ac1,ad2,ae3,af2),(aa1,ab2,ac1,ad2,ae3,af3),(aa1,ab2,ac1,ad2,ae3,af4),(aa1,ab2,ac1,ad3,ae1,af1),(aa1,ab2,ac1,ad3,ae1,af2),(aa1,ab2,ac1,ad3,ae1,af3),(aa1,ab2,ac1,ad3,ae1,af4),(aa1,ab2,ac1,ad3,ae2,af1),(aa1,ab2,ac1,ad3,ae2,af2),(aa1,ab2,ac1,ad3,ae2,af3),(aa1,ab2,ac1,ad3,ae2,af4),(aa1,ab2,ac1,ad3,ae3,af1),(aa1,ab2,ac1,ad3,ae3,af2),(aa1,ab2,ac1,ad3,ae3,af3),(aa1,ab2,ac1,ad3,ae3,af4),(aa1,ab2,ac1,ad4,ae1,af1),(aa1,ab2,ac1,ad4,ae1,af2),(aa1,ab2,ac1,ad4,ae1,af3),(aa1,ab2,ac1,ad4,ae1,af4),(aa1,ab2,ac1,ad4,ae2,af1),(aa1,ab2,ac1,ad4,ae2,af2),(aa1,ab2,ac1,ad4,ae2,af3),(aa1,ab2,ac1,ad4,ae2,af4),(aa1,ab2,ac1,ad4,ae3,af1),(aa1,ab2,ac1,ad4,ae3,af2),(aa1,ab2,ac1,ad4,ae3,af3),(aa1,ab2,ac1,ad4,ae3,af4),(aa1,ab2,ac2,ad1,ae1,af1),(aa1,ab2,ac2,ad1,ae1,af2),(aa1,ab2,ac2,ad1,ae1,af3),(aa1,ab2,ac2,ad1,ae1,af4),(aa1,ab2,ac2,ad1,ae2,af1),(aa1,ab2,ac2,ad1,ae2,af2),(aa1,ab2,ac2,ad1,ae2,af3),(aa1,ab2,ac2,ad1,ae2,af4),(aa1,ab2,ac2,ad1,ae3,af1),(aa1,ab2,ac2,ad1,ae3,af2),(aa1,ab2,ac2,ad1,ae3,af3),(aa1,ab2,ac2,ad1,ae3,af4),(aa1,ab2,ac2,ad2,ae1,af1),(aa1,ab2,ac2,ad2,ae1,af2),(aa1,ab2,ac2,ad2,ae1,af3),(aa1,ab2,ac2,ad2,ae1,af4),(aa1,ab2,ac2,ad2,ae2,af1),(aa1,ab2,ac2,ad2,ae2,af2),(aa1,ab2,ac2,ad2,ae2,af3),(aa1,ab2,ac2,ad2,ae2,af4),(aa2,ab2,ac2,ad2,ae3,af1),(aa1,ab2,ac2,ad2,ae3,af2),(aa1,ab2,ac2,ad2,ae3,af3),(aa1,ab2,ac2,ad2,ae3,af4),(aa1,ab2,ac2,ad3,ae1,af1),(aa1,ab2,ac2,ad3,ae1,af2),(aa1,ab2,ac2,ad3,ae1,af3),(aa1,ab2,ac2,ad3,ae1,af4),(aa1,ab2,ac2,ad3,ae2,af1),(aa1,ab2,ac2,ad3,ae2,af2),(aa1,ab2,ac2,ad3,ae2,af3),(aa1,ab2,ac2,ad3,ae2,af4),(aa1,ab2,ac2,ad3,ae3,af1),(aa1,ab2,ac2,ad3,ae3,af2),(aa1,ab2,ac2,ad3,ae3,af3),(aa1,ab2,ac2,ad3,ae3,af4),(aa1,ab2,ac2,ad4,ae1,af1),(aa1,ab2,ac2,ad4,ae1,af2),(aa1,ab2,ac2,ad4,ae1,af3),(aa1,ab2,ac2,ad4,ae1,af4),(aa1,ab2,ac2,ad4,ae2,af1),(aa1,ab2,ac2,ad4,ae2,af2),(aa1,ab2,ac2,ad4,ae2,af3),(aa1,ab2,ac2,ad4,ae2,af4),(aa1,ab2,ac2,ad4,ae3,af1),(aa1,ab2,ac2,ad4,ae3,af2),(aa1,ab2,ac2,ad4,ae3,af3),(aa1,ab2,ac2,ad4,ae3,af4),(aa1,ab3,ac1,ad1,ae1,af1),(aa1,ab3,ac1,ad1,ae1,af2),(aa1,ab3,ac1,ad1,ae1,af3),(aa1,ab3,ac1,ad1,ae1,af4),(aa1,ab3,ac1,ad1,ae2,af1),(aa1,ab3,ac1,ad1,ae2,af2),(aa1,ab3,ac1,ad1,ae2,af3),(aa1,ab3,ac1,ad1,ae2,af4),(aa1,ab3,ac1,ad1,ae3,af1),(aa1,ab3,ac1,ad1,ae3,af2),(aa1,ab3,ac1,ad1,ae3,af3),(aa1,ab3,ac1,ad1,ae3,af4),(aa1,ab3,ac1,ad2,ae1,af1),(aa1,ab3,ac1,ad2,ae1,af2),(aa1,ab3,ac1,ad2,ae1,af3),(aa1,ab3,ac1,ad2,ae1,af4), (aa1,ab3,ac1,ad2,ae2,af1),(aa1,ab3,ac1,ad2,ae2,af2),(aa1, ab3,ac1,ad2,ae2,af3),(aa1,ab3,ac1,ad2,ae2,af4),(aa1,ab3, ac1,ad2,ae3,af1),(aa1,ab3,ac1,ad2,ae3,af2),(aa1,ab3,ac1, ad2,ae3,af3),(aa1,ab3,ac1,ad2,ae3,af4),(aa1,ab3,ac1,ad3, ae1,af1),(aa1,ab3,ac1,ad3,ae1,af2),(aa1,ab3,ac1,ad3,ae1, af3),(aa1,ab3,ac1,ad3,ae1,af4),(aa1,ab3,ac1,ad3,ae2,af1), (aa1,ab3,ac1,ad3,ae2,af2),(aa1,ab3,ac1,ad3,ae2,af3),(aa1, ab3,ac1,ad3,ae2,af4),(aa1,ab3,ac1,ad3,ae3,af1),(aa1,ab3, ac1,ad3,ae3,af2),(aa1,ab3,ac1,ad3,ae3,af3),(aa1,ab3,ac1, ad3,ae3,af4),(aa1,ab3,ac1,ad4,ae1,af1),(aa1,ab3,ac1,ad4, ae1,af2),(aa1,ab3,ac1,ad4,ae1,af3),(aa1,ab3,ac1,ad4,ae1, af4),(aa1,ab3,ac1,ad4,ae2,af1),(aa1,ab3,ac1,ad4,ae2,af2), (aa1,ab3,ac1,ad4,ae2,af3),(aa1,ab3,ac1,ad4,ae2,af4),(aa1, ab3,ac1,ad4,ae3,af1),(aa1,ab3,ac1,ad4,ae3,af2),(aa1,ab3, ac1,ad4,ae3,af3),(aa1,ab3,ac1,ad4,ae3,af4),(aa1,ab3,ac2, ad1,ae1,af1),(aa1,ab3,ac2,ad1,ae1,af2),(aa1,ab3,ac2,ad1, ae1,af3),(aa1,ab3,ac2,ad1,ae1,af4),(aa1,ab3,ac2,ad1,ae2, af1),(aa1,ab3,ac2,ad1,ae2,af2),(aa1,ab3,ac2,ad1,ae2,af3), (aa1,ab3,ac2,ad1,ae2,af4),(aa1,ab3,ac2,ad1,ae3,af1),(aa1, ab3,ac2,ad1,ae3,af2),(aa1,ab3,ac2,ad1,ae3,af3),(aa1,ab3, ac2,ad1,ae3,af4),(aa1,ab3,ac2,ad2,ae1,af1),(aa1,ab3,ac2, ad2,ae1,af2),(aa1,ab3,ac2,ad2,ae1,af3),(aa1,ab3,ac2,ad2, ae1,af4),(aa1,ab3,ac2,ad2,ae2,af1),(aa1,ab3,ac2,ad2,ae2, af2),(aa1,ab3,ac2,ad2,ae2,af3),(aa1,ab3,ac2,ad2,ae2,af4), (aa1,ab3,ac2,ad2,ae3,af1),(aa1,ab3,ac2,ad2,ae3,af2),(aa1, ab3,ac2,ad2,ae3,af3),(aa1,ab3,ac2,ad2,ae3,af4),(aa1,ab3, ac2,ad3,ae1,af1),(aa1,ab3,ac2,ad3,ae1,af2),(aa1,ab3,ac2, ad3,ae1,af3),(aa1,ab3,ac2,ad3,ae1,af4),(aa1,ab3,ac2,ad3, ae2,af1),(aa1,ab3,ac2,ad3,ae2,af2),(aa1,ab3,ac2,ad3,ae2, af3),(aa1,ab3,ac2,ad3,ae2,af4),(aa1,ab3,ac2,ad3,ae3,af1), (aa1,ab3,ac2,ad3,ae3,af2),(aa1,ab3,ac2,ad3,ae3,af3),(aa1, ab3,ac2,ad3,ae3,af4),(aa1,ab3,ac2,ad4,ae1,af1),(aa1,ab3, ac2,ad4,ae1,af2),(aa1,ab3,ac2,ad4,ae1,af3),(aa1,ab3,ac2, ad4,ae1,af4),(aa1,ab3,ac2,ad4,ae2,af1),(aa1,ab3,ac2,ad4, ae2,af2),(aa1,ab3,ac2,ad4,ae2,af3),(aa1,ab3,ac2,ad4,ae2, af4),(aa1,ab3,ac2,ad4,ae3,af1),(aa1,ab3,ac2,ad4,ae3,af2), (aa1,ab3,ac2,ad4,ae3,af3),(aa1,ab3,ac2,ad4,ae3,af4),(aa1, ab4,ac1,ad1,ae1,af1),(aa1,ab4,ac1,ad1,ae1,af2),(aa1,ab4, ac1,ad1,ae1,af3),(aa1,ab4,ac1,ad1,ae1,af4),(aa1,ab4,ac1, ad1,ae2,af1),(aa1,ab4,ac1,ad1,ae2,af2),(aa1,ab4,ac1,ad1, ae2,af3),(aa1,ab4,ac1,ad1,ae2,af4),(aa1,ab4,ac1,ad1,ae3, af1),(aa1,ab4,ac1,ad1,ae3,af2),(aa1,ab4,ac1,ad1,ae3,af3), (aa1,ab4,ac1,ad1,ae3,af4),(aa1,ab4,ac1,ad2,ae1,af1),(aa1, ab4,ac1,ad2,ae1,af2),(aa1,ab4,ac1,ad2,ae1,af3),(aa1,ab4, ac1,ad2,ae1,af4),(aa1,ab4,ac1,ad2,ae2,af1),(aa1,ab4,ac1, ad2,ae2,af2),(aa1,ab4,ac1,ad2,ae2,af3),(aa1,ab4,ac1,ad2, ae2,af4),(aa1,ab4,ac1,ad2,ae3,af1),(aa1,ab4,ac1,ad2,ae3, af2),(aa1,ab4,ac1,ad2,ae3,af3),(aa1,ab4,ac1,ad2,ae3,af4), (aa1,ab4,ac1,ad3,ae1,af1),(aa1,ab4,ac1,ad3,ae1,af2),(aa1, ab4,ac1,ad3,ae1,af3),(aa1,ab4,ac1,ad3,ae1,af4),(aa1,ab4, ac1,ad3,ae2,af1),(aa1,ab4,ac1,ad3,ae2,af2),(aa1,ab4,ac1, ad3,ae2,af4),(aa1,ab4,ac1,ad3,ae2,af4),(aa1,ab4,ac1,ad3, ae3,af1),(aa1,ab4,ac1,ad3,ae3,af2),(aa1,ab4,ac1,ad3,ae3, af3),(aa1,ab4,ac1,ad3,ae3,af4),(aa1,ab4,ac1,ad4,ae1,af1), (aa1,ab4,ac1,ad4,ae1,af2),(aa1,ab4,ac1,ad4,ae1,af3),(aa1, ab4,ac1,ad4,ae1,af4),(aa1,ab4,ac1,ad4,ae2,af1),(aa1,ab4, ac1,ad4,ae2,af2),(aa1,ab4,ac1,ad4,ae2,af3),(aa1,ab4,ac1, ad4,ae2,af4),(aa1,ab4,ac1,ad4,ae3,af1),(aa1,ab4,ac1,ad4, ae3,af2),(aa1,ab4,ac1,ad4,ae3,af3),(aa1,ab4,ac1,ad4,ae3, af4),(aa1,ab4,ac2,ad1,ae1,af1),(aa1,ab4,ac2,ad1,ae1,af2), (aa1,ab4,ac2,ad1,ae1,af3),(aa1,ab4,ac2,ad1,ae1,af4),(aa1, ab4,ac2,ad1,ae2,af1),(aa1,ab4,ac2,ad1,ae2,af2),(aa1,ab4, ac2,ad1,ae2,af3),(aa1,ab4,ac2,ad1,ae2,af4),(aa1,ab4,ac2, ad1,ae3,af1),(aa1,ab4,ac2,ad1,ae3,af2),(aa1,ab4,ac2,ad1, ae3,af3),(aa1,ab4,ac2,ad1,ae3,af4),(aa1,ab4,ac2,ad2,ae1, af1),(aa1,ab4,ac2,ad2,ae1,af2),(aa1,ab4,ac2,ad2,ae1,af3), (aa1,ab4,ac2,ad2,ae1,af4),(aa1,ab4,ac2,ad2,ae2,af1),(aa1, ab4,ac2,ad2,ae2,af2),(aa1,ab4,ac2,ad2,ae2,af3),(aa1,ab4, ac2,ad2,ae2,af4),(aa1,ab4,ac2,ad2,ae3,af1),(aa1,ab4,ac2, ad2,ae3,af2),(aa1,ab4,ac2,ad2,ae3,af3),(aa1,ab4,ac2,ad2, ae3,af4),(aa1,ab4,ac2,ad3,ae1,af1),(aa1,ab4,ac2,ad3,ae1, af2),(aa1,ab4,ac2,ad3,ae1,af3),(aa1,ab4,ac2,ad3,ae1,af4), (aa1,ab4,ac2,ad3,ae2,af1),(aa1,ab4,ac2,ad3,ae2,af3),(aa1, ab4,ac2,ad3,ae2,af3),(aa1,ab4,ac2,ad3,ae2,af4),(aa1,ab4, ac2,ad3,ae3,af1),(aa1,ab4,ac2,ad3,ae3,af2),(aa1,ab4,ac2, ad3,ae3,af3),(aa1,ab4,ac2,ad3,ae3,af4),(aa1,ab4,ac2,ad4, ae1,af1),(aa1,ab4,ac2,ad4,ae1,af2),(aa1,ab4,ac2,ad4,ae1, af3),(aa1,ab4,ac2,ad4,ae1,af4),(aa1,ab4,ac2,ad4,ae2,af1), (aa1,ab4,ac2,ad4,ae2,af2),(aa1,ab4,ac2,ad4,ae2,af3),(aa1, ab4,ac2,ad4,ae2,af4),(aa1,ab4,ac2,ad4,ae3,af1),(aa1,ab4, ac2,ad4,ae3,af2),(aa1,ab4,ac2,ad4,ae3,af3),(aa1,ab4,ac2, ad4,ae3,af4), (aa1,ab5,ac1,ad1,ae1,af1),(aa1,ab5,ac1,ad1, ae1,af2),(aa1,ab5,ac1,ad1,ae1,af3),(aa1,ab5,ac1,ad1,ae1, af4),(aa1,ab5,ac1,ad1,ae2,af1),(aa1,ab5,ac1,ad1,ae2,af2), (aa1,ab5,ac1,ad1,ae2,af3),(aa1,ab5,ac1,ad1,ae2,af4),(aa1, ab5,ac1,ad1,ae3,af1),(aa1,ab5,ac1,ad1,ae3,af2),(aa1,ab5, ac1,ad1,ae3,af3),(aa1,ab5,ac1,ad1,ae3,af4),(aa1,ab5,ac1, ad2,ae1,af1),(aa1,ab5,ac1,ad2,ae1,af2),(aa1,ab5,ac1,ad2, ae1,af3),(aa1,ab5,ac1,ad2,ae1,af4),(aa1,ab5,ac1,ad2,ae2, af1),(aa1,ab5,ac1,ad2,ae2,af2),(aa1,ab5,ac1,ad2,ae2,af3), (aa1,ab5,ac1,ad2,ae2,af4),(aa1,ab5,ac1,ad2,ae3,af1),(aa1, ab5,ac1,ad2,ae3,af2),(aa1,ab5,ac1,ad2,ae3,af3),(aa1,ab5, ac1,ad2,ae3,af4),(aa1,ab5,ac1,ad3,ae1,af1),(aa1,ab5,ac1, ad3,ae1,af2),(aa1,ab5,ac1,ad3,ae1,af3),(aa1,ab5,ac1,ad3, ae1,af4),(aa1,ab5,ac1,ad3,ae2,af1),(aa1,ab5,ac1,ad3,ae2, af2),(aa1,ab5,ac1,ad3,ae2,af3),(aa1,ab5,ac1,ad3,ae2,af4), (aa1,ab5,ac1,ad3,ae3,af1),(aa1,ab5,ac1,ad3,ae3,af2),(aa1, ab5,ac1,ad3,ae3,af3),(aa1,ab5,ac1,ad3,ae3,af4),(aa1,ab5, ac1,ad4,ae1,af1),(aa1,ab5,ac1,ad4,ae1,af2),(aa1,ab5,ac1, ad4,ae1,af3),(aa1,ab5,ac1,ad4,ae1,af4),(aa1,ab5,ac1,ad4, ae2,af1),(aa1,ab5,ac1,ad4,ae2,af2),(aa1,ab5,ac1,ad4,ae2, af3),(aa1,ab5,ac1,ad4,ae2,af4),(aa1,ab5,ac1,ad4,ae3,af1), (aa1,ab5,ac1,ad4,ae3,af2),(aa1,ab5,ac1,ad4,ae3,af3),(aa1, ab5,ac1,ad4,ae3,af4),(aa1,ab5,ac2,ad1,ae1,af1),(aa1,ab5, ac2,ad1,ae1,af2),(aa1,ab5,ac2,ad1,ae1,af3),(aa1,ab5,ac2, ad1,ae1,af4),(aa1,ab5,ac2,ad1,ae2,af1),(aa1,ab5,ac2,ad1, ae2,af2),(aa1,ab5,ac2,ad1,ae2,af3),(aa1,ab5,ac2,ad1,ae2, af4),(aa1,ab5,ac2,ad1,ae3,af1),(aa1,ab5,ac2,ad1,ae3,af2), (aa1,ab5,ac2,ad1,ae3,af3),(aa1,ab5,ac2,ad1,ae3,af4),(aa1, ab5,ac2,ad2,ae1,af1),(aa1,ab5,ac2,ad2,ae1,af2),(aa1,ab1, ac2,ad2,ae1,af3),(aa1,ab5,ac2,ad2,ae1,af4),(aa1,ab5,ac2, ad2,ae2,af1),(aa1,ab5,ac2,ad2,ae2,af2),(aa1,ab5,ac2,ad2, ae2,af3),(aa1,ab5,ac2,ad2,ae2,af4),(aa1,ab5,ac2,ad2,ae3, af1),(aa1,ab5,ac2,ad2,ae3,af2),(aa1,ab5,ac2,ad2,ae3,af3), (aa1,ab5,ac2,ad2,ae3,af4),(aa1,ab5,ac2,ad3,ae1,af1),(aa1, ab5,ac2,ad3,ae1,af2),(aa1,ab5,ac2,ad3,ae1,af3),(aa1,ab5, ac2,ad3,ae1,af4),(aa1,ab5,ac2,ad3,ae2,af1),(aa1,ab5,ac2, ad3,ae2,af2),(aa1,ab5,ac2,ad3,ae2,af3),(aa1,ab5,ac2,ad3, ae2,af4),(aa1,ab5,ac2,ad3,ae3,af1),(aa1,ab5,ac2,ad3,ae3, af2),(aa1,ab5,ac2,ad3,ae3,af3),(aa1,ab5,ac2,ad3,ae3,af4), (aa1,ab5,ac2,ad4,ae1,af1),(aa1,ab5,ac2,ad4,ae1,af2),(aa1, ab5,ac2,ad4,ae1,af3),(aa1,ab5,ac2,ad4,ae1,af4),(aa1,ab5, ac2,ad4,ae2,af1),(aa1,ab5,ac2,ad4,ae2,af2),(aa1,ab5,ac2, ad4,ae2,af3),(aa1,ab1,ac2,ad4,ae2,af4),(aa1,ab5,ac2,ad4, ae3,af1),(aa1,ab5,ac2,ad4,ae3,af2),(aa1,ab5,ac2,ad4,ae3, af3),(aa1,ab5,ac2,ad4,ae3,af4),(aa1,ab6,ac1,ad1,ae1,af1), (aa1,ab6,ac1,ad1,ae1,af2),(aa1,ab6,ac1,ad1,ae1,af3),(aa1, ab6,ac1,ad1,ae1,af4),(aa1,ab6,ac1,ad1,ae2,af1),(aa1,ab6, ac1,ad1,ae2,af2),(aa1,ab6,ac1,ad1,ae2,af3),(aa1,ab6,ac1, ad1,ae2,af4),(aa1,ab6,ac1,ad1,ae3,af1),(aa1,ab6,ac1,ad1, ae3,af2),(aa1,ab6,ac1,ad1,ae3,af3),(aa1,ab6,ac1,ad1,ae3, af4),(aa1,ab6,ac1,ad2,ae1,af1),(aa1,ab6,ac1,ad2,ae1,af2), (aa1,ab6,ac1,ad2,ae1,af3),(aa1,ab6,ac1,ad2,ae1,af4),(aa1, ab6,ac1,ad2,ae2,af1),(aa1,ab6,ac1,ad2,ae2,af3),(aa1,ab6, ac1,ad2,ae2,af3),(aa1,ab6,ac1,ad2,ae2,af4),(aa1,ab6,ac1, ad2,ae3,af1),(aa1,ab6,ac1,ad2,ae3,af2),(aa1,ab6,ac1,ad2, ae3,af3),(aa1,ab6,ac1,ad2,ae3,af4),(aa1,ab6,ac1,ad3,ae1, af1),(aa1,ab6,ac1,ad3,ae1,af2),(aa1,ab6,ac1,ad3,ae1,af3), (aa1,ab6,ac1,ad3,ae1,af4),(aa1,ab6,ac1,ad3,ae2,af1),(aa1, ab6,ac1,ad3,ae2,af2),(aa1,ab6,ac1,ad3,ae2,af3),(aa1,ab6, ac1,ad3,ae2,af4),(aa1,ab6,ac1,ad3,ae3,af1),(aa1,ab6,ac1, ad3,ae3,af2),(aa1,ab6,ac1,ad3,ae3,af3),(aa1,ab6,ac1,ad3, ae3,af4),(aa1,ab6,ac1,ad4,ae1,af1),(aa1,ab6,ac1,ad4,ae1, af2),(aa1,ab6,ac1,ad4,ae1,af3),(aa1,ab6,ac1,ad4,ae1,af4), (aa1,ab6,ac1,ad4,ae2,af1),(aa1,ab6,ac1,ad4,ae2,af2),(aa1, ab6,ac1,ad4,ae2,af3),(aa1,ab6,ac1,ad4,ae2,af4),(aa1,ab6, ac1,ad4,ae3,af1),(aa1,ab6,ac1,ad4,ae3,af2),(aa1,ab6,ac1, ad4,ae3,af3),(aa1,ab6,ac1,ad4,ae3,af4),(aa1,ab6,ac2,ad1, ae1,af1),(aa1,ab6,ac2,ad1,ae1,af2),(aa1,ab6,ac2,ad1,ae1, af3),(aa1,ab6,ac2,ad1,ae1,af4),(aa1,ab6,ac2,ad1,ae2,af1), (aa1,ab6,ac2,ad1,ae2,af2),(aa1,ab6,ac2,ad1,ae2,af3),(aa1, ab6,ac2,ad1,ae2,af4),(aa1,ab6,ac2,ad1,ae3,af1),(aa1,ab6, ac2,ad1,ae3,af2),(aa1,ab6,ac2,ad1,ae3,af3),(aa1,ab6,ac2, ad1,ae3,af4),(aa1,ab6,ac2,ad2,ae1,af1),(aa1,ab6,ac2,ad2, ae1,af2),(aa1,ab6,ac2,ad2,ae1,af3),(aa1,ab6,ac2,ad2,ae1, af4),(aa1,ab6,ac2,ad2,ae2,af1),(aa1,ab6,ac2,ad2,ae2,af2), (aa1,ab6,ac2,ad2,ae2,af3),(aa1,ab6,ac2,ad2,ae2,af4),(aa1, ab6,ac2,ad2,ae3,af1),(aa1,ab6,ac2,ad2,ae3,af2),(aa1,ab6, ac2,ad2,ae3,af3),(aa1,ab6,ac2,ad2,ae3,af4),(aa1,ab6,ac2, ad3,ae1,af1),(aa1,ab6,ac2,ad3,ae1,af2),(aa1,ab6,ac2,ad3, ae1,af3),(aa1,ab6,ac2,ad3,ae1,af4),(aa1,ab6,ac2,ad3,ae2, af1),(aa1,ab6,ac2,ad3,ae2,af2),(aa1,ab6,ac2,ad3,ae2,af3), (aa1,ab6,ac2,ad3,ae2,af4),(aa1,ab6,ac2,ad3,ae3,af1),(aa1, ab6,ac2,ad3,ae3,af2),(aa1,ab6,ac2,ad3,ae3,af3),(aa1,ab6, ac2,ad3,ae3,af4),(aa1,ab6,ac2,ad4,ae1,af1),(aa1,ab6,ac2, ad4,ae1,af2),(aa1,ab6,ac2,ad4,ae1,af3),(aa1,ab6,ac2,ad4, ae1,af4),(aa1,ab6,ac2,ad4,ae2,af1),(aa1,ab6,ac2,ad4,ae2, af2),(aa1,ab6,ac2,ad4,ae2,af3),(aa1,ab6,ac2,ad4,ae2,af4), (aa1,ab6,ac2,ad4,ae3,af1),(aa1,ab6,ac2,ad4,ae3,af2),(aa1, ab6,ac2,ad4,ae3,af3),(aa1,ab6,ac2,ad4,ae3,af4),(aa1,ab7, ac1,ad1,ae1,af1),(aa1,ab7,ac1,ad1,ae1,af2),(aa1,ab7,ac1, ad1,ae1,af3),(aa1,ab7,ac1,ad1,ae1,af4),(aa1,ab7,ac1,ad1, ae2,af1),(aa1,ab7,ac1,ad1,ae2,af2),(aa1,ab7,ac1,ad1,ae2, af3),(aa1,ab7,ac1,ad1,ae2,af4),(aa1,ab7,ac1,ad1,ae3,af1), (aa1,ab7,ac1,ad1,ae3,af2),(aa1,ab7,ac1,ad1,ae3,af3),(aa1, ab7,ac1,ad1,ae3,af4),(aa1,ab7,ac1,ad2,ae1,af1),(aa1,ab7, ac1,ad2,ae1,af2),(aa1,ab7,ac1,ad2,ae1,af3),(aa1,ab7,ac1, ad2,ae1,af4),(aa1,ab7,ac1,ad2,ae2,af1),(aa1,ab7,ac1,ad2, ae2,af2),(aa1,ab7,ac1,ad2,ae2,af3),(aa1,ab7,ac1,ad2,ae2, af4),(aa1,ab7,ac1,ad2,ae3,af1),(aa1,ab7,ac1,ad2,ae3,af2), (aa1,ab7,ac1,ad2,ae3,af3),(aa1,ab7,ac1,ad2,ae3,af4),(aa1, ab7,ac1,ad3,ae1,af1),(aa1,ab7,ac1,ad3,ae1,af2),(aa1,ab7, ac1,ad3,ae1,af3),(aa1,ab7,ac1,ad3,ae1,af4),(aa1,ab7,ac1, ad3,ae2,af1),(aa1,ab7,ac1,ad3,ae2,af2),(aa1,ab7,ac1,ad3, ae2,af3),(aa1,ab7,ac1,ad3,ae2,af4),(aa1,ab7,ac1,ad3,ae3, af1),(aa1,ab7,ac1,ad3,ae3,af2),(aa1,ab7,ac1,ad3,ae3,af3), (aa1,ab7,ac1,ad3,ae3,af4),(aa1,ab7,ac1,ad4,ae1,af1),(aa1, ab7,ac1,ad4,ae1,af2),(aa1,ab7,ac1,ad4,ae1,af3),(aa1,ab7, ac1,ad4,ae1,af4),(aa1,ab7,ac1,ad4,ae2,af1),(aa1,ab7,ac1, ad4,ae2,af2),(aa1,ab7,ac1,ad4,ae2,af3),(aa1,ab7,ac1,ad4, ae2,af4),(aa1,ab7,ac1,ad4,ae3,af1),(aa1,ab7,ac1,ad4,ae3, af2),(aa1,ab7,ac1,ad4,ae3,af3),(aa1,ab7,ac1,ad4,ae3,af4), (aa1,ab7,ac2,ad1,ae1,af1),(aa1,ab7,ac2,ad1,ae1,af2),(aa1, ab7,ac2,ad1,ae1,af3),(aa1,ab7,ac2,ad1,ae1,af4),(aa1,ab7, ac2,ad1,ae2,af1),(aa1,ab7,ac2,ad1,ae2,af2),(aa1,ab7,ac2, ad1,ae2,af3),(aa1,ab7,ac2,ad1,ae2,af4),(aa1,ab7,ac2,ad1, ae3,af1),(aa1,ab7,ac2,ad1,ae3,af2),(aa1,ab7,ac2,ad1,ae3, af3),(aa1,ab7,ac2,ad1,ae3,af4),(aa1,ab7,ac2,ad2,ae1,af1), (aa1,ab7,ac2,ad2,ae1,af2),(aa1,ab7,ac2,ad2,ae1,af3),(aa1, ab7,ac2,ad2,ae1,af4),(aa1,ab7,ac2,ad2,ae2,af1),(aa1,ab7, ac2,ad2,ae2,af2),(aa1,ab7,ac2,ad2,ae2,af3),(aa1,ab7,ac2, ad2,ae2,af4),(aa1,ab7,ac2,ad2,ae3,af1),(aa1,ab7,ac2,ad2, ae3,af2),(aa1,ab7,ac2,ad2,ae3,af3),(aa1,ab7,ac2,ad2,ae3, af4),(aa1,ab7,ac2,ad3,ae1,af1),(aa1,ab7,ac2,ad3,ae1,af2), (aa1,ab7,ac2,ad3,ae1,af3),(aa1,ab7,ac2,ad3,ae1,af4),(aa1, ab7,ac2,ad3,ae2,af1),(aa1,ab7,ac2,ad3,ae2,af2),(aa1,ab7, ac2,ad3,ae2,af3),(aa1,ab7,ac2,ad3,ae2,af4),(aa1,ab7,ac2, ad3,ae3,af1),(aa1,ab7,ac2,ad3,ae3,af2),(aa1,ab7,ac2,ad3, ae3,af3),(aa1,ab7,ac2,ad3,ae3,af4),(aa1,ab7,ac2,ad4,ae1, af1),(aa1,ab7,ac2,ad4,ae1,af2),(aa1,ab7,ac2,ad4,ae1,af3), (aa1,ab7,ac2,ad4,ae1,af4),(aa1,ab7,ac2,ad4,ae2,af1),(aa1, ab7,ac2,ad4,ae2,af2),(aa1,ab7,ac2,ad4,ae2,af3),(aa1,ab7, ac2,ad4,ae2,af4),(aa1,ab7,ac2,ad4,ae3,af1),(aa1,ab7,ac2, ad4,ae3,af2),(aa1,ab7,ac2,ad4,ae3,af3),(aa1,ab7,ac2,ad4, ae3,af4),(aa1,ab8,ac1,ad1,ae1,af1),(aa1,ab8,ac1,ad1,ae1, af2),(aa1,ab8,ac1,ad1,ae1,af3),(aa1,ab8,ac1,ad1,ae1,af4), (aa1,ab8,ac1,ad1,ae2,af1),(aa1,ab8,ac1,ad1,ae2,af2),(aa1, ab8,ac1,ad1,ae2,af3),(aa1,ab8,ac1,ad1,ae2,af4),(aa1,ab8, ac1,ad1,ae3,af1),(aa1,ab8,ac1,ad1,ae3,af2),(aa1,ab8,ac1, ad1,ae3,af3),(aa1,ab8,ac1,ad1,ae3,af4),(aa1,ab8,ac1,ad2, ae1,af1),(aa1,ab8,ac1,ad2,ae1,af2),(aa1,ab8,ac1,ad2,ae1, af3),(aa1,ab8,ac1,ad2,ae1,af4),(aa1,ab8,ac1,ad2,ae2,af1), (aa1,ab8,ac1,ad2,ae2,af2),(aa1,ab8,ac1,ad2,ae2,af3),(aa1, ab8,ac1,ad2,ae2,af4),(aa1,ab8,ac1,ad2,ae3,af1),(aa1,ab8, ac1,ad2,ae3,af2),(aa1,ab8,ac1,ad2,ae3,af3),(aa1,ab8,ac1, ad2,ae3,af4),(aa1,ab8,ac1,ad3,ae1,af1),(aa1,ab8,ac1,ad3, ae1,af2),(aa1,ab8,ac1,ad3,ae1,af3),(aa1,ab8,ac1,ad3,ae1, af4),(aa1,ab8,ac1,ad3,ae2,af1),(aa1,ab8,ac1,ad3,ae2,af2), (aa1,ab8,ac1,ad3,ae2,af3),(aa1,ab8,ac1,ad3,ae2,af4),(aa1, ab8,ac1,ad3,ae3,af1),(aa1,ab8,ac1,ad3,ae3,af2),(aa1,ab8, ac1,ad3,ae3,af3),(aa1,ab8,ac1,ad3,ae3,af4),(aa1,ab8,ac1, ad4,ae1,af1),(aa1,ab8,ac1,ad4,ae1,af2),(aa1,ab8,ac1,ad4, ae1,af3),(aa1,ab8,ac1,ad4,ae1,af4),(aa1,ab8,ac1,ad4,ae2, af1),(aa1,ab8,ac1,ad4,ae2,af2),(aa1,ab8,ac1,ad4,ae2,af3), (aa1,ab8,ac1,ad4,ae2,af4),(aa1,ab8,ac1,ad4,ae3,af1),(aa1, ab8,ac1,ad4,ae3,af2),(aa1,ab8,ac1,ad4,ae3,af3),(aa1,ab8, ac1,ad4,ae3,af4),(aa1,ab8,ac2,ad1,ae1,af1),(aa1,ab8,ac2, ad1,ae1,af2),(aa1,ab8,ac2,ad1,ae1,af3),(aa1,ab8,ac2,ad1, ae1,af4),(aa1,ab8,ac2,ad1,ae2,af1),(aa1,ab8,ac2,ad1,ae2, af2),(aa1,ab8,ac2,ad1,ae2,af3),(aa1,ab1,ac2,ad1,ae2,af4), (aa1,ab8,ac2,ad1,ae3,af1),(aa1,ab8,ac2,ad1,ae3,af2),(aa1, ab8,ac2,ad1,ae3,af3),(aa1,ab8,ac2,ad1,ae3,af4),(aa1,ab8, ac2,ad2,ae1,af1),(aa1,ab8,ac2,ad2,ae1,af2),(aa1,ab8,ac2, ad2,ae1,af3),(aa1,ab8,ac2,ad2,ae1,af4),(aa1,ab8,ac2,ad2, ae2,af1),(aa1,ab8,ac2,ad2,ae2,af2),(aa1,ab8,ac2,ad2,ae2, af3),(aa1,ab8,ac2,ad2,ae2,af4),(aa1,ab8,ac2,ad2,ae3,af1), (aa1,ab8,ac2,ad2,ae3,af2),(aa1,ab8,ac2,ad2,ae3,af3),(aa1, ab8,ac2,ad2,ae3,af4),(aa1,ab8,ac2,ad3,ae1,af1),(aa1,ab8, ac2,ad3,ae1,af2),(aa1,ab8,ac2,ad3,ae1,af3),(aa1,ab8,ac2, ad3,ae1,af4),(aa1,ab8,ac2,ad3,ae2,af1),(aa1,ab8,ac2,ad3, ae2,af3),(aa1,ab8,ac2,ad3,ae2,af3),(aa1,ab8,ac2,ad3,ae2, af4),(aa1,ab8,ac2,ad3,ae3,af1),(aa1,ab8,ac2,ad3,ae3,af2), (aa1,ab8,ac2,ad3,ae3,af3),(aa1,ab8,ac2,ad3,ae3,af4),(aa1, ab8,ac2,ad4,ae1,af1),(aa1,ab8,ac2,ad4,ae1,af2),(aa1,ab8, ac2,ad4,ae1,af3),(aa1,ab8,ac2,ad4,ae1,af4),(aa1,ab8,ac2, ad4,ae2,af1),(aa1,ab8,ac2,ad4,ae2,af2),(aa1,ab8,ac2,ad4, ae2,af3),(aa1,ab8,ac2,ad4,ae2,af4),(aa1,ab8,ac2,ad4,ae3, af1),(aa1,ab8,ac2,ad4,ae3,af2),(aa1,ab8,ac2,ad4,ae3,af3), (aa1,ab8,ac2,ad4,ae3,af4),(aa2,ab1,ac1,ad1,ae1,af1),(aa2, ab1,ac1,ad1,ae1,af2),(aa2,ab1,ac1,ad1,ae1,af3),(aa2,ab1, ac1,ad1,ae1,af4),(aa2,ab1,ac1,ad1,ae2,af1),(aa2,ab1,ac1, ad1,ae2,af2),(aa2,ab1,ac1,ad1,ae2,af3),(aa2,ab1,ac1,ad1, ae2,af4),(aa2,ab1,ac1,ad1,ae3,af1),(aa2,ab1,ac1,ad1,ae3, af2),(aa2,ab1,ac1,ad1,ae3,af3),(aa2,ab1,ac1,ad1,ae3,af4), (aa2,ab1,ac1,ad2,ae1,af1),(aa2,ab1,ac1,ad2,ae1,af2),(aa2, ab1,ac1,ad2,ae1,af3),(aa2,ab1,ac1,ad2,ae1,af4),(aa2,ab1, ac1,ad2,ae2,af1),(aa2,ab1,ac1,ad2,ae2,af3),(aa2,ab1,ac1, ad2,ae2,af3),(aa2,ab1,ac1,ad2,ae2,af4),(aa2,ab1,ac1,ad2, ae3,af1),(aa2,ab1,ac1,ad2,ae3,af2),(aa2,ab1,ac1,ad2,ae3, af3),(aa2,ab1,ac1,ad2,ae3,af4),(aa2,ab1,ac1,ad3,ae1,af1), (aa2,ab1,ac1,ad3,ae1,af2),(aa2,ab1,ac1,ad3,ae1,af3),(aa2, ab1,ac1,ad3,ae1,af4),(aa2,ab1,ac1,ad3,ae2,af1),(aa2,ab1, ac1,ad3,ae2,af2),(aa2,ab1,ac1,ad3,ae2,af3),(aa2,ab1,ac1, ad3,ae2,af4),(aa2,ab1,ac1,ad3,ae3,af1),(aa2,ab1,ac1,ad3, ae3,af2),(aa2,ab1,ac1,ad3,ae1,af3),(aa2,ab1,ac1,ad3,ae3, af4),(aa2,ab1,ac1,ad4,ae1,af1),(aa2,ab1,ac1,ad4,ae1,af2), (aa2,ab1,ac1,ad4,ae1,af3),(aa2,ab1,ac1,ad4,ae1,af4),(aa2, ab1,ac1,ad4,ae2,af1),(aa2,ab1,ac1,ad4,ae2,af2),(aa2,ab1, ac1,ad4,ae2,af3),(aa2,ab1,ac1,ad4,ae2,af4),(aa2,ab1,ac1, ad4,ae3,af1),(aa2,ab1,ac1,ad4,ae3,af2),(aa2,ab1,ac1,ad4, ae3,af3),(aa2,ab1,ac1,ad4,ae3,af4),(aa2,ab1,ac2,ad1,ae1, af1),(aa2,ab1,ac2,ad1,ae1,af2),(aa2,ab1,ac2,ad1,ae1,af3), (aa2,ab1,ac2,ad1,ae1,af4),(aa2,ab1,ac2,ad1,ae2,af1),(aa2, ab1,ac2,ad1,ae2,af2),(aa2,ab1,ac2,ad1,ae2,af3),(aa2,ab1, ac2,ad1,ae2,af4),(aa2,ab1,ac2,ad1,ae3,af1),(aa2,ab1,ac2, ad1,ae3,af2),(aa2,ab1,ac2,ad1,ae3,af3),(aa2,ab1,ac2,ad1, ae3,af4),(aa2,ab1,ac2,ad2,ae1,af1),(aa2,ab1,ac2,ad2,ae1, af2),(aa2,ab1,ac2,ad2,ae1,af3),(aa2,ab1,ac2,ad2,ae1,af4), (aa2,ab1,ac2,ad2,ae1,af1),(aa2,ab1,ac2,ad2,ae2,af2),(aa2, ab2,ac2,ad2,ae2,af3),(aa2,ab1,ac2,ad2,ae2,af4),(aa2,ab1, ac2,ad2,ae3,af1),(aa2,ab1,ac2,ad2,ae3,af2),(aa2,ab1,ac2, ad2,ae3,af3),(aa2,ab1,ac2,ad2,ae3,af4),(aa2,ab1,ac2,ad3, ae1,af1),(aa2,ab1,ac2,ad3,ae1,af2),(aa2,ab1,ac2,ad3,ae1, af3),(aa2,ab1,ac2,ad3,ae1,af4),(aa2,ab1,ac2,ad3,ae2,af1), (aa2,ab1,ac2,ad3,ae2,af2),(aa2,ab1,ac2,ad3,ae2,af3),(aa2, ab1,ac2,ad3,ae2,af4),(aa2,ab1,ac2,ad3,ae3,af1),(aa2,ab1, ac2,ad3,ae3,af2),(aa2,ab1,ac2,ad3,ae3,af3),(aa2,ab1,ac2, ad3,ae3,af4),(aa2,ab1,ac2,ad4,ae1,af1),(aa2,ab1,ac2,ad4, ae1,af2),(aa2,ab1,ac2,ad4,ae1,af3),(aa2,ab1,ac2,ad4,ae1, af4),(aa2,ab1,ac2,ad4,ae2,af1),(aa2,ab1,ac2,ad4,ae2,af2), (aa2,ab1,ac2,ad4,ae2,af3),(aa2,ab1,ac2,ad4,ae2,af4),(aa2, ab1,ac2,ad4,ae3,af1),(aa2,ab1,ac2,ad4,ae3,af2),(aa2,ab1, ac2,ad4,ae3,af3),(aa2,ab1,ac2,ad4,ae3,af4),(aa2,ab2,ac1, ad1,ae1,af1),(aa2,ab2,ac1,ad1,ae1,af2),(aa2,ab2,ac1,ad1, ae1,af3),(aa2,ab2,ac1,ad1,ae1,af4),(aa2,ab2,ac1,ad1,ae2, af1),(aa2,ab2,ac1,ad1,ae2,af2),(aa2,ab2,ac1,ad1,ae2,af3), (aa2,ab2,ac1,ad1,ae2,af4),(aa2,ab2,ac1,ad1,ae3,af1),(aa2, ab2,ac1,ad1,ae3,af2),(aa2,ab2,ac1,ad1,ae3,af3),(aa2,ab2, ac1,ad1,ae3,af4),(aa2,ab2,ac1,ad2,ae1,af1),(aa2,ab2,ac1, ad2,ae1,af2),(aa2,ab2,ac1,ad2,ae1,af3),(aa2,ab2,ac1,ad2, ae1,af4),(aa2,ab2,ac1,ad2,ae2,af1),(aa2,ab2,ac1,ad2,ae2, af2),(aa2,ab2,ac1,ad2,ae2,af3),(aa2,ab2,ac1,ad2,ae2,af2), (aa2,ab2,ac1,ad2,ae3,af1),(aa2,ab2,ac1,ad2,ae3,af2),(aa2, ab2,ac1,ad2,ae3,af3),(aa2,ab2,ac1,ad2,ae3,af4),(aa1,ab2, ac1,ad3,ae1,af1),(aa2,ab2,ac1,ad3,ae1,af2),(aa2,ab2,ac1, ad3,ae1,af3),(aa2,ab2,ac1,ad3,ae1,af4),(aa2,ab2,ac1,ad3, ae2,af1),(aa2,ab2,ac1,ad3,ae2,af2),(aa2,ab2,ac1,ad3,ae2, af3),(aa2,ab2,ac1,ad3,ae2,af4),(aa2,ab2,ac1,ad3,ae3,af1), (aa2,ab2,ac1,ad3,ae3,af2),(aa2,ab2,ac1,ad3,ae3,af3),(aa2, ab2,ac1,ad3,ae3,af4),(aa2,ab2,ac1,ad4,ae1,af1),(aa2,ab2, ac1,ad4,ae1,af2),(aa2,ab2,ac1,ad4,ae1,af3),(aa2,ab2,ac1, ad4,ae1,af4),(aa2,ab2,ac1,ad4,ae2,af1),(aa2,ab2,ac1,ad4, ae2,af2),(aa2,ab2,ac1,ad4,ae2,af3),(aa2,ab2,ac1,ad4,ae2, af4),(aa2,ab2,ac1,ad4,ae3,af1),(aa2,ab2,ac1,ad4,ae3,af2), (aa2,ab2,ac1,ad4,ae3,af3),(aa2,ab2,ac1,ad4,ae3,af4),(aa2, ab2,ac2,ad1,ae1,af1),(aa2,ab2,ac2,ad1,ae1,af2),(aa2,ab2, ac2,ad1,ae1,af3),(aa2,ab2,ac2,ad1,ae1,af4),(aa2,ab2,ac2, ad1,ae2,af1),(aa2,ab2,ac2,ad1,ae2,af2),(aa2,ab2,ac2,ad1, ae2,af3),(aa2,ab2,ac2,ad1,ae2,af4),(aa2,ab2,ac2,ad1,ae3, af1),(aa2,ab2,ac2,ad1,ae3,af2),(aa2,ab2,ac2,ad1,ae3,af3), (aa2,ab2,ac2,ad1,ae3,af4),(aa2,ab2,ac2,ad2,ae1,af1),(aa2, ab2,ac2,ad2,ae1,af2),(aa2,ab2,ac2,ad2,ae1,af3),(aa2,ab2, ac2,ad2,ae1,af4),(aa2,ab2,ac2,ad2,ae2,af1),(aa2,ab2,ac2, ad2,ae2,af2),(aa2,ab2,ac2,ad2,ae2,af3),(aa2,ab2,ac2,ad2, ae2,af4),(aa2,ab2,ac2,ad2,ae3,af1),(aa2,ab2,ac2,ad2,ae3, af2),(aa2,ab2,ac2,ad2,ae3,af3),(aa2,ab2,ac2,ad2,ae3,af4), (aa2,ab2,ac2,ad3,ae1,af1),(aa2,ab2,ac2,ad3,ae1,af2),(aa2, ab2,ac2,ad3,ae1,af3),(aa2,ab2,ac2,ad3,ae1,af4),(aa2,ab2, ac2,ad3,ae2,af1),(aa2,ab2,ac2,ad3,ae2,af2),(aa2,ab2,ac2, ad3,ae2,af3),(aa2,ab2,ac2,ad3,ae2,af4),(aa2,ab2,ac2,ad3, ae3,af1),(aa2,ab2,ac2,ad3,ae3,af2),(aa2,ab2,ac2,ad3,ae3, af3),(aa2,ab2,ac2,ad3,ae3,af4),(aa2,ab2,ac2,ad4,ae1,af1), (aa2,ab2,ac2,ad4,ae1,af2),(aa2,ab2,ac2,ad4,ae1,af3),(aa2, ab2,ac2,ad4,ae1,af4),(aa2,ab2,ac2,ad4,ae2,af2),(aa2,ab2, ac2,ad4,ae2,af3),(aa2,ab2,ac2,ad4,ae2,af3),(aa2,ab2,ac2, ad4,ae2,af4),(aa2,ab2,ac2,ad4,ae3,af1),(aa2,ab2,ac2,ad4, ae3,af2),(aa2,ab2,ac2,ad4,ae3,af3),(aa2,ab2,ac2,ad4,ae3, af4),(aa2,ab3,ac1,ad1,ae1,af1),(aa2,ab3,ac1,ad1,ae1,af2), (aa2,ab3,ac1,ad1,ae1,af3),(aa2,ab3,ac1,ad1,ae1,af4),(aa2, ab3,ac1,ad1,ae2,af1),(aa2,ab3,ac1,ad1,ae2,af2),(aa2,ab3, ac1,ad1,ae2,af3),(aa2,ab3,ac1,ad1,ae2,af4),(aa2,ab3,ac1, ad1,ae3,af1),(aa2,ab3,ac1,ad1,ae3,af2),(aa2,ab3,ac1,ad1, ae3,af3),(aa2,ab3,ac1,ad1,ae3,af4), (aa2,ab3,ac1,ad2,ae1, af1),(aa2,ab3,ac1,ad2,ae1,af2),(aa2,ab3,ac1,ad2,ae1,af3), (aa2,ab3,ac1,ad2,ae1,af4),(aa2,ab3,ac1,ad2,ae2,af1),(aa2, ab3,ac1,ad2,ae2,af2),(aa2,ab3,ac1,ad2,ae2,af3),(aa2,ab3, ac1,ad2,ae2,af4),(aa2,ab3,ac1,ad2,ae3,af1),(aa2,ab3,ac1, ad2,ae3,af2),(aa2,ab3,ac1,ad2,ae3,af3),(aa2,ab3,ac1,ad2, ae3,af4),(aa2,ab3,ac1,ad3,ae1,af1),(aa2,ab3,ac1,ad3,ae1, af2),(aa2,ab3,ac1,ad3,ae1,af3),(aa2,ab3,ac1,ad3,ae1,af4), (aa2,ab3,ac1,ad3,ae2,af1),(aa2,ab3,ac1,ad3,ae2,af3),(aa2, ab3,ac1,ad3,ae2,af3),(aa2,ab3,ac1,ad3,ae2,af4),(aa2,ab3, ac1,ad3,ae3,af1),(aa2,ab3,ac1,ad3,ae3,af2),(aa2,ab3,ac1, ad3,ae3,af3),(aa2,ab3,ac1,ad3,ae3,af4),(aa2,ab3,ac1,ad4, ae1,af1),(aa2,ab3,ac1,ad4,ae1,af2),(aa2,ab3,ac1,ad4,ae1, af3),(aa2,ab1,ac1,ad4,ae1,af1),(aa2,ab3,ac1,ad4,ae2,af1), (aa2,ab3,ac1,ad4,ae2,af2),(aa2,ab3,ac1,ad4,ae2,af3),(aa2, ab3,ac1,ad4,ae2,af4),(aa2,ab3,ac1,ad4,ae3,af1),(aa2,ab3, ac1,ad4,ae3,af2),(aa2,ab3,ac1,ad4,ae3,af3),(aa2,ab3,ac1, ad4,ae3,af4),(aa2,ab3,ac2,ad1,ae1,af1),(aa2,ab3,ac2,ad1, ae1,af2),(aa2,ab3,ac2,ad1,ae1,af3),(aa2,ab3,ac2,ad1,ae1, af4),(aa2,ab3,ac2,ad1,ae2,af1),(aa2,ab3,ac2,ad1,ae2,af2), (aa2,ab3,ac2,ad1,ae2,af3),(aa2,ab3,ac2,ad1,ae2,af4),(aa2, ab3,ac2,ad1,ae3,af1),(aa2,ab3,ac2,ad1,ae3,af2),(aa2,ab3, ac2,ad1,ae3,af3),(aa2,ab3,ac2,ad1,ae3,af4),(aa2,ab3,ac2, ad2,ae1,af1),(aa2,ab3,ac2,ad2,ae1,af2),(aa2,ab3,ac2,ad2, ae1,af3),(aa2,ab3,ac2,ad2,ae1,af4),(aa2,ab3,ac2,ad2,ae2, af1),(aa2,ab3,ac2,ad2,ae2,af2),(aa2,ab3,ac2,ad2,ae2,af3), (aa2,ab3,ac2,ad2,ae2,af4),(aa2,ab3,ac2,ad2,ae3,af1) (aa2, ab3,ac2,ad2,ae3,af2),(aa2,ab3,ac2,ad2,ae3,af3),(aa2,ab3, ac2,ad2,ae3,af4),(aa2,ab3,ac2,ad3,ae1,af1),(aa2,ab3,ac2, ad3,ae1,af2),(aa2,ab3,ac2,ad3,ae1,af3),(aa2,ab3,ac2,ad3, ae1,af4),(aa2,ab3,ac2,ad3,ae2,af1),(aa2,ab3,ac2,ad3,ae2, af2),(aa2,ab3,ac2,ad3,ae2,af3),(aa2,ab3,ac2,ad3,ae2,af4), (aa2,ab3,ac2,ad3,ae3,af1),(aa2,ab3,ac2,ad3,ae3,af2),(aa2, ab3,ac2,ad3,ae3,af3),(aa2,ab3,ac2,ad3,ae3,af4),(aa2,ab3, ac2,ad4,ae1,af1),(aa2,ab3,ac2,ad4,ae1,af2),(aa2,ab3,ac2, ad4,ae1,af3),(aa2,ab3,ac2,ad4,ae1,af4),(aa2,ab3,ac2,ad4, ae2,af1),(aa2,ab3,ac2,ad4,ae2,af2),(aa2,ab3,ac2,ad4,ae2, af3),(aa2,ab3,ac2,ad4,ae2,af4),(aa2,ab3,ac2,ad4,ae3,af1), (aa2,ab3,ac2,ad4,ae3,af2),(aa2,ab3,ac2,ad4,ae3,af3),(aa2, ab3,ac2,ad4,ae3,af4),(aa2,ab4,ac1,ad1,ae1,af1),(aa2,ab4, ac1,ad1,ae1,af2),(aa2,ab4,ac1,ad1,ae1,af3),(aa2,ab4,ac1, ad1,ae1,af4),(aa2,ab4,ac1,ad1,ae2,af1),(aa2,ab4,ac1,ad1, ae2,af2),(aa2,ab4,ac1,ad1,ae2,af3),(aa2,ab4,ac1,ad1,ae2, af4),(aa2,ab4,ac1,ad1,ae3,af1),(aa2,ab4,ac1,ad1,ae3,af2), (aa2,ab4,ac1,ad1,ae3,af3),(aa2,ab4,ac1,ad1,ae3,af4),(aa2, ab4,ac1,ad2,ae1,af1),(aa2,ab4,ac1,ad2,ae1,af2),(aa2,ab4, ac1,ad2,ae1,af3),(aa2,ab4,ac1,ad2,ae1,af4),(aa2,ab4,ac1, ad2,ae2,af1),(aa2,ab4,ac1,ad2,ae2,af2),(aa2,ab4,ac1,ad2, ae2,af3),(aa2,ab4,ac1,ad2,ae2,af4),(aa2,ab4,ac1,ad2,ae3, af1),(aa2,ab4,ac1,ad2,ae3,af2),(aa2,ab4,ac1,ad2,ae3,af3), (aa2,ab4,ac1,ad2,ae3,af4),(aa2,ab4,ac1,ad3,ae1,af1),(aa2,ab4,ac1,ad3,ae1,af2),(aa2,ab4,ac1,ad3,ae1,af3),(aa2,ab4,ac1,ad3,ae1,af4),(aa2,ab4,ac1,ad3,ae2,af3),(aa2,ab4,ac1,ad3,ae2,af1),(aa2,ab4,ac1,ad3,ae2,af3),(aa2,ab4,ac1,ad3,ae2,af4),(aa2,ab4,ac1,ad3,ae3,af1),(aa2,ab4,ac1,ad3,ae3,af2),(aa2,ab4,ac1,ad3,ae3,af3),(aa2,ab4,ac1,ad3,ae3,af4),(aa2,ab4,ac1,ad4,ae1,af1),(aa2,ab4,ac1,ad4,ae1,af2),(aa2,ab4,ac1,ad4,ae1,af3),(aa2,ab4,ac1,ad4,ae1,af4),(aa2,ab4,ac1,ad4,ae2,af1),(aa2,ab4,ac1,ad4,ae2,af2),(aa2,ab4,ac1,ad4,ae2,af3),(aa2,ab4,ac1,ad4,ae2,af4),(aa2,ab4,ac1,ad4,ae3,af1),(aa2,ab4,ac1,ad4,ae3,af2),(aa2,ab4,ac1,ad4,ae3,af3),(aa2,ab4,ac1,ad4,ae3,af4),(aa2,ab4,ac2,ad1,ae1,af1),(aa2,ab4,ac2,ad1,ae1,af2),(aa2,ab4,ac2,ad1,ae1,af3),(aa2,ab4,ac2,ad1,ae1,af4),(aa2,ab4,ac2,ad1,ae2,af1),(aa2,ab4,ac2,ad1,ae2,af2),(aa2,ab4,ac2,ad1,ae2,af3),(aa2,ab4,ac2,ad1,ae2,af4),(aa2,ab4,ac2,ad1,ae3,af1),(aa2,ab4,ac2,ad1,ae3,af2),(aa2,ab4,ac2,ad1,ae3,af3),(aa2,ab4,ac2,ad1,ae3,af4),(aa2,ab4,ac2,ad2,ae1,af1),(aa2,ab4,ac2,ad2,ae1,af2),(aa2,ab4,ac2,ad2,ae1,af3),(aa2,ab4,ac2,ad2,ae1,af4),(aa2,ab4,ac2,ad2,ae2,af1),(aa2,ab4,ac2,ad2,ae2,af2),(aa2,ab4,ac2,ad2,ae2,af3),(aa2,ab4,ac2,ad2,ae2,af4),(aa2,ab4,ac2,ad2,ae3,af1),(aa2,ab4,ac2,ad2,ae3,af2),(aa2,ab4,ac2,ad2,ae3,af3),(aa2,ab4,ac2,ad2,ae3,af4),(aa2,ab4,ac2,ad3,ae1,af1),(aa2,ab4,ac2,ad3,ae1,af2),(aa2,ab4,ac2,ad3,ae1,af3),(aa2,ab4,ac2,ad3,ae1,af4),(aa2,ab4,ac2,ad3,ae2,af1),(aa2,ab4,ac2,ad3,ae2,af2),(aa2,ab4,ac2,ad3,ae2,af3),(aa2,ab4,ac2,ad3,ae2,af4),(aa2,ab4,ac2,ad3,ae3,af1),(aa2,ab4,ac2,ad3,ae3,af2),(aa2,ab4,ac2,ad3,ae3,af3),(aa2,ab4,ac2,ad3,ae3,af4),(aa2,ab4,ac2,ad4,ae1,af1),(aa2,ab4,ac2,ad4,ae1,af2),(aa2,ab4,ac2,ad4,ae1,af3),(aa2,ab4,ac2,ad4,ae1,af4),(aa2,ab4,ac2,ad4,ae2,af1),(aa2,ab4,ac2,ad4,ae2,af2),(aa2,ab4,ac2,ad4,ae2,af3),(aa2,ab4,ac2,ad4,ae2,af4),(aa2,ab4,ac2,ad4,ae3,af1),(aa2,ab4,ac2,ad4,ae3,af2),(aa2,ab4,ac2,ad4,ae3,af3),(aa2,ab4,ac2,ad4,ae3,af4),(aa2,ab5,ac1,ad1,ae1,af1),(aa2,ab5,ac1,ad1,ae1,af2),(aa2,ab5,ac1,ad1,ae1,af3),(aa2,ab5,ac1,ad1,ae1,af4),(aa2,ab5,ac1,ad1,ae2,af1),(aa2,ab5,ac1,ad1,ae2,af2),(aa2,ab5,ac1,ad1,ae2,af3),(aa2,ab5,ac1,ad1,ae2,af4),(aa2,ab5,ac1,ad1,ae3,af1),(aa2,ab5,ac1,ad1,ae3,af2),(aa2,ab5,ac1,ad1,ae3,af3),(aa2,ab5,ac1,ad1,ae3,af4),(aa2,ab5,ac1,ad2,ae1,af1),(aa2,ab5,ac1,ad2,ae1,af2),(aa2,ab5,ac1,ad2,ae1,af3),(aa2,ab5,ac1,ad2,ae1,af4),(aa2,ab5,ac1,ad2,ae2,af1),(aa2,ab5,ac1,ad2,ae2,af2),(aa2,ab5,ac1,ad2,ae2,af3),(aa2,ab5,ac1,ad2,ae2,af4),(aa2,ab5,ac1,ad2,ae3,af1),(aa2,ab5,ac1,ad2,ae3,af2),(aa2,ab5,ac1,ad2,ae3,af3),(aa2,ab5,ac1,ad2,ae3,af4),(aa2,ab5,ac1,ad3,ae1,af1),(aa2,ab5,ac1,ad3,ae1,af2),(aa2,ab5,ac1,ad3,ae1,af3),(aa2,ab5,ac1,ad3,ae1,af4),(aa2,ab5,ac1,ad3,ae2,af1),(aa2,ab5,ac1,ad3,ae2,af2),(aa2,ab5,ac1,ad3,ae2,af3),(aa2,ab5,ac1,ad3,ae2,af4),(aa2,ab5,ac1,ad3,ae3,af1),(aa2,ab5,ac1,ad3,ae3,af2),(aa2,ab5,ac1,ad3,ae3,af3),(aa2,ab5,ac1,ad3,ae3,af4),(aa2,ab5,ac1,ad4,ae1,af1),(aa2,ab5,ac1,ad4,ae1,af2),(aa2,ab5,ac1,ad4,ae1,af3),(aa2,ab5,ac1,ad4,ae1,af4),(aa2,ab5,ac1,ad4,ae2,af1),(aa2,ab5,ac1,ad4,ae2,af2),(aa2,ab5,ac1,ad4,ae2,af3),(aa2,ab5,ac1,ad4,ae2,af4),(aa2,ab5,ac1,ad4,ae3,af1),(aa2,ab5,ac1,ad4,ae3,af2),(aa2,ab5,ac1,ad4,ae3,af3),(aa2,ab5,ac1,ad4,ae3,af4),(aa2,ab5,ac2,ad1,ae1,af1),(aa2,ab5,ac2,ad1,ae1,af2),(aa2,ab5,ac2,ad1,ae1,af3),(aa2,ab5,ac2,ad1,ae1,af4),(aa2,ab5,ac2,ad1,ae2,af1),(aa2,ab5,ac2,ad1,ae2,af2),(aa2,ab5,ac2,ad1,ae2,af3),(aa2,ab5,ac2,ad1,ae2,af4),(aa2,ab5,ac2,ad1,ae3,af1),(aa2,ab5,ac2,ad1,ae3,af2),(aa2,ab5,ac2,ad1,ae3,af3),(aa2,ab5,ac2,ad1,ae3,af4),(aa2,ab5,ac2,ad2,ae1,af1),(aa2,ab5,ac2,ad2,ae1,af2),(aa2,ab5,ac2,ad2,ae1,af3),(aa2,ab5,ac2,ad2,ae1,af4),(aa2,ab5,ac2,ad2,ae2,af1),(aa2,ab5,ac2,ad2,ae2,af2),(aa2,ab5,ac2,ad2,ae2,af3),(aa2,ab5,ac2,ad2,ae2,af4),(aa2,ab5,ac2,ad2,ae3,af1),(aa2,ab5,ac2,ad2,ae3,af2),(aa2,ab5,ac2,ad2,ae3,af3),(aa2,ab5,ac2,ad2,ae3,af4),(aa2,ab5,ac2,ad3,ae1,af1),(aa2,ab5,ac2,ad3,ae1,af2),(aa2,ab5,ac2,ad3,ae1,af3),(aa2,ab5,ac2,ad3,ae1,af4),(aa2,ab5,ac2,ad3,ae2,af1),(aa2,ab5,ac2,ad3,ae2,af2),(aa2,ab5,ac2,ad3,ae2,af3),(aa2,ab5,ac2,ad3,ae2,af4),(aa2,ab5,ac2,ad3,ae3,af1),(aa2,ab5,ac2,ad3,ae3,af2),(aa2,ab5,ac2,ad3,ae3,af3),(aa2,ab5,ac2,ad3,ae3,af4),(aa2,ab5,ac2,ad4,ae1,af1),(aa2,ab5,ac2,ad4,ae1,af2),(aa2,ab5,ac2,ad4,ae1,af3),(aa2,ab5,ac2,ad4,ae1,af4),(aa2,ab5,ac2,ad4,ae2,af1),(aa2,ab5,ac2,ad4,ae2,af2),(aa2,ab5,ac2,ad4,ae2,af4),(aa2,ab5,ac2,ad4,ae2,af4),(aa2,ab5,ac2,ad4,ae3,af1),(aa2,ab5,ac2,ad4,ae3,af2),(aa2,ab5,ac2,ad4,ae3,af4),(aa2,ab5,ac2,ad4,ae3,af4),(aa2,ab6,ac1,ad1,ae1,af1),(aa2,ab6,ac1,ad1,ae1,af2),(aa2,ab6,ac1,ad1,ae1,af3),(aa2,ab6,ac1,ad1,ae1,af4),(aa2,ab6,ac1,ad1,ae2,af1),(aa2,ab6,ac1,ad1,ae2,af2),(aa2,ab6,ac1,ad1,ae2,af3),(aa2,ab6,ac1,ad1,ae2,af4),(aa2,ab6,ac1,ad1,ae3,af1),(aa2,ab6,ac1,ad1,ae3,af2),(aa2,ab6,ac1,ad1,ae3,af3),(aa2,ab6,ac1,ad1,ae3,af4),(aa2,ab6,ac1,ad2,ae1,af1),(aa2,ab6,ac1,ad2,ae1,af2),(aa2,ab6,ac1,ad2,ae1,af3),(aa2,ab6,ac1,ad2,ae1,af4),(aa2,ab6,ac1,ad2,ae2,af1),(aa2,ab6,ac1,ad2,ae2,af2),(aa2,ab6,ac1,ad2,ae2,af3),(aa2,ab6,ac1,ad2,ae2,af4),(aa2,ab6,ac1,ad2,ae3,af1),(aa2,ab6,ac1,ad2,ae3,af2),(aa2,ab6,ac1,ad2,ae3,af3),(aa2,ab6,ac1,ad2,ae3,af4),(aa2,ab6,ac1,ad3,ae1,af1),(aa2,ab6,ac1,ad3,ae1,af2),(aa2,ab6,ac1,ad3,ae1,af3),(aa2,ab6,ac1,ad3,ae1,af4),(aa2,ab6,ac1,ad3,ae2,af1),(aa2,ab6,ac1,ad3,ae2,af2),(aa2,ab6,ac1,ad3,ae2,af3),(aa2,ab6,ac1,ad3,ae2,af4),(aa2,ab6,ac1,ad3,ae3,af1),(aa2,ab6,ac1,ad3,ae3,af2),(aa2,ab6,ac1,ad3,ae3,af3),(aa2,ab6,ac1,ad3,ae3,af4),(aa2,ab6,ac1,ad4,ae1,af1),(aa2,ab6,ac1,ad4,ae1,af2),(aa2,ab6,ac1,ad4,ae1,af3),(aa2,ab6,ac1,ad4,ae1,af4),(aa2,ab6,ac1,ad4,ae2,af1),(aa2,ab6,ac1,ad4 af2),(aa2,ab6,ac1,ad4,ae2,af3),(aa2,ab6,ac1,ad4,ae2,af4),(aa2,ab6,ac1,ad4,ae3,af1),(aa2,ab6,ac1,ad4,ae3,af2),(aa2,ab6,ac1,ad4,ae3,af3),(aa2,ab6,ac1,ad4,ae3,af4),(aa2,ab6,ac2,ad1,ae1,af1),(aa2,ab6,ac2,ad1,ae1,af2),(aa2,ab6,ac2,ad1,ae1,af3),(aa2,ab6,ac2,ad1,ae1,af4),(aa2,ab6,ac2,ad1,ae2,af1),(aa2,ab6,ac2,ad1,ae2,af2),(aa2,ab6,ac2,ad1,ae2,af3),(aa2,ab6,ac2,ad1,ae2,af4),(aa2,ab6,ac2,ad1,ae3,af1),(aa2,ab6,ac2,ad1,ae3,af2),(aa2,ab6,ac2,ad1,ae3,af3),(aa2,ab6,ac2,ad1,ae3,af4),(aa2,ab6,ac2,ad2,ae1,af1),(aa2,ab6,ac2,ad2,ae1,af2),(aa2,ab6,ac2,ad2,ae1,af3),(aa2,ab6,ac2,ad2,ae1,af4) (aa2,ab6,ac2,ad2,ae2,af1),(aa2,ab6,ac2,ad2,ae2,af2),(aa2,ab6,ac2,ad2,ae2,af3),(aa2,ab6,ac2,ad2,ae2,af4),(aa2,ab6,ac2,ad2,ae3,af1),(aa2,ab6,ac2,ad2,ae3,af2),(aa2,ab6,ac2,ad2,ae3,af3),(aa2,ab6,ac2,ad2,ae3,af4),(aa2,ab6,ac2,ad3,ae1,af1),(aa2,ab6,ac2,ad3,ae1,af2),(aa2,ab6,ac2,ad3,ae1,af3),(aa2,ab6,ac2,ad3,ae1,af4),(aa2,ab6,ac2,ad3,ae2,af1),(aa2,ab6,ac2,ad3,ae2,af2),(aa2,ab6,ac2,ad3,ae2,af3),(aa2,ab6,ac2,ad3,ae2,af4),(aa2,ab6,ac2,ad3,ae3,af1),(aa2,ab6,ac2,ad3,ae3,af2),(aa2,ab6,ac2,ad3,ae3,af3),(aa2,ab6,ac2,ad3,ae3,af4),(aa2,ab6,ac2,ad4,ae1,af4),(aa2,ab6,ac2,ad4,ae1,af2),(aa2,ab6,ac2,ad4,ae1,af3),(aa2,ab6,ac2,ad4,ae1,af4),(aa2,ab6,ac2,ad4,ae2,af1),(aa2,ab6,ac2,ad4,ae2,af2),(aa2,ab6,ac2,ad4,ae2,af3),(aa2,ab6,ac2,ad4,ae2,af4),(aa2,ab6,ac2,ad4,ae3,af1),(aa2,ab6,ac2,ad4,ae3,af2),(aa2,ab6,ac2,ad4,ae3,af3),(aa2,ab6,ac2,ad4,ae3,af4),(aa2,ab7,ac1,ad1,ae1,af1),(aa2,ab7,ac1,ad1,ae1,af2),(aa2,ab7,ac1,ad1,ae1,af3),(aa2,ab7,ac1,ad1,ae1,af4),(aa2,ab7,ac1,ad1,ae2,af1),(aa2,ab7,ac1,ad1,ae2,af2),(aa2,ab7,ac1,ad1,ae2,af3),(aa2,ab7,ac1,ad1,ae2,af4),(aa2,ab7,ac1,ad1,ae3,af1),(aa2,ab7,ac1,ad1,ae3,af2),(aa2,ab7,ac1,ad1,ae3,af3),(aa2,ab7,ac1,ad1,ae3,af4),(aa2,ab7,ac1,ad2,ae1,af1),(aa2,ab7,ac1,ad2,ae1,af2),(aa2,ab7,ac1,ad2,ae1,af3),(aa2,ab7,ac1,ad2,ae1,af4),(aa2,ab7,ac1,ad2,ae2,af1),(aa2,ab7,ac1,ad2,ae2,af2),(aa2,ab7,ac1,ad2,ae2,af3),(aa2,ab7,ac1,ad2,ae2,af4),(aa2,ab7,ac1,ad2,ae3,af1),(aa2,ab7,ac1,ad2,ae3,af2),(aa2,ab7,ac1,ad2,ae3,af3),(aa2,ab7,ac1,ad2,ae3,af4),(aa2,ab7,ac1,ad3,ae1,af1),(aa2,ab7,ac1, ad3,ae1,af2),(aa2,ab7,ac1,ad3,ae1,af3),(aa2,ab7,ac1,ad3, ae1,af4),(aa2,ab7,ac1,ad3,ae2,af1),(aa2,ab7,ac1,ad3,ae2, af2),(aa2,ab7,ac1,ad3,ae2,af3),(aa2,ab7,ac1,ad3,ae2,af4), (aa2,ab7,ac1,ad3,ae3,af1),(aa2,ab7,ac1,ad3,ae3,af2),(aa2, ab7,ac1,ad3,ae3,af3),(aa2,ab7,ac1,ad3,ae3,af4),(aa2,ab7, ac1,ad4,ae1,af1),(aa2,ab7,ac1,ad4,ae1,af2),(aa2,ab7,ac1, ad4,ae1,af3),(aa2,ab7,ac1,ad4,ae1,af1),(aa2,ab7,ac1,ad4, ae2,af1),(aa2,ab7,ac1,ad4,ae2,af2),(aa2,ab7,ac1,ad4,ae2, af3),(aa2,ab7,ac1,ad4,ae2,af4),(aa2,ab7,ac1,ad4,ae3,af1), (aa2,ab7,ac1,ad4,ae3,af2),(aa2,ab7,ac1,ad4,ae3,af3),(aa2, ab7,ac1,ad4,ae3,af4),(aa2,ab7,ac2,ad1,ae1,af1),(aa2,ab7, ac2,ad1,ae1,af2),(aa2,ab7,ac2,ad1,ae1,af3),(aa2,ab7,ac2, ad1,ae1,af4),(aa2,ab7,ac2,ad1,ae2,af1),(aa2,ab7,ac2,ad1, ae2,af2),(aa2,ab7,ac2,ad1,ae2,af3),(aa2,ab7,ac2,ad1,ae2, af4),(aa2,ab7,ac2,ad1,ae3,af1),(aa2,ab7,ac2,ad1,ae3,af2), (aa2,ab7,ac2,ad1,ae3,af3),(aa2,ab1,ac2,ad1,ae3,af4),(aa2, ab7,ac2,ad2,ae1,af1),(aa2,ab7,ac2,ad2,ae1,af2),(aa2,ab7, ac2,ad2,ae1,af3),(aa2,ab7,ac2,ad2,ae1,af4),(aa2,ab7,ac2, ad2,ae2,af1),(aa2,ab7,ac2,ad2,ae2,af2),(aa2,ab7,ac2,ad2, ae2,af3),(aa2,ab7,ac2,ad2,ae2,af4),(aa2,ab7,ac2,ad2,ae3, af1),(aa2,ab7,ac2,ad2,ae3,af2),(aa2,ab7,ac2,ad2,ae3,af3), (aa2,ab7,ac2,ad2,ae3,af4),(aa2,ab7,ac2,ad3,ae1,af1),(aa2, ab7,ac2,ad3,ae1,af2),(aa2,ab7,ac2,ad3,ae1,af3),(aa2,ab7, ac2,ad3,ae1,af4),(aa2,ab7,ac2,ad3,ae2,af1),(aa2,ab7,ac2, ad3,ae2,af2),(aa2,ab7,ac2,ad3,ae2,af3),(aa2,ab7,ac2,ad3, ae2,af4),(aa2,ab7,ac2,ad3,ae3,af1),(aa2,ab7,ac2,ad3,ae3, af2),(aa2,ab7,ac2,ad3,ae3,af3),(aa2,ab7,ac2,ad3,ae3,af4), (aa2,ab7,ac2,ad4,ae1,af1),(aa2,ab7,ac2,ad4,ae1,af2),(aa2, ab7,ac2,ad4,ae1,af3),(aa2,ab7,ac2,ad4,ae2,af4),(aa2,ab7, ac2,ad4,ae2,af1),(aa2,ab7,ac2,ad4,ae2,af2),(aa2,ab7,ac2, ad4,ae2,af3),(aa2,ab7,ac2,ad4,ae2,af4),(aa2,ab7,ac2,ad4, ae3,af1),(aa2,ab7,ac2,ad4,ae3,af2),(aa2,ab7,ac2,ad4,ae3, af3),(aa2,ab7,ac2,ad4,ae3,af4),(aa2,ab8,ac1,ad1,ae1,af1), (aa2,ab8,ac1,ad1,ae1,af2),(aa2,ab8,ac1,ad1,ae1,af3),(aa2, ab8,ac1,ad1,ae1,af4),(aa2,ab8,ac1,ad1,ae2,af1),(aa2,ab8, ac1,ad1,ae2,af2),(aa2,ab8,ac1,ad1,ae2,af3),(aa2,ab8,ac1, ad1,ae2,af4),(aa2,ab8,ac1,ad1,ae3,af1),(aa2,ab8,ac1,ad1, ae3,af2),(aa2,ab8,ac1,ad1,ae3,af2),(aa2,ab8,ac1,ad1,ae3, af4),(aa2,ab8,ac1,ad2,ae1,af1),(aa2,ab8,ac1,ad2,ae1,af2), (aa2,ab8,ac1,ad2,ae1,af3),(aa2,ab8,ac1,ad2,ae1,af4),(aa2, ab8,ac1,ad2,ae2,af1),(aa2,ab8,ac1,ad2,ae2,af2),(aa2,ab8, ac1,ad2,ae2,af3),(aa2,ab8,ac1,ad2,ae2,af4),(aa2,ab8,ac1, ad2,ae3,af1),(aa2,ab8,ac1,ad2,ae3,af2),(aa2,ab8,ac1,ad2, ae3,af3),(aa2,ab8,ac1,ad2,ae3,af4),(aa2,ab8,ac1,ad3,ae1, af1),(aa2,ab8,ac1,ad3,ae1,af2),(aa2,ab8,ac1,ad3,ae1,af3), (aa2,ab8,ac1,ad3,ae1,af4),(aa2,ab8,ac1,ad3,ae2,af1),(aa2, ab8,ac1,ad3,ae2,af2),(aa2,ab8,ac1,ad3,ae2,af3),(aa2,ab8, ac1,ad3,ae2,af4),(aa2,ab8,ac1,ad3,ae3,af1),(aa2,ab8,ac1, ad2,ae3,af4),(aa2,ab8,ac1,ad3,ae3,af3),(aa2,ab8,ac1,ad3, ae3,af4),(aa2,ab8,ac1,ad4,ae1,af1),(aa2,ab8,ac1,ad4,ae1, af2),(aa2,ab8,ac1,ad4,ae1,af3),(aa2,ab8,ac1,ad4,ae1,af4), (aa2,ab8,ac1,ad4,ae2,af1),(aa2,ab8,ac1,ad4,ae2,af2),(aa2, ab8,ac1,ad4,ae2,af3),(aa2,ab8,ac1,ad4,ae2,af4),(aa2,ab8, ac1,ad4,ae3,af1),(aa2,ab8,ac1,ad4,ae3,af2),(aa2,ab8,ac1, ad4,ae3,af3),(aa2,ab8,ac1,ad4,ae3,af4),(aa2,ab8,ac2,ad1, ae1,af1),(aa2,ab8,ac2,ad1,ae1,af2),(aa2,ab8,ac2,ad1,ae1, af3),(aa2,ab8,ac2,ad1,ae1,af4),(aa2,ab8,ac2,ad1,ae2,af1), (aa2,ab8,ac2,ad1,ae2,af2),(aa2,ab8,ac2,ad1,ae2,af3),(aa2, ab8,ac2,ad1,ae2,af4),(aa2,ab8,ac2,ad1,ae3,af1),(aa2,ab8, ac2,ad1,ae3,af2),(aa2,ab8,ac2,ad1,ae3,af3),(aa2,ab8,ac2, ad1,ae3,af4),(aa2,ab8,ac2,ad2,ae1,af1),(aa2,ab8,ac2,ad2, ae1,af2),(aa2,ab8,ac2,ad2,ae1,af3),(aa2,ab8,ac2,ad2,ae1, af4),(aa2,ab8,ac2,ad2,ae2,af1),(aa2,ab8,ac2,ad2,ae2,af2), (aa2,ab8,ac2,ad2,ae2,af3),(aa2,ab8,ac2,ad2,ae2,af4),(aa2, ab8,ac2,ad2,ae3,af1),(aa2,ab8,ac2,ad2,ae3,af2),(aa2,ab8, ac2,ad2,ae3,af3),(aa2,ab8,ac2,ad2,ae3,af4),(aa2,ab8,ac2, ad3,ae1,af1),(aa2,ab8,ac2,ad2,ae1,af2),(aa2,ab8,ac2,ad3, ae1,af3),(aa2,ab8,ac2,ad3,ae1,af4),(aa2,ab8,ac2,ad3,ae2, af1),(aa2,ab8,ac2,ad3,ae2,af2),(aa2,ab8,ac2,ad3,ae2,af3), (aa2,ab8,ac2,ad3,ae2,af4),(aa2,ab8,ac2,ad3,ae3,af1),(aa2, ab8,ac2,ad3,ae3,af2),(aa2,ab8,ac2,ad3,ae3,af3),(aa2,ab8, ac2,ad3,ae3,af4),(aa2,ab8,ac2,ad4,ae1,af1),(aa2,ab8,ac2, ad4,ae1,af2),(aa2,ab8,ac2,ad4,ae1,af3),(aa2,ab8,ac2,ad4, ae1,af4),(aa2,ab8,ac2,ad4,ae2,af1),(aa2,ab8,ac2,ad4,ae2, af2),(aa2,ab8,ac2,ad4,ae2,af3),(aa2,ab8,ac2,ad4,ae2,af4), (aa2,ab8,ac2,ad4,ae3,af1),(aa2,ab8,ac2,ad4,ae3,af2),(aa2, ab8,ac2,ad4,ae3,af3),(aa2,ab8,ac2,ad4,ae3,af4).

As the compound represented by Formula (I) of the invention, the following compounds are exemplified.

A compound of Formula (I-c):

[Chemical Formula 81]

wherein $R^{3b}$ is:

(ba1) a hydrogen atom or halogen; or (ba2) a hydrogen atom;

$R^{2b}$ is:

(bb1) a group represented by the formula: $-(C(R^{11c})(R^{11d}))m'$-COOR wherein $R^{11c}$ is each independently a hydrogen atom, substituted or unsubstituted alkyl, substituted or unsubstituted alkenyl, or substituted or unsubstituted alkynyl;

$R^{11d}$ is each independently a hydrogen atom, substituted or unsubstituted alkyl, substituted or unsubstituted alkenyl, or substituted or unsubstituted alkynyl;

R is hydrogen or substituted or unsubstituted alkyl;

m' is an integer of 1 to 4;

(bb2) a group represented by the formula: $-(CH_2)m'$-COOH;

wherein m' is an integer of 1 to 3;

(bb3) unsubstituted alkyl, unsubstituted alkenyl or unsubstituted alkynyl;

(bb4) unsubstituted alkyl;

(bb5) a group represented by the formula: $-NH-C(=O)-(C(R^{8a})(R^{8b}))n-R^{13}$ wherein n is 0 or 1;

$R^{8a}$ and $R^{8b}$ are each independently a hydrogen atom or halogen;

$R^{13}$ is a hydrogen atom, substituted or unsubstituted alkyl, substituted or unsubstituted alkenyl, substituted or unsubstituted alkynyl, substituted or unsubstituted cycloalkyl, a substituted or unsubstituted non-aromatic heterocyclic group; substituted or unsubstituted aryl, substituted or unsubstituted heteroaryl, substituted or unsubstituted alkyloxy, substituted or unsubstituted alkenyloxy, substituted or unsubstituted alkynyloxy; or $-C(=O)-NH-(C(R^{8a'})(R^{8b'}))n'-R^{13'}$ wherein n' is 0 or 1;

$R^{8a'}$ and $R^{8b'}$ are each independently a hydrogen atom or halogen;

$R^{13'}$ is a hydrogen atom, substituted or unsubstituted alkyl, substituted or unsubstituted alkenyl, substituted or unsubstituted alkynyl, substituted or unsubstituted cycloalkyl, a substituted or unsubstituted non-aromatic heterocyclic group, substituted or unsubstituted aryl, substituted or unsubstituted heteroaryl, substituted or unsubstituted amino, substituted or unsubstituted carbamoyl, substituted or unsubstituted alkyloxy, substituted or unsubstituted alkenyloxy, substituted or unsubstituted alkynyloxy;

(bb6) a group represented by the formula: —NH—C(=O)—(C($R^{8a}$)($R^{8b}$))n-$R^{13}$ wherein n is 0 or 1;

$R^{8a}$ and $R^{8b}$ are each independently a hydrogen atom or halogen;

$R^{13}$ is a hydrogen atom, substituted or unsubstituted alkyl, substituted or unsubstituted alkenyl, substituted or unsubstituted alkynyl, a substituted or unsubstituted non-aromatic heterocyclic group, substituted or unsubstituted alkyloxy, substituted or unsubstituted alkenyloxy, substituted or unsubstituted alkynyloxy; or —C(=O)—NH—(C($R^{8a'}$)($R^{8b'}$))n'—$R^{13'}$ wherein n' is 0 or 1;

$R^{8a'}$ and $R^{8b'}$ are each independently a hydrogen atom or halogen;

$R^{13'}$ is a hydrogen atom, substituted or unsubstituted alkyl, substituted or unsubstituted alkenyl, substituted or unsubstituted alkynyl, a substituted or unsubstituted non-aromatic heterocyclic group, substituted or unsubstituted carbamoyl, or substituted or unsubstituted alkyloxy, substituted or unsubstituted alkenyloxy, substituted or unsubstituted alkynyloxy;

(bb7) a group represented by the formula: —NH—C(=O)—$R^{13}$ wherein $R^{13}$ is a hydrogen atom, substituted or unsubstituted alkyl, substituted or unsubstituted alkenyl, substituted or unsubstituted alkynyl, substituted or unsubstituted tetrahydropyranyl, substituted or unsubstituted tetrahydrothiopyranyl, substituted or unsubstituted alkyloxy, substituted or unsubstituted alkenyloxy, substituted or unsubstituted alkynyloxy; or

—C(=O)—NH—$R^{13'}$ wherein $R^{13'}$ is a hydrogen atom, substituted or unsubstituted alkyl, substituted or unsubstituted alkenyl, substituted or unsubstituted alkynyl, substituted or unsubstituted tetrahydropyranyl, substituted or unsubstituted tetrahydrothiopyranyl, substituted or unsubstituted carbamoylalkyl, substituted or unsubstituted alkyloxy, substituted or unsubstituted alkenyloxy, or substituted or unsubstituted alkynyloxy;

(bb8) a group represented by the formula: —NH—C(=O)—$R^{13}$ wherein $R^{13'}$ is a hydrogen atom, substituted or unsubstituted alkyl, substituted or unsubstituted tetrahydropyranyl, substituted or unsubstituted alkyloxy; or

—C(=O)—NH—$R^{13'}$ wherein $R^{13'}$ is a hydrogen atom, substituted or unsubstituted alkyl, substituted or unsubstituted tetrahydropyranyl, substituted or unsubstituted carbamoylalkyl or substituted or unsubstituted alkyloxy;

(bb9) nitro, substituted or unsubstituted alkyl, substituted or unsubstituted alkenyl, substituted or unsubstituted alkynyl, substituted or unsubstituted carbamoyl, substituted or unsubstituted sulfamoyl, or substituted or unsubstituted amino;

(bb10) substituted or unsubstituted alkyl;

(bb11) substituted or unsubstituted alkyl, substituted or unsubstituted alkyloxy, substituted or unsubstituted cycloalkyl, a substituted or unsubstituted non-aromatic heterocyclic group, substituted or unsubstituted aryl, substituted or unsubstituted heteroaryl, substituted or unsubstituted amino, or substituted or unsubstituted carbamoyl; or (bb12) substituted or unsubstituted heteroaryl, substituted or unsubstituted carbamoylalkylcarbamoyl, or substituted or unsubstituted heteroarylcarbamoyl;

$R^{9a}$ and $R^{9b}$ are each independently a hydrogen atom or halogen;

$R^6$ is a group represented by the formula:

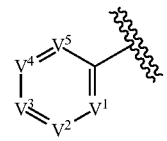

[Chemical Formula 82]

wherein =$V^1$—$V^2$=$V^3$—$V^4$=$V^5$— is (i): =C($R^{A'}$)—C($R^A$)=C($R^B$)—C($R^C$)=C($R^{C'}$)—, each symbol is as defined in the above (3);

(bc1) $R^6$ is a group represented by the formula:

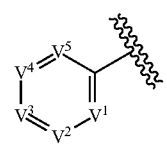

[Chemical Formula 83]

wherein =$V^1$—$V^2$=$V^3$—$V^4$=$V^5$— is (i): =C($R^{A'}$)—C($R^A$)=C($R^B$)—C($R^C$)=C($R^{C'}$)—, $R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl or alkylsilylalkynyl; or (bc2) $R^6$ is a group represented by the formula:

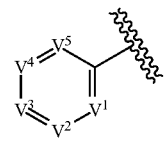

[Chemical Formula 84]

wherein =$V^1$—$V^2$=$V^3$—$V^4$=$V^5$— is (i): =C($R^{A'}$)—C($R^A$)=C($R^B$)—C($R^C$)=C($R^{C'}$)—, $R^A$, $R^{A'}$, $R^B$, $R^C$ and $R^{C'}$ are each independently a hydrogen atom or halogen;

$R^{16}$ is a hydrogen atom;

$R^7$ is a group represented by the formula:

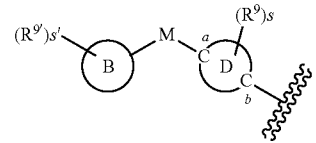

[Chemical Formula 85]

wherein ring D is benzene;

carbon atom a and carbon atom b are carbon atoms which constitute ring D;

-M- is —O—;
ring B is:
(bd1) an aromatic carbocyclic ring or an aromatic heterocyclic ring;
(bd2) benzene, thiazole, isothiazole, oxazole, isoxazole, furan, thiophen, thiadiazole, oxadiazole, pyridine, pyrimidine, pyrazine or pyridazine; or
(bd3) benzene, thiazole, thiadiazole, oxadiazole or pyridine;
(bd4) thiazole, isothiazole, oxazole, isoxazole, thiadiazole, oxadiazole, pyridine, pyrimidine, pyrazine or pyridazine;
s is 0 or 1;
$R^9$ are each independently:
(be1) halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;
(be2) halogen, or substituted or unsubstituted alkyl; or
(be3) halogen, hydroxy, cyano, substituted or unsubstituted alkyl, or substituted or unsubstituted alkyloxy;
s' is an integer of 0 to 2;
$R^{9'}$ are each independently:
(bf1) halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, or substituted sulfinyl;
(bf2) halogen, hydroxy, carboxy, cyano, substituted or unsubstituted alkyl, substituted or unsubstituted alkyloxy, substituted or unsubstituted alkyloxycarbonyl, substituted or unsubstituted carbamoyl, substituted or unsubstituted amino, substituted or unsubstituted sulfamoyl, substituted sulfonyl, or substituted sulfinyl; or
(bf3) halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl, or substituted or unsubstituted alkyloxycarbonyl,
or its pharmaceutically acceptable salt.

The compound represented by the formula (I-c) includes the compounds comprising the combination of some or all of options of the above. Specifically, the following combinations are included.
(ba1,bb1,bc1,bd1,be1,bf1),(ba1,bb1,bc1,bd1,be1,bf2),(ba1,bb1,bc1,bd1,be1,bf3),(ba1,bb1,bc1,bd1,be2,bf1),(ba1,bb1,bc1,bd1,be2,bf2),(ba1,bb1,bc1,bd1,be2,bf3),(ba1,bb1,bc1,bd1,be3,bf1),(ba1,bb1,bc1,bd1,be3,bf2),(ba1,bb1,bc1,bd1,be3,bf3),(ba1,bb1,bc1,bd2,be1,bf1),(ba1,bb1,bc1,bd2,be1,bf2),(ba1,bb1,bc1,bd2,be1,bf3),(ba1,bb1,bc1,bd2,be2,bf1),(ba1,bb1,bc1,bd2,be2,bf2),(ba1,bb1,bc1,bd2,be2,bf3),(ba1,bb1,bc1,bd2,be3,bf1),(ba1,bb1,bc1,bd2,be3,bf2),(ba1,bb1,bc1,bd2,be3,bf3),(ba1,bb1,bc1,bd3,be1,bf1),(ba1,bb1,bc1,bd3,be1,bf2),(ba1,bb1,bc1,bd3,be1,bf3),(ba1,bb1,bc1,bd3,be2,bf1),(ba1,bb1,bc1,bd3,be2,bf2),(ba1,bb1,bc1,bd3,be2,bf3),(ba1,bb1,bc1,bd3,be3,bf1),(ba1,bb1,bc1,bd3,be3,bf2),(ba1,bb1,bc1,bd3,be3,bf3),(ba1,bb1,bc1,bd4,be1,bf1),(ba1,bb1,bc1,bd4,be1,bf2),(ba1,bb1,bc1,bd4,be1,bf3),(ba1,bb1,bc1,bd4,be2,bf1),(ba1,bb1,bc1,bd4,be2,bf2),(ba1,bb1,bc1,bd4,be2,bf3),(ba1,bb1,bc1,bd4,be3,bf1),(ba1,bb1,bc1,bd4,be3,bf2),(ba1,bb1,bc1,bd4,be3,bf3),(ba1,bb1,bc2,bd1,be1,bf1),(ba1,bb1,bc2,bd1,be1,bf2),(ba1,bb1,bc2,bd1,be1,bf3),(ba1,bb1,bc2,bd1,be2,bf1),(ba1,bb1,bc2,bd1,be2,bf2),(ba1,bb1,bc2,bd1,be2,bf3),(ba1,bb1,bc2,bd1,be3,bf1),(ba1,bb1,bc2,bd1,be3,bf2),(ba1,bb1,bc2,bd1,be3,bf3),(ba1,bb1,bc2,bd2,be1,bf1),(ba1,bb1,bc2,bd2,be1,bf2),(ba1,bb1,bc2,bd2,be1,bf3),(ba1,bb1,bc2,bd2,be2,bf1),(ba1,bb1,bc2,bd2,be2,bf2),(ba1,bb1,bc2,bd2,be2,bf3),(ba1,bb1,bc2,bd2,be3,bf1),(ba1,bb1,bc2,bd2,be3,bf2),(ba1,bb1,bc2,bd2,be3,bf3),(ba1,bb1,bc2,bd3,be1,bf1),(ba1,bb1,bc2,bd3,be1,bf2),(ba1,bb1,bc2,bd3,be1,bf3),(ba1,bb1,bc2,bd3,be2,bf1),(ba1,bb1,bc2,bd3,be2,bf2),(ba1,bb1,bc2,bd3,be2,bf3),(ba1,bb1,bc2,bd3,be3,bf1),(ba1,bb1,bc2,bd3,be3,bf2),(ba1,bb1,bc2,bd3,be3,bf3),(ba1,bb1,bc2,bd4,be1,bf1),(ba1,bb1,bc2,bd4,be1,bf2),(ba1,bb1,bc2,bd4,be1,bf3),(ba1,bb1,bc2,bd4,be2,bf1),(ba1,bb1,bc2,bd4,be2,bf2),(ba1,bb1,bc2,bd4,be2,bf3),(ba1,bb1,bc2,bd4,be3,bf1),(ba1,bb1,bc2,bd4,be3,bf2),(ba1,bb1,bc2,bd4,be3,bf3),(ba1,bb2,bc1,bd1,be1,bf1),(ba1,bb2,bc1,bd1,be1,bf2),(ba1,bb2,bc1,bd1,be1,bf3),(ba1,bb2,bc1,bd1,be2,bf1),(ba1,bb2,bc1,bd1,be2,bf2),(ba1,bb2,bc1,bd1,be2,bf3),(ba1,bb2,bc1,bd1,be3,bf1),(ba1,bb2,bc1,bd1,be3,bf2),(ba1,bb2,bc1,bd1,be3,bf3),(ba1,bb2,bc1,bd2,be1,bf1),(ba1,bb2,bc1,bd2,be1,bf2),(ba1,bb2,bc1,bd2,be1,bf3),(ba1,bb2,bc1,bd2,be2,bf1),(ba1,bb2,bc1,bd2, be2,bf2),(ba1,bb2,bc1,bd2,be2,bf3),(ba1,bb2,bc1,bd2,be3,bf1),(ba1,bb2,bc1,bd2,be3,bf2),(ba1,bb2,bc1,bd2,be3,bf3),(ba1,bb2,bc1, bd3,be1,bf1),ba1,bb2,bc1,bd3,be1,bf2),(ba1,bb2,bc1,bd3,be1,bf3),(ba1, bb2,bc1,bd3,be2,bf1),(ba1,bb2,bc1,bd3,be2,bf2),(ba1,bb2,bc1,bd3,be2,bf3),(ba1,bb2,bc1,bd3,be3,bf1),(ba1,bb2,bc1,bd3,be3,bf2),(ba1,bb2,bc1,bd3,be3,bf3),(ba1,bb2,bc1,bd4,be1,bf1),(ba1,bb2,bc1,bd4,be1,bf2),(ba1,bb2,bc1,bd4,be1,bf3),(ba1,bb2,bc1,bd4,be2,bf1),(ba1,bb2,bc1,bd4,be2,bf2),(ba1,bb2,bc1,bd4,be2,bf3),(ba1,bb2,bc1,bd4,be3,bf1),(ba1,bb2,bc1,bd4,be3,bf2),(ba1,bb2,bc1,bd4,be3,bf3),(ba1,bb2,bc2,bd1,be1,bf1),(ba1,bb2,bc2,bd1,be1,bf2),(ba1,bb2,bc2,bd1,be1,bf3),(ba1,bb2,bc2,bd1,be2,bf2),(ba1,bb2,bc2,bd1,be2,bf2),(ba1,bb2,bc2,bd1,be2,bf3),(ba1,bb2,bc2,bd1,be3,bf1),(ba1,bb2,bc2,bd1,be3,bf2),(ba1,bb2,bc2,bd1,be3,bf3),(ba1,bb2,bc2,bd2,be1,bf1),(ba1,bb2,bc2,bd2,be1,bf2),(ba1,bb2,bc2,bd2,be1,bf3),(ba1,bb2,bc2,bd2,be2,bf1),(ba1,bb2,bc2,bd2,be2,bf2),(ba1,bb2,bc2,bd2,be2,bf3),(ba1,bb2,bc2,bd2,be3,bf1),(ba1,bb2,bc2,bd2,be3,bf2),(ba1,bb2,bc2,bd2,be3,bf3),(ba1,bb2,bc2,bd3,be1,bf1),(ba1,bb2,bc2,bd3,be1,bf2),(ba1,bb2,bc2,bd3,be1,bf3),(ba1,bb2,bc2,bd3,be2,bf1),(ba1,bb2,bc2, bd3,be2,bf2),(ba1,bb2,bc2,bd3,be2,bf3),(ba1,bb2,bc2,bd3,be3,bf1),(ba1,bb2,bc2,bd3,be3,bf2),(ba1,bb2,bc2,bd3,be3,bf3),(ba1,bb2,bc2,bd3,be3,bf3),(ba1,bb2,bc2,bd4,be1,bf1),(ba1,bb2,bc2,bd4,be1,bf2),(ba1,bb2,bc2,bd4,be1,bf3),(ba1,bb2,bc2,bd4,be2,bf1),(ba1,bb2,bc2,bd4,be2,bf2),(ba1,bb2,bc2,bd4,be2,bf3),(ba1,bb2,bc2,bd4,be3,bf1),(ba1,bb2,bc2,bd4,be3,bf2),(ba1,bb2,bc2,bd4,be3,bf3),(ba1,bb3,bc1,bd1,be1,bf1),(ba1,bb3,bc1,bd1,be1,bf2),(ba1,bb3,bc1,bd1,be1,bf3),(ba1,bb3,bc1,bd1,be2,bf1),(ba1,bb3,bc1,bd1,be2,bf2),(ba1,bb3,bc1,bd1,be2,bf3),(ba1,bb3,bc1,bd1,be3,bf1),(ba1,bb3,bc1,bd1,be3,bf2),(ba1,bb3,bc1,bd1,be3,bf3),(ba1,bb3,bc1,bd2,be1,bf1),(ba1,bb3,bc1,bd2,be1,bf2),(ba1,bb3,bc1,bd2,be2,bf1),(ba1,bb3,bc1,bd2,be2,bf1),(ba1,bb3,bc1,bd2,be2,bf2),(ba1,bb3,bc1,bd2,be2,bf3),(ba1,bb3,bc1,bd2,be3,bf1),(ba1,bb3,bc1,bd2,be3,bf2),(ba1,bb3,bc1,bd2,be3,bf3),(ba1,bb3,bc1,bd3,be1,bf1),(ba1,bb3,bc1,bd3,be1,bf2),(ba1,bb3,bc1,bd3,be1,bf3),(ba1,bb3,bc1,bd3,be2,bf1),(ba1,bb3,bc1,bd3,be2,bf2),(ba1,bb3,bc1,bd3,be2,bf3),(ba1,bb3,bc1,bd3,be3,bf1),(ba1,bb3,bc1,bd3,be3,bf2),(ba1,bb3,bc1,bd3,be3,bf3),(ba1,bb3,bc1,bd4,be1,bf1),(ba1,bb3,bc1,bd4,be1,bf2),(ba1,bb3,bc1,bd4,be1,bf3),(ba1,bb3,bc1,bd4,be2,bf1),(ba1,bb3,bc1,bd4,be2,bf2),(ba1,bb3,bc1,bd4,be2,bf3),(ba1,bb3,bc1,bd4,be3,bf1),(ba1,bb3,bc1,bd4,be3,bf2),(ba1,bb3,bc1,bd4,be3,bf3),(ba1,bb3,bc2,bd1,be1,bf1),(ba1,bb3,bc2,bd1,be1,bf2),(ba1,bb3,bc2,bd1,be1,bf3),(ba1,bb3,bc2,bd1,be2,bf1),(ba1,bb3,bc2,bd1,be2,bf2),(ba1,bb3,bc2,bd1,be2,bf3),(ba1,bb3, bc2,bd1,be3,bf1),(ba1,bb3,bc2,bd1,be3,bf2),(ba1,bb3,bc2,
bd1,be3,bf3),(ba1,bb3,bc2,bd2,be1,bf1),(ba1,bb3,bc2,bd2,
be1,bf2),(ba1,bb3,bc2,bd2,be1,bf3),(ba1,bb3,bc2,bd2,be2,
bf1),(ba1,bb3,bc2,bd2,be2,bf2),(ba1,bb3,bc2,bd2,be2,bf3),
(ba1,bb3,bc2,bd2,be3,bf1),(ba1,bb3,bc2,bd2,be3,bf2),(ba1,
bb3,bc2,bd2,be3,bf3),(ba1,bb3,bc2,bd3,be1,bf1),(ba1,bb3,
bc2,bd3,be1,bf2),(ba1,bb3,bc2,bd3,be1,bf3),(ba1,bb3,bc2,
bd3,be2,bf1),(ba1,bb3,bc2,bd3,be2,bf2),(ba1,bb3,bc2,bd3,
be2,bf3),(ba1,bb3,bc2,bd3,be3,bf1),(ba1,bb3,bc2,bd3,be3,
bf2),(ba1,bb3,bc2,bd3,be3,bf3) (ba1,bb3,bc2,bd3,be3,bf3),
(ba1,bb3,bc2,bd4,be1,bf2),(ba1,bb3,bc2,bd4,be1,bf3),(ba1,
bb3,bc2,bd4,be2,bf1),(ba1,bb3,bc2,bd4,be2,bf2),(ba1,bb3,
bc2,bd4,be2,bf3),(ba1,bb3,bc2,bd4,be3,bf1),(ba1,bb3,bc2,
bd4,be3,bf2),(ba1,bb3,bc2,bd4,be3,bf3),(ba1,bb4,bc1,bd1,
be1,bf1),(ba1,bb4,bc1,bd1,be1,bf2),(ba1,bb4,bc1,bd1,be1,
bf3),(ba1,bb4,bc1,bd1,be2,bf1),(ba1,bb4,bc1,bd1,be2,bf2),
(ba1,bb4,bc1,bd1,be2,bf3),(ba1,bb4,bc1,bd1,be3,bf1),(ba1,
bb4,bc1,bd1,be3,bf2),(ba1,bb4,bc1,bd1,be3,bf3),(ba1,bb4,
bc1,bd2,be1,bf1),(ba1,bb4,bc1,bd2,be1,bf2),(ba1,bb4,bc1,
bd2,be1,bf3),(ba1,bb4,bc1,bd2,be2,bf1),(ba1,bb4,bc1,bd2,
be2,bf2),(ba1,bb4,bc1,bd2,be2,bf3),(ba1,bb4,bc1,bd2,be3,
bf1),(ba1,bb4,bc1,bd2,be3,bf2),(ba1,bb4,bc1,bd2,be3,bf3),
(ba1,bb4,bc1,bd3,be1,bf1),(ba1,bb4,bc1,bd3,be1,bf2),(ba1,
bb4,bc1,bd3,be1,bf3),(ba1,bb4,bc1,bd3,be2,bf1),(ba1,bb4,
bc1,bd3,be2,bf2),(ba1,bb4,bc1,bd3,be2,bf3),(ba1,bb4,bc1,
bd3,be3,bf1),(ba1,bb4,bc1,bd3,be3,bf2),(ba1,bb4,bc1,bd3,
be3,bf3),(ba1,bb4,bc1,bd4,be1,bf1),(ba1,bb4,bc1,bd4,be1,
bf2),(ba1,bb4,bc1,bd4,be1,bf3),(ba1,bb4,bc1,bd4,be2,bf1),
(ba1,bb4,bc1,bd4,be2,bf2),(ba1,bb4,bc1,bd4,be2,bf3),(ba1,
bb4,bc1,bd4,be3,bf1),(ba1,bb4,bc1,bd4,be3,bf2),(ba1,bb4,
bc1,bd4,be3,bf3),(ba1,bb4,bc2,bd1,be1,bf1),(ba1,bb4,bc2,
bd1,be1,bf2),(ba1,bb4,bc2,bd1,be1,bf3),(ba1,bb4,bc2,bd1,
be2,bf1),(ba1,bb4,bc2,bd1,be2,bf2),(ba1,bb4,bc2,bd1,be2,
bf3),(ba1,bb4,bc2,bd1,be3,bf1),(ba1,bb4,bc2,bd1,be3,bf2),
(ba1,bb4,bc2,bd1,be3,bf3),(ba1,bb4,bc2,bd2,be1,bf1),(ba1,
bb4,bc2,bd2,be1,bf2),(ba1,bb4,bc2,bd2,be1,bf3),(ba1,bb4,
bc2,bd2,be2,bf1),(ba1,bb4,bc2,bd2,be2,bf2),(ba1,bb4,bc2,
bd2,be2,bf3),(ba1,bb4,bc2,bd2,be3,bf1),(ba1,bb4,bc2,bd2,
be3,bf2),(ba1,bb4,bc2,bd2,be3,bf3),(ba1,bb4,bc2,bd3,be1,
bf1),(ba1,bb4,bc2,bd3,be1,bf2),(ba1,bb4,bc2,bd3,be1,bf3),
(ba1,bb4,bc2,bd3,be2,bf1),(ba1,bb4,bc2,bd3,be2,bf2),(ba1,
bb4,bc2,bd3,be2,bf3),(ba1,bb4,bc2,bd3,be3,bf1),(ba1,bb4,
bc2,bd3,be3,bf2),(ba1,bb4,bc2,bd3,be3,bf3),(ba1,bb4,bc2,
bd4,be1,bf1),(ba1,bb4,bc2,bd4,be1,bf2),(ba1,bb4,bc2,bd4,
be1,bf3),(ba1,bb4,bc2,bd4,be2,bf1),(ba1,bb4,bc2,bd4, be2,
bf2),(ba1,bb4,bc2,bd4,be2,bf3),(ba1,bb4,bc2,bd4,be3,bf1),
(ba1,bb4,bc2,bd4,be3,bf2),(ba1,bb4,bc2,bd4,be3,bf3),(ba1,
bb5,bc1,bd1,be1,bf1),(ba1,bb5,bc1,bd1,be1,bf2),(ba1,bb5,
bc1,bd1,be1,bf3),(ba1,bb5,bc1,bd1,be2,bf1),(ba1,bb5,bc1,
bd1,be2,bf2),(ba1,bb5,bc1,bd1,be2,bf3),(ba1,bb5,bc1,bd1,
be3,bf1),(ba1,bb5,bc1,bd1,be3,bf2),(ba1,bb5,bc1,bd1,be3,
bf3),(ba1,bb5,bc1,bd2,be1,bf1),(ba1,bb5,bc1,bd2,be1,bf2),
(ba1,bb5,bc1,bd2,be1,bf3),(ba1,bb5,bc1,bd2,be2,bf1),(ba1,
bb5,bc1,bd2,be2,bf2),(ba1,bb5,bc1,bd2,be2,bf3),(ba1,bb5,
bc1,bd2,be3,bf1),(ba1,bb5,bc1,bd2,be3,bf2),(ba1,bb5,bc1,
bd2,be3,bf3),(ba1,bb5,bc1,bd3,be1,bf1),(ba1,bb5,bc1,bd3,
be1,bf2),(ba1,bb5,bc1,bd3,be1,bf3),(ba1,bb5,bc1,bd3,be2,
bf1),(ba1,bb5,bc1,bd3,be2,bf2),(ba1,bb5,bc1,bd3,be2,bf3),
(ba1,bb5,bc1,bd3,be3,bf1),(ba1,bb5,bc1,bd3,be3,bf2),(ba1,
bb5,bc1,bd3,be3,bf3),(ba1,bb5,bc1,bd4,be1,bf1),(ba1,bb5,
bc1,bd4,be1,bf2),(ba1,bb5,bc1,bd4,be1,bf3),(ba1,bb5,bc1,
bd4,be2,bf1),(ba1,bb5,bc1,bd4,be2,bf2),(ba1,bb5,bc1,bd4,
be2,bf3),(ba1,bb5,bc1,bd4,be3,bf1),(ba1,bb5,bc1,bd4,be3,
bf2),(ba1,bb5,bc1,bd4,be3,bf3),(ba1,bb5,bc2,bd1,be1,bf1),
(ba1,bb5,bc2,bd1,be1,bf2),(ba1,bb5,bc2,bd1,be1,bf3),(ba1,
bb5,bc2, bd1,be2,bf1),(ba1,bb5,bc2,bd1,be2,bf2),(ba1,bb5,
bc2,bd1,be2,bf3),(ba1,bb5,bc2,bd1,be3,bf1),(ba1,bb5,bc2,
bd1,be3,bf2),(ba1,bb5,bc2,bd1,be3,bf3),(ba1,bb5,bc2,bd2,
be1,bf1),(ba1,bb5,bc2,bd2,be1,bf2),(ba1,bb5,bc2,bd2,be1,
bf3),(ba1,bb5,bc2,bd2,be2,bf1),(ba1,bb5,bc2,bd2,be2,bf2),
(ba1,bb5,bc2,bd2,be2,bf3),(ba1,bb5,bc2,bd2,be3,bf1),(ba1,
bb5,bc2,bd2,be3,bf2),(ba1,bb5,bc2,bd2,be3,bf3),(ba1,bb5,
bc2,bd3,be1,bf1),(ba1,bb5,bc2,bd3,be1,bf2),(ba1,bb5,bc2,
bd3,be1,bf3),(ba1,bb1,bc2,bd3,be2,bf1),(ba1,bb5,bc2,bd3,
be2,bf2),(ba1,bb5,bc2,bd3,be2,bf3),(ba1,bb5,bc2,bd3,be3,
bf1),(ba1,bb5,bc2,bd3,be3,bf2),(ba1,bb5,bc2,bd3,be3,bf3),
(ba1,bb5,bc2,bd4,be1,bf1),(ba1,bb5,bc2,bd4,be1,bf2),(ba1,
bb5,bc2,bd4,be1,bf3),(ba1,bb5,bc2,bd4,be2,bf1),(ba1,bb5,
bc2,bd4,be2,bf2),(ba1,bb5,bc2,bd4,be2,bf3),(ba1,bb5,bc2,
bd4,be3,bf1),(ba1,bb5,bc2,bd4,be3,bf2),(ba1,bb5,bc2,bd4,
be3,bf3),(ba1,bb6,bc1,bd1,be1,bf1),(ba1,bb6,bc1,bd1,be1,
bf2),(ba1,bb6,bc1,bd1,be1,bf3),(ba1,bb6,bc1,bd1,be2,bf1),
(ba1,bb6,bc1,bd1,be2,bf2),(ba1,bb6,bc1,bd1,be2,bf3),(ba1,
bb6,bc1,bd1,be3,bf1),(ba1,bb6,bc1,bd1,be3,bf2),(ba1,bb6,
bc1,bd1,be3,bf3),(ba1,bb6,bc1,bd2,be1,bf1),(ba1,bb6,bc1,
bd2,be1,bf2),(ba1,bb6,bc1,bd2,be1,bf3),(ba1,bb6,bc1,bd2,
be2,bf1),(ba1,bb6,bc1,bd2,be2,bf2),(ba1,bb6,bc1,bd2,be2,
bf3),(ba1,bb6,bc1,bd2,be3,bf1),(ba1,bb6,bc1,bd2,be3,bf2),
(ba1,bb6,bc1,bd2,be3,bf3),(ba1,bb6,bc1,bd3,be1,bf1),(ba1,
bb6,bc1,bd3,be1,bf2),(ba1,bb6,bc1,bd3,be1,bf3),(ba1,bb6,
bc1,bd3,be2,bf1),(ba1,bb6,bc1,bd3,be2,bf2),(ba1,bb6,bc1,
bd3,be2,bf3),(ba1,bb6,bc1,bd3,be3,bf1),(ba1,bb6,bc1,bd3,
be3,bf2),(ba1,bb6,bc1,bd3,be3,bf3),(ba1,bb6,bc1,bd4,be1,
bf1),(ba1,bb6,bc1,bd4,be1,bf2),(ba1,bb6,bc1,bd4,be1,bf3),
(ba1,bb6,bc1,bd4,be2,bf1),(ba1,bb6,bc1,bd4,be2,bf2),(ba1,
bb6,bc1,bd4,be2,bf3),(ba1,bb6,bc1,bd4,be3,bf1),(ba1,bb6,
bc1,bd4,be3,bf2),(ba1,bb6,bc1,bd4,be3,bf3),(ba1,bb6,bc2,
bd1,be1,bf1),(ba1,bb6,bc2,bd1,be1,bf2),(ba1,bb6,bc2,bd1,
be1,bf3),(ba1,bb6,bc2,bd1,be2,bf1),(ba1,bb6,bc2,bd1,be2,
bf2),(ba1,bb6,bc2,bd1,be2,bf3),(ba1,bb6,bc2,bd1,be3,bf1),
(ba1,bb6,bc2,bd1,be3,bf2),(ba1,bb6,bc2,bd1,be3,bf3),(ba1,
bb6,bc2,bd2,be1,bf1),(ba1,bb6,bc2,bd2,be1,bf2),(ba1,bb6,
bc2,bd2,be1,bf3),(ba1,bb6,bc2,bd2,be2,bf2),(ba1,bb6,bc2,
bd2,be2,bf2),(ba1,bb6,bc2,bd2,be2,bf3),(ba1,bb6,bc2,bd2,
be3,bf1),(ba1,bb6,bc2,bd2,be3,bf2),(ba1,bb6,bc2,bd2,be3,
bf3),(ba1,bb6,bc2,bd3,be1,bf1),(ba1,bb6,bc2,bd3,be1,bf2),
(ba1,bb6,bc2,bd3,be1,bf3),(ba1,bb6,bc2,bd3,be2,bf1),(ba1,
bb6,bc2,bd3,be2,bf2),(ba1,bb6,bc2,bd3,be2,bf3),(ba1,bb6,
bc2,bd3,be3,bf1),(ba1,bb6,bc2,bd3,be3,bf2),(ba1,bb6,bc2,
bd3,be3,bf3),(ba1,bb6,bc2,bd4,be1,bf1),(ba1,bb6,bc2,bd4,
be1,bf2),(ba1,bb6,bc2,bd4,be1,bf3),(ba1,bb6,bc2,bd4,be2,
bf1),(ba1,bb6,bc2,bd4,be2,bf2),(ba1,bb6,bc2,bd4,be2,bf3),
(ba1,bb6,bc2,bd4,be3,bf1),(ba1,bb6,bc2,bd4,be3,bf2),(ba1,
bb6,bc2,bd4,be3,bf3),(ba1,bb7,bc1,bd1,be1,bf1),(ba1,bb7,
bc1,bd1,be1,bf2),(ba1,bb7,bc1,bd1,be1,bf3),(ba1,bb7,bc1,
bd1,be2,bf1),(ba1,bb7,bc1,bd1,be2,bf2),(ba1,bb7,bc1,bd1,
be2,bf3),(ba1,bb7,bc1,bd1,be3,bf1),(ba1,bb7,bc1,bd1,be3,
bf2),(ba1,bb7,bc1,bd1,be3,bf3),(ba1,bb7,bc1,bd2,be1,bf1),
(ba1,bb7,bc1,bd2,be1,bf2),(ba1,bb7,bc1,bd2,be1,bf3),(ba1,
bb7,bc1,bd2,be2,bf1),(ba1,bb7,bc1,bd2,be2,bf2),(ba1,bb7,
bc1,bd2,be2,bf3),(ba1,bb7,bc1,bd2,be3,bf1),(ba1,bb7,bc1,
bd2,be3,bf2),(ba1,bb7,bc1,bd2,be3,bf3),(ba1,bb7,bc1,bd3,
be1,bf1),(ba1,bb7,bc1,bd3,be1,bf2),(ba1,bb7,bc1,bd3,be1,
bf3),(ba1,bb7,bc1,bd3,be2,bf1),(ba1,bb7,bc1,bd3,be2,bf2),
(ba1,bb7,bc1,bd3,be2,bf3),(ba1,bb7,bc1,bd3,be3,bf1),(ba1,
bb7,bc1,bd3,be3,bf2),(ba1,bb7,bc1,bd3,be3,bf3),(ba1,bb7,
bc1,bd4,be1,bf1),(ba1,bb7,bc1,bd4,be1,bf2),(ba1,bb7,bc1,
bd4,be1,bf3),(ba1,bb7,bc1,bd4,be2,bf1),(ba1,bb7,bc1,bd4,
be2,bf2),(ba1,bb7,bc1,bd4,be2,bf3),(ba1,bb7,bc1,bd4,be3,
bf1),(ba1,bb7,bc1,bd4,be3,bf2),(ba1,bb7,bc1,bd4,be3,bf3),
(ba1,bb7,bc2,bd1,be1,bf1),(ba1,bb7,bc2,bd1,be1,bf2),(ba1,
bb7,bc2,bd1,be1,bf3),(ba1,bb7,bc2,bd1,be2,bf1),(ba1,bb7,
bc2,bd1,be2,bf2),(ba1,bb7,bc2,bd1,be2,bf3),(ba1,bb7,bc2,
bd1,be3,bf1),(ba1,bb7,bc2,bd1,be3,bf2),(ba1,bb7,bc2,bd1, be3,bf3),(ba1,bb7,bc2,bd2,be1,bf1),(ba1,bb7,bc2,bd2,be1,bf2),(ba1,bb7,bc2,bd2,be1,bf3),(ba1,bb7,bc2,bd2,be2,bf1),(ba1,bb7,bc2,bd2,be2,bf2),(ba1,bb7,bc2,bd2,be2,bf3),(ba1,bb7,bc2,bd2,be3,bf1),(ba1,bb7,bc2,bd2,be3,bf2),(ba1,bb7,bc2,bd2,be3,bf3),(ba1,bb7,bc2,bd3,be1,bf1),(ba1,bb7,bc2,bd3,be1,bf2),(ba1,bb7,bc2,bd3,be1,bf3),(ba1,bb7,bc2,bd3,be2,bf1),(ba1,bb7,bc2,bd3,be2,bf2),(ba1,bb7,bc2,bd3,be2,bf3),(ba1,bb7,bc2,bd3,be3,bf1),(ba1,bb7,bc2,bd3,be3,bf2),(ba1,bb7,bc2,bd3,be3,bf3),(ba1,bb7,bc2,bd4,be1,bf1),(ba1,bb7,bc2,bd4,be1,bf2),(ba1,bb7,bc2,bd4,be1,bf3),(ba1,bb7,bc2,bd4,be2,bf1),(ba1,bb7,bc2,bd4,be2,bf2),(ba1,bb7,bc2,bd4,be2,bf3),(ba1,bb7,bc2,bd4,be3,bf1),(ba1,bb7,bc2,bd4,be3,bf2),(ba1,bb7,bc2,bd4,be3,bf3),(ba1,bb8,bc1,bd1,be1,bf1),(ba1,bb8,bc1,bd1,be1,bf2),(ba1,bb8,bc1,bd1,be1,bf3),(ba1,bb8,bc1,bd1,be2,bf1),(ba1,bb8,bc1,bd1,be2,bf2),(ba1,bb8,bc1,bd1,be2,bf3),(ba1,bb8,bc1,bd1,be3,bf1),(ba1,bb8,bc1,bd1,be3,bf2),(ba1,bb8,bc1,bd1,be3,bf3),(ba1,bb8,bc1,bd2, be1,bf1),(ba1,bb8,bc1,bd2,be1,bf2),(ba1,bb8,bc1,bd2,be1,bf3),(ba1,bb8,bc1,bd2,be2,bf1),(ba1,bb8,bc1,bd2,be2,bf2),(ba1,bb8,bc1,bd2,be2,bf3),(ba1,bb8,bc1,bd2,be3,bf1),(ba1,bb8,bc1,bd2,be3,bf2),(ba1,bb8,bc1,bd2,be3,bf3),(ba1,bb8,bc1,bd3,be1,bf1),(ba1,bb8,bc1,bd3,be1,bf2),(ba1,bb8,bc1,bd3,be1,bf3),(ba1,bb8,bc1,bd3,be2,bf1),(ba1,bb8,bc1,bd3,be2,bf2),(ba1,bb8,bc1,bd3,be2,bf3),(ba1,bb8,bc1,bd3,be3,bf1),(ba1,bb8,bc1,bd3,be3,bf2),(ba1,bb8,bc1,bd3,be3,bf3),(ba1,bb8,bc1,bd4,be1,bf1),(ba1,bb8,bc1,bd4,be1,bf2),(ba1,bb8,bc1,bd4,be1,bf3),(ba1,bb8,bc1,bd4,be2,bf1),(ba1,bb8,bc1,bd4,be2,bf2),(ba1,bb8,bc1,bd4,be2,bf3),(ba1,bb8,bc1,bd4,be3,bf1),(ba1,bb8,bc1,bd4,be3,bf2),(ba1,bb8,bc1,bd4,be3,bf3),(ba1,bb8,bc2,bd1,be1,bf1),(ba1,bb8,bc2,bd1,be1,bf2),(ba1,bb8,bc2,bd1,be1,bf3),(ba1,bb8,bc2,bd1,be2,bf1),(ba1,bb8,bc2,bd1,be2,bf2),(ba1,bb8,bc2,bd1,be2,bf3),(ba1,bb8,bc2,bd1,be3,bf1),(ba1,bb8,bc2,bd1,be3,bf2),(ba1,bb8,bc2,bd1,be3,bf3),(ba1,bb8,bc2,bd2,be1,bf1),(ba1,bb8,bc2,bd2,be1,bf2),(ba1,bb8,bc2,bd2,be1,bf3),(ba1,bb8,bc2,bd2,be2,bf1),(ba1,bb8,bc2,bd2,be2,bf2),(ba1,bb8,bc2,bd2,be2,bf3),(ba1,bb8,bc2,bd2,be3,bf1),(ba1,bb8,bc2,bd2,be3,bf2),(ba1,bb8,bc2,bd2,be3,bf3),(ba1,bb8,bc2,bd3,be1,bf1),(ba1,bb8,bc2,bd3,be1,bf2),(ba1,bb8,bc2,bd3,be1,bf3),(ba1,bb8,bc2,bd3,be2,bf1),(ba1,bb8,bc2,bd3,be2,bf2),(ba1,bb8,bc2,bd3,be2,bf3),(ba1,bb8,bc2,bd3,be3,bf1),(ba1,bb8,bc2,bd3,be3,bf2),(ba1,bb8,bc2,bd3,be3,bf3),(ba1,bb8,bc2,bd4,be1,bf1),(ba1,bb8,bc2,bd4,be1,bf2),(ba1,bb8,bc2,bd4,be1,bf3),(ba1,bb8,bc2,bd4,be2,bf1),(ba1,bb8,bc2,bd4,be2,bf2),(ba1,bb8,bc2,bd4,be2,bf3),(ba1,bb8,bc2,bd4,be3,bf1),(ba1,bb8,bc2,bd4,be3,bf2),(ba1,bb8,bc2,bd4,be3,bf3),(ba1,bb9,bc1,bd1,be1,bf1),(ba1,bb9,bc1,bd1,be1,bf2),(ba1,bb9,bc1,bd1,be1,bf3),(ba1,bb9,bc1,bd1,be2,bf1),(ba1,bb9,bc1,bd1,be2,bf2),(ba1,bb9,bc1,bd1,be2,bf3),(ba1,bb9,bc1,bd1,be3,bf1),(ba1,bb9,bc1,bd1,be3,bf2),(ba1,bb9,bc1,bd1,be3,bf3),(ba1,bb9,bc1,bd2,be1,bf1),(ba1,bb9,bc1,bd2,be1,bf2),(ba1,bb9,bc1,bd2,be1,bf3),(ba1,bb9,bc1,bd2,be2,bf1),(ba1,bb9,bc1,bd2,be2,bf2),(ba1,bb9,bc1,bd2,be2,bf3),(ba1,bb9,bc1,bd2,be3,bf1),(ba1,bb9,bc1,bd2,be3,bf2),(ba1,bb9,bc1,bd2,be3,bf3),(ba1,bb9,bc1,bd3,be1,bf1),(ba1,bb9,bc1,bd3,be1,bf2),(ba1,bb9,bc1,bd3,be1,bf3),(ba1,bb9,bc1,bd3,be2,bf1),(ba1,bb9,bc1,bd3,be2,bf2),(ba1,bb9,bc1,bd3,be2,bf3),(ba1,bb9,bc1,bd3,be3,bf1),(ba1,bb9,bc1,bd3,be3,bf2),(ba1,bb9,bc1,bd3,be3,bf3),(ba1,bb9,bc1,bd4,be1,bf1),(ba1,bb9,bc1,bd4,be1,bf2),(ba1,bb9,bc1,bd4,be1,bf3),(ba1,bb9,bc1,bd4,be2,bf1),(ba1, bb9,bc1,bd4,be2,bf2),(ba1,bb9,bc1,bd4,be2,bf3),(ba1,bb9,bc1,bd4,be3,bf1),(ba1,bb9,bc1,bd4,be3,bf2),(ba1,bb9,bc1,bd4,be3,bf3),(ba1,bb9,bc2,bd1,be1,bf1),(ba1,bb9,bc2,bd1,be1,bf2),(ba1,bb9,bc2,bd1,be1,bf3),(ba1,bb9,bc2,bd1,be2,bf1),(ba1,bb9,bc2,bd1,be2,bf2),(ba1,bb9,bc2,bd1,be2,bf3),(ba1,bb9,bc2,bd1,be3,bf1),(ba1,bb9,bc2,bd1,be3,bf2),(ba1,bb9,bc2,bd1,be3,bf3),(ba1,bb9,bc2,bd2,be1,bf1),(ba1,bb9,bc2,bd2,be1,bf2),(ba1,bb9,bc2,bd2,be1,bf3),(ba1,bb9,bc2,bd2,be2,bf1),(ba1,bb9,bc2,bd2,be2,bf2),(ba1,bb9,bc2,bd2,be2,bf3),(ba1,bb9,bc2,bd2,be3,bf1),(ba1,bb9,bc2,bd2,be3,bf2),(ba1,bb9,bc2,bd2,be3,bf3),(ba1,bb9,bc2,bd3,be1,bf1),(ba1,bb9,bc2,bd3,be1,bf2),(ba1,bb9,bc2,bd3,be1,bf3),(ba1,bb9,bc2,bd3,be2,bf1),(ba1,bb9,bc2,bd3,be2,bf2),(ba1,bb9,bc2,bd3,be2,bf3),(ba1,bb9,bc2,bd3,be3,bf1),(ba1,bb9,bc2,bd3,be3,bf2),(ba1,bb9,bc2,bd3,be3,bf3),(ba1,bb9,bc2,bd4,be1,bf1),(ba1,bb9,bc2,bd4,be1,bf2),(ba1,bb9,bc2,bd4,be1,bf3),(ba1,bb9,bc2,bd4,be2,bf1),(ba1,bb9,bc2,bd4,be2,bf2),(ba1,bb9,bc2,bd4,be2,bf3),(ba1,bb9,bc2,bd4,be3,bf1),(ba1,bb9,bc2,bd4,be3,bf2),(ba1,bb9,bc2,bd4,be3,bf3),(ba1,bb10,bc1,bd1,be1,bf1),(ba1,bb10,bc1,bd1,be1,bf2),(ba1,bb10,bc1,bd1,be1,bf3),(ba1,bb10,bc1,bd1,be2,bf1),(ba1,bb10,bc1,bd1,be2,bf2),(ba1,bb10,bc1,bd1,be2,bf3),(ba1,bb10,bc1,bd1,be3,bf1),(ba1,bb10,bc1,bd1,be3,bf2),(ba1,bb10,bc1,bd1,be3,bf3),(ba1,bb10,bc1,bd2,be1,bf1),(ba1,bb10,bc1,bd2,be1,bf2),(ba1,bb10,bc1,bd2,be1,bf3),(ba1,bb10,bc1,bd2,be2,bf1),(ba1,bb10,bc1,bd2,be2,bf2),(ba1,bb10,bc1,bd2,be2,bf3),(ba1,bb10,bc1,bd2,be3,bf1),(ba1,bb10,bc1,bd2,be3,bf2),(ba1,bb10,bc1,bd2,be3,bf3),(ba1,bb10,bc1,bd3,be1,bf1),(ba1,bb10,bc1,bd3,be1,bf2),(ba1,bb10,bc1,bd3,be1,bf3),(ba1,bb10,bc1,bd3,be2,bf1),(ba1,bb10,bc1,bd3,be2,bf2),(ba1,bb10,bc1,bd3,be2,bf3),(ba1,bb10,bc1,bd3,be3,bf1),(ba1,bb10,bc1,bd3,be3,bf2),(ba1,bb10,bc1,bd3,be3,bf3),(ba1,bb10,bc1,bd4,be1 bf1),(ba1,bb10,bc1,bd4,be1,bf2),(ba1,bb10,bc1,bd4,be1,bf3),(ba1,bb10,bc1,bd4,be2,bf1),(ba1,bb10,bc1,bd4,be2,bf2),(ba1,bb10,bc1,bd4,be2,bf3),(ba1,bb10,bc1,bd4,be3,bf1),(ba1,bb10,bc1,bd4,be3,bf2),(ba1,bb10,bc1,bd4,be3,bf3),(ba1,bb10,bc2,bd1,be1,bf1),(ba1,bb10,bc2,bd1,be1,bf2),(ba1,bb10,bc2,bd1,be1,bf3),(ba1,bb10,bc2,bd1,be2,bf1),(ba1,bb10,bc2,bd1,be2,bf2),(ba1,bb10,bc2,bd1,be2,bf3),(ba1,bb10,bc2,bd1,be3,bf1),(ba1,bb10,bc2,bd1,be3,bf2),(ba1,bb10,bc2,bd1,be3,bf3),(ba1,bb10,bc2,bd2,be1,bf1),(ba1,bb10,bc2,bd2,be1,bf2),(ba1,bb10,bc2,bd2,be1,bf3),(ba1,bb10,bc2,bd2,be2,bf1),(ba1,bb10,bc2,bd2,be2,bf2),(ba1,bb10,bc2,bd2,be2,bf3),(ba1,bb10,bc2,bd2,be3,bf1),(ba1,bb10,bc2,bd2,be3,bf2),(ba1,bb10,bc2,bd2,be3,bf3),(ba1,bb10,bc2,bd3,be1,bf1),(ba1,bb10,bc2,bd3,be1,bf2),(ba1,bb10,bc2,bd3,be1,bf3),(ba1,bb10,bc2,bd3,be2,bf1),(ba1,bb10,bc2,bd3,be2,bf2),(ba1,bb10,bc2,bd3,be2,bf3),(ba1,bb10,bc2,bd3,be3,bf1),(ba1,bb10,bc2,bd3,be3,bf2),(ba1,bb10,bc2,bd3,be3,bf3),(ba1,bb10,bc2,bd4,be1,bf1),(ba1,bb10,bc2,bd4,be1,bf2),(ba1,bb10,bc2,bd4,be1,bf3),(ba1,bb10,bc2,bd4,be2,bf1),(ba1,bb2,bc2,bd4,be2,bf2),(ba1,bb10,bc2,bd4,be3,bf1),(ba1,bb10,bc2,bd4,be3,bf2),(ba1,bb10,bc2,bd4,be3,bf3),(ba1,bb11,bc1,bd1,be1,bf1),(ba1,bb10,bc1,bd1,be1,bf2),(ba1,bb11,bc1,bd1,be1,bf3),(ba1,bb11,bc1,bd1,be2,bf1),(ba1,bb11,bc1,bd1,be2,bf2),(ba1,bb11,bc1,bd1,be2,bf3),(ba1,bb11,bc1,bd1,be3,bf1),(ba1,bb1,bc1,bd1,be3,bf2),(ba1,bb11,bc1,bd1,be3,bf3),(ba1,bb1,bc1,bd2,be1,bf1),(ba1,bb11,bc1,bd2,be1,bf2),(ba1,bb11,bc1,bd2,be1,bf3),(ba1,bb11,bc1,bd2,be2,bf1),(ba11,bb11,bc1,bd2,be2,bf2),(ba1,bb11,bc1,bd2,be2,bf3),(ba1,bb11,bc1,bd2,be3,bf1),(ba1,bb11,bc1,bd2,be3,bf2),(ba1,bb11,bc1,bd2,be3,bf3),(ba1,bb1,bc1,bd3,be1,bf1),(ba1,bb11,bc1,bd3,be1,bf2),(ba1,bb11,bc1,bd3,be1,bf3),(ba1,bb11,bc1,bd3,be2,bf1),(ba1,bb11,bc1,bd3,be2,bf2),(ba1,bb1,bc1,bd3,be2,bf3),(ba1,bb11,bc1,bd3,be3,bf1),(ba1,bb11,bc1,bd3,be3,bf2),(ba1,bb1,bc1,bd3,be3,bf3),(ba1,bb11,bc1,bd4,be1,bf1),(ba1,bb11,bc1,bd4,be1,bf2),(ba1,bb11,bc1,bd4,be1,bf3),(ba1,bb11,bc1,bd4,be2,bf1),(ba1,bb11,bc1,bd4,be2,bf2),(ba1,bb11,bc1,bd4,be2,bf3),(ba1,bb11,bc1,bd4,be3,bf1),(ba1,bb11,bc1,bd4,be3,bf2),(ba1,bb11,bc1,bd4,be3,bf3),(ba1,bb11,bc2,bd1,be1,bf1),(ba1,bb11,bc2,bd1,be1, bf2),(ba1,bb11,bc2,bd1,be1,bf3),(ba1,bb1,bc2,bd1,be2, bf1),(ba1,bb11,bc2,bd1,be2,bf2),(ba1,bb11,bc2,bd1,be2, bf3),(ba1,bb11,bc2,bd1,be3,bf1),(ba1,bb11,bc2,bd1,be3, bf2),(ba1,bb11,bc2,bd1,be3,bf3),(ba1,bb11,bc2,bd2,be1, bf1),(ba1,bb1,bc2,bd2,be1,bf2),(ba1,bb11,bc2,bd2,be1, bf3),(ba1,bb11,bc2,bd2,be2,bf1),(ba1,bb11,bc2,bd2,be2, bf2),(ba1,bb11,bc2,bd2,be2,bf3),(ba1,bb11,bc2,bd2,be3, bf1),(ba1,bb11,bc2,bd2,be3,bf2),(ba1,bb11,bc2,bd2,be3, bf3),(ba1,bb11,bc2,bd3,be1,bf1),(ba1,bb11,bc2,bd3,be1, bf2),(ba1,bb1,bc2,bd3,be1,bf3),(ba1,bb11,bc2,bd3,be2, bf1),(ba1,bb11,bc2,bd3,be2,bf2),(ba1,bb11,bc2,bd3,be2, bf3),(ba1,bb11,bc2,bd3,be3,bf1),(ba1,bb11,bc2,bd3,be3, bf2),(ba1,bb11,bc2,bd3,be3,bf3),(ba1,bb1,bc2,bd4,be1, bf1),(ba1,bb11,bc2,bd4,be1,bf2),(ba1,bb1,bc2,bd4,be1, bf3),(ba1,bb11,bc2,bd4,be2,bf1),(ba1,bb11,bc2,bd4,be2, bf2),(ba1,bb11,bc2,bd4,be2,bf3),(ba1,bb11,bc2,bd4,be3, bf1),(ba1,bb11,bc2,bd4,be3,bf2),(ba1,bb11,bc2,bd4,be3, bf3),(ba1,bb12,bc1,bd1,be1,bf1),(ba1,bb12,bc1,bd1,be1, bf2),(ba1,bb12,bc1,bd1,be1,bf3),(ba1,bb12,bc1,bd1,be2, bf1),(ba1,bb12,bc1,bd1,be2,bf2),(ba1,bb12,bc1,bd1,be2, bf3),(ba1,bb12,bc1,bd1,be3,bf1),(ba1,bb12,bc1,bd1,be3, bf2),(ba1,bb12,bc1,bd1,be3,bf3),(ba1,bb12,bc1,bd2,be1, bf1),(ba1,bb12,bc1,bd2,be1,bf2),(ba1,bb12,bc1,bd2,be1, bf3),(ba1,bb12,bc1,bd2,be2,bf1),(ba1,bb12,bc1,bd2,be2, bf2),(ba1,bb12,bc1,bd2,be2,bf3),(ba1,bb12,bc1,bd2,be3, bf1),(ba1,bb12,bc1,bd2,be3,bf2),(ba1,bb12,bc1,bd2,be3, bf3),(ba1,bb12,bc1,bd3,be1,bf1),(ba1,bb12,bc1,bd3,be1, bf2),(ba1,bb2,bc1,bd3,be1,bf3),(ba1,bb12,bc1,bd3,be2, bf1),(ba1,bb12,bc1,bd3,be2,bf2),(ba11,bb12,bc1,bd3,be2, bf3),(ba1,bb12,bc1,bd3,be3,bf1),(ba1,bb12,bc1,bd3,be2, bf3),(ba1,bb12,bc1,bd3,be3,bf3),(ba1,bb12,bc1,bd4,be1, bf1),(ba1,bb12,bc1,bd4,be1,bf2),(ba1,bb12,bc1,bd4,be1, bf3),(ba1,bb12,bc1,bd4,be2,bf1),(ba1,bb12,bc1,bd4,be2, bf2),(ba1,bb12,bc1,bd4,be2,bf3),(ba1,bb12,bc1,bd4,be3, bf1),(ba1,bb12,bc1,bd4,be3,bf2),(ba1,bb12,bc1,bd4,be3, bf3),(ba1,bb12,bc2,bd1,be1,bf1),(ba1,bb12,bc2,bd1,be1, bf2),(ba1,bb12,bc2,bd1,be1,bf3),(ba1,bb12,bc2,bd1,be2, bf1),(ba1,bb12,bc2,bd1,be2,bf2),(ba1,bb12,bc2,bd1,be2, bf3),(ba1,bb12,bc2,bd1,be3,bf1),(ba1,bb12,bc2,bd1,be3, bf2),(ba1,bb12,bc2,bd1,be3,bf3),(ba1,bb12,bc2,bd2,be1, bf1),(ba1,bb2,bc2,bd2,be1,bf2),(ba1,bb12,bc2,bd2,be1, bf3),(ba1,bb12,bc2,bd2,be2,bf1),(ba1,bb12,bc2,bd2,be2, bf2),(ba1,bb12,bc2,bd2,be2,bf3),(ba1,bb12,bc2,bd2,be3, bf1),(ba1,bb12,bc2,bd2,be3,bf2),(ba1,bb12,bc2,bd2,be3, bf3),(ba1,bb12,bc2,bd3,be1,bf1),(ba1,bb12,bc2,bd3,be1, bf2),(ba1,bb12,bc2,bd3,be1,bf3),(ba1,bb12,bc2,bd3,be2, bf1),(ba1,bb12,bc2,bd3,be2,bf2),(ba1,bb12,bc2,bd3,be2, bf3),(ba1,bb12,bc2,bd3,be3,bf1),(ba1,bb12,bc2,bd3,be3, bf2),(ba1,bb12,bc2,bd3,be3,bf3),(ba1,bb12,bc2,bd4,be1, bf1),(ba1,bb2,bc2,bd4,be1,bf2),(ba1,bb12,bc2,bd4,be1, bf3),(ba1,bb12,bc2,bd4,be2,bf1),(ba1,bb12,bc2,bd4,be2, bf2),(ba1,bb12,bc2,bd4,be2,bf3),(ba1,bb12,bc2,bd4,be3, bf1),(ba1,bb12,bc2,bd4,be3,bf2),(ba1,bb12,bc2,bd4,be3, bf3),(ba2,bb1,bc1,bd1,be1,bf1),(ba2,bb1,bc1,bd1,be1,bf2), (ba2,bb1,bc1,bd1,be1,bf3),(ba2,bb1,bc1,bd1,be2,bf1),(ba2, bb1,bc1,bd1,be2,bf2),(ba2,bb1,bc1,bd1,be2,bf3),(ba2,bb1, bc1,bd1,be3,bf1),(ba2,bb1,bc1,bd1,be3,bf2),(ba2,bb1,bc1, bd1,be3,bf3),(ba2,bb1,bc1,bd2,be1,bf1),(ba2,bb1,bc1,bd2, be1,bf2),(ba2,bb1,bc1,bd2,be1,bf3),(ba2,bb1,bc1,bd2,be2, bf1),(ba2,bb1,bc1,bd2,be2,bf2),(ba2,bb1,bc1,bd2,be2,bf3), (ba2,bb1,bc1,bd2,be3,bf1),(ba2,bb1,bc1,bd2,be3,bf2),(ba2, bb1,bc1,bd2,be3,bf3),(ba2,bb1,bc1,bd3,be1,bf1),(ba2,bb1, bc1,bd3,be1,bf2),(ba2,bb1,bc1,bd3,be1,bf3),(ba2,bb1,bc1, bd3,be2,bf1),(ba2,bb1,bc1,bd3,be2,bf2),(ba2,bb1,bc1,bd3, be2,bf3),(ba2,bb1,bc1,bd3,be3,bf1),(ba2,bb1,bc1,bd3,be3, bf2),(ba2,bb1,bc1,bd3,be3,bf3),(ba2,bb1,bc1,bd4,be1,bf1), (ba2,bb1,bc1,bd4,be1,bf2),(ba2,bb1,bc1,bd4,be1,bf3),(ba2, bb1,bc1,bd4,be2,bf1),(ba2,bb1,bc1,bd4,be2,bf2),(ba2,bb1, bc1,bd4,be2,bf3),(ba2,bb1,bc1,bd4,be3,bf1),(ba2,bb1,bc1, bd4,be3,bf2),(ba2,bb1,bc1,bd4,be3,bf3),(ba2,bb1,bc2,bd1, be1,bf1),(ba2,bb1,bc2,bd1,be1,bf2),(ba2,bb1,bc2,bd1,be1, bf3),(ba2,bb1,bc2,bd1,be2,bf1),(ba2,bb1,bc2,bd1,be2,bf2), (ba2,bb1,bc2,bd1,be2,bf3),(ba2,bb1,bc2,bd1,be3,bf1),(ba2, bb1,bc2,bd1,be3,bf2),(ba2,bb1,bc2,bd1,be3,bf3),(ba2,bb1, bc2,bd2,be1,bf1),(ba2,bb1,bc2,bd2,be1,bf2),(ba2,bb1,bc2, bd2,be1,bf3),(ba2,bb1,bc2,bd2,be2,bf1),(ba2,bb1,bc2,bd2, be2,bf2),(ba2,bb1,bc2,bd2,be2,bf3),(ba2,bb1,bc2,bd2,be3, bf1),(ba2,bb1,bc2,bd2,be3,bf2),(ba2,bb1,bc2,bd2,be3,bf3), (ba2,bb1,bc2,bd3,be1,bf1),(ba2,bb1,bc2,bd3,be1,bf2),(ba2, bb1,bc2,bd3,be1,bf3),(ba2,bb1,bc2,bd3,be2,bf1),(ba2,bb1, bc2,bd3,be2,bf2),(ba2,bb1,bc2,bd3,be2,bf3),(ba2,bb1,bc2, bd3,be3,bf1),(ba2,bb1,bc2,bd3,be3,bf2),(ba2,bb1,bc2,bd3, be3,bf3),(ba2,bb1,bc2,bd4,be1,bf1),(ba2,bb1,bc2,bd4,be1, bf2),(ba2,bb1,bc2,bd4,be1,bf3),(ba2,bb1,bc2,bd4,be2,bf1), (ba2,bb1,bc2,bd4,be2,bf2),(ba2,bb1,bc2,bd4,be2,bf3),(ba2, bb1,bc2,bd4,be3,bf1),(ba2,bb1,bc2,bd4,be3,bf2),(ba2,bb1, bc2,bd4,be3,bf3),(ba2,bb2,bc1,bd1,be1,bf1),(ba2,bb2,bc1, bd1,be1,bf2),(ba2,bb2,bc1,bd1,be1,bf3),(ba2,bb2,bc1,bd1, be2,bf1),(ba2,bb2,bc1,bd1,be2,bf2),(ba2,bb2,bc1,bd1,be2, bf3),(ba2,bb2,bc1,bd1,be3,bf1),(ba2,bb1,bc1,bd1,be3,bf2), (ba2,bb2,bc1,bd1,be3,bf3),(ba2,bb2,bc1,bd2,be1,bf1),(ba2, bb2,bc1,bd2,be1,bf2),(ba2,bb2,bc1,bd2,be1,bf3),(ba2,bb2, bc1,bd2,be2,bf1),(ba2,bb2,bc1,bd2,be2,bf2),(ba2,bb2,bc1, bd2,be2,bf3),(ba2,bb2,bc1,bd2,be3,bf1),(ba2,bb2,bc1,bd2, be3,bf2),(ba2,bb2,bc1,bd2,be3,bf3),(ba2,bb2,bc1,bd3,be1, bf1),(ba2,bb2,bc1,bd3,be1,bf2),(ba2,bb2,bc1,bd3,be1,bf3), (ba2,bb2,bc1,bd3,be2,bf1),(ba2,bb2,bc1,bd3,be2,bf2),(ba2, bb2,bc1,bd3,be2,bf3),(ba2,bb2,bc1,bd3,be3,bf1),(ba2,bb2, bc1,bd3,be3,bf2),(ba2,bb2,bc1,bd3,be3,bf3),(ba2,bb2,bc1, bd4,be1,bf1),(ba2,bb2,bc1,bd4,be1,bf2),(ba2,bb2,bc1,bd4, be1,bf3),(ba2,bb2,bc1,bd4,be2,bf1),(ba2,bb2,bc1,bd4,be2, bf2),(ba2,bb2,bc1, bd4,be2,bf3),(ba2,bb2,bc1,bd4,be3,bf1), (ba2,bb2,bc1,bd4,be3,bf2),(ba2,bb2,bc1,bd4,be3,bf3),(ba2, bb2,bc2,bd1,be1,bf1),(ba2,bb2,bc2,bd1,be1,bf1),(2),(ba2, bb2,bc2,bd1,be1,bf3),(ba2,bb2,bc2,bd1,be2,bf1),(ba2,bb2, bc2,bd1,be2,bf2),(ba2,bb2,bc2,bd1,be2,bf3),(ba2,bb2,bc2, bd1,be3,bf1),(ba2,bb2,bc2,bd1,be3,bf2),(ba2,bb2,bc2,bd1, be3,bf3),(ba2,bb2,bc2,bd2,be1,bf1),(ba2,bb2,bc2,bd2,be1, bf2),(ba2,bb2,bc2,bd2,be1,bf3),(ba2,bb2,bc2,bd2,be2,bf1), (ba2,bb2,bc2,bd2,be2,bf2),(ba2,bb2,bc2,bd2,be2,bf3),(ba2, bb2,bc2,bd2,be3,bf1),(ba2,bb2,bc2,bd2,be3,bf2),(ba2,bb2, bc2,bd2,be3,bf3),(ba2,bb2,bc2,bd3,be1,bf1),(ba2,bb2,bc2, bd3,be1,bf2),(ba2,bb2,bc2,bd3,be1,bf3),(ba2,bb2,bc2,bd3, be2,bf1),(ba2,bb2,bc2,bd3,be2,bf2),(ba2,bb2,bc2,bd3,be2, bf3),(ba2,bb2,bc2,bd3,be3,bf1),(ba2,bb2,bc2,bd3,be3,bf2), (ba2,bb2,bc2,bd3,be3,bf3),(ba2,bb2,bc2,bd4,be1,bf1),(ba2, bb2,bc2,bd4,be1,bf2),(ba2,bb2,bc2,bd4,be1,bf3),(ba2,bb2, bc2,bd4,be2,bf1),(ba2,bb2,bc2,bd4,be2,bf2),(ba2,bb2,bc2, bd4,be2,bf3),(ba2,bb2,bc2,bd4,be3,bf1),(ba2,bb2,bc2,bd4, be3,bf2),(ba2,bb2,bc2,bd4,be3,bf3),(ba2,bb3,bc1,bd1,be1, bf1),(ba2,bb3,bc1,bd1,be1,bf2),(ba2,bb3,bc1,bd1,be1,bf3), (ba2,bb3,bc1,bd1,be2,bf1),(ba2,bb3,bc1,bd1,be2,bf2),(ba2, bb3,bc1,bd1,be2,bf3),(ba2,bb3,bc1,bd1,be3,bf1),(ba2,bb3, bc1,bd1,be3,bf2),(ba2,bb3,bc1,bd1,be3,bf3),(ba2,bb3,bc1, bd2,be1,bf1),(ba2,bb3,bc1,bd2,be1,bf2),(ba2,bb3,bc1,bd2, be1,bf3),(ba2,bb3,bc1,bd2,be2,bf1),(ba2,bb3,bc1,bd2,be2, bf2),(ba2,bb3,bc1,bd2,be2,bf3),(ba2,bb3,bc1,bd2,be3,bf1), (ba2,bb3,bc1,bd2,be3,bf2),(ba2,bb3,bc1,bd2, be3,bf3),(ba2, bb3,bc1,bd3,be1,bf1),(ba2,bb3,bc1,bd3,be1,bf2),(ba2,bb3, bc1,bd3,be1,bf3),(ba2,bb3,bc1,bd3,be2,bf1),(ba2,bb3,bc1, bd3,be2,bf2),(ba2,bb3,bc1,bd3,be2,bf3),(ba2,bb3,bc1,bd3, be3,bf1),(ba2,bb3,bc1,bd3,be3,bf2),(ba2,bb3,bc1,bd3,be3, bf3),(ba2,bb3,bc1,bd4,be1,bf1),(ba2,bb3,bc1,bd4,be1,bf2), (ba2,bb3,bc1,bd4,be1,bf3),(ba2,bb3,bc1,bd4,be2,bf1),(ba2, bb3,bc1,bd4,be2,bf2),(ba2, bb3,bc1,bd4,be2,bf3),(ba2,bb3, bc1,bd4,be3,bf1),(ba2,bb3,bc1,bd4,be3,bf2),(ba2,bb3,bc1, bd4,be3,bf3),(ba2,bb3,bc2,bd1,be1,bf1),(ba2,bb3,bc2,bd1, be1,bf2),(ba2,bb3,bc2,bd1,be1,bf3),(ba2,bb3,bc2,bd1,be2, bf1),(ba2,bb3,bc2,bd1,be2,bf2),(ba2,bb3,bc2,bd1,be2,bf3), (ba2,bb3,bc2,bd1,be3,bf1),(ba2,bb3,bc2,bd1,be3,bf2),(ba2, bb3,bc2,bd1,be3,bf3),(ba2,bb3,bc2,bd2,be1,bf1),(ba2,bb3, bc2,bd2,be1,bf2),(ba2,bb3,bc2,bd2,be1,bf3),(ba2,bb3,bc2, bd2,be2,bf1),(ba2,bb3,bc2,bd2,be2,bf2),(ba2,bb3,bc2,bd2, be2,bf3),(ba2,bb3,bc2,bd2,be3,bf1),(ba2,bb3,bc2,bd2,be3, bf2),(ba2,bb3,bc2,bd2,be3,bf3),(ba2,bb3,bc2,bd3,be1,bf1), (ba2,bb3,bc2,bd3,be1,bf2),(ba2,bb3,bc2,bd3,be1,bf3),(ba2, bb3,bc2,bd3,be2,bf1),(ba2,bb3,bc1,bd3,be2,bf2),(ba2,bb3, bc2,bd3,be2,bf3),(ba2,bb3,bc2,bd3,be3,bf1),(ba2,bb3,bc2, bd3,be3,bf2),(ba2,bb3,bc2,bd3,be3,bf3),(ba2,bb3,bc2,bd4, be1,bf1),(ba2,bb3,bc2,bd4,be1, bf2),(ba2,bb3,bc2,bd4,be1, bf3),(ba2,bb3,bc2,bd4,be2,bf1),(ba2,bb3,bc2,bd4,be2,bf2), (ba2,bb3,bc2,bd4,be2,bf3),(ba2,bb3,bc2,bd4,be3,bf1),(ba2, bb3,bc2, bd4,be3,bf2),(ba2,bb3,bc2,bd4,be3,bf3),(ba2,bb4, bc1,bd1,be1,bf1),(ba2,bb4,bc1,bd1,be1,bf2),(ba2,bb4,bc1, bd1,be1,bf3),(ba2,bb4,bc1,bd1,be2,bf1),(ba2,bb4,bc1,bd1, be2,bf2),(ba2,bb4,bc1,bd1,be2,bf3),(ba2,bb4,bc1,bd1,be3, bf1),(ba2,bb4,bc1,bd1,be3,bf2),(ba2,bb4,bc1,bd1,be3,bf3), (ba2,bb4,bc1, bd2,be1,bf1),(ba2,bb4,bc1,bd2,be1,bf2),(ba2, bb4,bc1,bd2,be1,bf3),(ba2,bb4,bc1,bd2,be2,bf1),(ba2,bb4, bc1,bd2,be2,bf2),(ba2,bb4,bc1,bd2,be2,bf3),(ba2,bb4,bc1, bd2,be3,bf1),(ba2,bb4,bc1, bd2,be3,bf2),(ba2,bb4,bc1,bd2, be3,bf3),(ba2,bb4,bc1,bd3,be1,bf1),(ba2,bb4,bc1,bd3,be1, bf2),(ba2,bb4,bc1,bd3,be1,bf3),(ba2,bb4,bc1,bd3,be2,bf1), (ba2,bb4,bc1,bd3,be2,bf2),(ba2,bb4,bc1,bd3,be2,bf3),(ba2, bb4,bc1,bd3,be3,bf1),(ba2,bb4,bc1,bd3,be3,bf2),(ba2,bb4, bc1,bd3,be3,bf3),(ba2,bb4,bc1,bd4,be1,bf1),(ba2,bb4,bc1, bd4,be1,bf2),(ba2,bb4,bc1,bd4,be1,bf3),(ba2,bb4,bc1,bd4, be2,bf1),(ba2,bb4,bc1,bd4,be2,bf2),(ba2,bb4,bc1,bd4,be2, bf3),(ba2,bb4,bc1,bd4,be3,bf1),(ba2,bb4,bc1,bd4,be3,bf2), (ba2,bb4,bc1,bd4,be3,bf3),(ba2,bb4,bc2,bd1,be1,bf1),(ba2, bb4,bc2,bd1,be1,bf2),(ba2,bb3,bc2,bd1,be1,bf3),(ba2,bb4, bc2,bd1,be2,bf1),(ba2,bb4,bc2,bd1,be2,bf2),(ba2,bb4,bc2, bd1,be2,bf3),(ba2,bb4,bc2,bd1,be3,bf1),(ba2,bb4,bc2,bd1, be3,bf2),(ba2,bb4,bc2,bd1,be3,bf3),(ba2,bb4,bc2,bd2,be1, bf1),(ba2,bb4,bc2,bd2,be1,bf2),(ba2,bb4,bc2,bd2,be1,bf3), (ba2,bb4,bc2,bd2,be2,bf1),(ba2,bb4,bc2,bd2,be2,bf2),(ba2, bb4,bc2,bd2,be2,bf3),(ba2,bb4,bc2,bd2,be3,bf1),(ba2,bb4, bc2,bd2,be3,bf2),(ba2,bb4,bc2,bd2,be3,bf3),(ba2,bb4,bc2, bd3,be1,bf1),(ba2,bb4,bc2,bd3,be1,bf2),(ba2,bb4,bc2,bd3, be1,bf3),(ba2,bb4,bc2,bd3,be2,bf1),(ba2,bb4,bc2,bd3,be2, bf2),(ba2,bb4,bc2,bd3,be2,bf3),(ba2,bb4,bc2,bd3,be3,bf1), (ba2,bb4,bc2,bd3,be3,bf2),(ba2,bb4,bc2,bd3,be3,bf3),(ba2, bb4,bc2,bd4,be1,bf1),(ba2,bb4,bc2,bd4,be1,bf2),(ba2,bb4, bc2,bd4,be1,bf3),(ba2,bb4,bc2,bd4,be2,bf1),(ba2,bb4,bc2, bd4,be2,bf2),(ba2,bb4,bc2,bd4,be2,bf3),(ba2,bb4,bc2,bd4, be3,bf1),(ba2,bb4,bc2,bd4,be3,bf2),(ba2,bb4,bc2,bd4,be3, bf3),(ba2,bb5,bc1,bd1,be1,bf1),(ba2,bb5,bc1,bd1,be1,bf2), (ba2,bb5,bc1,bd1,be1,bf3),(ba2,bb5,bc1,bd1,be2,bf1),(ba2, bb5,bc1,bd1,be2,bf2),(ba2,bb5,bc1,bd1,be2,bf3),(ba2,bb5, bc1,bd1,be3,bf1),(ba2,bb5,bc1,bd1,be3,bf2),(ba2,bb5,bc1, bd1,be3,bf3),(ba2,bb5,bc1,bd2,be1,bf1),(ba2,bb5,bc1,bd2, be1,bf2),(ba2,bb5,bc1,bd2,be1,bf3),(ba2,bb5,bc1,bd2,be2, bf1),(ba2,bb5,bc1,bd2,be2,bf2),(ba2,bb5,bc1,bd2,be2,bf3), (ba2,bb5,bc1,bd2,be3,bf1),(ba2,bb5,bc1,bd2,be3,bf2),(ba2, bb5,bc1,bd2,be3,bf3),(ba2,bb5,bc1,bd3,be1,bf1),(ba2,bb5, bc1,bd3,be1,bf2),(ba2,bb5,bc1,bd3,be1,bf3),(ba2,bb5,bc1, bd3,be2,bf1),(ba2,bb5,bc1,bd3,be2,bf2),(ba2,bb5,bc1,bd3, be2,bf3),(ba2,bb5,bc1,bd3,be3,bf1),(ba2,bb5,bc1,bd3,be3, bf2),(ba2,bb5,bc1,bd3,be3,bf3),(ba2,bb5,bc1,bd4,be1,bf1), (ba2,bb5,bc1,bd4,be1,bf2),(ba2,bb5,bc1,bd4,be1,bf3),(ba2, bb5,bc1,bd4,be2,bf1),(ba2,bb5,bc1,bd4,be2,bf2),(ba2,bb5, bc1,bd4,be2,bf3),(ba2,bb5,bc1,bd4,be3,bf1),(ba2,bb5,bc1, bd4,be3,bf2),(ba2,bb5,bc1,bd4,be3,bf3),(ba2,bb5,bc2,bd1, be1,bf1),(ba2,bb5,bc2,bd1,be1,bf2),(ba2,bb5,bc2,bd1,be1, bf3),(ba2,bb5,bc2,bd1,be2,bf1),(ba2,bb5,bc2,bd1,be2,bf2), (ba2,bb5,bc2,bd1,be2,bf3),(ba2,bb5,bc2,bd1,be3,bf1),(ba2, bb5,bc2,bd1,be3,bf2),(ba2,bb5,bc2,bd1,be3,bf3),(ba2,bb5, bc2,bd2,be1,bf1),(ba2,bb5,bc2,bd2,be1,bf2),(ba2,bb5,bc2, bd2,be1,bf3),(ba2,bb5,bc2,bd2,be2,bf1),(ba2,bb5,bc2,bd2, be2,bf2),(ba2,bb5,bc2,bd2,be2,bf3),(ba2,bb5,bc2,bd2,be3, bf1),(ba2,bb5,bc2,bd2,be3,bf2),(ba2,bb5,bc2, bd2,be3,bf3), (ba2,bb5,bc2,bd3,be1,bf1),(ba2,bb5,bc2,bd3,be1,bf2),(ba2, bb5,bc2,bd3,be1,bf3),(ba2,bb5,bc2,bd3,be2,bf1),(ba2,bb5, bc2,bd3,be2,bf2),(ba2,bb5,bc2,bd3,be2,bf3),(ba2,bb5,bc2, bd3,be3,bf1),(ba2,bb5,bc2,bd3,be3,bf2),(ba2,bb5,bc2,bd3, be3,bf3),(ba2,bb5,bc2,bd4,be1,bf1),(ba2,bb5,bc2,bd4,be1, bf2),(ba2,bb5,bc2,bd4,be1,bf3),(ba2,bb5,bc2,bd4,be2,bf1), (ba2,bb5,bc2,bd4,be2,bf2),(ba2 bb5,bc2,bd4,be2,bf3),(ba2, bb5,bc2,bd4,be3,bf1),(ba2,bb5,bc2,bd4,be3,bf2),(ba2,bb5, bc2,bd4,be3,bf3),(ba2,bb6,bc1,bd1,be1,bf1),(ba2,bb6,bc1, bd1,be1,bf2),(ba2,bb6,bc1,bd1,be2,bf3),(ba2,bb6,bc1,bd1, be2,bf1),(ba2,bb6,bc1,bd1,be2,bf2),(ba2,bb6,bc1,bd1,be2, bf3),(ba2,bb6,bc1,bd1,be3,bf1),(ba2,bb6,bc1,bd1,be3,bf2), (ba2,bb6,bc1,bd1,be3,bf3),(ba2,bb6,bc1,bd2,be1,bf1),(ba2, bb6,bc1,bd2,be1,bf2),(ba2,bb6,bc1,bd2,be1,bf3),(ba2,bb6, bc1,bd2,be2,bf1),(ba2,bb6,bc1,bd2,be2,bf2),(ba2,bb6,bc1, bd2,be2,bf3),(ba2,bb6,bc1,bd2,be3,bf1),(ba2,bb6,bc1,bd2, be3,bf2),(ba2,bb6,bc1,bd2,be3,bf3),(ba2,bb6,bc1,bd3,be1, bf1),(ba2,bb6,bc1,bd3,be1,bf2),(ba2,bb6,bc1,bd3,be1,bf3), (ba2,bb6,bc1,bd3,be2,bf1),(ba2,bb6,bc1,bd3,be2,bf2),(ba2, bb6,bc1,bd3,be2,bf3),(ba2,bb6,bc1,bd3,be3,bf1),(ba2,bb6, bc1,bd3,be3,bf2),(ba2,bb6,bc1,bd3,be3,bf3),(ba2,bb6,bc1, bd4,be1,bf1),(ba2,bb6,bc1, bd4,be1,bf2),(ba2,bb6,bc1,bd4, be1,bf3),(ba2,bb6,bc1,bd3,be2,bf1),(ba2,bb6,bc1,bd4,be2, bf2),(ba2,bb6,bc1,bd4, be2,bf3),(ba2,bb6,bc1,bd4,be3,bf1), (ba2,bb6,bc1,bd4,be3,bf2),(ba2,bb6,bc1,bd4,be3,bf3),(ba2, bb6,bc2,bd1,be1,bf1),(ba2,bb6,bc2,bd1,be1,bf2),(ba2,bb6, bc2,bd1,be1,bf3),(ba2,bb6,bc2,bd1,be2,bf1),(ba2,bb6,bc2, bd1,be2,bf2),(ba2,bb6,bc2,bd1,be2,bf3),(ba2,bb6,bc2,bd1, be3,bf1),(ba2,bb6,bc2,bd1,be3,bf2),(ba2,bb6,bc2,bd1,be3, bf3),(ba2,bb6,bc2,bd2,be1,bf1),(ba2,bb6,bc2,bd2,be1,bf2), (ba2,bb6,bc2,bd2,be1,bf3),(ba2,bb6,bc2,bd2,be2,bf1),(ba2, bb6,bc2,bd2,be2,bf2),(ba2,bb6,bc2,bd2,be2,bf3),(ba2,bb6, bc2,bd2,be3,bf1),(ba2,bb6,bc2,bd2,be3,bf2),(ba2,bb6,bc2, bd2,be3,bf3),(ba2,bb6,bc2, bd3,be1,bf1),(ba2,bb6,bc2,bd3, be1,bf2),(ba2,bb6,bc2,bd3,be1,bf3),(ba2,bb6,bc2,bd3,be2, bf1),(ba2,bb6,bc2,bd3,be2,bf2),(ba2,bb6,bc2,bd3,be2,bf3), (ba2,bb6,bc2,bd3,be3,bf1),(ba2,bb6,bc2,bd3,be3,bf2),(ba2, bb6,bc2,bd3,be3,bf3),(ba2,bb6,bc2,bd4,be1,bf1),(ba2,bb6, bc2,bd4,be1,bf2),(ba2,bb6,bc2,bd4,be1,bf3),(ba2,bb6,bc2, bd4,be2,bf1),(ba2,bb6,bc2,bd4,be2,bf2),(ba2,bb6,bc2,bd4, be2,bf3),(ba2,bb6,bc2,bd4,be3,bf2),(ba2,bb6,bc2,bd4,be2, bf2),(ba2,bb6,bc2,bd4,be3,bf3),(ba2,bb7,bc1,bd1,be1,bf1), (ba2,bb7,bc1,bd1,be1,bf2),(ba2,bb7,bc1,bd1,be1,bf3),(ba2, bb7,bc1,bd1,be2,bf1),(ba2,bb7,bc1,bd1,be2,bf2),(ba2,bb7, bc1,bd1,be2,bf3),(ba2,bb7,bc1,bd1,be3,bf1),(ba2,bb7,bc1, bd1,be3,bf2),(ba2,bb7,bc1,bd1,be3,bf3),(ba2,bb7,bc1,bd2, be1,bf1),(ba2,bb7,bc1,bd2,be1,bf2),(ba2,bb7,bc1,bd2,be1, bf3),(ba2,bb7,bc1,bd2,be2,bf1),(ba2,bb7,bc1,bd2,be2,bf2), (ba2,bb7,bc1,bd2,be2,bf3),(ba2,bb7,bc1,bd2,be3,bf1),(ba2, bb7,bc1,bd2,be3,bf2),(ba2,bb7,bc1,bd2,be3,bf3),(ba2,bb7, bc1,bd3,be1,bf1),(ba2,bb7,bc1,bd3,be1,bf2),(ba2,bb7,bc1, bd3,be1,bf3),(ba2,bb7,bc1,bd3,be2,bf1),(ba2,bb7,bc1,bd3, be2,bf2),(ba2,bb7,bc1,bd3,be2,bf3),(ba2,bb7,bc1,bd3,be3, bf1),(ba2,bb7,bc1,bd3,be3,bf2),(ba2,bb7,bc1,bd3,be3,bf3), (ba2,bb7,bc1,bd4,be1,bf1),(ba2,bb7,bc1,bd4,be1,bf2),(ba2, bb7,bc1,bd4,be1,bf3),(ba2,bb7,bc1,bd4,be2,bf1),(ba2,bb7, bc1,bd4,be2,bf2),(ba2,bb7,bc1,bd4,be2,bf3),(ba2,bb7,bc1, bd4,be3,bf1),(ba2,bb7,bc1,bd4,be3,bf2),(ba2,bb7,bc1,bd4, be3,bf3),(ba2,bb7,bc2,bd1,be1,bf1),(ba2,bb7,bc2,bd1,be1, bf2),(ba2,bb7,bc2,bd1,be1,bf3),(ba2,bb7,bc2,bd1,be2,bf1), (ba2,bb7,bc2,bd1,be2,bf2),(ba2,bb7,bc2,bd1,be2,bf3),(ba2, bb7,bc2,bd1,be3,bf1),(ba2,bb7,bc2,bd1,be3,bf2),(ba2,bb7, bc2,bd1,be3,bf3),(ba2,bb7,bc2,bd2,be1,bf1),(ba2,bb7,bc2, bd2,be1,bf2),(ba2,bb7,bc2,bd2,be1,bf3),(ba2,bb7,bc2,bd2, be2,bf1),(ba2,bb7,bc2,bd2,be2,bf2),(ba2,bb7,bc2,bd2,be2, bf3),(ba2,bb7,bc2,bd2,be3,bf1),(ba2,bb7,bc2,bd2,be3,bf2), (ba2,bb7,bc2,bd2,be3,bf3),(ba2,bb7,bc2, bd3,be1,bf1),(ba2, bb7,bc2,bd3,be1,bf2),(ba2,bb7,bc2,bd3,be1,bf3),(ba2,bb7, bc2,bd3,be2,bf1),(ba2,bb7,bc2,bd3,be2,bf2),(ba2,bb7,bc2, bd3,be2,bf3),(ba2,bb7,bc2,bd3,be3,bf1),(ba2,bb7,bc2,bd3, be3,bf2),(ba2,bb7,bc2,bd3,be3,bf3),(ba2,bb7,bc2,bd4,be1, bf1),(ba2,bb7,bc2,bd4,be1,bf2),(ba2,bb7,bc2,bd4,be1,bf3), (ba2,bb7,bc2,bd4,be2,bf1),(ba2,bb7,bc2,bd4,be2,bf2),(ba2, bb7,bc2,bd4,be2,bf3),(ba2,bb7,bc2,bd4,be3,bf1),(ba2,bb7, bc2,bd4,be3,bf2),(ba2,bb7,bc2,bd4,be3,bf3),(ba2,bb8,bc1, bd1,be1,bf1),(ba2,bb8,bc1,bd1,be1,bf2),(ba2,bb8,bc1,bd1, be1,bf3),(ba2,bb8,bc1,bd1,be2,bf1),(ba2,bb8,bc1,bd1,be2, bf2),(ba2,bb8,bc1,bd1,be2,bf3),(ba2,bb8,bc1,bd1,be3,bf1), (ba2,bb8,bc1,bd1,be3,bf2),(ba2,bb8,bc1,bd1,be3,bf3),(ba2, bb8,bc1,bd2,be1,bf1),(ba2,bb8,bc1,bd2,be1,bf2),(ba2,bb8, bc1,bd2,be1,bf3),(ba2,bb8,bc1,bd2,be2,bf1),(ba2,bb8,bc1, bd2,be2,bf2),(ba2,bb8,bc1, bd2,be2,bf3),(ba2,bb8,bc1,bd2, be3,bf1),(ba2,bb8,bc1,bd2,be3,bf2),(ba2,bb8,bc1,bd2,be3, bf3),(ba2,bb8,bc1,bd3,be1,bf1),(ba2,bb8,bc1, bd3,be1,bf2), (ba2,bb8,bc1,bd3,be1,bf3),(ba2,bb8,bc1,bd3,be2,bf1),(ba2, bb8,bc1,bd3,be2,bf2),(ba2,bb8,bc1,bd3, be2,bf3),(ba2,bb8, bc1,bd3,be3,bf1),(ba2,bb8,bc1,bd3,be3,bf2),(ba2,bb8,bc1, bd3,be3,bf3),(ba2,bb8,bc1,bd4,be1,bf1),(ba2,bb8,bc1,bd4, be1,bf2),(ba2,bb8,bc1,bd4,be1,bf3),(ba2,bb8,bc1,bd4,be2, bf1),(ba2,bb8,bc1,bd4,be2,bf2),(ba2,bb8,bc1,bd4,be2,bf3), (ba2,bb8,bc1,bd4,be3,bf1),(ba2,bb8,bc1,bd4,be3,bf2),(ba2, bb8,bc1,bd4,be3,bf3),(ba2,bb8,bc2,bd1,be1,bf1),(ba2,bb8, bc2,bd1,be1,bf2),(ba2,bb8,bc2,bd1,be1,bf3),(ba2,bb8,bc2, bd1,be2,bf1),(ba2,bb8,bc2,bd1,be2,bf2),(ba2,bb8,bc2,bd1, be2,bf3),(ba2,bb8,bc2,bd1,be3,bf1),(ba2,bb8,bc2,bd1,be3, bf2),(ba2,bb8,bc2,bd1,be3,bf3),(ba2,bb8,bc2,bd2,be1,bf1), (ba2,bb8,bc2,bd2,be1,bf2),(ba2,bb8,bc2,bd2,be1,bf3),(ba2, bb8,bc2,bd2,be2,bf1),(ba2,bb8,bc2,bd2,be2,bf2),(ba2,bb8, bc2,bd2,be2,bf3),(ba2,bb8,bc2,bd2,be3,bf1),(ba2,bb8,bc2, bd2,be3,bf2),(ba2,bb8,bc2,bd2,be3,bf3),(ba2,bb8,bc2,bd3, be1,bf1),(ba2,bb8,bc2,bd3,be1,bf2),(ba2,bb8,bc2,bd3,be1, bf3),(ba2,bb8,bc2,bd3,be2,bf1),(ba2,bb8,bc2,bd3,be2,bf2), (ba2,bb8,bc2,bd3,be3,bf3),(ba2,bb8,bc2,bd3,be3,bf1),(ba2, bb8,bc2,bd3,be3,bf2),(ba2,bb8,bc2,bd3,be3,bf3),(ba2,bb8, bc2,bd4,be1,bf1),(ba2,bb8,bc2,bd4,be1,bf2),(ba2,bb8,bc2, bd4,be1,bf3),(ba2,bb8,bc2,bd4,be2,bf1),(ba2,bb8,bc2,bd4, be2,bf2),(ba2,bb8,bc2,bd4,be2,bf3),(ba2,bb8,bc2,bd4,be3, bf1),(ba2,bb8,bc2,bd4,be3,bf2),(ba2,bb8,bc2,bd4,be3,bf3), (ba2,bb9,bc1,bd1,be1,bf1),(ba2,bb9,bc1,bd1,be1,bf2),(ba2, bb9,bc1,bd1,be1,bf3),(ba2,bb9,bc1,bd1,be2,bf1),(ba2,bb9, bc1,bd1,be2,bf2),(ba2,bb9,bc1,bd1,be2,bf3),(ba2,bb9,bc1, bd1,be3,bf1),(ba2,bb9,bc1,bd1,be3,bf2),(ba2,bb9,bc1,bd1, be3,bf3),(ba2, bb9,bc1,bd2,be1,bf1),(ba2,bb9,bc1,bd2,be1, bf2),(ba2,bb9,bc1,bd2,be1,bf3),(ba2,bb9,bc1,bd2,be2,bf1), (ba2,bb9,bc1,bd2,be2,bf2),(ba2,bb9,bc1,bd2,be2,bf3),(ba2, bb9,bc1,bd2,be3,bf1),(ba2,bb9,bc1,bd2,be3,bf2),(ba2,bb9, bc1,bd2,be3,bf3),(ba2,bb9,bc1,bd3,be1,bf1),(ba2,bb9,bc1, bd3,be1,bf2),(ba2,bb9,bc1,bd3,be1,bf3),(ba2,bb9,bc1,bd3, be2,bf1),(ba2,bb9,bc1,bd3,be2,bf2),(ba2,bb9,bc1,bd3,be2, bf3),(ba2,bb9,bc1,bd3,be3,bf1),(ba2,bb9,bc1,bd3,be3,bf2), (ba2,bb9,bc1,bd3,be3,bf3),(ba2,bb9,bc1,bd4,be1,bf1),(ba2, bb9,bc1,bd4,be1,bf2),(ba2,bb9,bc1,bd4,be1,bf3),(ba2,bb9, bc1,bd4,be2,bf1),(ba2,bb9,bc1,bd4,be2,bf2),(ba2,bb9,bc1, bd4,be2,bf3),(ba2,bb9,bc1,bd4,be3,bf1),(ba2,bb9,bc1,bd4, be3,bf2),(ba2,bb9,bc1,bd4,be3,bf3),(ba2,bb9,bc2,bd1,be1, bf1),(ba2,bb9,bc2,bd1,be1,bf2),(ba2,bb9,bc2,bd1,be1,bf3), (ba2,bb9,bc2,bd1,be2,bf1),(ba2,bb9,bc2,bd1,be2,bf2),(ba2, bb9,bc2,bd1,be2,bf3),(ba2,bb9,bc2,bd1,be3,bf1),(ba2,bb9, bc2,bd1,be3,bf2),(ba2,bb9,bc2,bd1,be3,bf3),(ba2,bb9,bc2, bd2,be1,bf1),(ba2,bb9,bc2,bd2,be1,bf2),(ba2,bb9,bc2,bd2, be1,bf3),(ba2,bb9,bc2,bd2,be2,bf1),(ba2,bb9,bc2,bd2,be2, bf2),(ba2,bb9,bc2,bd2,be2,bf3),(ba2,bb9,bc2,bd2,be3,bf1), (ba2,bb9,bc1,bd2,be3,bf2),(ba2,bb9,bc2,bd2,be3,bf3),(ba2, bb9,bc2,bd3,be1,bf1),(ba2,bb9,bc2,bd3,be1,bf2),(ba2,bb9, bc2,bd3,be1,bf3),(ba2,bb9,bc2,bd3,be2,bf1),(ba2,bb9,bc2, bd3,be2,bf2),(ba2,bb9,bc2,bd3,be2,bf3),(ba2,bb9,bc2,bd3, be3,bf1),(ba2,bb9,bc2,bd3,be3,bf2),(ba2,bb9,bc2,bd3,be3, bf3),(ba2,bb9,bc2,bd4,be1,bf1),(ba2,bb9,bc2,bd4,be1,bf2), (ba2,bb9,bc2,bd4,be1,bf3),(ba2,bb9,bc2,bd4,be2,bf1),(ba2, bb9,bc2,bd4,be2,bf2),(ba2,bb9,bc2,bd4,be2,bf3),(ba2,bb9, bc2,bd4,be3,bf1),(ba2,bb9,bc2,bd4,be3,bf2),(ba2,bb9,bc2, bd4,be3,bf3),(ba2,bb10,bc1,bd1,be1,bf1),(ba2,bb10,bc1, bd1,be1,bf2),(ba2,bb10,bc1,bd1,be1,bf3),(ba2,bb10,bc1, bd1,be2,bf1),(ba2,bb10,bc1,bd1,be2,bf2),(ba2,bb10,bc1, bd1,be2,bf3),(ba2,bb10,bc1,bd1,be3,bf1),(ba2,bb10,bc1, bd1,be3,bf2),(ba2,bb10,bc1,bd1,be3,bf3),(ba2,bb10,bc1, bd2,be1,bf1),(ba2,bb10,bc1,bd2,be1,bf2),(ba2,bb10,bc1, bd2,be1,bf3),(ba2,bb10,bc1,bd2,be2,bf1),(ba2,bb10,bc1, bd2,be2,bf2),(ba2,bb10,bc1,bd2,be2,bf3),(ba2,bb10,bc1, bd2,be3,bf1),(ba2,bb10,bc1,bd2,be3,bf2),(ba2,bb10,bc1, bd2,be3,bf3),(ba2,bb10,bc1,bd3,be1,bf1),(ba2,bb10,bc1, bd3,be1,bf2),(ba2,bb10,bc1,bd3,be1,bf3),(ba2,bb10,bc1, bd3,be2,bf1),(ba2,bb10,bc1,bd3,be2,bf2),(ba2,bb10,bc1, bd3,be2,bf3),(ba2,bb10,bc1,bd3,be3,bf1),(ba2,bb10,bc1, bd3,be1,bf2),(ba2,bb10,bc1,bd3,be3,bf3),(ba2,bb10,bc1, bd4,be1,bf1),(ba2,bb10,bc1,bd4,be1,bf2),(ba2,bb10,bc1, bd4,be1,bf3),(ba2,bb10,bc1,bd4,be2,bf1),(ba2,bb10,bc1, bd4,be2,bf2),(ba2,bb10,bc1,bd4,be2,bf3),(ba2,bb10,bc1, bd4,be3,bf1),(ba2,bb10,bc1,bd4,be3,bf2),(ba2,bb10,bc1, bd4,be3,bf3),(ba2,bb10,bc2,bd1,be1,bf1),(ba2,bb10,bc2, bd1,be1,bf2),(ba2,bb10,bc2,bd1,be1,bf3),(ba2,bb10,bc2, bd1,be2,bf1),(ba2,bb10,bc2,bd1,be2,bf2),(ba2,bb10,bc2, bd1,be2,bf3),(ba2,bb10,bc2,bd1,be3,bf1),(ba2,bb10,bc2, bd1,be3,bf2),(ba2,bb10,bc2,bd1,be3,bf3),(ba2,bb10,bc2, bd2,be1,bf1),(ba2,bb10,bc2,bd2,be1,bf2),(ba2,bb10,bc2, bd2,be1,bf3),(ba2,bb10,bc2,bd2,be2,bf1),(ba2,bb10,bc2, bd2,be2,bf2),(ba2,bb10,bc2,bd2,be2,bf3),(ba2,bb10,bc2, bd2,be3,bf1),(ba2,bb10,bc2,bd2,be3,bf2),(ba2,bb10,bc2, bd2,be3,bf3),(ba2,bb10,bc2,bd3,be1,bf1),(ba2,bb10,bc2, bd3,be1,bf2),(ba2,bb10,bc2,bd3,be1,bf3),(ba2,bb10,bc2, bd3,be2,bf1),(ba2,bb10,bc2,bd3,be2,bf2),(ba2,bb10,bc2, bd3,be2,bf3),(ba2,bb10,bc2,bd3,be3,bf1),(ba2,bb10,bc2, bd3,be3,bf2),(ba2,bb10,bc2,bd3,be3,bf3),(ba2,bb10,bc2, bd4,be1,bf1),(ba2,bb10,bc2,bd4,be1,bf2),(ba2,bb10,bc2, bd4,be1,bf3),(ba2,bb10,bc2,bd4,be2,bf1),(ba2,bb10,bc2, bd4,be2,bf2),(ba2,bb10,bc2,bd4,be2,bf3),(ba2,bb10,bc2, bd4,be3,bf1),(ba2,bb10,bc2,bd4,be3,bf2),(ba2,bb10,bc2, bd4,be3,bf3),(ba2,bb11,bc1,bd1,be1,bf1),(ba2,bb11,bc1, bd1,be1,bf2),(ba2,bb11,bc1,bd1,be1,bf3),(ba2,bb11,bc1, bd1,be2,bf1),(ba2,bb11,bc1,bd1,be2,bf2),(ba2,bb11,bc1, bd1,be2,bf3),(ba2,bb11,bc1,bd1,be3,bf1),(ba2,bb11,bc1, bd1,be3,bf2),(ba2,bb11,bc1,bd1,be3,bf3),(ba2,bb11,bc1, bd2,be1,bf1),(ba2,bb11,bc1,bd2,be1,bf2),(ba2,bb11,bc1, bd2,be1,bf3),(ba2,bb11,bc1,bd2,be2,bf1),(ba2,bb11,bc1, bd2,be2,bf2),(ba2,bb11,bc1,bd2,be2,bf3),(ba2,bb11,bc1, bd2,be3,bf1),(ba2,bb11,bc1,bd2,be3,bf2),(ba2,bb11,bc1, bd3,be1,bf1),(ba2,bb11,bc1,bd3,be1,bf3),(ba2,bb11,bc1, bd3,be2,bf1),(ba2,bb11,bc1,bd3,be2,bf2),(ba2,bb11,bc1, bd3,be2,bf3),(ba2,bb11,bc1,bd3,be3,bf1),(ba2,bb11,bc1, bd3,be3,bf2),(ba2,bb11,bc1,bd3,be3,bf3),(ba2,bb11,bc1, bd4,be1,bf1),(ba2,bb11,bc1,bd4,be1,bf2),(ba2,bb11,bc1, bd4,be1,bf3),(ba2,bb11,bc1,bd4,be2,bf1),(ba2,bb11,bc1, bd4,be2,bf2),(ba2,bb11,bc1,bd4,be2,bf3),(ba2,bb11,bc1, bd4,be3,bf1),(ba2,bb11,bc1,bd4,be3,bf2),(ba2,bb11,bc1, bd4,be3,bf3),(ba2,bb11,bc2,bd1,be1,bf1),(ba2,bb11,bc2, bd1,be1,bf2),(ba2,bb11,bc2,bd1,be1,bf3),(ba2,bb11,bc2, bd1,be2,bf1),(ba2,bb11,bc2,bd1,be2,bf2),(ba2,bb11,bc2, bd1,be2,bf3),(ba2,bb11,bc2,bd1,be3,bf1),(ba2,bb11,bc2, bd1,be3,bf2),(ba2,bb11,bc2,bd1,be3,bf3),(ba2,bb11,bc2, bd2,be1,bf1),(ba2,bb11,bc2,bd2,be1,bf2),(ba2,bb11,bc2, bd2,be1,bf3),(ba2,bb11,bc2,bd2,be2,bf1),(ba2,bb11,bc2, bd2,be2,bf2),(ba2,bb11,bc2,bd2,be2,bf3),(ba2,bb11,bc2, bd2,be3,bf1),(ba2,bb11,bc2,bd2,be3,bf2),(ba2,bb11,bc2, bd2,be3,bf3),(ba2,bb11,bc2,bd3,be1,bf1),(ba2,bb11,bc2, bd3,be1,bf2),(ba2,bb11,bc2,bd3,be1,bf3),(ba2,bb11,bc2, bd3,be2,bf1),(ba2,bb11,bc2,bd3,be2,bf2),(ba2,bb11,bc2, bd3,be2,bf3),(ba2,bb11,bc2,bd3,be3,bf1),(ba2,bb11,bc2, bd3,be3,bf2),(ba2,bb11,bc2,bd3,be3,bf3),(ba2,bb11,bc2, bd4,be1,bf1),(ba2,bb11,bc2,bd4,be1,bf2),(ba2,bb11,bc2, bd4,be1,bf3),(ba2,bb11,bc2,bd4,be2,bf1),(ba2,bb11,bc2, bd4,be2,bf2),(ba2,bb11,bc2,bd4,be2,bf3),(ba2,bb11,bc2, bd4,be3,bf1),(ba2,bb11,bc2,bd4,be3,bf2),(ba2,bb11,bc2, bd4,be3,bf3),(ba2,bb12,bc1,bd1,be1,bf1),(ba2,bb2,bc1,bd1, be1,bf2),(ba2,bb12,bc1,bd1,be1,bf3),(ba2,bb12,bc1,bd1, be2,bf1),(ba2,bb12,bc1,bd1,be2,bf2),(ba2,bb12,bc1,bd1, be2,bf3),(ba2,bb12,bc1,bd1,be3,bf1),(ba2,bb12,bc1,bd1, be3,bf2),(ba2,bb12,bc1,bd1,be3,bf3),(ba2,bb12,bc1,bd2, be1,bf1),(ba2,bb12,bc1,bd2,be1,bf2),(ba2,bb12,bc1,bd2, be1,bf3),(ba2,bb12,bc1,bd2,be2,bf1),(ba2,bb12,bc1,bd2, be2,bf2),(ba2,bb12,bc1,bd2,be2,bf3),(ba2,bb12,bc1,bd2, be3,bf1),(ba2,bb12,bc1,bd2,be3,bf2),(ba2,bb12,bc1,bd2, be3,bf3),(ba2,bb12,bc1,bd3,be1,bf1),(ba2,bb12,bc1,bd3, be1,bf2),(ba2,bb12,bc1,bd3,be1,bf3),(ba2,bb12,bc1,bd3, be2,bf1),(ba2,bb12,bc1,bd3,be2,bf2),(ba2,bb12,bc1,bd3, be2,bf3),(ba2,bb12,bc1,bd3,be3,bf1),(ba2,bb12,bc1,bd3, be3,bf2),(ba2,bb12,bc1,bd3,be3,bf3),(ba2,bb12,bc1,bd4, be1,bf1),(ba2,bb12,bc1,bd4,be1,bf2),(ba2,bb12,bc1,bd4, be3,bf3),(ba2,bb12,bc1,bd4,be2,bf1),(ba2,bb12,bc1,bd4, be2,bf2),(ba2,bb12,bc1,bd4,be2,bf3),(ba2,bb2,bc1,bd4,be3, bf1),(ba2,bb12,bc1,bd4,be3,bf2),(ba2,bb12,bc1,bd4,be3, bf3),(ba2,bb12,bc2,bd1,be1,bf1),(ba2,bb12,bc2,bd1,be1, bf2),(ba2,bb12,bc2,bd1,be1,bf3),(ba2,bb12,bc2,bd1,be2, bf1),(ba2,bb12,bc2,bd1,be2,bf2),(ba2,bb12,bc2,bd1,be2, bf3),(ba2,bb12,bc2,bd1,be3,bf1),(ba2,bb12,bc2,bd1,be3, bf2),(ba2,bb12,bc2,bd1,be3,bf3),(ba2,bb12,bc2,bd2,be1, bf1),(ba2,bb12,bc2,bd2,be1,bf2),(ba2,bb12,bc2,bd2,be1, bf3),(ba2,bb12,bc2,bd2,be2,bf1),(ba2,bb12,bc2,bd2,be2, bf2),(ba2,bb12,bc2,bd2,be2,bf3),(ba2,bb12,bc2,bd2,be3, bf1),(ba2,bb12,bc2,bd2,be3,bf2),(ba2,bb12,bc2,bd2,be3, bf3),(ba2,bb12,bc2,bd3,be1,bf1),(ba2,bb12,bc2,bd3,be1, bf2),(ba2,bb12,bc2,bd3,be1,bf3),(ba2,bb12,bc2,bd3,be2, bf1),(ba2,bb12,bc2,bd3,be2,bf2),(ba2,bb12,bc2,bd3,be2, bf3),(ba2,bb12,bc2,bd3,be3,bf1),(ba2,bb12,bc2,bd3,be3, bf2),(ba2,bb12,bc2,bd3,be3,bf3),(ba2,bb12,bc2,bd4,be1, bf1),(ba2,bb12,bc2,bd4,be1,bf2),(ba2,bb12,bc2,bd4,be1, bf3),(ba2,bb12,bc2,bd4,be2,bf1),(ba2,bb12,bc2,bd4,be2, bf2),(ba2,bb12,bc2,bd4,be2,bf3),(ba2,bb12,bc2,bd4,be3, bf1),(ba2,bb12,bc2,bd4,be3,bf2),(ba2,bb12,bc2,bd4,be3, bf3).

As the compound represented by Formula (I) of the invention, the following compounds are exemplified.

A compound wherein the group represented by the formula:

[Chemical Formula 86]

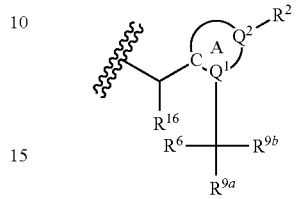

is a group represented by the formula

[Chemical Formula 87]

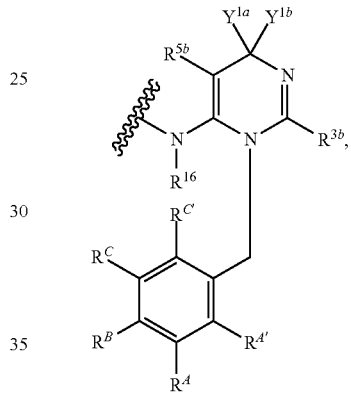

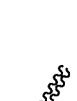

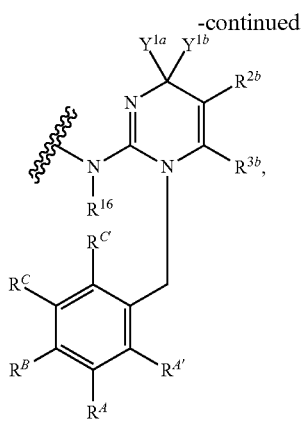
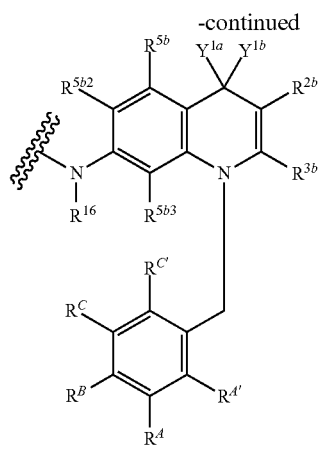
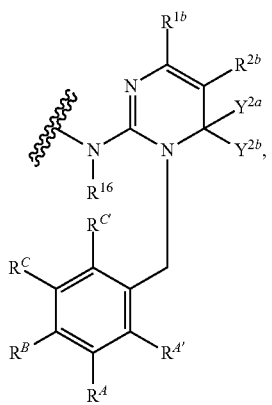
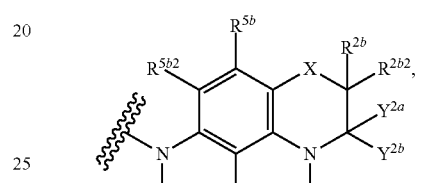
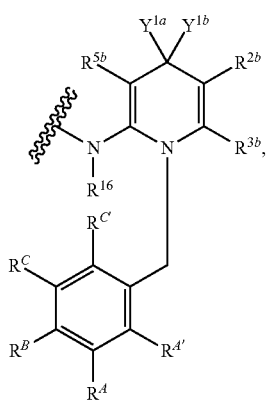
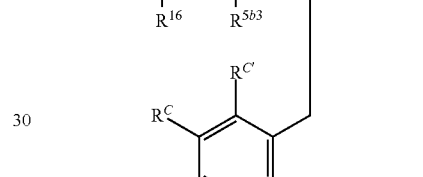
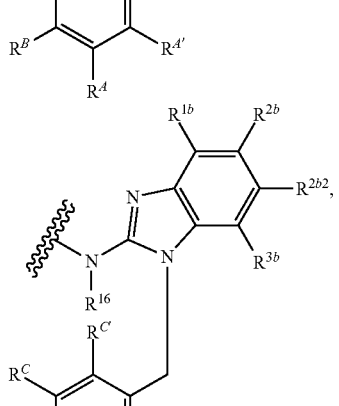
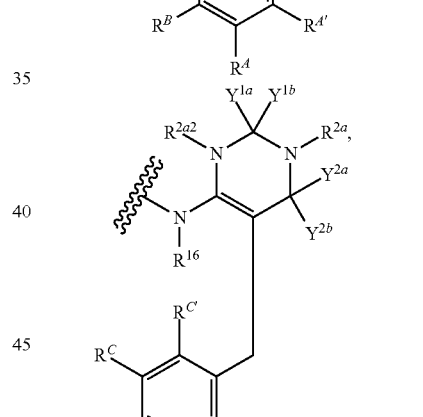
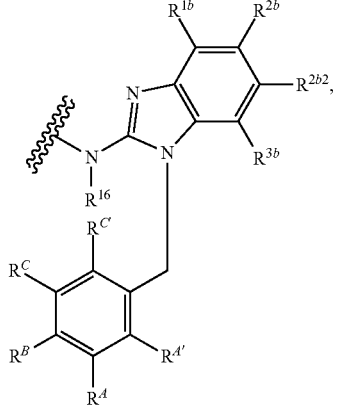
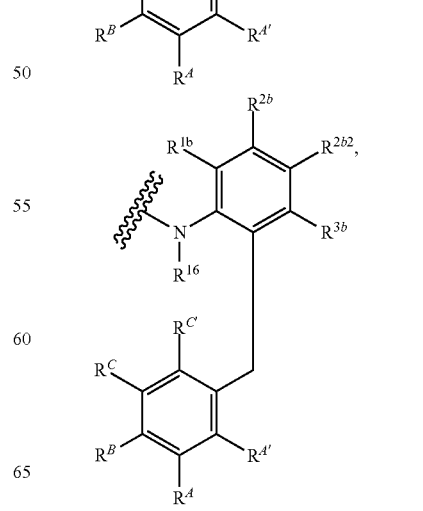

aromatic heterocyclic group, substituted or unsubstituted aryl, substituted or unsubstituted heteroaryl, substituted or unsubstituted amino, or substituted or unsubstituted carbamoyl;

$R^{2b}$ and $R^{2b2}$ are each independently a hydrogen atom, substituted or unsubstituted alkyl, substituted or unsubstituted cycloalkyl, a substituted or unsubstituted non-aromatic heterocyclic group, substituted or unsubstituted aryl, substituted or unsubstituted heteroaryl, substituted or unsubstituted amino または substituted or unsubstituted carbamoyl, a group represented by the formula: —NH—C(=O)—(C($R^{8a}$)($R^{8b}$))n-$R^{13}$ wherein n is an integer of 0 to 4;

$R^{8a}$ are each independently a hydrogen atom, halogen, hydroxy, or, substituted or unsubstituted alkyl;

$R^{8b}$ are each independently a hydrogen atom, halogen, hydroxy, or, substituted or unsubstituted alkyl;

$R^{13}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group represented by the formula: —C(=O)—NH—(C($R^{8a'}$)($R^{8b'}$))n'—$R^{13'}$ wherein n' is an integer of 0 to 4;

$R^{8a'}$ are each independently a hydrogen atom, halogen, hydroxy, or substituted or unsubstituted alkyl;

$R^{8b'}$ are each independently a hydrogen atom, halogen, hydroxy, or substituted or unsubstituted alkyl;

$R^{13'}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino or substituted or unsubstituted guanidyl;

$R^7$ is a group represented the formula;

[Chemical Formula 88]

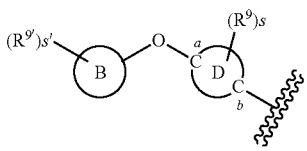

wherein $R^{2a}$ is substituted or unsubstituted alkyl, substituted or unsubstituted cycloalkyl, a substituted or unsubstituted nonwherein ring D is benzene or pyridine;

carbon atom a and carbon atom b are carbon atoms which constitute ring D; ring B is thiazole, isothiazole, oxazole, isoxazole, thiadiazole, oxadiazole, pyridine, pyrimidine, pyrazine or pyridazine;

s and s' are each independently integers of 0 to 3;

$R^9$ are each independently halogen, hydroxy, cyano, substituted or unsubstituted alkyl or substituted or unsubstituted alkyloxy;

$R^{9'}$ are each independently halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl;

$R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;

other symbols are as defined in the above (5).

In the above-mentioned compound, s' is preferably an integer of 1 to 3.

A general synthesis method for the compound of the present invention is shown below. The starting materials and reaction reagents used for synthesis are either commercially available or that can be manufactured using commercially available compounds according to a widely known method in the art.

Compounds of the present invention of the formulas (I) and (II) may be manufactured by the following synthesis routes:

[Method A]

[Chemical Formula 89]

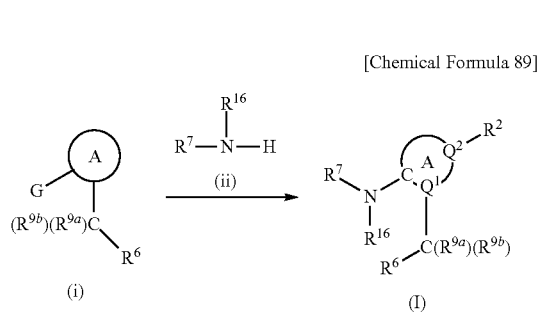

wherein G represents a leaving group such as halogen, substituted or unsubstituted alkylthio, substituted or unsubstituted alkylsulfinyl, or substituted or unsubstituted alkylsulfonyl; and the other symbols are as defined in the above (1α)

In other words, the compound of the present invention of the formulas (I) and (II) may be manufactured by reacting Compound (i) with Compound (ii) in the absence of solvent or in an appropriate solvent in the presence of a palladium catalyst and a base or an acid if necessary.

In this reaction, the amount of Compound (ii) to be used may be one or more equivalents and preferably 1 to 5 equivalents relative to 1 equivalent of Compound (i).

Examples of a base appropriate for use include metal hydroxide (e.g., sodium hydroxide, potassium hydroxide, tripotassium phosphate, etc.), metal hydride (e.g., sodium hydride, lithium hydride, etc.), metal carboxylate (e.g., sodium carbonate, potassium carbonate, cesium carbonate, etc.), and metal alkoxide (e.g., sodium methoxide, sodium ethoxide, potassium t-butoxide, etc.), and the amount thereof to be used may be one or more equivalents and preferably 1 to 5 equivalents relative to 1 equivalent of Compound (i).

Examples of an acid appropriate for use include acetic acid and phosphoric acid, and the amount thereof to be used may be one or more equivalents and preferably 1 to 5 equivalents relative to 1 equivalent of Compound (i).

Examples of a palladium catalyst appropriate for use include tris(dibenzylideneacetone)dipalladium(0), palladium acetate(II), dichlorobis(triphenylphosphine)palladium (II), and tetrakis(triphenylphosphine)palladium(II), and the amount thereof to be used may be 0.001 equivalent or more and preferably 0.01 to 1 equivalent relative to 1 equivalent of Compound (i).

Examples of solvent appropriate for use include alcohols (e.g., t-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 250° C., under microwave irradiation as necessary, and preferably between 0 and 200° C. The reaction time may be between 10 minutes and 80 hours, which varies depending on the compound.

The obtained desired compound of the formulas (I) and (II) may be purified as necessary by a conventional method (e.g., column chromatography, recrystallization, etc.).

[Method B]

[Chemical Formula 90]

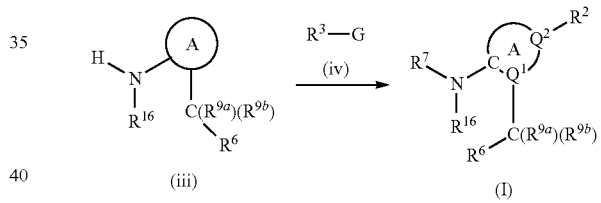

wherein the symbols are as defined in Method A.

In other words, the compound of the present invention of the formula (I) may be manufactured by reacting Compound (iii) with Compound (iv) in the absence of solvent or in an appropriate solvent, if necessary, in the presence of a palladium catalyst and a base or an acid.

In this reaction, the amount of Compound (iii) to be used may be one or more equivalents and preferably 1 to 5 equivalents relative to 1 equivalent of Compound (iv).

Examples of a base appropriate for use include metal hydroxide (e.g., sodium hydroxide, potassium hydroxide, tripotassium phosphate, etc.), metal hydride (e.g., sodium hydride, lithium hydride, etc.), metal carboxylate (e.g., sodium carbonate, potassium carbonate, cesium carbonate, etc.), and metal alkoxide (e.g., sodium methoxide, sodium ethoxide, potassium t-butoxide, etc.), and the amount thereof to be used may be one or more equivalents and preferably 1 to 5 equivalents relative to 1 equivalent of Compound (iii).

Examples of a palladium catalyst appropriate for use include tris(dibenzylideneacetone)dipalladium(0), palladium acetate(II), dichlorobis(triphenylphosphine)palladium (II), and tetrakis(triphenylphosphine)palladium(II), and the amount thereof to be used may be 0.001 equivalent or more and preferably 0.01 to 1 equivalent relative to 1 equivalent of Compound (iii).

Examples of a solvent appropriate for use include alcohols (e.g., t-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 250° C., under microwave irradiation as necessary, and preferably between 0 and 200° C. The reaction time may be between 10 minutes and 80 hours, which varies depending on the compound.

The obtained desired compound of the formula (I) may be purified as necessary by a conventional method (e.g., column chromatography, recrystallization, etc.).

[Method C]

[Chemical Formula 91]

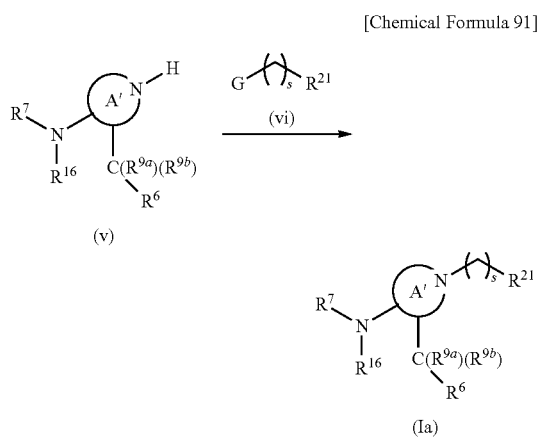

wherein A' is a nitrogen-containing heterocyclic ring; $R^{21}$ is a substituent selected from Substituent Group B; a is an integer from 1 to 4; and the other symbols are as defined in Method A.

In other words, the compound of the present invention of the formula (Ia) may be manufactured by reacting Compound (v) with Compound (vi) in an appropriate solvent in the presence of a base.

In this reaction, the amount of Compound (vi) to be used may be one or more equivalents and preferably 1 to 5 equivalents relative to 1 equivalent of Compound (v).

Examples of a base appropriate for use include metal hydroxide (e.g., sodium hydroxide, potassium hydroxide, tripotassium phosphate, etc.), metal hydride (e.g., sodium hydride, lithium hydride, etc.), metal carboxylate (e.g., sodium carbonate, potassium carbonate, cesium carbonate, etc.), metal alkoxide (e.g., sodium methoxide, sodium ethoxide, potassium t-butoxide, etc.), and metal alkyl (e.g., butyl-lithium, etc.), and the amount thereof to be used may be one or more equivalents and preferably 1 to 5 equivalents relative to 1 equivalent of Compound (v).

Examples of a solvent appropriate for use include alcohols (e.g., t-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 250° C., under microwave irradiation as necessary, and preferably between 0 and 200° C. The reaction time may be between 10 minutes and 80 hours, which varies depending on the compound.

The obtained desired Compound (Ia) may be purified as necessary by a conventional method (e.g., column chromatography, recrystallization, etc.).

[Method D]

[Chemical Formula 92]

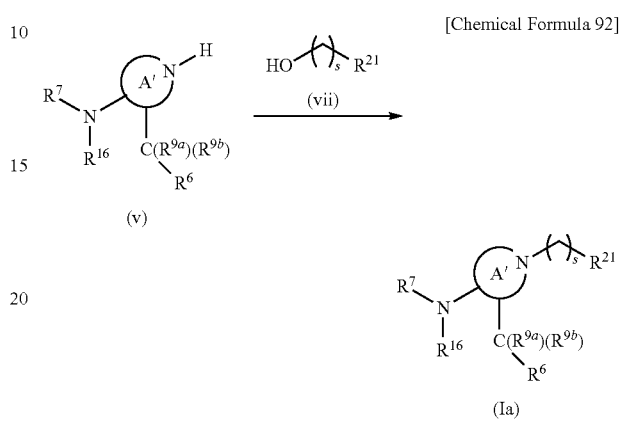

wherein the symbols are as defined in Method C.

In other words, the compound of the present invention of the formula (Ia) may be manufactured by subjecting Compound (v) and Compound (vii) to condensation reaction, such as Mitsunobu reaction.

In this reaction, the amount of Compound (vii) to be used may be one or more equivalents and preferably 1 to 5 equivalents relative to 1 equivalent of Compound (v).

Examples of alkylphosphines appropriate for use include triphenylphosphine and tributylphosphine, and the amount thereof to be used may be one or more equivalents and preferably 1 to 5 equivalents relative to 1 equivalent of Compound (v).

Examples of azodicarboxylates appropriate for use include diethyl azodicarboxylate and di-2-methoxyethyl azodicarboxylate, and the amount thereof to be used may be one or more equivalents and preferably 1 to 5 equivalents relative to 1 equivalent of Compound (v).

Examples of a solvent appropriate for use include aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), and mixed solvents thereof.

The reaction temperature is between −10 and 200° C. and preferably between 0 and 120° C. The reaction time may be between 10 minutes and 80 hours, which varies depending on the compound.

The obtained desired Compound (Ia) may be purified as necessary by a conventional method (e.g., column chromatography, recrystallization, etc.).

[Method E]

[Chemical Formula 93]

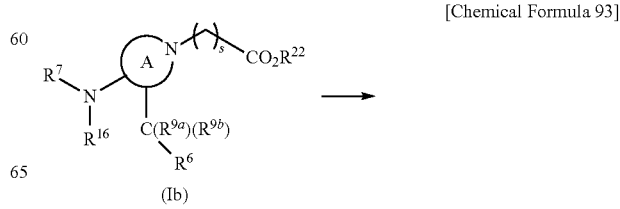

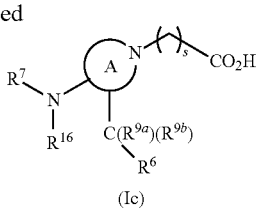

(Ic)

wherein $R^{22}$ is substituted or unsubstituted alkyl; and the other symbols are as defined in Method C.

In other words, the compound of the present invention of the formula (Ic) may be manufactured by subjecting Compound (Ib) obtained by Method A, Method B, Method C, or Method D to hydrolysis in the presence of a base or an acid.

Examples of a base appropriate for use include metal hydroxide (e.g., sodium hydroxide, potassium hydroxide, lithium hydroxide, etc.) and metal carboxylate (e.g., sodium carbonate, potassium carbonate, cesium carbonate, etc.), and the amount thereof to be used may be one or more equivalents and preferably 1 to 5 equivalents relative to 1 equivalent of Compound (Ib).

Examples of an acid appropriate for use include hydrochloric acid, trifluoroacetic acid, and para-toluenesulfonic acid, and the amount thereof to be used may be one or more equivalents and preferably 1 to 5 equivalents relative to 1 equivalent of Compound (Ib).

Examples of a solvent appropriate for use include alcohols (e.g., methanol, ethanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 200° C. and preferably between 0 to 120° C. The reaction time may be between 10 minutes and 80 hours, which varies depending on the compound.

The obtained desired Compound (Ic) may be purified as necessary by a conventional method (e.g., column chromatography, recrystallization, etc.).

[Method F]

[Chemical Formula 94]

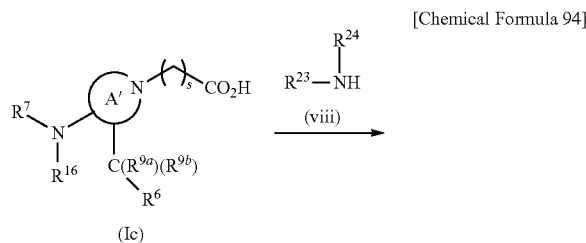

wherein $R^{23}$ and $R^{24}$ are each independently hydrogen, substituted or unsubstituted alkyl, substituted or unsubstituted arylalkyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, or substituted or unsubstituted acyl; and the other symbols are as defined in Method C.

In other words, the compound of the present invention of the formula (Id) may be manufactured by subjecting Compound (Ic) obtained by Method E and Compound (viii) to condensation in an appropriate solvent.

Examples of a condensation agents appropriate for use include condensation agents such as 1-hydroxybenzotriazole or HOAt, 1-ethyl-3-(3-dimethylaminopropyl) carbodiimide hydrochloride, HATU, and PyBOp, and bases such as triethylamine and diisopropylethylamine, and the amount thereof to be used may be one or more equivalents and preferably 1 to 5 equivalents relative to 1 equivalent of Compound (Ic).

Examples of a solvent appropriate for use include aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, and mixed solvents thereof.

The reaction temperature is between −10 and 200° C. and preferably between 0 and 120° C. The reaction time may be between 10 minutes and 80 hours, which varies depending on the compound.

The obtained desired Compound (Id) may be purified as necessary by a conventional method (e.g., column chromatography, recrystallization, etc.).

[Method G]

[Chemical Formula 95]

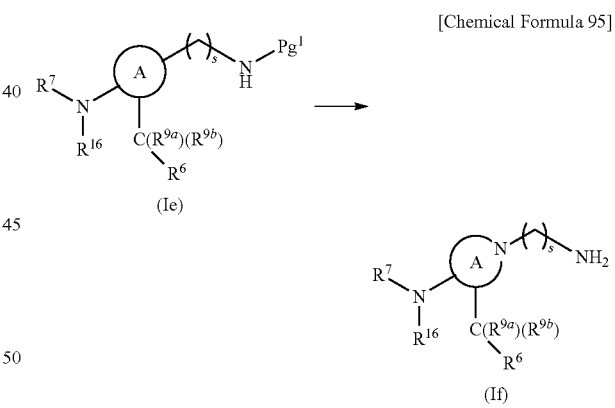

wherein $Pg^1$ is an appropriate protecting group for an amino group; and the other symbols are as defined in Method C.

In other words, the compound of the present invention of the formula (If) may be manufactured by subjecting Compound (Ie) obtained by Method A, Method B, Method C, or Method D to deprotection in an appropriate solvent in the presence of an acid.

Examples of an acid appropriate for use include hydrochloric acid, trifluoroacetic acid, and para-toluenesulfonic acid, and the amount thereof to be used may be 0.01 equivalent or more and preferably 0.5 to 3 equivalents relative to 1 equivalent of Compound (Ie).

Examples of a solvent appropriate for use include alcohols (e.g., methanol, ethanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), water, and mixed solvents thereof.

The reaction temperature is between −10 and 200° C. and preferably between 0 and 120° C. The reaction time may be between 10 minutes and 80 hours, which varies depending on the compound.

The obtained desired Compound (If) may be purified as necessary by a conventional method (e.g., column chromatography, recrystallization, etc.) or salt formation.

[Method H]

dimethoxyethane, etc.), N,N-dimethylformamide, DMSO, NMP, and mixed solvents thereof.

The reaction temperature is between −10 and 200° C. and preferably between 0 and 120° C. The reaction time may be between 10 minutes and 80 hours, which varies depending on the compound.

The obtained desired Compound (Ig) may be purified as necessary by a conventional method (e.g., column chromatography, recrystallization, etc.).

[Method I]

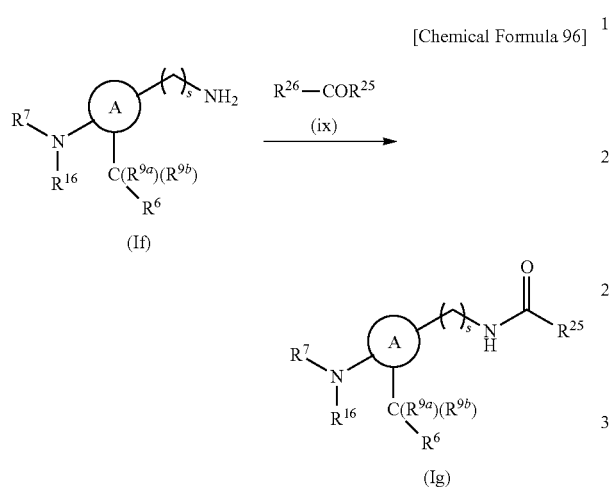

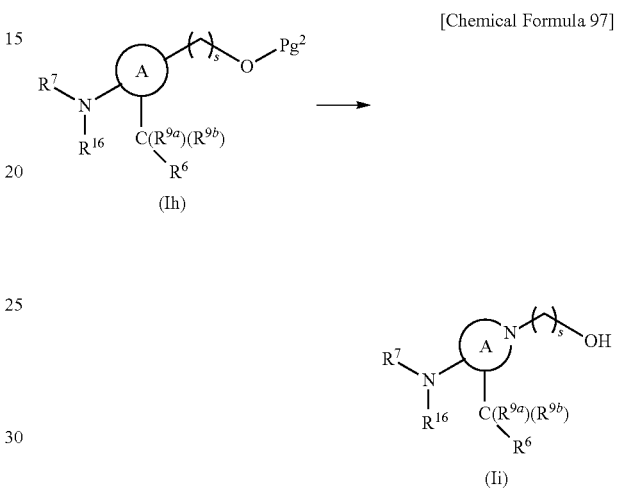

wherein $R^{25}$ is substituted or unsubstituted alkyl, substituted or unsubstituted arylalkyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, or substituted or unsubstituted acyl; $R^{26}$ is hydroxy or halogen; and the other symbols are as defined in Method C.

In other words, the compound of the present invention of the formula (Ig) may be manufactured by reacting Compound (If) obtained by Method G with Compound (ix) in an appropriate solvent in the presence of a base or a condensation agent.

Examples of a base appropriate for use include triethylamine, diisopropylethylamine, and pyridine, and the amount thereof to be used may be one or more equivalents and preferably 1 to 5 equivalents relative to 1 equivalent of Compound (If).

Examples of a condensation agents appropriate for use include condensation agents such as 1-hydroxybenzotriazole or HOAt, 1-ethyl-3-(3-dimethylaminopropyl) carbodiimide hydrochloride, HATU, and PyBOp, and bases such as triethylamine and diisopropylethylamine, and the amount thereof to be used may be one or more equivalents and preferably 1 to 5 equivalents relative to 1 equivalent of Compound (If).

Examples of a solvent appropriate for use include halogenated hydrocarbons (e.g., dichloromethane, chloroform, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, wherein $Pg^2$ is an appropriate protecting group for a hydroxy group; and the other symbols are as defined in Method C.

In other words, the compound of the present invention of the formula (Ii) may be manufactured by subjecting Compound (Ih) obtained by Method A, Method B, Method C, or Method D to deprotection in an appropriate solvent in the presence of an acid.

Examples of an acid appropriate for use include hydrochloric acid, trifluoroacetic acid, and para-toluenesulfonic acid, and the amount thereof to be used may be 0.01 equivalent or more and preferably 0.5 to 3 equivalents relative to 1 equivalent of Compound (Ih).

Examples of a solvent appropriate for use include alcohols (e.g., methanol, ethanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), water, and mixed solvents thereof.

The reaction temperature is between −10 and 200° C. and preferably between 0 and 120° C. The reaction time may be between 10 minutes and 80 hours, which varies depending on the compound.

The obtained desired Compound (Ii) may be purified as necessary by a conventional method (e.g., column chromatography, recrystallization, etc.).

The compounds of Formula (I), Formula (II), and the like are not limited to specific isomers but include all possible isomers (e.g., keto-enol isomers, imine-enamine isomers, diastereoisomers, enantiomers, rotamers or the like), racemates or mixtures thereof. For example, a compound of Formula (I) includes the following tautomer.

[Chemcial Formula 98]

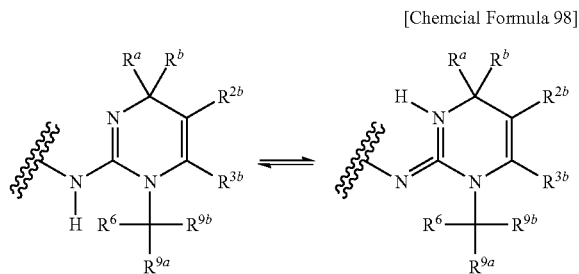

In addition, one or more hydrogen atoms, carbon atoms or other atoms of the compound of Formula (I) can be replaced by an isotope of the hydrogen atom, carbon atom or other atoms. Compounds of Formula (I), Formula (II), and the like include all radiolabeled forms of compounds of Formula (I), Formula (II), and the like. The "radiolabeled," "radiolabeled form" and the like of the compound of Formula (I), Formula (II), and the like are encompassed by the present invention and useful as a research and/or diagnostic tool in metabolism pharmacokinetic studies and in binding assays. It is also useful for a medicament.

One or more hydrogen, carbon and/or other atoms in the compounds of Formula (I), Formula (II), and the like may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds of Formula (I), Formula (II), and the like include the compounds replaced with these isotopes. The compounds replaced with the above isotopes are useful as medicines and include all of radiolabeled compounds of the compound of Formula (I), Formula (II), and the like. A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds of Formula (I), Formula (II), and the like can be prepared using well-known methods in this field of the invention. For example, a tritium-labeled compound of Formula (I), Formula (II), and the like can be prepared by introducing a tritium to a certain compound of Formula (I), Formula (II), and the like, through a catalytic dehalogenation reaction using a tritium. This method comprises reacting with an appropriately-halogenated precursor of the compound of Formula (I), Formula (II), and the like with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds of Formula (I), Formula (II), and the like include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds of Formula (I), Formula (II), and the like of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds of Formula (I), Formula (II), and the like. When the compounds of Formula (I), Formula (II), and the like or pharmaceutically acceptable salts thereof are allowed to stand in the atmosphere, the compounds may absorb water, resulting in attachment of adsorbed water or formation of hydrates. Recrystallization of the compounds of Formula (I), Formula (II), and the like or pharmaceutically acceptable salts thereof may produce crystal polymorphs.

The compounds of Formula (I), Formula (II), and the like of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of Formula (I), Formula (II), and the like through enzymatic oxidation, reduction, hydrolysis or the like under physiological conditions in vivo, compounds that are converted to the compounds of Formula (I), Formula (II), and the like through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds of Formula (I), Formula (II), and the like or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_8-$, $CH_2FSO_3-$, $CF_3CH_2SO_3-$, $p-CH_3O-PhSO_3-$, $PhSO_3-$ and $p-CH_3PhSO_3$.

The compound of the Formula (I), Formula (II), and the like has an antagonistic activity on $P2X_3$ and/or $P2X_3$/s receptor, and therefore, is useful as a therapeutic agent for diseases associated with a $P2X_3$ and/or $P2X_{2/3}$ receptor. Since $P2X_3$ and/or $P2X_{2/3}$ receptor is believed to associate with pain, diseases in urinary system and respiratory disease (Nature 407, 26, 1011-1015 (2000), Nature, Vol. 407, No.

26, 1015-1017 (2000), Non-Patent Document 1, Non-Patent Document 2, Non-Patent Documents 9-11 etc.), the compound of the invention is useful in the treatment, alleviation of symptoms and/or prevention of diseases, such as for example, pain associated with rheumatoid arthritis, pain associated with osteoarthritis, headache, migraine, orofacial pain, toothache, glossagra, pain associated with temporomandibular arthrosis, trigeminal neuralgia, shoulder pain, pain associated with hernia of intervertebral disk, pain associated with cervical spondylosis deformans, pain associated with spinal canal stenosis, pain associated with thoracic outlet syndrome, pain associated with traumatic brachial plexus injury syndrome, pain associated with shoulder-hand syndrome, pain associated with whiplash injury, chest pain, abdominal pain, colic pain, pain associated with cholelithiasis, pain associated with pancreatitis, pain associated with urinary calculosis, pain associated with irritable bowel syndrome, lumbar backache, sciatica, pain associated with bone fracture, pain associated with osteoporosis, joint pain, pain associated with gout, pain associated with cauda equina syndrome, pain associated with ankylosing spondylitis, sore muscle, pain associated with painful spasm, pain associated with myofascial pain syndrome, pain associated with fibromyalgia syndrome, complex regional pain syndrome, pain associated with arteriosclerosis obliterans, pain associated with Buerger's disease, pain associated with Raynaud's phenomenon, pain associated with zoster, causalgic pain, pain associated with entrapment neuropathy, pain associated with carpal canal syndrome, pain associated with diabetes, pain associated with Guillain-Barre syndrome, pain associated with Hansen's disease, pain associated with drug therapy, pain associated with radiation therapy, pain associated with cord injury, pain associated with syringomyelia, pain associated with stroke, thalamic pain, pain associated with deafferentation, sympathetically-maintained pain, ABC syndrome, multiple sclerosis, pain associated with skin disease, cancer pain, postoperative pain, pain associated with injury, pain associated with gangrene, pain associated with somatoform disorder, pain associated with somatization disorder, pain associated with depression, pain associated with Parkinson's disease, knee joint pain, pain associated with arthritis, neuropathic pain such as menstrual pain, intermenstrual pain, labor pain, etc., inflammatory pain, nociceptive pain, psychogenic pain, pains associated with endometriosis, and the like; Overactive bladder, urge incontinence, stress urinary incontinence, reflex incontinence, urinary urgency, neurogenic bladder, unstable bladder, urethritis, urinary tract infections, interstitial cystitis, cystitis, bladder cancer, chemotherapy-induced urinary tract disorder, urinary tract disorders associated with brain disorders such as stroke etc., voiding dysfunction and/or pain, etc. associated with prostatic hyperplasia and/or prostatitis, etc., and the like;
And chronic obstructive pulmonary disease (COPD), asthma, bronchospasm, chronic cough, and the like.

"A pharmaceutical composition having an improving effect of urination disorder" includes a pharmaceutical composition for use to improve the treatment and/or prevention of urination disorder.

The compound of the present invention or the pharmaceutical composition of the present invention can be a drug with reduced side-effect such as effect on motor function because it has a high affinity for ATP receptor, especially P2X$_3$ receptor, and also has high subtype selectivity and high selectivity for other receptors. Also, the compound encompassed by the present invention or the pharmaceutical composition encompassed by the present invention is advantageous because of its high P2X3 receptor inhibitor activity in the presence of RSA, high metabolic stability, high oral absorption, good bioavailability, low clearance, long half-life, prolonged duration of action, low activity of hepatic enzyme inhibition, high unbound fraction in serum and/or high safety etc.

When administering the pharmaceutical composition of the present invention, it can be administered in any method of orally and parenterally methods. In case of oral administration, any forms, which are usually used, such as tablets, powders, capsules, and the like may prepared according to the usual method and administered. In case of parenteral administration, any forms, which are usually used, such as injections and the like can be preferably administered. The compound of the present invention has high oral absorption and is preferably used as an oral agent.

Various pharmaceutical additives such as excipients, binders, disintegrating agents and lubricants suitable for the dosage form can be mixed as necessary in an effective amount of the compound of the present invention, to make the compound into a pharmaceutical composition.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The compound of the present invention can be used in combination of other drugs (hereinafter referred to as a co-administered drug) to increase the activity of the compound, reduce the dose of the compound, or the like. In this case, the timing of administration for a compound of the present invention and the co-administered drug is not limited. They can be administered to the subjects to be treated, at a time or at different times. Furthermore, a compound of the present invention and the co-administered drug can be administered as two formulations independently comprising each active ingredient or a single formulation comprising the both active ingredients.

The dose for co-administered drugs may be appropriately selected in reference to the clinical dose. The compounding ratio of the compounds of the present invention and co-administered drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of co-administered drugs.

In specific embodiments of the compounds of the present invention, compounds of the following Formula (VI), Formula (V), and Formula (VI) having the following $R^r$, $R^o$, and $R^q$ are provided:

[Chemical Formula 99]

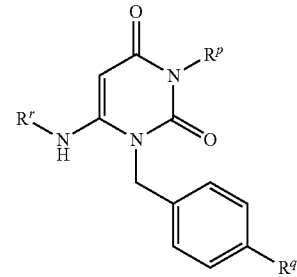

(IV)

TABLE 1

| Compound No | R$^r$ | R$^p$ | R$^q$ |
| --- | --- | --- | --- |
| P-001 | 4-(3-Me-1,2,4-thiadiazol-5-yl)O—Ph | (CH$_2$)$_2$COOH | 4-Cl |
| P-002 | 4-(3-Me-1,2,4-thiadiazol-5-yl)O-3-F—Ph | (CH$_2$)$_2$COOH | 4-Cl |
| P-003 | 4-(4-Pyridyl)O—Ph | (CH$_2$)$_2$COOH | 4-Cl |
| P-004 | 4-(5-CN-2-Pyridyl)O—Ph | (CH$_2$)$_2$COOH | 4-Cl |
| P-005 | 4-(6-CN-2-Pyridyl)O—Ph | (CH$_2$)$_2$COOH | 4-Cl |
| P-006 | 4-(2-CN-4-Pyridyl)O—Ph | (CH$_2$)$_2$COOH | 4-Cl |
| P-007 | 4-(3-F-2-Pyridyl)O—Ph | (CH$_2$)$_2$COOH | 4-Cl |
| P-008 | 4-(3-F-2-Pyridyl)O-3-Me—Ph | (CH$_2$)$_2$COOH | 4-Cl |
| P-009 | 4-(6-F-2-Pyridyl)O—Ph | (CH$_2$)$_2$COOH | 4-Cl |
| P-010 | 4-(6-F-2-Pyridyl)O-3-Me—Ph | (CH$_2$)$_2$COOH | 4-Cl |
| P-011 | 4-(5-F-3-Pyridyl)O—Ph | (CH$_2$)$_2$COOH | 4-Cl |
| P-012 | 4-(2-F-4-Pyridyl)O—Ph | (CH$_2$)$_2$COOH | 4-Cl |
| P-013 | 4-(2-F-4-Pyridyl)O-3-Me—Ph | (CH$_2$)$_2$COOH | 4-Cl |
| P-014 | 4-(2-Cl-4-Pyridyl)O—Ph | (CH$_2$)$_2$COOH | 4-Cl |
| P-015 | 4-(2-Cl-4-Pyridyl)O-3-Me—Ph | (CH$_2$)$_2$COOH | 4-Cl |
| P-016 | 4-(6-MeO-3-Pyridyl)O—Ph | (CH$_2$)$_2$COOH | 4-Cl |
| P-017 | 4-(1-Me-6-oxo-3-Pyridyl)O—Ph | (CH$_2$)$_2$COOH | 4-Cl |
| P-018 | 4-(6-H$_2$NCO-2-Pyridyl)O—Ph | (CH$_2$)$_2$COOH | 4-Cl |
| P-019 | 4-(2-Pyrimidyl)O—Ph | (CH$_2$)$_2$COOH | 4-Cl |
| P-020 | 4-(2-Pyrazinyl)O—Ph | (CH$_2$)$_2$COOH | 4-Cl |
| P-021 | 4-(2-Pyrazinyl)O-3-Me—Ph | (CH$_2$)$_2$COOH | 4-Cl |
| P-022 | 4-(6-Me-2-Pyrazinyl)O—Ph | (CH$_2$)$_2$COOH | 4-Cl |
| P-023 | 4-(5-CN-2-Pyrazinyl)O—Ph | (CH$_2$)$_2$COOH | 4-Cl |
| P-024 | 4-(4-Pyridazinyl)O—Ph | (CH$_2$)$_2$COOH | 4-Cl |
| P-025 | 2-Et-3-Me-benzofuran-5-yl | (CH$_2$)$_2$COOH | 4-Cl |
| P-026 | 2-Et-benzothiazol-6-yl | (CH$_2$)$_2$COOH | 4-Cl |
| P-027 | 3-F-4-i-PrO—Ph | CH$_2$COH(CH$_2$OH)$_2$ | 4-Cl |
| P-028 | 3-Cl-4-EtO—Ph | CH$_2$COH(CH$_2$OH)$_2$ | 4-Cl |
| P-029 | 3-Me-4-i-PrO—Ph | CH$_2$COH(CH$_2$OH)$_2$ | 4-Cl |
| P-030 | 4-c-BuO—Ph | CH$_2$COH(CH$_2$OH)$_2$ | 4-Cl |
| P-031 | 4-c-PrCH$_2$O—Ph | CH$_2$COH(CH$_2$OH)$_2$ | 4-Cl |
| P-032 | 4-(3-isoxazolyl)O—Ph | CH$_2$COH(CH$_2$OH)$_2$ | 4-Cl |
| P-033 | 4-(2-thiazolyl)O—Ph | CH$_2$COH(CH$_2$OH)$_2$ | 4-Cl |
| P-034 | 4-(6-F-2-Pyridyl)O—Ph | CH$_2$COH(CH$_2$OH)$_2$ | 4-Cl |
| P-035 | 4-(3-Pyridazinyl)O—Ph | CH$_2$COH(CH$_2$OH)$_2$ | 4-Cl |
| P-036 | 2-Et-benzofuran-5-yl | CH$_2$COH(CH$_2$OH)$_2$ | 4-Cl |
| P-037 | 2-Et-3-Me-benzofuran-5-yl | CH$_2$COH(CH$_2$OH)$_2$ | 4-Cl |
| P-038 | 4-(3-HOCO-5-F—PhO)—Ph | Et | 4-Cl |
| P-039 | 4-(4-HOCO-3-F—PhO)—Ph | Et | 4-Cl |
| P-040 | 4-(3-HOCOCH=CH—PhO)—Ph | Et | 4-Cl |
| P-041 | 4-(3-HOCOCH$_2$CH$_2$—PhO)—Ph | Et | 4-Cl |
| P-042 | 4-(5-HOCO-2-furanyl)O—Ph | Pr | 4-Cl |
| P-043 | 4-(4-HOCO-2-oxazolyl)O—Ph | Pr | 4-Cl |
| P-044 | 4-(4-HOCO-2-oxazolyl)O-3-F—Ph | Et | 4-Cl |
| P-045 | 4-(4-HOCO-2-oxazolyl)O-3-F—Ph | Pr | 4-Cl |

TABLE 2

| Compound No | R$^r$ | R$^p$ | R$^q$ |
| --- | --- | --- | --- |
| P-046 | 4-(4-HOCO-2-oxazolyl)O-3-Me—Ph | Pr | 4-Cl |
| P-047 | 4-(5-HOCO-3-isoxazolyl)O—Ph | Et | 4-Cl |
| P-048 | 4-(5-HOCO-3-isoxazolyl)O—Ph | Pr | 4-Cl |
| P-049 | 4-(4-HOCO-2-thiazolyl)O—Ph | Et | 4-Cl |
| P-050 | 4-(4-HOCO-2-thiazolyl)O—Ph | Pr | 4-Cl |
| P-051 | 4-(4-HOCO-5-Me-2-thiazolyl)O—Ph | Et | 4-Cl |
| P-052 | 4-(4-HOCO-5-Me-2-thiazolyl)O—Ph | Pr | 4-Cl |
| P-053 | 4-(5-HOCO-2-thiazolyl)O—Ph | Pr | 4-Cl |
| P-054 | 4-(4-HOCO-2-thiazolyl)O-3-Me—Ph | Et | 4-Cl |
| P-055 | 4-(4-HOCO-2-thiazolyl)O—F—Me—Ph | Et | 4-Cl |
| P-056 | 4-(5-HOCO-2-thiazolyl)O-3-Me—Ph | Et | 4-Cl |
| P-057 | 4-(5-HOCO-2-thiazolyl)O-3-MeO—Ph | Et | 4-Cl |
| P-058 | 4-(5-HOCO-2-thiazolyl)O-3-F—Ph | Et | 4-Cl |
| P-059 | 4-(5-HOCO-3-isothiazolyl)O—Ph | Et | 4-Cl |
| P-060 | 4-(5-HOCO-3-isothiazolyl)O—Ph | Pr | 4-Cl |
| P-061 | 4-(4-HOCO-2-Pyridyl)O—Ph | Et | 4-Cl |
| P-062 | 4-(4-HOCO-2-Pyridyl)O—Ph | Pr | 4-Cl |
| P-063 | 4-(5-HOCO-2-Pyridyl)O—Ph | Et | 4-Cl |
| P-064 | 4-(5-HOCO-2-Pyridyl)O—Ph | Pr | 4-Cl |
| P-065 | 4-(6-HOCO-2-Pyridyl)O—Ph | Pr | 4-Cl |
| P-066 | 4-(6-HOCO-2-Pyridyl)O—Ph | Pr | 4-F |
| P-067 | 4-(5-HOCO-3-Pyridyl)O—Ph | Et | 4-Cl |
| P-068 | 4-(5-HOCO-3-Pyridyl)O—Ph | Pr | 4-Cl |
| P-069 | 4-(6-HOCO-3-Pyridyl)O—Ph | Et | 4-Cl |
| P-070 | 4-(6-HOCO-3-Pyridyl)O—Ph | Pr | 4-Cl |
| P-071 | 4-(2-HOCO-4-Pyridyl)O—Ph | Et | 4-Cl |
| P-072 | 4-(2-HOCO-4-Pyridyl)O—Ph | Et | 4-F |
| P-073 | 4-(2-HOCO-4-Pyridyl)O—Ph | Pr | 4-Cl |
| P-074 | 4-(2-HOCO-4-Pyridyl)O—Ph | Pr | 4-F |
| P-075 | 4-(2-HOCO-4-Pyridyl)O-3-F—Ph | Et | 4-Cl |
| P-076 | 4-(4-HOCO-2-Pyridyl)O-3-Me—Ph | Et | 4-Cl |
| P-077 | 4-(4-HOCO-2-Pyridyl)O-3-Me—Ph | Pr | 4-Cl |
| P-078 | 4-(5-HOCO-2-Pyridyl)O-3-Me—Ph | Et | 4-Cl |
| P-079 | 4-(5-HOCO-2-Pyridyl)O-3-Me—Ph | Pr | 4-Cl |
| P-080 | 4-(5-HOCO-2-Pyridyl)O-3-Me—Ph | Pr | 4-F |
| P-081 | 4-(6-HOCO-2-Pyridyl)O-3-Me—Ph | Pr | 4-Cl |
| P-082 | 4-(6-HOCO-2-Pyridyl)O-3-Me—Ph | Pr | 4-F |
| P-083 | 4-(5-HOCO-3-Pyridyl)O-3-Me—Ph | Et | 4-Cl |
| P-084 | 4-(5-HOCO-3-Pyridyl)O-3-Me—Ph | Pr | 4-Cl |
| P-085 | 4-(5-HOCO-3-Pyridyl)O-3-Me—Ph | Pr | 4-F |
| P-086 | 4-(6-HOCO-3-Pyridyl)O-3-Me—Ph | Et | 4-Cl |
| P-087 | 4-(6-HOCO-3-Pyridyl)O-3-Me—Ph | Pr | 4-Cl |
| P-088 | 4-(2-HOCO-4-Pyridyl)O-3-Me—Ph | Et | 4-Cl |
| P-089 | 4-(2-HOCO-4-Pyridyl)O-3-Me—Ph | Pr | 4-Cl |
| P-090 | 4-(2-HOCO-4-Pyridyl)O-3-Me—Ph | Pr | 4-F |

TABLE 3

| Compound No | $R^r$ | $R^p$ | $R^q$ |
|---|---|---|---|
| P-091 | 4-(6-HOCO-2-Pyridyl)O-3-MeO—Ph | Et | 4-Cl |
| P-092 | 4-(2-HOCO-4-Pyridyl)O-3-MeO—Ph | Et | 4-Cl |
| P-093 | 4-(6-HOCOCH$_2$NH-3-Pyridyl)O—Ph | Et | 4-Cl |
| P-094 | 4-(2-HOCOCH$_2$NH-4-Pyridyl)O—Ph | Et | 4-Cl |
| P-095 | 4-(4-HOCO-2-Pyrimidyl)O—Ph | Et | 4-Cl |
| P-096 | 4-(4-HOCO-2-Pyrimidyl)O—Ph | Pr | 4-Cl |
| P-097 | 4-(5-HOCO-2-Pyrimidyl)O—Ph | Et | 4-Cl |
| P-098 | 4-(6-HOCO-4-Pyrimidyl)O—Ph | Et | 4-Cl |
| P-099 | 4-(6-HOCO-4-Pyrimidyl)O-3-Me—Ph | Et | 4-Cl |
| P-100 | 4-(6-HOCO-4-Pyrimidyl)O-3-Me—Ph | Pr | 4-Cl |
| P-101 | 4-(6-HOCO-4-Pyrimidyl)O-3-Me—Ph | Pr | 4-F |
| P-102 | 4-(2-HOCO-5-Pyrimidyl)O—Ph | Et | 4-Cl |
| P-103 | 4-(5-HOCO-2-Pyrazinyl)O—Ph | Et | 4-Cl |
| P-104 | 4-(5-HOCO-2-Pyrazinyl)O—Ph | Pr | 4-Cl |
| P-105 | 4-(5-HOCO-2-Pyrazinyl)O-3-Me—Ph | Et | 4-Cl |
| P-106 | 4-(5-HOCO-2-Pyrazinyl)O-3-Me—Ph | Pr | 4-Cl |
| P-107 | 4-(5-HOCO-2-Pyrazinyl)O-3-Me—Ph | Pr | 4-F |
| P-108 | 4-(6-HOCO-2-Pyrazinyl)O—Ph | Et | 4-Cl |
| P-109 | 4-(6-HOCO-2-Pyrazinyl)O—Ph | Pr | 4-Cl |
| P-110 | 4-(6-HOCO-3-Pyridazinyl)O—Ph | Et | 4-Cl |
| P-111 | 4-(6-HOCO-3-Pyridazinyl)O—Ph | Pr | 4-Cl |
| P-112 | 4-(6-HOCO-3-Pyridazinyl)O-3-Me—Ph | Et | 4-Cl |
| P-113 | 4-(6-HOCO-3-Pyridazinyl)O-3-Me—Ph | Pr | 4-Cl |
| P-114 | 4-(4-H$_2$NCO-2-thiazolyl)O—Ph | Me | 4-Cl |
| P-115 | 4-(4-H$_2$NCO-2-thiazolyl)O—Ph | Et | 4-Cl |
| P-116 | 4-(5-H$_2$NCO-2-thiazolyl)O—Ph | Me | 4-Cl |
| P-117 | 4-(4-H$_2$NCO-2-Pyridyl)O—Ph | Me | 4-Cl |
| P-118 | 4-(5-H$_2$NCO-2-Pyridyl)O—Ph | Me | 4-Cl |
| P-119 | 4-(6-H$_2$NCO-2-Pyridyl)O—Ph | Me | 4-Cl |
| P-120 | 4-(6-H$_2$NCO-3-Pyridyl)O—Ph | Et | 4-Cl |
| P-121 | 4-(2-H$_2$NCO-4-Pyridyl)O—Ph | Me | 4-Cl |
| P-122 | 4-(6-H$_2$NCOCH$_2$NH-3-Pyridyl)O—Ph | Et | 4-Cl |
| P-123 | 4-(2-H$_2$NCOCH$_2$NH-4-Pyridyl)O—Ph | Et | 4-Cl |
| P-124 | 4-(2-H$_2$NCOCH$_2$O-4-Pyridyl)O—Ph | Et | 4-Cl |
| P-125 | 4-(4-H$_2$NCO-2-Pyrimidyl)O—Ph | Et | 4-Cl |
| P-126 | 4-(2-H$_2$NCO-4-Pyrimidyl)O—Ph | Et | 4-Cl |
| P-127 | 4-(5-H$_2$NCO-2-Pyrazinyl)O—Ph | Et | 4-Cl |
| P-128 | 4-(5-H$_2$NCO-2-Pyrazinyl)O—Ph | Me | 4-Cl |
| P-129 | 4-(6-H$_2$NCO-2-Pyrazinyl)O—Ph | Et | 4-Cl |
| P-130 | 4-(6-H$_2$NCO-2-Pyrazinyl)O—Ph | Me | 4-Cl |
| P-131 | 4-(6-H$_2$NCO-3-Pyridazinyl)O—Ph | Et | 4-Cl |
| P-132 | 4-(6-H$_2$NCO-3-Pyridazinyl)O—Ph | Me | 4-Cl |

TABLE 3-continued

| Compound No | $R^r$ | $R^p$ | $R^q$ |
|---|---|---|---|
| P-133 | 4-(6-H$_2$NCO-3-Pyridazinyl)O-3-Me—Ph | Et | 4-Cl |
| P-134 | 4-(4-CN-2-Pyridyl)O—Ph | Me | 4-Cl |
| P-135 | 4-(5-CN-2-Pyridyl)O—Ph | Me | 4-Cl |

TABLE 4

| Compound No | $R^r$ | $R^p$ | $R^q$ |
|---|---|---|---|
| P-136 | 4-(6-CN-3-Pyridyl)O—Ph | Me | 4-Cl |
| P-137 | 4-(2-CN-4-Pyridyl)O—Ph | Me | 4-Cl |
| P-138 | 4-(6-NCNHCO-2-Pyridyl)O—Ph | Et | 4-Cl |
| P-139 | 4-(6-AcNH-3-Pyridyl)O—Ph | Me | 4-Cl |
| P-140 | 4-(2-AcNH-4-Pyridyl)O—Ph | Me | 4-Cl |
| P-141 | 4-(2-AcNH-4-Pyridyl)O—Ph | Et | 4-F |
| P-142 | 4-(2-CN-4-Pyrimidyl)O—Ph | Et | 4-Cl |
| P-143 | 4-(2-CN-5-Pyrimidyl)O—Ph | Me | 4-Cl |
| P-144 | 4-(5-CN-2-Pyrazinyl)O—Ph | Et | 4-Cl |
| P-145 | 4-(5-CN-2-Pyrazinyl)O—Ph | Et | 4-F |
| P-146 | 4-(5-CN-2-Pyrazinyl)O—Ph | Me | 4-Cl |
| P-147 | 4-(6-CN-3-Pyridazinyl)O—Ph | Et | 4-Cl |

[Chemical Formula 100]

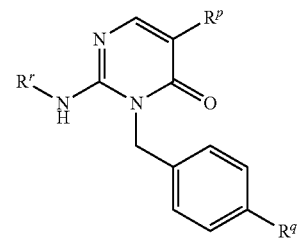

(V)

TABLE 5

| Compound No | $R^r$ | $R^p$ | $R^q$ |
|---|---|---|---|
| Q-001 | 4-(3-Me-1,2,4-thiadiazol-5-yl)O—Ph | CONH$_2$ | 4-Cl |
| Q-002 | 4-(3-Me-1,2,4-thiadiazol-5-yl)O-3-F—Ph | CONH$_2$ | 4-Cl |
| Q-003 | 4-(4-Pyridyl)O—Ph | CONH$_2$ | 4-Cl |
| Q-004 | 4-(5-CN-2-Pyridyl)O—Ph | CONH$_2$ | 4-Cl |
| Q-005 | 4-(6-CN-2-Pyridyl)O—Ph | CONH$_2$ | 4-Cl |
| Q-006 | 4-(2-CN-4-Pyridyl)O—Ph | CONH$_2$ | 4-Cl |
| Q-007 | 4-(3-F-2-Pyridyl)O—Ph | CONH$_2$ | 4-Cl |
| Q-008 | 4-(3-F-2-Pyridyl)O-3-Me—Ph | CONH$_2$ | 4-Cl |
| Q-009 | 4-(6-F-2-Pyridyl)O—Ph | CONH$_2$ | 4-Cl |
| Q-010 | 4-(6-F-2-Pyridyl)O-3-Me—Ph | CONH$_2$ | 4-Cl |
| Q-011 | 4-(5-F-3-Pyridyl)O—Ph | CONH$_2$ | 4-Cl |
| Q-012 | 4-(2-F-4-Pyridyl)O—Ph | CONH$_2$ | 4-Cl |
| Q-013 | 4-(2-F-4-Pyridyl)O-3-Me—Ph | CONH$_2$ | 4-Cl |
| Q-014 | 4-(2-Cl-4-Pyridyl)O—Ph | CONH$_2$ | 4-Cl |
| Q-015 | 4-(2-Cl-4-Pyridyl)O-3-Me—Ph | CONH$_2$ | 4-Cl |
| Q-016 | 4-(6-MeO-3-Pyridyl)O—Ph | CONH$_2$ | 4-Cl |
| Q-017 | 4-(1-Me-6-oxo-3-Pyridyl)O—Ph | CONH$_2$ | 4-Cl |
| Q-018 | 4-(3-HOCO—PhO)—Ph | CONH$_2$ | 4-Cl |
| Q-019 | 4-(3-HOCO-5-F—PhO)—Ph | CONH$_2$ | 4-Cl |
| Q-020 | 4-(5-HOCO-2-thiazolyl)O—Ph | CONH$_2$ | 4-Cl |
| Q-021 | 4-(5-HOCO-4-Me-2-thiazolyl)O—Ph | CONH$_2$ | 4-Cl |
| Q-022 | 4-(6-HOCO-2-Pyridyl)O—Ph | CONH$_2$ | 4-Cl |
| Q-023 | 4-(5-HOCO-3-Pyridyl)O—Ph | CONH$_2$ | 4-Cl |
| Q-024 | 4-(6-H$_2$NCO-2-Pyridyl)O—Ph | CONH$_2$ | 4-Cl |
| Q-025 | 4-(2-Pyrimidyl)O—Ph | CONH$_2$ | 4-Cl |
| Q-026 | 4-(2-Pyrazinyl)O—Ph | CONH$_2$ | 4-Cl |
| Q-027 | 4-(2-Pyrazinyl)O-3-Me—Ph | CONH$_2$ | 4-Cl |
| Q-028 | 4-(6-Me-2-Pyrazinyl)O—Ph | CONH$_2$ | 4-Cl |
| Q-029 | 4-(5-CN-2-Pyrazinyl)O—Ph | CONH$_2$ | 4-Cl |

TABLE 5-continued

| Compound No | R$^r$ | R$^p$ | R$^q$ |
|---|---|---|---|
| Q-030 | 4-(4-Pyridazinyl)O—Ph | CONH$_2$ | 4-Cl |
| Q-031 | 2-Et-benzothiazol-6-yl | CONH$_2$ | 4-Cl |
| Q-032 | 4-(3-Me-1,2,4-thiadiazol-5-yl)O—Ph | CONH-4-THP | 4-Cl |
| Q-033 | 4-(3-Me-1,2,4-thiadiazol-5-yl)O-3-F—Ph | CONH-4-THP | 4-Cl |
| Q-034 | 4-(4-Pyridyl)O—Ph | CONH-4-THP | 4-Cl |
| Q-035 | 4-(5-CN-2-Pyridyl)O—Ph | CONH-4-THP | 4-Cl |
| Q-036 | 4-(6-CN-2-Pyridyl)O—Ph | CONH-4-THP | 4-Cl |
| Q-037 | 4-(2-CN-4-Pyridyl)O—Ph | CONH-4-THP | 4-Cl |
| Q-038 | 4-(3-F-2-Pyridyl)O—Ph | CONH-4-THP | 4-Cl |
| Q-039 | 4-(3-F-2-Pyridyl)O-3-Me—Ph | CONH-4-THP | 4-Cl |
| Q-040 | 4-(6-F-2-Pyridyl)O—Ph | CONH-4-THP | 4-Cl |
| Q-041 | 4-(6-F-2-Pyridyl)O-3-Me—Ph | CONH-4-THP | 4-Cl |
| Q-042 | 4-(5-F-3-Pyridyl)O—Ph | CONH-4-THP | 4-Cl |
| Q-043 | 4-(2-F-4-Pyridyl)O—Ph | CONH-4-THP | 4-Cl |
| Q-044 | 4-(2-F-4-Pyridyl)O-3-Me—Ph | CONH-4-THP | 4-Cl |
| Q-045 | 4-(2-Cl-4-Pyridyl)O—Ph | CONH-4-THP | 4-Cl |

TABLE 6

| Compound No | R$^r$ | R$^p$ | R$^q$ |
|---|---|---|---|
| Q-046 | 4-(2-Cl-4-Pyridyl)O-3-Me—Ph | CONH-4-THP | 4-Cl |
| Q-047 | 4-(6-MeO-3-Pyridyl)O—Ph | CONH-4-THP | 4-Cl |
| Q-048 | 4-(1-Me-6-oxo-3-Pyridyl)O—Ph | CONH-4-THP | 4-Cl |
| Q-049 | 4-(6-H$_2$NCO-2-Pyridyl)O—Ph | CONH-4-THP | 4-Cl |
| Q-050 | 4-(2-Pyrimidyl)O—Ph | CONH-4-THP | 4-Cl |
| Q-051 | 4-(2-Pyrazinyl)O—Ph | CONH-4-THP | 4-Cl |
| Q-052 | 4-(2-Pyrazinyl)O-3-Me—Ph | CONH-4-THP | 4-Cl |
| Q-053 | 4-(6-Me-2-Pyrazinyl)O—Ph | CONH-4-THP | 4-Cl |
| Q-054 | 4-(5-CN-2-Pyrazinyl)O—Ph | CONH-4-THP | 4-Cl |
| Q-055 | 4-(4-Pyridazinyl)O—Ph | CONH-4-THP | 4-Cl |
| Q-056 | 2-Et-benzothiazol-6-yl | CONH-4-THP | 4-Cl |
| Q-057 | 4-(3-Me-1,2,4-thiadiazol-5-yl)O—Ph | NHCO-4-THP | 4-Cl |
| Q-058 | 4-(3-Me-1,2,4-thtadiazol-5-yl)O-3-F—Ph | NHCO-4-THP | 4-Cl |
| Q-059 | 4-(4-Pyridyl)O—Ph | NHCO-4-THP | 4-Cl |
| Q-060 | 4-(5-CN-2-Pyridyl)O—Ph | NHCO-4-THP | 4-Cl |
| Q-061 | 4-(6-CN-2-Pyridyl)O—Ph | NHCO-4-THP | 4-Cl |
| Q-062 | 4-(2-CN-4-Pyridyl)O—Ph | NHCO-4-THP | 4-Cl |
| Q-063 | 4-(3-F-2-Pyridyl)O—Ph | NHCO-4-THP | 4-Cl |
| Q-064 | 4-(3-F-2-Pyridyl)O-3-Me—Ph | NHCO-4-THP | 4-Cl |
| Q-065 | 4-(6-F-2-Pyridyl)O—Ph | NHCO-4-THP | 4-Cl |
| Q-066 | 4-(6-F-2-Pyridyl)O-3-Me—Ph | NHCO-4-THP | 4-Cl |
| Q-067 | 4-(2-F-4-Pyridyl)O—Ph | NHCO-4-THP | 4-Cl |
| Q-068 | 4-(2-F-4-Pyridyl)O-3-Me—Ph | NHCO-4-THP | 4-Cl |
| Q-069 | 4-(2-Cl-4-Pyridyl)O—Ph | NHCO-4-THP | 4-Cl |
| Q-070 | 4-(2-Cl-4-Pyridyl)O-3-Me—Ph | NHCO-4-THP | 4-Cl |
| Q-071 | 4-(6-MeO-3-Pyridyl)O—Ph | NHCO-4-THP | 4-Cl |
| Q-072 | 4-(1-Me-6-oxo-3-Pyridyl)O—Ph | NHCO-4-THP | 4-Cl |
| Q-073 | 4-(3-HOCO—PhO)—Ph | NHCO-4-THP | 4-Cl |
| Q-074 | 4-(3-HOCO-5-F—PhO)—Ph | NHCO-4-THP | 4-Cl |
| Q-076 | 4-(5-HOCO-2-thiazolyl)O—Ph | NHCO-4-THP | 4-Cl |
| Q-076 | 4-(5-HOCO-4-Me-2-thiazolyl)O—Ph | NHCO-4-THP | 4-Cl |
| Q-077 | 4-(6-HOCO-2-Pyridyl)O—Ph | NHCO-4-THP | 4-Cl |
| Q-079 | 4-(2-Pyrimidyl)O—Ph | NHCO-4-THP | 4-Cl |
| Q-080 | 4-(2-Pyrazinyl)O—Ph | NHCO-4-THP | 4-Cl |
| Q-081 | 4-(2-Pyrazinyl)O-3-Me—Ph | NHCO-4-THP | 4-Cl |
| Q-082 | 4-(6-Me-2-Pyrazinyl)O—Ph | NHCO-4-THP | 4-Cl |
| Q-083 | 4-(5-CN-2-Pyrazinyl)O—Ph | NHCO-4-THP | 4-Cl |
| Q-084 | 4-(4-Pyridazinyl)O—Ph | NHCO-4-THP | 4-Cl |
| Q-085 | 4-(3-Me-1,2,4-thiadiazol-5-yl)O—Ph | NHAc | 4-Cl |
| Q-086 | 4-(3-Me-1,2,4-thiadiazol-5-yl)O-3-F—Ph | NHAc | 4-Cl |
| Q-087 | 4-(4-Pyridyl)O—Ph | NHAc | 4-Cl |
| Q-088 | 4-(5-CN-2-Pyridyl)O—Ph | NHAc | 4-Cl |
| Q-089 | 4-(6-CN-2-Pyridyl)O—Ph | NHAc | 4-Cl |
| Q-090 | 4-(2-CN-4-Pyridyl)O—Ph | NHAc | 4-Cl |

TABLE 7

| Compound No | R^r | R^p | R^q |
|---|---|---|---|
| Q-091 | 4-(3-F-2-Pyridyl)O—Ph | NHAc | 4-Cl |
| Q-092 | 4-(3-F-2-Pyridyl)O-3-Me—Ph | NHAc | 4-Cl |
| Q-093 | 4-(6-F-2-Pyridyl)O—Ph | NHAc | 4-Cl |
| Q-094 | 4-(6-F-2-Pyridyl)O-3-Me—Ph | NHAc | 4-Cl |
| Q-095 | 4-(5-F-3-Pyridyl)O—Ph | NHAc | 4-Cl |
| Q-096 | 4-(2-F-4-Pyridyl)O—Ph | NHAc | 4-Cl |
| Q-097 | 4-(2-F-4-Pyridyl)O-3-Me—Ph | NHAc | 4-Cl |
| Q-098 | 4-(2-Cl-4-Pyridyl)O—Ph | NHAc | 4-Cl |
| Q-099 | 4-(2-Cl-4-Pyridyl)O-3-Me—Ph | NHAc | 4-Cl |
| Q-100 | 4-(6-MeO-3-Pyridyl)O—Ph | NHAc | 4-Cl |
| Q-101 | 4-(1-Me-6-oxo-3-Pyridyl)O—Ph | NHAc | 4-Cl |
| Q-102 | 4-(3-HOCO—PhO)—Ph | NHAc | 4-Cl |
| Q-103 | 4-(3-HOCO-5-F—PhO)—Ph | NHAc | 4-Cl |
| Q-104 | 4-(5-HOCO-2-thiazolyl)O—Ph | NHAc | 4-Cl |
| Q-105 | 4-(5-HOCO-4-Me-2-thiazolyl)O—Ph | NHAc | 4-Cl |
| Q-106 | 4-(6-HOCO-2-Pyridyl)O—Ph | NHAc | 4-Cl |
| Q-107 | 4-(5-HOCO-3-Pyridyl)O—Ph | NHAc | 4-Cl |
| Q-108 | 4-(6-H$_2$NCO-2-Pyridyl)O—Ph | NHAc | 4-Cl |
| Q-109 | 4-(2-Pyrimidyl)O—Ph | NHAc | 4-Cl |
| Q-110 | 4-(2-Pyrazinyl)O—Ph | NHAc | 4-Cl |
| Q-111 | 4-(2-Pyrazinyl)O-3-Me—Ph | NHAc | 4-Cl |
| Q-112 | 4-(6-Me-2-Pyrazinyl)O—Ph | NHAc | 4-Cl |
| Q-113 | 4-(5-CN-2-Pyrazinyl)O—Ph | NHAc | 4-Cl |
| Q-114 | 4-(4-Pyridazinyl)O—Ph | NHAc | 4-Cl |
| Q-115 | 2-Et-3-Me-benzofuran-5-yl | NHAc | 4-Cl |
| Q-116 | 2-Et-benzothiazol-6-yl | NHAc | 4-Cl |
| Q-117 | 4-(3-Me-1,2,4-thiadiazol-5-yl)O—Ph | NHCOEt | 4-Cl |
| Q-118 | 4-(3-Me-1,2,4-thiadiazol-5-yl)O-3-F—Ph | NHCOEt | 4-Cl |
| Q-119 | 4-(4-Pyridyl)O—Ph | NHCOEt | 4-Cl |
| Q-120 | 4-(5-CN-2-Pyridyl)O—Ph | NHCOEt | 4-Cl |
| Q-121 | 4-(2-CN-4-Pyridyl)O—Ph | NHCOEt | 4-Cl |
| Q-122 | 4-(3-F-2-Pyridyl)O—Ph | NHCOEt | 4-Cl |
| Q-123 | 4-(3-F-2-Pyridyl)O-3-Me—Ph | NHCOEt | 4-Cl |
| Q-124 | 4-(6-F-2-Pyridyl)O—Ph | NHCOEt | 4-Cl |
| Q-125 | 4-(6-F-2-Pyridyl)O-3-Me—Ph | NHCOEt | 4-Cl |
| Q-126 | 4-(5-F-3-Pyridyl)O—Ph | NHCOEt | 4-Cl |
| Q-127 | 4-(2-F-4-Pyridyl)O—Ph | NHCOEt | 4-Cl |
| Q-128 | 4-(2-F-4-Pyridyl)O-3-Me—Ph | NHCOEt | 4-Cl |
| Q-129 | 4-(2-Cl-4-Pyridyl)O—Ph | NHCOEt | 4-Cl |
| Q-130 | 4-(2-Cl-4-Pyridyl)O-3-Me—Ph | NHCOEt | 4-Cl |
| Q-131 | 4-(6-MeO-3-Pyridyl)O—Ph | NHCOEt | 4-Cl |
| Q-132 | 4-(1-Me-6-oxo-3-Pyridyl)O—Ph | NHCOEt | 4-Cl |
| Q-133 | 4-(3-HOCO—PhO)—Ph | NHCOEt | 4-Cl |
| Q-134 | 4-(3-HOCO-5-F—PhO)—Ph | NHCOEt | 4-Cl |
| Q-135 | 4-(5-HOCO-2-thiazolyl)O—Ph | NHCOEt | 4-Cl |

TABLE 8

| Compound No | R^r | R^p | R^q |
|---|---|---|---|
| Q-136 | 4-(5-HOCO-4-Me-2-thiazolyl)O—Ph | NHCOEt | 4-Cl |
| Q-137 | 4-(6-HOCO-2-Pyridyl)O—Ph | NHCOEt | 4-Cl |
| Q-138 | 4-(5-HOCO-3-Pyridyl)O—Ph | NHCOEt | 4-Cl |
| Q-139 | 4-(6-H$_2$NCO-2-Pyridyl)O—Ph | NHCOEt | 4-Cl |
| Q-140 | 4-(2-Pyrimidyl)O—Ph | NHCOEt | 4-Cl |
| Q-141 | 4-(2-Pyrazinyl)O—Ph | NHCOEt | 4-Cl |
| Q-142 | 4-(2-Pyrazinyl)O-3-Me—Ph | NHCOEt | 4-Cl |
| Q-143 | 4-(6-Me-2-Pyrazinyl)O—Ph | NHCOEt | 4-Cl |
| Q-144 | 4-(5-CN-2-Pyrazinyl)O—Ph | NHCOEt | 4-Cl |
| Q-145 | 4-(4-Pyridazinyl)O—Ph | NHCOEt | 4-Cl |
| Q-146 | 2-Et-3-Me-benzofuran-5-yl | NHCOEt | 4-Cl |
| Q-147 | 2-Et-benzothiazol-6-yl | NHCOEt | 4-Cl |
| Q-148 | 3-Cl-4-i-PrO—Ph | NHCOOMe | 4-Cl |
| Q-149 | 4-(3-Me-1,2,4-thiadiazol-5-yl)O—Ph | NHCOOMe | 4-Cl |
| Q-150 | 4-(3-Me-1,2,4-thiadiazol-5-yl)O-3-F—Ph | NHCOOMe | 4-Cl |
| Q-151 | 4-(4-Pyridyl)O—Ph | NHCOOMe | 4-Cl |
| Q-152 | 4-(5-CN-2-Pyridyl)O—Ph | NHCOOMe | 4-Cl |
| Q-153 | 4-(2-CN-4-Pyridyl)O—Ph | NHCOOMe | 4-Cl |
| Q-154 | 4-(3-F-2-Pyridyl)O—Ph | NHCOOMe | 4-Cl |
| Q-155 | 4-(3-F-2-Pyridyl)O-3-Me—Ph | NHCOOMe | 4-Cl |
| Q-156 | 4-(6-F-2-Pyridyl)O—Ph | NHCOOMe | 4-Cl |
| Q-157 | 4-(6-F-2-Pyridyl)O-3-Me—Ph | NHCOOMe | 4-Cl |
| Q-158 | 4-(5-F-3-Pyridyl)O—Ph | NHCOOMe | 4-Cl |
| Q-159 | 4-(2-F-4-Pyridyl)O—Ph | NHCOOMe | 4-Cl |
| Q-160 | 4-(2-F-4-Pyridyl)O-3-Me—Ph | NHCOOMe | 4-Cl |

TABLE 8-continued

| Compound No | $R^r$ | $R^p$ | $R^q$ |
|---|---|---|---|
| Q-161 | 4-(2-Cl-4-Pyridyl)O—Ph | NHCOOMe | 4-Cl |
| Q-162 | 4-(2-Cl-4-Pyridyl)O-3-Me—Ph | NHCOOMe | 4-Cl |
| Q-163 | 4-(6-MeO-3-Pyridyl)O—Ph | NHCOOMe | 4-Cl |
| Q-164 | 4-(1-Me-6-oxo-3-Pyridyl)O—Ph | NHCOOMe | 4-Cl |
| Q-165 | 4-(3-HOCO—PhO)—Ph | NHCOOMe | 4-Cl |
| Q-166 | 4-(3-HOCO-5-F—PhO)—Ph | NHCOOMe | 4-Cl |
| Q-167 | 4-(5-HOCO-2-thiazolyl)O—Ph | NHCOOMe | 4-Cl |
| Q-168 | 4-(5-HOCO-4-Me-2-thiazolyl)O—Ph | NHCOOMe | 4-Cl |
| Q-169 | 4-(6-HOCO-2-Pyridyl)O—Ph | NHCOOMe | 4-Cl |
| Q-170 | 4-(5-HOCO-3-Pyridyl)O—Ph | NHCOOMe | 4-Cl |
| Q-171 | 4-(2-Pyrimidyl)O—Ph | NHCOOMe | 4-Cl |
| Q-172 | 4-(2-Pyrazinyl)O—Ph | NHCOOMe | 4-Cl |
| Q-173 | 4-(2-Pyrazinyl)O-3-Me—Ph | NHCOOMe | 4-Cl |
| Q-174 | 4-(6-Me-2-Pyrazinyl)O—Ph | NHCOOMe | 4-Cl |
| Q-175 | 4-(5-CN-2-Pyrazinyl)O—Ph | NHCOOMe | 4-Cl |
| Q-176 | 4-(4-Pyridazinyl)O—Ph | NHCOOMe | 4-Cl |
| Q-177 | 2-Et-3-Me-benzofuran-5-yl | NHCOOMe | 4-Cl |
| Q-178 | 2-Et-benzothiazol-6-yl | NHCOOMe | 4-Cl |

[Chemical Formula 101]

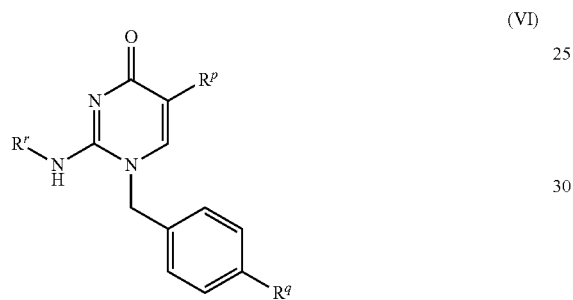

(VI)

TABLE 9

| Compound No | $R^r$ | $R^p$ | $R^q$ |
|---|---|---|---|
| R-001 | 4-(3-Me-1,2,4-thiadiazol-5-yl)O—Ph | $(CH_2)_2COOH$ | 4-Cl |
| R-002 | 4-(3-Me-1,2,4-thiadiazol-5-yl)O-3-F—Ph | $(CH_2)_2COOH$ | 4-Cl |
| R-003 | 4-(4-Pyridyl)O—Ph | $(CH_2)_2COOH$ | 4-Cl |
| R-004 | 4-(5-CN-2-Pyridyl)O—Ph | $(CH_2)_2COOH$ | 4-Cl |
| R-005 | 4-(6-CN-2-Pyridyl)O—Ph | $(CH_2)_2COOH$ | 4-Cl |
| R-006 | 4-(2-CN-4-Pyridyl)O—Ph | $(CH_2)_2COOH$ | 4-Cl |
| R-007 | 4-(3-F-2-Pyridyl)O—Ph | $(CH_2)_2COOH$ | 4-Cl |
| R-008 | 4-(3-F-2-Pyridyl)O-3-Me—Ph | $(CH_2)_2COOH$ | 4-Cl |
| R-009 | 4-(6-F-2-Pyridyl)O—Ph | $(CH_2)_2COOH$ | 4-Cl |
| R-010 | 4-(6-F-2-Pyridyl)O-3-Me—Ph | $(CH_2)_2COOH$ | 4-Cl |
| R-011 | 4-(5-F-3-Pyridyl)O—Ph | $(CH_2)_2COOH$ | 4-Cl |
| R-012 | 4-(2-F-4-Pyridyl)O—Ph | $(CH_2)_2COOH$ | 4-Cl |
| R-013 | 4-(2-F-4-Pyridyl)O-3-Me—Ph | $(CH_2)_2COOH$ | 4-Cl |
| R-014 | 4-(2-Cl-4-Pyridyl)O—Ph | $(CH_2)_2COOH$ | 4-Cl |
| R-015 | 4-(2-Cl-4-Pyridyl)O-3-Me—Ph | $(CH_2)_2COOH$ | 4-Cl |
| R-016 | 4-(6-MeO-3-Pyridyl)O—Ph | $(CH_2)_2COOH$ | 4-Cl |
| R-017 | 4-(1-Me-6-oxo-3-Pyridyl)O—Ph | $(CH_2)_2COOH$ | 4-Cl |
| R-018 | 4-(6-$H_2$NCO-2-Pyridyl)O—Ph | $(CH_2)_2COOH$ | 4-Cl |
| R-019 | 4-(2-Pyrimidyl)O—Ph | $(CH_2)_2COOH$ | 4-Cl |
| R-020 | 4-(2-Pyrazinyl)O—Ph | $(CH_2)_2COOH$ | 4-Cl |
| R-021 | 4-(2-Pyrazinyl)O-3-Me—Ph | $(CH_2)_2COOH$ | 4-Cl |
| R-022 | 4-(6-Me-2-Pyrazinyl)O—Ph | $(CH_2)_2COOH$ | 4-Cl |
| R-023 | 4-(5-CN-2-Pyrazinyl)O—Ph | $(CH_2)_2COOH$ | 4-Cl |
| R-024 | 4-(4-Pyridazinyl)O—Ph | $(CH_2)_2COOH$ | 4-Cl |
| R-025 | 2-Et-3-Me-benzofuran-5-yl | $(CH_2)_2COOH$ | 4-Cl |
| R-026 | 2-Et-benzothiazol-6-yl | $(CH_2)_2COOH$ | 4-Cl |
| R-027 | 4-(3-Me-1,2,4-thiadiazol-5-yl)O—Ph | CONH—i-Pr | 4-Cl |
| R-028 | 4-(3-Me-1,2,4-thiadiazol-5-yl)O-3-F—Ph | CONH—i-Pr | 4-Cl |
| R-029 | 4-(4-Pyridyl)O—Ph | CONH—i-Pr | 4-Cl |
| R-030 | 4-(5-CN-2-Pyridyl)O—Ph | CONH—i-Pr | 4-Cl |
| R-031 | 4-(6-CN-2-Pyridyl)O—Ph | CONH—i-Pr | 4-Cl |
| R-032 | 4-(2-CN-4-Pyridyl)O—Ph | CONH—i-Pr | 4-Cl |

TABLE 9-continued

| Compound No | $R^r$ | $R^p$ | $R^q$ |
|---|---|---|---|
| R-033 | 4-(3-F-2-Pyridyl)O—Ph | CONH—i-Pr | 4-Cl |
| R-034 | 4-(3-F-2-Pyridyl)O-3-Me—Ph | CONH—i-Pr | 4-Cl |
| R-035 | 4-(6-F-2-Pyridyl)O—Ph | CONH—i-Pr | 4-Cl |
| R-036 | 4-(6-F-2-Pyridyl)O-3-Me—Ph | CONH—i-Pr | 4-Cl |
| R-037 | 4-(5-F-3-Pyridyl)O—Ph | CONH—i-Pr | 4-Cl |
| R-038 | 4-(2-F-4-Pyridyl)O—Ph | CONH—i-Pr | 4-Cl |
| R-039 | 4-(2-F-4-Pyridyl)O-3-Me—Ph | CONH—i-Pr | 4-Cl |
| R-040 | 4-(2-Cl-4-Pyridyl)O—Ph | CONH—i-Pr | 4-Cl |
| R-041 | 4-(2-Cl-4-Pyridyl)O-3-Me—Ph | CONH—i-Pr | 4-Cl |
| R-042 | 4-(6-MeO-3-Pyridyl)O—Ph | CONH—i-Pr | 4-Cl |
| R-043 | 4-(1-Me-6-oxo-3-Pyridyl)O—Ph | CONH—i-Pr | 4-Cl |
| R-044 | 4-(6-H$_2$NCO-2-Pyridyl)O—Ph | CONH—i-Pr | 4-Cl |
| R-045 | 4-(2-Pyrimidyl)O—Ph | CONH—i-Pr | 4-Cl |

TABLE 10

| Compound No | $R^r$ | $R^p$ | $R^q$ |
|---|---|---|---|
| R-046 | 4-(2-Pyrazinyl)O—Ph | CONH—i-Pr | 4-Cl |
| R-047 | 4-(2-Pyrazinyl)O-3-Me—Ph | CONH—i-Pr | 4-Cl |
| R-048 | 4-(6-Me-2-Pyrazinyl)O—Ph | CONH—i-Pr | 4-Cl |
| R-049 | 4-(5-CN-2-Pyrazinyl)O—Ph | CONH—i-Pr | 4-Cl |
| R-050 | 4-(4-Pyridazinyl)O—Ph | CONH—i-Pr | 4-Cl |
| R-051 | 2-Et-benzothiazol-6-yl | CONH—i-Pr | 4-Cl |
| R-052 | 3-Cl-4-i-PrO—Ph | CONH-4-THP | 4-Cl |
| R-053 | 4-(3-Me-1,2,4-thiadiazol-5-yl)O—Ph | CONH-4-THP | 4-Cl |
| R-054 | 4-(3-Me-1,2,4-thiadiazol-5-yl)O-3-F—Ph | CONH-4-THP | 4-Cl |
| R-055 | 4-(4-Pyridyl)O—Ph | CONH-4-THP | 4-Cl |
| R-056 | 4-(5-CN-2-Pyridyl)O—Ph | CONH-4-THP | 4-Cl |
| R-057 | 4-(6-CN-2-Pyridyl)O—Ph | CONH-4-THP | 4-Cl |
| R-058 | 4-(2-CN-4-Pyridyl)O—Ph | CONH-4-THP | 4-Cl |
| R-059 | 4-(3-F-2-Pyridyl)O—Ph | CONH-4-THP | 4-Cl |
| R-060 | 4-(3-F-2-Pyridyl)O-3-Me—Ph | CONH-4-THP | 4-Cl |
| R-061 | 4-(6-F-2-Pyridyl)O—Ph | CONH-4-THP | 4-Cl |
| R-062 | 4-(6-F-2-Pyridyl)O-3-Me—Ph | CONH-4-THP | 4-Cl |
| R-063 | 4-(5-F-3-Pyridyl)O—Ph | CONH-4-THP | 4-Cl |
| R-064 | 4-(2-F-4-Pyridyl)O—Ph | CONH-4-THP | 4-Cl |
| R-065 | 4-(2-F-4-Pyridyl)O-3-Me—Ph | CONH-4-THP | 4-Cl |
| R-066 | 4-(2-Cl-4-Pyridyl)O—Ph | CONH-4-THP | 4-Cl |
| R-067 | 4-(2-Cl-4-Pyridyl)O-3-Me—Ph | CONH-4-THP | 4-Cl |
| R-068 | 4-(6-MeO-3-Pyridyl)O—Ph | CONH-4-THP | 4-Cl |
| R-069 | 4-(1-Me-6-oxo-3-Pyridyl)O—Ph | CONH-4-THP | 4-Cl |
| R-070 | 4-(6-H$_2$NCO-2-Pyridyl)O—Ph | CONH-4-THP | 4-Cl |
| R-071 | 4-(2-Pyrimidyl)O—Ph | CONH-4-THP | 4-Cl |
| R-072 | 4-(2-Pyrazinyl)O—Ph | CONH-4-THP | 4-Cl |
| R-073 | 4-(2-Pyrazinyl)O-3-Me—Ph | CONH-4-THP | 4-Cl |
| R-074 | 4-(6-Me-2-Pyrazinyl)O—Ph | CONH-4-THP | 4-Cl |
| R-075 | 4-(5-CN-2-Pyrazinyl)O—Ph | CONH-4-THP | 4-Cl |
| R-076 | 4-(4-Pyridazinyl)O—Ph | CONH-4-THP | 4-Cl |
| R-077 | 2-Et-benzothiazol-6-yl | CONH-4-THP | 4-Cl |
| R-078 | 4-(3-Me-1,2,4-thiadiazol-5-yl)O—Ph | CONHCHEt$_2$ | 4-Cl |
| R-079 | 4-(3-Me-1,2,4-thiadiazol-5-yl)O-3-F—Ph | CONHCHEt$_2$ | 4-Cl |
| R-080 | 4-(4-Pyridyl)O—Ph | CONHCHEt$_2$ | 4-Cl |
| R-081 | 4-(5-CN-2-Pyridyl)O—Ph | CONHCHEt$_2$ | 4-Cl |
| R-082 | 4-(6-CN-2-Pyridyl)O—Ph | CONHCHEt$_2$ | 4-Cl |
| R-083 | 4-(2-CN-4-Pyridyl)O—Ph | CONHCHEt$_2$ | 4-Cl |
| R-084 | 4-(3-F-2-Pyridyl)O—Ph | CONHCHEt$_2$ | 4-Cl |
| R-085 | 4-(3-F-2-Pyridyl)O-3-Me—Ph | CONHCHEt$_2$ | 4-Cl |
| R-086 | 4-(6-F-2-Pyridyl)O—Ph | CONHCHEt$_2$ | 4-Cl |
| R-087 | 4-(6-F-2-Pyridyl)O-3-Me—Ph | CONHCHEt$_2$ | 4-Cl |
| R-088 | 4-(5-F-3-Pyridyl)O—Ph | CONHCHEt$_2$ | 4-Cl |
| R-089 | 4-(2-F-4-Pyridyl)O—Ph | CONHCHEt$_2$ | 4-Cl |
| R-090 | 4-(2-F-4-Pyridyl)O-3-Me—Ph | CONHCHEt$_2$ | 4-Cl |

TABLE 11

| Compound No | $R^r$ | $R^p$ | $R^q$ |
|---|---|---|---|
| R-091 | 4-(2-Cl-4-Pyridyl)O—Ph | CONHCHEt$_2$ | 4-Cl |
| R-092 | 4-(2-Cl-4-Pyridyl)O-3-Me—Ph | CONHCHEt$_2$ | 4-Cl |
| R-093 | 4-(6-MeO-3-Pyridyl)O—Ph | CONHCHEt$_2$ | 4-Cl |
| R-094 | 4-(1-Me-6-oxo-3-Pyridyl)O—Ph | CONHCHEt$_2$ | 4-Cl |
| R-095 | 4-(6-H$_2$NCO-2-Pyridyl)O—Ph | CONHCHEt$_2$ | 4-Cl |
| R-096 | 4-(2-Pyrimidyl)O—Ph | CONHCHEt$_2$ | 4-Cl |
| R-097 | 4-(2-Pyrazinyl)O—Ph | CONHCHEt$_2$ | 4-Cl |
| R-098 | 4-(2-Pyrazinyl)O-3-Me—Ph | CONHCHEt$_2$ | 4-Cl |
| R-099 | 4-(6-Me-2-Pyrazinyl)O—Ph | CONHCHEt$_2$ | 4-Cl |
| R-100 | 4-(5-CN-2-Pyrazinyl)O—Ph | CONHCHEt$_2$ | 4-Cl |

143

TABLE 11-continued

| Compound No | R$^r$ | R$^p$ | R$^q$ |
|---|---|---|---|
| R-101 | 4-(4-Pyridazinyl)O—Ph | CONHCHEt$_2$ | 4-Cl |
| R-102 | 2-Et-benzothiazol-6-yl | CONHCHEt$_2$ | 4-Cl |

In the above tables, Me is methyl, Et is ethyl, Pr is propyl, i-Pr is isopropyl, c-Pr is cyclopropyl, s-Bu is sec-butyl, c-Bu is cyclobutyl, Ph is phenyl, Bn is benzyl, THP is tetrahydropyranyl, and Ac is acetyl.

In specific embodiments of the compounds of the present invention, the following compound is provided:

[Chemical Formula 102]

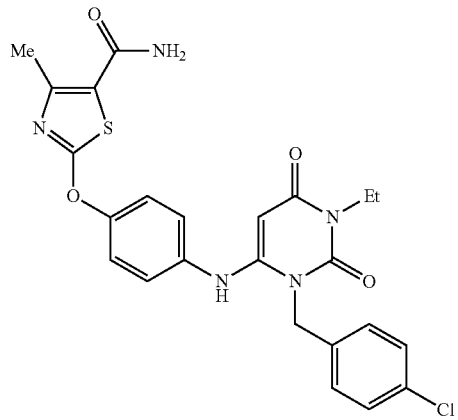

In the above tables, Me is methyl, and Et is ethyl.

Following examples illustrate the present invention in more detail, but the present invention is not limited by these examples. The meaning of each abbreviation is as follows:

Me: methyl
Et: ethyl
Boc: tert-butyloxycarbonyl
Bn: benzyl
TMS: tetramethylsilane
DIPEA: N,N-diisopropylethylamine
DMSO: dimethyl sulfoxide
DMF: dimethylformamide
THF: tetrahydrofuran
DBU: 1,8-diazabicyclo[5.4.0]undeca-7-ene
HOAt: 1-hydroxy-7-azabenzotriazole
HOBt: 1-hydroxybenzotriazole
HATU: 2-(7-azabenzotriazole-1-yl)-1,1,3,3-tetramethyluronium hexafluorophosphate
HBTU: 2-(1H-benzotriazol-1-yl)-1,1,3,3-tetramethyluronium hexafluorophosphate
PyBOP: benzotriazole-1-yl-oxytrispyrrolidinophosphonium hexafluorophosphate
rt: room temperature
M: mol/L

144

Example 1

(1) Preparation of 5-ethoxycarbonyl-1-(4-chlorobenzyl)-2-(methylthio)pyrimidin-4(1H)-one and 5-ethoxycarbonyl-3-(4-chlorobenzyl)-2-(methylthio)pyrimidin-6(1H)-one

[Chemical Formula 103]

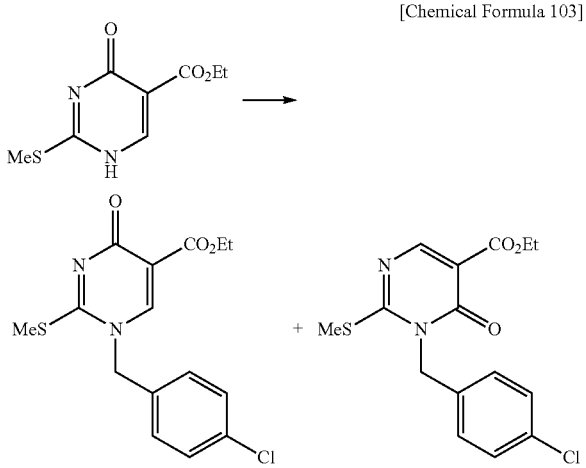

4-Chlorobenzyl bromide (2.11 g, 10.27 mmol) was added to mixture of 5-ethoxycarbonyl-2-(methylthio)pyrimidin-4(1H)-one (2.0 g, 9.34 mmol), diisopropylethylamine (2.46 mL, 14 mmol) and dichloromethane (20 mL), and stirred overnight at room temperature. The reaction mixture was concentrated, and the resulting residue was purified by silica-gel column chromatography (ethyl acetate/hexane) to give 5-ethoxycarbonyl-1-(4-chlorobenzyl)-2-(methylthio)pyrimidin-4(1H)-one (1.68 g, yield: 53%) as white solid, 1H-NMR (CDCl3) δ: 1.35 (3H, t, J=7.2 Hz), 2.61 (3H, s), 4.34 (2H, q, J=7.2 Hz), 5.06 (2H, s), 7.18 (2H, d, J=8.5 Hz), 7.39-7.41 (2H, m), 8.05 (1H, s)

and 5-ethoxycarbonyl-3-(4-chlorobenzyl)-2-(methylthio)pyrimidin-6(1H)-one (0.86 g, yield: 27%) as white solid.

1H-NMR (CDCl3) δ: 1.37 (4H, t, J=7.2 Hz), 2.60 (3H, s), 4.37 (2H, q, J=7.2 Hz), 5.28 (2H, s), 7.26-7.34 (4H, m), 8.56 (1H, s).

(2) Preparation of 5-ethoxycarbonyl-3-(4-chlorobenzyl)-2-(2-ethyl-3-methylbenzofuran-5-ylamino)pyrimidin-6(1H)-one (I-014)

[Chemical Formula 104]

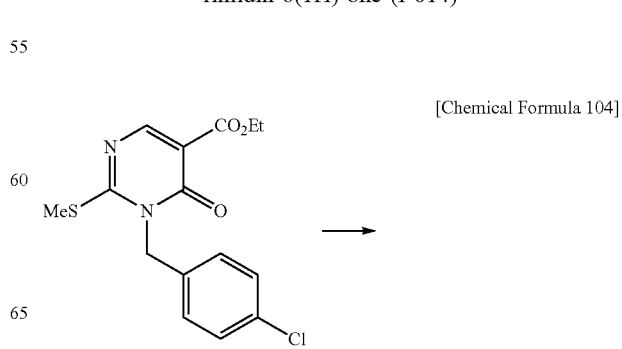

145

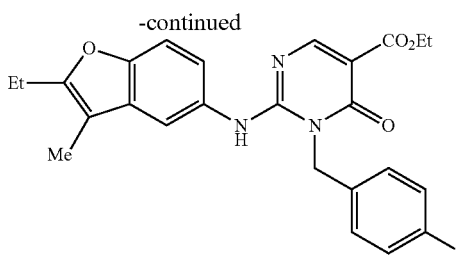

Mixture of 5-ethoxycarbonyl-3-(4-chlorobenzyl)-2-(methylthio)pyrimidin-6(1H)-one (0.678 g, 2 mmol), 5-amino-2-ethyl-3-methylbenzofurane (0.526 g, 3.00 mmol), t-butanol (15 mL), and acetic acid (1.72 mL) was stirred under heating at reflux for 6 hours. The reaction mixture was added to mixture of saturated sodium hydrogen carbonate aqueous solution (50 mL) and water (50 mL), and extracted with ethyl acetate (150 mL). The organic phase was washed by saturated saline (100 mL), and dried over anhydrous magnesium sulfate. After concentrated in vacuo, the residue was purified by silica-gel column chromatography (ethyl acetate/hexane) to give 5-ethoxycarbonyl-3-(4-chlorobenzyl)-2-(2-ethyl-3-methylbenzofuran-5-ylamino)pyrimidin-6(1H)-one (0.9 g, yield: 97%) as colorless amorphous.

1H NMR (CDCl3) δ: 1.25-1.29 (4H, m), 1.36 (3H, t, J=7.0 Hz), 1.57 (3H, s), 2.73 (3H, q, J=7.5 Hz), 4.34 (2H, q, J=7.1 Hz), 5.39 (2H, s), 6.64 (1H, s), 6.85 (1H, dd, J=8.5, 2.3 Hz), 7.24 (1H, d, J=2.3 Hz), 7.30-7.42 (5H, m), 8.59 (1H, s).

Example 2

Preparation of 5-hydroxycarbonyl-3-(4-chlorobenzyl)-2-(2-ethyl-3-methylbenzofuran-5-ylamino)pyrimidin-6(1H)-one (I-016)

[Chemical Formula 105]

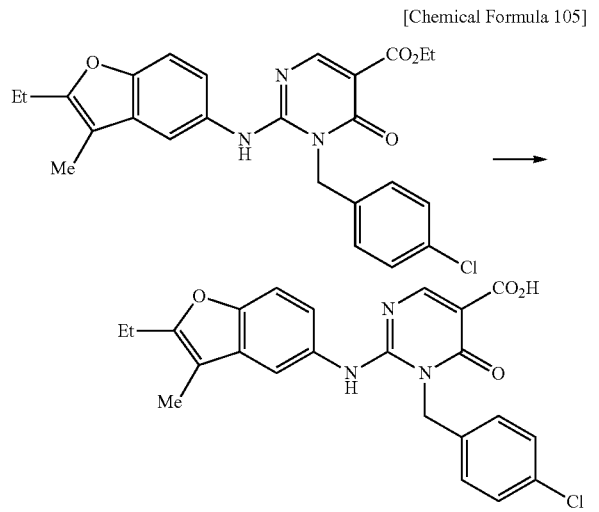

4 mol/L Lithium hydroxide (3 mL) was added to mixture of 5-ethoxycarbonyl-3-(4-chlorobenzyl)-2-(2-ethyl-3-methylbenzofuran-5-ylamino)pyrimidin-6(1H)-one (0.839 g, 1.8 mmol), ethanol (3 mL), THF (3 mL) and water (4 mL), and stirred at 80° C. for 9 hours. The reaction mixture was poured into water (100 mL), acidified by 2 mol/L hydrochloride, and extracted with ethyl acetate (150 mL). The organic phase was washed by saturated saline (100 mL), and dried over anhydrous magnesium sulfate. After concentrated in vacuo, ethyl acetate and hexane were added to the residue, and the resulting powder was filtered to give 5-hydroxycarbonyl-3-(4-chlorobenzyl)-2-(2-ethyl-3-methylbenzofuran-5-ylamino)pyrimidin-6(1H)-one (0.54 g, yield: 81%) as white powder.

1H NMR (DMSO-d6) δ: 1.22 (3H, t, J=7.5 Hz), 2.12 (3H, s), 2.76 (2H, q, J=7.5 Hz), 5.46 (2H, s), 7.13 (1H, m), 7.36-7.47 (6H, m), 8.46 (1H, s), 9.94 (1H, s), 12.77 (1H, s).

Example 3

Preparation of 1-(4-chlorobenzyl)-2-(2-ethyl-3-methylbenzofuran-5-ylamino)-5-(tetrahydro-2H-pyran-4-ylcarbamoyl)pyrimidin-6(1H)-one (I-019)

[Chemical Formula 106]

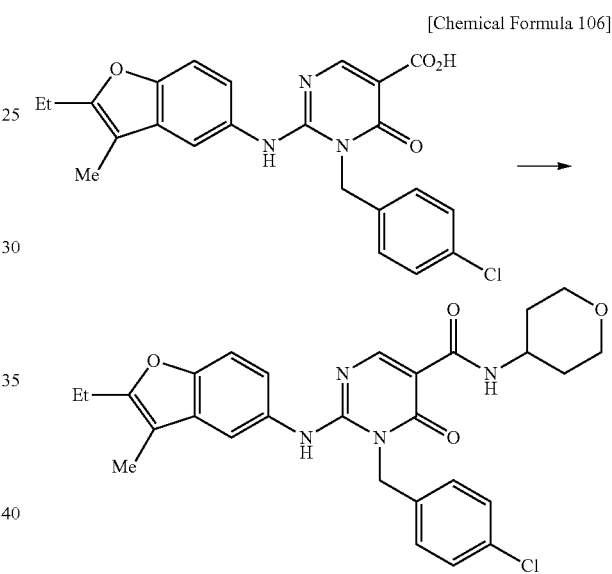

4-Aminotetrahydro-2H-pyran (36 mg, 0.36 mmol), 1-hydroxybenzotriazole hydrate (55 mg, 0.36 mmol), 4-dimethylaminopyridine (3.7 mg, 0.03 mmol) and 1-ethyl-3-(3-dimethylaminopropyl)carbodiimide hydrochloride (69 mg, 0.36 mmol) were added to mixture of 5-hydroxycarbonyl-3-(4-chlorobenzyl)-2-(2-ethyl-3-methylbenzofuran-5-ylamino)pyrimidin-6(1H)-one (131 mg, 0.3 mmol) and DMF (2 mL), and stirred at room temperature for 4 hours. The reaction mixture was added to water (100 mL), extracted with ethyl acetate (100 mL). The organic phase was washed by saturated sodium hydrogen carbonate aqueous solution (100 mL) and saturated saline (1.00 mL), and dried over anhydrous magnesium sulfate. After concentrated in vacuo, the residue was purified by silica-gel column chromatography (ethyl acetate/hexane). Ethyl acetate and hexane were added to the resulting mixture, and the resulting powder was filtered to give 1-(4-chlorobenzyl)-2-(2-ethyl-3-methylbenzofuran-5-ylamino)-5-(tetrahydro-2H-pyran-4-ylcarbamoyl)pyrimidin-6(1H)-one (0.09 g, yield: 58%) as white powder.

1H-NMR (CDCl3) δ: 1.27 (3H, t, J=7.5 Hz), 1.59-1.66 (2H, m), 1.98 (2H, d, J=10.3 Hz), 2.11 (3H, s), 2.73 (2H, q, J=7.5 Hz), 3.50-3.56 (2H, m), 3.95-3.99 (2H, m), 4.18 (1H, m), 5.41 (2H, s), 6.60 (1H, s), 6.86 (1H, dd, J=8.5, 2.3 Hz), 7.25-7.33 (4H, m), 7.45 (2H, d, J=8.3 Hz), 8.79 (1H, s), 8.95 (1H, d, J=7.8 Hz).

Example 4

(1) Preparation of 3-(4-chlorobenzyl)-2-(methyl-thio)-5-nitropyrimidin-6(1H)-one

[Chemical Formula 107]

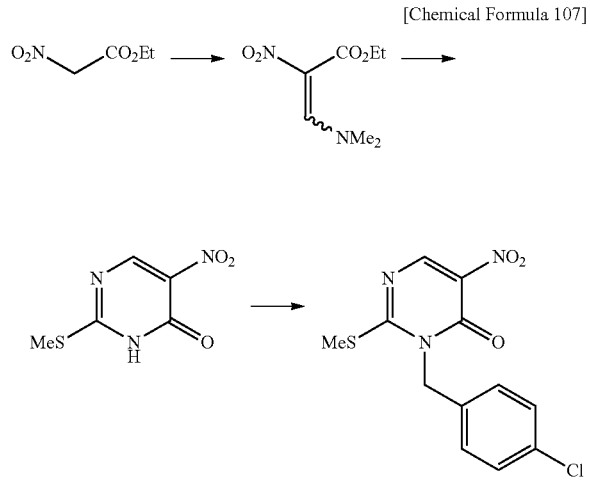

1,1-Dimethoxy-N,N-dimethylmethaneamine (26.2 g, 220 mmol) was added to ethyl nitroacetate (13.98 g, 105 mmol), stirred at room temperature for 1.5 hours, and then stirred at 100° C. for 1 hour. The reaction mixture was concentrated in vacuo to give crude product of ethyl 3-(dimethylamino)-2-nitroacrylate (20.66 g) as orange oil.

S-Methylthiourea-1/2 sulfate (17.54 g, 63.0 mmol) and sodium ethoxide (10.72 g, 158 mmol) were added to mixture of ethyl 3-(dimethylamino)-2-nitroacrylate (19.76 g, 105 mmol) and ethanol (100 mL), and stirred at room temperature for 3 hours. The reaction mixture was added to sodium ethoxide (10.72 g, 158 mmol), and stirred at room temperature for 2 hours. The reaction mixture was adjusted to pH 4 by 2 mol/L hydrochloride under ice-cooling, and the resulting solid was filtered to give crude product of 2-(methyl-thio)-5-nitropyrimidin-6(1H)-one (15.8 g) as yellow solid.

Potassium carbonate (17.50 g, 127 mmol) was added to mixture of 2-(methylthio)-5-nitropyrimidin-6(1H)-one (15.8 g, 84 mmol), 4-chlorobenzyl bromide (19.08 g, 93 mmol) and DMF (100 mL), and stirred at room temperature for 16 hours. The reaction mixture was added to water (500 mL), and extracted with ethyl acetate (300 mL×3). The organic phase was washed by water (300 mL) and saturated saline (300 mL), dried over anhydrous magnesium sulfate. After concentrated in vacuo, the residue was purified by silica-gel column chromatography (ethyl acetate/hexane). Ethyl acetate and hexane were added to the resulting mixture, and the resulting solid was filtered to give 3-(4-chlorobenzyl)-2-(methylthio)-5-nitropyrimidin-6(1H)-one (1.09 g, yield: 4%) as pale yellow solid.

1H-NMR (CDCl8) δ: 2.68 (3H, s), 5.32 (2H, s), 7.29-7.38 (4H, m), 8.84 (1H, s)

(2) Preparation of 3-(4-chlorobenzyl)-2-[4-(6-cyano-2-pyridyloxy)phenylamino]-5-nitropyrimidin-6(1H)-one (I-002)

[Chemical Formula 108]

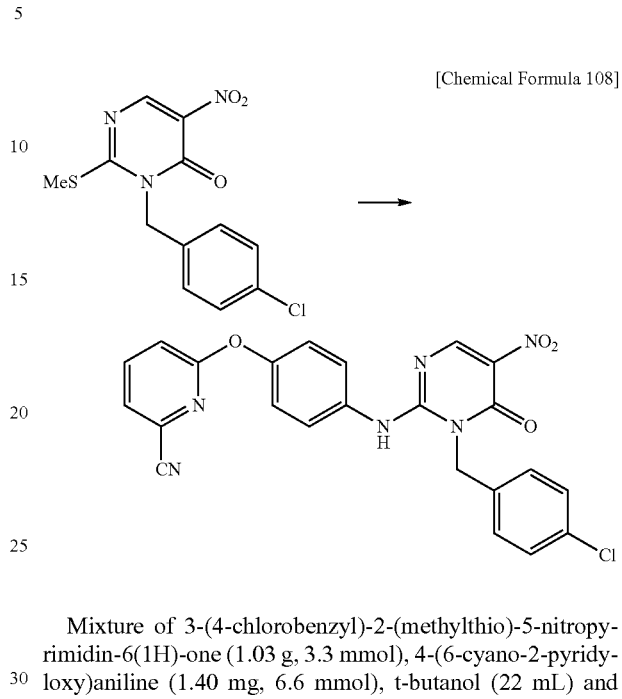

Mixture of 3-(4-chlorobenzyl)-2-(methylthio)-5-nitropyrimidin-6(1H)-one (1.03 g, 3.3 mmol), 4-(6-cyano-2-pyridyloxy)aniline (1.40 mg, 6.6 mmol), t-butanol (22 mL) and acetic acid (2.83 mL) was stirred under heating at reflux for 6 hours. The reaction mixture was added to mixture of saturated sodium hydrogen carbonate aqueous solution (50 mL) and water (50 mL), extracted with ethyl acetate (1.50 mL). The organic phase was washed by saturated saline (100 mL), dried over anhydrous magnesium sulfate. After concentrated in vacuo, the residue was purified by silica-gel column chromatography (ethyl acetate/hexane) to give 3-(4-chlorobenzyl)-2-[4-(6-cyano-2-pyridyloxy)phenylamino]-5-nitropyrimidin-6(1H)-one (0.62 g, yield 89%) as yellow amorphous.

1H NMR (CDCl3) δ: 5.42 (2H, s), 7.01 (1H, br s), 7.12-7.26 (5H, m), 7.34 (2H, d, J=8.3 Hz), 7.41-7.48 (4H, m), 7.83 (1H, dd, J=8.4, 7.4 Hz), 8.95 (1H, s).

Example 5

Preparation of 5-amino-3-(4-chlorobenzyl)-2-[4-(6-cyano-2-pyridyloxy)phenylamino]pyrimidin-6(1H)-one (I-003)

[Chemical Formula 109]

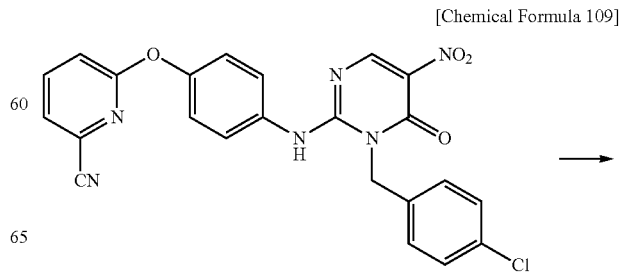

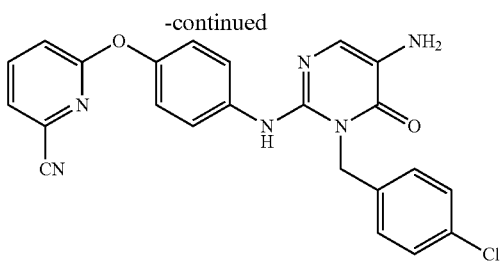

Iron powder (282 mg, 5.05 mmol) and aminoacetic acid hydrochloride (225 mg, 4.21 mmol) were added to mixture of 3-(4-chlorobenzyl)-2-[4-(6-cyano-2-pyridyloxy)phenylamino]-5-nitropyrimidin-6(1H)-one (0.4 g, 0.842 mmol), methanol (6.0 mL), water (2.0 mL) and THF (8 mL), and stirred under heating at reflux for 1.5 hours. After filtered, the reaction mixture was added to water (150 mL), and extracted with ethyl acetate (150 mL). The organic phase was washed by saturated saline (150 mL), dried over anhydrous sodium sulfate. After concentrated in vacuo, the residue was purified by silica-gel column chromatography (ethyl acetate/hexane) to give 5-amino-1-(4-chlorobenzyl)-2-[4-(6-cyano-2-pyridyloxy)phenylamino]pyrimidin-6(1H)-one (0.29 g, yield: 78%) as yellow amorphous.

1H NMR (CDCl3) δ: 3.65 (2H, s), 5.39 (2H, s), 5.91 (1H, s), 7.06 (2H, d, J=8.9 Hz), 7.13 (1H, d, J=8.3 Hz), 7.18 (2H, d, J=8.9 Hz), 7.29-7.33 (3H, m), 7.37-7.44 (3H, m), 7.78 (1H, dd, J=8.3, 7.4 Hz).

Example 6

Preparation of 3-(4-chlorobenzyl)-2-[4-(6-carbamoyl-2-pyridyloxy)phenylamino]-5-nitropyrimidin-6(1H)-one (I-004)

[Chemical Formula 110]

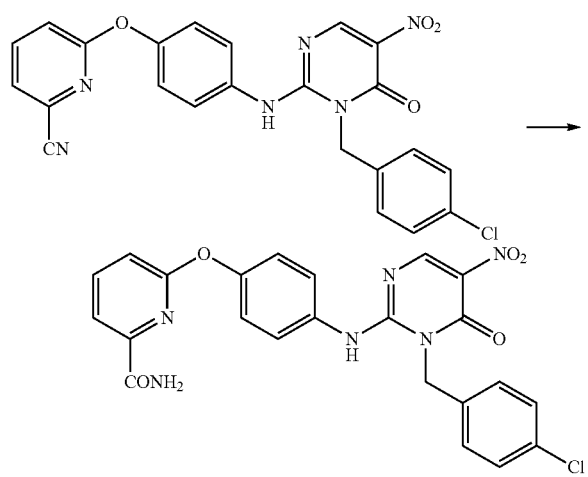

2 mol/L Sodium hydroxide (0.42 mL, 0.84 mmol) was added to DMSO solution (2 mL) of 3-(4-chlorobenzyl)-2-[4-(6-cyano-2-pyridyloxy)phenylamino]-5-nitropyrimidin-6(1H)-one (200 mg, 0.421 mmol), and stirred overnight at room temperature. The reaction mixture was added to water (100 mL), acidified by 2 mol/L hydrochloride, and then extracted with ethyl acetate (150 mL). The organic phase was washed by saturated saline (100 mL), and dried over anhydrous sodium sulfate. After concentrated in vacuo, the residue was purified by silica-gel column chromatography (ethyl acetate/hexane) to give 3-(4-chlorobenzyl)-2-[4-(6-carbamoyl-2-pyridyloxy)phenylamino]-5-nitropyrimidin-6(1H)-one (145 mg, yield: 70%) as yellow amorphous.

1H NMR (CDCl3) δ: 5.33 (1H, s), 5.46 (2H, s), 7.11-7.18 (4H, m), 7.25-7.32 (31H, m), 7.35 (2H, d, J=8.5 Hz), 7.44 (2H, d, J=8.5 Hz), 7.87-7.92 (2H, m), 8.94 (1H, s).

Example 7

Preparation of 3-(4-chlorobenzyl)-2-[4-(6-cyano-2-pyridyloxy)phenylamino]-5-(methoxycarbonylamino)pyrimidin-6(1H)-one (I-005)

[Chemical Formula 111]

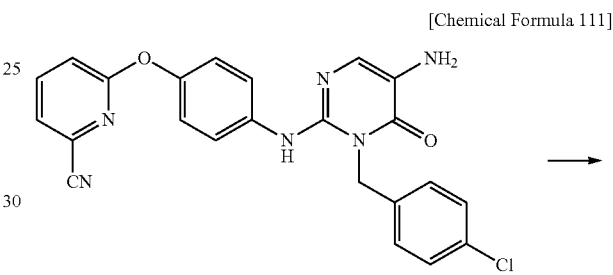

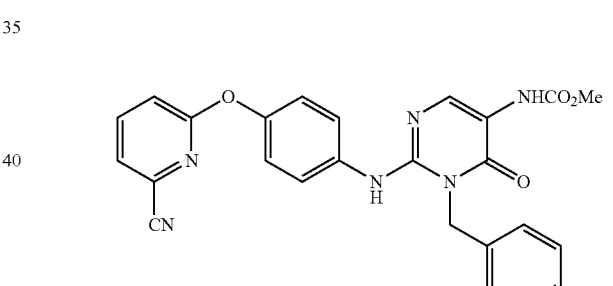

Sodium carbonate (79 mg, 0.742 mmol) and methyl chlorocarbonate (0.023 mL, 0.297 mmol) were added to THF solution (2 mL) of 5-amino-3-(4-chlorobenzyl)-2-[4-(6-cyano-2-pyridyloxy)phenylamino]pyrimidin-6(1H)-one (110 mg, 0.247 mmol), and stirred at room temperature for 5 hours. The reaction mixture was poured into water (100 mL), extracted with ethyl acetate (100 mL). The organic phase was washed by saturated saline (100 mL), dried over anhydrous sodium sulfate. After concentrated in vacuo, the residue was purified by silica-gel column chromatography (ethyl acetate/hexane) to give 3-(4-chlorobenzyl)-2-[4-(6-cyano-2-pyridyloxy)phenylamino]-5-(methoxycarbonylamino)pyrimidin-6(1H)-one (62 mg, yield: 50%) as pale yellow solid.

1H NMR (CDCl3) δ: 3.79 (3H, s), 5.39 (2H, s), 6.12 (1H, s), 7.09 (2H, d, J=8.8 Hz), 7.14-7.20 (1H, m), 7.15 (1H, d, J=8.5 Hz), 7.22-7.28 (2H, m), 7.30 (2H, d, J=8.4 Hz), 7.40 (1H, d, J=7.3 Hz), 7.44 (2H, d, J=8.4 Hz), 7.79 (1H, t, J=7.9 Hz), 8.51 (1H, s).

Example 8

(1) Preparation of 5-bromo-1-(4-chlorobenzyl)-2-(methylthio)pyrimidin-6(1H)-one

[Chemical Formula 112]

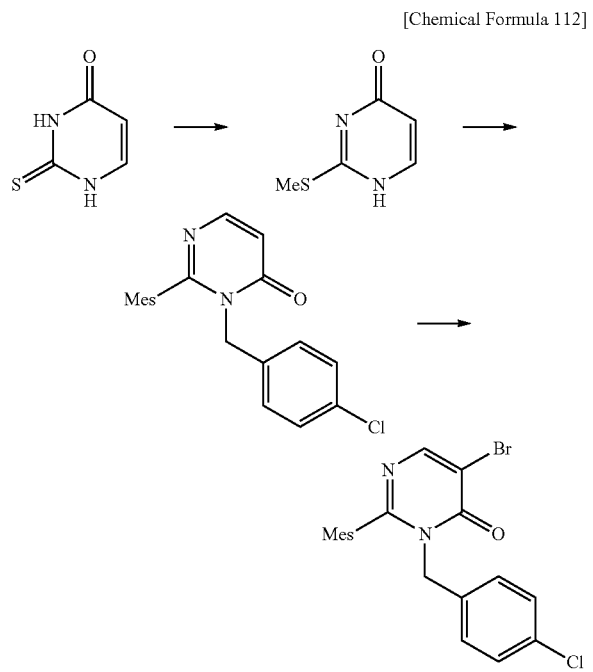

1 mol/L Sodium hydroxide (107 mL, 215 mmol) and methyl iodide (12.8 mL, 205 mmol) were added to mixture of 2-thiouracil (25.0 g, 195 mmol) and ethanol (250 mL), and stirred at 60° C. for 7 hours. The reaction mixture was concentrated, and 2 mol/L hydrochloride was added to the residue. The resulting solid was filtered to give 2-(methylthio)pyrimidin-4(1H)-one (14.6 g, yield: 53%) as colorless solid.

1H-NMR (δ ppm TMS/DMSO-d6): 2.47 (3H, s), 6.09 (1H, d, J=5.6 Hz), 7.86 (1H, d, J=5.6 Hz), 12.67 (1H, brs).

Potassium carbonate (1.4.6 g, 1.06 mmol) and 4-chlorobenzyl bromide (15.9 g, 77.0 mmol) were added to mixture of 2-(methylthio)pyrimidin-4(1H)-one (10.0 g, 70.3 mmol) and DMF (200 mL), and stirred at room temperature for 20 hours. The reaction mixture was added to water, and extracted with chloroform. The extract was washed by saturated saline, dried overanhydrous sodium sulfate, and then concentrated in vacuo. The resulting residue was purified by silica-gel column chromatography (ethyl acetate/hexane) to give 1-(4-chlorobenzyl)-2-(methylthio)pyrimidin-6(1H)-one (7.3 g, yield: 39%) as colorless solid.

1H-NMR (δ ppm TMS/DMSO-d6): 2.50 (3H, s), 5.21 (2H, s), 6.28 (1H, d, J=6.3 Hz), 7.25 (2H, d, J=7.8 Hz), 7.40 (2H, d, J=7.8 Hz), 7.90 (1H, d, J=6.3 Hz).

N-Bromosuccinimide (5.47 g, 30.7 mmol) was added to mixture of 1-(4-chlorobenzyl)-2-(methylthio)pyrimidin-6(1H)-one (4.00 g, 1.5.0 mmol) and dichloromethane (40 mL), and stirred at room temperature for 2 hours. The reaction mixture was concentrated in vacuo, and the resulting residue was washed by methanol to give 5-bromo-1-(4-chlorobenzyl)-2-(methylthio)pyrimidin-6(1H)-one (3.25 g, yield: 63%) as colorless solid.

1H-NMR (δ ppm TMS/DMSO-d6): 2.52 (3H, s), 5.25 (2H, s), 7.27 (2H, d, J=8.1 Hz), 7.41 (2H, d, J=8.1 Hz), 8.31 (1H, s).

(2) Preparation of 1-(4-chlorobenzyl)-2-(2-ethyl-3-methylbenzofuran-5-ylamino)-5-(tetrahydro-2H-pyran-4-ylcarbonylamino)pyrimidin-6(1H)-one (I-030)

[Chemical Formula 113]

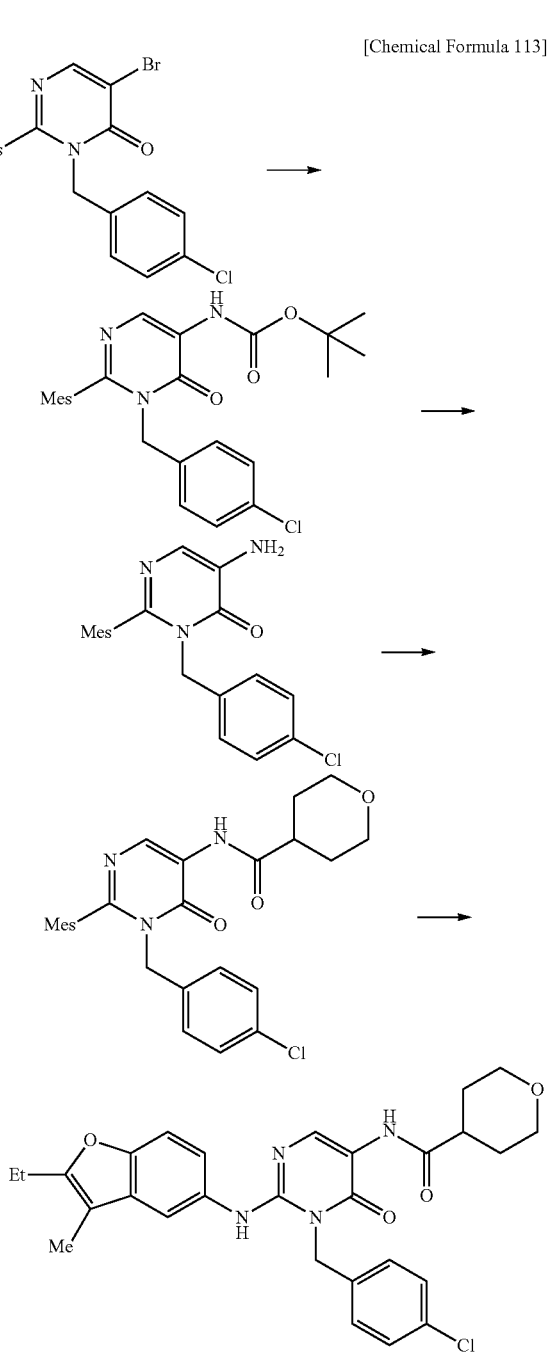

t-Butyl carbamate ester (588 mg, 5.02 mmol), tris(dibenzylideneacetone)dipalladium(0) (329 mg, 0.359 mmol), 4,5-bis(diphenylphosphino)-9,9-dimethylxanthene (623 mg, 1.08 mmol) and cesium carbonate (1.64 g, 5.02 mmol) were added to mixture of 5-bromo-1-(4-chlorobenzyl)-2-(methylthio)pyrimidin-6(1H)-one (1.24 g, 3.59 mmol) and dioxane (15 mL), and stirred under heating at reflux for 20 hours. The reaction mixture was added to water, and extracted with ethyl acetate. The extract was washed by saturated saline, dried overanhydrous sodium sulfate, and then concentrated in vacuo. The resulting residue was purified by silica-gel column chromatography (ethyl acetate/hexane) to give 5-(t-butoxycarbonyl)amino-1-(4-chlorobenzyl)-2-(methylthio) pyrimidin-6(1H)-one (136 mg, yield: 10%) as pale yellow solid.

1H-NMR (δ ppm TMS/DMSO-d6): 1.44 (9H, s), 2.50 (3H, s), 5.24 (2H, s), 7.25 (2H, d, J=7.8 Hz), 7.40 (2H, d, J=7.8 Hz), 8.02 (1H, s), 8.26 (1H, s).

Trifluoroacetic acid (0.36 mL, 4.7 mmol) was added to mixture of 5-(t-butoxycarbonyl)amino-1-(4-chlorobenzyl)-2-(methylthio)pyrimidin-6(1H)-one (90.0 mg, 0.236 mmol) and chloroform (1 mL), and stirred at room temperature for 20 hours. The reaction mixture was concentrated, and methanol (1 mL), THF (1 mL), water (1 mL) and small amount of potassium carbonate were added to the residue, and stirred at 50° C. for 2 hours. The reaction mixture was added to water, and extracted with ethyl acetate. The extract was washed by saturated saline, dried over anhydrous sodium sulfate, and then concentrated in vacuo to give 5-amino-1-(4-chlorobenzyl)-2-(methylthio)pyrimidin-6 (1H)-one (70 mg, yield: 100%) as pale yellow solid.

1H-NMR (δ ppm TMS/DMSO-d6): 2.42 (3H, s), 4.92 (2H, s), 5.22 (2H, s), 7.23 (2H, d, J=8.1 Hz), 7.32 (1H, s), 7.39 (2H, d, J=8.1 Hz).

Sodium carbonate (15 mg, 0.14 mmol) and tetrahydro-2H-pyran-4-carbonyl chloride (26 mg, 0.18 mmol) were added to mixture of 5-amino-1-(4-chlorobenzyl)-2-(methylthio)pyrimidin-6(1H)-one (33.2 mg, 0.118 mmol) and THF (0.5 mL) under ice-cooling, and stirred under ice-cooling for 2 hours. The reaction mixture was added to saturated sodium hydrogen carbonate aqueous solution, and extracted with ethyl acetate. The extract was washed by saturated saline, dried over anhydrous sodium sulfate, and then concentrated in vacuo to give 3-(4-chlorobenzyl)-2-methylthio-5-(tetrahydro-2H-pyran-4-ylcarbonylamino)pyrimidin-6(1H)-one (48 mg, yield: 100%) as pale yellow solid.

1H-NMR (δ ppm TMS/DMSO-d6): 1.54-1.70 (4H, m), 2.50 (3H, s), 2.83-2.92 (1H, m), 3.27-3.35 (2H, m), 3.84-3.91 (2H, m), 5.25 (2H, s), 7.27 (2H, d, J=7.8 Hz), 7.41 (2H, d, J=7.8 Hz), 8.70 (1H, s), 9.31 (1H, s).

m-Chloroperoxybenzoic acid (138 mg, 0.559 mmol) was added to mixture of 3-(4-chlorobenzyl)-2-methylthio-5-(tetrahydro-2H-pyran-4-ylcarbonylamino)pyrimidin-6(1H)-one (200 mg, 0.508 mmol) and dichloromethane (5 mL) under ice-cooling, and stirred under ice-cooling for 1 hour. The reaction mixture was added to 5-amino-2-ethyl-3-methylbenzofurane (133 mg, 0.762 mmol), and stirred at 50; for 1.5 hours. The reaction mixture was added to saturated sodium hydrogen carbonate aqueous solution, and extracted with dichloromethane. The extract was washed by saturated saline, dried overanhydrous sodium sulfate, and then concentrated in vacuo. The resulting residue was purified by silica-gel column chromatography (ethyl acetate/hexane) to give 1-(4-chlorobenzyl)-2-(2-ethyl-3-methylbenzofuran-5-ylamino)-5-(tetrahydro-2H-pyran-4-ylcarbonylamino)pyrimidin-6(1H)-one (105 mg, yield: 40%) as colorless solid.

1H NMR (CDCl3) δ: 1.26 (3H, t, J=7.5 Hz), 1.84-1.93 (4H, m), 2.10 (3H, s), 2.52-2.57 (1H, m), 2.72 (2H, q, J=7.5 Hz), 3.45 (2H, td, J=11.2, 2.8 Hz), 4.02-4.08 (2H, m), 5.38 (2H, s), 6.09 (1H, s), 6.83 (1H, dd, J=8.5, 2.3 Hz), 7.26-7.30 (4H, m), 7.43 (2H, d, J=8.5 Hz), 7.80 (1H, s), 8.82 (1H, s).

Example 9

(1) Preparation of 6-chloro-1-(4-chlorobenzyl)-3-ethylpyrimidin-2,4(1H,3H)-dione

[Chemical Formula 114]

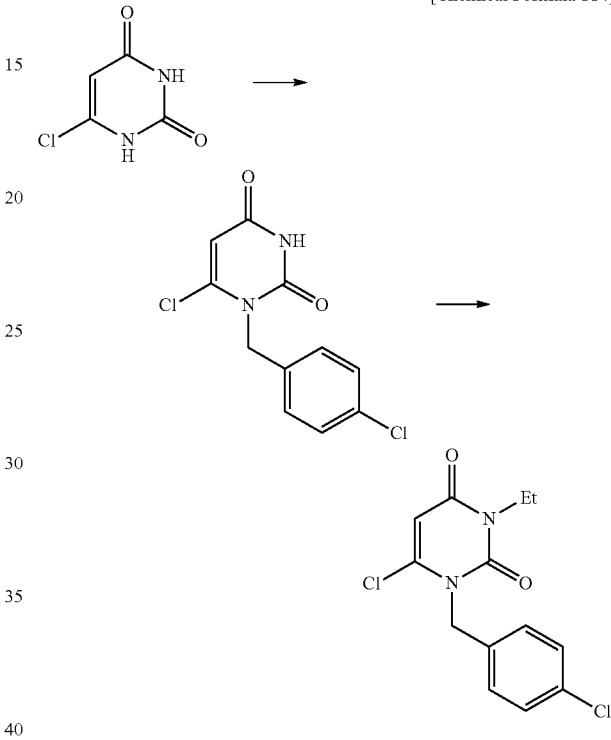

60% Sodium hydride (1.64 g, 40.9 mmol) and lithium bromide (2.96 g, 34.18 mmol) were added to mixture of 6-chlorouracil (5.00 g, 34.1 mmol) and DMF (100 mL), and stirred at room temperature for 1 hour. The reaction mixture was added to 4-chlorobenzyl bromide (7.71 g, 37.5 mmol), and then stirred for 21 hours. The reaction mixture was added to water (100 mL), and the resulting solid was filtered. The solid was purified by silica-gel column chromatography (ethyl acetate/hexane), and solidified by methanol/ethyl acetate/hexane to give 6-chloro-1-(4-chlorobenzyl)pyrimidin-2,4(1H,3H)-dione (3.87 g, yield: 42%) as colorless solid.

1H-NMR (δ ppm TMS/DMSO-d6): 5.14 (2H, s), 5.96 (1H, s), 7.31 (2H, d, J=8.0 Hz), 7.43 (2H, d, J=8.0 Hz), 11.76 (1H, s).

Cesium carbonate (5.77 g, 17.71 mmol) and bromoethane (0.793 ml, 10.62 mmol) were added to DMF solution (24 mL) of 6-chloro-1-(4-chlorobenzyl)pyrimidin-2,4(1H,3H)-dione (2.4 g, 8.85 mmol), and stirred at room temperature for 3 hours. The reaction mixture was added to water, and extracted with ethyl acetate. The extract was washed by saturated saline, dried overanhydrous sodium sulfate, and then concentrated in vacuo. The residue was purified by silica-gel column chromatography (ethyl acetate/hexane) to give 6-chloro-1-(4-chlorobenzyl)-3-ethylpyrimidin-2,4(1H, 3H)-dione (2.52 g, yield: 95%) as white solid.

1H-NMR (δ ppm TMS/DMSO-d6): 1.13 (3H, t, J=7.2 Hz), 3.84 (2H, q, J=7.2 Hz), 5.20 (2H, s), 6.12 (1H, s), 7.06-7.61 (4H, m).

(2) 1-(4-chlorobenzyl)-3-ethyl-6-[4-(3-methoxycarbonylphenoxy)phenylamino]pyrimidin-2,4(1H,3H)-dione(I-008)の Preparation

[Chemical Formula 115]

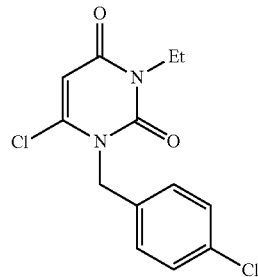

→

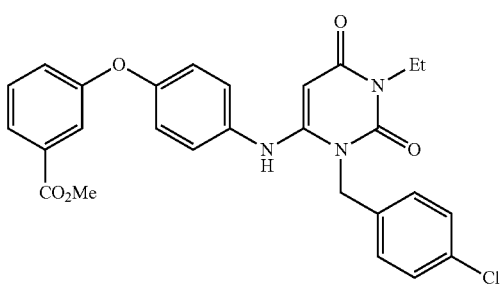

Palladium acetate (II) (37.5 mg, 0.167 mmol), 4,5-bis(diphenylphosphino)-9,9-dimethylxanthene (145 mg, 0.251 mmol) and cesium carbonate (762 mg, 2.340 mmol) were added to dioxane solution (10 mL) of 6-chloro-1-(4-chlorobenzyl)-3-ethylpyrimidin-2,4(1H,3H)-dione (500 mg, 1.67 mmol) and (3-methoxycarbonylphenoxy)aniline, and stirred under heating at reflux for 1 hour. The reaction mixture was added to water, and extracted with ethyl acetate. The extract was washed by saturated saline, dried over anhydrous sodium sulfate, and then concentrated in vacuo. The residue was purified by silica-gel column chromatography (ethyl acetate/hexane), the resulting mixture was added to hexane, and the resulting powder was filtered to give 1-(4-chlorobenzyl)-3-ethyl-6-[4-(3-methoxycarbonylphenoxy)phenylamino]pyrimidin-2,4(1H,3H)-dione (623 mg, yield: 74%) as pale sand powder.

1H-NMR (δ ppm TMS/DMSO-d6): 1.07 (3H, t, J=7.2 Hz), 3.80 (2H, q, J=7.2 Hz), 3.83 (3H, s), 4.61 (1H, s), 5.30 (2H, s), 7.12 (2H, d, J=8.0 Hz), 7.21 (2H, d, J=8.0 Hz), 7.29-7.45 (6H, m), 7.56 (1H, t, J=8.0 Hz), 7.73 (1H, d, J=8.0 Hz), 8.62 (1H, s).

Example 10

1-(4-chlorobenzyl)-3-ethyl-6-[4-(3-hydroxycarbonylphenoxy)phenylamino]pyrimidin-2,4(1H,3H)-dione(I-023)の Preparation

[Chemical Formula 116]

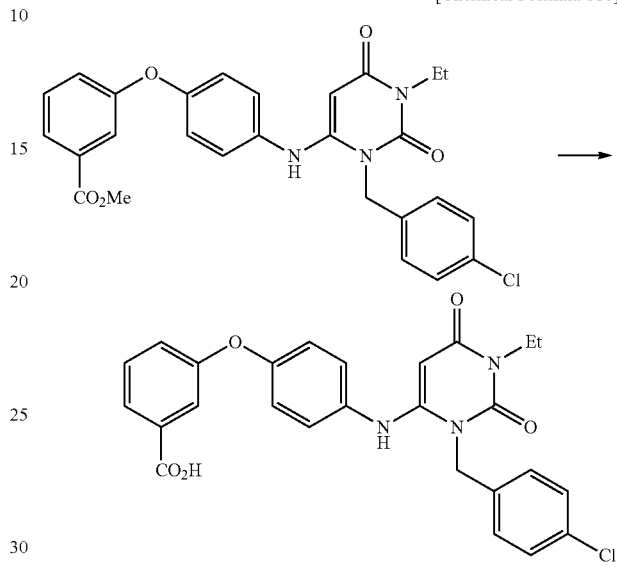

2 mol/L Sodium hydroxide (2.22 mL) was added to mixture of 1-(4-chlorobenzyl)-3-ethyl-6-[4-(3-methoxycarbonylphenoxy)phenylamino]pyrimidin-2,4(1H, 3H)-dione (562 mg, 1.111 mmol), methanol (2.8 mL) and THF (5.6 mL), and stirred at room temperature for 3 hours. The reaction mixture was poured into water, acidified by 1 mol/L citric acid aqueous solution, and then extracted with ethyl acetate. The organic phase was washed by saturated saline, dried over anhydrous magnesium sulfate, and concentrated in vacuo. The residue was purified by silica-gel column chromatography (ethyl acetate/hexane) to give 1-(4-chlorobenzyl)-3-ethyl-6-[4-(3-hydroxycarbonylphenoxy)phenylamino]pyrimidin-2,4(1H,3H)-dione (548 mg, yield: 100%) as pale yellow amorphous.

1H-NMR (δ ppm TMS/DMSO-d6): 1.06 (3H, t, J=7.2 Hz), 3.80 (2H, q, J=7.2 Hz), 4.62 (1H, s), 5.29 (2H, s), 7.12 (2H, d, J=8.0 Hz), 7.21 (2H, d, J=8.0 Hz), 7.29-7.45 (6H, m), 7.53 (1H, t, J=8.0 Hz), 7.71 (1H, d, J=8.0 Hz), 8.61 (1H, s), 13.17 (1H, brs).

Example 11

Preparation of 5-bromo-1-(4-chlorobenzyl)-2-[4-(6-cyano-2-pyridyloxy)phenylamino]pyrimidin-6(1H)-one (I-176)

[Chemical Formula 117]

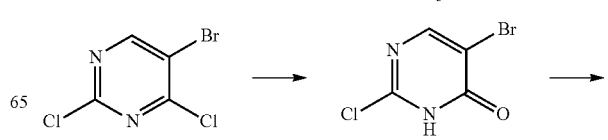

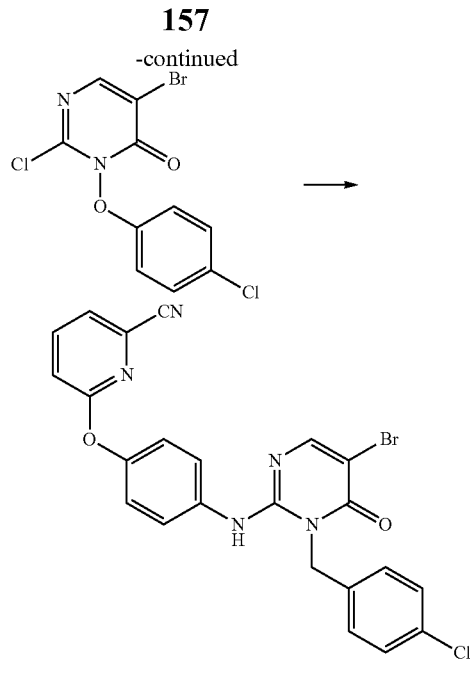

Step 1

1 mol/L Sodium hydroxide (150 mL) was added to mixture of 5-bromo-2,4-dichloropyrimidine (25 g, 110 mmol) and THF (50 mL), and stirred at room temperature for 3.5 hours, the reaction mixture was neutralized with 2 mol/L hydrochloride, and extracted with chloroform (150 mL). The organic phase was washed by saturated saline (100 mL), and dried over anhydrous magnesium sulfate. After concentrated in vacuo, the residue was added to chloroform and hexane, and the resulting powder was filtered to give 5-bromo-2-chloropyrimidin-4(3H)-one (6.15 g, yield: 27%) as white powder.

1H-NMR (δ ppm TMS/DMSO-d6): 8.37 (1H, s).

Step 2

Lithium hydrate (0.245 g, 31 mmol) was added to mixture of 5-bromo-2-chloropyrimidin-4(3H)-one (6.15 g, 29 mmol), 4-chlorobenzyl 4-methylbenzenesulfonate (11.33 g, 38 mmol) and dioxane (60 mL), and stirred at 65° C. for 11 hours. The reaction mixture was poured into 5% citric acid aqueous solution (200 mL), and extracted with ethyl acetate (200 mL×2). The organic phase was washed by saturated saline (200 mL), and dried over anhydrous magnesium sulfate. After concentrated in vacuo, the residue was purified by silica-gel column chromatography (ethyl acetate/hexane) to give 5-bromo-2-chloro-1-(4-chlorobenzyl)pyrimidin-6(1H)-one (4.93 g, yield: 50%) as white solid.

1H-NMR (δ ppm TMS/DMSO-d6): 5.36 (2H, s), 7.34 (2H, d, J=8.0 Hz), 7.44 (2H, d, J=7.9 Hz), 8.35 (1H, s).

Step 3

A drop of hydrochloride (4 mol/L dioxane solution) was added to mixture of 5-bromo-2-chloro-1-(4-chlorobenzyl)pyrimidin-6(1H)-one (300 mg, 0.9 mmol), 4-(6-cyano-2-pyridyloxy)aniline (304 mg, 1.44 mmol) and t-butanol (3 mL), and stirred at 100° C. for 1 hours. The reaction mixture was added to water (100 mL), and extracted with ethyl acetate (0.100 mL). The organic phase was washed by saturated sodium hydrogen carbonate aqueous solution (100 mL) and saturated saline (100 mL), dried overanhydrous magnesium sulfate, and then concentrated in vacuo. The residue was purified by silica-gel column chromatography (ethyl acetate/hexane), and powdered by ethyl acetate and hexane to give 5-bromo-1-(4-chlorobenzyl)-2-[4-(6-cyano-2-pyridyloxy)phenylamino]pyrimidin-6(1H)-one (268 mg, yield: 59%) as white solid.

1H-NMR (δ ppm TMS/DMSO-d6): 5.44 (2H, s), 7.17 (2H, d, J=8.7 Hz), 7.31 (2H, d, J=8.0 Hz), 7.39-7.49 (5H, m), 7.79 (1H, d, J=7.3 Hz), 7.98-8.14 (2H, m), 9.16 (1H, s).

Example 12

Preparation of 1-(4-chlorobenzyl)-2-[4-(6-cyano-2-pyridyloxy)phenylamino]-5-phenylpyrimidin-6(1H)-one (I-408)

[Chemical Formula 118]

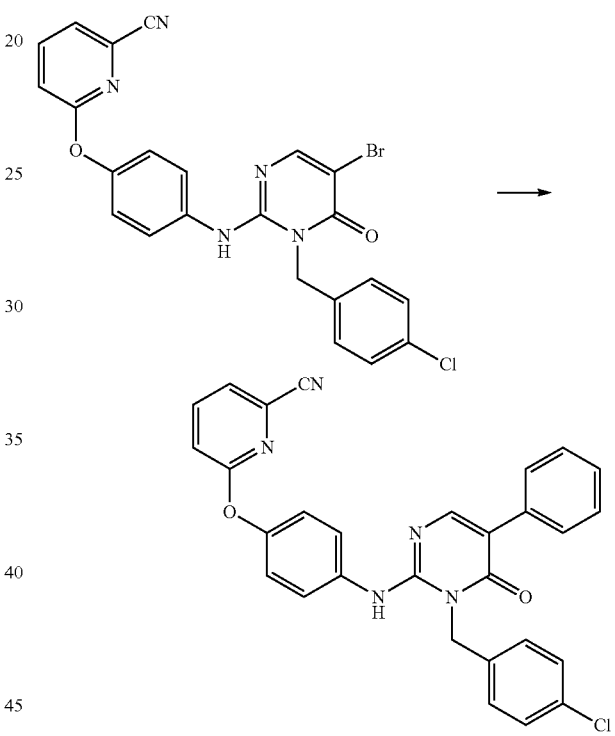

After purged with nitrogen, dichloromethane adduct of [1,1'-bis(diphenylphosphino)ferrocene]dichloropalladium (II) (28 mg, 0.03 mmol) was added to mixture of 5-bromo-1-(4-chlorobenzyl)-2-[4-(6-cyano-2-pyridyloxy)phenylamino]pyrimidin-6(1H)-one (1.50 mg, 0.3 mmol), phenylboronic acid (40 mg, 0.33 mmol), 2 mol/L sodium carbonate aqueous solution (0.59 mL, 1.2 mmol) and THF (1.5 mL), and stirred under heating at reflux for 4 hours. The reaction mixture was added to saturated chloride ammonium aqueous solution, extracted with ethyl acetate. The organic phase was washed by saturated saline, dried over anhydrous magnesium sulfate, and then concentrated in vacuo. The residue was purified by silica-gel column chromatography (ethyl acetate/n-hexane) to give 1-(4-chlorobenzyl)-2-[4-(6-cyano-2-pyridyloxy)phenylamino]-5-phenylpyrimidin-6(1H)-one (66 mg, yield: 44%) as colorless amorphous.

1H-NMR (δ ppm TMS/CDCl3): 5.43 (2H, s), 6.39 (1H, s), 7.08-7.20 (4H, m), 7.27-7.46 (11H, m), 7.68 (2H, d, J=7.5 Hz), 7.80 (1H, dd, J=8.3, 7.5 Hz), 7.96 (1H, s).

Reference Example 1

Preparation of 1-(4-chlorobenzyl)-5-ethoxycarbonyl-2-[4-(4-methoxybenzyloxy)phenylamino]pyrimidin-6(1H)-one

[Chemical Formula 119]

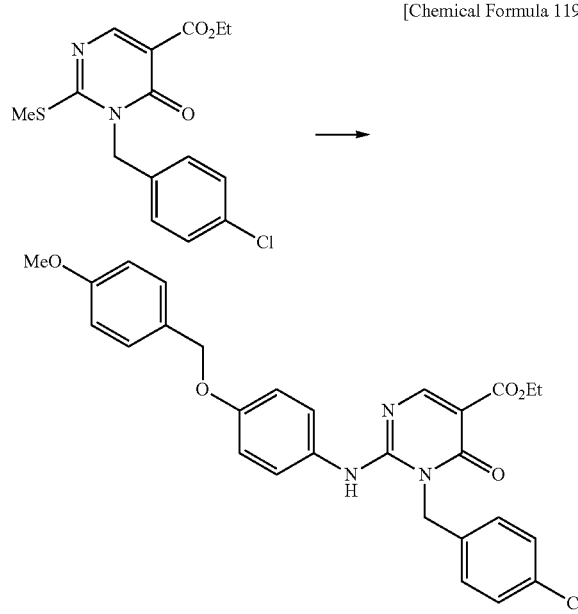

Mixture of 5-ethoxycarbonyl-1-(4-chlorobenzyl)-2-(methylthio)pyrimidin-6(1H)-one (1.25 g, 3.7 mmol), 4-(4-methoxybenzyloxy)aniline (1.69 g, 7.4 mmol), t-butanol (25 mL) and acetic acid (3.17 mL) was stirred under heating at reflux for 15 hours. The reaction mixture was added to mixture of saturated sodium hydrogen carbonate aqueous solution (100 mL) and water (100 mL), and extracted with ethyl acetate (150 mL). The organic phase was washed by 0.1 M hydrochloride (100 mL) and saturated saline (100 mL), and dried over anhydrous sodium sulfate. After concentrated in vacuo, the residue was purified by silica-gel column chromatography (ethyl acetate/hexane) to give 1-(4-chlorobenzyl)-5-ethoxycarbonyl-2-[4-(4-methoxybenzyloxy)phenylamino]pyrimidin-6(1H)-one (1.52 g, yield: 79%) as pale brown amorphous.

1H-NMR (δ ppm TMS/CDCl3): 1.36 (3H, t, J=7.0 Hz), 3.81 (3H, s), 4.34 (2H, q, J=7.0 Hz), 4.96 (2H, s), 5.36 (2H, s), 6.52 (1H, s), 6.87-6.98 (4H, m), 7.07 (2H, d, J=8.0 Hz), 7.28-7.36 (4H, m), 7.40 (2H, d, J=7.5 Hz), 8.59 (1H, s).

Reference Example 2

Preparation of 1-(4-chlorobenzyl)-2-[4-(4-methoxybenzyloxy)phenylamino]-5-(5-methyloxazol-2-yl)pyrimidin-6(1H)-one

[Chemical Formula 120]

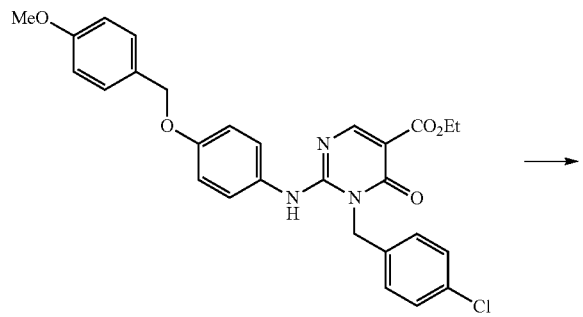

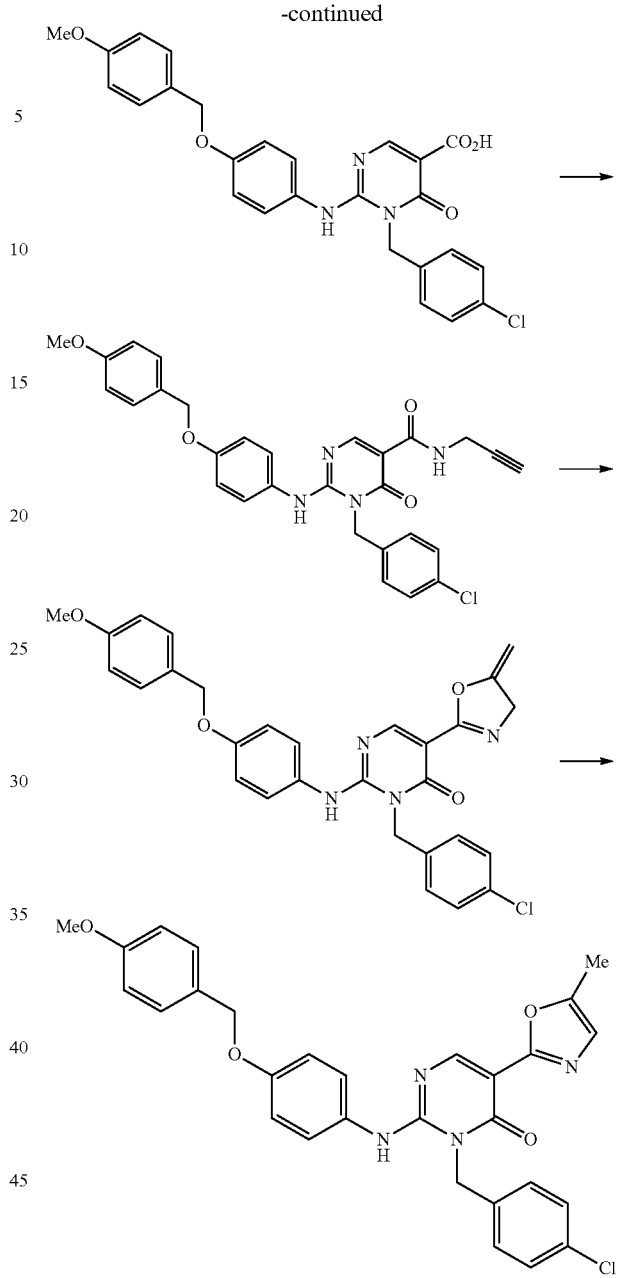

Step 1

4 mol/L Lithium hydroxide (2.88 mL) was added to mixture of 1-(4-chlorobenzyl)-5-ethoxycarbonyl-2-[4-(4-methoxybenzyloxy)phenylamino]pyrimidin-6(1H)-one (1.5 g, 2.9 mmol), ethanol (15 mL), THF (15 mL) and water (15 mL), and stirred at 80° C. for 23 hours. The reaction mixture was poured into water (100 mL), acidified by 2 mol/L hydrochloride, and then extracted with ethyl acetate (150 mL). The organic phase was washed by saturated saline (100 mL), and dried over anhydrous magnesium sulfate. After concentrated in vacuo, the residue was added to ethyl acetate, and the resulting powder was filtered to give 1-(4-chlorobenzyl)-5-hydroxycarbonyl-2-[4-(4-methoxybenzyloxy)phenylamino]pyrimidin-6(1H)-one (0.99 g, yield: 70%) as white powder.

1H-NMR (δ ppm TMS/DMSO-d6): 3.76 (3H, s), 5.02 (21H, s), 5.42 (2H, s), 6.95 (2H, d, J=8.3 Hz), 7.01 (2H, d, J=8.5 Hz), 7.16-7.24 (2H, m), 7.31-7.41 (4H, m), 7.45 (2H, d, J=8.0 Hz), 8.47 (1H, s), 9.78 (1H, s), 12.79 (1H, br s).

Step 2

Propargylamine (66 mg, 1.2 mmol), 1-hydroxybenzotriazole (162 mg, 1.2 mmol), 4-dimethylaminopyridine (12 mg, 0.1 mmol) and 1-ethyl-3-(3-dimethylaminopropyl)carbodiimide hydrochloride (229 mg, 1.2 mmol) were added to mixture of 1-(4-chlorobenzyl)-5-hydroxycarbonyl-2-[4-(4-methoxybenzyloxy)phenylamino]pyrimidin-6(1H)-one (490 mg, 1 mmol) and DMF (5 mL), and stirred overnight at room temperature. The reaction mixture was added to water (100 mL), and extracted with ethyl acetate (100 mL). The organic phase was washed by saturated sodium hydrogen carbonate aqueous solution (100 mL) and saturated saline (100 mL), and dried over anhydrous magnesium sulfate. After concentrated in vacuo, the residue was purified by silica-gel column chromatography (ethyl acetate/hexane) to give 1-(4-chlorobenzyl)-5-propargylcarbamoyl-2-[4-(4-methoxybenzyloxy)phenylamino]pyrimidin-6(1H)-one (429 mg, yield: 81%) as white solid.

Step 3

Zinc iodide (241 mg, 0.76 mmol) was added to mixture of 1-(4-chlorobenzyl)-5-propargylcarbamoyl-2-[4-(4-methoxybenzyloxy)phenylamino]pyrimidin-6(1H)-one (400 mg, 0.76 mmol) and dichloromethane (4 mL), and stirred at room temperature for 8 hours. The reaction mixture was added to water (100 mL), and extracted with ethyl acetate (100 mL). The organic phase was washed by saturated sodium hydrogen carbonate aqueous solution (100 mL) and saturated saline (100 mL), and dried over anhydrous sodium sulfate. After concentrated in vacuo, 1-(4-chlorobenzyl)-5-(5-methylene-4,5-dihydrooxazol-2-yl)-2-[4-(4-methoxybenzyloxy)phenylamino]pyrimidin-6(1H)-one (457 mg) was given as the crude product.

1H-NMR (δ ppm TMS/CDCl3): 3.80 (3H, s), 4.09-4.45 (2H, m), 4.83 (1H, br s), 4.90-4.98 (2H, m), 5.28-5.94 (2H, m), 6.65-6.99 (5H, m), 7.04-7.24 (2H, m), 7.27-7.47 (6H, m), 8.48 (1H, br s).

Step 4

DBU (222 mg, 1.46 mmol) was added to mixture of the crude product of 1-(4-chlorobenzyl)-5-(5-methylene-4,5-dihydrooxazol-2-yl)-2-[4-(4-methoxybenzyloxy)phenylamino]pyrimidin-6(1H)-one (386 mg, 0.73 mmol) and toluene (4 mL), and stirred at 80° C. for 3 hours. The reaction mixture was added to water (100 mL), and extracted with ethyl acetate (100 mL). The organic phase was washed by 5% citric acid aqueous solution (100 mL) and saturated saline (100 mL), and dried over anhydrous sodium sulfate. After concentrated in vacuo, the residue was purified by silica-gel column chromatography (ethyl acetate/hexane) to give 1-(4-chlorobenzyl)-2-[4-(4-methoxybenzyloxy)phenylamino]-5-(5-methyloxazol-2-yl)pyrimidin-6(1H)-one (246 mg, yield: 64%) as pale brown amorphous.

1H-NMR (δ ppm TMS/CDCl3): 2.38 (3H, s), 3.81 (3H, s), 4.97 (2H, s), 5.41 (2H, s), 6.41 (1H, s), 6.81 (1H, s), 6.92 (4H, dd, J=8.8, 6.8 Hz), 7.10 (2H, d, J=8.8 Hz), 7.33 (4H, d, J=8.4 Hz), 7.40 (2H, d, J=8.4 Hz), 8.46 (1H, s).

Example 13

Preparation of 1-(4-chlorobenzyl)-2-[4-(6-cyano-2-pyridyloxy)phenylamino]-5-(5-methyloxazol-2-yl)pyrimidin-6(1H)-one (I-278)

[Chemical Formula 121]

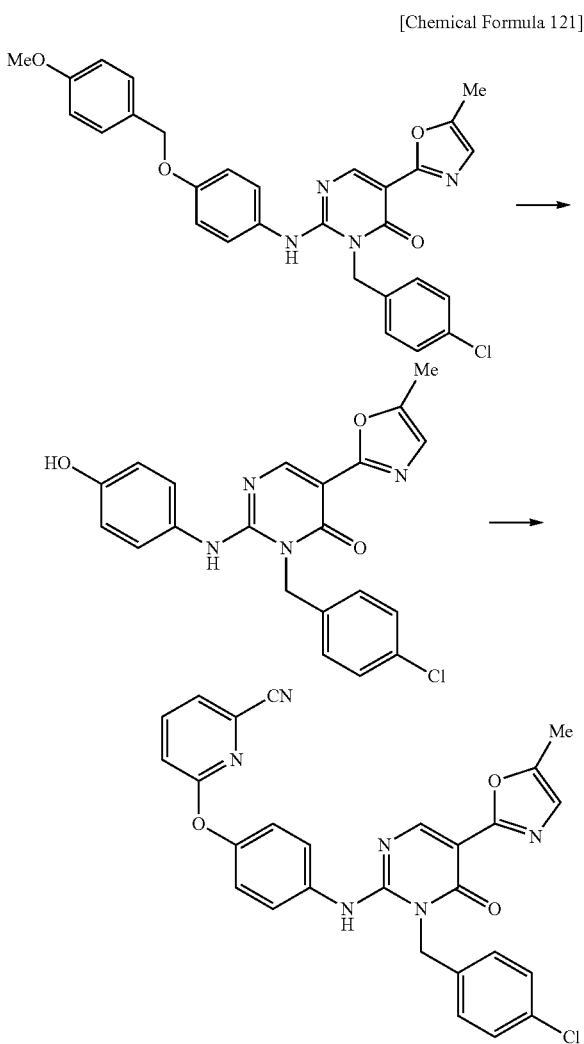

Step 1

Trifluoroacetic acid (1.9 mL) was added to 1-(4-chlorobenzyl)-2-[4-(4-methoxybenzyloxy)phenylamino]-5-(5-methyloxazol-2-yl)pyrimidin-6(1H)-one (246 mg, 0.465 mmol) and anisole (98 mg, 0.92 mmol), and stirred at room temperature for 1 hour. The reaction mixture was concentrated in vacuo, and the residue was purified by silica-gel column chromatography (methanol/water/chloroform) to give 1-(4-chlorobenzyl)-2-(4-hydroxyphenyl)amino]-5-(5-methyloxazol-2-yl)pyrimidin-6(1H)-one (221 mg, yield: 99%, purity: 85%) as yellow solid.

1H-NMR (δ ppm TMS/DMSO-d6): 2.32 (3H, s), 5.41 (2H, s), 6.75 (2H, d, J=8.2 Hz), 6.93 (1H, s), 7.08 (2H, d, J=8.3 Hz), 7.32 (2H, d, J=8.0 Hz), 7.44 (2H, d, J=7.9 Hz), 8.27 (1H, s), 9.30 (2H, br s).

Step 2

2-Chloro-6-cyanopyridine (138 mg, 1 mmol) and cesium carbonate (325 mg, 1 mmol) were added to mixture of 1-(4-chlorobenzyl)-2-(4-hydroxyphenyl)amino-5-(5-methyloxazol-2-yl)pyrimidin-6(1H)-one (160 mg, 0.33 mmol, purity: 85%) and DMF (5 mL), and stirred at 80° C. for 1.5 hours. The reaction mixture was added to water (100 mL), and extracted with ethyl acetate (100 mL). The organic phase was washed by saturated sodium hydrogen carbonate aqueous solution (100 mL) and saturated saline (100 mL), and dried over anhydrous sodium sulfate. After concentrated in vacuo, the residue was purified by silica-gel column chromatography (ethyl acetate/hexane) to give 1-(4-chlorobenzyl)-2-[4-(6-cyano-2-pyridyloxy)phenylamino]-5-(5-methyloxazol-2-yl)pyrimidin-6(1H)-one (87.8 mg, yield: 52%) as brown amorphous.

1H-NMR (δ ppm TMS/CDCl3): 2.39 (3H, s), 5.45 (2H, s), 6.81 (2H, d, J=13.9 Hz), 7.12 (2H, d, J=8.3 Hz), 7.17 (1H, d, J=8.4 Hz), 7.29 (2H, d, J=8.3 Hz), 7.36 (2H, d, J=8.2 Hz), 7.41 (3H, d, J=7.9 Hz), 7.81 (1H, t, J=7.7 Hz), 8.50 (1H, s).

Example 14

Preparation of 1-(4-chlorobenzyl)-2-[4-(6-hydroxycarbonyl-2-pyridyloxy)phenylamino]-5-(5-methyloxazol-2-yl)pyrimidin-6(1H)-one (I-290)

[Chemical Formula 122]

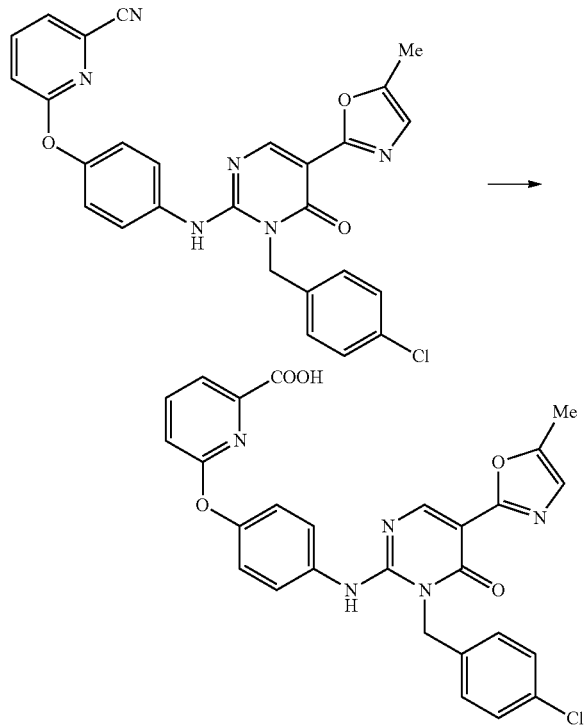

2 mol/L Lithium hydroxide (0.32 mL) was added to mixture of 1-(4-chlorobenzyl)-2-[4-(6-cyano-2-pyridyloxy)phenylamino]-5-(5-methyloxazol-2-yl)pyrimidin-6(1H)-one (34 mg, 0.06 mmol) and DMSO (0.32 mL), and stirred at 60° for 7 hours. The reaction mixture was poured into water, acidified by 2 mol/L hydrochloride, and then extracted with chloroform. The organic phase was washed by saturated saline, and dried over anhydrous sodium sulfate. After concentrated in vacuo, the residue was purified by silica-gel column chromatography (methanol/water/chloroform) to give 1-(4-chlorobenzyl)-2-[4-(6-hydroxycarbonyl-2-pyridyloxy)phenylamino]-5-(5-methyloxazol-2-yl)pyrimidin-6(1H)-one (32.4 mg, yield: 95%) as yellow solid.

1H-NMR (δ ppm TMS/DMSO-d6): 2.31 (3H, s), 5.46 (2H, s), 6.86 (1H, s), 7.14-7.28 (3H, m), 7.30-7.57 (6H, m), 7.79 (1H, d, J=7.4 Hz), 8.02 (1H, t, J=7.8 Hz), 8.30 (1H, s), 9.38 (1H, s), 13.23 (1H, br s).

Example 15

Preparation of 1-(4-chlorobenzyl)-2-[4-(6-fluoro-2-pyridyloxy)phenylamino]-5-(3-methyl-1,2,4-oxadiazol-5-yl)pyrimidin-4(1H)-one (I-190)

[Chemical Formula 123]

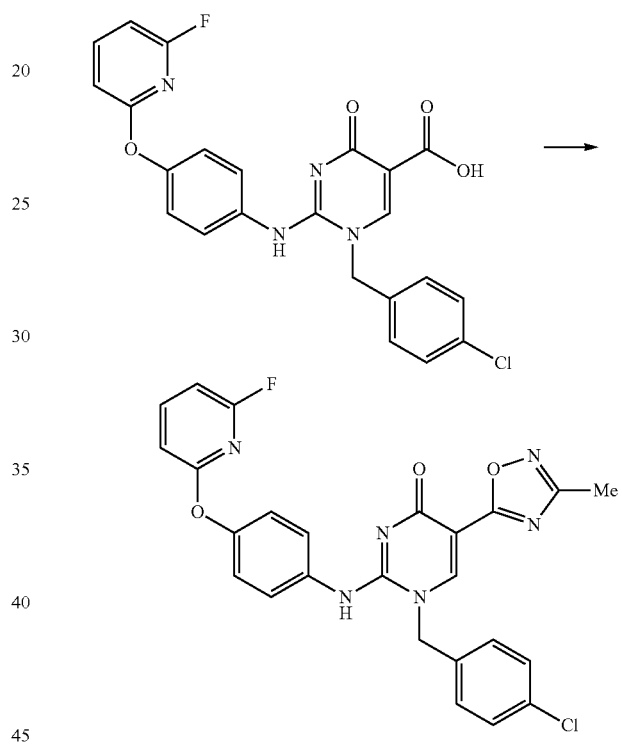

HBTU (0.21 g, 0.55 mmol), HOBt (14 mg, 0.1 mmol) and diisopropylethylamine (0.32 g, 2.5 mmol) were added to mixture of 1-(4-chlorobenzyl)-2-[4-(6-fluoro-2-pyridyloxy)phenylamino]-5-hydroxycarbonylpyrimidin-4(1H)-one (0.23 g, 0.5 mmol) and DMF (2 mL), and stirred at room temperature for 10 minutes. The reaction mixture was added to acetamidoxime (41 mg, 0.55 mmol), stirred at room temperature for 1 hour, and stirred at 110° C. for 14 hours. The reaction mixture was added to water (100 mL), and extracted with ethyl acetate (100 mL). The organic phase was washed by saturated saline (100 mL), dried over anhydrous magnesium sulfate, and then concentrated in vacuo. The residue was purified by silica-gel column chromatography (ethyl acetate/hexane) to give 1-(4-chlorobenzyl)-2-[4-(6-fluoro-2-pyridyloxy)phenylamino]-5-(3-methyl-1,2,4-oxadiazol-5-yl)pyrimidin-4(1H)-one (23 mg, yield: 9.1%) as pale yellow amorphous.

1H-NMR (δ ppm TMS/CDCl3): 2.42 (3H, s), 5.17 (2H, s), 6.62 (1H, d, J=7.8 Hz), 6.80 (1H, d, J=7.8 Hz), 6.87 (2H, d, J=8.0 Hz), 7.15-7.33 (3H, m), 7.40 (4H, s), 7.78 (1H, q, J=7.9 Hz), 8.35 (1H, s).

Example 16

Preparation of 1-(4-chlorobenzyl)-2-[4-(6-fluoro-2-pyridyloxy)phenylamino]-5-methoxypyrimidin-4(1H)-one (I-351)

[Chemical Formula 124]

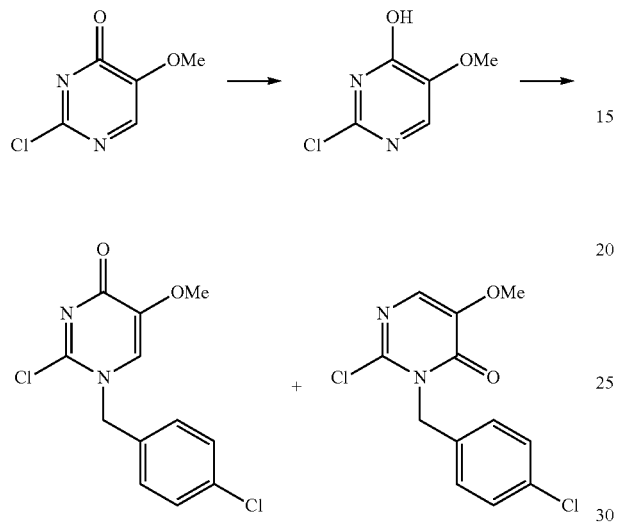

Step 1

2 mol/L Sodium hydroxide (20 mL) was added to mixture of 2,4-dichloro-5-methoxypyrimidine (5 g, 27.9 mmol), THF (10 mL) and water (10 mL), and stirred overnight at room temperature. The reaction mixture was added to water, acidified by 2 mol/L hydrochloride, and extracted with ethyl acetate. The organic phase was washed by saturated saline, dried over anhydrous magnesium sulfate, and concentrated in vacuo. The residue was washed by hexane to give 2-chloro-5-methoxypyrimidin-4-ol (2.53 g, yield: 56%) as white solid.

1H-NMR (δ ppm TMS/DMSO-d6): 4.00 (3H, s), 7.6 (1H, s), 8.66 (1H, s).

Step 2

DIPEA (4.11 mL, 23.5 mmol) was added to mixture of 2-chloro-5-methoxypyrimidin-4-ol (2.53 g, 15.8 mmol), 4-chlorobenzyl bromide (3.55 g, 17.3 mmol), and dichloromethane (40 mL), and stirred at room temperature for 3 days. The reaction mixture was added to saturated chloride ammonium aqueous solution, and extracted with dichloromethane. The organic phase was dried over anhydrous magnesium sulfate, and concentrated in vacuo. The residue was purified by silica-gel column chromatography (chloroform/methanol), 2-chloro-1-(4-chlorobenzyl)-5-methoxypyrimidin-4(1H)-one (1.3 g, yield: 16%) as white solid, 1H-NMR (δ ppm TMS/DMSO-d6): 3.69 (3H, s), 5.28 (2H, s), 7.33 (2H, d, J=12 Hz), 7.48 (2H, d, J=12 Hz), 7.85 (1H, s)

and 2-chloro-3-(4-chlorobenzyl)-5-methoxypyrimidin-4(3H)-one (1.2 g, yield: 15%) as white solid.

1H-NMR (δ ppm TMS/DMSO-d6): 3.79 (3H, s), 5.31 (2H, s), 7.28 (2H, d, J=8.0 Hz), 7.42 (2H, d, J=8.0 Hz), 7.55 (1H, s).

[Chemical Formula 125]

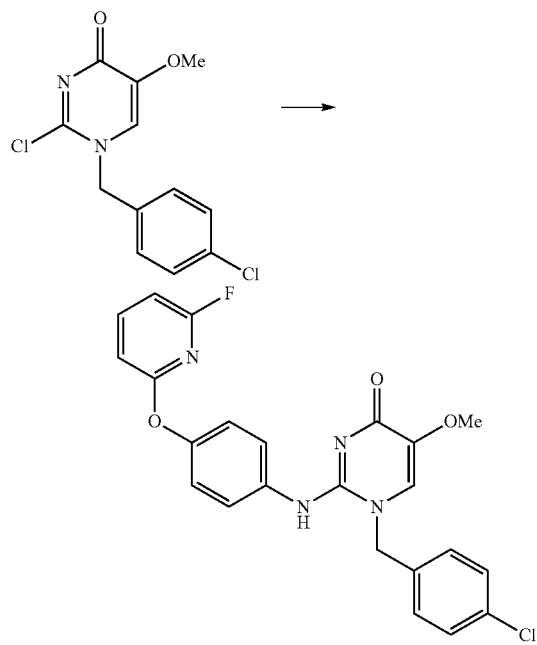

Step 3

A drop of 4 mol/L hydrochloride dioxane solution was added to mixture of 2-chloro-1-(4-chlorobenzyl)-5-methoxypyrimidin-4(1H)-one (200 mg, 0.7 mmol), 4-(6-fluoropyridin-2-yloxy)aniline (215 mg, 1.05 mmol) and ethanol (4 mL), and stirred at 120° C. under microwave for 15 minutes. The reaction mixture was concentrated in vacuo, the residue was purified by silica-gel column chromatography (chloroform/methanol), and then the resulting crude product was washed by hexane to give 1-(4-chlorobenzyl)-2-(4-(6-fluoropyridin-2-yloxy)phenylamino)-5-methoxypyrimidin-4(1H)-one (98.7 mg, yield: 31%) as white solid.

1H-NMR (δ ppm TMS/DMSO-d6): 3.60 (3H, s), 5.25 (2H, s), 6.85-6.89 (2H, m), 7.10 (2H, d, J=8.8 Hz), 7.31-7.33 (3H, m), 7.43-7.47 (4H, m), 8.00 (1H, q, J=8.2 Hz), 8.65 (1H, s).

Example 17

Preparation of 1-(4-chlorobenzyl)-2-[4-(6-fluoro-2-pyridyloxy)phenylamino]-5-(hydroxycarbonylmethyloxy)methylpyrimidin-4(1H)-one (I-428)

[Chemical Formula 126]

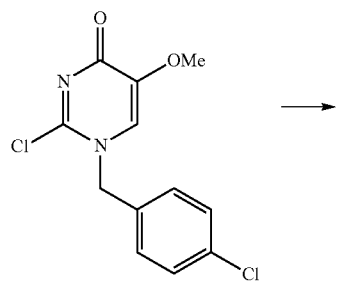

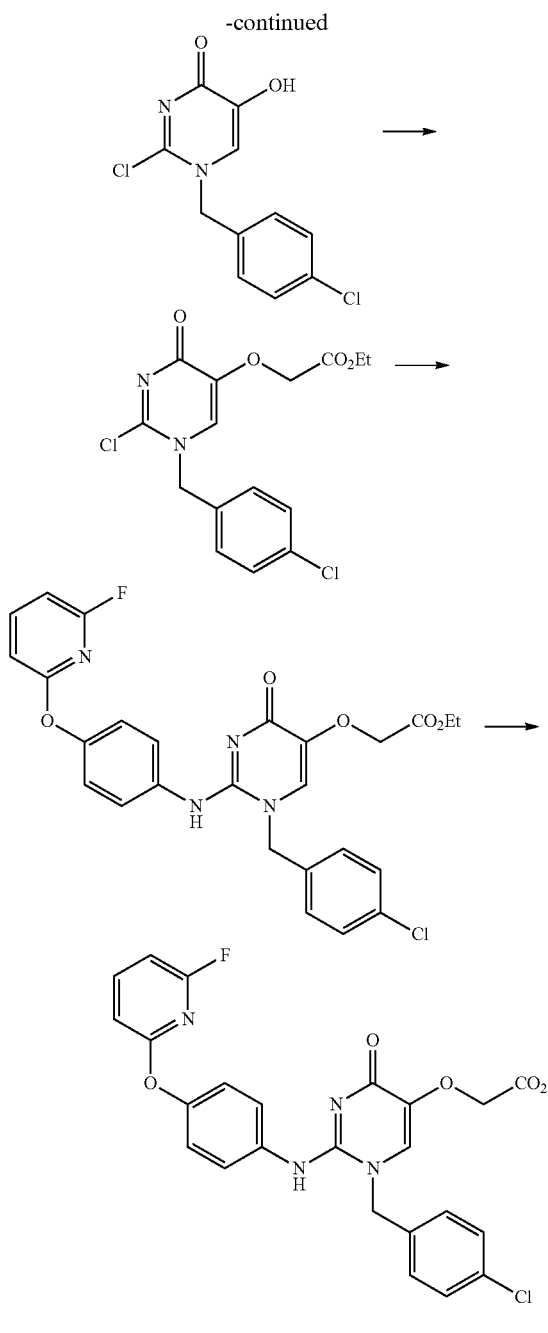

din-4(1H)-one (200 mg, 0.738 mmol), potassium carbonate (153 mg, 1.107 mmol) and acetonitrile (4 mL)/DMA (4 mL), stirred at 90° C. for 3 hours. The reaction mixture was added to water, and extracted with ethyl acetate. The extract was washed by saturated saline, dried overanhydrous magnesium sulfate, and then concentrated in vacuo to give 2-chloro-1-(4-chlorobenzyl)-5-(ethoxycarbonylmethyloxy)methylpyrimidin-4(1H)-one as crude product.

Step 3

4-(6-Fluoropyridin-2-yloxy)aniline (226 mg, 1.107 mmol), ethanol (4 mL) and a drop of 4 mol/L hydrochloride dioxane solution was added to the crude product of 2-chloro-1-(4-chlorobenzyl)-5-(ethoxycarbonylmethyloxy)methylpyrimidin-4(1H)-one, stirred at 120° C. under microwave for 15 minutes, and then concentrated in vacuo. The residue was added to ethanol (1 mL), THF (1 mL) and, 2 mol/L lithium hydroxide (2.0 mL), and stirred overnight at room temperature. The reaction mixture was added to 2 mol/L hydrochloride aqueous solution and acidified, and the resulting precipitate was filtered and purified by reversed phase silica-gel column chromatography (acetonitrile/water) to give 1-(4-chlorobenzyl)-2-[4-(6-fluoro-2-pyridyloxy)phenylamino]-5-(hydroxycarbonylmethyloxy)methylpyrimidin-4(1H)-one (4.4 mg, yield: 1.2%) as white solid.

1H-NMR (δ ppm TMS/DMSO-d6): 3.36 (1H, br s), 4.24 (2H, s), 5.25 (2H, s), 6.85-6.89 (2H, m), 7.10 (2H, d, J=8.0 Hz), 7.33 (2H, d, J=8.0 Hz), 7.42-7.46 (5H, m), 8.00 (1H, q, J=8.0 Hz), 8.77 (1H, s).

Example 18

Preparation of 1-(4-chlorobenzyl)-3-dimethylamino-6-[4-(5-fluoro-2-pyridyloxy)phenylamino]benzene (I-464)

[Chemical Formula 127]

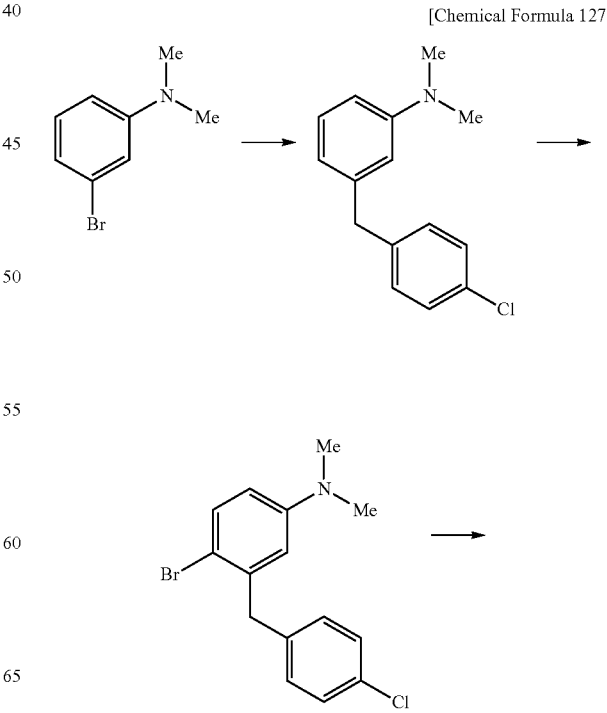

Step 1

1 mol/L Boron tribromide methylene chloride solution (50.5 mL, 50.5 mmol) was added to dichloromethane solution (120 mL) of 2-chloro-1-(4-chlorobenzyl)-5-methoxypyrimidin-4(1H)-one (6.0 g, 21.0 mmol) at 0° C., and stirred at 0° C. for 5.5 hours. The reaction mixture was added to saturated sodium hydrogen carbonate aqueous solution, and the resulting precipitate was filtered and then washed by ethyl acetate to give 2-chloro-1-(4-chlorobenzyl)-5-hydroxypyrimidin-4(1H)-one (5.97 g, yield: 105%, white solid) as crude product.

1H-NMR (δ ppm TMS/DMSO-d6): 4.07 (1H, br s), 5.25 (2H, s), 7.31-7.32 (2H, m), 7.46-7.49 (2H, m), 7.72 (1H, s).

Step 2

Ethyl bromoacetate (185 mg, 1.107 mmol) was added to mixture of 2-chloro-1-(4-chlorobenzyl)-5-hydroxypyrimi- -continued

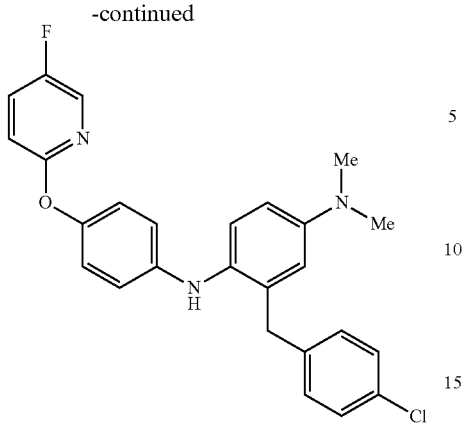

Step 1

4-Chlorobenzylzinc chloride (0.5 mol/L THF solution, 10 mL, 5 mmol), triphenylphosphine (65.5 mg, 0.25 mmol) and palladium acetate (II) (28 mg, 0.13 mmol) were added to mixture of 3-bromo-1-dimethylaminobenzene (500 mg, 2.5 mmol) and THF (3 mL), and stirred under heating at reflux for 3 hours under nitrogen atmosphere. The reaction mixture was added to water (200 mL), and extracted with ethyl acetate (200 mL). The organic phase was washed by saturated saline (200 mL), dried over anhydrous sodium sulfate, and then concentrated in vacuo. The residue was purified by silica-gel column chromatography (ethyl acetate/hexane) to give 1-(4-chlorobenzyl)-3-dimethylaminobenzene (558 mg, yield: 91%) as colorless oil.

1H-NMR (δ ppm TMS/CDCl$_3$): 2.89 (6H, s), 3.87 (2H, s), 6.48-6.59 (4H, m), 7.08-7.22 (4H, m).

Step 2

N-Bromosuccinimide (418 mg, 2.4 mmol) was added to mixture of 1-(4-chlorobenzyl)-3-dimethylaminobenzene (550 m g, 2.2 mmol) and dichloromethane (14 mL), and stirred at 0° C. for 1 hour. The reaction mixture was added to water (100 mL), and extracted with chloroform (100 mL). The organic phase was washed by saturated saline (100 mL), dried overanhydrous sodium sulfate, and then concentrated in vacuo. The residue was purified by silica-gel column chromatography (ethyl acetate/hexane) to give 6-bromo-1-(4-chlorobenzyl)-3-dimethylaminobenzene (683 mg, yield: 95%) as colorless oil.

1H-NMR (δ ppm TMS/CDCl$_3$): 2.88 (6H, s), 4.02 (2H, s), 6.47-6.49 (2H, m), 7.11 (2H, m), 7.24 (2H, m), 7.35 (1H, m).

Step 3

After purged with nitrogen, mixture of 6-bromo-1-(4-chlorobenzyl)-3-dimethylaminobenzene (100 mg, 0.31 mmol), 4-(5-fluoro-2-pyridyloxy)aniline (94 mg, 0.46 mmol), Davephos(2-(dicyclohexylphosphino)-2'-(dimethylamino)biphenyl) (12.1 mg, 0.03 mmol), sodium tert-butoxide (44.4 mg, 0.46 mmol) and dioxane (2 mL) was added to Pd$_2$(dba)$_3$ (9.5 mg, 0.01 mmol), and stirred at 100 for 1 hour. The reaction mixture was added to water (100 mL), and extracted with ethyl acetate (100 mL). The organic phase was washed by saturated saline (100 mL), dried over anhydrous magnesium sulfate, and then concentrated in vacuo. The residue was purified by silica-gel column chromatography (ethyl acetate/hexane) to give 1-(4-chlorobenzyl)-3-dimethylamino-6-[4-(5-fluoro-2-pyridyloxy)phenylamino]benzene (108 mg, yield: 78%) as brown oil.

1H-NMR (δ ppm TMS/CDCl$_3$): 2.93 (6H, s), 3.88 (2H, s), 4.91 (1H, s), 6.60-6.65 (5H, m), 6.82 (1H, dd, J=9.0, 3.5 Hz), 6.90 (2H, d, J=8.8 Hz), 7.08 (2H, d, J=8.3 Hz), 7.14 (1H, d, J=8.8 Hz), 7.23 (1H, d, J=8.5 Hz), 7.37-7.40 (1H, m), 8.02 (1H, d, J=3.0 Hz).

Example 19

Preparation of 3-t-butyl-1-(4-chlorobenzyl)-5-[4-(6-carbamoyl-2-pyridyloxy)phenylamino]pyrazole (I-468)

[Chemical Formula 128]

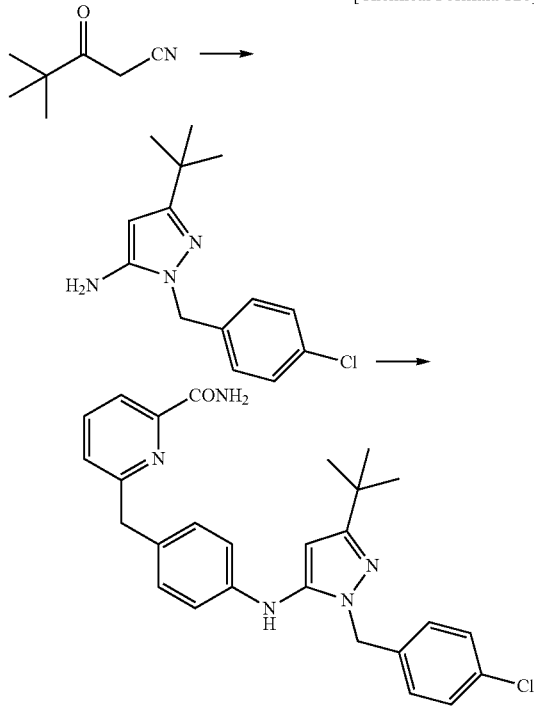

Step 1

Pivaloylacetonitrile (245 mg, 2 mmol) was added to mixture of 4-chlorobenzylhydrazine dihydrochloride (449 mg, 2 mmol), ethanol (3 mL) triethylamine (0.57 mL, 4.1 mmol), and stirred under heating at reflux for 7 hours. The reaction mixture was concentrated in vacuo. The resulting residue was purified by silica-gel column chromatography (ethyl acetate/hexane) to give 5-amino-3-t-butyl-1-(4-chlorobenzyl)pyrazole (290 mg, yield: 56%) as colorless solid.

1H-NMR (δ ppm TMS/DMSO-d6): 1.16 (9H, s), 5.04 (2H, s), 5.10 (2H, s), 5.19 (1H, s), 7.11 (2H, d, J=8.1 Hz), 7.37 (2H, d, J=8.1 Hz).

Step 2

1-Bromo-4-(6-cyano-2-pyridyloxy)benzene (393 mg, 1.4 mmol), tris(dibenzylideneacetone)dipalladium(0) (12 mg, 0.014 mmol), 4,5-bis(diphenylphosphino)-9,9-dimethylxanthene (19 mg, 0.03 mmol), and sodium phenoxide trihydrate (281 mg, 1.6 mmol) were added to mixture of 5-amino-3-t-butyl-1-(4-chlorobenzyl)pyrazole (290 mg, 1.1 mmol) and dioxane (1 mL), and stirred at 170° C. under microwave for 1 hours. The reaction mixture was added to saturated sodium hydrogen carbonate aqueous solution, and extracted with ethyl acetate. The organic phase was washed by saturated saline, dried over anhydrous sodium sulfate, and then concentrated in vacuo. The resulting residue was purified by silica-gel column chromatography (ethyl acetate/hexane) to give 3-t-butyl-1-(4-chlorobenzyl)-5-[4-(6-carbamoyl-2-pyridyloxy)phenylamino]pyrazole (20 mg, yield: 16%) as pale yellow solid.

1H-NMR (δ ppm TMS/DMSO-d6): 1.23 (9H, s), 5.20 (2H, s), 5.96 (1H, s), 6.89 (2H, d, J=8.4 Hz), 7.01-7.09 (3H, m), 7.22-7.30 (1H, m), 7.36-7.40 (2H, m), 7.48 (1H, s), 7.67-7.81 (3H, m), 7.90-8.03 (2H, m).

Example 20

Preparation of 5-(4-chlorobenzyl)-6-[4-(6-cyano-2-pyridyloxy)phenylamino]-3-ethylpyrimidin-2,4(1H,3H)-dione (I-456)

[Chemical Formula 129]

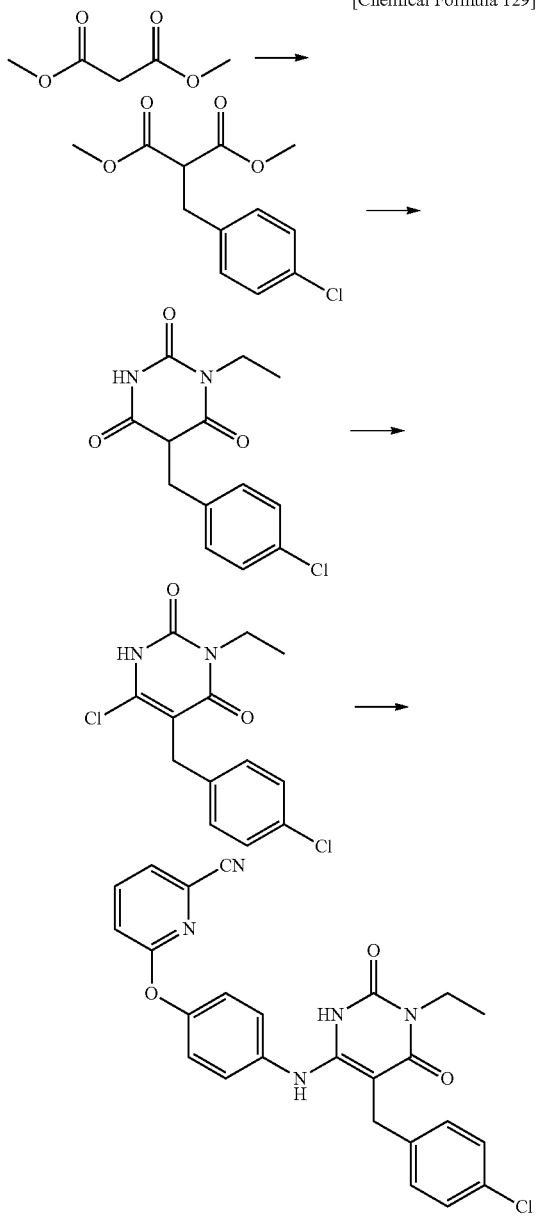

Step 1

Dimethyl malonate (10.0 g, 76 mmol) was added to mixture of 60% sodium hydride (3.03 g, 76 mmol) and DMF (100 mL) under ice-cooling, stirred at room temperature for 30 minutes, then added to mixture of 4-chlorobenzyl bromide (15.55 g, 76 mmol) and DMF (20 mL) under ice-cooling, and then stirred at room temperature for 80 minutes. The reaction mixture was added to ice water (450 mL), and extracted with ethyl acetate (200 mL). The organic phase was washed by saturated saline (50 mL×2), dried over anhydrous magnesium sulfate, and then concentrated in vacuo. The residue was purified by silica-gel column chromatography (ethyl acetate/hexane) to give dimethyl 2-(4-chlorobenzyl)malonate (9.39 g, yield: 48%) as colorless oil.

1H-NMR (δ ppm TMS/CDCl$_3$): 3.19 (2H, d, J=7.8 Hz), 3.64 (1H, t, J=7.8 Hz), 3.71 (6H, s), 7.13 (2H, d, J=8.0 Hz), 7.25 (2H, d, J=8.0 Hz).

Step 2

1-Ethylurea (1.66 g, 19 mmol) and sodium methoxide (5 mol/L methanol solution, 3.76 mL, 19 mmol) were added to mixture of dimethyl 2-(4-chlorobenzyl)malonate (4.83 g, 19 mmol) and methanol (46 mL), and stirred under heating at reflux for 22.5 hours. The reaction mixture was added to 1 mol/L citric acid aqueous solution (20 mL), concentrated in vacuo, then added to water (10 mL), and then extracted with ethyl acetate. The organic phase was washed by saturated saline, dried over anhydrous magnesium sulfate, and then concentrated in vacuo. The residue was purified by silica-gel column chromatography (ethyl acetate/hexane) to give 5-(4-chlorobenzyl)-1-ethylpyrimidin-2,4,6(1H,3H,5H)-trione (3.73 g, yield: 71%) as white solid.

1H-NMR (δ ppm TMS/CDCl3): 1.07 (3H, t, J=7.2 Hz), 3.46 (1H, dd, J=5.0, 13.8 Hz), 3.50 (1H, dd, J=5.0, 13.8 Hz), 3.70-3.88 (33H, m), 7.07 (2H, d, J=8.4 Hz), 7.22 (2H, d, J=8.4 Hz), 8.32 (1H, brs).

Step 3

Benzyltriethylammonium chloride (1.44 g, 6.3 mmol) was added to mixture of 5-(4-chlorobenzyl)-1-ethylpyrimidin-2,4,6(1H,3H,5H)-trione (0.89 g, 3.2 mmol) and phosphorus oxychloride (8.9 mL), stirred at 70° C. for 2 hours. The reaction mixture was added to ice water (45 ml), and extracted with ethyl acetate. The organic phase was washed by saturated sodium hydrogen carbonate aqueous solution and saturated saline, dried over anhydrous magnesium sulfate, and then concentrated in vacuo. The residue was purified by silica-gel column chromatography (ethyl acetate/hexane) to give 6-chloro-5-(4-chlorobenzyl)-1-ethyl-2,4(1H,3H)-dione (354 mg, yield: 37%) as white solid;

1H-NMR (δ ppm TMS/CDCl3): 1.22 (3H, t, J=7.0 Hz), 3.78 (2H, s), 3.97 (2H, q, J=7.0 Hz), 7.25 (4H, s), 10.36 (1H, s).

Step 4

4-(6-Cyano-2-pyridyloxy)aniline (115 mg, 0.54 mmol), palladium acetate (II) (12.2 mg, 0.054 mmol), 4,5-bis(diphenylphosphino)-9,9-dimethylxanthene (47.3 mg, 0.082 mmol) and cesium carbonate (248 mg, 0.76 mmol) were added to mixture of 6-chloro-5-(4-chlorobenzyl)-1-ethyl-2,4(1H,3H)-dione (195 mg, 0.65 mmol) and dioxane (4 mL), and stirred under heating at reflux for 2.5 hours. The reaction mixture was added to water, extracted with ethyl acetate. The organic phase was washed by saturated saline, dried over anhydrous magnesium sulfate, and then concentrated in vacuo. The residue was purified by silica-gel column chromatography (ethyl acetate/hexane) and solidified by ethanol and dichloromethane to give 5-(4-chlorobenzyl)-6-[4-(6-cyano-2-pyridyloxy)phenylamino]-3-ethylpyrimidin-2,4(1H,3H)-dione (118 mg, yield: 46%) as pale yellow solid.

1H-NMR (δ ppm TMS/DMSO-d6): 1.08 (3H, t, J=6.7 Hz), 3.70 (2H, s), 3.78 (2H, q, J=6.7 Hz), 7.09 (2H, d, J=8.4 Hz), 7.15 (2H, d, J=8.4 Hz), 7.21 (2H, d, J=8.0 Hz), 7.27

(2H, d, J=8.0 Hz), 7.39 (1H, d, J=8.4 Hz), 7.79 (1H, d, J=7.3 Hz), 8.09 (1H, t, J=7.9 Hz), 8.48 (1H, s), 10.74 (1H, s).

Example 21

Preparation of 3-(4-chloro-benzyl)-1-isopropyl-4-[4-(6-methoxycarbonyl-2-pyridyloxy)phenylamino]pyridin-2(1H)-one (I-465)

[Chemical Formula 130]

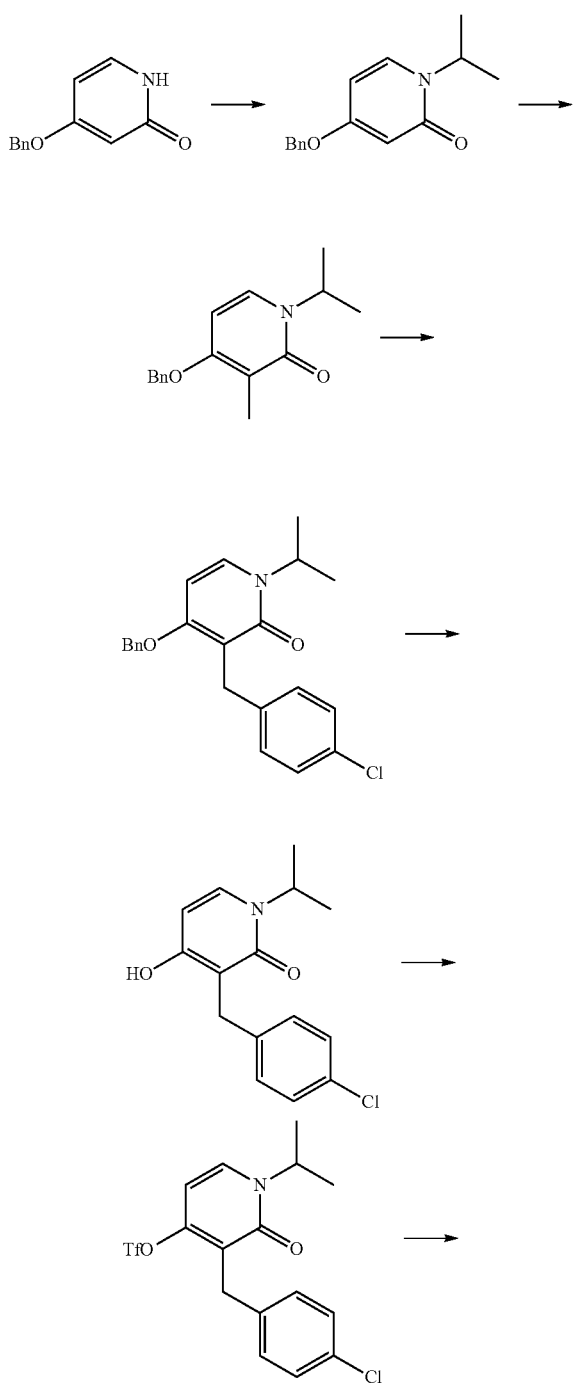

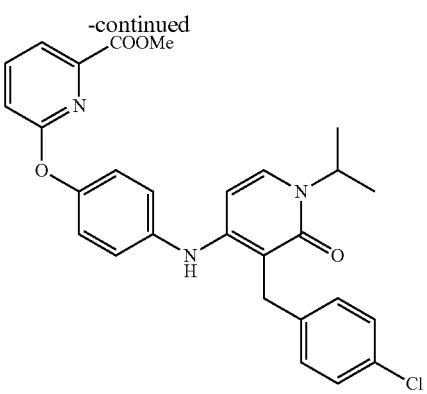

Step 1

60% Sodium hydride (4.77 g, 119 mmol) was added to mixture of 4-benzyloxy-2-pyridin-2(1H)-one (20 g, 99 mmol) and DMF (150 mL) under ice-cooling, stirred under ice-cooling for 30 minutes, then added to isopropyl iodide (10.91 mL, 109 mmol) under ice-cooling, and stirred at room temperature for 2 hours then at 80° C. for 3 hours. The reaction mixture was added to ice water and extracted with ethyl acetate. The organic phase was washed by saturated saline, dried over anhydrous magnesium sulfate, and then concentrated in vacuo. The residue was purified by silica-gel column chromatography (ethyl acetate/hexane) to give 4-benzyloxy-1-isopropyl-2-pyridin-2(1H)-one (2.71 g, yield: 11%) as yellow solid.

1H-NMR (δ ppm TMS/CDCl3): δ: 1.32 (6H, d, J=6.9 Hz), 4.98 (2H, s), 5.16-5.29 (1H, m), 5.96-6.05 (2H, m), 7.20 (1H, d, J=7.5 Hz), 7.32-7.44 (5H, m).

Step 2

N-Iodosuccinimide (2.64 g, 11.8 mmol) was added to mixture of 4-benzyloxy-1-isopropyl-2-pyridin-2(1H)-one (2.60 g, 10.7 mmol) and acetonitrile (50 mL), and stirred at room temperature for 2.5 hours. The reaction mixture was added to ethyl acetate, washed by saturated sodium hydrogen carbonate aqueous solution and saturated saline, then dried over anhydrous magnesium sulfate, and then concentrated in vacuo. The residue was purified by silica-gel column chromatography (ethyl acetate/hexane) to give 4-benzyloxy-3-iodo-1-isopropyl-2-pyridin-2(1H)-one (4.59 g, yield: 100%) as yellow oil.

1H-NMR (5 ppm TMS/CDCl3): δ: 1.34 (6H, d, J=6.8 Hz), 5.21-5.33 (3H, m), 6.03 (1H, d, J=7.7 Hz), 7.27-7.48 (6H, m).

Step 3

4-Chlorobenzylzinc chloride (0.5 mol/L THF solution, 28 mL, 14 mmol), triphenylphosphine (244 mg, 0.93 mmol) and palladium acetate (II) (105 mg, 0.47 mmol) were added to mixture of 4-benzyloxy-3-iodo-1-isopropyl-2-pyridin-2(1H)-one (2 g, 4.7 mmol) and THF (12 mL), and stirred under heating at reflux for 3 hours. The reaction mixture was added to water (200 mL), and extracted with ethyl acetate (200 mL). The organic phase was washed by saturated sodium hydrogen carbonate aqueous solution and saturated saline (200 mL), dried over anhydrous magnesium sulfate, and then concentrated in vacuo. The residue was purified by silica-gel column chromatography (ethyl acetate/hexane) to give 3-(4-chloro-benzyl)-4-benzyloxy-1-isopropyl-2-pyridin-2(1H)-one (1.43 g, yield: 78%) as yellow solid.

1H-NMR (δ ppm TMS/CDCl3): δ: 1.31 (6H, d, J=6.8 Hz), 3.90 (2H, s), 5.11 (2H, s), 5.22-5.35 (1H, m), 6.12 (1H, d, J=7.9 Hz), 7.13-7.44 (10H, m).

Step 4

Boron tribromide (1 mol/L dichloromethane solution, 7.2 mL, 7.2 mmol) was added to mixture of 3-(4-chloro-benzyl)-4-benzyloxy-1-isopropyl-2-pyridin-2(1H)-one (1.2 g, 3.3 mmol) and dichloromethane (5 mL) under ice-cooling, and stirred at room temperature for 2 hours. The reaction mixture was added to half-saturated sodium hydrogen carbonate aqueous solution (200 mL), and extracted with 10% methanol/chloroform (200 mL). The organic phase was washed by saturated saline (200 mL), dried over anhydrous sodium sulfate, and then concentrated in vacuo. The residue was solidified by ethyl acetate/hexane to give 3-(4-chloro-benzyl)-4-hydroxy-1-isopropyl-2-pyridin-2(1H)-one (0.84 g, yield: 92%) as white solid.

1H-NMR (δ ppm TMS/CDCl$_3$): δ: 1.22 (6H, d, J=6.8 Hz), 3.67 (2H, s), 4.94-5.11 (1H, m), 6.02 (1H, d, J=7.7 Hz), 7.19-7.31 (4H, m), 7.48 (1H, d, J=7.7 Hz), 10.40 (1H, br s).

Step 5

Trifluoromethanesulfonic anhydride (1.52 mL, 9 mmol) was added to mixture of 3-(4-chloro-benzyl)-4-hydroxy-1-isopropyl-2-pyridin-2(1H)-one (0.83 g, 3 mmol), pyridine (0.72 mL, 9 mmol), THF (8 mL) and dichloromethane (16 mL) under ice-cooling, and stirred at room temperature for 1 hour. The reaction mixture was concentrated in vacuo, added to ethyl acetate, and washed by 5% citric acid aqueous solution and saturated saline. The organic phase was dried over anhydrous sodium sulfate, then concentrated in vacuo, and the resulting residue was purified by silica-gel column chromatography (ethyl acetate/hexane) to give 3-(4-chloro-benzyl)-4-trifluoromethanesulfonyloxy-1-isopropyl-2-pyridin-2(1H)-one (1.35 g, yield: 99%) as colorless oil.

1H-NMR (δ ppm TMS/CDCl$_3$): δ: 1.36 (6H, d, J=6.8 Hz), 3.93 (2H, s), 5.15-5.28 (1H, m), 6.31 (1H, d, J=7.9 Hz), 7.20-7.30 (4H, m), 7.34 (1H, d, J=7.8 Hz).

Step 6

4-(6-Methoxycarbonyl-2-pyridyloxy)aniline (223 mg, 0.92 mmol), palladium acetate (II) (14 mg, 0.06 mmol), 4,5-bis(diphenylphosphino)-9,9-dimethylxanthene (53 mg, 0.09 mmol) and cesium carbonate (278 mg, 0.85 mmol) were added to mixture of 3-(4-chloro-benzyl)-4-trifluoromethanesulfonyloxy-1-isopropyl-2-pyridin-2(1H)-one (277 mg, 0.61 mmol) and dioxane (5 mL), and stirred at 100° C. for 0.5 hours. The reaction mixture was added to water, and extracted with ethyl acetate. The organic phase was washed by saturated saline, dried over anhydrous sodium sulfate, and then concentrated in vacuo. The residue was purified by silica-gel column chromatography (ethyl acetate/hexane) to give 3-(4-chloro-benzyl)-1-isopropyl-4-[4-(6-methoxycarbonyl-2-pyridyloxy)phenylamino]pyridin-2(1H)-one (260 mg, yield: 85%) as yellow amorphous.

1H-NMR (δ ppm TMS/CDCl3): δ: 1.35 (6H, d, J=6.7 Hz), 3.94 (3H, s), 4.04 (2H, s), 5.26-5.41 (1H, m), 5.75 (1H, s), 6.12 (1H, d, J=7.7 Hz), 7.01 (3H, t, J=9.0 Hz), 7.14 (3H, d, J=8.0 Hz), 7.22-7.31 (4H, m), 7.77-7.90 (2H, m).

Example 22

Preparation of 1-(4-chloro-benzyl)-2-[4-(5-fluoro-2-pyridyloxy)phenylamino]-5-(ethoxycarbonyl)pyridin-4(1H)-one (I-463)

[Chemical Formula 131]

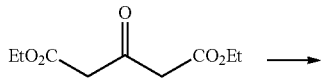

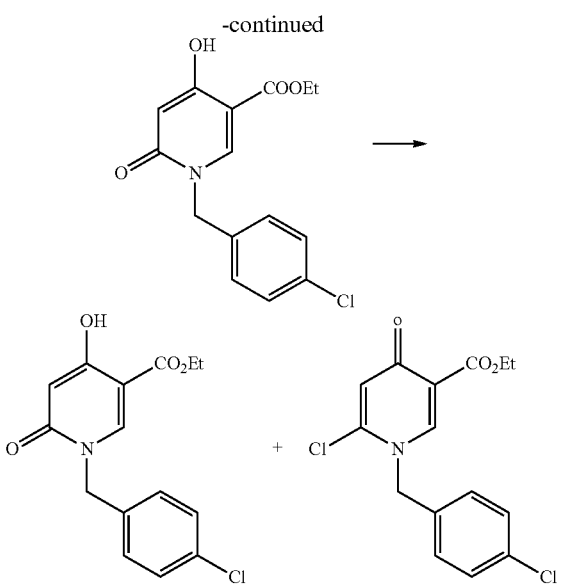

Step 1

Acetic anhydride (3.78 mL, 40 mmol) was added to mixture of ethyl 1,3-acetonedicarbonate ester (4.04 g, 20 mmol) and ethyl orthoformate (3.33 mL, 20 mmol), and stirred under heating at reflux for 1 hour. The reaction mixture was concentrated, and the residue was added to 4-chloro-benzylamine (2.83 g, 20 mmol) and stirred at room temperature for 1 hour, then at 120° C. for 6 hours. The reaction mixture was added to 0.5 mol/L hydrochloride (150 mL), and extracted with ethyl acetate (150 mL). The organic phase was washed by saturated saline (150 mL), dried over anhydrous magnesium sulfate, and then concentrated in vacuo. The residue purified by silica-gel column chromatography (ethyl acetate/hexane) to give 1-(4-chloro-benzyl)-5-ethoxycarbonyl-4-hydroxypyridin-2(1H)-one (1.56 g, yield: 25%) as pale brown oil.

1H-NMR (δ ppm TMS/CDCl3): 1.37 (3H, t, J=7.2 Hz), 4.36 (2H, q, J=7.1 Hz), 5.11 (2H, s), 5.98 (1H, s), 7.25 (2H, d, J=8.8 Hz), 7.32-7.35 (2H, m), 8.09 (1H, s), 10.65 (1H, a).

Step 2

Mixture of 1-(4-chloro-benzyl)-5-ethoxycarbonyl-4-hydroxypyridin-2(1H)-one (1.23 g, 4 mmol) and phosphorus oxychloride (3.72 ml) was stirred at 90° C. for 1 hour. The reaction mixture was added to mixture of ice water (100 mL) and saturated sodium hydrogen carbonate aqueous solution (100 mL), and extracted with ethyl acetate (150 mL). The organic phase was washed by saturated saline (200 mL), dried over anhydrous magnesium sulfate, and then concentrated in vacuo. The residue was purified by silica-gel column chromatography (ethyl acetate/hexane) to give 4-chloro-1-(4-chloro-benzyl)-5-(ethoxycarbonyl)pyridin-2(1H)-one (0.67 g, yield: 51%) as pale brown solid, 1H-NMR (δ ppm TMS/CDCl3): 1.35 (3H, t, J=7.1 Hz), 4.32 (2H, q, J=7.1 Hz), 5.10 (2H, s), 6.69 (1H, s), 7.26 (2H, d, J=6.9 Hz), 7.34 (2H, d, J=7.8 Hz), 8.17 (1H, s).

and 2-chloro-1-(4-chloro-benzyl)-5-(ethoxycarbonyl)pyridin-4(1H)-one (0.12 g, yield: 9%) as pale brown solid.

1H-NMR (δ ppm TMS/CDCl3): 1.37 (3H, t, J=7.0 Hz), 4.36 (2H, q, J=7.0 Hz), 5.22 (2H, s), 6.66 (1H, s), 7.12 (2H, d, J=7.7 Hz), 7.40 (2H, d, J=7.8 Hz), 8.23 (1H, s).

[Chemical Formula 132]

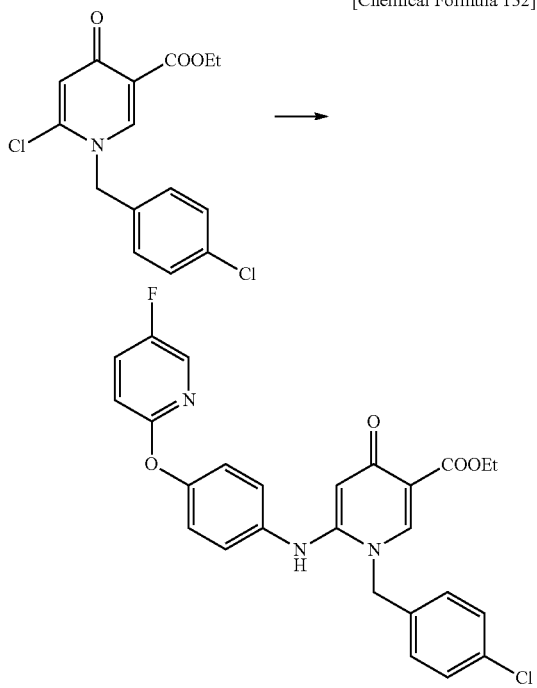

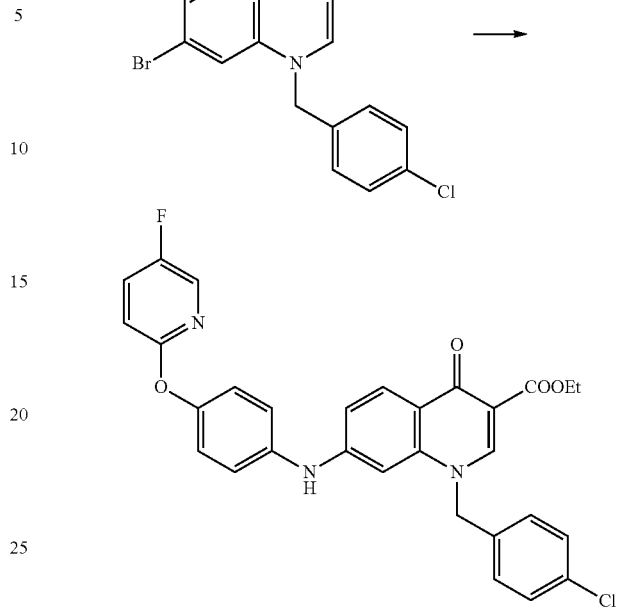

Step 3

4-(5-Fluoro-2-pyridyloxy)aniline (47 mg, 0.23 mmol), palladium acetate (II) (3.4 mg, 0.015 mmol), 4,5-bis(diphenylphosphino)-9,9-dimethylxanthene (13.3 mg, 0.023 mmol) and cesium carbonate (74.9 mg, 0.23 mmol) were added to mixture of 2-chloro-1-(4-chloro-benzyl)-5-(ethoxycarbonyl)pyridin-4(1H)-one (50 mg, 0.15 mmol) and dioxane (1 mL), and stirred at 100° C. for 1 hour. The reaction mixture was added to water, and extracted with ethyl acetate. The organic phase was washed by saturated saline, dried over anhydrous sodium sulfate, and then concentrated in vacuo. The residue purified by silica-gel column chromatography (ethyl acetate/hexane) to give 1-(4-chlorobenzyl)-2-[4-(5-fluoro-2-pyridyloxy)phenylamino]-5-(ethoxycarbonyl)pyridin-4(1H)-one (46.1 mg, yield: 61%) as pale brown solid.

1H-NMR (δ ppm TMS/CDCl3): 1.35 (3H, t, J=7.2 Hz), 4.34 (2H, q, J=13.7 Hz), 5.21 (2H, d, J=12.3 Hz), 5.82 (1H, s), 6.80-6.85 (3H, m), 7.04 (2H, d, J=8.5 Hz), 7.32-7.47 (5H, m), 8.02-8.04 (2H, m), 10.34 (1H, s).

Example 23

Preparation of 1-(4-chlorobenzyl)-7-[4-(5-fluoro-2-pyridyloxy)phenylamino]-3-(ethoxycarbonyl)quinolin-4(1H)-one (I-459)

[Chemical Formula 133]

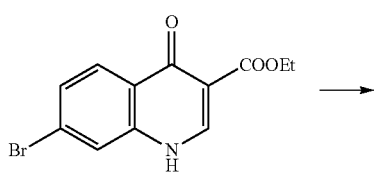

Step 1

Potassium carbonate (0.7 g, 5.1 mmol) and 4-chlorobenzyl bromide (0.76 g, 3.7 mmol) were added to mixture of 7-bromo-3-(ethoxycarbonyl)quinolin-4(1H)-one (1.0 g, 3.4 mmol) and acetonitrile (20 mL), and stirred under heating at reflux for 7 hours. The insoluble matter was removed by filtering, and the filtrate was washed by ethyl acetate and concentrated in vacuo. The resulting solid was washed by water and hexane to give 7-bromo-1-(4-chlorobenzyl)-3-(ethoxycarbonyl)quinolin-4(1H)-one (1.11 g, yield: 78%) as colorless solid.

1H-NMR (δ ppm TMS/DMSO-d6): 1.29 (3H, t, J=6.0 Hz), 4.24 (2H, q, J=6.0 Hz), 5.69 (2H, s), 7.28 (2H, d, J=8.0 Hz), 7.44 (2H, d, J=8.0 Hz), 7.61 (1H, d, J=8.0 Hz), 7.85 (1H, s), 8.14 (1H, d, J=8.0 Hz), 8.89 (1H, s).

Step 2

4-(5-Fluoro-2-pyridyloxy)aniline (291 mg, 1.43 mmol), palladium acetate (II) (21.4 mg, 0.095 mmol), 4,5-bis(diphenylphosphino)-9,9-dimethylxanthene (83 mg, 0.14 mmol) and cesium carbonate (465 mg, 1.43 mmol) were added to mixture of 7-bromo-1-(4-chlorobenzyl)-3-(ethoxycarbonyl)quinolin-4(1H)-one (400 mg, 0.95 mmol) and dioxane (16 mL), and stirred under heating at reflux for 5 hours. The reaction mixture was added to water, acidified by 5% citric acid aqueous solution, and extracted with ethyl acetate. The organic phase was washed by saturated saline, dried over anhydrous sodium sulfate, and then concentrated in vacuo. The residue was solidified by ethyl acetate to give 1-(4-chlorobenzyl)-7-[4-(5-fluoro-2-pyridyloxy)phenylamino]-3-(ethoxycarbonyl)quinolin-4(1H)-one (260 mg, yield: 50%) as pale brown solid.

1H-NMR (δ ppm TMS/CDCl3): 1.42 (3H, t, J=7.0 Hz), 4.40 (2H, q, J=7.1 Hz), 5.17 (2H, s), 6.11 (1H, s), 6.59 (1H, s), 6.82-7.09 (8H, m), 7.32 (2H, d, J=7.8 Hz), 7.48 (1H, m), 8.05 (1H, br s), 8.35 (1H, d, J=8.7 Hz), 8.51 (1H, s).

Example 24

Preparation of 1-(4-chlorobenzyl)-2-[4-(6-cyano-2-pyridyloxy)phenylamino]benzimidazole (I-453)

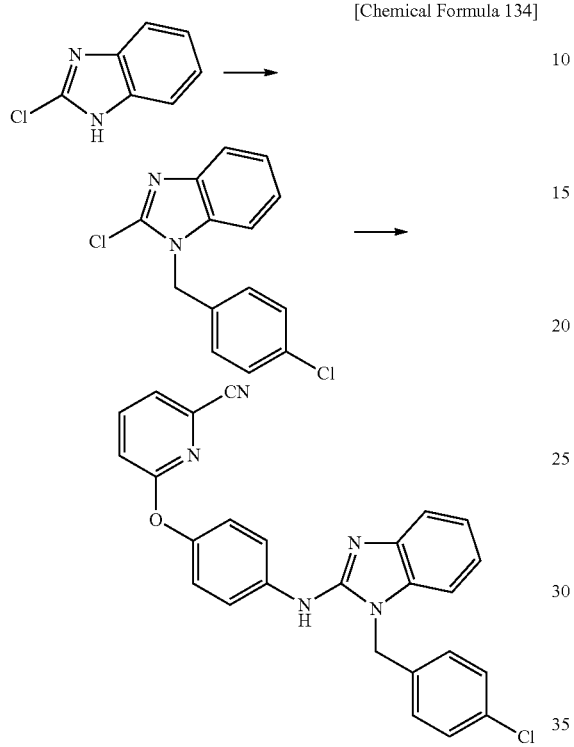

[Chemical Formula 134]

Step 1

60% Sodium hydride (1.42 g, 35.4 mmol) was added to mixture of 2-chlorobenzimidazole (5 g, 32.8 mmol) and DMF (50 mL) under ice-cooling, stirred at room temperature for 30 minutes, then added to 4-chlorobenzyl bromide (7.61 g, 37 mmol), and then stirred overnight at room temperature. The reaction mixture was added to saturated chloride ammonium aqueous solution (200 mL), and extracted with ethyl acetate (30 mL×3). The organic phase was washed by 1 mol/L hydrochloride (30 mL), saturated sodium hydrogen carbonate aqueous solution (30 mL), and saturated saline (30 mL), dried over anhydrous magnesium sulfate, and then concentrated in vacuo. The residue was purified by silica-gel column chromatography (ethyl acetate/hexane) to give 1-(4-chlorobenzyl)-2-chlorobenzimidazole (7.45 g, yield: 82%) as pale yellow solid.

1H-NMR (δ ppm TMS/CDCl3): 5.36 (2H, s), 7.11 (2H, d, J=8.2 Hz), 7.20-7.31 (5H, m), 7.72 (1H, d, J=7.8 Hz).

Step 2

Hydrochloride (4 mol/L dioxane solution, 0.09 mL) was added to mixture of 1-(4-chlor-chlorobenzyl)-2-chlorobenzimidazole (100 mg, 0.36 mmol), 4-(6-cyano-2-pyridyloxy)aniline (91 mg, 0.43 mmol) and 2-propanol (2 mL), and stirred at 1.50° C. under microwave for 20 minutes. The reaction mixture was added to water (20 mL), and extracted with ethyl acetate (30 mL×3). The organic phase was washed by saturated sodium hydrogen carbonate aqueous solution (10 mL) and saturated saline (10 mL), dried over anhydrous magnesium sulfate, and then concentrated in vacuo. The residue was powdered by ethyl acetate to give 1-(4-chlorobenzyl)-2-[4-(6-cyano-2-pyridyloxy)phenylamino]benzimidazole (105 mg, yield: 65%) as white solid.

1H-NMR (δ ppm TMS/DMSO-d6): 5.56 (2H, s), 7.00 (1H, t, J=7.5 Hz), 7.07 (1H, t, J=7.5 Hz), 7.17-7.22 (5H, m), 7.38-7.42 (4H, m), 7.78 (1H, d, J=7.3 Hz), 7.96 (2H, d, J=8.7 Hz), 8.08 (1H, t, J=7.9 Hz), 9.22 (1H, s).

Example 25

Preparation of 4-(4-chlorobenzyl)-6-[4-(6-cyano-2-pyridyloxy)phenylamino]-2H-1,4-benzooxazin-3(4H)-one (I-460)

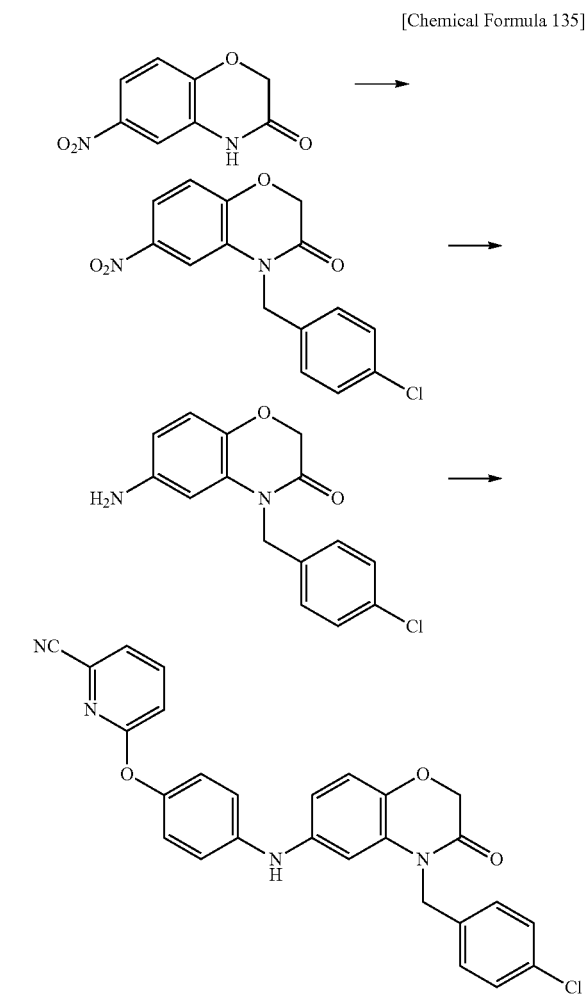

[Chemical Formula 135]

Step 1

Potassium carbonate (3.2 g, 28.2 mmol) and 4-chlorobenzyl bromide (3.49 g, 17 mmol) were added to mixture of 6-nitro-2H-1,4-benzooxazin-3(4H)-one (3 g, 15.4 mmol) and DMF (30 mL), and stirred at room temperature for 1 hour, then at 60° C. for 20 minutes. The reaction mixture was added to ice water (200 mL), and the resulting precipitate was filtered and then solidified by ethyl acetate to give 4-(4-chlorobenzyl)-6-nitro-2H-1,4-benzooxazin-3(4H)-one (3.08 g, yield: 63%) as pale yellow solid.

1H-NMR (δ ppm TMS/CDCl3): 4.85 (2H, s), 5.18 (2H, s), 7.08 (1H, d, J=8.9 Hz), 7.20-7.29 (2H, m), 7.34 (2H, d, J=8.0 Hz), 7.81 (1H, s), 7.91 (1H, d, J=8.8 Hz).

Step 2

Tin chloride (II) dihydrate (5.66 g, 25 mmol) was added to mixture of 4-(4-chlorobenzyl)-6-nitro-2H-1,4-benzooxazin-3(4H)-one (2 g, 6.3 mmol) and acetonitrile (40 mL), and stirred under heating at reflux for 5 hours. The reaction mixture was added to half-saturated sodium hydrogen carbonate aqueous solution (200 mL), and the resulting precipitate was filtered and solidified by ethyl acetate to give 6-amino-4-(4-chlorobenzyl)-2H-1,4-benzooxazin-3(4H)-one (1.01 g, yield: 61%) as pale brown solid.

1H-NMR (δ ppm TMS/CDCl3): 3.46 (2H, br s), 4.64 (2H, s), 5.07 (2H, s), 6.16 (1H, s), 6.30 (1H, d, J=8.5 Hz), 6.81 (1H, d, J=8.5 Hz), 7.18 (2H, d, J=8.0 Hz), 7.30 (2H, d, J=8.0 Hz).

Step 3

2-(4-Bromophenoxy)-6-cyanopyridine (263 mg, 1 mmol), palladium acetate (II) (21.5 mg, 0.1 mmol), 4,5-bis(diphenylphosphino)-9,9-dimethylxanthene (83 mg, 0.1.4 mmol), and cesium carbonate (467 mg, 1.4 mmol) were added to mixture of 6-amino-4-(4-chlorobenzyl)-2H-1,4-benzooxazin-3(4H)-one (400 mg, 1.4 mmol) and dioxane (16 mL), and stirred at 105° C. for 8 hours. The reaction mixture was added to water, acidified by 5% citric acid aqueous solution, and extracted with ethyl acetate. The organic phase was washed saturated saline, dried over anhydrous sodium sulfate, and then concentrated in vacuo. The residue was purified by silica-gel column chromatography (ethyl acetate/hexane) and solidified by ethyl acetate to give 4-(4-chlorobenzyl)-6-[4-(6-cyano-2-pyridyloxy)phenylamino]-2H-1,4-benzooxazin-3(4H)-one (71 mg, yield: 15%) as pale orange solid.

1H-NMR (δ ppm TMS/CDCl3): 4.71 (2H, s), 5.09 (2H, s), 5.51 (1H, br s), 6.59 (1H, s), 6.64 (1H, d, J=8.5 Hz), 6.76 (2H, d, J=8.4 Hz), 6.90-6.96 (3H, m), 7.12-7.20 (3H, m), 7.29 (2H, d, J=7.9 Hz), 7.41 (1H, d, J=7.3 Hz), 7.80 (1H, t, J=7.8 Hz).

Example 26

Preparation of 4-(4-fluorobenzyl)-6-[4-(5-fluoro-2-pyridyloxy)phenylamino]-2-methylthiopyrimidine (I-479)

[Chemical Formula 136]

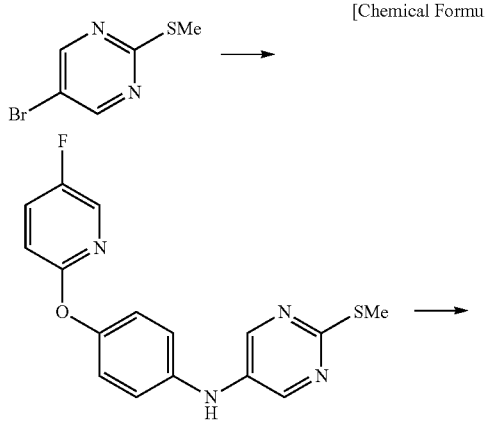

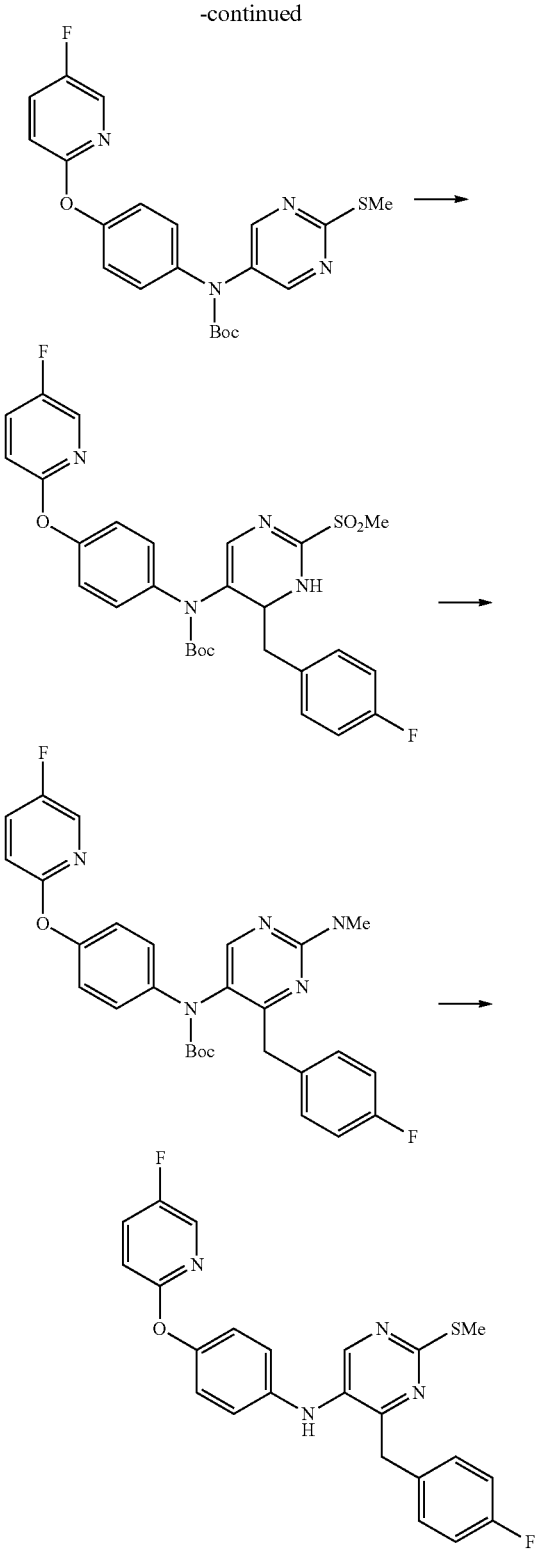

Step 1

After purged with nitrogen, mixture of 5-bromo-2-(methylthio)pyrimidine (1.0 g, 4.9 mmol), tris(dibenzylideneacetone)dipaliadium(0) (0.45 g, 0.49 mmol), 4,5-bis(diphenylphosphino)-9,9-dimethylxanthene (0.56 mg, 0.98 mmol), cesium carbonate (2.38 g, 7.3 mmol) and dioxane (20 mL) was added to 4-(5-fluoro-2-pyridyloxy)aniline (1.0 g, 4.9 mmol), and stirred under heating at reflux for 24 hours. The reaction mixture was added to saturated chloride ammonium aqueous solution, and extracted with ethyl acetate. The organic phase was washed by saturated saline, dried over anhydrous sodium sulfate, and then concentrated in vacuo. The resulting residue was purified by silica-gel column chromatography (ethyl acetate/hexane). The resulting mixture was solidified by diisopropyl ether to give 5-[4-(5-fluoro-2-pyridyloxy)phenylamino]-2-(methylthio)pyrimidine (0.51 g, yield: 32%) as pale yellow solid.

1H-NMR (δ ppm TMS/CDCl3): 2.57 (3H, s), 5.48 (1H, s), 6.89-6.95 (1H, m), 7.03-7.11 (4H, m), 7.45 (1H, m), 8.02 (1H, s), 8.40 (2H, s).

Step 2

Di-t-butyl dicarbonate (0.44 g, 2.0 mmol) was added to mixture of 5-[4-(5-fluoro-2-pyridyloxy)phenylamino]-2-(methylthio)pyrimidine (0.51 g, 1.55 mmol), 4-dimethylaminopyridine (95 mg, 0.78 mmol) and dichloromethane (5 mL), and stirred at room temperature for 2 hours. The reaction mixture was added to di-t-butyl dicarbonate (6.16 g, 28.2 mmol), and stirred at room temperature for 16 hours. The reaction mixture was concentrated in vacuo, and the residue was purified by silica-gel column chromatography (ethyl acetate/hexane) to give 5-[4-(5-fluoro-2-pyridyloxy)phenyl(t-butoxycarbonyl)amino]-2-(methylthio)pyrimidine (0.65 g, yield: 94%) as yellow solid.

1H-NMR (5 ppm TMS/CDCl3): 1.47 (9H, s), 2.56 (3H, s), 6.92 (1H dd, J=8.8, 3.5 Hz), 7.11 (2H, d, J=9.0 Hz), 7.23 (2H, d, J=9.0 Hz), 7.45 (1H, m), 8.03 (1H, d, J=3.3 Hz), 8.45 (2H, s).

Step 3

0.25 mol/L 4-Fluorobenzylmagnesium bromide THF solution (17.5 mL, 4.4 mmol) was added dropwise to mixture of 5-[4-(5-fluoro-2-pyridyloxy)phenyl(t-butoxycarbonyl)amino]-2-(methylthio)pyrimidine (625 g, 1.46 mmol) and THF (3.1 mL) at room temperature, and stirred at room temperature for 1 hour. The reaction mixture was added slowly to saturated chloride ammonium aqueous solution (20 mL), then to water (200 mL), and extracted with ethyl acetate (200 mL). The organic phase was dried over anhydrous sodium sulfate, and concentrated in vacuo. The residue was purified by silica-gel column chromatography (ethyl acetate/hexane) to give 4-(4-fluorobenzyl)-5-[4-(5-fluoro-2-pyridyloxy)phenyl(t-butoxycarbonyl)amino]-2-(methylthio)-1,6-dihydropyrimidine (0.58 g, yield: 74%) as colorless oil.

Step 4

2,3-Dichloro-5,6-dicyano-1,4-benzoquinone (0.27 g, 1.2 mmol) was added to mixture of 4-(4-fluorobenzyl)-5-[4-(5-fluoro-2-pyridyloxy)phenyl(t-butoxycarbonyl)amino]-2-(methylthio)-1,6-dihydropyrimidine (0.58 g, 1.1 mmol) and THF (3.1 mL), and stirred at room temperature for 2 hours. The reaction mixture was concentrated in vacuo, and the resulting residue was purified by silica-gel column chromatography (ethyl acetate/hexane) to give 4-(4-fluorobenzyl)-5-[4-(5-fluoro-2-pyridyloxy)phenyl(t-butoxycarbonyl)amino]-2-(methylthio)pyrimidine (0.35 g, yield: 45%) as colorless amorphous.

1H-NMR (δ ppm TMS/CDCl3): 1.36 (9H, s), 2.54 (3H, s), 3.88 (2H, s), 6.87-7.14 (9H, m), 7.44 (1H, m), 8.01 (1H, d, J=3.3 Hz), 8.34 (2H, s).

Step 5

4 mol/L hydrochloride dioxane solution (0.5 mL) was added to mixture of 4-(4-fluorobenzyl)-5-[4-(5-fluoro-2-pyridyloxy)phenyl(t-butoxycarbonyl)amino]-2-(methylthio) pyrimidine (50 mg, 0.09 mmol) and dichloromethane (1 mL), and stirred at room temperature for 2 hours. The reaction mixture was added to saturated sodium hydrogen carbonate aqueous solution, and extracted with ethyl acetate. The organic phase was dried over anhydrous sodium sulfate, and concentrated in vacuo. The residue was purified by reverse-phase HPLC (water/acetonitrile) to give 4-(4-fluorobenzyl)-6-[4-(5-fluoro-2-pyridyloxy)phenylamino]-2-methylthiopyrimidine (23 mg, yield: 57%) as yellow oil.

1H-NMR (δ ppm TMS/CDCl3): 2.57 (3H, s), 4.06 (2H, s), 5.00 (1H, s), 6.74 (2H, dd, J=6.7, 2.1 Hz), 6.88 (1H, dd, J=9.0, 3.0 Hz), 6.98-7.02 (4H, m), 7.18-7.21 (2H, m), 7.43 (1H, m), 8.01 (1H, d, J=3.0 Hz), 8.41 (1H, s).

Example 27

Preparation of 2-dimethylamino-4-(4-fluorobenzyl)-5-[4-(5-fluoro-2-pyridyloxy)phenylamino]pyrimidine (I-481)

[Chemical Formula 137]

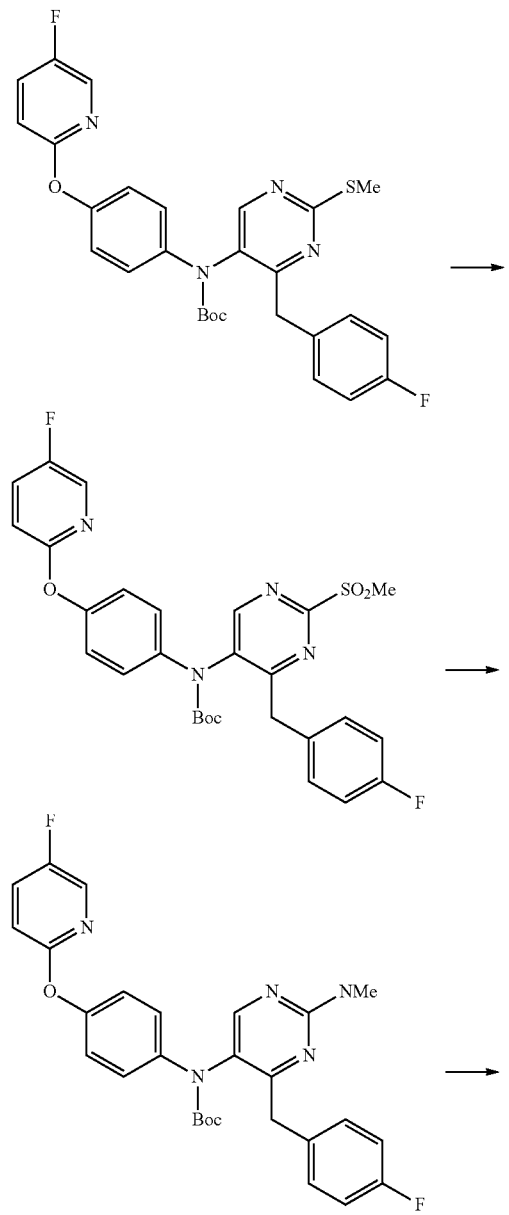

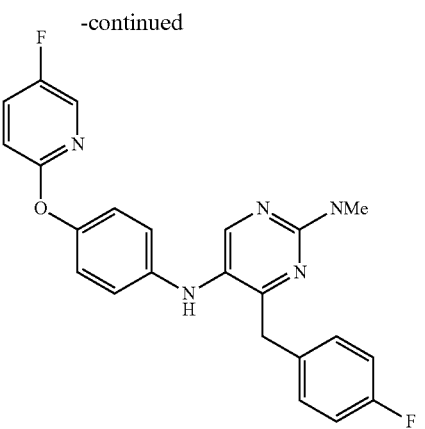

Step 1 m-Chloroperoxybenzoic acid (70% wt, 355 mg, 1.44 mmol) was added to mixture of 4-(4-fluorobenzyl)-5-[4-(5-fluoro-2-pyridyloxy)phenyl(t-butoxycarbonyl)amino]-2-(methylthio)pyrimidine (350 mg, 0.65 mmol) and dichloromethane (7 mL) at 0° C., and stirred at 0° C. for 2 hours. The reaction mixture was added to saturated sodium hydrogen carbonate aqueous solution, and extracted with ethyl acetate. The organic phase was dried over anhydrous sodium sulfate, and concentrated in vacuo to give 4-(4-fluorobenzyl)-5-[4-(5-fluoro-2-pyridyloxy)phenyl(t-butoxycarbonyl)amino]-2-(methanesulfonyl)pyrimidine as crude product.

Step 2

The crude product was added to 2 mol/L dimethylamine THF solution (5.2 mL, 10.4 mmol) and 4-dimethylaminopyridine (25.4 mg, 0.2 mmol), and stirred at room temperature for 1 hour. The reaction mixture was concentrated in vacuo, and the resulting residue was purified by silica-gel column chromatography (ethyl acetate/hexane) to give 2-dimethylamino-4-(4-fluorobenzyl)-5-[4-(5-fluoro-2-pyridyloxy)phenyl(t-butoxycarbonyl)amino]pyrimidine (220 mg, yield: 80%) as pale yellow amorphous.

Step 3

2-Dimethylamino-4-(4-fluorobenzyl)-5-[4-(5-fluoro-2-pyridyloxy)phenyl(t-butoxycarbonyl)amino]pyrimidine (215 mg, 0.4 mmol) was solved in 4 mol/L hydrochloride dioxane solution (2 mL), and stirred at room temperature for 1 hour. The reaction mixture was added to saturated sodium hydrogen carbonate aqueous solution, and extracted with ethyl acetate. The organic phase was dried over anhydrous sodium sulfate, and concentrated in vacuo. The residue was purified by reverse-phase HPLC (water/acetonitrile) to give 2-dimethylamino-4-(4-fluorobenzyl)-5-[4-(5-fluoro-2-pyridyloxy)phenylamino]pyrimidine (112 mg, yield: 64%) as red oil.

1H-NMR (δ ppm TMS/DMSO-d6): 3.12 (6H, s), 3.90 (2H, s), 6.55 (2H, d, J=8.0 Hz), 6.91 (2H, d, J=8.0 Hz), 6.98-7.02 (1H, m), 7.08 (2H, t, J=8.4 Hz), 7.24-7.28 (2H, m), 7.80 (1H, t, J=8.3 Hz), 8.15-8.18 (2H, m).

The compounds used as intermediates are commercially available or can be synthesized by the method described in the following documents.

JP63112566

JP60112483

WO2006129609

Journal of Combinatorial Chemistry (2009), 11(6), 1050-1060.

Annali di Chimica, 1959, 49 2083-8.

J. Chem. Soc., Perkin Trans. 1, 1997, 2665-2672.

J. Chem. Soc., Perkin Trans. 1, 1997, 2673-2678.

J. Chem. Soc., Perkin Trans. 1, 1998, 3245-3252.

J. Org. Chem. 1987, 52, 3426-3434.

Tetrahedron (2004), 60(1), 211-217.

Journal of Fluorine Chemistry (2007), 128(7), 748-754.

Synlett, 2007, 2331-2336.

Liebigs Annalen der Chemie (1984), (6), 1193-204.

European Journal of Medicinal Chemistry (1988), 23(1), 53-62.

Journal of Heterocyclic Chemistry (1978), 15(1), 77-80.

Bulletin of the Korean Chemical Society (2004), 25(7), 991-996

Chemische Berichte (1978), 111(3), 982-95

Journal of Medicinal Chemistry (2006), 49(2), 441-444.

The following compounds were synthesized according to the method described in the general synthetic procedures and Examples. The chemical structures of the compounds and the physical properties of them are described below.

(Method of Identification for the Compound)

LC/MS data of compound of the present invention were measured under any one of the following 5 conditions (Methods 1 to 6), and a retention time (RT (min)) and [M+H]$^+$ are shown.

(Method 1)

Column: Luna C18(2) (5 μm, i.d.4.6×50 mm) (Phenomenex)

Flow rate: 3 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 100% solvent [B] for 3 minutes was performed, and 100% solvent [B] was maintained for 1 minute.

(Method 2)

Column: Xbridge C18 (5 μm, i.d. 4.6×50 mm) (Waters)

Flow rate: 3 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 100% solvent [B] for 3 minutes was performed, and 1.00% solvent [B] was maintained for 1 minute.

(Method 3)

Column: Shim-pack XR-ODS (2.2 μm, i.d.50×3.0 mm) (Shimadzu)

Flow rate: 1.6 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 100% solvent [B] for 3 minutes was performed, and 100% solvent [B] was maintained for 1 minute.

(Method 4)

Column: Develosil RPAq XR-ODS (i.d.50×3.0 mm)

Flow rate: 1.5 mL/min

IV detection wavelength: 254 nm

Mobile phase: [A] is 0.1% formic acid-containing aqueous solution, and [B] is 0.1% formic acid-containing acetonitrile solution Gradient: 60% solvent [B] was maintained for 0.5 minute, linear gradient of 60% to 100% solvent [B] for 4.5 minutes was performed, and 100% solvent [B] was maintained for 1 minute.

(Method 5)
Column: ACQUITY UPLC (registered trademark) BEH C18 (1.7 μm i.d.2.1×50 mm)
Flow rate: 0.8 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 10% to 100% solvent [B] for 3.5 minutes was performed, and 100% solvent [B] was maintained for 0.5 minute.

(Method 6)
Column: Shim-pack XR-ODS (2.2 μm, i.d.50×3.0 mm) (Shimadzu)
Flow rate: 1.6 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 10% to 50% solvent [B] for 3 minutes was performed, and 50% solvent [B] was maintained for 1 minute.

TABLE 12

| Structure | Compound No | RT (min) | [M + H] | Method |
|---|---|---|---|---|
| 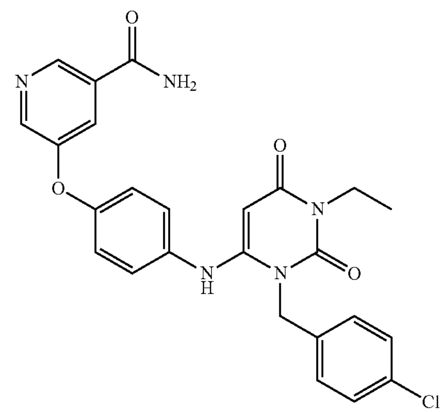 [SMILES: CCn1c(=O)cc(Nc2ccc(Oc3cncc(C(N)=O)c3)cc2)n(Cc2ccc(Cl)cc2)c1=O] | I-001 | 1.75 | 492 | 3 |
| 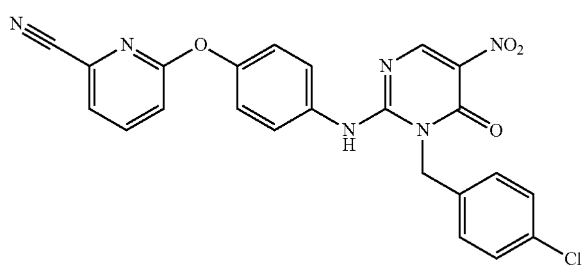 [SMILES: N#Cc1cccc(Oc2ccc(Nc3ncc([N+](=O)[O-])c(=O)n3Cc3ccc(Cl)cc3)cc2)n1] | I-002 | 2.18 | 475 | 3 |
| 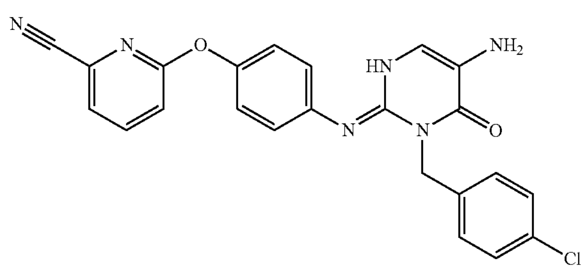 [SMILES: N#Cc1cccc(Oc2ccc(/N=c3\[nH]cc(N)c(=O)n3Cc3ccc(Cl)cc3)cc2)n1] | I-003 | 1.74 | 445 | 3 |

TABLE 13
| Structure | Compound No | RT (min) | [M + H] | Method |
|---|---|---|---|---|
| 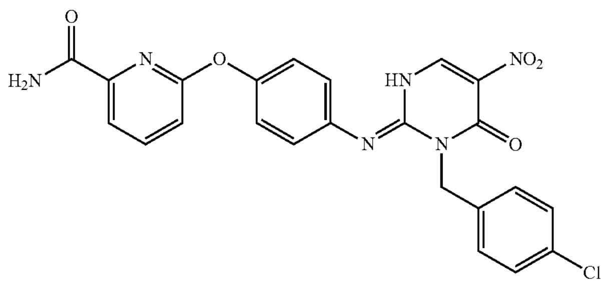 [SMILES: NC(=O)c1cccc(Oc2ccc(/N=c3\[nH]cc([N+](=O)[O-])c(=O)n3Cc3ccc(Cl)cc3)cc2)n1] | I-004 | 1.89 | 493 | 3 |
| 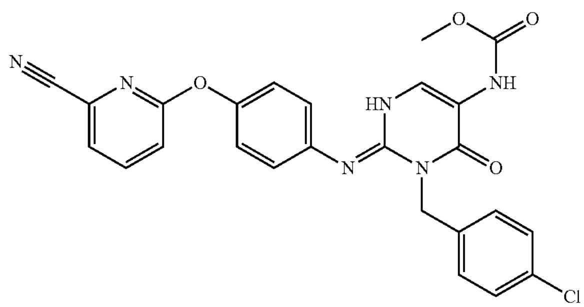 [SMILES: COC(=O)Nc1c[nH]/c(=N\c2ccc(Oc3cccc(C#N)n3)cc2)n(Cc2ccc(Cl)cc2)c1=O] | I-005 | 2.19 | 503 | 3 |
| 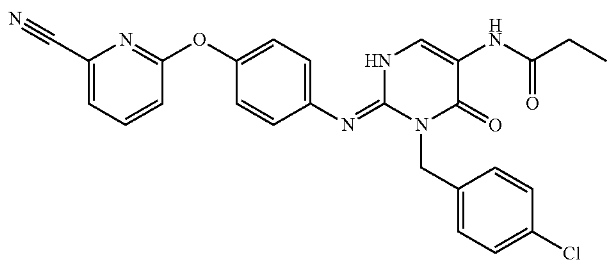 [SMILES: CCC(=O)Nc1c[nH]/c(=N\c2ccc(Oc3cccc(C#N)n3)cc2)n(Cc2ccc(Cl)cc2)c1=O] | I-006 | 2.16 | 501 | 3 |
TABLE 14
| Structure | Compound No | RT (min) | [M + H] | Method |
|---|---|---|---|---|
| 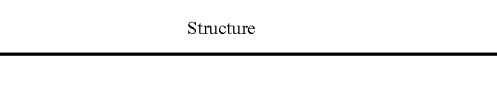 | I-007 | 1.88 | 521 | 3 |

TABLE 14-continued

| Structure | Compound No | RT (min) | [M + H] | Method |
|---|---|---|---|---|
| 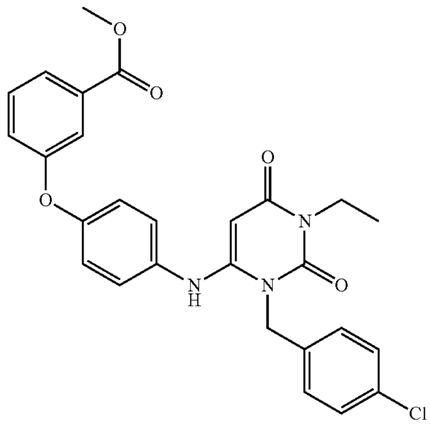 [SMILES: CCn1c(=O)cc(Nc2ccc(Oc3cccc(C(=O)OC)c3)cc2)n(Cc2ccc(Cl)cc2)c1=O] | I-008 | 2.42 | 506 | 3 |
| 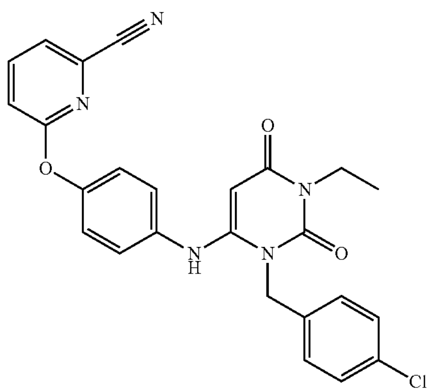 | I-009 | 2.19 | 474 | 3 |

TABLE 15

| Structure | Compound No | RT (min) | [M + H] | Method |
|---|---|---|---|---|
| 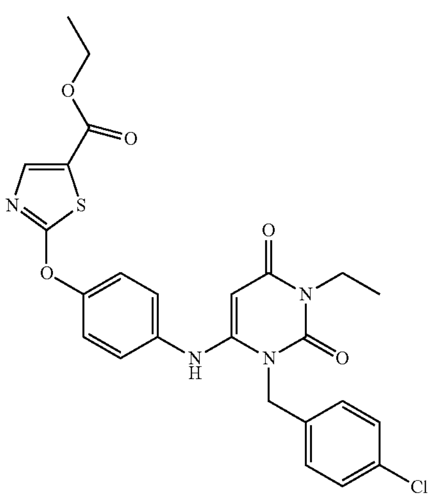 [SMILES: CCOC(=O)c1cnc(Oc2ccc(Nc3cc(=O)n(CC)c(=O)n3Cc3ccc(Cl)cc3)cc2)s1] | I-010 | 2.37 | 527 | 3 |

TABLE 15-continued

| Structure | Compound No | RT (min) | [M + H] | Method |
|---|---|---|---|---|
| 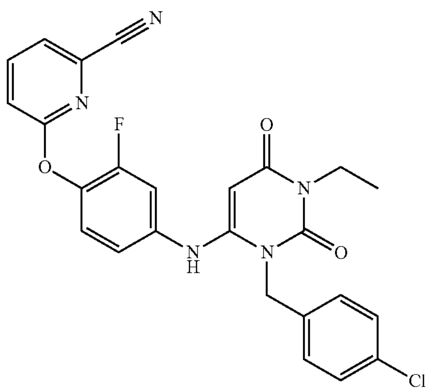 [SMILES: CCn1c(=O)cc(Nc2ccc(Oc3cccc(C#N)n3)c(F)c2)n(Cc2ccc(Cl)cc2)c1=O] | I-011 | 2.23 | 492 | 3 |
| 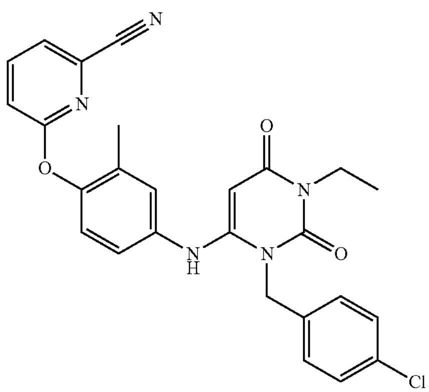 [SMILES: CCn1c(=O)cc(Nc2ccc(Oc3cccc(C#N)n3)c(C)c2)n(Cc2ccc(Cl)cc2)c1=O] | I-012 | 2.27 | 488 | 3 |

TABLE 16

| Structure | Compound No | RT (min) | [M + H] | Method |
|---|---|---|---|---|
| 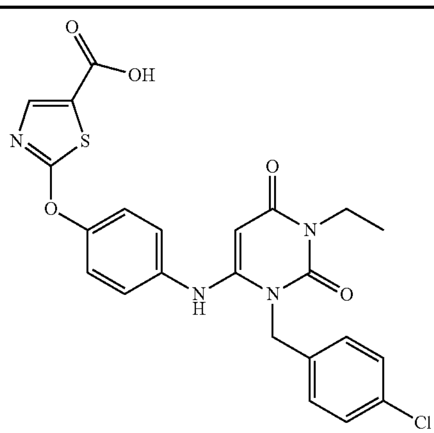 | I-013 | 1.92 | 499 | 3 |

TABLE 16-continued

| Structure | Compound No | RT (min) | [M + H] | Method |
|---|---|---|---|---|
| 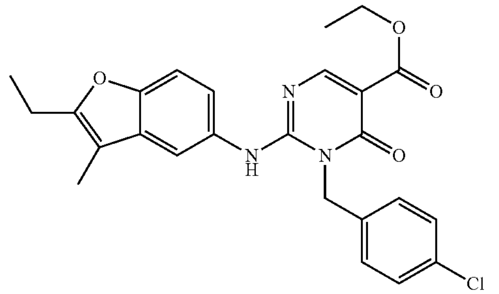 [SMILES: CCOC(=O)c1cnc(Nc2ccc3oc(CC)c(C)c3c2)n(Cc2ccc(Cl)cc2)c1=O] | I-014 | 2.60 | 466 | 3 |
| 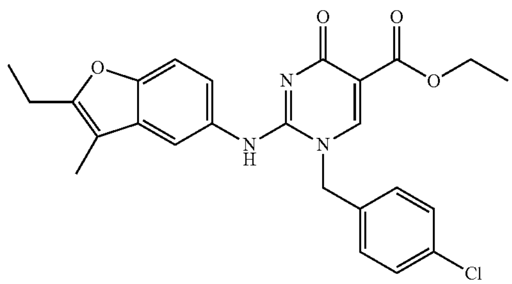 [SMILES: CCOC(=O)c1cn(Cc2ccc(Cl)cc2)c(Nc2ccc3oc(CC)c(C)c3c2)nc1=O] | I-015 | 2.63 | 466 | 3 |

TABLE 17

| Structure | Compound No | RT (min) | [M + H] | Method |
|---|---|---|---|---|
| 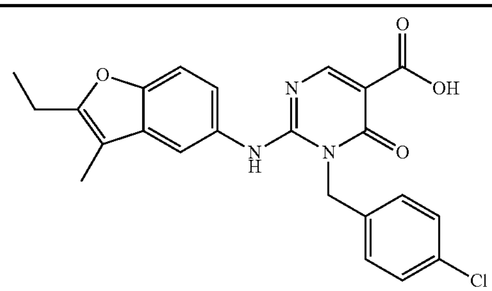 | I-016 | 2.49 | 438 | 3 |
| 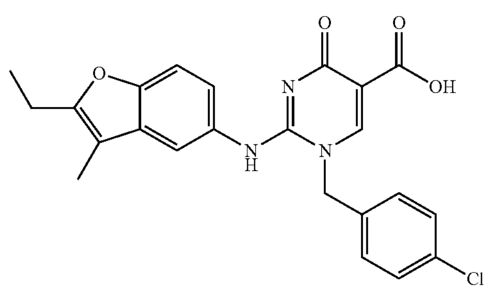 [SMILES: CCc1oc2ccc(Nc3nc(=O)c(C(=O)O)cn3Cc3ccc(Cl)cc3)cc2c1C] | I-017 | 2.32 | 438 | 3 |
| 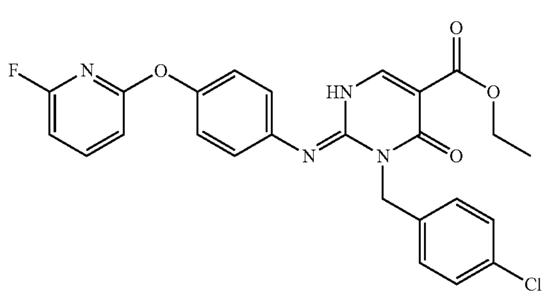 [SMILES: CCOC(=O)c1c[nH]/c(=N\c2ccc(Oc3cccc(F)n3)cc2)n(Cc2ccc(Cl)cc2)c1=O] | I-018 | 2.37 | 495 | 3 |

TABLE 18

| Structure | Compound No | RT (min) | [M + H] | Method |
|---|---|---|---|---|
| 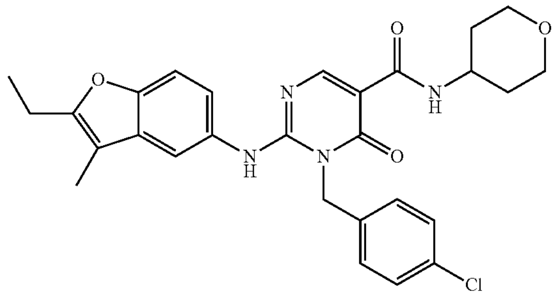 [SMILES: CCc1oc2ccc(Nc3ncc(C(=O)NC4CCOCC4)c(=O)n3Cc3ccc(Cl)cc3)cc2c1C] | I-019 | 2.49 | 521 | 3 |
| 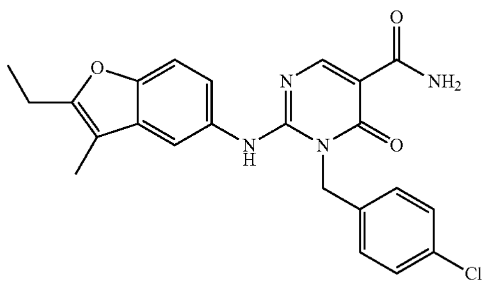 [SMILES: CCc1oc2ccc(Nc3ncc(C(N)=O)c(=O)n3Cc3ccc(Cl)cc3)cc2c1C] | I-020 | 2.29 | 437 | 3 |
| 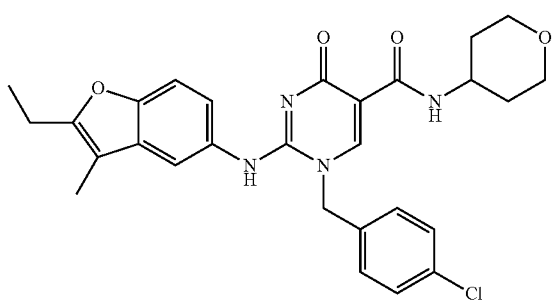 [SMILES: CCc1oc2ccc(Nc3nc(=O)c(C(=O)NC4CCOCC4)cn3Cc3ccc(Cl)cc3)cc2c1C] | I-021 | 2.46 | 521 | 3 |

TABLE 19

| Structure | Compound No | RT (min) | [M + H] | Method |
|---|---|---|---|---|
| 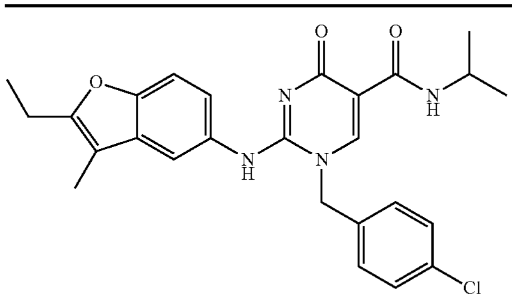 | I-022 | 2.63 | 479 | 3 |

TABLE 19-continued
| Structure | Compound No | RT (min) | [M + H] | Method |
|---|---|---|---|---|
| 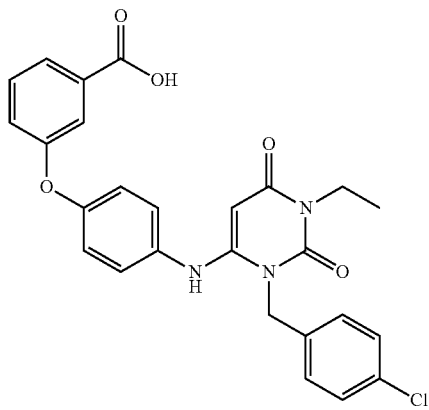 | I-023 | 2.08 | 492 | 3 |
| 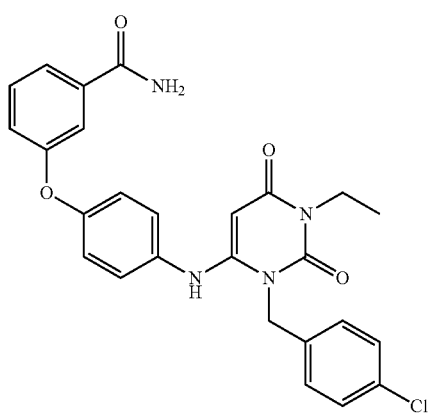 [SMILES: CCn1c(=O)cc(Nc2ccc(Oc3cccc(C(N)=O)c3)cc2)n(Cc2ccc(Cl)cc2)c1=O] | I-024 | 1.90 | 491 | 3 |
TABLE 20
| Structure | Compound No | RT (min) | [M + H] | Method |
|---|---|---|---|---|
| 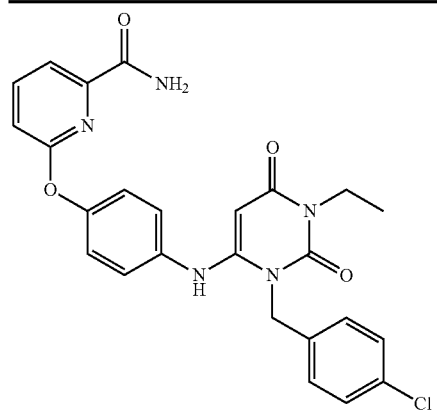 | I-025 | 1.91 | 492 | 3 |

TABLE 20-continued

| Structure | Compound No | RT (min) | [M + H] | Method |
|---|---|---|---|---|
| 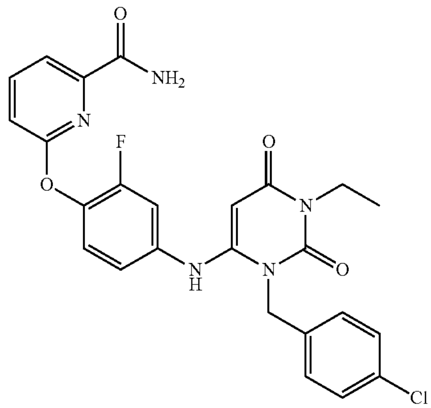 [SMILES: CCn1c(=O)cc(Nc2ccc(Oc3cccc(C(N)=O)n3)c(F)c2)n(Cc2ccc(Cl)cc2)c1=O] | I-026 | 1.97 | 510 | 3 |
| 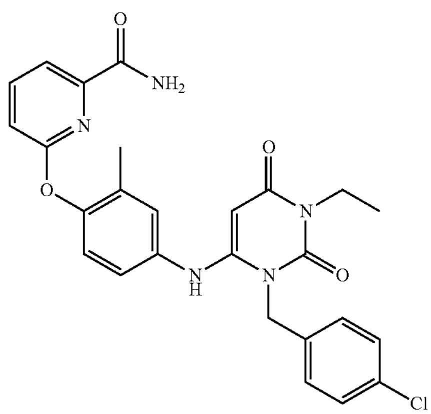 | I-027 | 2.00 | 506 | 3 |

TABLE 21

| Structure | Compound No | RT (min) | [M + H] | Method |
|---|---|---|---|---|
| 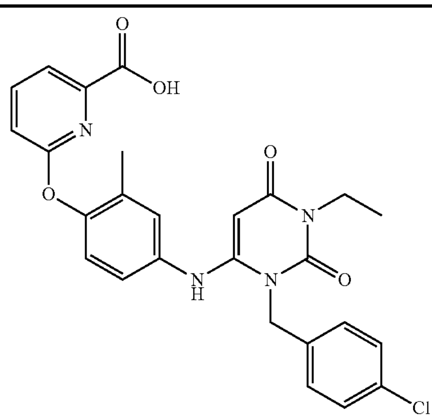 | I-028 | 2.03 | 507 | 3 |

TABLE 21-continued

| Structure | Compound No | RT (min) | [M + H] | Method |
|---|---|---|---|---|
| 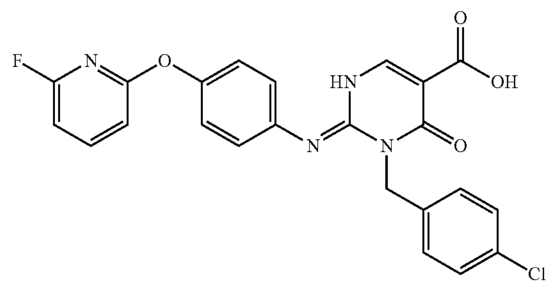 | I-029 | 2.29 | 467 | 3 |
| 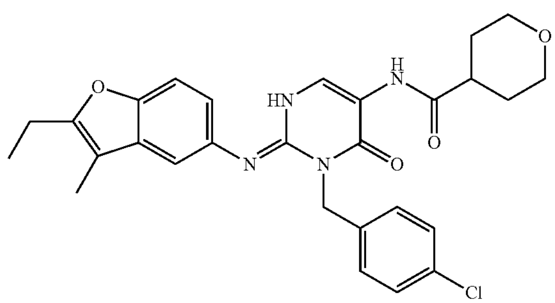 [SMILES: CCc1oc2ccc(/N=c3\[nH]cc(NC(=O)C4CCOCC4)c(=O)n3Cc3ccc(Cl)cc3)cc2c1C] | I-030 | 2.39 | 521 | 3 |

TABLE 22

| Structure | Compound No | RT (min) | [M + H] | Method |
|---|---|---|---|---|
| 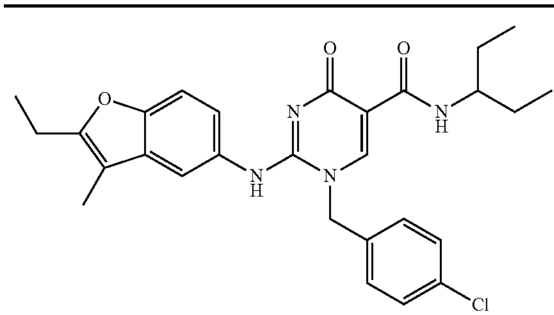 | I-031 | 2.83 | 507 | 3 |
| 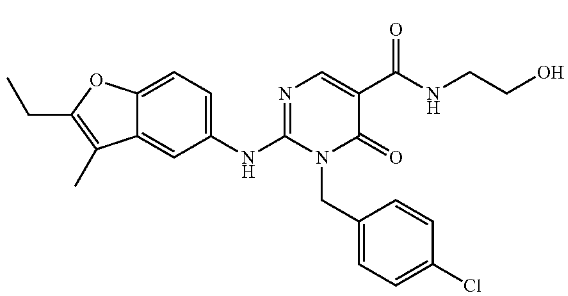 [SMILES: CCc1oc2ccc(Nc3ncc(C(=O)NCCO)c(=O)n3Cc3ccc(Cl)cc3)cc2c1C] | I-032 | 2.21 | 481 | 3 |

TABLE 22-continued
| Structure | Compound No | RT (min) | [M + H] | Method |
|---|---|---|---|---|
| 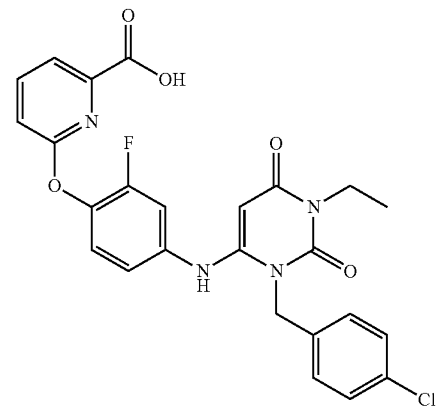 [SMILES: CCn1c(=O)cc(Nc2ccc(Oc3cccc(C(=O)O)n3)c(F)c2)n(Cc2ccc(Cl)cc2)c1=O] | I-033 | 2.01 | 511 | 3 |
TABLE 23
| Structure | Compound No | RT (min) | [M + H] | Method |
|---|---|---|---|---|
| 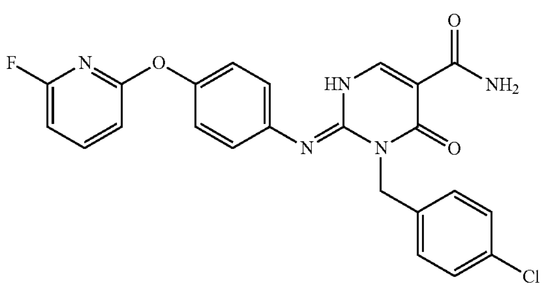 [SMILES: NC(=O)c1c[nH]/c(=N\c2ccc(Oc3cccc(F)n3)cc2)n(Cc2ccc(Cl)cc2)c1=O] | I-034 | 2.10 | 466 | 3 |
| 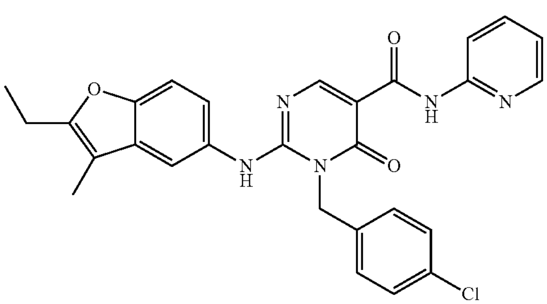 [SMILES: CCc1oc2ccc(Nc3ncc(C(=O)Nc4ccccn4)c(=O)n3Cc3ccc(Cl)cc3)cc2c1C] | I-035 | 2.39 | 515 | 3 |
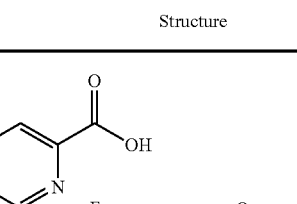

TABLE 23-continued

| Structure | Compound No | RT (min) | [M + H] | Method |
|---|---|---|---|---|
| 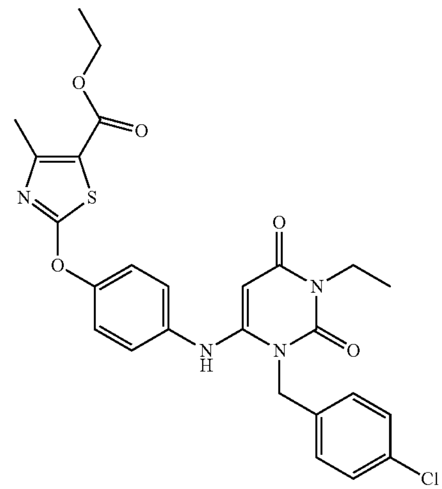 [SMILES: CCOC(=O)c1sc(Oc2ccc(Nc3cc(=O)n(CC)c(=O)n3Cc3ccc(Cl)cc3)cc2)nc1C] | I-036 | 2.47 | 541 | 3 |

TABLE 24

| Structure | Compound No | RT (min) | [M + H] | Method |
|---|---|---|---|---|
| 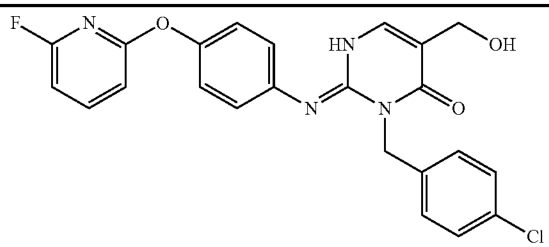 | I-037 | 2.03 | 453 | 3 |
| 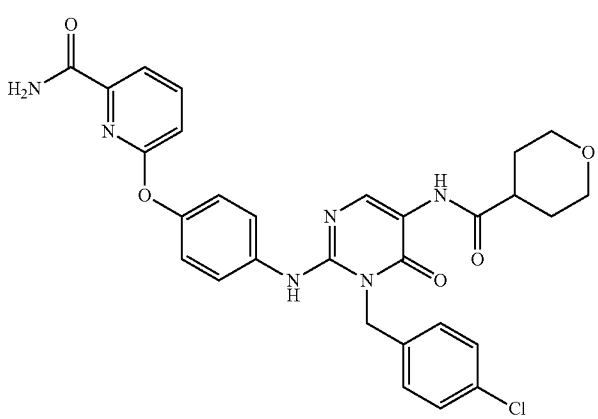 [SMILES: NC(=O)c1cccc(Oc2ccc(Nc3ncc(NC(=O)C4CCOCC4)c(=O)n3Cc3ccc(Cl)cc3)cc2)n1] | I-038 | 1.84 | 575 | 3 |

TABLE 24-continued

| Structure | Compound No | RT (min) | [M + H] | Method |
|---|---|---|---|---|
| 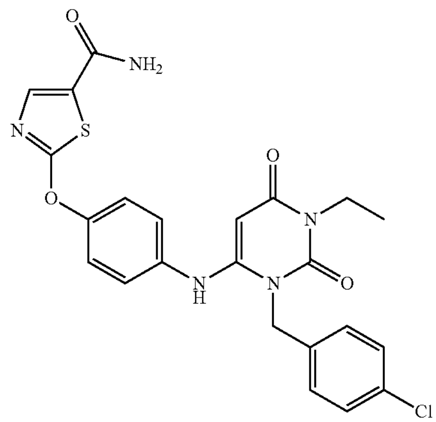 | I-039 | 1.77 | 498 | 3 |

TABLE 25

| Structure | Compound No | RT (min) | [M + H] | Method |
|---|---|---|---|---|
| 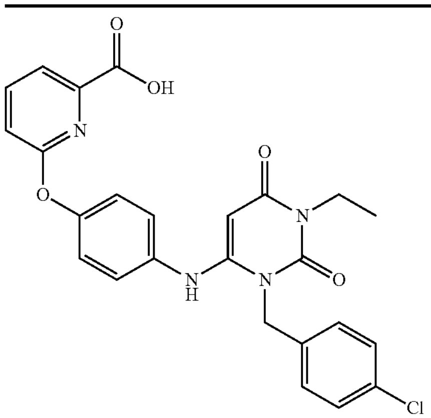 | I-040 | 1.93 | 493 | 3 |
| 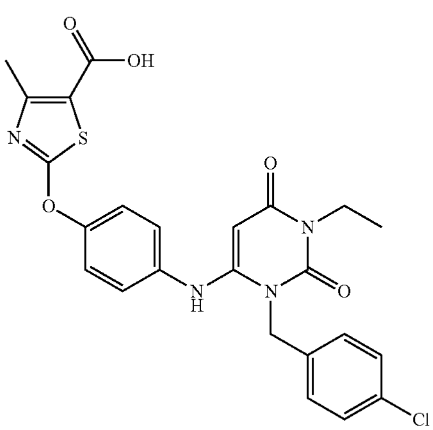 [SMILES: CCn1c(=O)cc(Nc2ccc(Oc3nc(C)c(C(=O)O)s3)cc2)n(Cc2ccc(Cl)cc2)c1=O] | I-041 | 1.97 | 513 | 3 |

TABLE 26

| Structure | Compound No | RT (min) | [M + H] | Method |
|---|---|---|---|---|
| 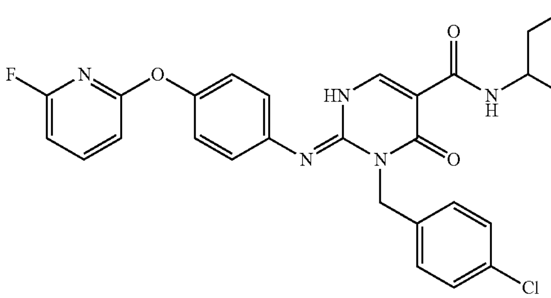 | I-042 | 550 | 2.30 | 3 |
| 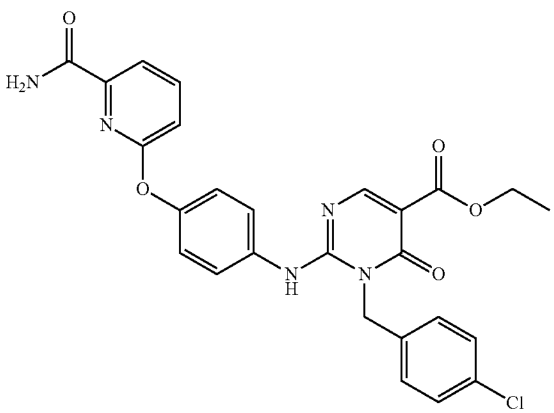 [SMILES: CCOC(=O)c1cnc(Nc2ccc(Oc3cccc(C(N)=O)n3)cc2)n(Cc2ccc(Cl)cc2)c1=O] | I-043 | 520 | 1.96 | 3 |
| 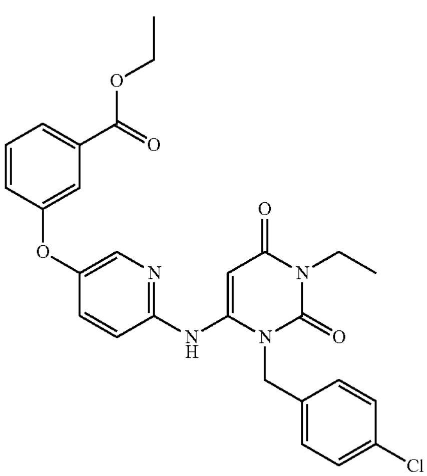 [SMILES: CCOC(=O)c1cccc(Oc2ccc(Nc3cc(=O)n(CC)c(=O)n3Cc3ccc(Cl)cc3)nc2)c1] | I-044 | 521 | 2.45 | 3 |

TABLE 27

| Structure | Compound No | RT (min) | [M + H] | Method |
|---|---|---|---|---|
| (structure) | I-045 | 422 | 2.45 | 3 |
| (structure) | I-046 | 424 | 2.17 | 3 |
| (structure) | I-047 | 557 | 2.42 | 3 |

TABLE 28

| Structure | Compound No | RT (min) | [M + H] | Method |
|---|---|---|---|---|
| (structure) | I-048 | 506 | 2.48 | 3 |
| (structure) | I-049 | 507 | 1.58 | 3 |

TABLE 28-continued

| Structure | Compound No | RT (min) | [M + H] | Method |
|---|---|---|---|---|
| 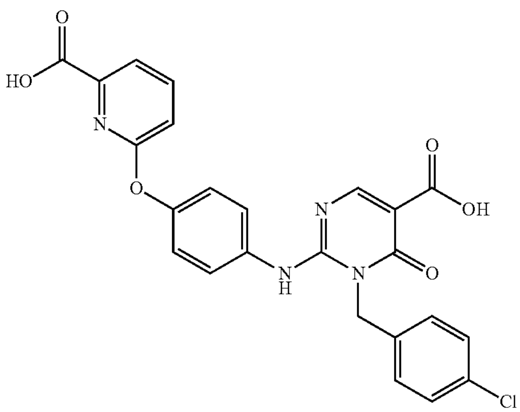 [SMILES: O=C(O)c1cccc(Oc2ccc(Nc3ncc(C(=O)O)c(=O)n3Cc3ccc(Cl)cc3)cc2)n1] | I-050 | 493 | 2.00 | 3 |

TABLE 29

| Structure | Compound No | RT (min) | [M + H] | Method |
|---|---|---|---|---|
| 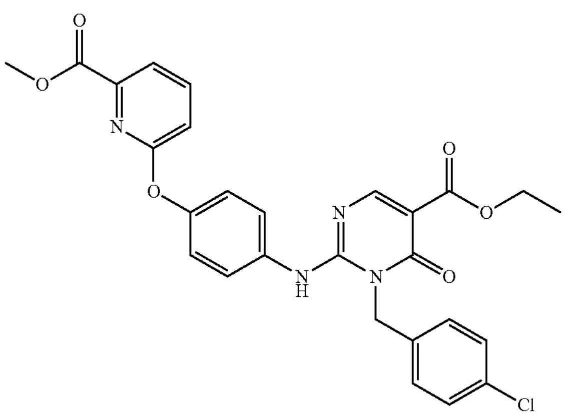 [SMILES: CCOC(=O)c1cnc(Nc2ccc(Oc3cccc(C(=O)OC)n3)cc2)n(Cc2ccc(Cl)cc2)c1=O] | I-051 | 535 | 2.27 | 3 |
| 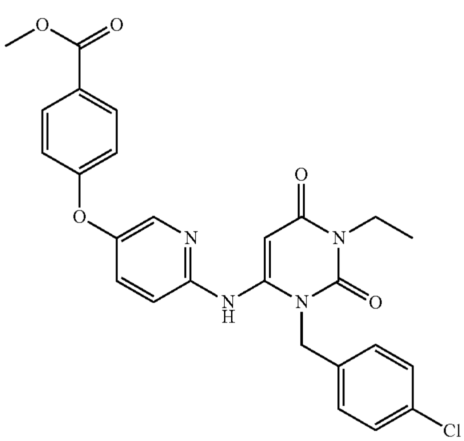 [SMILES: CCn1c(=O)cc(Nc2ccc(Oc3ccc(C(=O)OC)cc3)cn2)n(Cc2ccc(Cl)cc2)c1=O] | I-052 | 507 | 2.29 | 3 |

TABLE 29-continued

| Structure | Compound No | RT (min) | [M + H] | Method |
|---|---|---|---|---|
| (structure of I-053) | I-053 | 493 | 1.97 | 3 |

TABLE 30

| Structure | Compound No | RT (min) | [M + H] | Method |
|---|---|---|---|---|
| (structure of I-054) | I-054 | 493 | 1.95 | 3 |
| (structure of I-055) | I-055 | 521 | 2.03 | 3 |

TABLE 30-continued
| Structure | Compound No | RT (min) | [M + H] | Method |
|---|---|---|---|---|
| 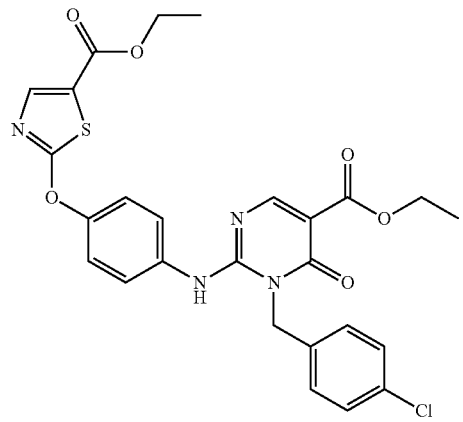 [SMILES: CCOC(=O)c1cnc(Oc2ccc(Nc3ncc(C(=O)OCC)c(=O)n3Cc3ccc(Cl)cc3)cc2)s1] | I-056 | 555 | 2.52 | 3 |
TABLE 31
| Structure | Compound No | RT (min) | [M + H] | Method |
|---|---|---|---|---|
| 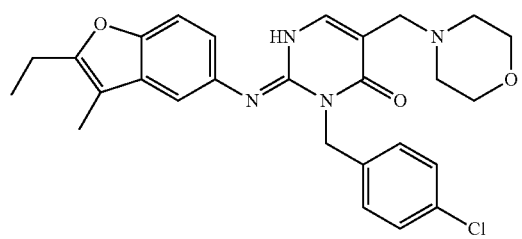 [SMILES: CCc1oc2ccc(/N=c3\[nH]cc(CN4CCOCC4)c(=O)n3Cc3ccc(Cl)cc3)cc2c1C] | I-057 | 493 | 1.58 | 3 |
| 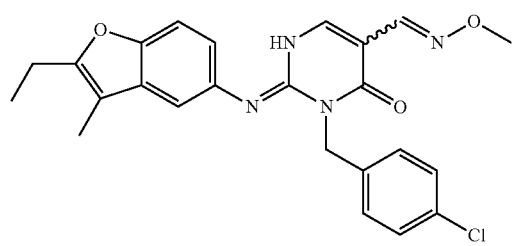 [SMILES: CCc1oc2ccc(/N=c3\[nH]cc(C=NOC)c(=O)n3Cc3ccc(Cl)cc3)cc2c1C] | I-058 | 451 | 2.71 | 3 |
| 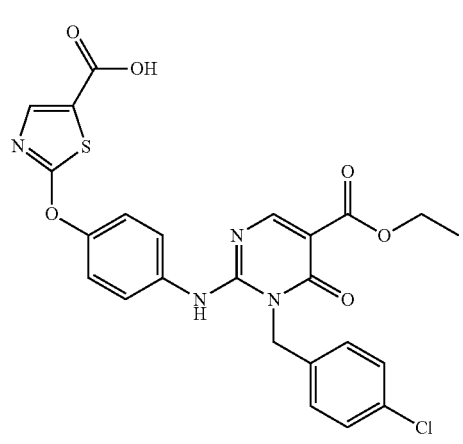 [SMILES: CCOC(=O)c1cnc(Nc2ccc(Oc3ncc(C(=O)O)s3)cc2)n(Cc2ccc(Cl)cc2)c1=O] | I-059 | 527 | 2.02 | 3 |

TABLE 32

| Structure | Compound No | RT (min) | [M + H] | Method |
|---|---|---|---|---|
| 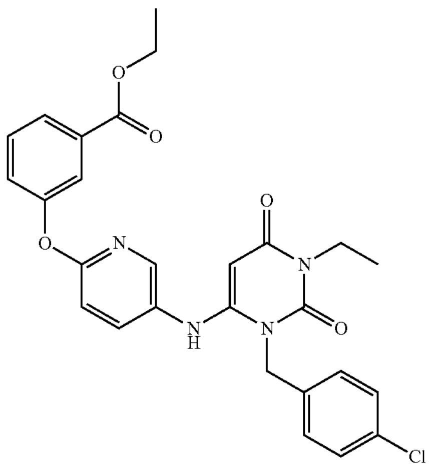 [SMILES: CCOC(=O)c1cccc(Oc2ccc(Nc3cc(=O)n(CC)c(=O)n3Cc3ccc(Cl)cc3)cn2)c1] | I-060 | 521 | 2.35 | 3 |
| 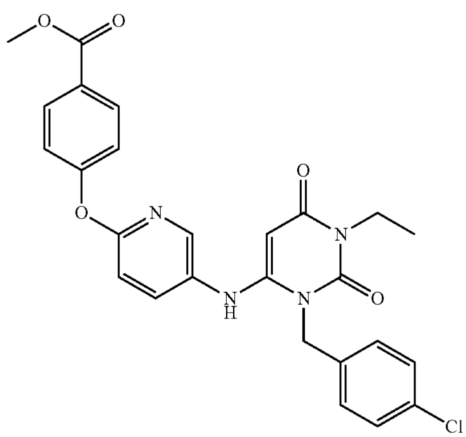 [SMILES: CCn1c(=O)cc(Nc2ccc(Oc3ccc(C(=O)OC)cc3)nc2)n(Cc2ccc(Cl)cc2)c1=O] | I-061 | 507 | 2.20 | 3 |
| 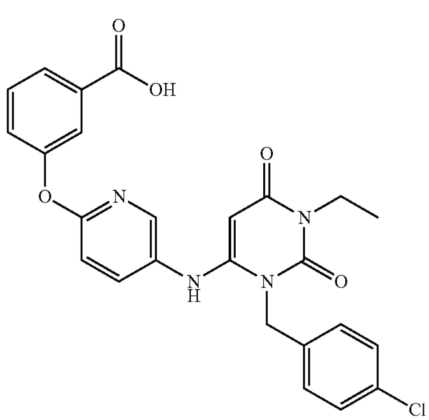 [SMILES: CCn1c(=O)cc(Nc2ccc(Oc3cccc(C(=O)O)c3)nc2)n(Cc2ccc(Cl)cc2)c1=O] | I-062 | 493 | 1.90 | 3 |

TABLE 33

| Structure | Compound No | RT (min) | [M + H] | Method |
|---|---|---|---|---|
| (structure) | I-063 | 493 | 1.90 | 3 |
| (structure) | I-064 | 446 | 1.84 | 3 |
| (structure) | I-065 | 452 | 1.86 | 3 |

TABLE 34

| Structure | Compound No | RT (min) | [M + H] | Method |
|---|---|---|---|---|
| 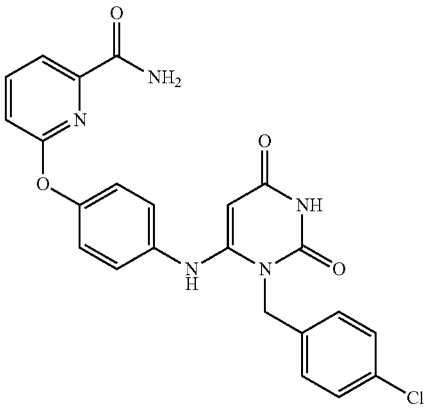 [SMILES: NC(=O)c1cccc(Oc2ccc(Nc3cc(=O)[nH]c(=O)n3Cc3ccc(Cl)cc3)cc2)n1] | I-066 | 464 | 1.60 | 3 |
| 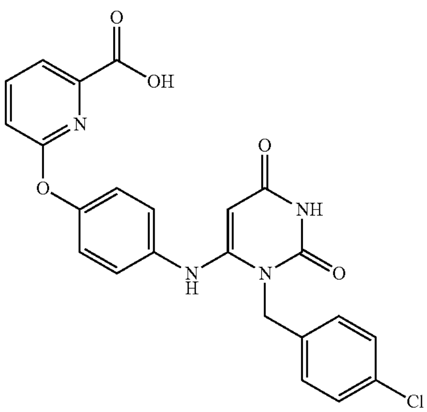 [SMILES: O=C(O)c1cccc(Oc2ccc(Nc3cc(=O)[nH]c(=O)n3Cc3ccc(Cl)cc3)cc2)n1] | I-067 | 465 | 1.62 | 3 |
| 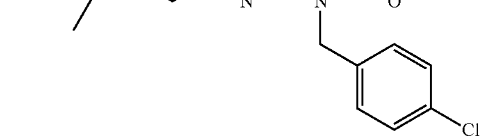 | I-068 | 438 | 2.20 | 3 |

TABLE 35

| Structure | Compound No | RT (min) | [M + H] | Method |
|---|---|---|---|---|
| *(structure)* | I-069 | 463 | 1.63 | 3 |
| *(structure)* | I-070 | 480 | 2.11 | 3 |
| *(structure)* | I-071 | 454 | 2.29 | 3 |

TABLE 36

| Structure | Compound No | RT (min) | [M + H] | Method |
|---|---|---|---|---|
| *(structure)* | I-072 | 480 | 2.55 | 3 |

TABLE 36-continued

| Structure | Compound No | RT (min) | [M + H] | Method |
|---|---|---|---|---|
| (structure I-073) | I-073 | 436 | 2.50 | 3 |
| (structure I-074) | I-074 | 452 | 2.15 | 3 |

TABLE 37

| Structure | Compound No | RT (min) | [M + H] | Method |
|---|---|---|---|---|
| (structure I-075) | I-075 | 475 | 2.09 | 3 |
| (structure I-076) | I-076 | 493 | 1.70 | 3 |

TABLE 37-continued
| Structure | Compound No | RT (min) | [M + H] | Method |
|---|---|---|---|---|
| 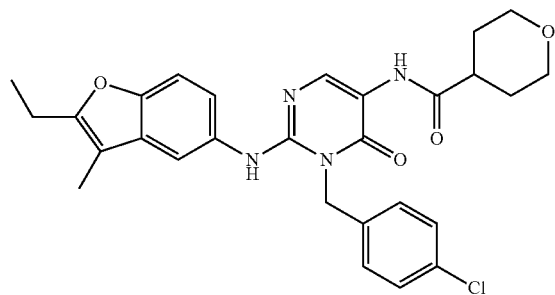 [SMILES: CCc1oc2ccc(Nc3ncc(NC(=O)C4CCOCC4)c(=O)n3Cc3ccc(Cl)cc3)cc2c1C] | I-077 | 487 | 2.16 | 3 |
TABLE 38
| Structure | Compound No | RT (min) | [M + H] | Method |
|---|---|---|---|---|
| 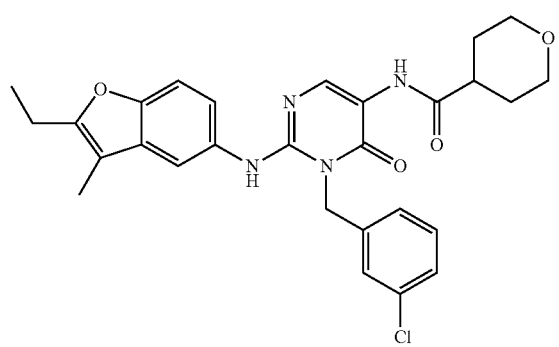 [SMILES: CCc1oc2ccc(Nc3ncc(NC(=O)C4CCOCC4)c(=O)n3Cc3cccc(Cl)c3)cc2c1C] | I-078 | 521 | 2.33 | 3 |
| 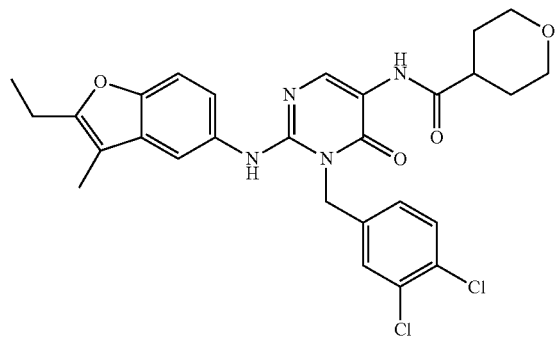 [SMILES: CCc1oc2ccc(Nc3ncc(NC(=O)C4CCOCC4)c(=O)n3Cc3ccc(Cl)c(Cl)c3)cc2c1C] | I-079 | 555 | 2.49 | 3 |
| 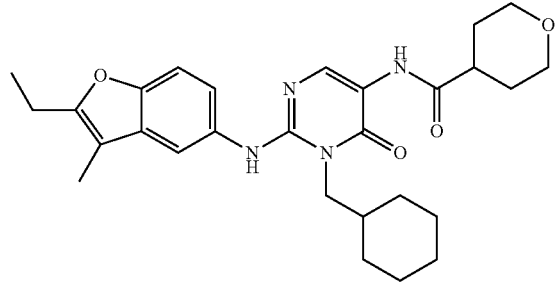 [SMILES: CCc1oc2ccc(Nc3ncc(NC(=O)C4CCOCC4)c(=O)n3CC3CCCCC3)cc2c1C] | I-080 | 493 | 2.33 | 3 |

TABLE 39

| Structure | Compound No | RT (min) | [M + H] | Method |
|---|---|---|---|---|
| 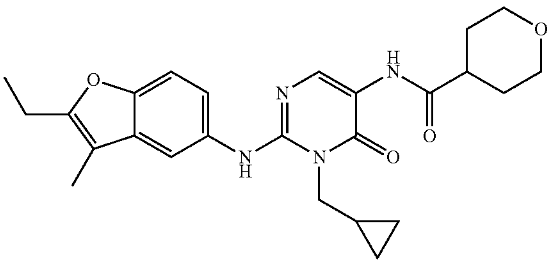 [SMILES: CCc1oc2ccc(Nc3ncc(NC(=O)C4CCOCC4)c(=O)n3CC3CC3)cc2c1C] | I-081 | 451 | 1.95 | 3 |
| 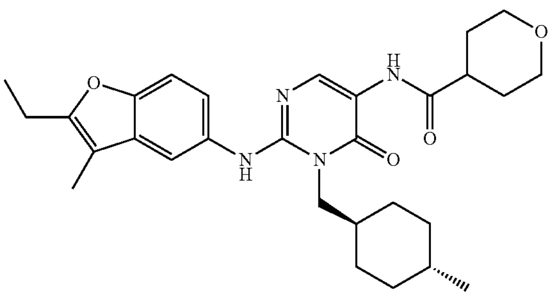 [SMILES: CCc1oc2ccc(Nc3ncc(NC(=O)C4CCOCC4)c(=O)n3C[C@H]3CC[C@H](C)CC3)cc2c1C] | I-082 | 507 | 2.47 | 3 |
| 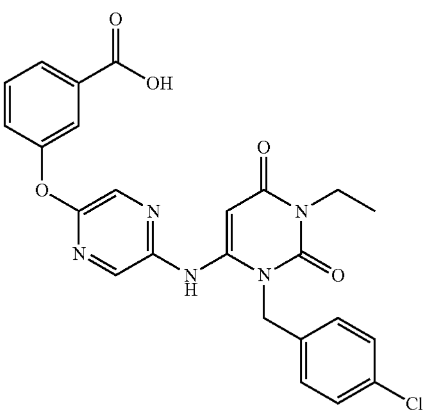 [SMILES: CCn1c(=O)cc(Nc2cnc(Oc3cccc(C(=O)O)c3)cn2)n(Cc2ccc(Cl)cc2)c1=O] | I-083 | 494 | 1.87 | 3 |

TABLE 40

| Structure | Compound No | RT (min) | [M + H] | Method |
|---|---|---|---|---|
| 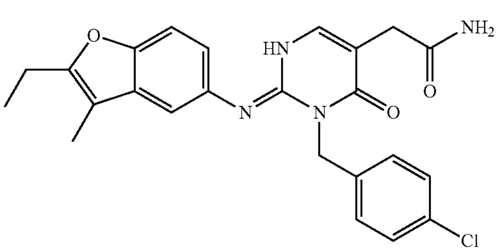 [SMILES: CCc1oc2ccc(/N=c3\[nH]cc(CC(N)=O)c(=O)n3Cc3ccc(Cl)cc3)cc2c1C] | I-084 | 451 | 2.00 | 3 |

TABLE 40-continued

| Structure | Compound No | RT (min) | [M + H] | Method |
|---|---|---|---|---|
| 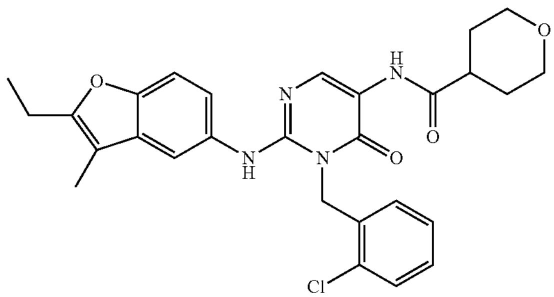 [SMILES: CCc1oc2ccc(Nc3ncc(NC(=O)C4CCOCC4)c(=O)n3Cc3ccccc3Cl)cc2c1C] | I-085 | 521 | 2.31 | 3 |
| 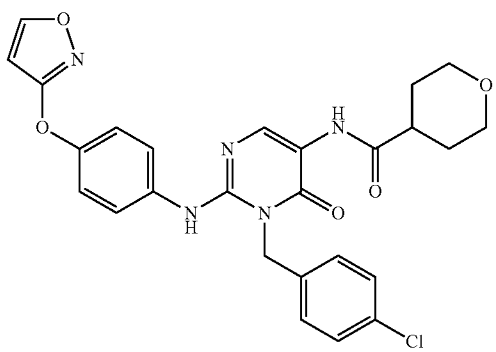 [SMILES: O=C(Nc1cnc(Nc2ccc(Oc3ccon3)cc2)n(Cc2ccc(Cl)cc2)c1=O)C1CCOCC1] | I-086 | 522 | 1.93 | 3 |

TABLE 41

| Structure | Compound No | RT (min) | [M + H] | Method |
|---|---|---|---|---|
| 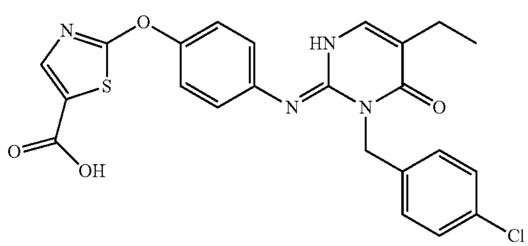 [SMILES: CCc1c[nH]/c(=N\c2ccc(Oc3ncc(C(=O)O)s3)cc2)n(Cc2ccc(Cl)cc2)c1=O] | I-087 | 483 | 2.08 | 3 |
| 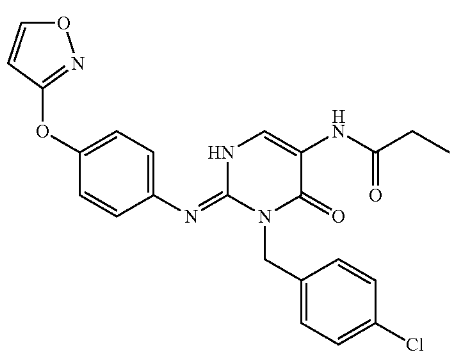 [SMILES: CCC(=O)Nc1c[nH]/c(=N\c2ccc(Oc3ccon3)cc2)n(Cc2ccc(Cl)cc2)c1=O] | I-088 | 466 | 1.95 | 3 |

TABLE 41-continued
| Structure | Compound No | RT (min) | [M + H] | Method |
|---|---|---|---|---|
| 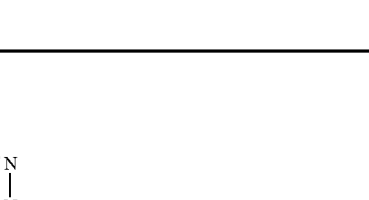 | I-089 | 507 | 1.62 | 3 |
TABLE 42
| Structure | Compound No | RT (min) | [M + H] | Method |
|---|---|---|---|---|
| 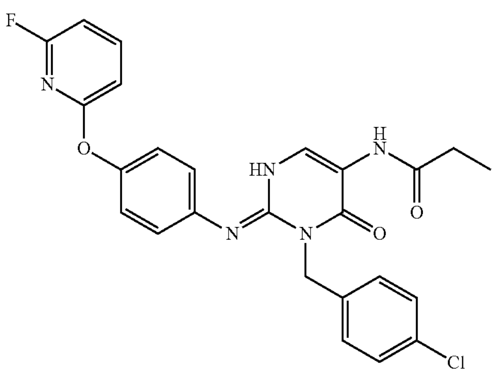 [SMILES: CCC(=O)Nc1c[nH]/c(=N\c2ccc(Oc3cccc(F)n3)cc2)n(Cc2ccc(Cl)cc2)c1=O] | I-090 | 494 | 2.20 | 3 |
| 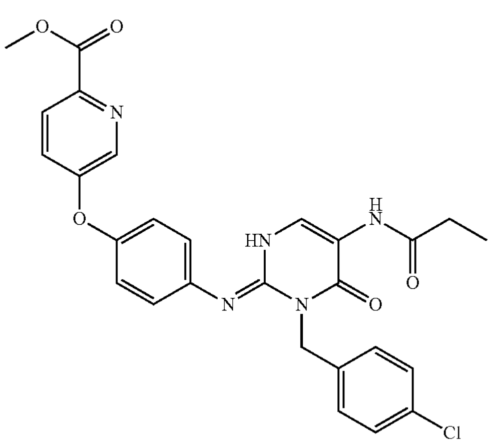 [SMILES: CCC(=O)Nc1c[nH]/c(=N\c2ccc(Oc3ccc(C(=O)OC)nc3)cc2)n(Cc2ccc(Cl)cc2)c1=O] | I-091 | 534 | 3.37 | 3 |

TABLE 42-continued

| Structure | Compound No | RT (min) | [M + H] | Method |
|---|---|---|---|---|
| (structure) | I-092 | 520 | 1.75 | 3 |

TABLE 43

| Structure | Compound No | RT (min) | [M + H] | Method |
|---|---|---|---|---|
| (structure) | I-093 | 519 | 1.83 | 3 |
| (structure) | I-094 | 521 | 1.73 | 3 |
| (structure) | I-095 | 519 | 1.80 | 3 |

TABLE 44

| Structure | Compound No | RT (min) | [M + H] | Method |
|---|---|---|---|---|
| (structure of I-096) | I-096 | 467 | 2.08 | 3 |
| (structure of I-097) | I-097 | 520 | 1.73 | 3 |
| (structure of I-098) | I-098 | 534 | 1.92 | 3 |

TABLE 45

| Structure | Compound No | RT (min) | [M + H] | Method |
|---|---|---|---|---|
| (structure of I-099) | I-099 | 439 | 2.01 | 3 |

TABLE 45-continued

| Structure | Compound No | RT (min) | [M + H] | Method |
|---|---|---|---|---|
| 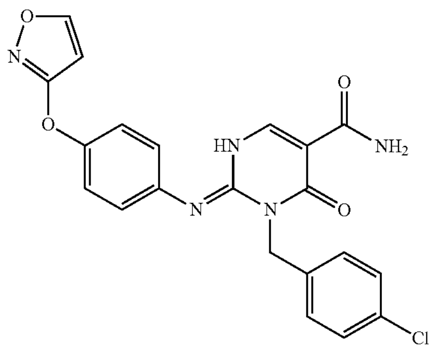 [SMILES: NC(=O)c1c[nH]/c(=N\c2ccc(Oc3ccon3)cc2)n(Cc2ccc(Cl)cc2)c1=O] | I-100 | 438 | 1.83 | 3 |
| 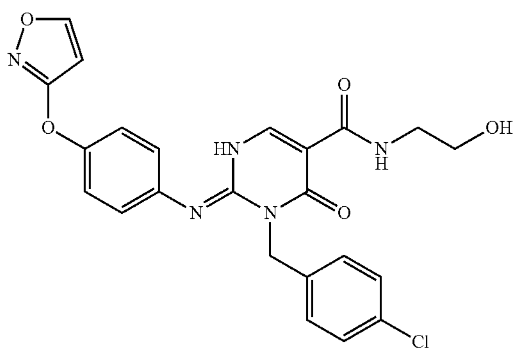 [SMILES: O=C(NCCO)c1c[nH]/c(=N\c2ccc(Oc3ccon3)cc2)n(Cc2ccc(Cl)cc2)c1=O] | I-101 | 482 | 1.76 | 3 |

TABLE 46

| Structure | Compound No | RT (min) | [M + H] | Method |
|---|---|---|---|---|
| 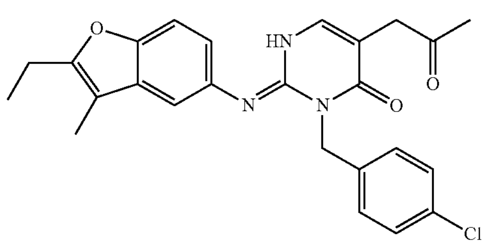 [SMILES: CCc1oc2ccc(/N=c3\[nH]cc(CC(C)=O)c(=O)n3Cc3ccc(Cl)cc3)cc2c1C] | I-102 | 450 | 2.32 | 3 |
| 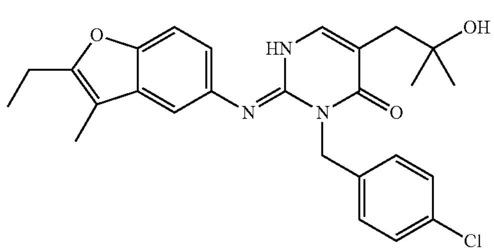 [SMILES: CCc1oc2ccc(/N=c3\[nH]cc(CC(C)(C)O)c(=O)n3Cc3ccc(Cl)cc3)cc2c1C] | I-103 | 466 | 2.33 | 3 |

TABLE 46-continued
| Structure | Compound No | RT (min) | [M + H] | Method |
|---|---|---|---|---|
| 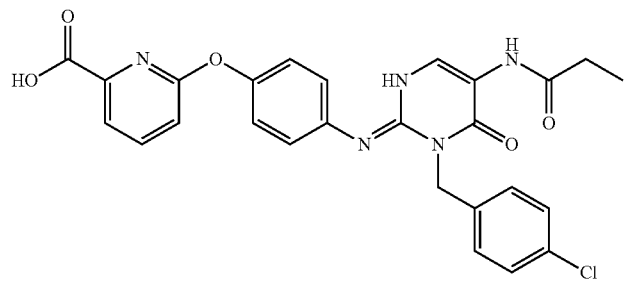 [SMILES: CCC(=O)Nc1c[nH]/c(=N\c2ccc(Oc3cccc(C(=O)O)n3)cc2)n(Cc2ccc(Cl)cc2)c1=O] | I-104 | 520 | 1.87 | 3 |
TABLE 47
| Structure | Compound No | RT (min) | [M + H] | Method |
|---|---|---|---|---|
| 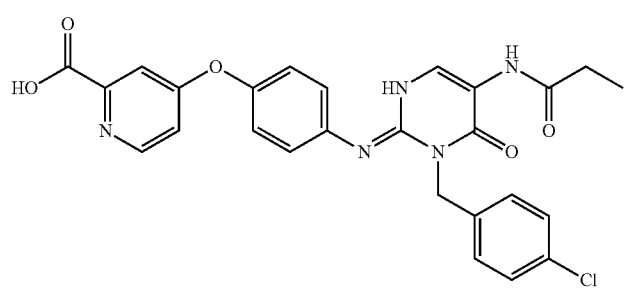 | I-105 | 529 | 1.43 | 3 |
| 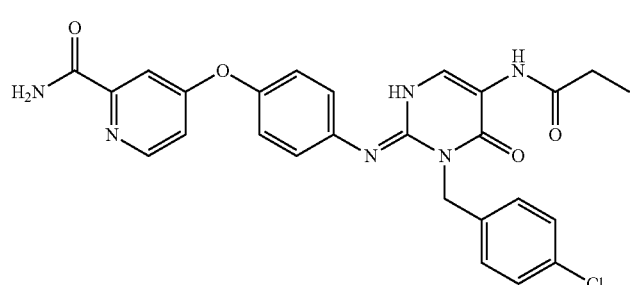 | I-106 | 519 | 1.81 | 3 |
| 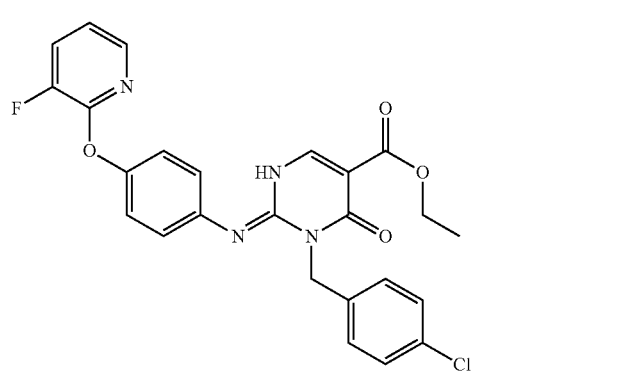 [SMILES: CCOC(=O)c1c[nH]/c(=N\c2ccc(Oc3ncccc3F)cc2)n(Cc2ccc(Cl)cc2)c1=O] | I-107 | 495 | 2.25 | 3 |

TABLE 48

| Structure | Compound No | RT (min) | [M + H] | Method |
|---|---|---|---|---|
| 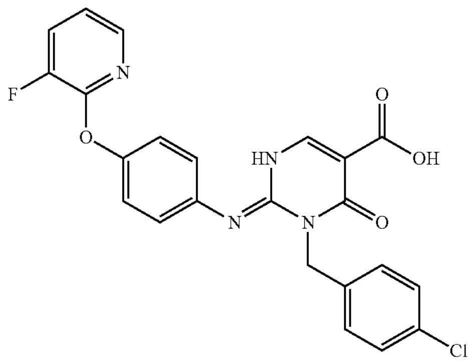 [SMILES: O=C(O)c1c[nH]/c(=N\c2ccc(Oc3ncccc3F)cc2)n(Cc2ccc(Cl)cc2)c1=O] | I-108 | 467 | 2.18 | 3 |
| 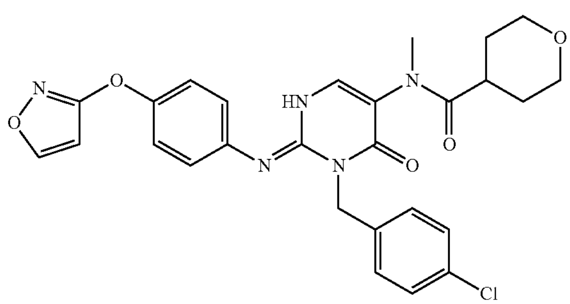 [SMILES: CN(C(=O)C1CCOCC1)c1c[nH]/c(=N\c2ccc(Oc3ccon3)cc2)n(Cc2ccc(Cl)cc2)c1=O] | I-109 | 536 | 1.86 | 3 |
| 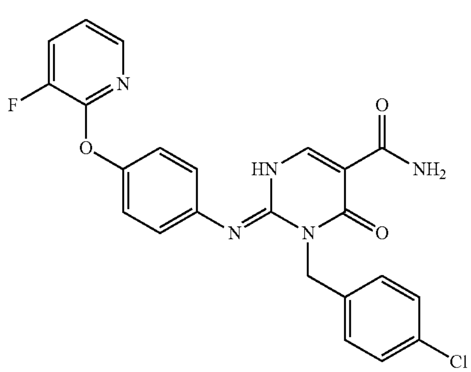 | I-110 | 466 | 2.01 | 3 |

TABLE 49

| Structure | Compound No | RT (min) | [M + H] | Method |
|---|---|---|---|---|
| (structure of I-111) | I-111 | 510 | 1.94 | 3 |
| (structure of I-112) | I-112 | 509 | 2.39 | 3 |
| (structure of I-113) | I-113 | 520 | 2.39 | 3 |

TABLE 50

| Structure | Compound No | RT (min) | [M + H] | Method |
|---|---|---|---|---|
| (structure of I-114) | I-114 | 511 | 2.03 | 3 |

TABLE 50-continued
| Structure | Compound No | RT (min) | [M + H] | Method |
|---|---|---|---|---|
| 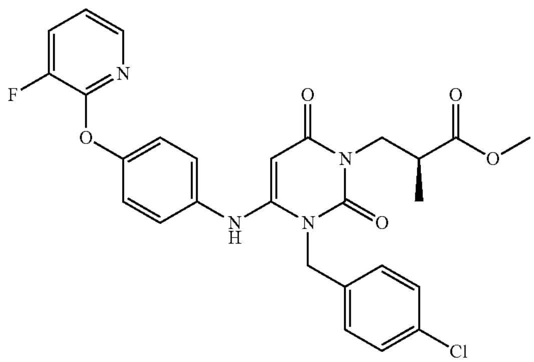 [SMILES: COC(=O)[C@@H](C)Cn1c(=O)cc(Nc2ccc(Oc3ncccc3F)cc2)n(Cc2ccc(Cl)cc2)c1=O] | I-115 | 539 | 2.17 | 3 |
| 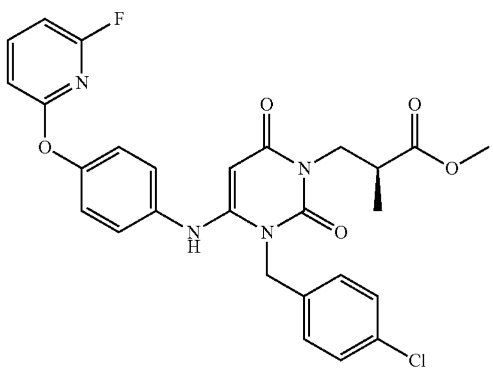 [SMILES: COC(=O)[C@@H](C)Cn1c(=O)cc(Nc2ccc(Oc3cccc(F)n3)cc2)n(Cc2ccc(Cl)cc2)c1=O] | I-116 | 539 | 2.23 | 3 |
TABLE 51
| Structure | Compound No | RT (min) | [M + H] | Method |
|---|---|---|---|---|
| 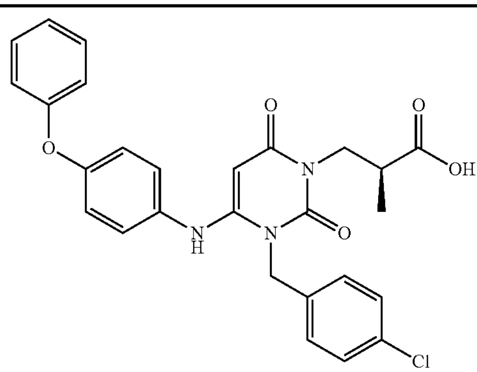 | I-117 | 506 | 2.15 | 3 |
| 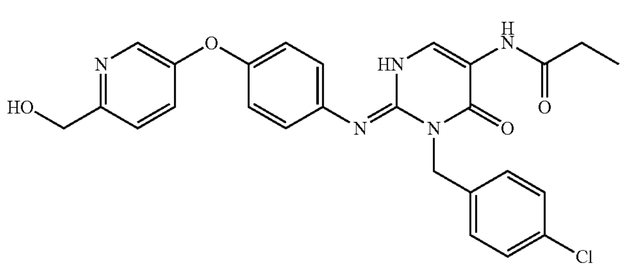 [SMILES: CCC(=O)Nc1c[nH]/c(=N\c2ccc(Oc3ccc(CO)nc3)cc2)n(Cc2ccc(Cl)cc2)c1=O] | I-118 | 506 | 1.58 | 3 |
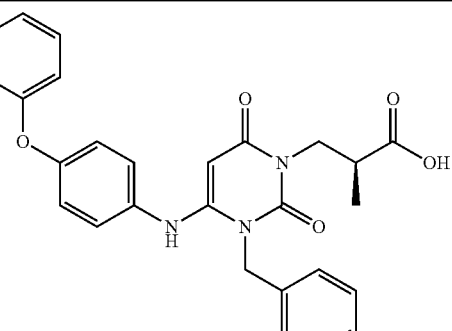

TABLE 51-continued

| Structure | Compound No | RT (min) | [M + H] | Method |
|---|---|---|---|---|
| (3-fluoropyridin-2-yloxy-phenylamino uracil with 4-chlorobenzyl and (S)-2-methylpropanoic acid) | I-119 | 525 | 1.94 | 3 |

TABLE 52

| Structure | Compound No | RT (min) | [M + H] | Method |
|---|---|---|---|---|
| (6-fluoropyridin-2-yloxy-phenylamino uracil with 4-chlorobenzyl and (S)-2-methylpropanoic acid) | I-120 | 525 | 1.99 | 3 |
| (isoxazol-3-yloxy-phenylamino uracil with 4-chlorobenzyl and (S)-2-methylpropanoic acid) | I-121 | 497 | 1.79 | 3 |

TABLE 52-continued
| Structure | Compound No | RT (min) | [M + H] | Method |
|---|---|---|---|---|
| 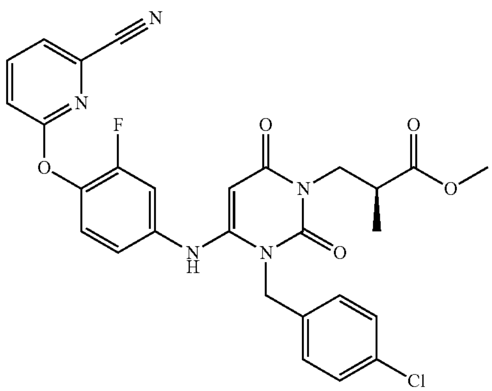 [SMILES: COC(=O)[C@@H](C)Cn1c(=O)cc(Nc2ccc(Oc3cccc(C#N)n3)c(F)c2)n(Cc2ccc(Cl)cc2)c1=O] | I-122 | 564 | 2.20 | 3 |
TABLE 53
| Structure | Compound No | RT (min) | [M + H] | Method |
|---|---|---|---|---|
| 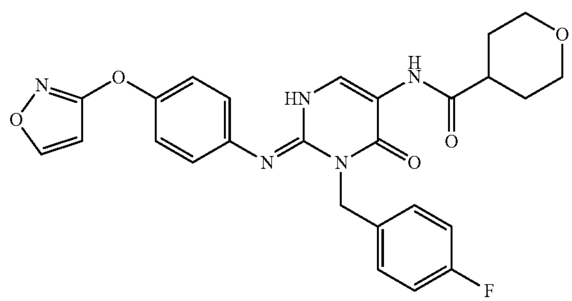 [SMILES: O=C(Nc1c[nH]/c(=N\c2ccc(Oc3ccon3)cc2)n(Cc2ccc(F)cc2)c1=O)C1CCOCC1] | I-123 | 506 | 1.79 | 3 |
| 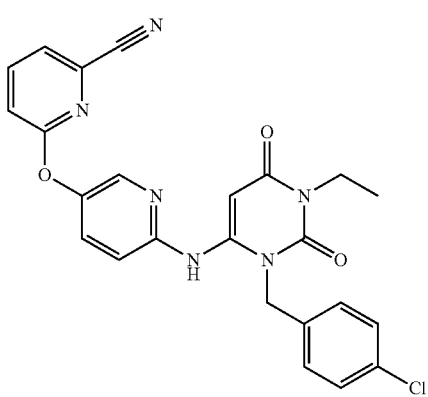 | I-124 | 475 | 2.01 | 3 |

TABLE 53-continued

| Structure | Compound No | RT (min) | [M + H] | Method |
|---|---|---|---|---|
| 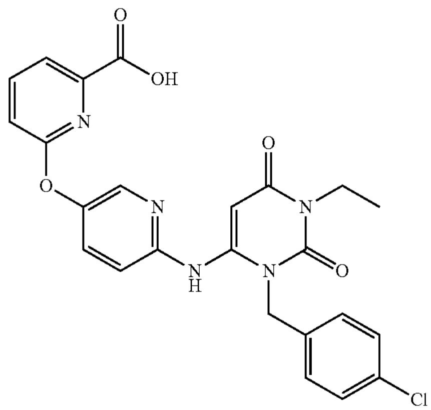 | I-125 | 494 | 1.79 | 3 |

TABLE 54

| Structure | Compound No | RT (min) | [M + H] | Method |
|---|---|---|---|---|
| 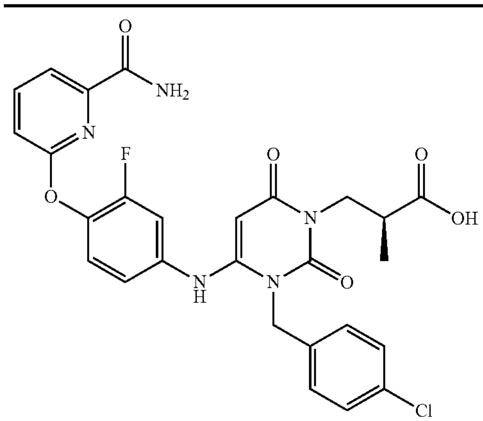 | I-126 | 568 | 1.75 | 3 |
| 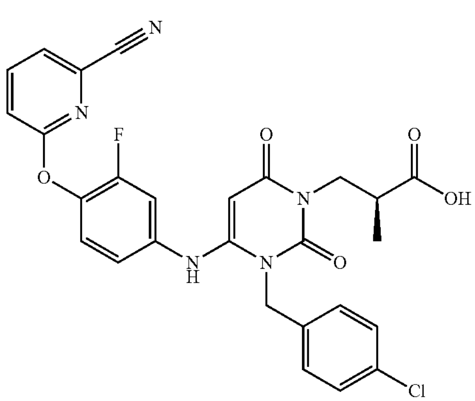 [SMILES: C[C@@H](Cn1c(=O)cc(Nc2ccc(Oc3cccc(C#N)n3)c(F)c2)n(Cc2ccc(Cl)cc2)c1=O)C(=O)O] | I-127 | 550 | 1.96 | 3 |

TABLE 54-continued

| Structure | Compound No | RT (min) | [M + H] | Method |
|---|---|---|---|---|
| 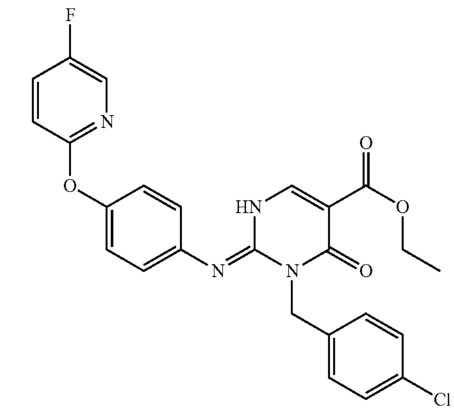 [SMILES: CCOC(=O)c1c[nH]/c(=N\c2ccc(Oc3ccc(F)cn3)cc2)n(Cc2ccc(Cl)cc2)c1=O] | I-128 | 495 | 2.27 | 3 |

TABLE 55

| Structure | Compound No | RT (min) | [M + H] | Method |
|---|---|---|---|---|
| 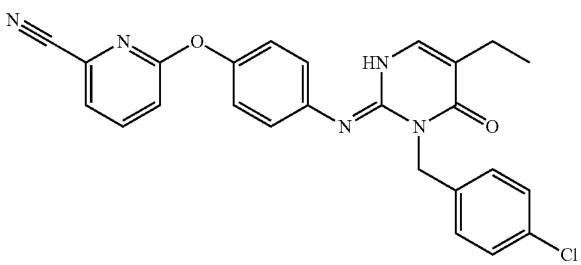 [SMILES: CCc1c[nH]/c(=N\c2ccc(Oc3cccc(C#N)n3)cc2)n(Cc2ccc(Cl)cc2)c1=O] | I-129 | 458 | 2.33 | 3 |
| 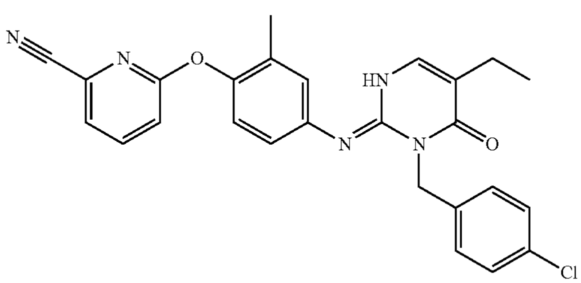 [SMILES: CCc1c[nH]/c(=N\c2ccc(Oc3cccc(C#N)n3)c(C)c2)n(Cc2ccc(Cl)cc2)c1=O] | I-130 | 472 | 2.39 | 3 |
| 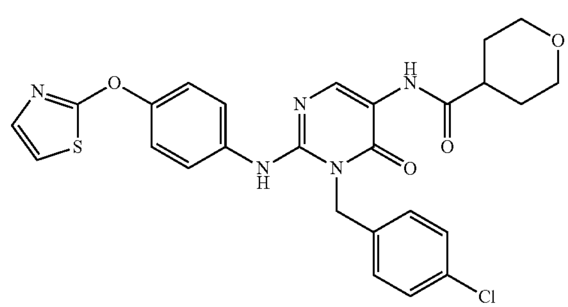 [SMILES: O=C(Nc1cnc(Nc2ccc(Oc3nccs3)cc2)n(Cc2ccc(Cl)cc2)c1=O)C1CCOCC1] | I-131 | 538 | 2.02 | 3 |

TABLE 56

| Structure | Compound No | RT (min) | [M + H] | Method |
|---|---|---|---|---|
| 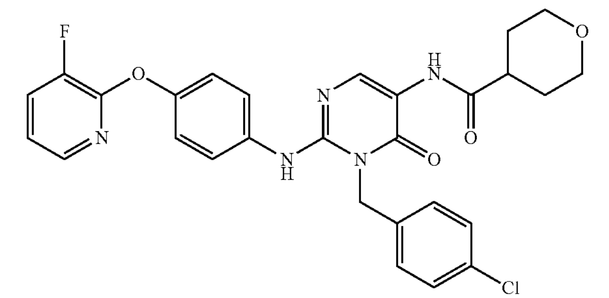 [SMILES: O=C(Nc1cnc(Nc2ccc(Oc3ncccc3F)cc2)n(Cc2ccc(Cl)cc2)c1=O)C1CCOCC1] | I-132 | 550 | 2.09 | 3 |
| 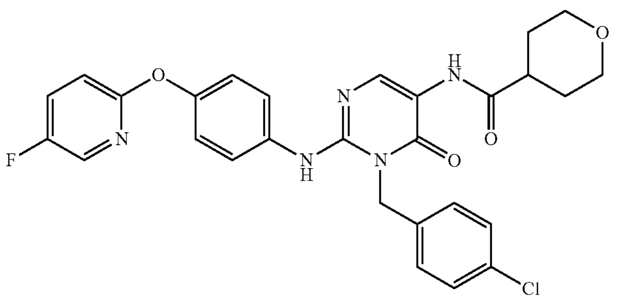 [SMILES: O=C(Nc1cnc(Nc2ccc(Oc3ccc(F)cn3)cc2)n(Cc2ccc(Cl)cc2)c1=O)C1CCOCC1] | I-133 | 550 | 2.09 | 3 |
| 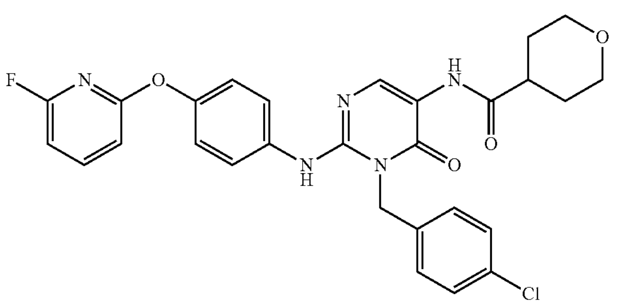 [SMILES: O=C(Nc1cnc(Nc2ccc(Oc3cccc(F)n3)cc2)n(Cc2ccc(Cl)cc2)c1=O)C1CCOCC1] | I-134 | 550 | 2.14 | 3 |

TABLE 57

| Structure | Compound No | RT (min) | [M + H] | Method |
|---|---|---|---|---|
| 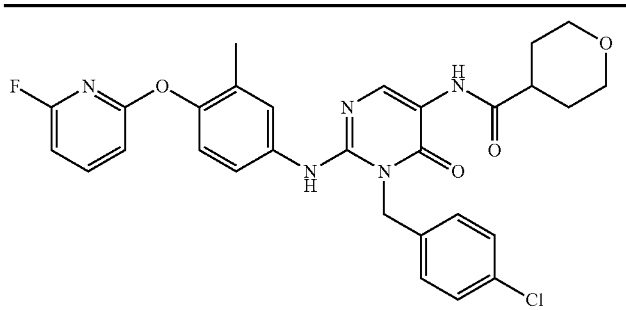 | I-135 | 564 | 2.23 | 3 |

TABLE 57-continued

| Structure | Compound No | RT (min) | [M + H] | Method |
|---|---|---|---|---|
| (structure) | I-136 | 547 | 1.96 | 3 |
| (structure) | I-137 | 547 | 1.77 | 3 |

TABLE 58

| Structure | Compound No | RT (min) | [M + H] | Method |
|---|---|---|---|---|
| (structure) | I-138 | 502 | 2.08 | 3 |
| (structure) | I-139 | 480 | 2.13 | 3 |

TABLE 58-continued

| Structure | Compound No | RT (min) | [M + H] | Method |
|---|---|---|---|---|
| 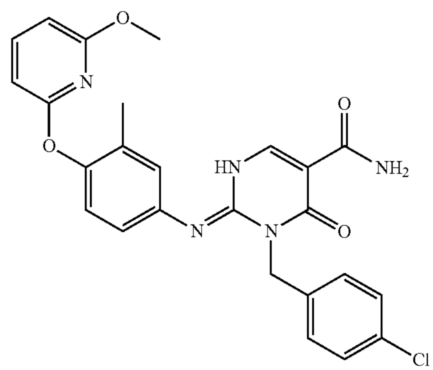 [SMILES: COc1cccc(Oc2ccc(/N=c3\[nH]cc(C(N)=O)c(=O)n3Cc3ccc(Cl)cc3)cc2C)n1] | I-140 | 492 | 2.20 | 3 |

TABLE 59

| Structure | Compound No | RT (min) | [M + H] | Method |
|---|---|---|---|---|
| 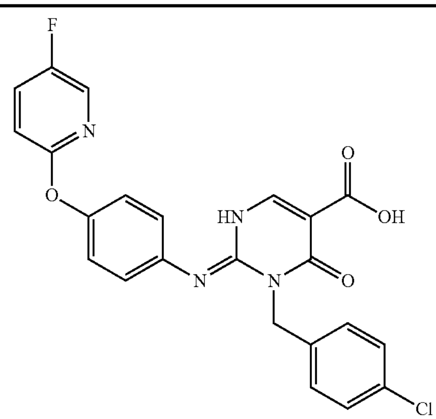 | I-141 | 467 | 2.18 | 3 |
| 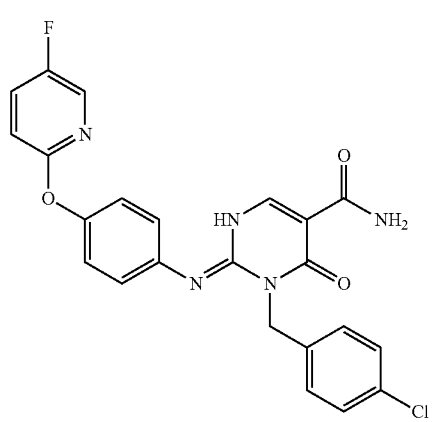 [SMILES: NC(=O)c1c[nH]/c(=N\c2ccc(Oc3ccc(F)cn3)cc2)n(Cc2ccc(Cl)cc2)c1=O] | I-142 | 466 | 2.00 | 3 |

TABLE 59-continued

| Structure | Compound No | RT (min) | [M + H] | Method |
|---|---|---|---|---|
| (structure) | I-143 | 558 | 2.02 | 3 |

TABLE 60

| Structure | Compound No | RT (min) | [M + H] | Method |
|---|---|---|---|---|
| (structure) | I-144 | 477 | 2.10 | 3 |
| (structure) | I-145 | 491 | 2.02 | 3 |
| (structure) | I-146 | 491 | 1.79 | 3 |

TABLE 61

| Structure | Compound No | RT (min) | [M + H] | Method |
|---|---|---|---|---|
| (structure) | I-147 | 470 | 2.50 | 3 |
| (structure) | I-148 | 491 | 2.09 | 3 |
| (structure) | I-149 | 522 | 1.68 | 3 |

TABLE 62

| Structure | Compound No | RT (min) | [M + H] | Method |
|---|---|---|---|---|
| (structure) | I-150 | 508 | 1.46 | 3 |

TABLE 62-continued
| Structure | Compound No | RT (min) | [M + H] | Method |
|---|---|---|---|---|
| 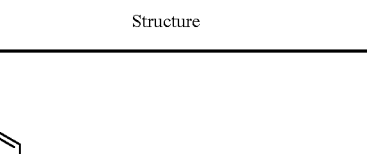 | I-151 | 505 | 2.21 | 3 |
| 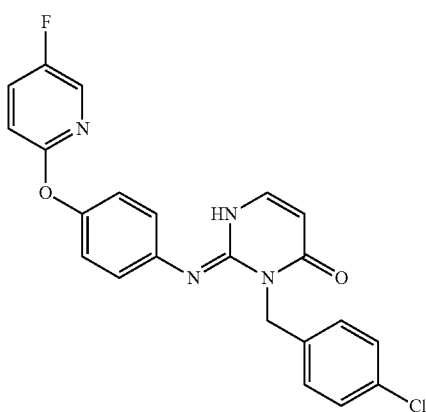 [SMILES: O=c1cc[nH]/c(=N\c2ccc(Oc3ccc(F)cn3)cc2)n1Cc1ccc(Cl)cc1] | I-152 | 423 | 2.25 | 3 |
TABLE 63
| Structure | Compound No | RT (min) | [M + H] | Method |
|---|---|---|---|---|
| 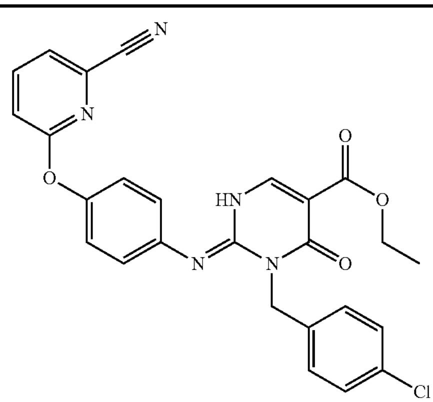 | I-153 | 502 | 2.21 | 3 |

TABLE 63-continued

| Structure | Compound No | RT (min) | [M + H] | Method |
|---|---|---|---|---|
| 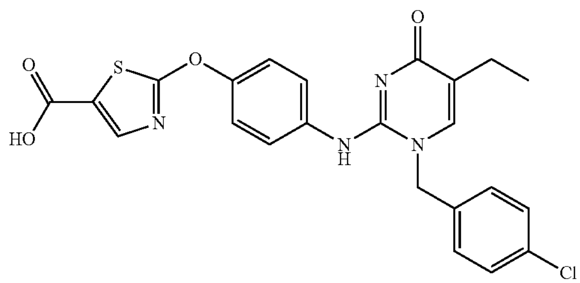 [SMILES: CCc1cn(Cc2ccc(Cl)cc2)c(Nc2ccc(Oc3ncc(C(=O)O)s3)cc2)nc1=O] | I-154 | 483 | 1.87 | 3 |
| 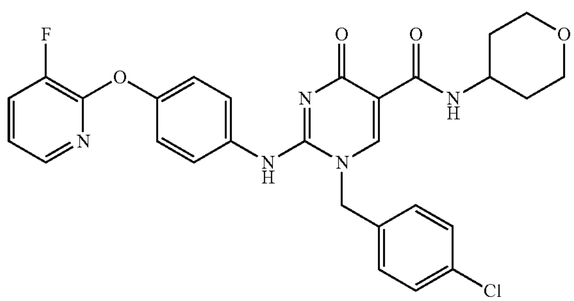 [SMILES: O=C(NC1CCOCC1)c1cn(Cc2ccc(Cl)cc2)c(Nc2ccc(Oc3ncccc3F)cc2)nc1=O] | I-155 | 550 | 2.12 | 3 |

TABLE 64

| Structure | Compound No | RT (min) | [M + H] | Method |
|---|---|---|---|---|
| 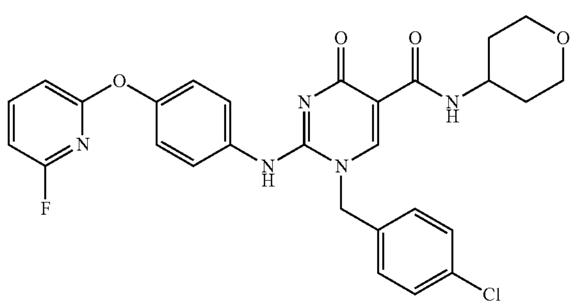 [SMILES: O=C(NC1CCOCC1)c1cn(Cc2ccc(Cl)cc2)c(Nc2ccc(Oc3cccc(F)n3)cc2)nc1=O] | I-156 | 550 | 2.15 | 3 |
| 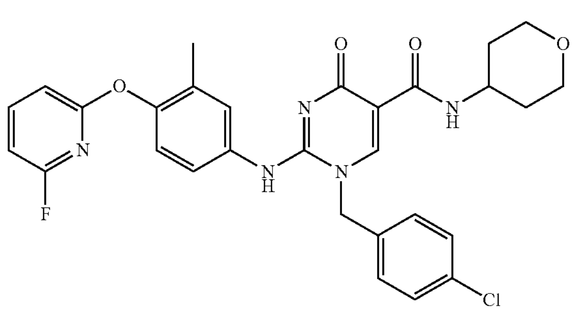 [SMILES: Cc1cc(Nc2nc(=O)c(C(=O)NC3CCOCC3)cn2Cc2ccc(Cl)cc2)ccc1Oc1cccc(F)n1] | I-157 | 564 | 2.25 | 3 |

TABLE 64-continued

| Structure | Compound No | RT (min) | [M + H] | Method |
|---|---|---|---|---|
| 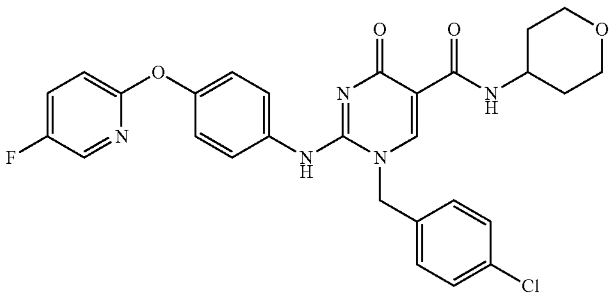 [SMILES: O=C(NC1CCOCC1)c1cn(Cc2ccc(Cl)cc2)c(Nc2ccc(Oc3ccc(F)cn3)cc2)nc1=O] | I-158 | 550 | 2.12 | 3 |

TABLE 65

| Structure | Compound No | RT (min) | [M + H] | Method |
|---|---|---|---|---|
| 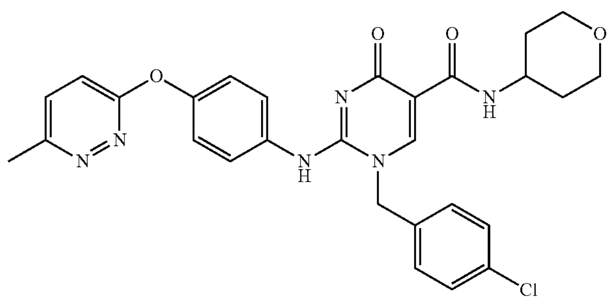 [SMILES: Cc1ccc(Oc2ccc(Nc3nc(=O)c(C(=O)NC4CCOCC4)cn3Cc3ccc(Cl)cc3)cc2)nn1] | I-159 | 547 | 1.80 | 3 |
| 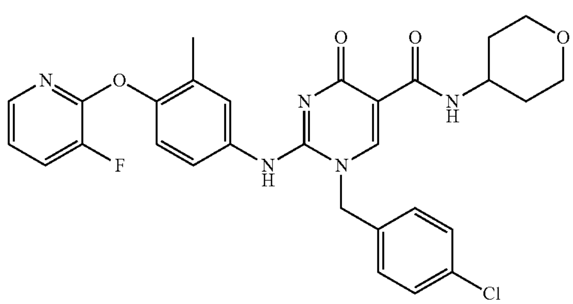 [SMILES: Cc1cc(Nc2nc(=O)c(C(=O)NC3CCOCC3)cn2Cc2ccc(Cl)cc2)ccc1Oc1ncccc1F] | I-160 | 564 | 2.24 | 3 |
| 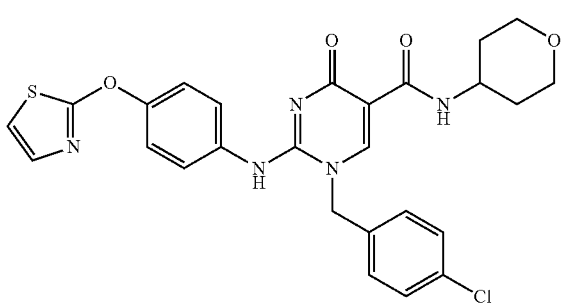 [SMILES: O=C(NC1CCOCC1)c1cn(Cc2ccc(Cl)cc2)c(Nc2ccc(Oc3nccs3)cc2)nc1=O] | I-161 | 538 | 2.03 | 3 |

TABLE 66

| Structure | Compound No | RT (min) | [M + H] | Method |
|---|---|---|---|---|
| (structure) | I-162 | 564 | 2.26 | 3 |
| (structure) | I-163 | 506 | 1.46 | 5 |

TABLE 67

| Structure | Compound No | RT (min) | [M + H] | Method |
|---|---|---|---|---|
| (structure) | I-164 | 488 | 2.23 | 3 |
| (structure) | I-165 | 507 | 2.00 | 3 |

TABLE 67-continued

| Structure | Compound No | RT (min) | [M + H] | Method |
|---|---|---|---|---|
| 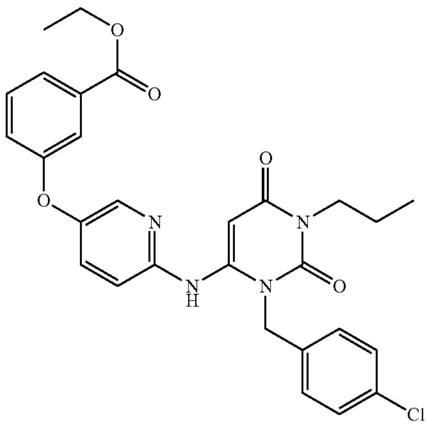 [SMILES: CCCn1c(=O)cc(Nc2ccc(Oc3cccc(C(=O)OCC)c3)cn2)n(Cc2ccc(Cl)cc2)c1=O] | I-166 | 535 | 2.48 | 3 |
| 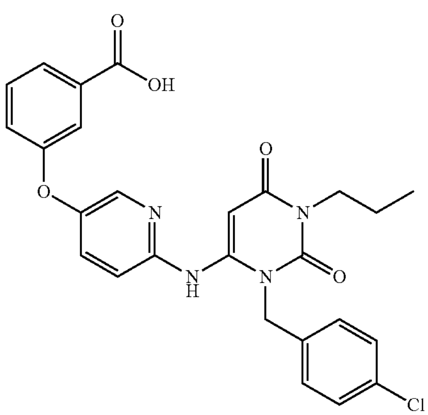 [SMILES: CCCn1c(=O)cc(Nc2ccc(Oc3cccc(C(=O)O)c3)cn2)n(Cc2ccc(Cl)cc2)c1=O] | I-167 | 507 | 2.04 | 3 |
| 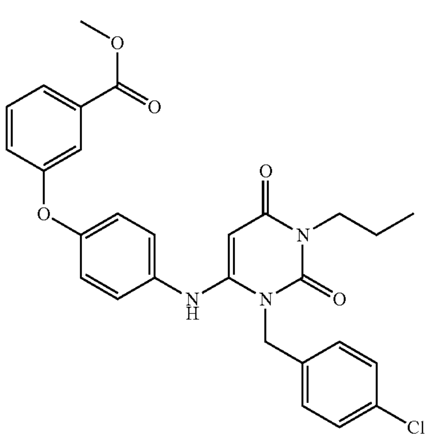 [SMILES: CCCn1c(=O)cc(Nc2ccc(Oc3cccc(C(=O)OC)c3)cc2)n(Cc2ccc(Cl)cc2)c1=O] | I-168 | 520 | 2.45 | 3 |

TABLE 68

| Structure | Compound No | RT (min) | [M + H] | Method |
|---|---|---|---|---|
| 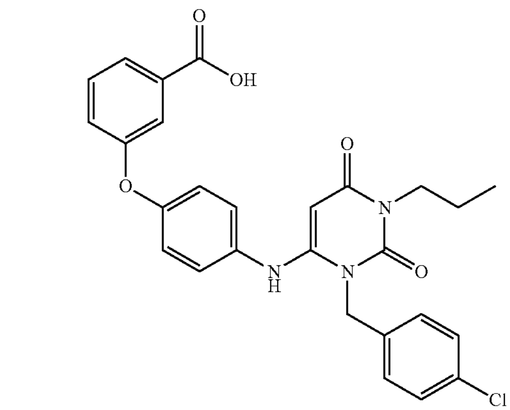 [SMILES: CCCn1c(=O)cc(Nc2ccc(Oc3cccc(C(=O)O)c3)cc2)n(Cc2ccc(Cl)cc2)c1=O] | I-169 | 506 | 2.13 | 3 |
| 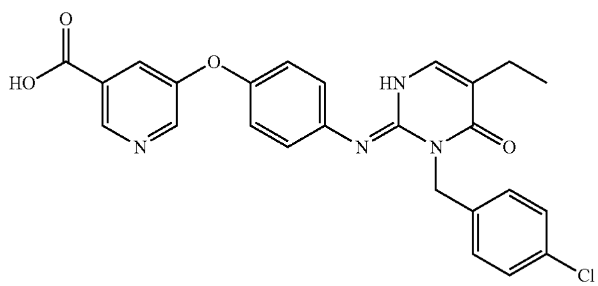 [SMILES: CCc1c[nH]/c(=N\c2ccc(Oc3cncc(C(=O)O)c3)cc2)n(Cc2ccc(Cl)cc2)c1=O] | I-170 | 477 | 1.92 | 3 |
| 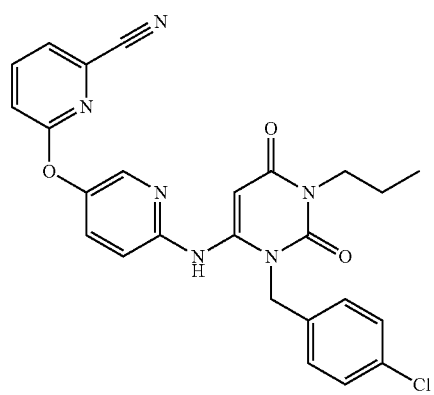 [SMILES: CCCn1c(=O)cc(Nc2ccc(Oc3cccc(C#N)n3)cn2)n(Cc2ccc(Cl)cc2)c1=O] | I-171 | 489 | 2.13 | 3 |
| 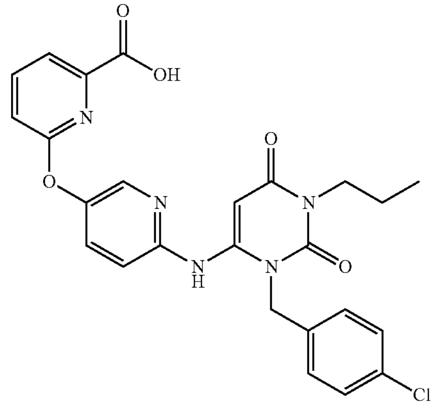 [SMILES: CCCn1c(=O)cc(Nc2ccc(Oc3cccc(C(=O)O)n3)cn2)n(Cc2ccc(Cl)cc2)c1=O] | I-172 | 508 | 1.92 | 3 |

TABLE 68-continued
| Structure | Compound No | RT (min) | [M + H] | Method |
|---|---|---|---|---|
| 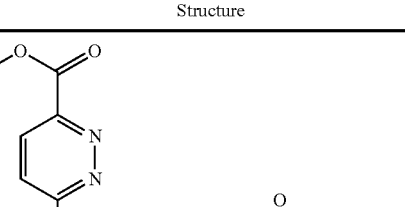 | I-173 | 508 | 1.85 | 3 |
TABLE 69
| Structure | Compound No | RT (min) | [M + H] | Method |
|---|---|---|---|---|
| 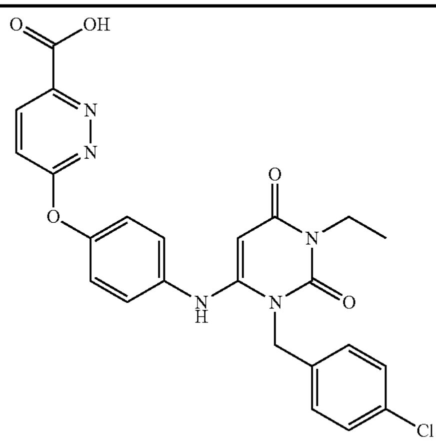 | I-174 | 494 | 1.71 | 3 |
| 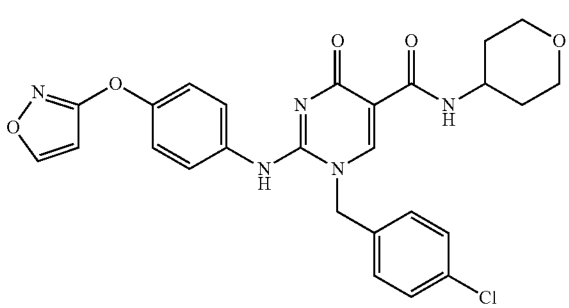 [SMILES: O=C(NC1CCOCC1)c1cn(Cc2ccc(Cl)cc2)c(Nc2ccc(Oc3ccon3)cc2)nc1=O] | I-175 | 522 | 1.92 | 3 |
| 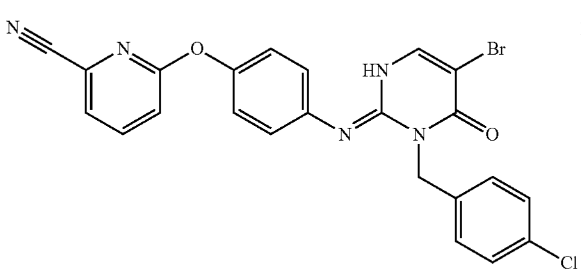 [SMILES: N#Cc1cccc(Oc2ccc(/N=c3\[nH]cc(Br)c(=O)n3Cc3ccc(Cl)cc3)cc2)n1] | I-176 | 508 | 2.33 | 3 |

TABLE 69-continued

| Structure | Compound No | RT (min) | [M + H] | Method |
|---|---|---|---|---|
| 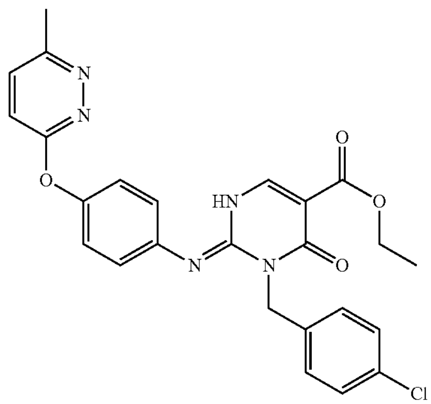 [SMILES: CCOC(=O)c1c[nH]/c(=N\c2ccc(Oc3ccc(C)nn3)cc2)n(Cc2ccc(Cl)cc2)c1=O] | I-177 | 492 | 1.91 | 3 |
| 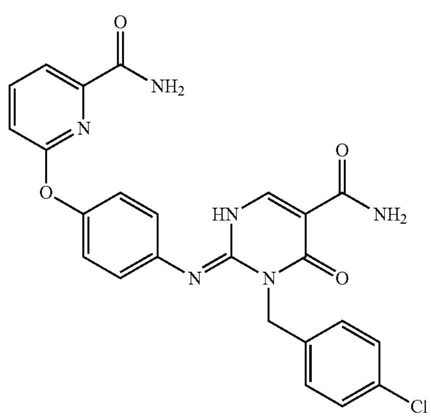 [SMILES: NC(=O)c1cccc(Oc2ccc(/N=c3\[nH]cc(C(N)=O)c(=O)n3Cc3ccc(Cl)cc3)cc2)n1] | I-178 | 491 | 1.70 | 3 |

TABLE 70

| Structure | Compound No | RT (min) | [M + H] | Method |
|---|---|---|---|---|
| 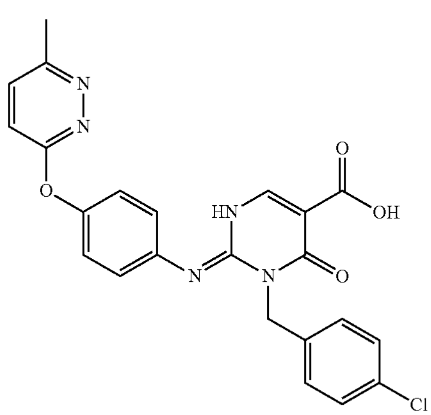 [SMILES: Cc1ccc(Oc2ccc(/N=c3\[nH]cc(C(=O)O)c(=O)n3Cc3ccc(Cl)cc3)cc2)nn1] | I-179 | 464 | 1.96 | 3 |

TABLE 70-continued

| Structure | Compound No | RT (min) | [M + H] | Method |
|---|---|---|---|---|
| (structure) | I-180 | 463 | 1.71 | 3 |
| (structure) | I-181 | 493 | 1.38 | 3 |
| (structure) | I-182 | 621 | 2.35 | 3 |
| (structure) | I-183 | 508 | 1.75 | 3 |

TABLE 71

| Structure | Compound No | RT (min) | [M + H] | Method |
|---|---|---|---|---|
| 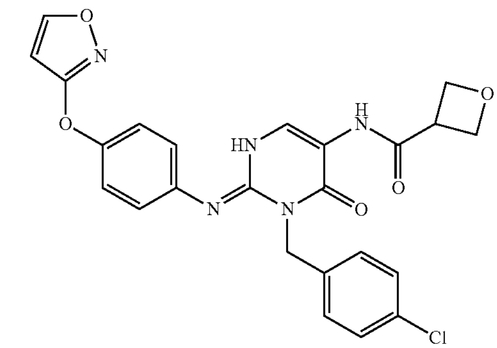 [SMILES: O=C(Nc1c[nH]/c(=N\c2ccc(Oc3ccon3)cc2)n(Cc2ccc(Cl)cc2)c1=O)C1COC1] | I-184 | 494 | 1.79 | 3 |
| 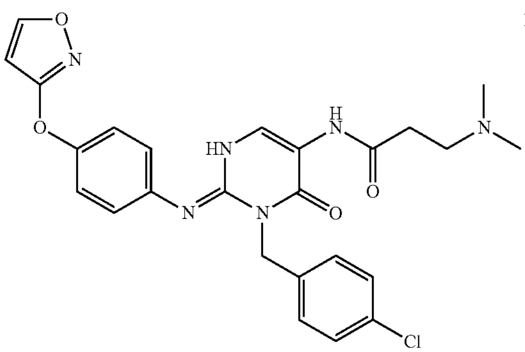 [SMILES: CN(C)CCC(=O)Nc1c[nH]/c(=N\c2ccc(Oc3ccon3)cc2)n(Cc2ccc(Cl)cc2)c1=O] | I-185 | 509 | 1.29 | 3 |
| 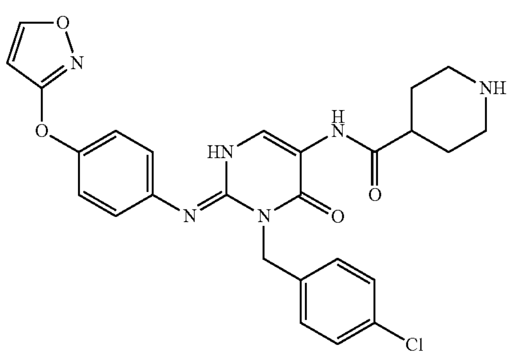 [SMILES: O=C(Nc1c[nH]/c(=N\c2ccc(Oc3ccon3)cc2)n(Cc2ccc(Cl)cc2)c1=O)C1CCNCC1] | I-186 | 521 | 1.28 | 3 |
| 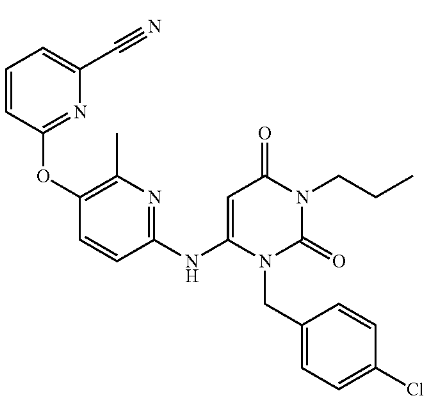 [SMILES: CCCn1c(=O)cc(Nc2ccc(Oc3cccc(C#N)n3)c(C)n2)n(Cc2ccc(Cl)cc2)c1=O] | I-187 | 503 | 2.22 | 3 |

TABLE 71-continued

| Structure | Compound No | RT (min) | [M + H] | Method |
|---|---|---|---|---|
| 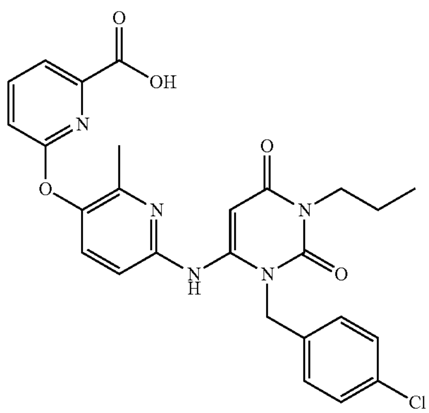 [SMILES: CCCn1c(=O)cc(Nc2ccc(Oc3cccc(C(=O)O)n3)c(C)n2)n(Cc2ccc(Cl)cc2)c1=O] | I-188 | 522 | 2.01 | 3 |

TABLE 72

| Structure | Compound No | RT (min) | [M + H] | Method |
|---|---|---|---|---|
| 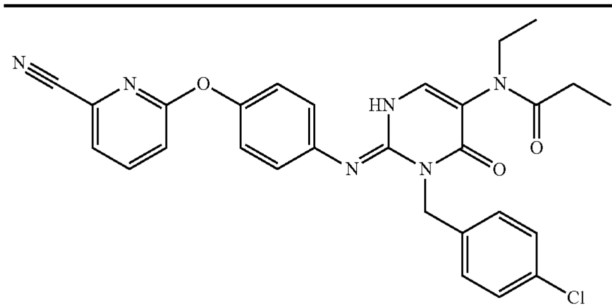 | I-189 | 529 | 2.13 | 3 |
| 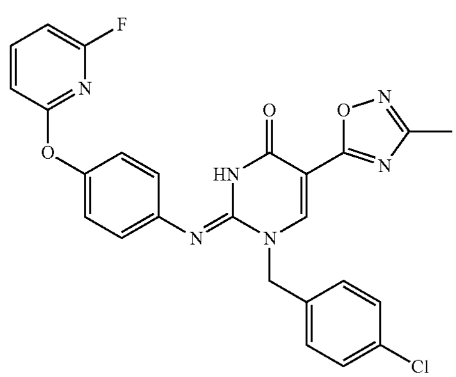 [SMILES: Cc1noc(-c2cn(Cc3ccc(Cl)cc3)/c(=N/c3ccc(Oc4cccc(F)n4)cc3)[nH]c2=O)n1] | I-190 | 505 | 2.22 | 3 |
| 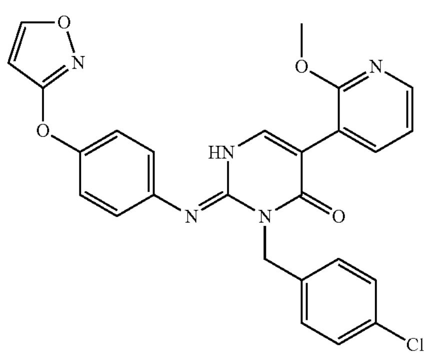 [SMILES: COc1ncccc1-c1c[nH]/c(=N\c2ccc(Oc3ccon3)cc2)n(Cc2ccc(Cl)cc2)c1=O] | I-191 | 501 | 2.62 | 2 |

TABLE 72-continued

| Structure | Compound No | RT (min) | [M + H] | Method |
|---|---|---|---|---|
| 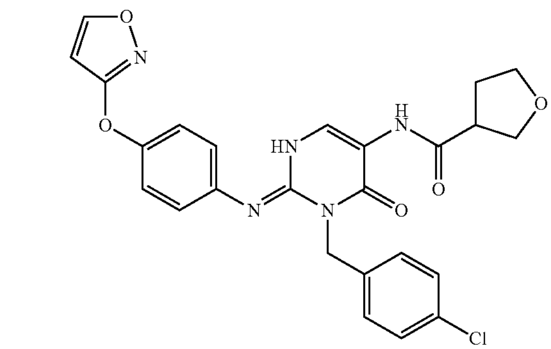 [SMILES: O=C(Nc1c[nH]/c(=N\c2ccc(Oc3ccon3)cc2)n(Cc2ccc(Cl)cc2)c1=O)C1CCOC1] | I-192 | 508 | 1.86 | 3 |
| 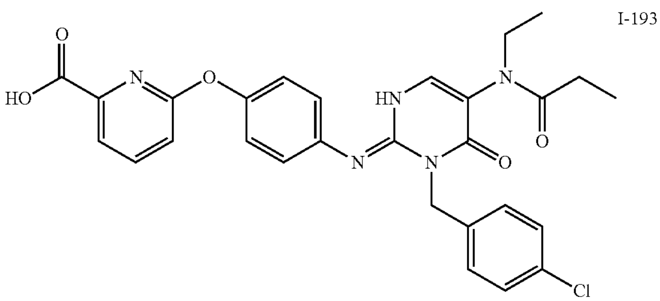 | I-193 | 548 | 1.92 | 3 |
| 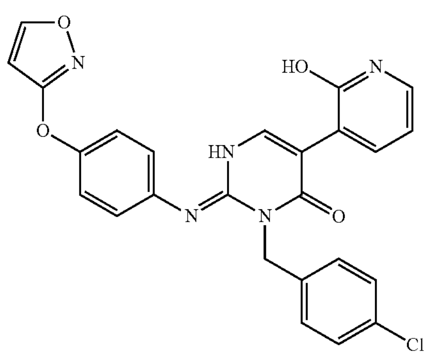 [SMILES: O=c1c(-c2cccnc2O)c[nH]/c(=N\c2ccc(Oc3ccon3)cc2)n1Cc1ccc(Cl)cc1] | I-194 | 487 | 1.84 | 3 |

TABLE 73

| Structure | Compound No | RT (min) | [M + H] | Method |
|---|---|---|---|---|
| 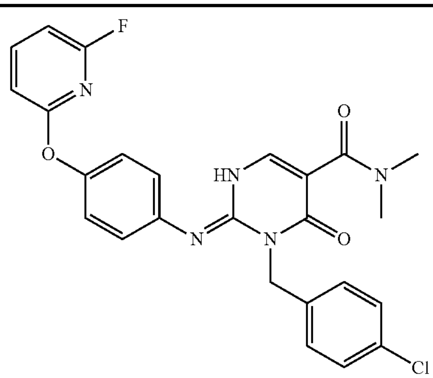 | I-195 | 493 | 2.00 | 3 |

TABLE 73-continued

| Structure | Compound No | RT (min) | [M + H] | Method |
|---|---|---|---|---|
| 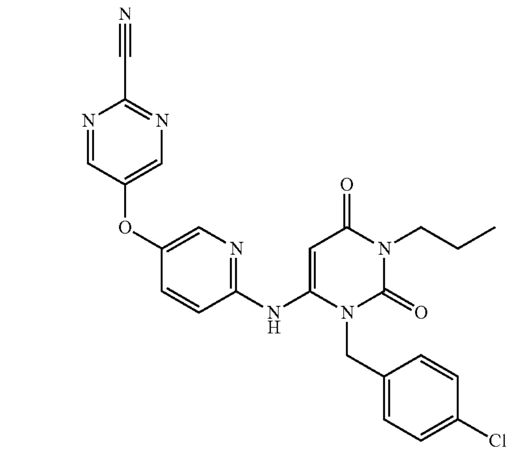 [SMILES: CCCn1c(=O)cc(Nc2ccc(Oc3cnc(C#N)nc3)cn2)n(Cc2ccc(Cl)cc2)c1=O] | I-196 | 490 | 2.09 | 3 |
| 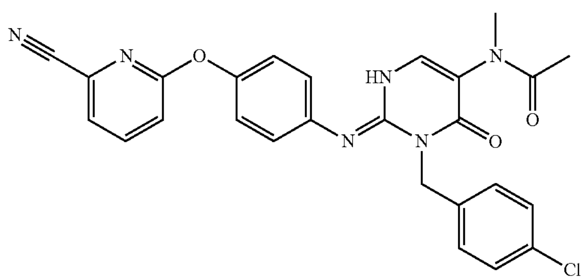 [SMILES: CC(=O)N(C)c1c[nH]/c(=N\c2ccc(Oc3cccc(C#N)n3)cc2)n(Cc2ccc(Cl)cc2)c1=O] | I-197 | 501 | 1.95 | 3 |
| 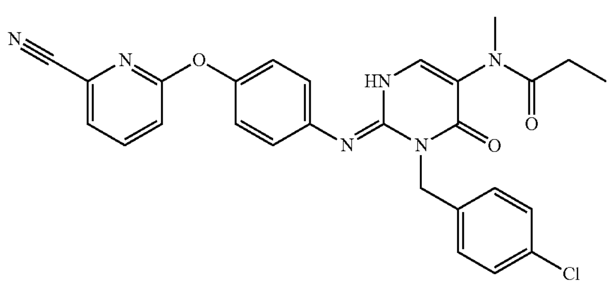 [SMILES: CCC(=O)N(C)c1c[nH]/c(=N\c2ccc(Oc3cccc(C#N)n3)cc2)n(Cc2ccc(Cl)cc2)c1=O] | I-198 | 515 | 2.05 | 3 |
| 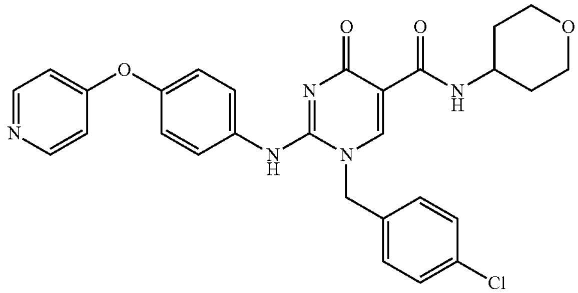 [SMILES: O=C(NC1CCOCC1)c1cn(Cc2ccc(Cl)cc2)c(Nc2ccc(Oc3ccncc3)cc2)nc1=O] | I-199 | 532 | 1.27 | 3 |

TABLE 73-continued
| Structure | Compound No | RT (min) | [M + H] | Method |
|---|---|---|---|---|
| 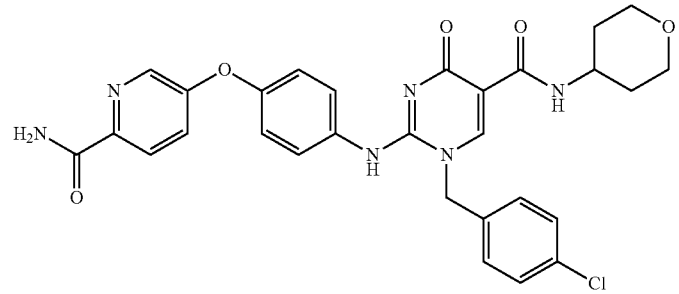 | I-200 | 575 | 1.76 | 3 |
TABLE 74
| Structure | Compound No | RT (min) | [M + H] | Method |
|---|---|---|---|---|
| 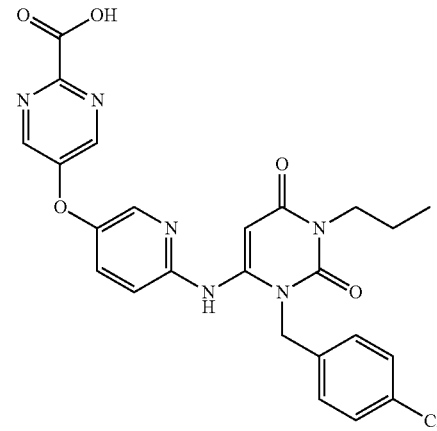 [SMILES: CCCn1c(=O)cc(Nc2ccc(Oc3cnc(C(=O)O)nc3)cn2)n(Cc2ccc(Cl)cc2)c1=O] | I-201 | 509 | 1.70 | 3 |
| 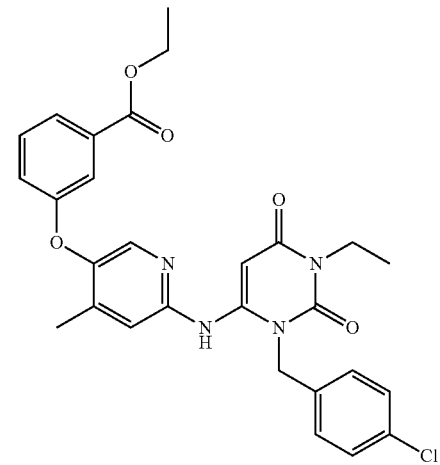 [SMILES: CCOC(=O)c1cccc(Oc2cnc(Nc3cc(=O)n(CC)c(=O)n3Cc3ccc(Cl)cc3)cc2C)c1] | I-202 | 535 | 2.44 | 3 |

TABLE 74-continued
| Structure | Compound No | RT (min) | [M + H] | Method |
|---|---|---|---|---|
| 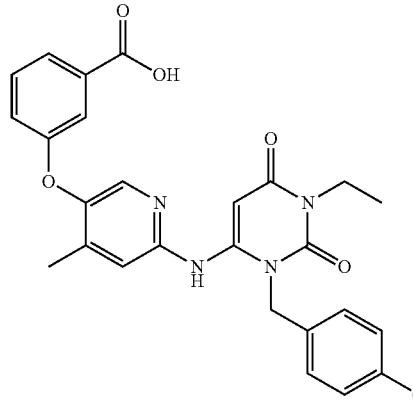 | I-203 | 507 | 1.98 | 3 |
| 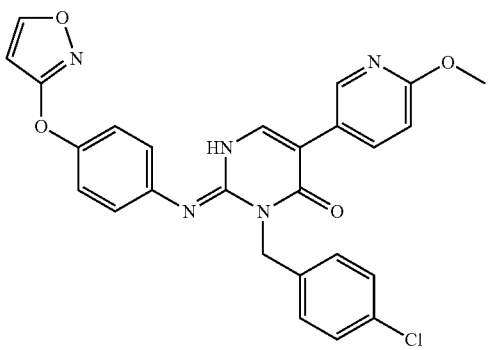 [SMILES: COc1ccc(-c2c[nH]/c(=N\c3ccc(Oc4ccon4)cc3)n(Cc3ccc(Cl)cc3)c2=O)cn1] | I-204 | 501 | 2.26 | 3 |
| 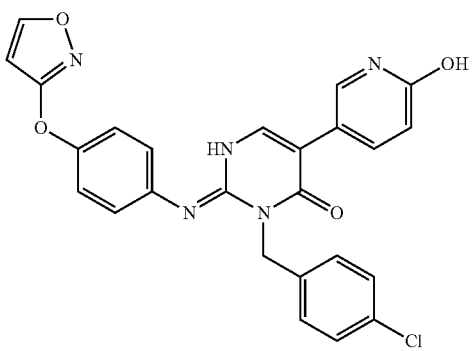 [SMILES: O=c1c(-c2ccc(O)nc2)c[nH]/c(=N\c2ccc(Oc3ccon3)cc2)n1Cc1ccc(Cl)cc1] | I-205 | 487 | 1.74 | 3 |

TABLE 75

| Structure | Compound No | RT (min) | [M + H] | Method |
|---|---|---|---|---|
| 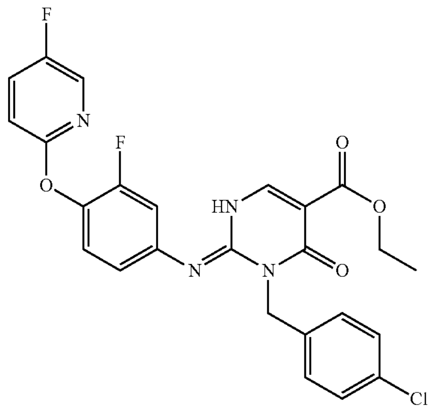 [SMILES: CCOC(=O)c1c[nH]/c(=N\c2ccc(Oc3ccc(F)cn3)c(F)c2)n(Cc2ccc(Cl)cc2)c1=O] | I-206 | 513 | 2.36 | 3 |
| 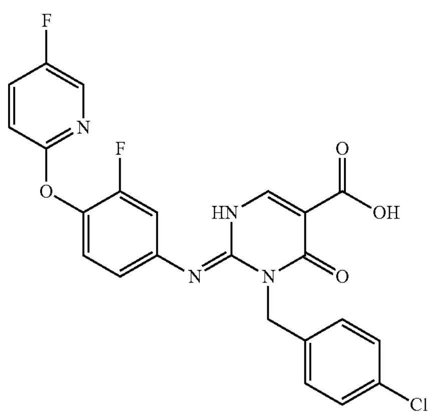 [SMILES: O=C(O)c1c[nH]/c(=N\c2ccc(Oc3ccc(F)cn3)c(F)c2)n(Cc2ccc(Cl)cc2)c1=O] | I-207 | 485 | 2.30 | 3 |
| 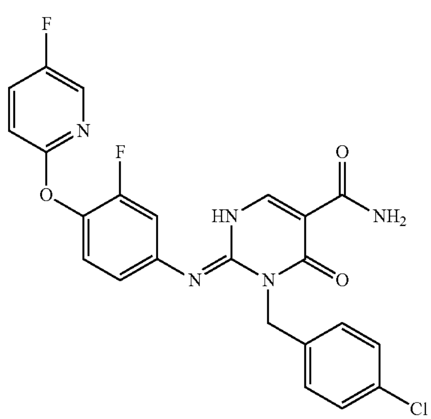 [SMILES: NC(=O)c1c[nH]/c(=N\c2ccc(Oc3ccc(F)cn3)c(F)c2)n(Cc2ccc(Cl)cc2)c1=O] | I-208 | 484 | 2.14 | 3 |

TABLE 75-continued

| Structure | Compound No | RT (min) | [M + H] | Method |
|---|---|---|---|---|
| 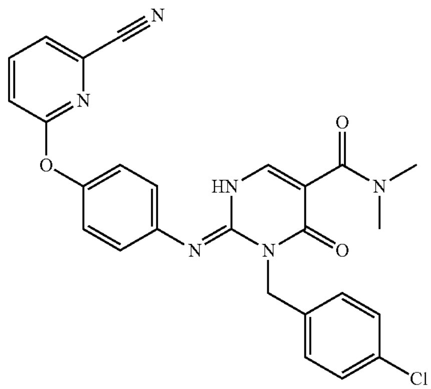 [SMILES: CN(C)C(=O)c1c[nH]/c(=N\c2ccc(Oc3cccc(C#N)n3)cc2)n(Cc2ccc(Cl)cc2)c1=O] | I-209 | 501 | 1.97 | 3 |
| 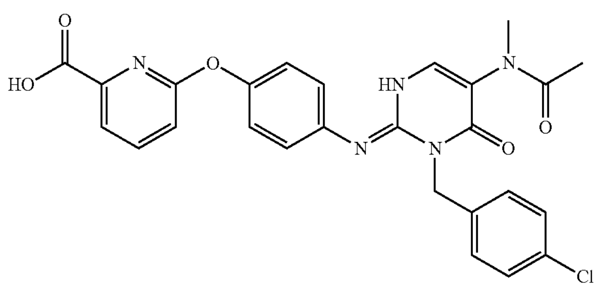 [SMILES: CC(=O)N(C)c1c[nH]/c(=N\c2ccc(Oc3cccc(C(=O)O)n3)cc2)n(Cc2ccc(Cl)cc2)c1=O] | I-210 | 520 | 1.72 | 3 |

TABLE 76

| Structure | Compound No | RT (min) | [M + H] | Method |
|---|---|---|---|---|
| 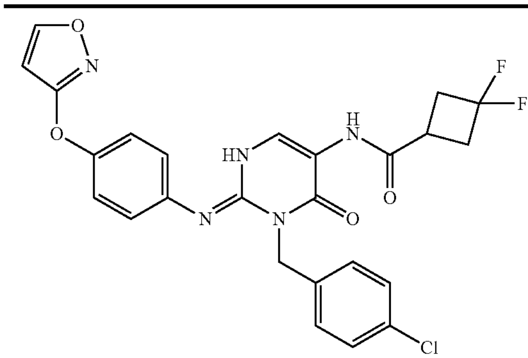 | I-211 | 528 | 2.16 | 3 |
| 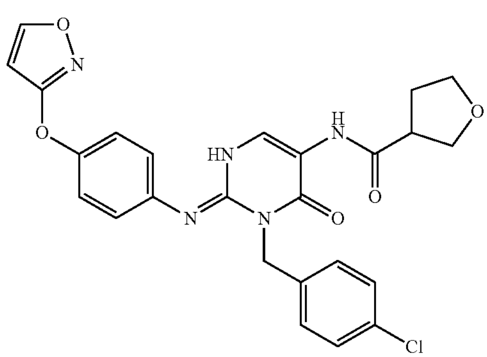 [SMILES: O=C(Nc1c[nH]/c(=N\c2ccc(Oc3ccon3)cc2)n(Cc2ccc(Cl)cc2)c1=O)C1CCOC1] | I-212 | 508 | 1.88 | 3 |

TABLE 76-continued

| Structure | Compound No | RT (min) | [M + H] | Method |
|---|---|---|---|---|
| 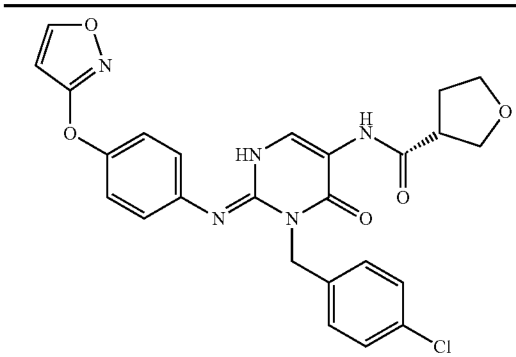 | I-213 | 508 | 2.09 | 3 |
| 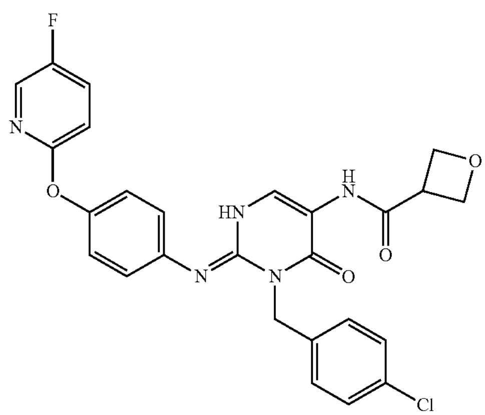 [SMILES: O=C(Nc1c[nH]/c(=N\c2ccc(Oc3ccc(F)cn3)cc2)n(Cc2ccc(Cl)cc2)c1=O)C1COC1] | I-214 | 522 | 1.96 | 3 |
| 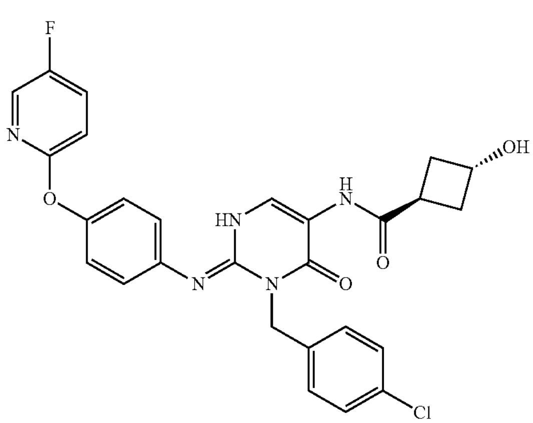 [SMILES: O=c1c(NC(=O)[C@H]2C[C@H](O)C2)c[nH]/c(=N\c2ccc(Oc3ccc(F)cn3)cc2)n1Cc1ccc(Cl)cc1] | I-215 | 536 | 1.90 | 3 |

TABLE 77

| Structure | Compound No | RT (min) | [M + H] | Method |
|---|---|---|---|---|
| (structure) | I-216 | 557 | 2.06 | 3 |
| (structure) | I-217 | 575 | 1.79 | 3 |
| (structure) | I-218 | 510 | 2.10 | 3 |
| (structure) | I-219 | 510 | 2.06 | 3 |

TABLE 77-continued
| Structure | Compound No | RT (min) | [M + H] | Method |
|---|---|---|---|---|
| 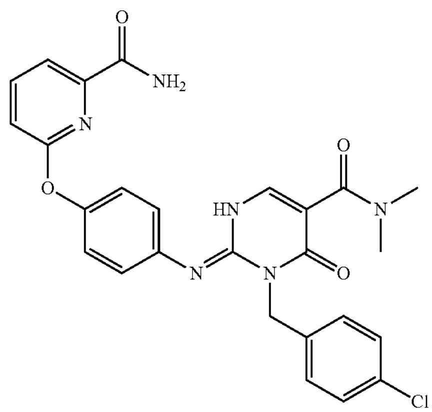 [SMILES: CN(C)C(=O)c1c[nH]/c(=N\c2ccc(Oc3cccc(C(N)=O)n3)cc2)n(Cc2ccc(Cl)cc2)c1=O] | I-220 | 519 | 1.67 | 3 |
| 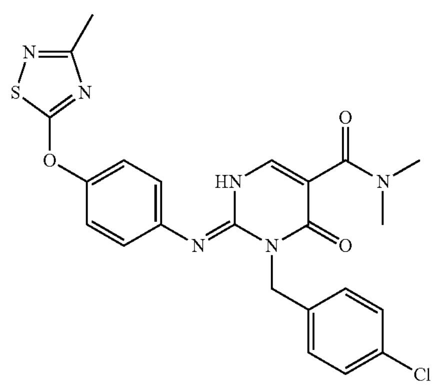 [SMILES: Cc1nsc(Oc2ccc(/N=c3\[nH]cc(C(=O)N(C)C)c(=O)n3Cc3ccc(Cl)cc3)cc2)n1] | I-221 | 497 | 1.88 | 3 |
TABLE 78
| Structure | Compound No | RT (min) | [M + H] | Method |
|---|---|---|---|---|
| 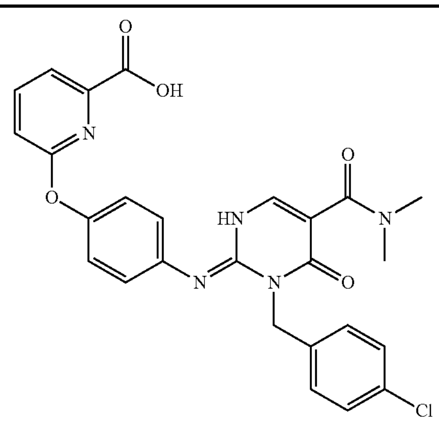 | I-222 | 520 | 1.72 | 3 |
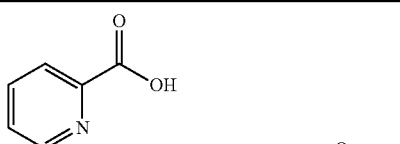

TABLE 78-continued

| Structure | Compound No | RT (min) | [M + H] | Method |
|---|---|---|---|---|
| 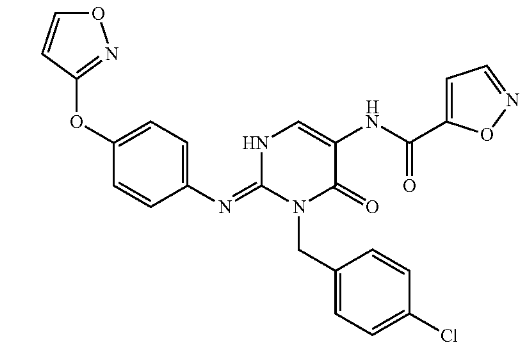 [SMILES: O=C(Nc1c[nH]/c(=N\c2ccc(Oc3ccon3)cc2)n(Cc2ccc(Cl)cc2)c1=O)c1ccno1] | I-223 | 505 | 2.03 | 3 |
| 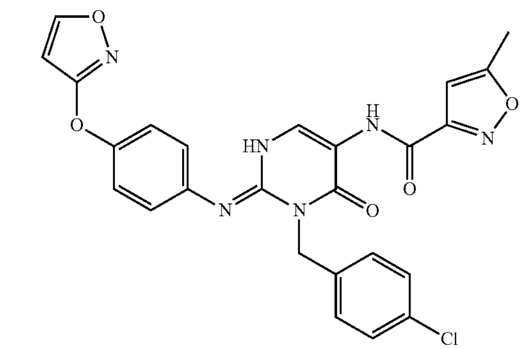 [SMILES: Cc1cc(C(=O)Nc2c[nH]/c(=N\c3ccc(Oc4ccon4)cc3)n(Cc3ccc(Cl)cc3)c2=O)no1] | I-224 | 519 | 2.29 | 3 |
| 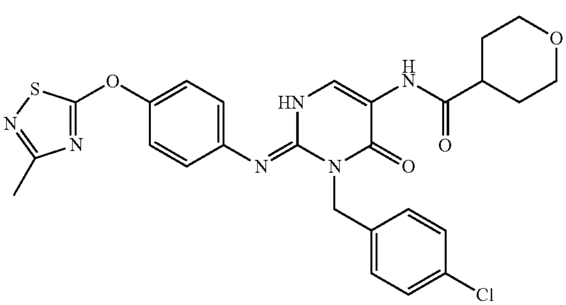 [SMILES: Cc1nsc(Oc2ccc(/N=c3\[nH]cc(NC(=O)C4CCOCC4)c(=O)n3Cc3ccc(Cl)cc3)cc2)n1] | I-225 | 553 | 2.04 | 3 |
| 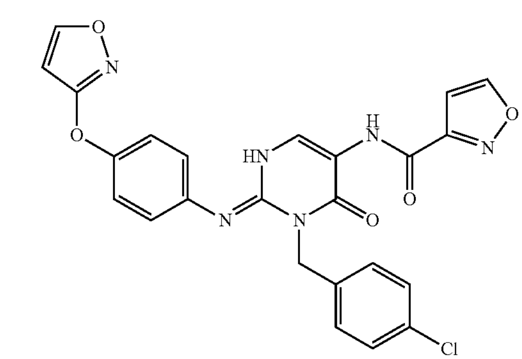 [SMILES: O=C(Nc1c[nH]/c(=N\c2ccc(Oc3ccon3)cc2)n(Cc2ccc(Cl)cc2)c1=O)c1ccon1] | I-226 | 505 | 2.16 | 3 |

TABLE 78-continued

| Structure | Compound No | RT (min) | [M + H] | Method |
|---|---|---|---|---|
| 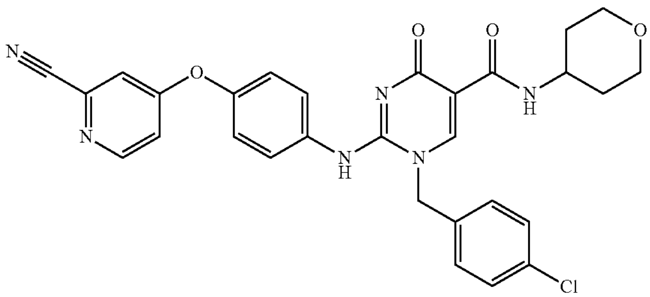 [SMILES: N#Cc1cc(Oc2ccc(Nc3nc(=O)c(C(=O)NC4CCOCC4)cn3Cc3ccc(Cl)cc3)cc2)ccn1] | I-227 | 557 | 2.05 | 3 |

TABLE 79

| Structure | Compound No | RT (min) | [M + H] | Method |
|---|---|---|---|---|
| 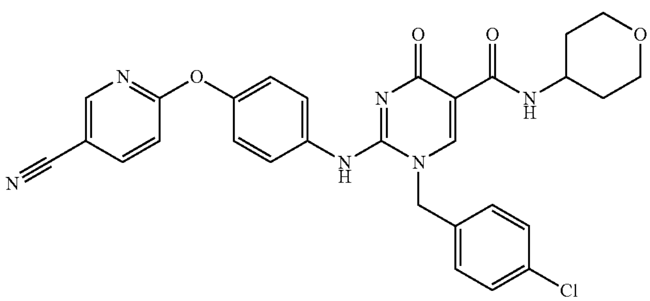 [SMILES: N#Cc1ccc(Oc2ccc(Nc3nc(=O)c(C(=O)NC4CCOCC4)cn3Cc3ccc(Cl)cc3)cc2)nc1] | I-228 | 557 | 2.04 | 3 |
| 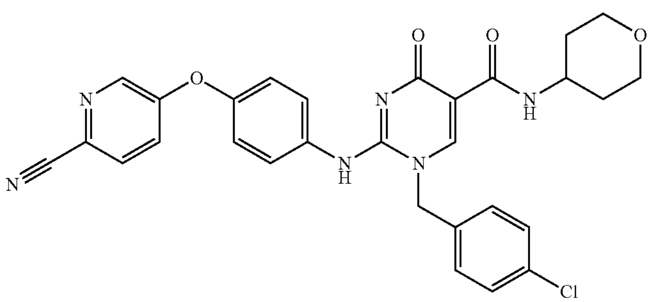 [SMILES: N#Cc1ccc(Oc2ccc(Nc3nc(=O)c(C(=O)NC4CCOCC4)cn3Cc3ccc(Cl)cc3)cc2)cn1] | I-229 | 557 | 2.06 | 3 |
| 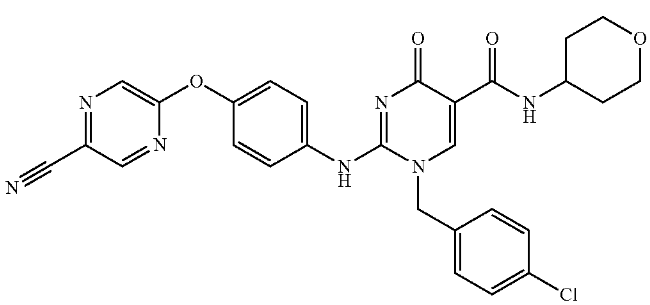 [SMILES: N#Cc1cnc(Oc2ccc(Nc3nc(=O)c(C(=O)NC4CCOCC4)cn3Cc3ccc(Cl)cc3)cc2)cn1] | I-230 | 558 | 2.02 | 3 |

TABLE 79-continued

| Structure | Compound No | RT (min) | [M + H] | Method |
|---|---|---|---|---|
| 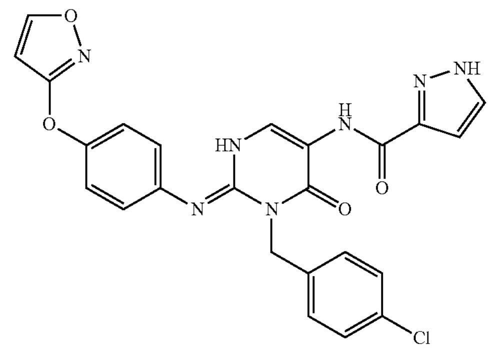 [SMILES: O=C(Nc1c[nH]/c(=N\c2ccc(Oc3ccon3)cc2)n(Cc2ccc(Cl)cc2)c1=O)c1cc[nH]n1] | I-231 | 461 | 1.93 | 3 |
| 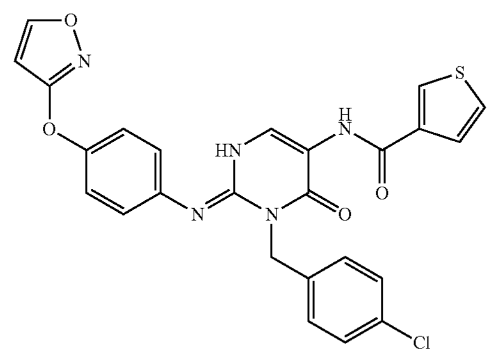 [SMILES: O=C(Nc1c[nH]/c(=N\c2ccc(Oc3ccon3)cc2)n(Cc2ccc(Cl)cc2)c1=O)c1ccsc1] | I-232 | 477 | 2.45 | 3 |
| 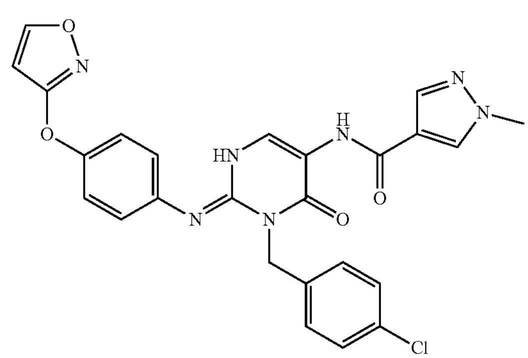 [SMILES: Cn1cc(C(=O)Nc2c[nH]/c(=N\c3ccc(Oc4ccon4)cc3)n(Cc3ccc(Cl)cc3)c2=O)cn1] | I-233 | 475 | 1.97 | 3 |

TABLE 80

| Structure | Compound No | RT (min) | [M + H] | Method |
|---|---|---|---|---|
| 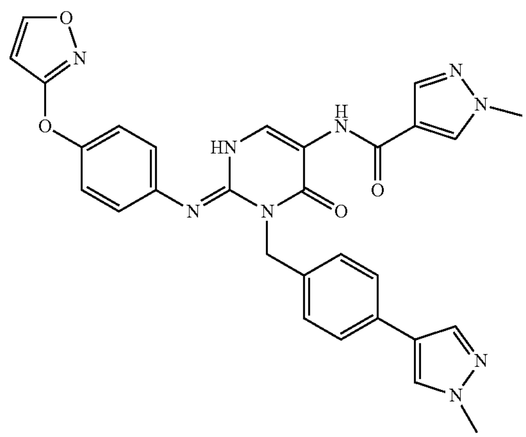 [SMILES: Cn1cc(C(=O)Nc2c[nH]/c(=N\c3ccc(Oc4ccon4)cc3)n(Cc3ccc(-c4cnn(C)c4)cc3)c2=O)cn1] | I-234 | 521 | 1.65 | 3 |
| 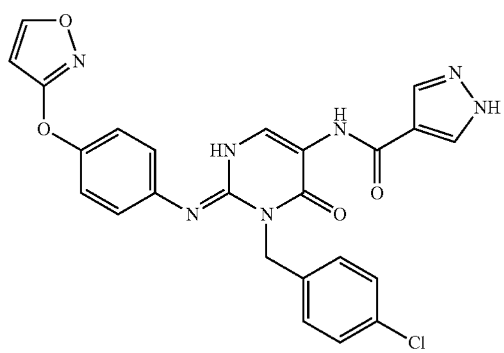 [SMILES: O=C(Nc1c[nH]/c(=N\c2ccc(Oc3ccon3)cc2)n(Cc2ccc(Cl)cc2)c1=O)c1cn[nH]c1] | I-235 | 461 | 1.82 | 3 |
| 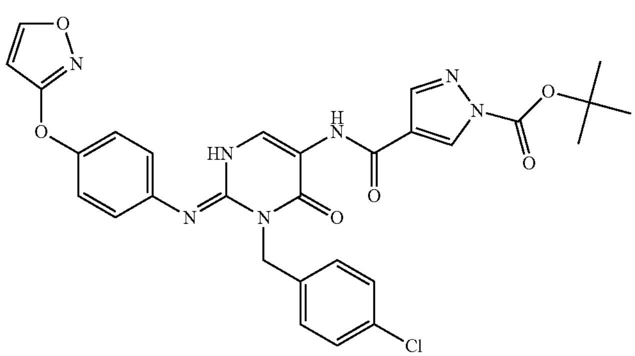 [SMILES: CC(C)(C)OC(=O)n1cc(C(=O)Nc2c[nH]/c(=N\c3ccc(Oc4ccon4)cc3)n(Cc3ccc(Cl)cc3)c2=O)cn1] | I-236 | 561 | 2.43 | 3 |
| 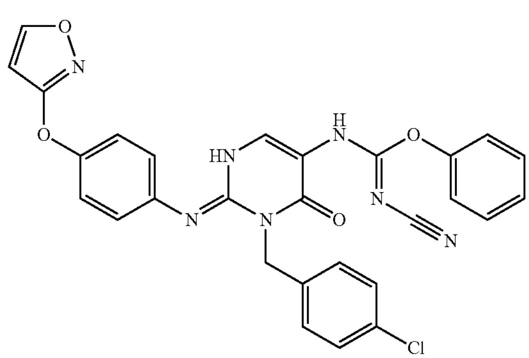 [SMILES: N#C/N=C(/Nc1c[nH]/c(=N\c2ccc(Oc3ccon3)cc2)n(Cc2ccc(Cl)cc2)c1=O)Oc1ccccc1] | I-237 | 554 | 2.14 | 3 |

TABLE 80-continued

| Structure | Compound No | RT (min) | [M + H] | Method |
|---|---|---|---|---|
| (structure) | I-238 | 538 | 1.40 | 3 |

TABLE 81

| Structure | Compound No | RT (min) | [M + H] | Method |
|---|---|---|---|---|
| (structure) | I-239 | 575 | 1.68 | 3 |
| (structure) | I-240 | 575 | 1.78 | 3 |
| (structure) | I-241 | 534 | 1.83 | 3 |

TABLE 81-continued

| Structure | Compound No | RT (min) | [M + H] | Method |
|---|---|---|---|---|
| 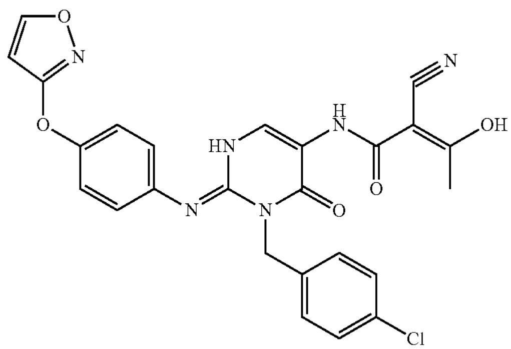 [SMILES: C/C(O)=C(/C#N)C(=O)Nc1c[nH]/c(=N\c2ccc(Oc3ccon3)cc2)n(Cc2ccc(Cl)cc2)c1=O] | I-242 | 519 | 2.16 | 3 |
| 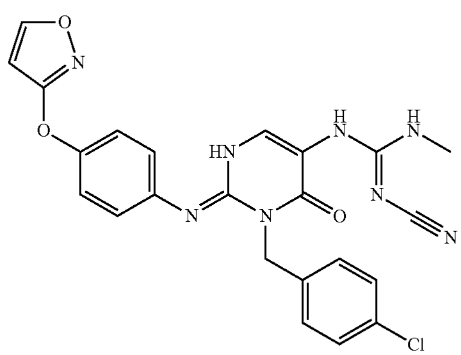 [SMILES: CN/C(=N\C#N)Nc1c[nH]/c(=N\c2ccc(Oc3ccon3)cc2)n(Cc2ccc(Cl)cc2)c1=O] | I-243 | 491 | 1.72 | 3 |
| 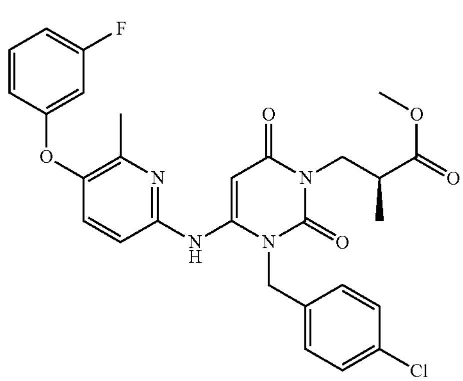 [SMILES: COC(=O)[C@@H](C)Cn1c(=O)cc(Nc2ccc(Oc3cccc(F)c3)c(C)n2)n(Cc2ccc(Cl)cc2)c1=O] | I-244 | 553 | 2.44 | 3 |

TABLE 82

| Structure | Compound No | RT (min) | [M + H] | Method |
|---|---|---|---|---|
| 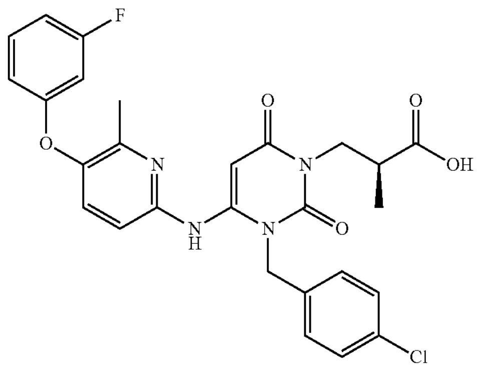 [SMILES: Cc1nc(Nc2cc(=O)n(C[C@H](C)C(=O)O)c(=O)n2Cc2ccc(Cl)cc2)ccc1Oc1cccc(F)c1] | I-245 | 539 | 2.20 | 3 |
| 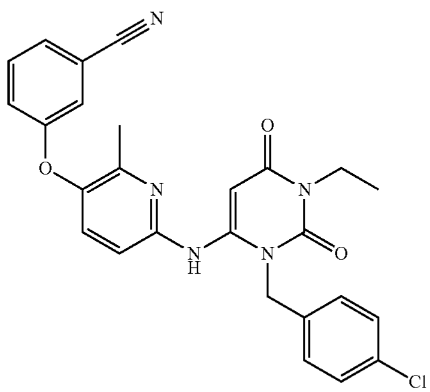 [SMILES: CCn1c(=O)cc(Nc2ccc(Oc3cccc(C#N)c3)c(C)n2)n(Cc2ccc(Cl)cc2)c1=O] | I-246 | 488 | 2.23 | 3 |
| 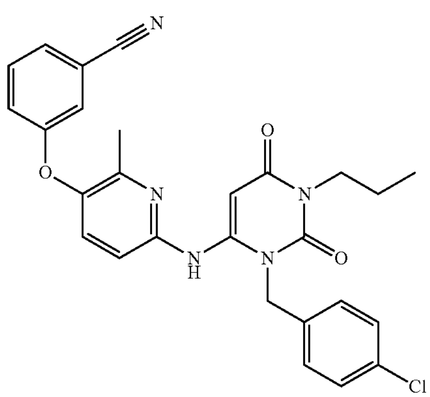 [SMILES: CCCn1c(=O)cc(Nc2ccc(Oc3cccc(C#N)c3)c(C)n2)n(Cc2ccc(Cl)cc2)c1=O] | I-247 | 502 | 2.36 | 3 |
| 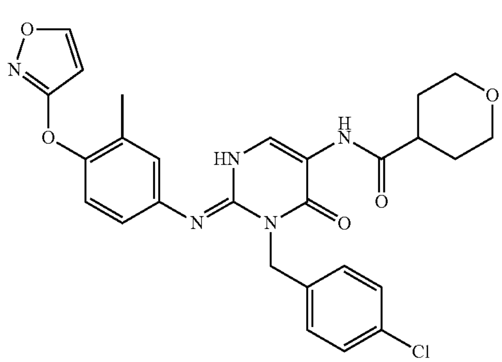 [SMILES: Cc1cc(/N=c2\[nH]cc(NC(=O)C3CCOCC3)c(=O)n2Cc2ccc(Cl)cc2)ccc1Oc1ccon1] | I-248 | 536 | 2.00 | 3 |

TABLE 82-continued
| Structure | Compound No | RT (min) | [M + H] | Method |
|---|---|---|---|---|
| 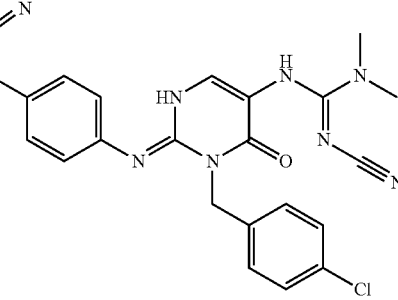 | I-249 | 554 | 2.13 | 3 |
TABLE 83
| Structure | Compound No | RT (min) | [M + H] | Method |
|---|---|---|---|---|
| 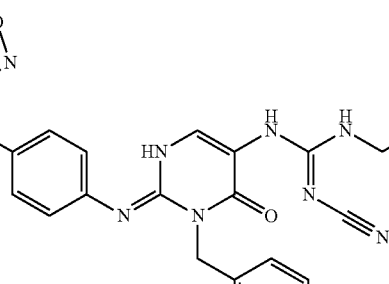 | I-250 | 505 | 1.68 | 3 |
| 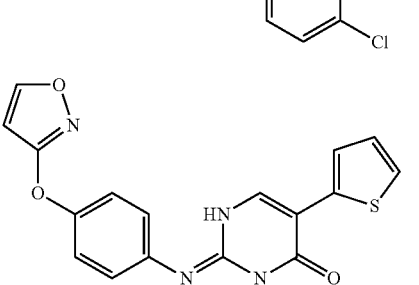 | I-251 | 505 | 1.81 | 3 |
| 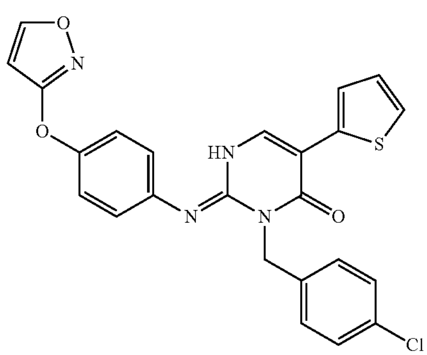 [SMILES: O=c1c(-c2cccs2)c[nH]/c(=N\c2ccc(Oc3ccon3)cc2)n1Cc1ccc(Cl)cc1] | I-252 | 477 | 2.43 | 3 |

TABLE 83-continued

| Structure | Compound No | RT (min) | [M + H] | Method |
|---|---|---|---|---|
| 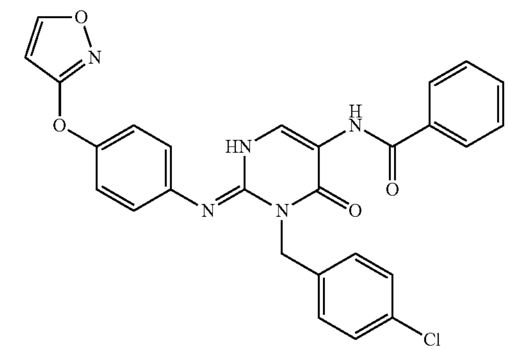 [SMILES: O=C(Nc1c[nH]/c(=N\c2ccc(Oc3ccon3)cc2)n(Cc2ccc(Cl)cc2)c1=O)c1ccccc1] | I-253 | 514 | 2.28 | 3 |
| 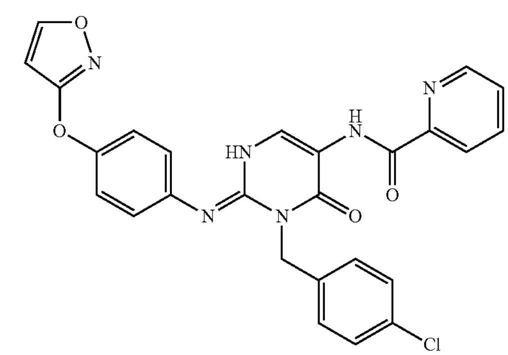 [SMILES: O=C(Nc1c[nH]/c(=N\c2ccc(Oc3ccon3)cc2)n(Cc2ccc(Cl)cc2)c1=O)c1ccccn1] | I-254 | 515 | 2.32 | 3 |
| 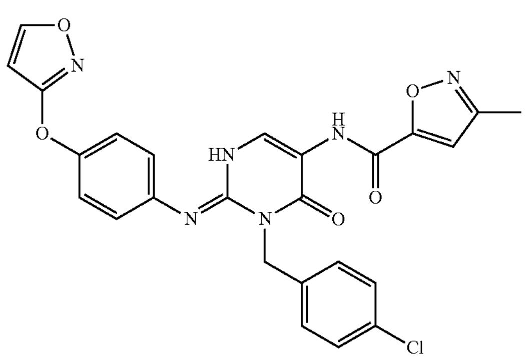 [SMILES: Cc1cc(C(=O)Nc2c[nH]/c(=N\c3ccc(Oc4ccon4)cc3)n(Cc3ccc(Cl)cc3)c2=O)on1] | I-255 | 519 | 2.14 | 3 |

TABLE 84

| Structure | Compound No | RT (min) | [M + H] | Method |
|---|---|---|---|---|
| 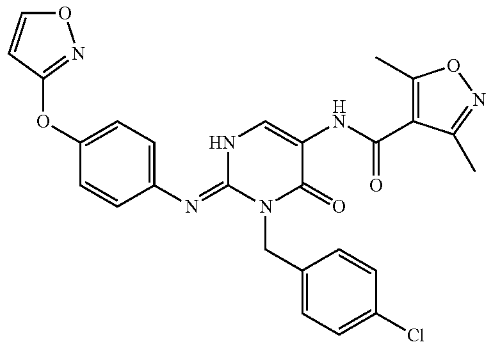 [SMILES: Cc1noc(C)c1C(=O)Nc1c[nH]/c(=N\c2ccc(Oc3ccon3)cc2)n(Cc2ccc(Cl)cc2)c1=O] | I-256 | 533 | 2.16 | 3 |
| 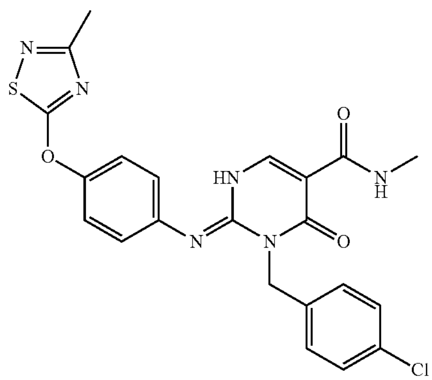 | I-257 | 483 | 2.07 | 3 |
| 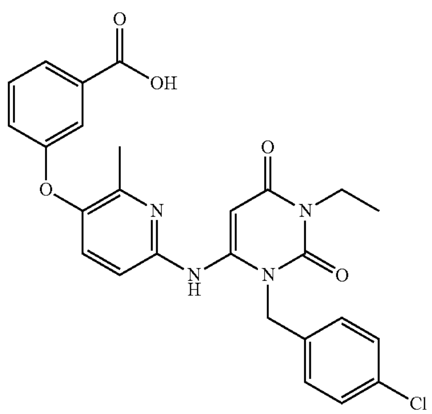 [SMILES: CCn1c(=O)cc(Nc2ccc(Oc3cccc(C(=O)O)c3)c(C)n2)n(Cc2ccc(Cl)cc2)c1=O] | I-258 | 507 | 2.00 | 3 |
| 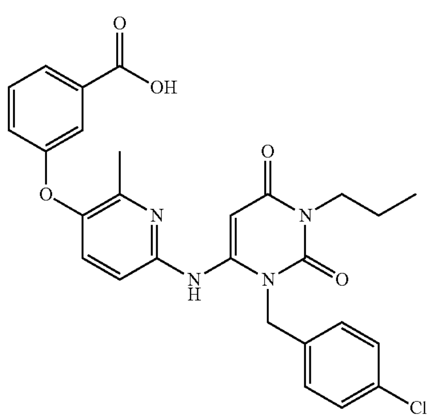 [SMILES: CCCn1c(=O)cc(Nc2ccc(Oc3cccc(C(=O)O)c3)c(C)n2)n(Cc2ccc(Cl)cc2)c1=O] | I-259 | 521 | 2.12 | 3 |

TABLE 84-continued
| Structure | Compound No | RT (min) | [M + H] | Method |
|---|---|---|---|---|
| 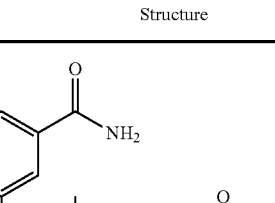 | I-260 | 506 | 1.82 | 3 |
TABLE 85
| Structure | Compound No | RT (min) | [M + H] | Method |
|---|---|---|---|---|
| 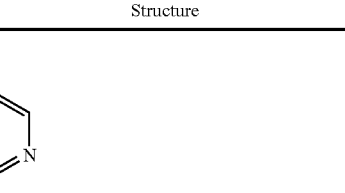 | I-261 | 448 | 2.18 | 3 |
| 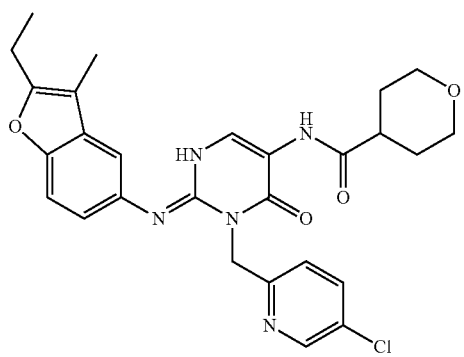 [SMILES: CCc1oc2ccc(/N=c3\[nH]cc(NC(=O)C4CCOCC4)c(=O)n3Cc3ccc(Cl)cn3)cc2c1C] | I-262 | 523 | 2.33 | 3 |

TABLE 85-continued

| Structure | Compound No | RT (min) | [M + H] | Method |
|---|---|---|---|---|
| (structure) | I-263 | 471 | 2.43 | 3 |
| (structure) | I-264 | 519 | 2.07 | 3 |
| (structure) | I-265 | 515 | 1.83 | 3 |

TABLE 86

| Structure | Compound No | RT (min) | [M + H] | Method |
|---|---|---|---|---|
| (structure) | I-266 | 515 | 1.82 | 3 |

TABLE 86-continued

| Structure | Compound No | RT (min) | [M + H] | Method |
|---|---|---|---|---|
| 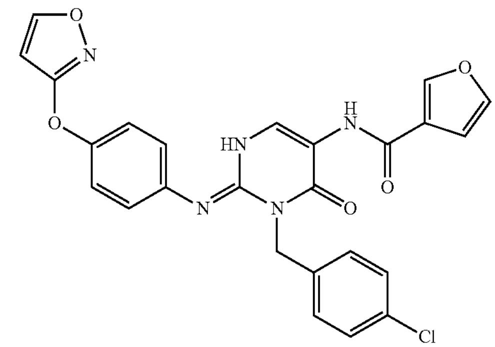 [SMILES: O=C(Nc1c[nH]/c(=N\c2ccc(Oc3ccon3)cc2)n(Cc2ccc(Cl)cc2)c1=O)c1ccoc1] | I-267 | 504 | 2.08 | 3 |
| 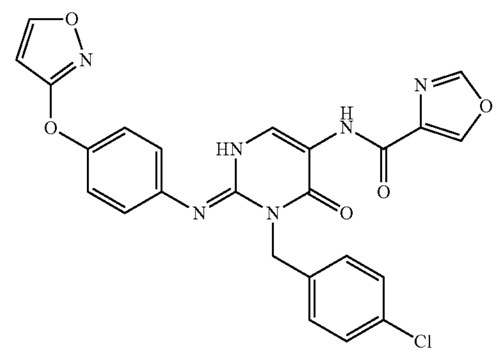 [SMILES: O=C(Nc1c[nH]/c(=N\c2ccc(Oc3ccon3)cc2)n(Cc2ccc(Cl)cc2)c1=O)c1cocn1] | I-268 | 505 | 2.07 | 3 |
| 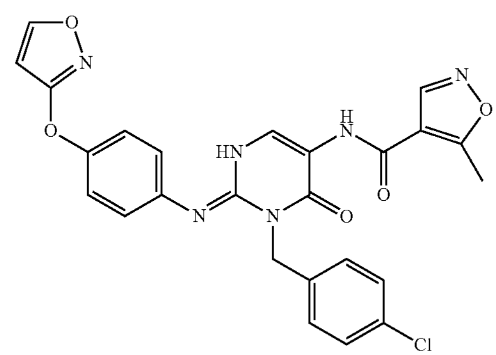 [SMILES: Cc1oncc1C(=O)Nc1c[nH]/c(=N\c2ccc(Oc3ccon3)cc2)n(Cc2ccc(Cl)cc2)c1=O] | I-269 | 519 | 2.07 | 3 |
| 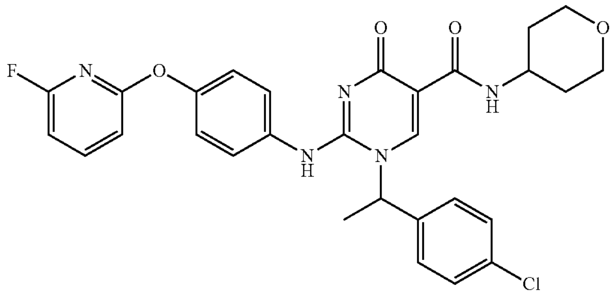 [SMILES: CC(c1ccc(Cl)cc1)n1cc(C(=O)NC2CCOCC2)c(=O)nc1Nc1ccc(Oc2cccc(F)n2)cc1] | I-270 | 530 | 3.02 | 3 |

TABLE 86-continued

| Structure | Compound No | [M + H] | RT (min) | Method |
|---|---|---|---|---|
| *(structure)* | I-271 | 513 | 2.59 | 3 |

TABLE 87

| Structure | Compound No | [M + H] | RT (min) | Method |
|---|---|---|---|---|
| *(structure)* | I-272 | 472 | 1.72 | 2 |
| *(structure)* | I-273 | 472 | 1.71 | 2 |

TABLE 87-continued

| Structure | Compound No | RT (min) | [M + H] | Method |
|---|---|---|---|---|
| 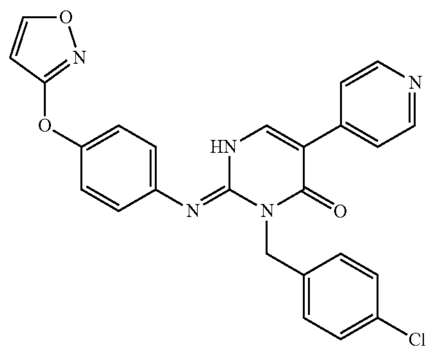 [SMILES: O=c1c(-c2ccncc2)c[nH]/c(=N\c2ccc(Oc3ccon3)cc2)n1Cc1ccc(Cl)cc1] | I-274 | 472 | 1.67 | 2 |
| 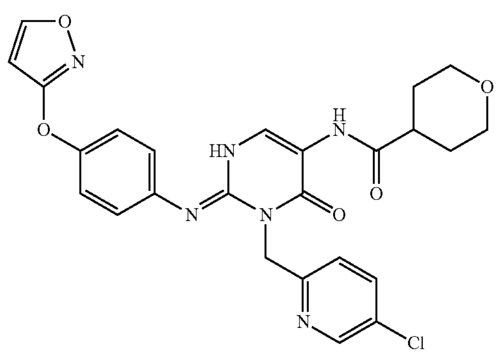 [SMILES: O=C(Nc1c[nH]/c(=N\c2ccc(Oc3ccon3)cc2)n(Cc2ccc(Cl)cn2)c1=O)C1CCOCC1] | I-275 | 523 | 1.93 | 2 |
| 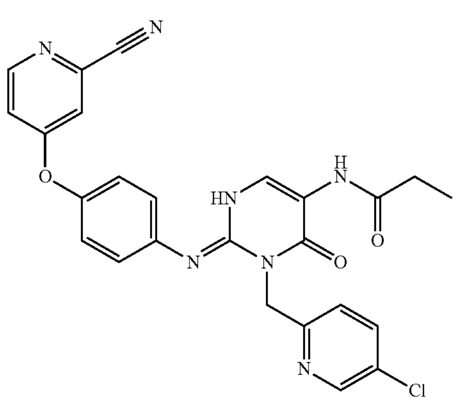 [SMILES: CCC(=O)Nc1c[nH]/c(=N\c2ccc(Oc3ccnc(C#N)c3)cc2)n(Cc2ccc(Cl)cn2)c1=O] | I-276 | 502 | 1.99 | 3 |

TABLE 88

| Structure | Compound No | RT (min) | [M + H] | Method |
|---|---|---|---|---|
| 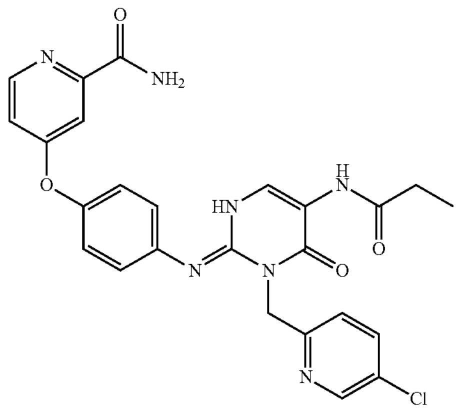 [SMILES: CCC(=O)Nc1c[nH]/c(=N\c2ccc(Oc3ccnc(C(N)=O)c3)cc2)n(Cc2ccc(Cl)cn2)c1=O] | I-277 | 520 | 1.72 | 3 |
| 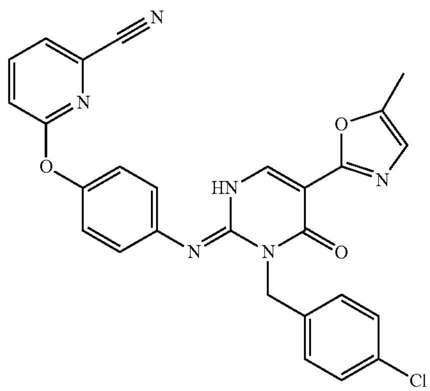 [SMILES: Cc1cnc(-c2c[nH]/c(=N\c3ccc(Oc4cccc(C#N)n4)cc3)n(Cc3ccc(Cl)cc3)c2=O)o1] | I-278 | 511 | 2.07 | 3 |
| 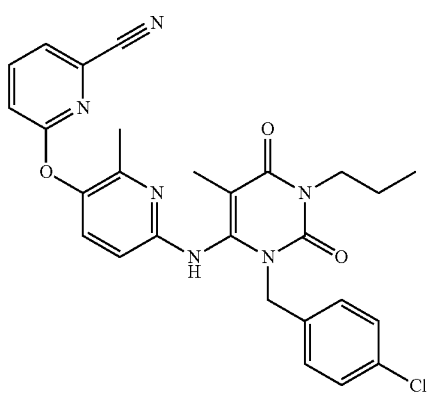 | I-279 | 517 | 2.28 | 3 |
| 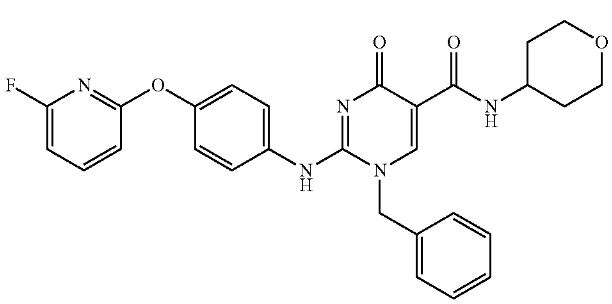 [SMILES: O=C(NC1CCOCC1)c1cn(Cc2ccccc2)c(Nc2ccc(Oc3cccc(F)n3)cc2)nc1=O] | I-280 | 516 | 1.95 | 3 |

TABLE 88-continued
| Structure | Compound No | RT (min) | [M + H] | Method |
|---|---|---|---|---|
| 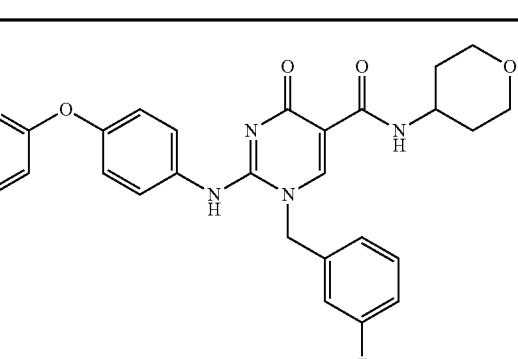 | I-281 | 534 | 2.00 | 3 |
| 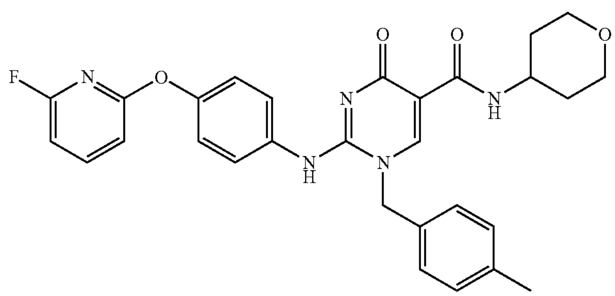 [SMILES: Cc1ccc(Cn2cc(C(=O)NC3CCOCC3)c(=O)nc2Nc2ccc(Oc3cccc(F)n3)cc2)cc1] | I-282 | 530 | 2.07 | 3 |
TABLE 89
| Structure | Compound No | RT (min) | [M + H] | Method |
|---|---|---|---|---|
| 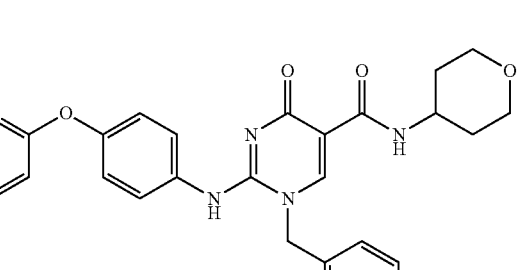 | I-283 | 534 | 2.00 | 3 |
| 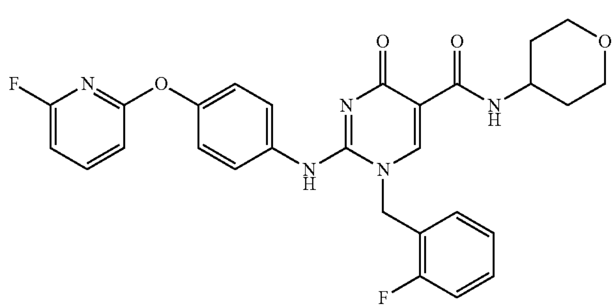 [SMILES: O=C(NC1CCOCC1)c1cn(Cc2ccccc2F)c(Nc2ccc(Oc3cccc(F)n3)cc2)nc1=O] | I-284 | 534 | 2.01 | 3 |

TABLE 89-continued

| Structure | Compound No | RT (min) | [M + H] | Method |
|---|---|---|---|---|
| 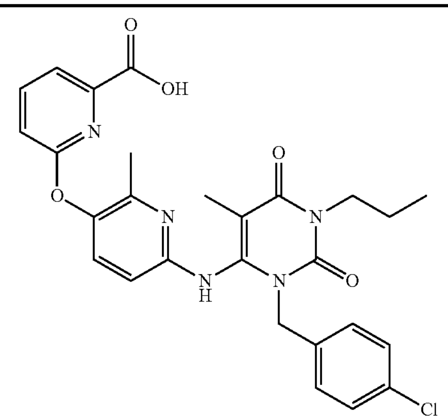 | I-285 | 536 | 2.04 | 3 |
| 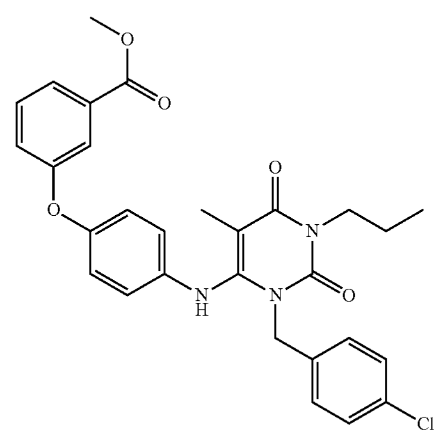 [SMILES: CCCn1c(=O)c(C)c(Nc2ccc(Oc3cccc(C(=O)OC)c3)cc2)n(Cc2ccc(Cl)cc2)c1=O] | I-286 | 534 | 2.62 | 3 |
| 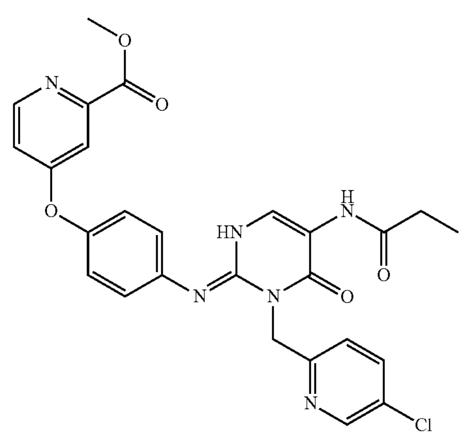 [SMILES: CCC(=O)Nc1c[nH]/c(=N\c2ccc(Oc3ccnc(C(=O)OC)c3)cc2)n(Cc2ccc(Cl)cn2)c1=O] | I-287 | 535 | 1.84 | 3 |

TABLE 90

| Structure | Compound No | RT (min) | [M + H] | Method |
|---|---|---|---|---|
| 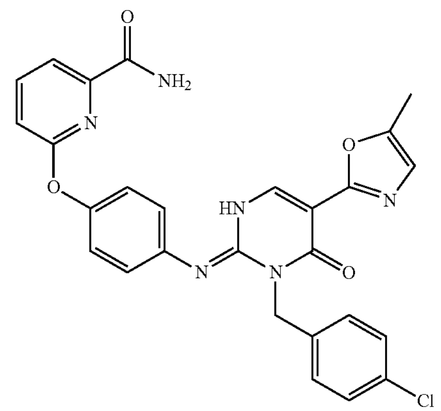 [SMILES: Cc1cnc(-c2c[nH]/c(=N\c3ccc(Oc4cccc(C(N)=O)n4)cc3)n(Cc3ccc(Cl)cc3)c2=O)o1] | I-288 | 5291 | 1.80 | 3 |
| 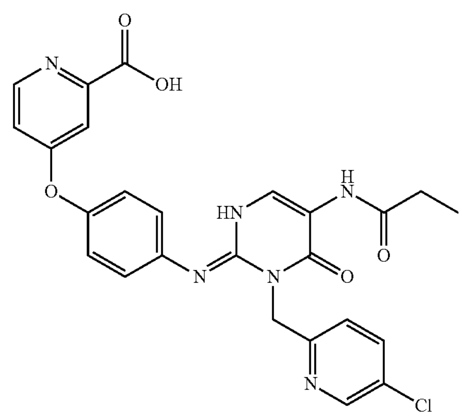 [SMILES: CCC(=O)Nc1c[nH]/c(=N\c2ccc(Oc3ccnc(C(=O)O)c3)cc2)n(Cc2ccc(Cl)cn2)c1=O] | I-289 | 521 | 1.30 | 3 |
| 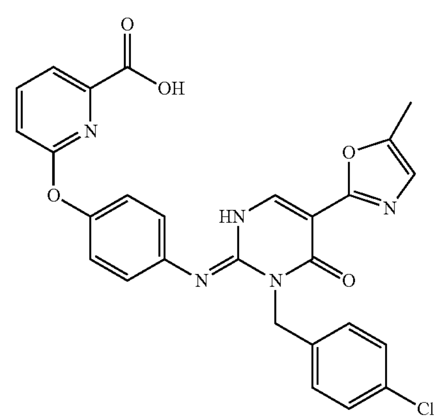 [SMILES: Cc1cnc(-c2c[nH]/c(=N\c3ccc(Oc4cccc(C(=O)O)n4)cc3)n(Cc3ccc(Cl)cc3)c2=O)o1] | I-290 | 530 | 1.84 | 3 |
| 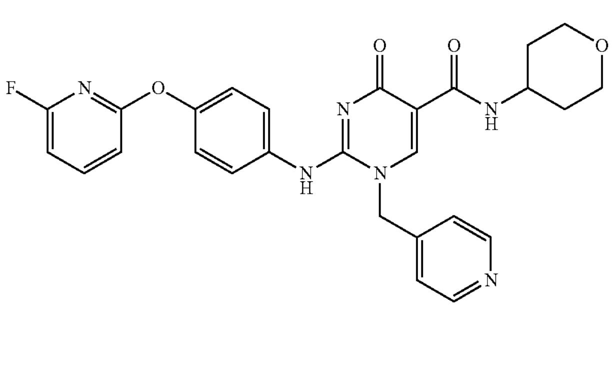 [SMILES: O=C(NC1CCOCC1)c1cn(Cc2ccncc2)c(Nc2ccc(Oc3cccc(F)n3)cc2)nc1=O] | I-291 | 517 | 1.23 | 3 |

TABLE 90-continued

| Structure | Compound No | RT (min) | [M + H] | Method |
|---|---|---|---|---|
| (structure) | I-292 | 517 | 1.35 | 3 |

TABLE 91

| Structure | Compound No | RT (min) | [M + H] | Method |
|---|---|---|---|---|
| (structure) | I-293 | 520 | 2.25 | 3 |
| (structure) | I-294 | 476 | 1.94 | 3 |
| (structure) | I-295 | 517 | 1.69 | 3 |

TABLE 91-continued

| Structure | Compound No | RT (min) | [M + H] | Method |
|---|---|---|---|---|
| (structure) | I-296 | 517 | 1.49 | 3 |
| (structure) | I-297 | 551 | 1.97 | 3 |
| (structure) | I-298 | 548 | 1.67 | 3 |

TABLE 92

| Structure | Compound No | RT (min) | [M + H] | Method |
|---|---|---|---|---|
| (structure) | I-299 | 551 | 1.99 | 3 |

TABLE 92-continued

| Structure | Compound No | RT (min) | [M + H] | Method |
|---|---|---|---|---|
| 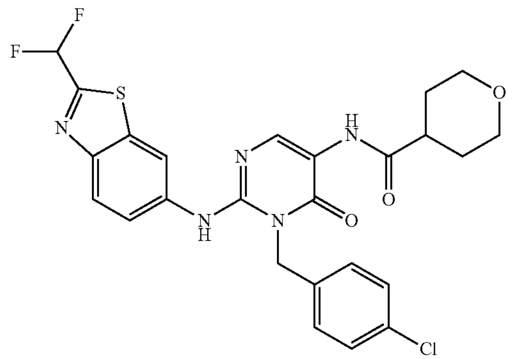 [SMILES: O=C(Nc1cnc(Nc2ccc3nc(C(F)F)sc3c2)n(Cc2ccc(Cl)cc2)c1=O)C1CCOCC1] | I-300 | 546 | 2.12 | 3 |
| 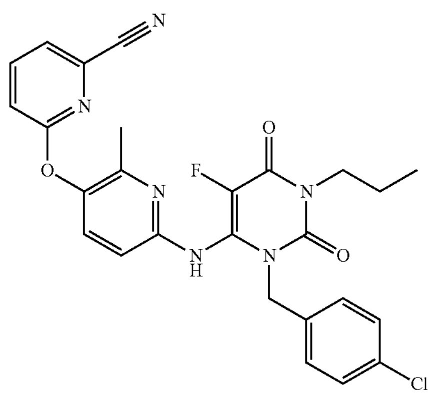 [SMILES: CCCn1c(=O)c(F)c(Nc2ccc(Oc3cccc(C#N)n3)c(C)n2)n(Cc2ccc(Cl)cc2)c1=O] | I-301 | 521 | 2.28 | 3 |
| 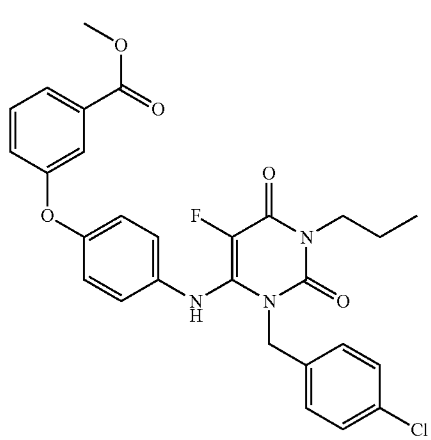 [SMILES: CCCn1c(=O)c(F)c(Nc2ccc(Oc3cccc(C(=O)OC)c3)cc2)n(Cc2ccc(Cl)cc2)c1=O] | I-302 | 538 | 2.55 | 3 |

TABLE 92-continued

| Structure | Compound No | RT (min) | [M + H] | Method |
|---|---|---|---|---|
| (structure of I-303) | I-303 | 524 | 2.19 | 3 |

TABLE 93

| Structure | Compound No | RT (min) | [M + H] | Method |
|---|---|---|---|---|
| (structure of I-304) | I-304 | 550 | 2.23 | 5 |
| (structure of I-305) | I-305 | 535 | 1.96 | 5 |

TABLE 93-continued

| Structure | Compound No | RT (min) | [M + H] | Method |
|---|---|---|---|---|
| 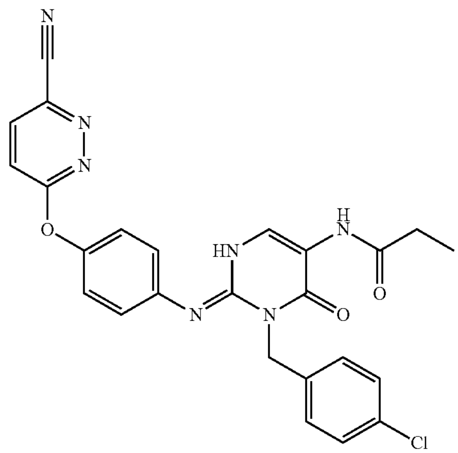 [SMILES: CCC(=O)Nc1c[nH]/c(=N\c2ccc(Oc3ccc(C#N)nn3)cc2)n(Cc2ccc(Cl)cc2)c1=O] | I-306 | 502 | 2.06 | 5 |
| 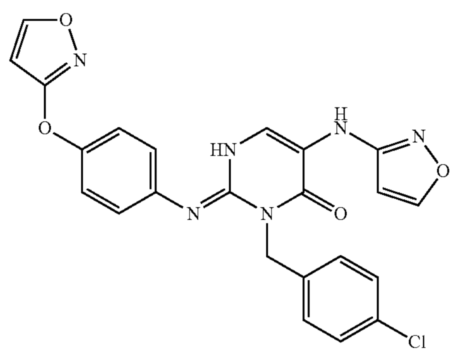 [SMILES: O=c1c(Nc2ccon2)c[nH]/c(=N\c2ccc(Oc3ccon3)cc2)n1Cc1ccc(Cl)cc1] | I-307 | 477 | 2.22 | 5 |
| 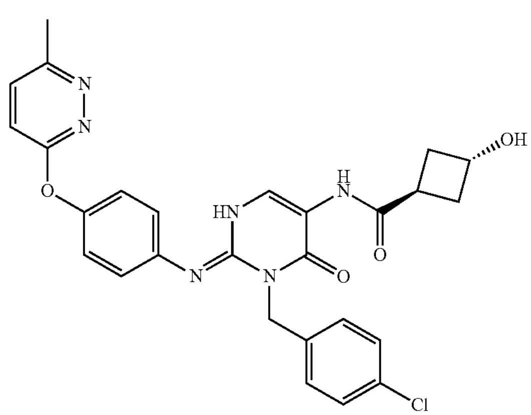 [SMILES: Cc1ccc(Oc2ccc(/N=c3\[nH]cc(NC(=O)[C@H]4C[C@H](O)C4)c(=O)n3Cc3ccc(Cl)cc3)cc2)nn1] | I-308 | 533 | 1.67 | 5 |

TABLE 94

| Structure | Compound No | RT (min) | [M + H] | Method |
|---|---|---|---|---|
| (structure shown) | I-309 | 520 | 1.68 | 3 |
| (structure shown) | I-310 | 512 | 2.15 | 3 |
| (structure shown) | I-311 | 565 | 2.37 | 3 |

TABLE 94-continued

| Structure | Compound No | RT (min) | [M + H] | Method |
|---|---|---|---|---|
| 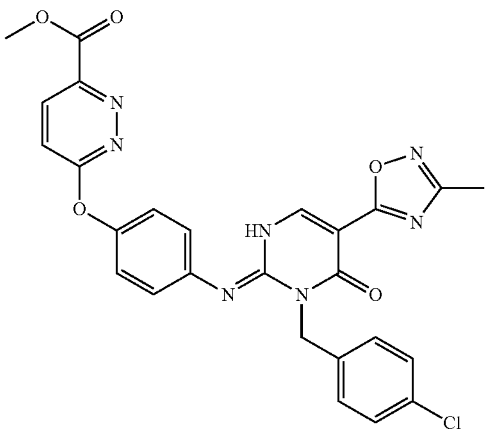 | I-312 | 546 | 1.91 | 3 |
| 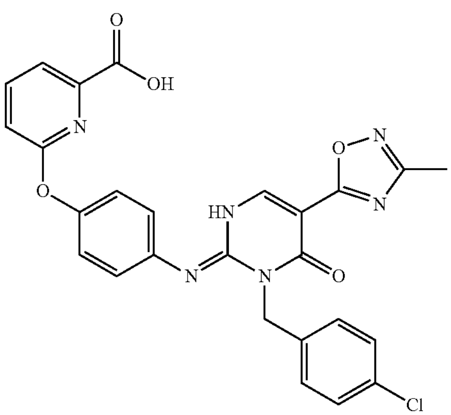 | I-313 | 531 | 1.91 | 3 |

TABLE 95

| Structure | Compound No | RT (min) | [M + H] | Method |
|---|---|---|---|---|
| 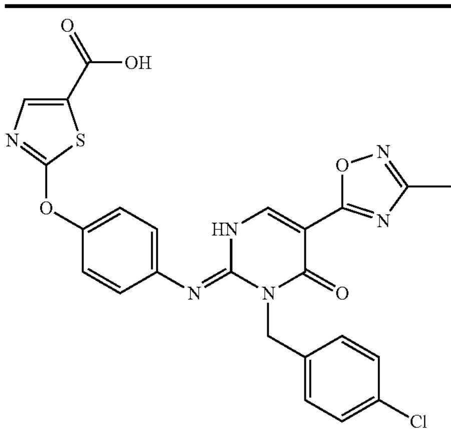 | I-314 | 537 | 1.89 | 3 |

TABLE 95-continued
| Structure | Compound No | RT (min) | [M + H] | Method |
|---|---|---|---|---|
| 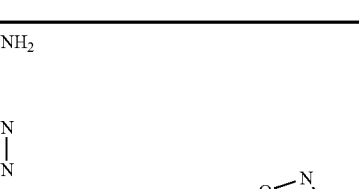 | I-315 | 531 | 1.73 | 3 |
| 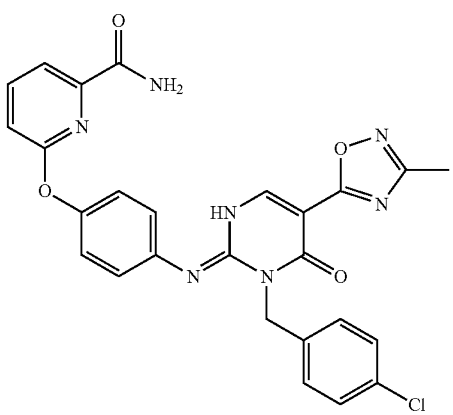 [SMILES: Cc1noc(-c2c[nH]/c(=N\c3ccc(Oc4cccc(C(N)=O)n4)cc3)n(Cc3ccc(Cl)cc3)c2=O)n1] | I-316 | 530 | 1.86 | 3 |
| 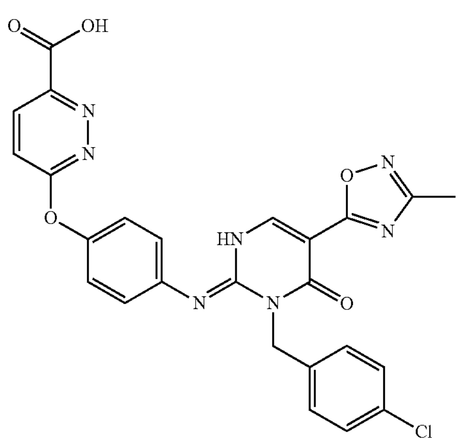 [SMILES: Cc1noc(-c2c[nH]/c(=N\c3ccc(Oc4ccc(C(=O)O)nn4)cc3)n(Cc3ccc(Cl)cc3)c2=O)n1] | I-317 | 532 | 1.74 | 3 |

TABLE 95-continued

| Structure | Compound No | RT (min) | [M + H] | Method |
|---|---|---|---|---|
| 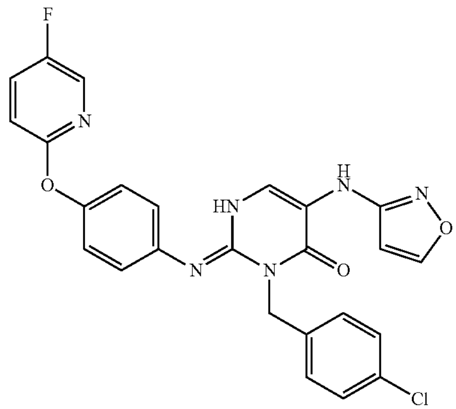 [SMILES: O=c1c(Nc2ccon2)c[nH]/c(=N\c2ccc(Oc3ccc(F)cn3)cc2)n1Cc1ccc(Cl)cc1] | I-318 | 505 | 2.22 | 3 |

TABLE 96

| Structure | Compound No | RT (min) | [M + H] | Method |
|---|---|---|---|---|
| 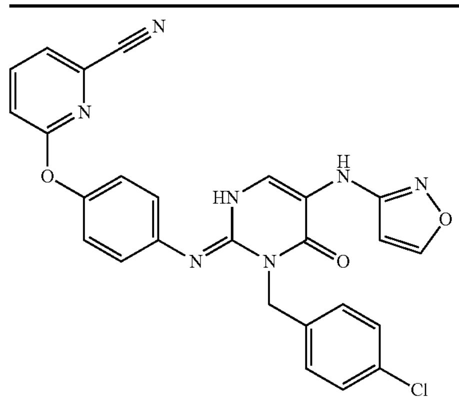 | I-319 | 512 | 2.19 | 3 |
| 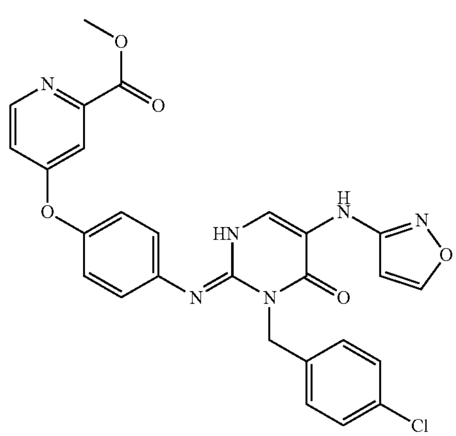 [SMILES: COC(=O)c1cc(Oc2ccc(/N=c3\[nH]cc(Nc4ccon4)c(=O)n3Cc3ccc(Cl)cc3)cc2)ccn1] | I-320 | 545 | 2.02 | 3 |

TABLE 96-continued
| Structure | Compound No | RT (min) | [M + H] | Method |
|---|---|---|---|---|
| 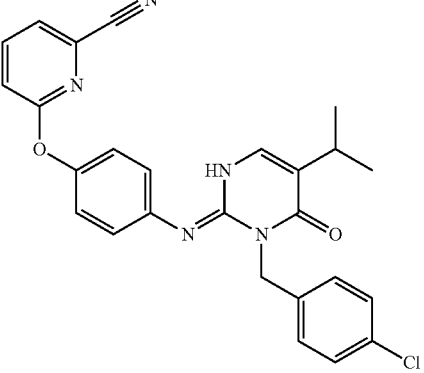 | I-321 | 472 | 2.43 | 3 |
| 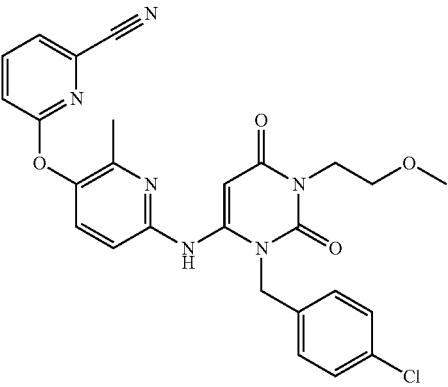 [SMILES: COCCn1c(=O)cc(Nc2ccc(Oc3cccc(C#N)n3)c(C)n2)n(Cc2ccc(Cl)cc2)c1=O] | I-322 | 519 | 2.01 | 3 |
| 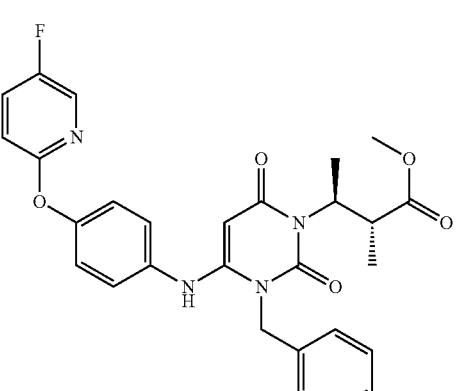 | I-323 | 553 | 2.31 | 3 |

TABLE 97

| Structure | Compound No | RT (min) | [M + H] | Method |
|---|---|---|---|---|
| 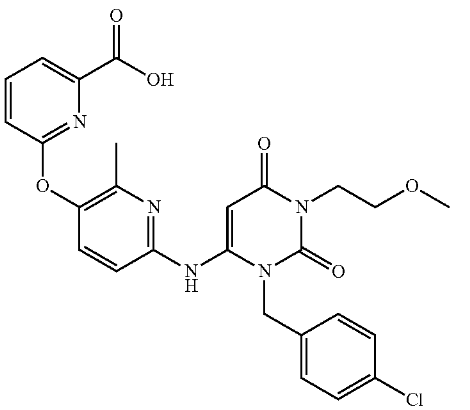 [SMILES: COCCn1c(=O)cc(Nc2ccc(Oc3cccc(C(=O)O)n3)c(C)n2)n(Cc2ccc(Cl)cc2)c1=O] | I-324 | 536 | 1.80 | 3 |
| 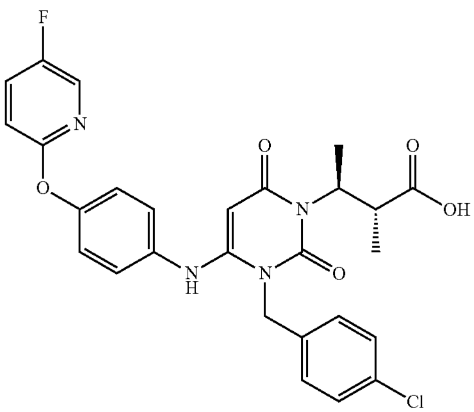 [SMILES: C[C@@H](C(=O)O)[C@H](C)n1c(=O)cc(Nc2ccc(Oc3ccc(F)cn3)cc2)n(Cc2ccc(Cl)cc2)c1=O] | I-325 | 539 | 2.01 | 3 |
| 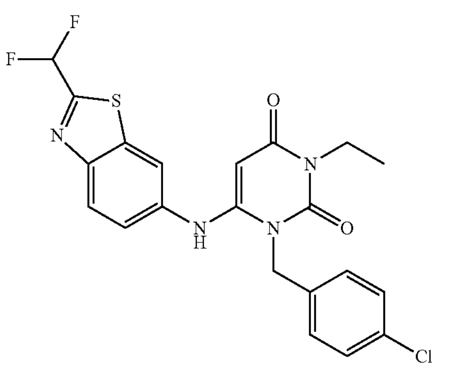 [SMILES: CCn1c(=O)cc(Nc2ccc3nc(C(F)F)sc3c2)n(Cc2ccc(Cl)cc2)c1=O] | I-326 | 463 | 2.11 | 3 |
| 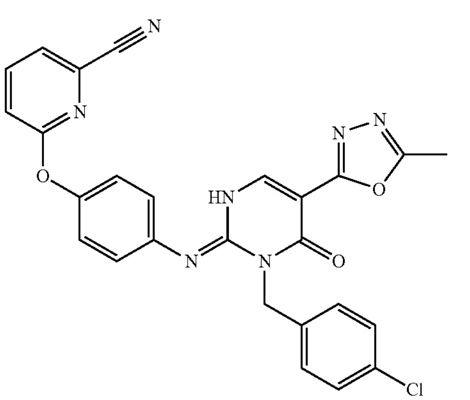 [SMILES: Cc1nnc(-c2c[nH]/c(=N\c3ccc(Oc4cccc(C#N)n4)cc3)n(Cc3ccc(Cl)cc3)c2=O)o1] | I-327 | 512 | 1.96 | 3 |

TABLE 97-continued

| Structure | Compound No | RT (min) | [M + H] | Method |
|---|---|---|---|---|
| 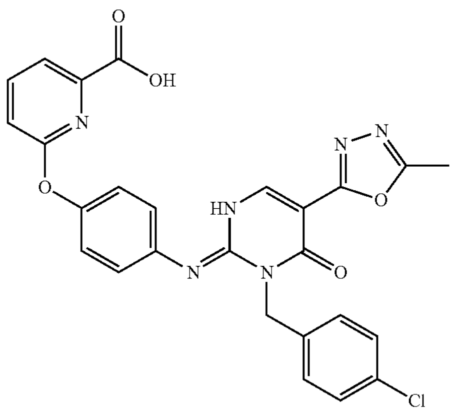 [SMILES: Cc1nnc(-c2c[nH]/c(=N\c3ccc(Oc4cccc(C(=O)O)n4)cc3)n(Cc3ccc(Cl)cc3)c2=O)o1] | I-328 | 531 | 1.75 | 3 |

TABLE 98

| Structure | Compound No | RT (min) | [M + H] | Method |
|---|---|---|---|---|
| 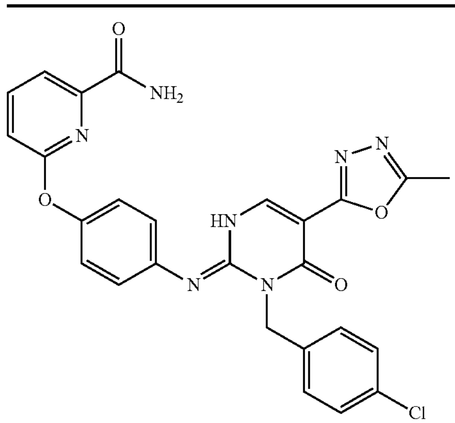 | I-329 | 530 | 1.70 | 3 |
| 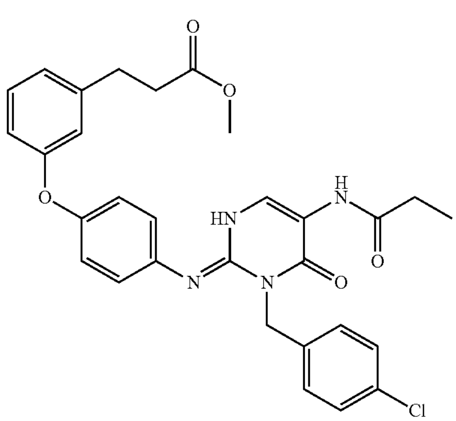 [SMILES: CCC(=O)Nc1c[nH]/c(=N\c2ccc(Oc3cccc(CCC(=O)OC)c3)cc2)n(Cc2ccc(Cl)cc2)c1=O] | I-330 | 561 | 2.35 | 3 |

TABLE 98-continued

| Structure | Compound No | RT (min) | [M + H] | Method |
|---|---|---|---|---|
| 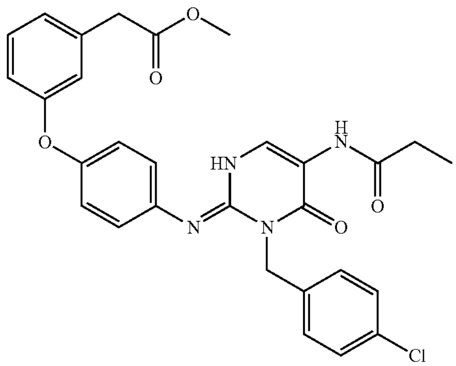 [SMILES: CCC(=O)Nc1c[nH]/c(=N\c2ccc(Oc3cccc(CC(=O)OC)c3)cc2)n(Cc2ccc(Cl)cc2)c1=O] | I-331 | 547 | 2.26 | 3 |
| 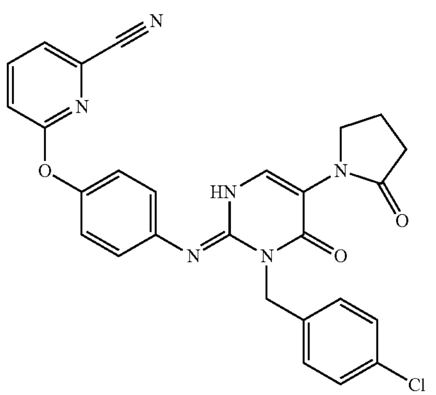 [SMILES: N#Cc1cccc(Oc2ccc(/N=c3\[nH]cc(N4CCCC4=O)c(=O)n3Cc3ccc(Cl)cc3)cc2)n1] | I-332 | 513 | 1.95 | 3 |
| 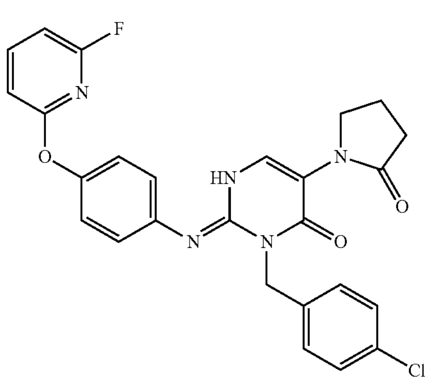 [SMILES: O=C1CCCN1c1c[nH]/c(=N\c2ccc(Oc3cccc(F)n3)cc2)n(Cc2ccc(Cl)cc2)c1=O] | I-333 | 506 | 2.02 | 3 |

TABLE 99

| Structure | Compound No | RT (min) | [M + H] | Method |
|---|---|---|---|---|
| 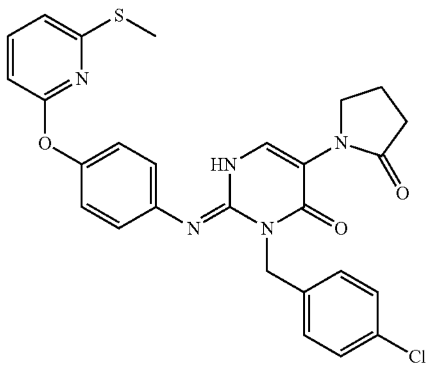 [SMILES: CSc1cccc(Oc2ccc(/N=c3\[nH]cc(N4CCCC4=O)c(=O)n3Cc3ccc(Cl)cc3)cc2)n1] | I-334 | 534 | 2.21 | 3 |
| 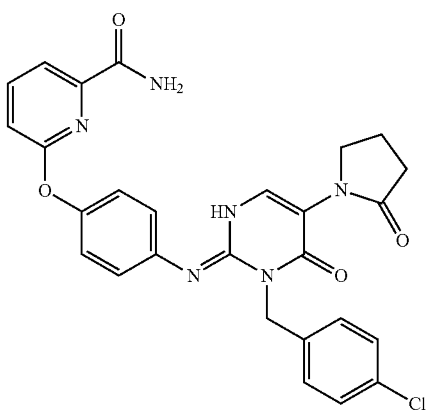 [SMILES: NC(=O)c1cccc(Oc2ccc(/N=c3\[nH]cc(N4CCCC4=O)c(=O)n3Cc3ccc(Cl)cc3)cc2)n1] | I-335 | 531 | 1.69 | 3 |
| 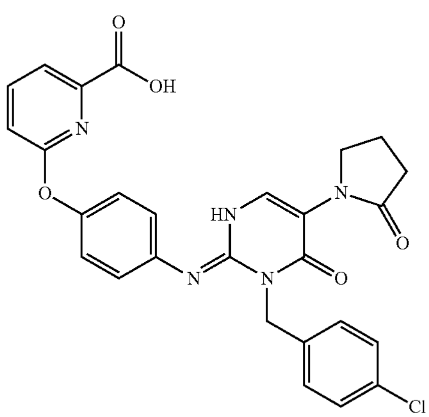 [SMILES: O=C(O)c1cccc(Oc2ccc(/N=c3\[nH]cc(N4CCCC4=O)c(=O)n3Cc3ccc(Cl)cc3)cc2)n1] | I-336 | 532 | 1.73 | 3 |
| 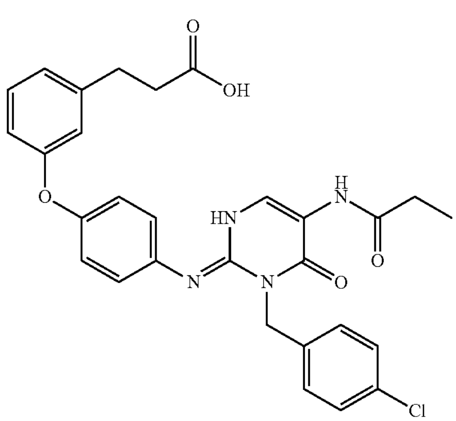 [SMILES: CCC(=O)Nc1c[nH]/c(=N\c2ccc(Oc3cccc(CCC(=O)O)c3)cc2)n(Cc2ccc(Cl)cc2)c1=O] | I-337 | 547 | 2.05 | 3 |

TABLE 99-continued

| Structure | Compound No | RT (min) | [M + H] | Method |
|---|---|---|---|---|
| (structure) | I-338 | 2.34 | 568 | 3 |

TABLE 100

| Structure | Compound No | RT (min) | [M + H] | Method |
|---|---|---|---|---|
| (structure) | I-339 | 2.04 | 554 | 3 |
| (structure) | I-340 | 2.25 | 503 | 3 |

TABLE 100-continued

| Structure | Compound No | RT (min) | [M + H] | Method |
|---|---|---|---|---|
| 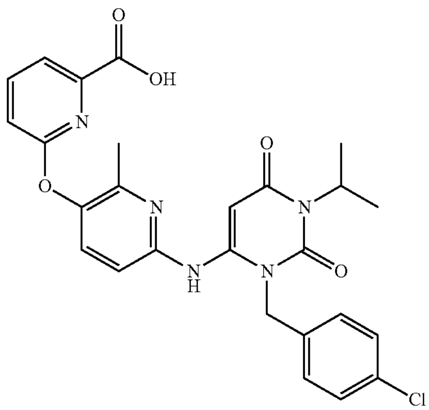 [SMILES: Cc1nc(Nc2cc(=O)n(C(C)C)c(=O)n2Cc2ccc(Cl)cc2)ccc1Oc1cccc(C(=O)O)n1] | I-341 | 522 | 2.03 | 3 |
| 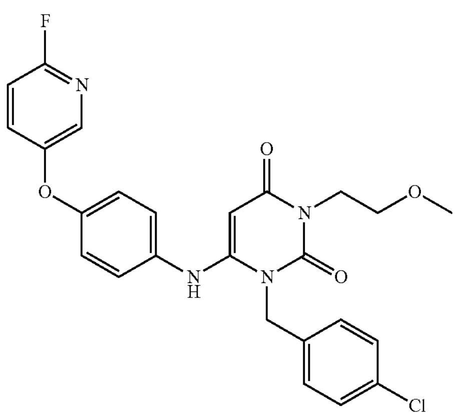 [SMILES: COCCn1c(=O)cc(Nc2ccc(Oc3ccc(F)nc3)cc2)n(Cc2ccc(Cl)cc2)c1=O] | I-342 | 497 | 2.05 | 3 |
| 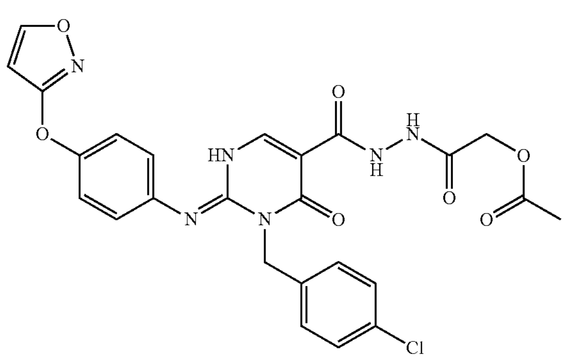 [SMILES: CC(=O)OCC(=O)NNC(=O)c1c[nH]/c(=N\c2ccc(Oc3ccon3)cc2)n(Cc2ccc(Cl)cc2)c1=O] | I-343 | 553 | 1.80 | 3 |

TABLE 101

| Structure | Compound No | RT (min) | [M + H] | Method |
|---|---|---|---|---|
| (structure) | I-344 | 476 | 2.08 | 3 |
| (structure) | I-345 | 477 | 2.09 | 2 |
| (structure) | I-346 | 466 | 1.77 | 3 |
| (structure) | I-347 | 495 | 1.71 | 3 |

TABLE 101-continued

| Structure | Compound No | RT (min) | [M + H] | Method |
|---|---|---|---|---|
| 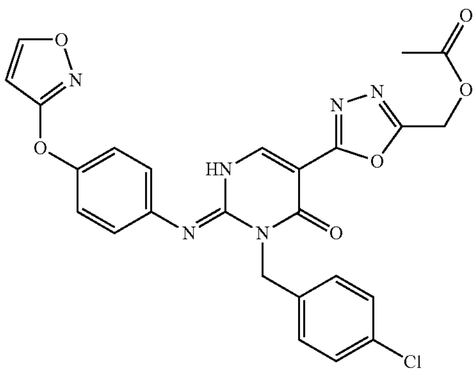 [SMILES: CC(=O)OCc1nnc(-c2c[nH]/c(=N\c3ccc(Oc4ccon4)cc3)n(Cc3ccc(Cl)cc3)c2=O)o1] | I-348 | 535 | 1.98 | 2 |

TABLE 102

| Structure | Compound No | RT (min) | [M + H] | Method |
|---|---|---|---|---|
| 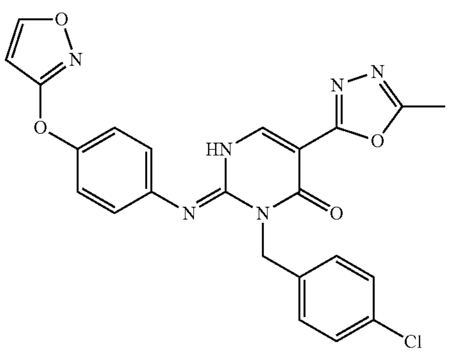 [SMILES: Cc1nnc(-c2c[nH]/c(=N\c3ccc(Oc4ccon4)cc3)n(Cc3ccc(Cl)cc3)c2=O)o1] | I-349 | 477 | 1.88 | 2 |
| 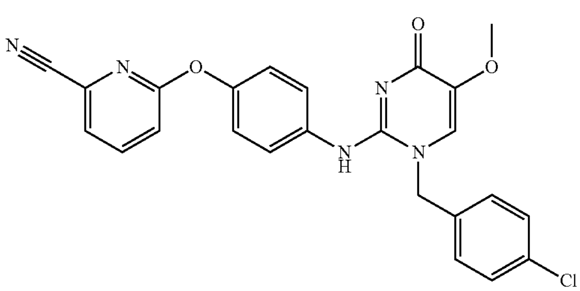 [SMILES: COc1cn(Cc2ccc(Cl)cc2)c(Nc2ccc(Oc3cccc(C#N)n3)cc2)nc1=O] | I-350 | 460 | 1.73 | 3 |
| 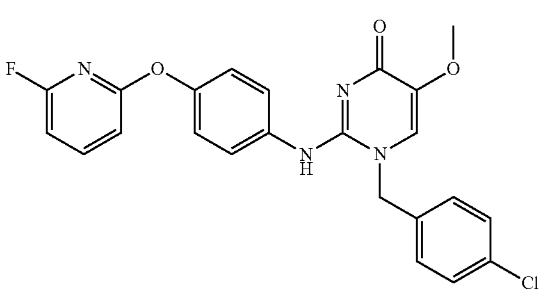 [SMILES: COc1cn(Cc2ccc(Cl)cc2)c(Nc2ccc(Oc3cccc(F)n3)cc2)nc1=O] | I-351 | 453 | 1.78 | 3 |

TABLE 102-continued

| Structure | Compound No | RT (min) | [M + H] | Method |
|---|---|---|---|---|
| 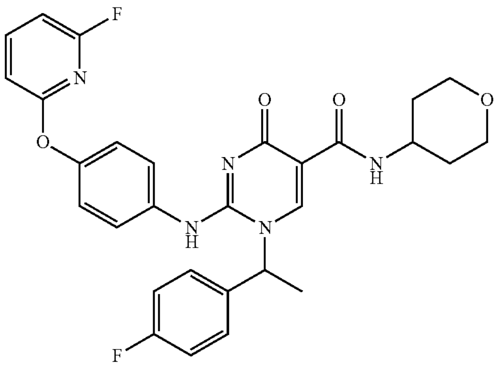 [SMILES: CC(c1ccc(F)cc1)n1cc(C(=O)NC2CCOCC2)c(=O)nc1Nc1ccc(Oc2cccc(F)n2)cc1] | I-352 | 548 | 2.08 | 3 |
| 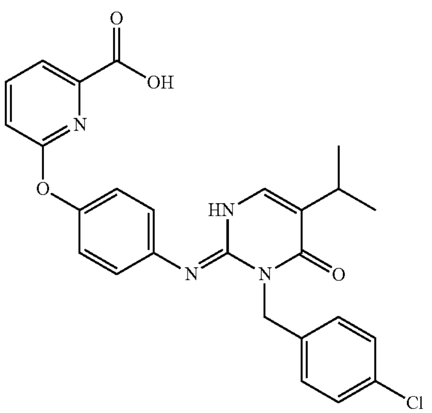 [SMILES: CC(C)c1c[nH]/c(=N\c2ccc(Oc3cccc(C(=O)O)n3)cc2)n(Cc2ccc(Cl)cc2)c1=O] | I-353 | 491 | 2.14 | 3 |

TABLE 103

| Structure | Compound No | RT (min) | [M + H] | Method |
|---|---|---|---|---|
| 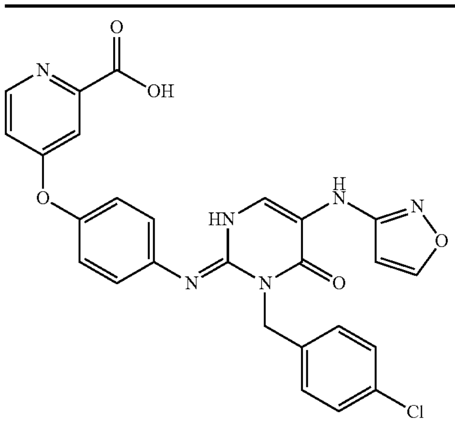 | I-354 | 531 | 1.52 | 3 |

TABLE 103-continued

| Structure | Compound No | RT (min) | [M + H] | Method |
|---|---|---|---|---|
| 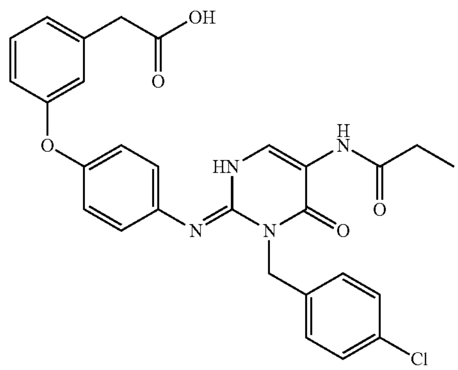 [SMILES: CCC(=O)Nc1c[nH]/c(=N\c2ccc(Oc3cccc(CC(=O)O)c3)cc2)n(Cc2ccc(Cl)cc2)c1=O] | I-355 | 533 | 1.97 | 3 |
| 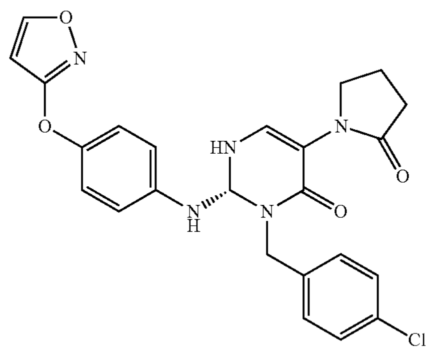 [SMILES: O=C1CCCN1C1=CN[C@@H](Nc2ccc(Oc3ccon3)cc2)N(Cc2ccc(Cl)cc2)C1=O] | I-356 | 478 | 1.80 | 3 |
| 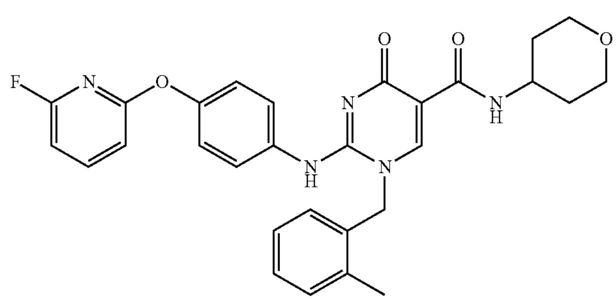 [SMILES: Cc1ccccc1Cn1cc(C(=O)NC2CCOCC2)c(=O)nc1Nc1ccc(Oc2cccc(F)n2)cc1] | I-357 | 530 | 2.04 | 3 |
| 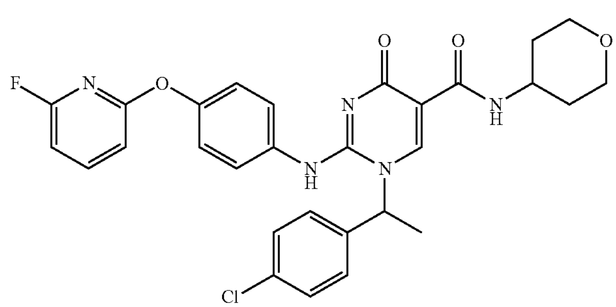 [SMILES: CC(c1ccc(Cl)cc1)n1cc(C(=O)NC2CCOCC2)c(=O)nc1Nc1ccc(Oc2cccc(F)n2)cc1] | I-358 | 564 | 2.28 | 3 |

TABLE 103-continued

| Structure | Compound No | RT (min) | [M + H] | Method |
|---|---|---|---|---|
| *(structure of I-359)* | I-359 | 546 | 2.14 | 3 |

TABLE 104

| Structure | Compound No | RT (min) | [M + H] | Method |
|---|---|---|---|---|
| *(structure of I-360)* | I-360 | 554 | 2.14 | 3 |
| *(structure of I-361)* | I-361 | 540 | 1.90 | 3 |

TABLE 104-continued

| Structure | Compound No | RT (min) | [M + H] | Method |
|---|---|---|---|---|
| 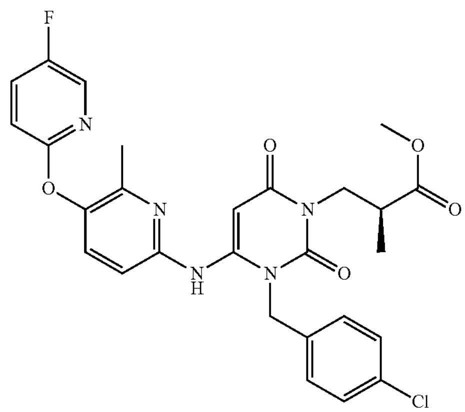 [SMILES: COC(=O)[C@@H](C)Cn1c(=O)cc(Nc2ccc(Oc3ccc(F)cn3)c(C)n2)n(Cc2ccc(Cl)cc2)c1=O] | I-362 | 554 | 2.20 | 3 |
| 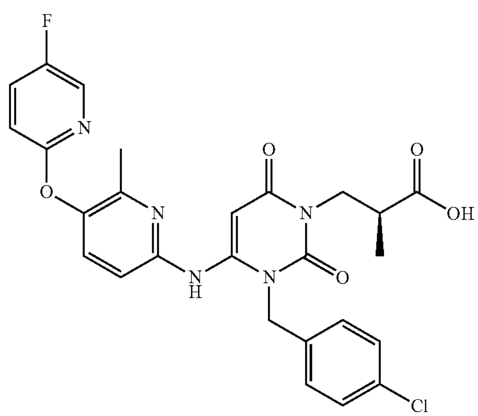 [SMILES: Cc1nc(Nc2cc(=O)n(C[C@H](C)C(=O)O)c(=O)n2Cc2ccc(Cl)cc2)ccc1Oc1ccc(F)cn1] | I-363 | 540 | 1.94 | 3 |
| 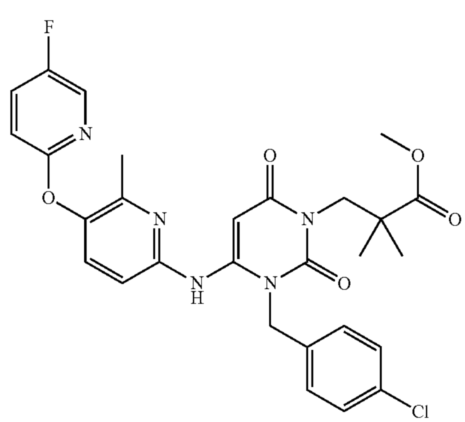 [SMILES: COC(=O)C(C)(C)Cn1c(=O)cc(Nc2ccc(Oc3ccc(F)cn3)c(C)n2)n(Cc2ccc(Cl)cc2)c1=O] | I-364 | 568 | 2.31 | 3 |

TABLE 105
| Structure | Compound No | RT (min) | [M + H] | Method |
|---|---|---|---|---|
| 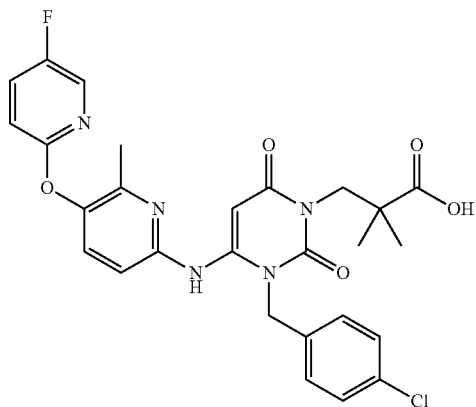 [SMILES: Cc1nc(Nc2cc(=O)n(CC(C)(C)C(=O)O)c(=O)n2Cc2ccc(Cl)cc2)ccc1Oc1ccc(F)cn1] | I-365 | 554 | 2.02 | 3 |
| 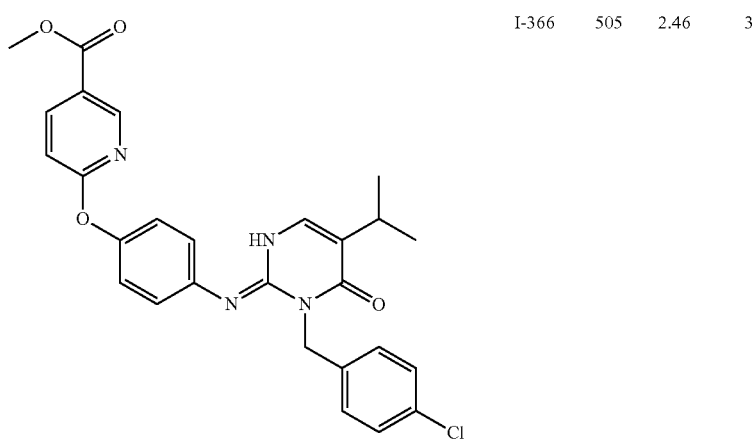 | I-366 | 505 | 2.46 | 3 |
| 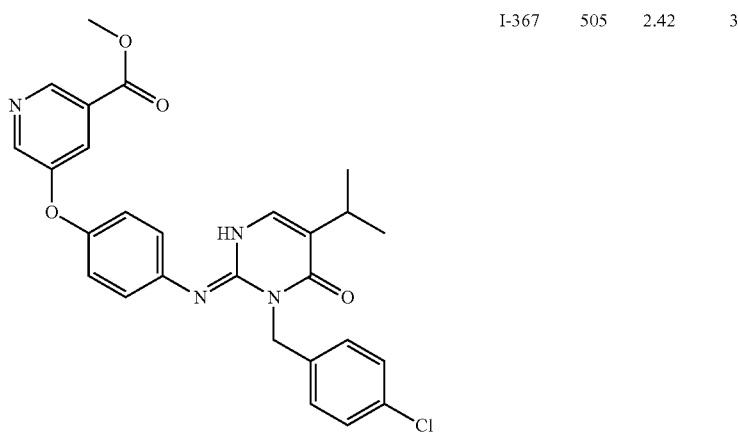 | I-367 | 505 | 2.42 | 3 |

TABLE 105-continued
| Structure | Compound No | RT (min) | [M + H] | Method |
|---|---|---|---|---|
| 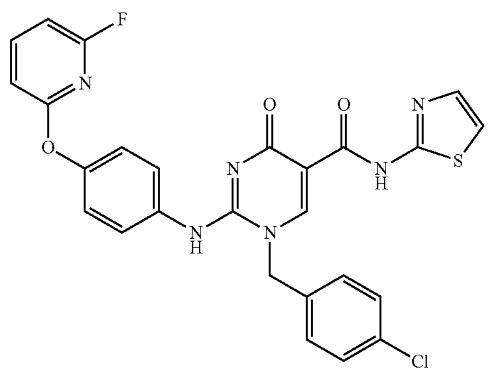 [SMILES: O=C(Nc1nccs1)c1cn(Cc2ccc(Cl)cc2)c(Nc2ccc(Oc3cccc(F)n3)cc2)nc1=O] | I-368 | 549 | 1.85 | 2 |
| 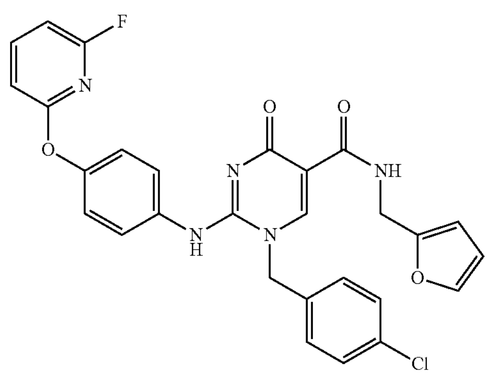 [SMILES: O=C(NCc1ccco1)c1cn(Cc2ccc(Cl)cc2)c(Nc2ccc(Oc3cccc(F)n3)cc2)nc1=O] | I-369 | 546 | 2.46 | 2 |
TABLE 106
| Structure | Compound No | RT (min) | [M + H] | Method |
|---|---|---|---|---|
| 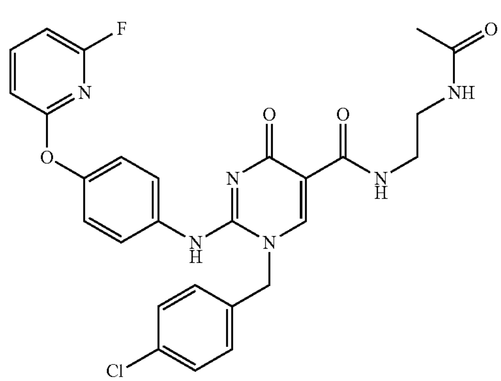 [SMILES: CC(=O)NCCNC(=O)c1cn(Cc2ccc(Cl)cc2)c(Nc2ccc(Oc3cccc(F)n3)cc2)nc1=O] | I-370 | 551 | 1.97 | 2 |
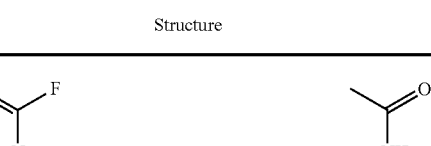

TABLE 106-continued
| Structure | Compound No | RT (min) | [M + H] | Method |
|---|---|---|---|---|
| 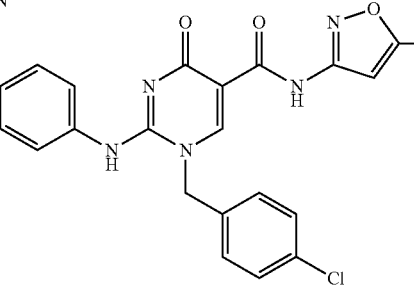 | I-371 | 547 | 2.51 | 2 |
| 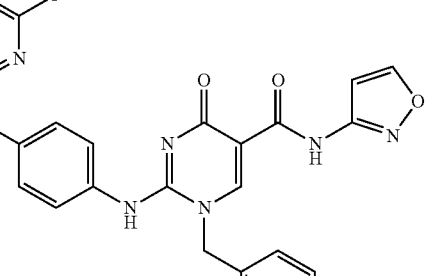 | I-372 | 533 | 2.43 | 2 |
| 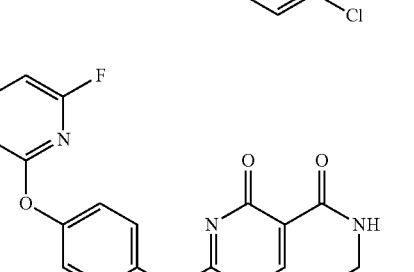 | I-373 | 538 | 2.27 | 2 |
| 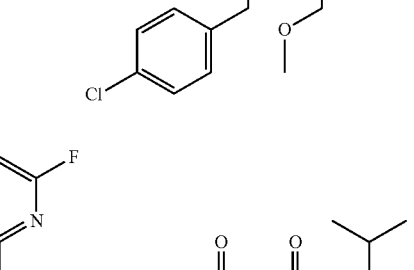 | I-374 | 522 | 2.53 | 2 |

TABLE 107

| Structure | Compound No | RT (min) | [M + H] | Method |
|---|---|---|---|---|
| 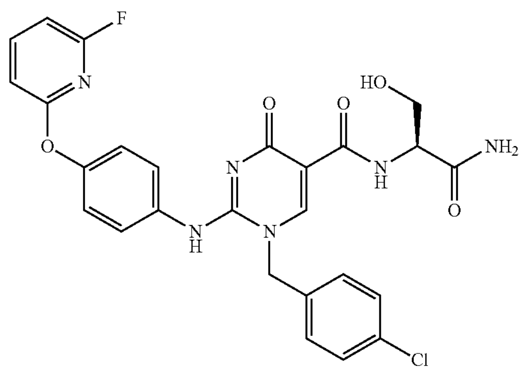 [SMILES: NC(=O)[C@H](CO)NC(=O)c1cn(Cc2ccc(Cl)cc2)c(Nc2ccc(Oc3cccc(F)n3)cc2)nc1=O] | I-375 | 553 | 1.88 | 2 |
| 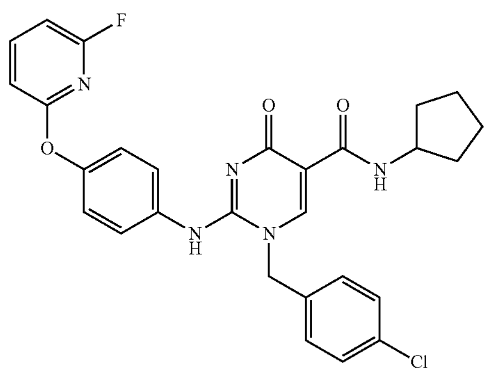 [SMILES: O=C(NC1CCCC1)c1cn(Cc2ccc(Cl)cc2)c(Nc2ccc(Oc3cccc(F)n3)cc2)nc1=O] | I-376 | 534 | 2.56 | 2 |
| 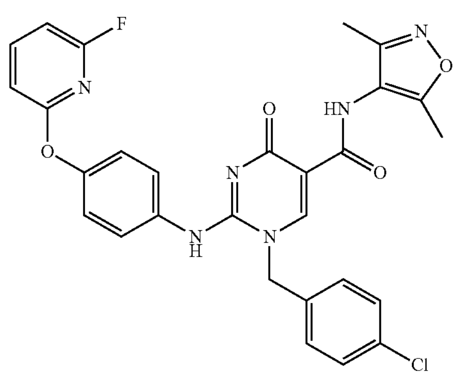 [SMILES: Cc1noc(C)c1NC(=O)c1cn(Cc2ccc(Cl)cc2)c(Nc2ccc(Oc3cccc(F)n3)cc2)nc1=O] | I-377 | 561 | 2.38 | 2 |
| 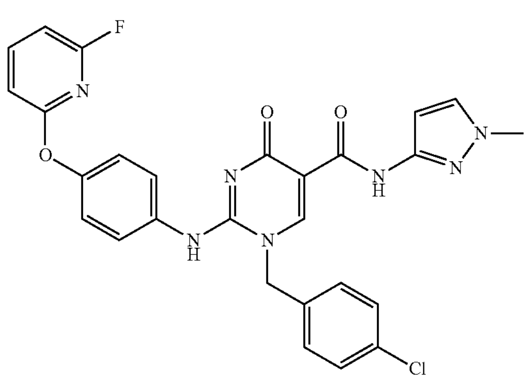 [SMILES: Cn1ccc(NC(=O)c2cn(Cc3ccc(Cl)cc3)c(Nc3ccc(Oc4cccc(F)n4)cc3)nc2=O)n1] | I-378 | 546 | 2.28 | 2 |

TABLE 107-continued
| Structure | Compound No | RT (min) | [M + H] | Method |
|---|---|---|---|---|
| 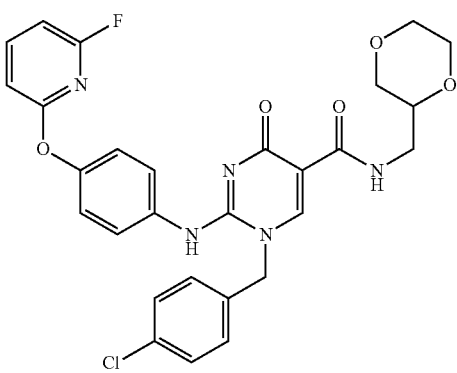 [SMILES: O=C(NCC1COCCO1)c1cn(Cc2ccc(Cl)cc2)c(Nc2ccc(Oc3cccc(F)n3)cc2)nc1=O] | I-379 | 566 | 2.19 | 2 |
TABLE 108
| Structure | Compound No | RT (min) | [M + H] | Method |
|---|---|---|---|---|
| 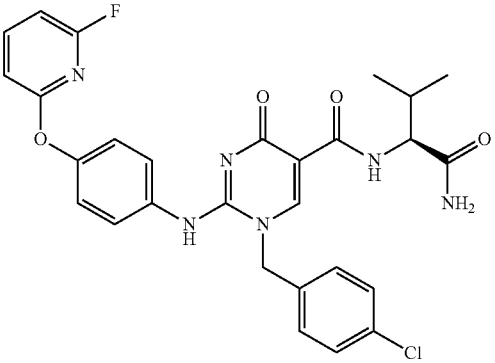 [SMILES: CC(C)[C@H](NC(=O)c1cn(Cc2ccc(Cl)cc2)c(Nc2ccc(Oc3cccc(F)n3)cc2)nc1=O)C(N)=O] | I-380 | 565 | 2.16 | 2 |
| 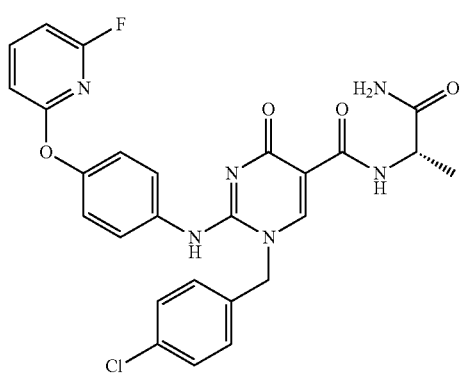 [SMILES: C[C@H](NC(=O)c1cn(Cc2ccc(Cl)cc2)c(Nc2ccc(Oc3cccc(F)n3)cc2)nc1=O)C(N)=O] | I-381 | 537 | 2.01 | 2 |

TABLE 108-continued

| Structure | Compound No | RT (min) | [M + H] | Method |
|---|---|---|---|---|
| 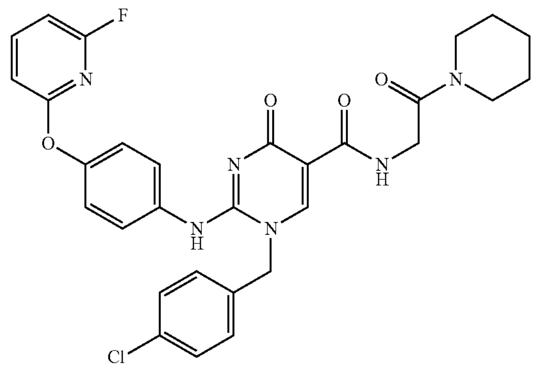 [SMILES: O=C(NCC(=O)N1CCCCC1)c1cn(Cc2ccc(Cl)cc2)c(Nc2ccc(Oc3cccc(F)n3)cc2)nc1=O] | I-382 | 591 | 2.31 | 2 |
| 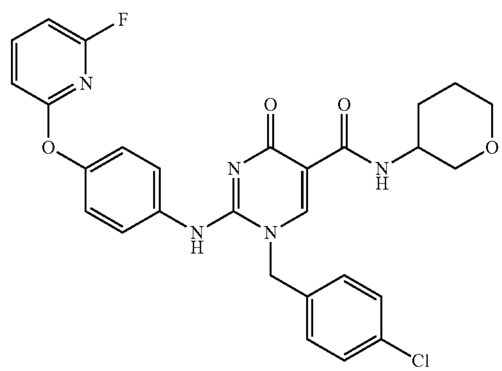 [SMILES: O=C(NC1CCCOC1)c1cn(Cc2ccc(Cl)cc2)c(Nc2ccc(Oc3cccc(F)n3)cc2)nc1=O] | I-383 | 550 | 2.30 | 2 |
| 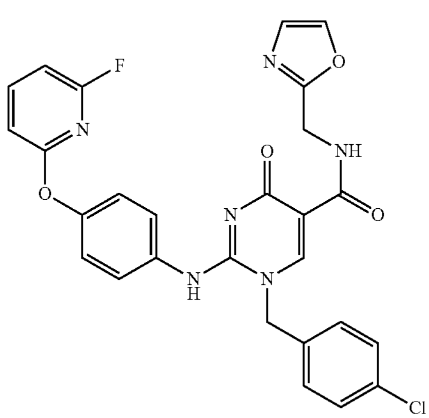 [SMILES: O=C(NCc1ncco1)c1cn(Cc2ccc(Cl)cc2)c(Nc2ccc(Oc3cccc(F)n3)cc2)nc1=O] | I-384 | 547 | 2.19 | 2 |

TABLE 109

| Structure | Compound No | RT (min) | [M + H] | Method |
|---|---|---|---|---|
| 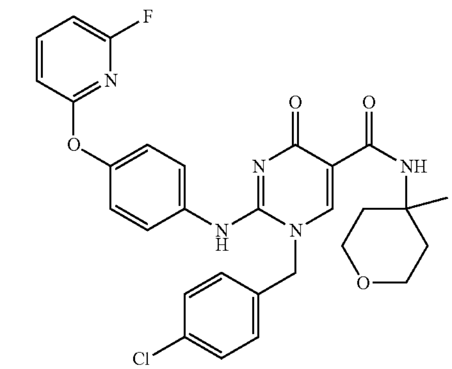 [SMILES: CC1(NC(=O)c2cn(Cc3ccc(Cl)cc3)c(Nc3ccc(Oc4cccc(F)n4)cc3)nc2=O)CCOCC1] | I-385 | 564 | 2.37 | 2 |
| 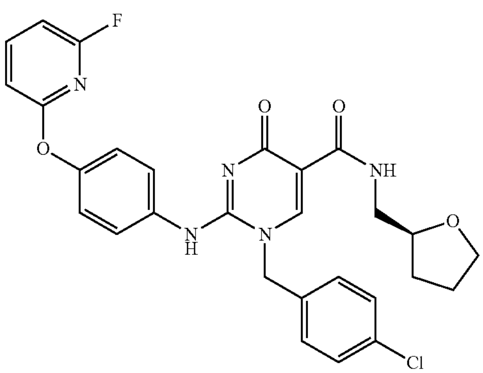 [SMILES: O=C(NC[C@@H]1CCCO1)c1cn(Cc2ccc(Cl)cc2)c(Nc2ccc(Oc3cccc(F)n3)cc2)nc1=O] | I-386 | 550 | 2.30 | 2 |
| 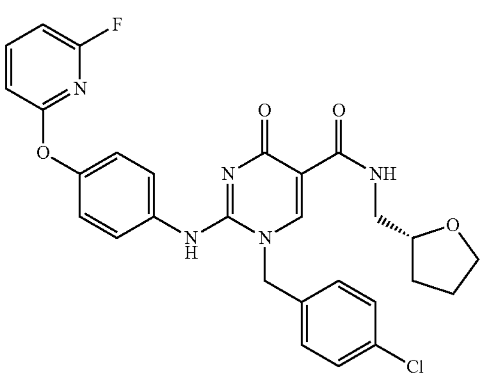 [SMILES: O=C(NC[C@H]1CCCO1)c1cn(Cc2ccc(Cl)cc2)c(Nc2ccc(Oc3cccc(F)n3)cc2)nc1=O] | I-387 | 550 | 2.30 | 2 |
| 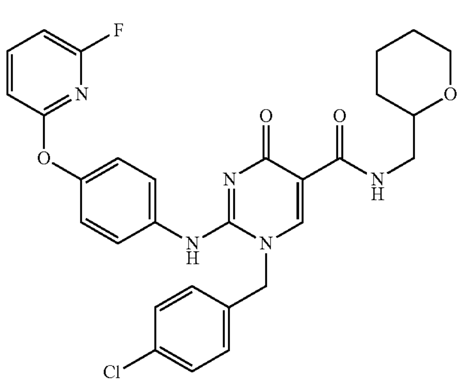 [SMILES: O=C(NCC1CCCCO1)c1cn(Cc2ccc(Cl)cc2)c(Nc2ccc(Oc3cccc(F)n3)cc2)nc1=O] | I-388 | 564 | 2.45 | 2 |

TABLE 109-continued
| Structure | Compound No | RT (min) | [M + H] | Method |
|---|---|---|---|---|
| 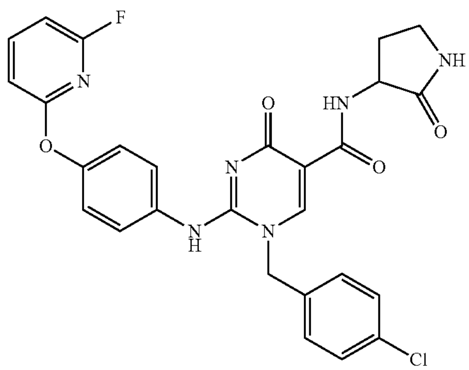 [SMILES: O=C(NC1CCNC1=O)c1cn(Cc2ccc(Cl)cc2)c(Nc2ccc(Oc3cccc(F)n3)cc2)nc1=O] | I-389 | 549 | 2.00 | 2 |
TABLE 110
| Structure | Compound No | RT (min) | [M + H] | Method |
|---|---|---|---|---|
| 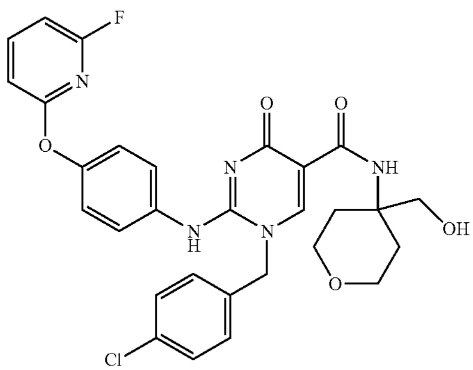 [SMILES: O=C(NC1(CO)CCOCC1)c1cn(Cc2ccc(Cl)cc2)c(Nc2ccc(Oc3cccc(F)n3)cc2)nc1=O] | I-390 | 580 | 2.10 | 2 |
| 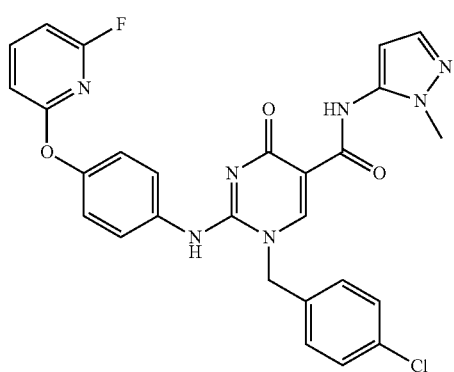 [SMILES: Cn1nccc1NC(=O)c1cn(Cc2ccc(Cl)cc2)c(Nc2ccc(Oc3cccc(F)n3)cc2)nc1=O] | I-391 | 546 | 2.24 | 2 |

TABLE 110-continued

| Structure | Compound No | RT (min) | [M + H] | Method |
|---|---|---|---|---|
| 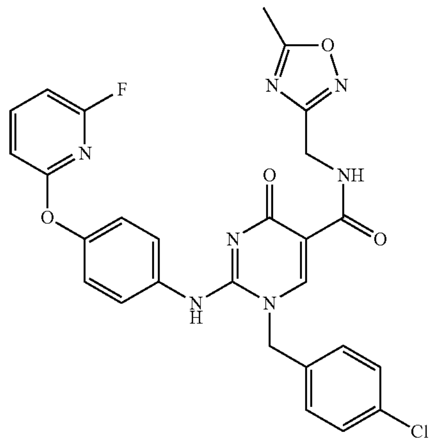 [SMILES: Cc1nc(CNC(=O)c2cn(Cc3ccc(Cl)cc3)c(Nc3ccc(Oc4cccc(F)n4)cc3)nc2=O)no1] | I-392 | 562 | 2.24 | 2 |
| 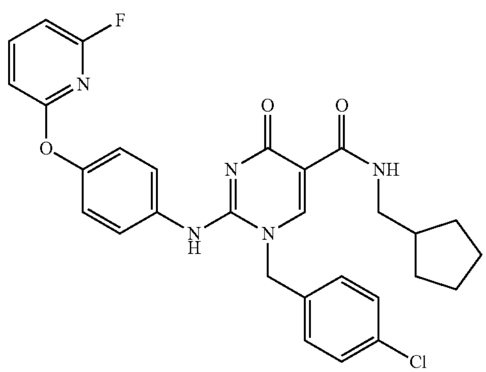 [SMILES: O=C(NCC1CCCC1)c1cn(Cc2ccc(Cl)cc2)c(Nc2ccc(Oc3cccc(F)n3)cc2)nc1=O] | I-393 | 548 | 2.70 | 2 |
| 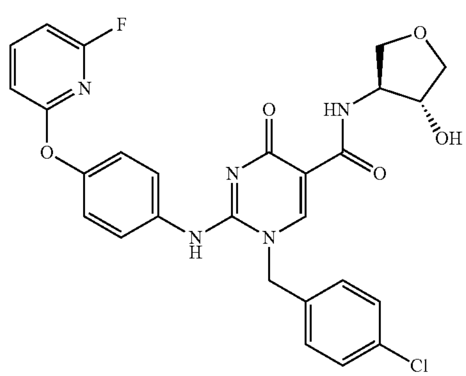 [SMILES: O=C(N[C@H]1COC[C@@H]1O)c1cn(Cc2ccc(Cl)cc2)c(Nc2ccc(Oc3cccc(F)n3)cc2)nc1=O] | I-394 | 552 | 2.03 | 2 |

TABLE 111

| Structure | Compound No | RT (min) | [M + H] | Method |
|---|---|---|---|---|
| 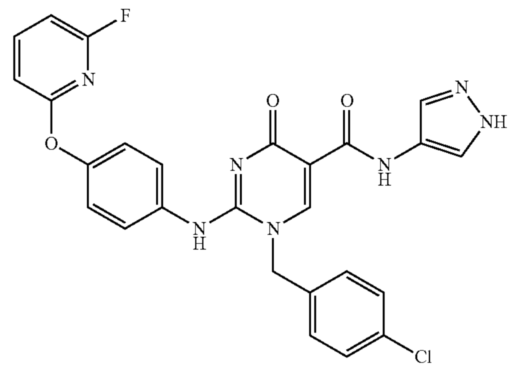 [SMILES: O=C(Nc1cn[nH]c1)c1cn(Cc2ccc(Cl)cc2)c(Nc2ccc(Oc3cccc(F)n3)cc2)nc1=O] | I-395 | 532 | 2.11 | 2 |
| 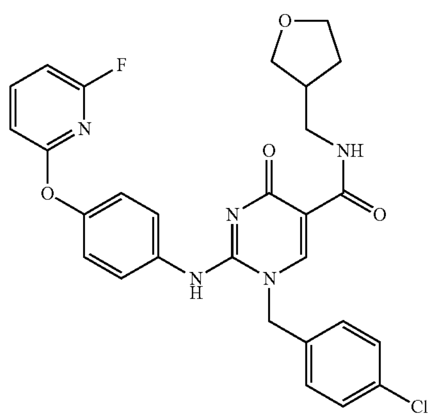 [SMILES: O=C(NCC1CCOC1)c1cn(Cc2ccc(Cl)cc2)c(Nc2ccc(Oc3cccc(F)n3)cc2)nc1=O] | I-396 | 550 | 2.21 | 2 |
| 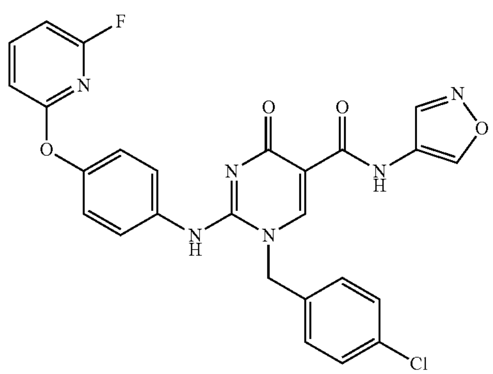 [SMILES: O=C(Nc1cnoc1)c1cn(Cc2ccc(Cl)cc2)c(Nc2ccc(Oc3cccc(F)n3)cc2)nc1=O] | I-397 | 533 | 2.39 | 2 |
| 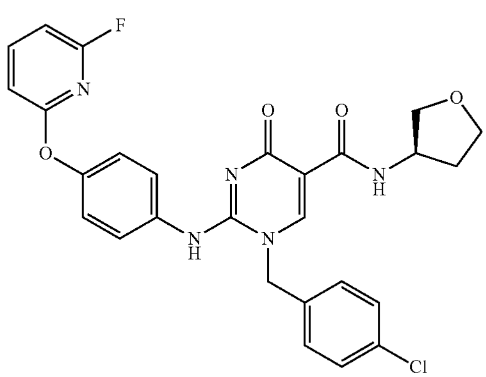 [SMILES: O=C(N[C@@H]1CCOC1)c1cn(Cc2ccc(Cl)cc2)c(Nc2ccc(Oc3cccc(F)n3)cc2)nc1=O] | I-398 | 536 | 2.18 | 2 |

TABLE 111-continued
| Structure | Compound No | RT (min) | [M + H] | Method |
|---|---|---|---|---|
| 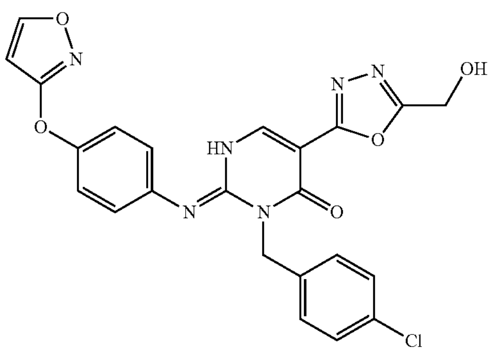 [SMILES: O=c1c(-c2nnc(CO)o2)c[nH]/c(=N\c2ccc(Oc3ccon3)cc2)n1Cc1ccc(Cl)cc1] | I-399 | 493 | 1.66 | 3 |
TABLE 112
| Structure | Compound No | RT (min) | [M + H] | Method |
|---|---|---|---|---|
| 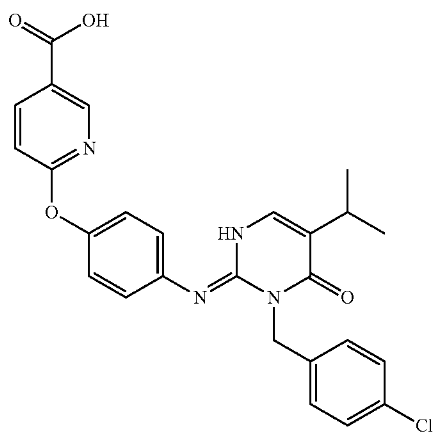 [SMILES: CC(C)c1c[nH]/c(=N\c2ccc(Oc3ccc(C(=O)O)cn3)cc2)n(Cc2ccc(Cl)cc2)c1=O] | I-400 | 491 | 2.13 | 3 |
| 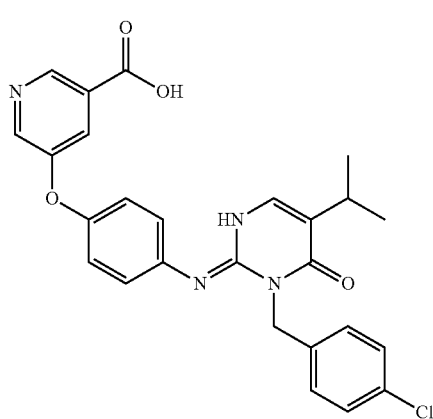 [SMILES: CC(C)c1c[nH]/c(=N\c2ccc(Oc3cncc(C(=O)O)c3)cc2)n(Cc2ccc(Cl)cc2)c1=O] | I-401 | 491 | 2.05 | 3 |

TABLE 112-continued

| Structure | Compound No | RT (min) | [M + H] | Method |
|---|---|---|---|---|
| (structure) | I-402 | 552 | 2.07 | 3 |
| (structure) | I-403 | 478 | 1.53 | 3 |
| (structure) | I-404 | 479 | 1.54 | 3 |

TABLE 113

| Structure | Compound No | RT (min) | [M + H] | Method |
|---|---|---|---|---|
| (structure) | I-405 | 562 | 1.98 | 3 |

TABLE 113-continued

| Structure | Compound No | RT (min) | [M + H] | Method |
|---|---|---|---|---|
| 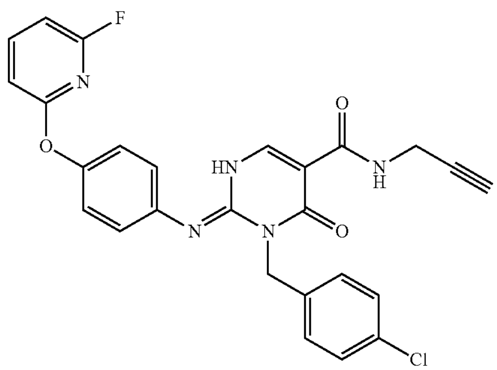 [SMILES: C#CCNC(=O)c1c[nH]/c(=N\c2ccc(Oc3cccc(F)n3)cc2)n(Cc2ccc(Cl)cc2)c1=O] | I-406 | 504 | 2.27 | 3 |
| 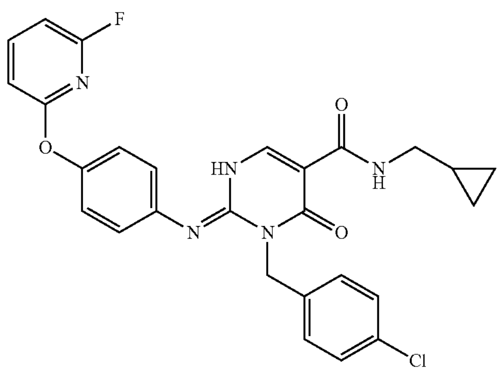 [SMILES: O=C(NCC1CC1)c1c[nH]/c(=N\c2ccc(Oc3cccc(F)n3)cc2)n(Cc2ccc(Cl)cc2)c1=O] | I-407 | 520 | 2.43 | 3 |
| 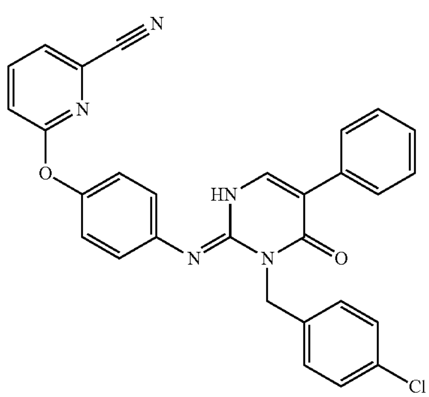 [SMILES: N#Cc1cccc(Oc2ccc(/N=c3\[nH]cc(-c4ccccc4)c(=O)n3Cc3ccc(Cl)cc3)cc2)n1] | I-408 | 506 | 2.55 | 3 |
| 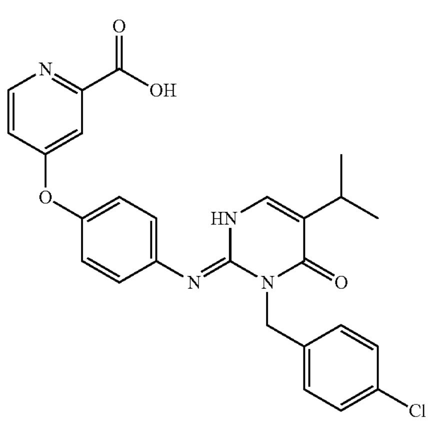 | I-409 | 491 | 1.72 | 3 |

TABLE 114

| Structure | Compound No | RT (min) | [M + H] | Method |
|---|---|---|---|---|
| 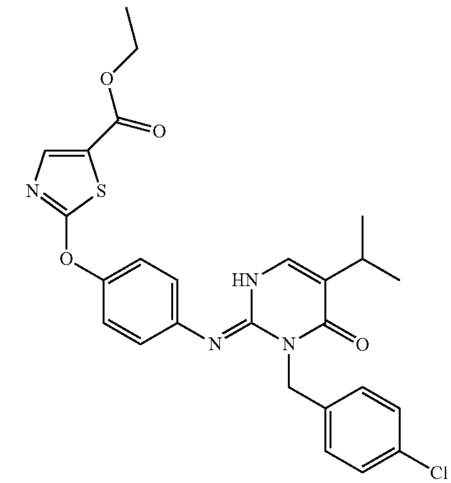 [SMILES: CCOC(=O)c1cnc(Oc2ccc(/N=c3\[nH]cc(C(C)C)c(=O)n3Cc3ccc(Cl)cc3)cc2)s1] | I-410 | 525 | 2.32 | 3 |
| 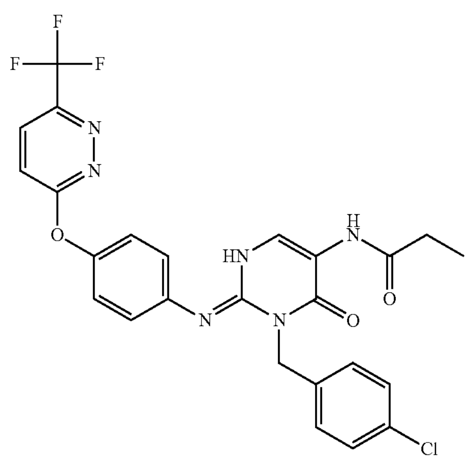 [SMILES: CCC(=O)Nc1c[nH]/c(=N\c2ccc(Oc3ccc(C(F)(F)F)nn3)cc2)n(Cc2ccc(Cl)cc2)c1=O] | I-411 | 545 | 2.13 | 3 |
| 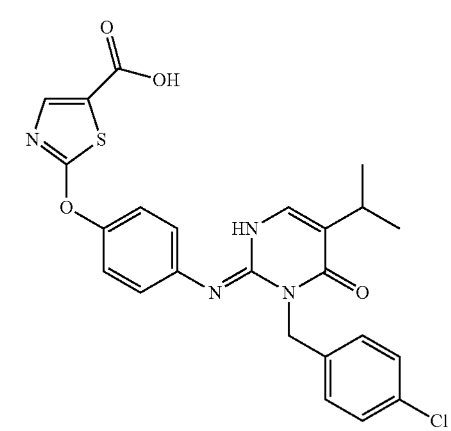 [SMILES: CC(C)c1c[nH]/c(=N\c2ccc(Oc3ncc(C(=O)O)s3)cc2)n(Cc2ccc(Cl)cc2)c1=O] | I-412 | 497 | 2.22 | 3 |

TABLE 114-continued

| Structure | Compound No | RT (min) | [M + H] | Method |
|---|---|---|---|---|
| (structure) | I-413 | 492 | 1.90 | 3 |
| (structure) | I-414 | 492 | 1.76 | 3 |

TABLE 115

| Structure | Compound No | RT (min) | [M + H] | Method |
|---|---|---|---|---|
| (structure) | I-415 | 506 | 1.88 | 3 |
| (structure) | I-416 | 506 | 2.04 | 3 |

TABLE 115-continued

| Structure | Compound No | RT (min) | [M + H] | Method |
|---|---|---|---|---|
| 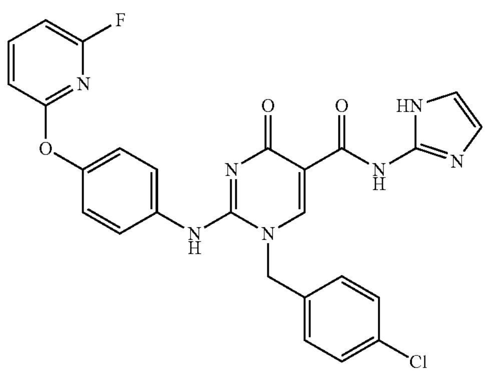 [SMILES: O=C(Nc1ncc[nH]1)c1cn(Cc2ccc(Cl)cc2)c(Nc2ccc(Oc3cccc(F)n3)cc2)nc1=O] | I-417 | 532 | 1.47 | 3 |
| 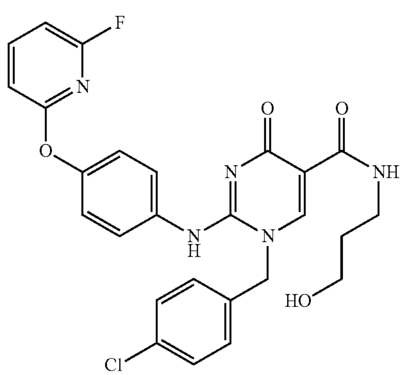 [SMILES: O=C(NCCCO)c1cn(Cc2ccc(Cl)cc2)c(Nc2ccc(Oc3cccc(F)n3)cc2)nc1=O] | I-418 | 524 | 1.95 | 3 |
| 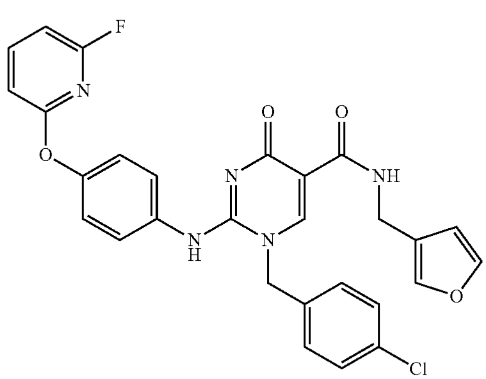 [SMILES: O=C(NCc1ccoc1)c1cn(Cc2ccc(Cl)cc2)c(Nc2ccc(Oc3cccc(F)n3)cc2)nc1=O] | I-419 | 546 | 2.29 | 3 |

TABLE 116

| Structure | Compound No | RT (min) | [M + H] | Method |
|---|---|---|---|---|
| 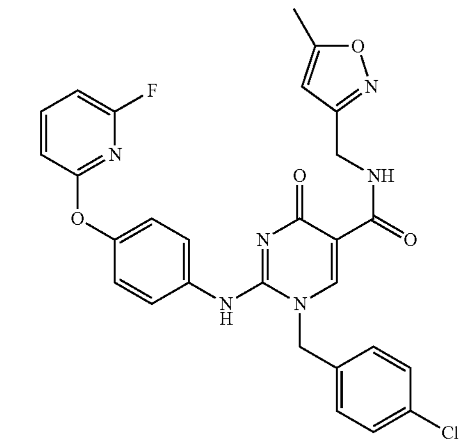 [SMILES: Cc1cc(CNC(=O)c2cn(Cc3ccc(Cl)cc3)c(Nc3ccc(Oc4cccc(F)n4)cc3)nc2=O)no1] | I-420 | 561 | 2.21 | 3 |
| 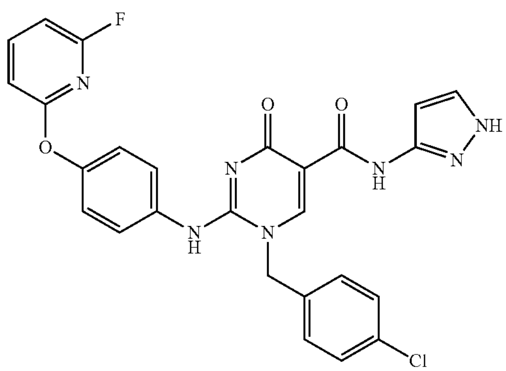 [SMILES: O=C(Nc1cc[nH]n1)c1cn(Cc2ccc(Cl)cc2)c(Nc2ccc(Oc3cccc(F)n3)cc2)nc1=O] | I-421 | 532 | 2.05 | 3 |
| 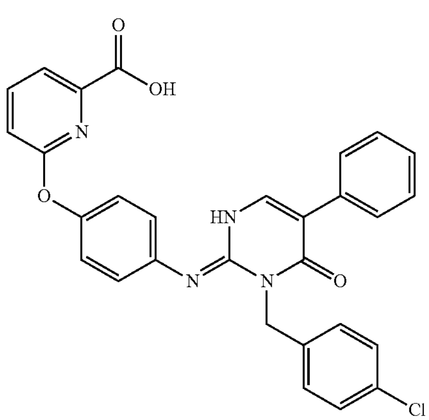 [SMILES: O=C(O)c1cccc(Oc2ccc(/N=c3\[nH]cc(-c4ccccc4)c(=O)n3Cc3ccc(Cl)cc3)cc2)n1] | I-422 | 525 | 2.29 | 3 |

TABLE 116-continued

| Structure | Compound No | RT (min) | [M + H] | Method |
|---|---|---|---|---|
| 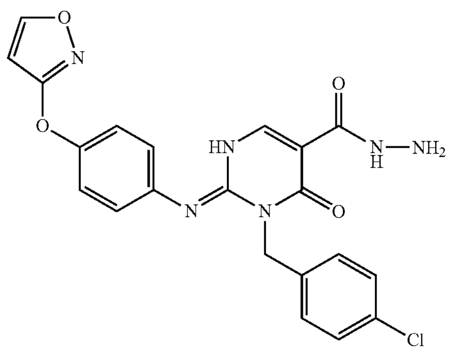 [SMILES: NNC(=O)c1c[nH]/c(=N\c2ccc(Oc3ccon3)cc2)n(Cc2ccc(Cl)cc2)c1=O] | I-423 | 453 | 1.64 | 3 |
| 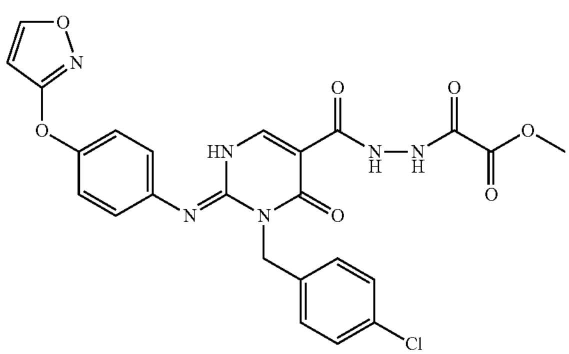 [SMILES: COC(=O)C(=O)NNC(=O)c1c[nH]/c(=N\c2ccc(Oc3ccon3)cc2)n(Cc2ccc(Cl)cc2)c1=O] | I-424 | 539 | 1.83 | 3 |

TABLE 117

| Structure | Compound No | RT (min) | [M + H] | Method |
|---|---|---|---|---|
| 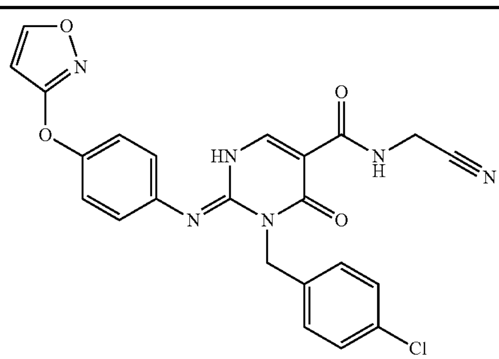 | I-425 | 477 | 1.95 | 3 |

TABLE 117-continued

| Structure | Compound No | RT (min) | [M + H] | Method |
|---|---|---|---|---|
| 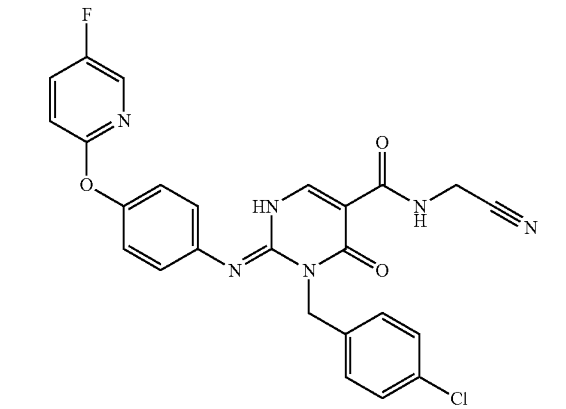 [SMILES: N#CCNC(=O)c1c[nH]/c(=N\c2ccc(Oc3ccc(F)cn3)cc2)n(Cc2ccc(Cl)cc2)c1=O] | I-426 | 505 | 2.12 | 3 |
| 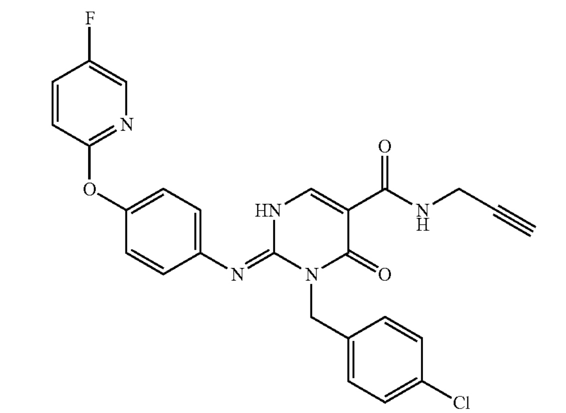 [SMILES: C#CCNC(=O)c1c[nH]/c(=N\c2ccc(Oc3ccc(F)cn3)cc2)n(Cc2ccc(Cl)cc2)c1=O] | I-427 | 504 | 2.23 | 3 |
| 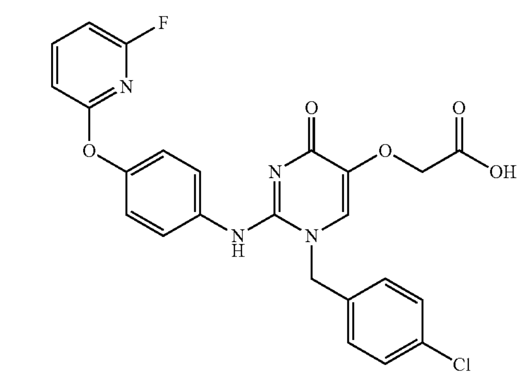 [SMILES: O=C(O)COc1cn(Cc2ccc(Cl)cc2)c(Nc2ccc(Oc3cccc(F)n3)cc2)nc1=O] | I-428 | 497 | 1.75 | 3 |
| 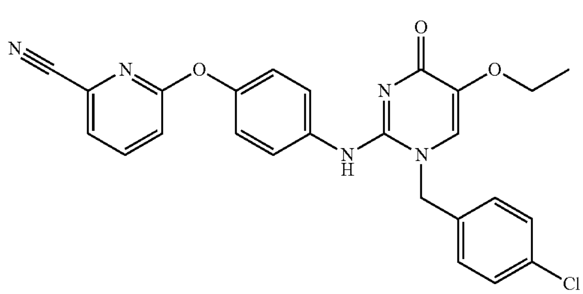 [SMILES: CCOc1cn(Cc2ccc(Cl)cc2)c(Nc2ccc(Oc3cccc(C#N)n3)cc2)nc1=O] | I-429 | 474 | 1.83 | 3 |

TABLE 118

| Structure | Compound No | RT (min) | [M + H] | Method |
|---|---|---|---|---|
| 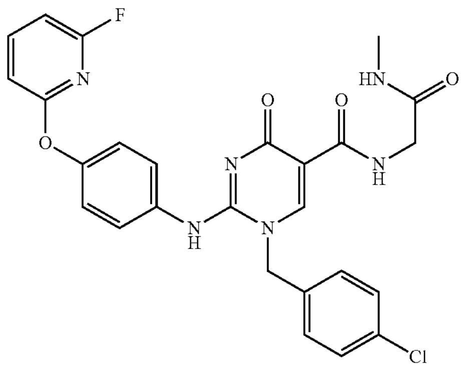 [SMILES: CNC(=O)CNC(=O)c1cn(Cc2ccc(Cl)cc2)c(Nc2ccc(Oc3cccc(F)n3)cc2)nc1=O] | I-430 | 537 | 1.89 | 3 |
| 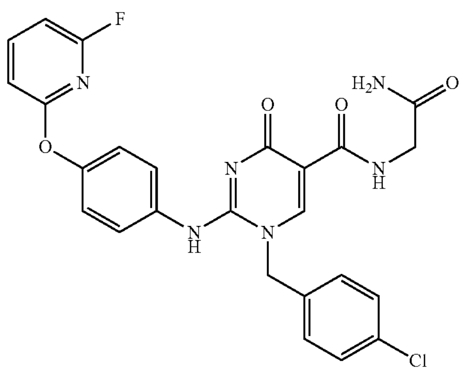 [SMILES: NC(=O)CNC(=O)c1cn(Cc2ccc(Cl)cc2)c(Nc2ccc(Oc3cccc(F)n3)cc2)nc1=O] | I-431 | 523 | 1.84 | 3 |
| 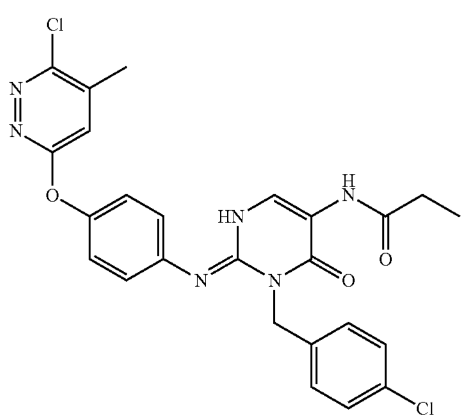 [SMILES: CCC(=O)Nc1c[nH]/c(=N\c2ccc(Oc3cc(C)c(Cl)nn3)cc2)n(Cc2ccc(Cl)cc2)c1=O] | I-432 | 525 | 2.08 | 3 |
| 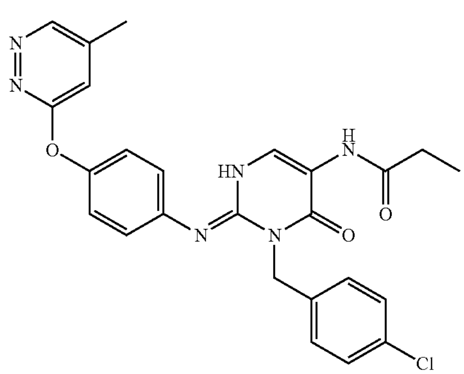 [SMILES: CCC(=O)Nc1c[nH]/c(=N\c2ccc(Oc3cc(C)cnn3)cc2)n(Cc2ccc(Cl)cc2)c1=O] | I-433 | 491 | 1.83 | 3 |

TABLE 118-continued
| Structure | Compound No | RT (min) | [M + H] | Method |
|---|---|---|---|---|
| 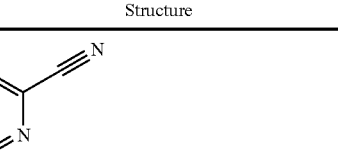 | I-434 | 472 | 2.43 | 3 |
TABLE 119
| Structure | Compound No | RT (min) | [M + H] | Method |
|---|---|---|---|---|
| 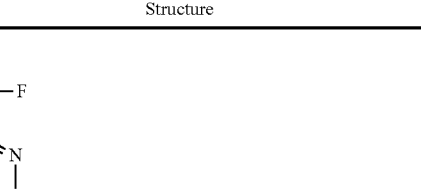 | I-435 | 601 | 2.09 | 3 |
| 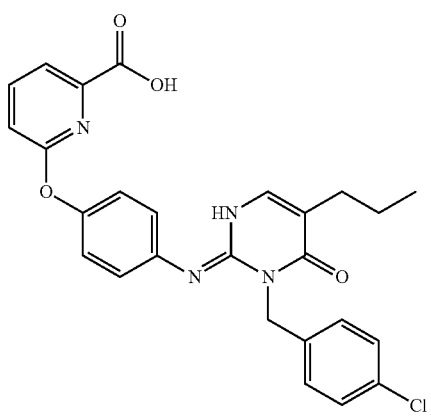 [SMILES: CCCc1c[nH]/c(=N\c2ccc(Oc3cccc(C(=O)O)n3)cc2)n(Cc2ccc(Cl)cc2)c1=O] | I-436 | 491 | 2.13 | 3 |

TABLE 119-continued
| Structure | Compound No | RT (min) | [M + H] | Method |
|---|---|---|---|---|
| 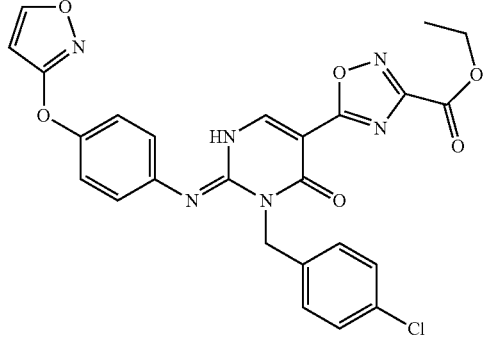 [SMILES: CCOC(=O)c1noc(-c2c[nH]/c(=N\c3ccc(Oc4ccon4)cc3)n(Cc3ccc(Cl)cc3)c2=O)n1] | I-437 | 535 | 2.18 | 3 |
| 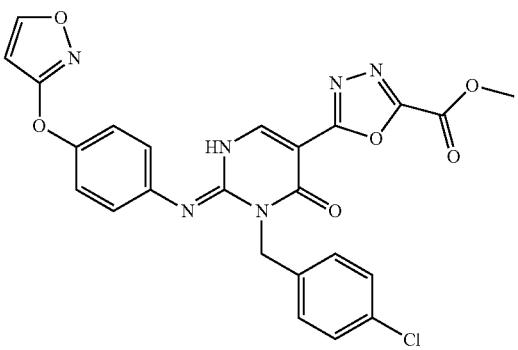 [SMILES: COC(=O)c1nnc(-c2c[nH]/c(=N\c3ccc(Oc4ccon4)cc3)n(Cc3ccc(Cl)cc3)c2=O)o1] | I-438 | 521 | 1.96 | 3 |
| 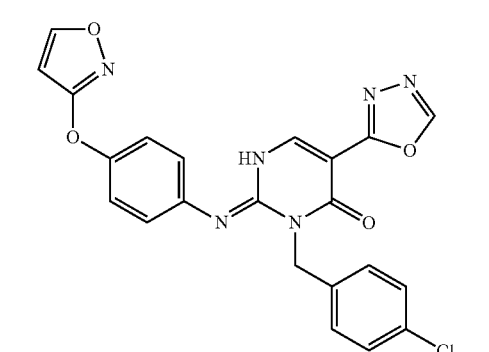 | I-439 | 463 | 1.78 | 3 |

TABLE 120

| Structure | Compound No | RT (min) | [M + H] | Method |
|---|---|---|---|---|
| 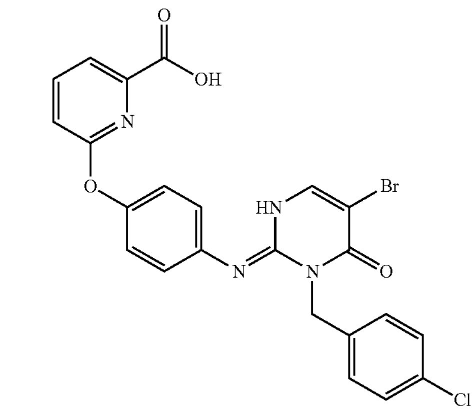 [SMILES: O=C(O)c1cccc(Oc2ccc(/N=c3\[nH]cc(Br)c(=O)n3Cc3ccc(Cl)cc3)cc2)n1] | I-440 | 529 | 2.06 | 3 |
| 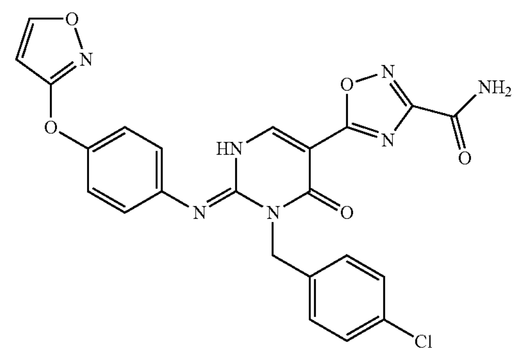 [SMILES: NC(=O)c1noc(-c2c[nH]/c(=N\c3ccc(Oc4ccon4)cc3)n(Cc3ccc(Cl)cc3)c2=O)n1] | I-441 | 506 | 1.77 | 3 |
| 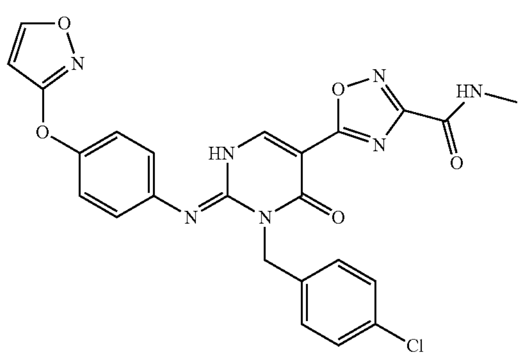 [SMILES: CNC(=O)c1noc(-c2c[nH]/c(=N\c3ccc(Oc4ccon4)cc3)n(Cc3ccc(Cl)cc3)c2=O)n1] | I-442 | 520 | 1.85 | 3 |
| 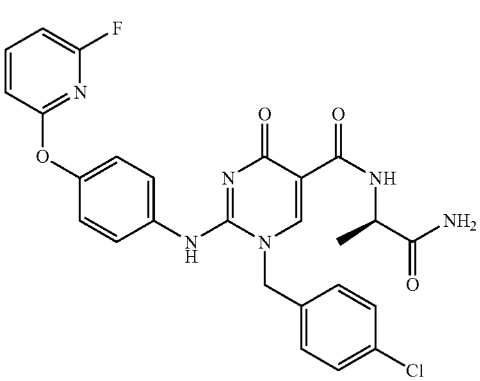 [SMILES: C[C@@H](NC(=O)c1cn(Cc2ccc(Cl)cc2)c(Nc2ccc(Oc3cccc(F)n3)cc2)nc1=O)C(N)=O] | I-443 | 537 | 1.91 | 3 |

TABLE 120-continued

| Structure | Compound No | RT (min) | [M + H] | Method |
|---|---|---|---|---|
| 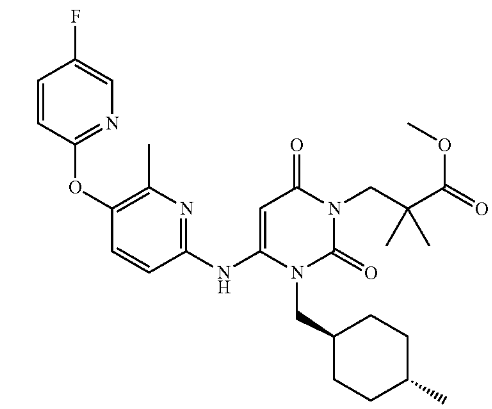 [SMILES: COC(=O)C(C)(C)Cn1c(=O)cc(Nc2ccc(Oc3ccc(F)cn3)c(C)n2)n(C[C@H]2CC[C@H](C)CC2)c1=O] | I-444 | 554 | 2.52 | 3 |

TABLE 121

| Structure | Compound No | RT (min) | [M + H] | Method |
|---|---|---|---|---|
| 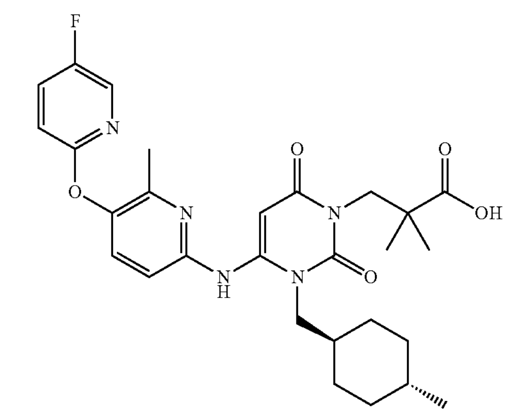 [SMILES: Cc1nc(Nc2cc(=O)n(CC(C)(C)C(=O)O)c(=O)n2C[C@H]2CC[C@H](C)CC2)ccc1Oc1ccc(F)cn1] | I-445 | 540 | 2.21 | 3 |
| 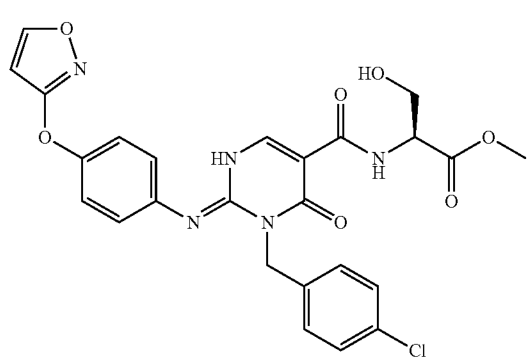 [SMILES: COC(=O)[C@H](CO)NC(=O)c1c[nH]/c(=N\c2ccc(Oc3ccon3)cc2)n(Cc2ccc(Cl)cc2)c1=O] | I-446 | 540 | 1.82 | 3 |

TABLE 121-continued

| Structure | Compound No | RT (min) | [M + H] | Method |
|---|---|---|---|---|
| 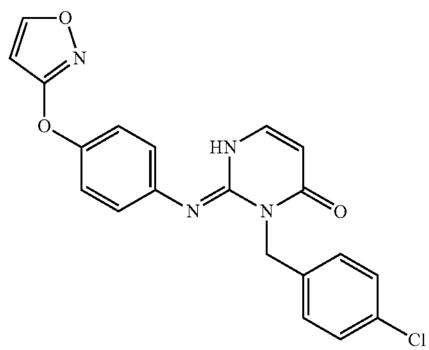 [SMILES: O=c1cc[nH]/c(=N\c2ccc(Oc3ccon3)cc2)n1Cc1ccc(Cl)cc1] | I-447 | 395 | 1.92 | 3 |
| 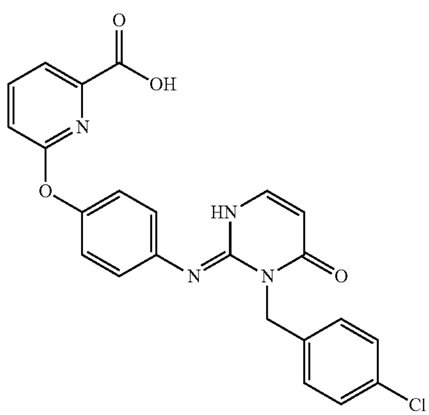 [SMILES: O=C(O)c1cccc(Oc2ccc(/N=c3\[nH]ccc(=O)n3Cc3ccc(Cl)cc3)cc2)n1] | I-448 | 449 | 1.80 | 3 |
| 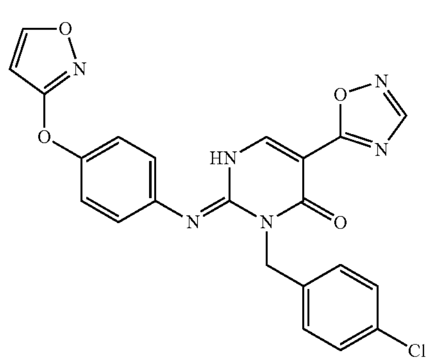 [SMILES: O=c1c(-c2ncno2)c[nH]/c(=N\c2ccc(Oc3ccon3)cc2)n1Cc1ccc(Cl)cc1] | I-449 | 463 | 2.03 | 3 |

TABLE 122

| Structure | Compound No | RT (min) | [M + H] | Method |
|---|---|---|---|---|
| 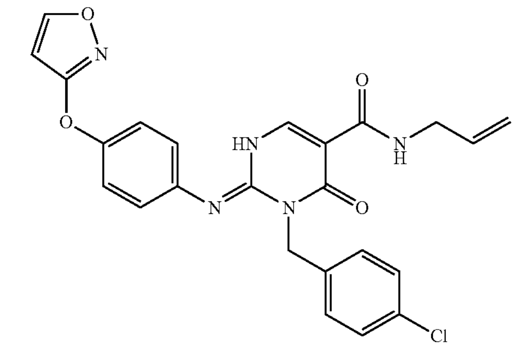 [SMILES: C=CCNC(=O)c1c[nH]/c(=N\c2ccc(Oc3ccon3)cc2)n(Cc2ccc(Cl)cc2)c1=O] | I-450 | 478 | 2.16 | 3 |
| 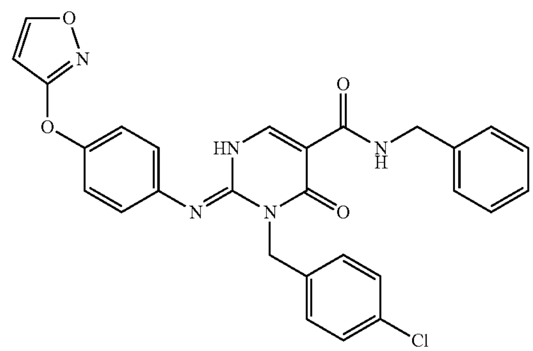 [SMILES: O=C(NCc1ccccc1)c1c[nH]/c(=N\c2ccc(Oc3ccon3)cc2)n(Cc2ccc(Cl)cc2)c1=O] | I-451 | 528 | 2.35 | 3 |
| 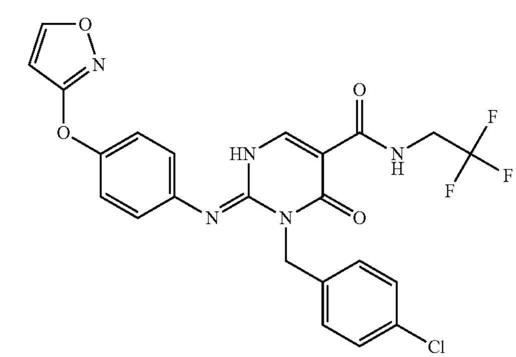 [SMILES: O=C(NCC(F)(F)F)c1c[nH]/c(=N\c2ccc(Oc3ccon3)cc2)n(Cc2ccc(Cl)cc2)c1=O] | I-452 | 520 | 2.24 | 3 |
| 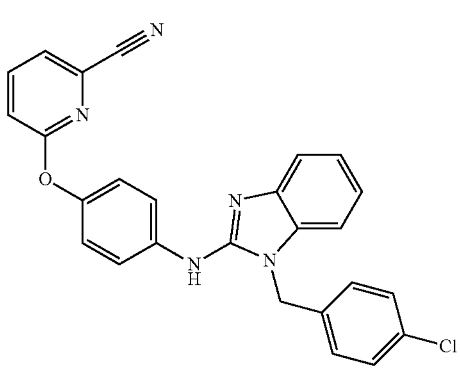 [SMILES: N#Cc1cccc(Oc2ccc(Nc3nc4ccccc4n3Cc3ccc(Cl)cc3)cc2)n1] | I-453 | 452 | 1.63 | 3 |

TABLE 122-continued

| Structure | Compound No | RT (min) | [M + H] | Method |
|---|---|---|---|---|
| 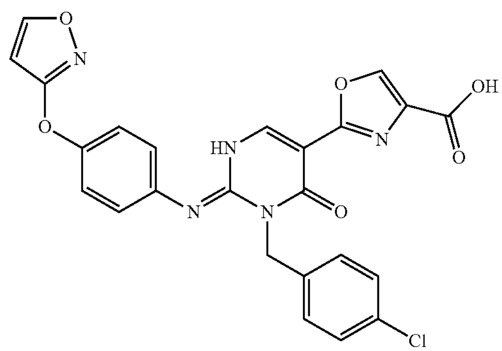 [SMILES: O=C(O)c1coc(-c2c[nH]/c(=N\c3ccc(Oc4ccon4)cc3)n(Cc3ccc(Cl)cc3)c2=O)n1] | I-454 | 506 | 1.80 | 3 |
| 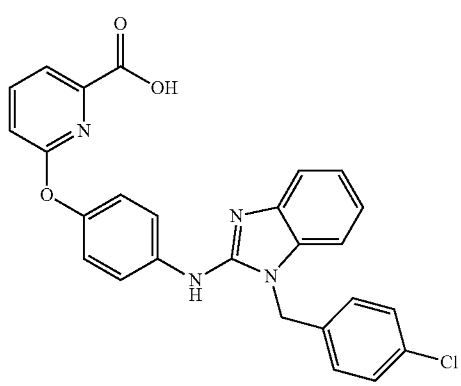 [SMILES: O=C(O)c1cccc(Oc2ccc(Nc3nc4ccccc4n3Cc3ccc(Cl)cc3)cc2)n1] | I-456 | 471 | 1.49 | 3 |

TABLE 123

| Structure | Compound No | RT (min) | [M + H] | Method |
|---|---|---|---|---|
| 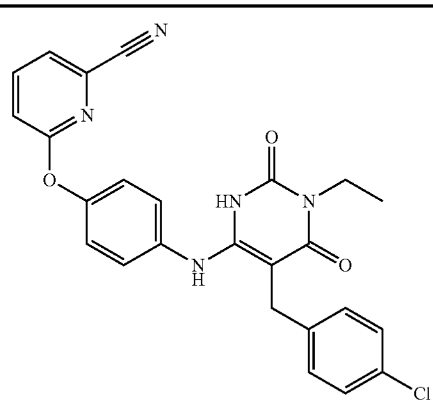 | I-456 | 474 | 2.02 | 3 |

TABLE 123-continued

| Structure | Compound No | RT (min) | [M + H] | Method |
|---|---|---|---|---|
| 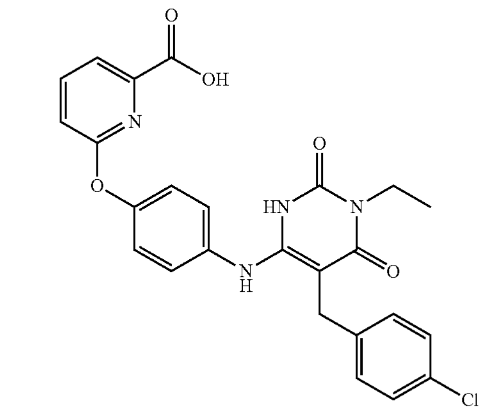 [SMILES: CCn1c(=O)[nH]c(Nc2ccc(Oc3cccc(C(=O)O)n3)cc2)c(Cc2ccc(Cl)cc2)c1=O] | I-457 | 493 | 1.83 | 3 |
| 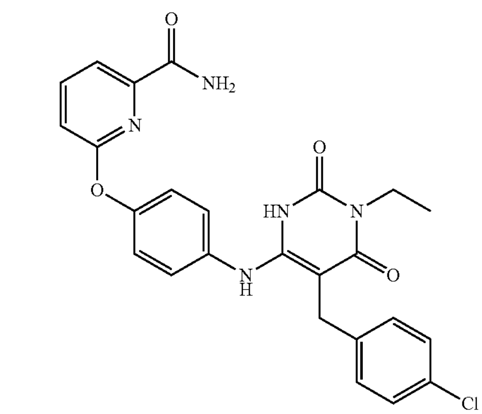 [SMILES: CCn1c(=O)[nH]c(Nc2ccc(Oc3cccc(C(N)=O)n3)cc2)c(Cc2ccc(Cl)cc2)c1=O] | I-458 | 492 | 1.79 | 3 |
| 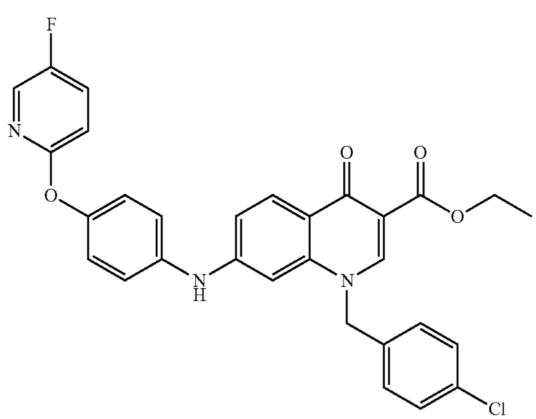 [SMILES: CCOC(=O)c1cn(Cc2ccc(Cl)cc2)c2cc(Nc3ccc(Oc4ccc(F)cn4)cc3)ccc2c1=O] | I-459 | 544 | 2.17 | 3 |

TABLE 123-continued
| Structure | Compound No | RT (min) | [M + H] | Method |
|---|---|---|---|---|
| 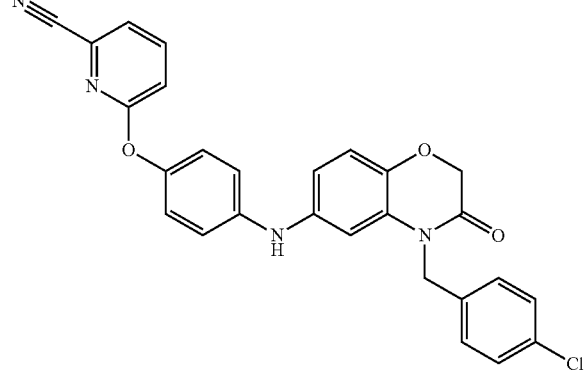 | I-460 | 483 | 2.37 | 3 |
TABLE 124
| Structure | Compound No | RT (min) | [M + H] | Method |
|---|---|---|---|---|
| 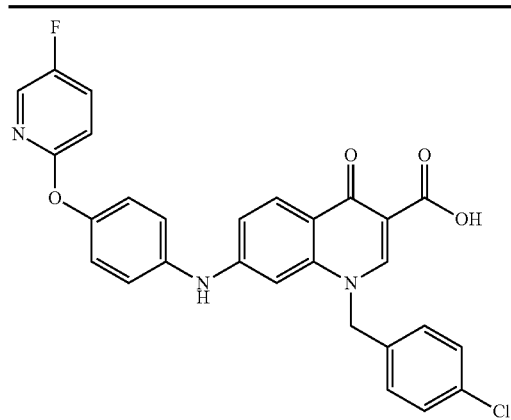 | I-461 | 516 | 2.20 | 3 |
| 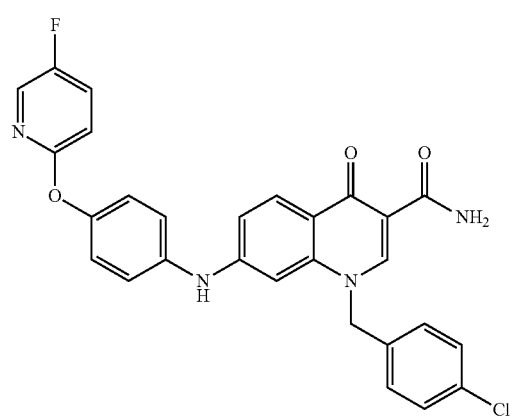 [SMILES: NC(=O)c1cn(Cc2ccc(Cl)cc2)c2cc(Nc3ccc(Oc4ccc(F)cn4)cc3)ccc2c1=O] | I-462 | 515 | 2.01 | 3 |

TABLE 124-continued

| Structure | Compound No | RT (min) | [M + H] | Method |
|---|---|---|---|---|
| 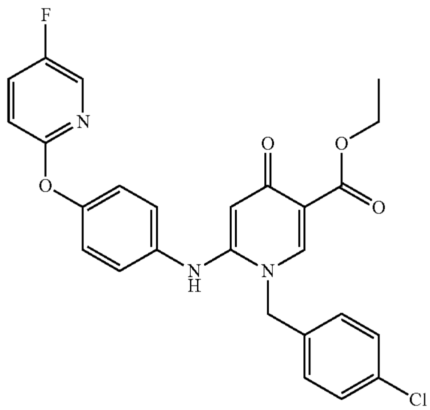 [SMILES: CCOC(=O)c1cn(Cc2ccc(Cl)cc2)c(Nc2ccc(Oc3ccc(F)cn3)cc2)cc1=O] | I-463 | 494 | 1.73 | 3 |
| 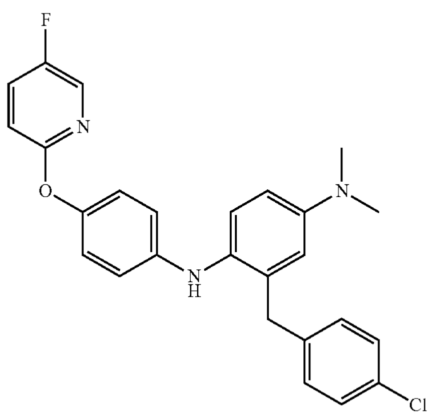 [SMILES: CN(C)c1ccc(Nc2ccc(Oc3ccc(F)cn3)cc2)c(Cc2ccc(Cl)cc2)c1] | I-464 | 448 | 2.21 | 3 |
| 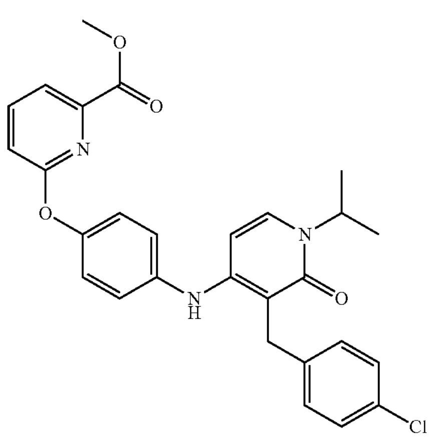 [SMILES: COC(=O)c1cccc(Oc2ccc(Nc3ccn(C(C)C)c(=O)c3Cc3ccc(Cl)cc3)cc2)n1] | I-465 | 504 | 2.27 | 3 |

TABLE 125
| Structure | Compound No | RT (min) | [M + H] | Method |
|---|---|---|---|---|
| 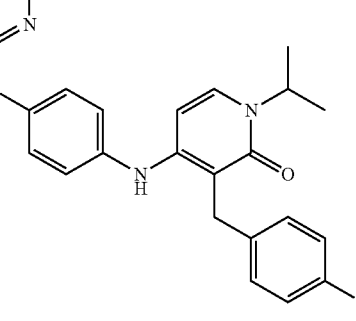 | I-466 | 490 | 2.03 | 3 |
| 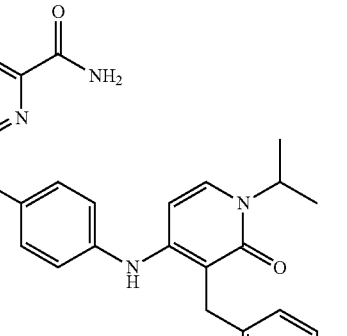 | I-467 | 489 | 2.01 | 3 |
| 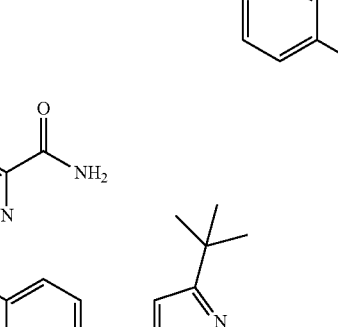 | I-468 | 476 | 2.34 | 3 |
| 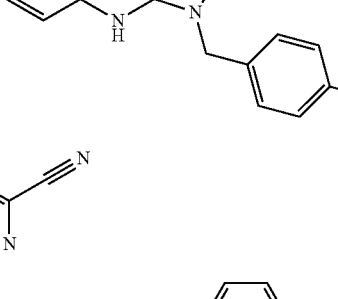 | I-469 | 436 | 1.51 | 3 |

TABLE 125-continued

| Structure | Compound No | RT (min) | [M + H] | Method |
|---|---|---|---|---|
| (structure) | I-470 | 455 | 1.38 | 3 |

TABLE 126

| Structure | Compound No | RT (min) | [M + H] | Method |
|---|---|---|---|---|
| (structure) | I-471 | 531 | 2.39 | 3 |
| (structure) | I-472 | 517 | 2.17 | 3 |

TABLE 126-continued

| Structure | Compound No | RT (min) | [M + H] | Method |
|---|---|---|---|---|
| 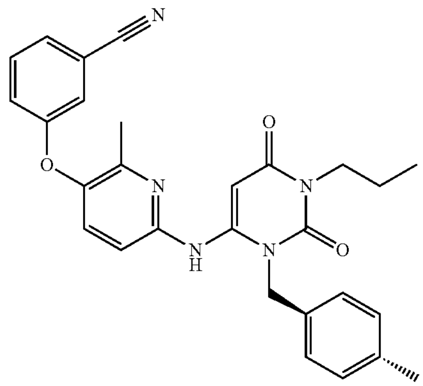 | I-473 | 488 | 2.56 | 3 |
| 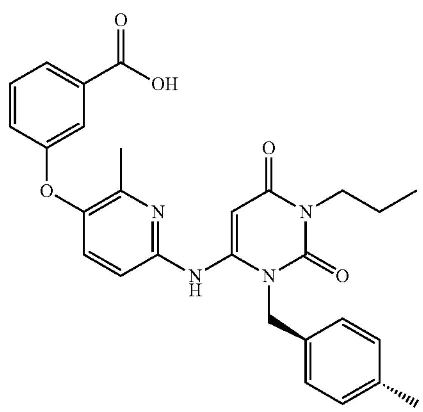 | I-474 | 507 | 2.33 | 3 |
| 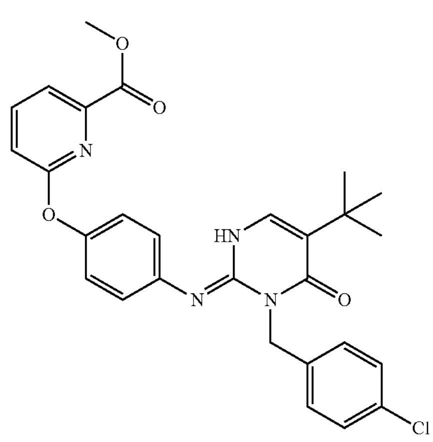 [SMILES: COC(=O)c1cccc(Oc2ccc(/N=c3\[nH]cc(C(C)(C)C)c(=O)n3Cc3ccc(Cl)cc3)cc2)n1] | I-475 | 519 | 2.51 | 3 |

TABLE 127

| Structure | Compound No | RT (min) | [M + H] | Method |
|---|---|---|---|---|
| 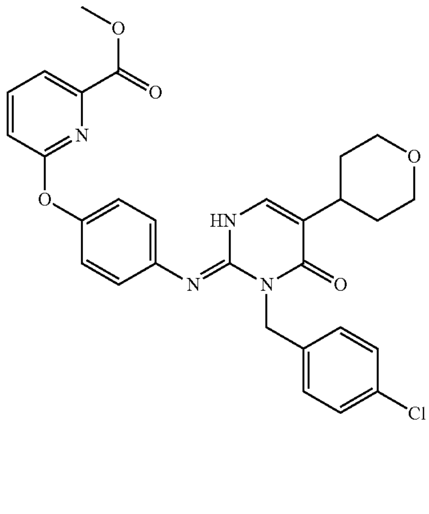 [SMILES: COC(=O)c1cccc(Oc2ccc(/N=c3\[nH]cc(C4CCOCC4)c(=O)n3Cc3ccc(Cl)cc3)cc2)n1] | I-476 | 547 | 2.16 | 3 |
| 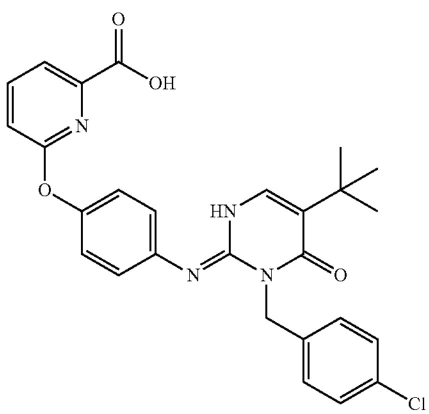 [SMILES: CC(C)(C)c1c[nH]/c(=N\c2ccc(Oc3cccc(C(=O)O)n3)cc2)n(Cc2ccc(Cl)cc2)c1=O] | I-477 | 505 | 2.26 | 3 |
| 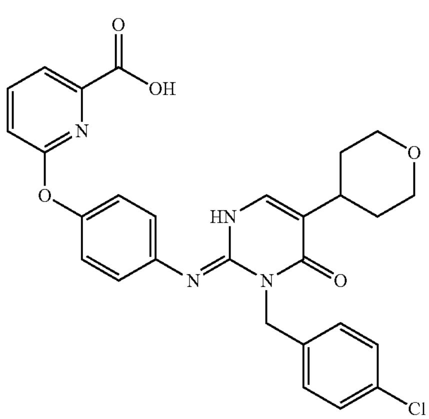 [SMILES: O=C(O)c1cccc(Oc2ccc(/N=c3\[nH]cc(C4CCOCC4)c(=O)n3Cc3ccc(Cl)cc3)cc2)n1] | I-478 | 533 | 1.93 | 3 |

TABLE 127-continued

| Structure | Compound No | RT (min) | [M + H] | Method |
|---|---|---|---|---|
| 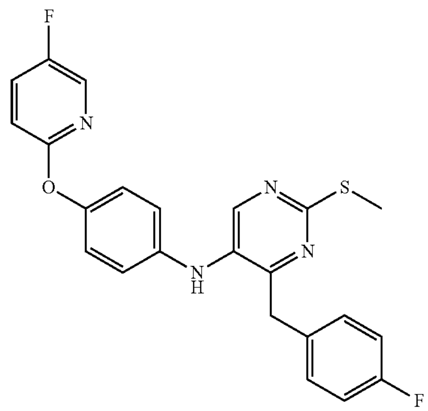 [SMILES: CSc1ncc(Nc2ccc(Oc3ccc(F)cn3)cc2)c(Cc2ccc(F)cc2)n1] | I-479 | 437 | 2.52 | 3 |
| 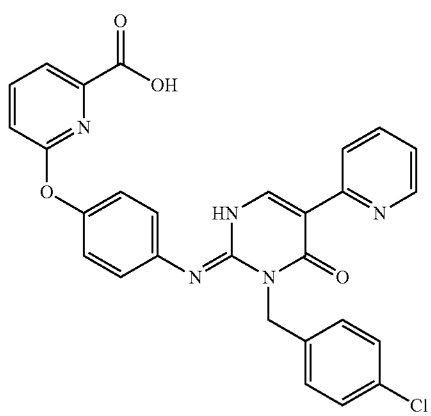 [SMILES: O=C(O)c1cccc(Oc2ccc(/N=c3\[nH]cc(-c4ccccn4)c(=O)n3Cc3ccc(Cl)cc3)cc2)n1] | I-480 | 526 | 1.44 | 3 |

TABLE 128

| Structure | Compound No | RT (min) | [M + H] | Method |
|---|---|---|---|---|
| 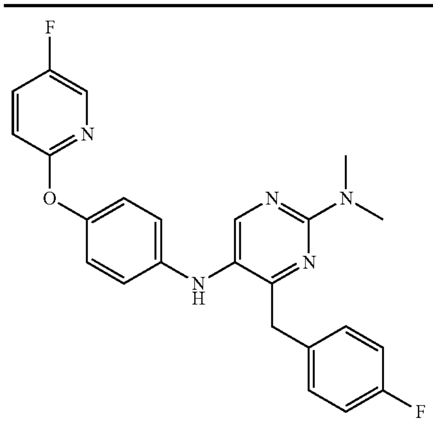 | I-481 | 434 | 2.50 | 3 |

TABLE 128-continued

| Structure | Compound No | RT (min) | [M + H] | Method |
|---|---|---|---|---|
| (structure shown) | I-482 | 504 | 2.24 | 3 |
| (structure shown) | I-483 | 532 | 1.90 | 3 |

TEST EXAMPLES

Test Example 1-1

Evaluation of Human P2X$_3$ Receptor Inhibitory Activity

Stably expressing cell line (C6BU-1 cell transfected with human P2X$_3$ receptor gene (GenBank accession number Y07683) was used. The cells were seeded in a 96-well microtiter plate at a concentration of 8000 cells/well and cultured in the medium (7.0% fetal bovine serum, 7.0% horse serum, 1% antibiotic and antifungal in DMEM) for one day at 37° C. under 5% carbon dioxide atmosphere. The medium was replaced with 4 µM Fluo-3-AM solution (20 mM HEPES, 137 mM NaCl, 5.27 mM KCl, 0.9 mM MgCl$_2$, 1.26 mM CaCl$_2$, 5.6 mM D-glucose, 2.5 mM probenecid, 1% BSA, and 0.08% Pluronic F-127, pH 7.5) and incubated at 37° C. under 5% dioxide carbon atmosphere for one hour. The plate was washed with washing buffer (20 mM HEPES, 137 mM NaCl, 5.27 mM KCl, 0.9 mM MgCl$_2$, 1.26 mM CaCl$_2$, 5.6 mM D-glucose, 2.5 mM probenecid, pH7.5), and each well was added with 40 µL of this buffer. The plate was placed in High-Throughput Screening System. FDSS 3000 (Hamamatsu Photonics K.K.). Measurement of fluorescence intensity by FDSS 3000 was started, and 40 µL of DMSO solutions containing different concentrations of the test compound as prepared by dilution with dilution buffer (20 mM HEPES, 137 mM NaCl, 5.27 mM KCl, 0.9 mM MgCl$_2$, 1.26 mM CaCl$_2$, 5.68 mM D-glucose, 2.5 mM probenecid, 0.1% Pluronic F-127, pH7.5) were dispensed to each well through the built-in automatic dispenser. Five minutes after, 50 nM ATP solution (50 µL) prepared by dilution with the dilution buffer was dispensed through the built-in automatic dispenser, and the measurement of fluorescence intensity was continued for 4 min. For each well, the specific maximum fluorescence intensity was calculated as the ratio of the maximum fluorescence intensity after addition of the ATP solution to the fluorescence intensity at the starting of the measurement. The 50% inhibitory concentration (IC$_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. IC$_{50}$ was calculated using Microsoft Excel (Microsoft Corporation) and XLfit (idbs Ltd.)

Test Example 1-2

Evaluation of Human P2X$_3$ Receptor Inhibitory Activity

Stably expressing cell line (C6BU-1 cell transfected with human P2X$_3$ receptor gene (GenBank accession number Y07683) was used. The cells were seeded in a 384-well microtiter plate at a concentration of 3000 cells/well and cultured in the medium (7.0% fetal bovine serum, 7.0% horse serum, 1% antibiotic and antifungal in DMEM) for one day at 37° C. under 5% carbon dioxide atmosphere. The medium was replaced with 4 μM Fluo-3-AM solution (20 mM HEPES, 1.37 mM NaCl, 5.27 mM KCl, 0.9 mM $MgCl_2$, 1.26 mM $CaCl_2$, 5.6 mM D-glucose, 2.5 mM probenecid, 0.5% BSA, and 0.04% Pluronic F-127, pH 7.5) and incubated at 37° C. under 5% dioxide carbon atmosphere for one hour. The plate was washed with washing buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, pH7.5), and each well was added with 20 μL of this buffer. The plate was placed in High-Throuphput Screening System FLIPR 384 (Molecular Device Co.). Measurement of fluorescence intensity by FLIPR 384 was started, and 20 μL of DMSO solutions containing different concentrations of the test compound as prepared by dilution with dilution buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH 7.5) were dispensed to each well through the built-in automatic dispenser. Five minutes after, 150 nM ATP solution (25 μL) prepared by dilution with the dilution buffer was dispensed through the built-in automatic dispenser, and the measurement of fluorescence intensity was continued for 4 min. For each well, the specific maximum fluorescence intensity was calculated as the ratio of the maximum fluorescence intensity after addition of the ATP solution to the fluorescence intensity at the starting of the measurement. The 50% inhibitory concentration ($IC_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. The specific maximum fluorescence intensity and $IC_{50}$ were calculated using Spotfire (Science & Technology Systems, Inc.)

The data of the compounds of the present invention are as shown in the following Tables. The data of the compounds I-001 to I-300 are the results by the method mentioned in Test Example 1-1, and the data of the compounds I-301 to I-483 are the results by the method mentioned in Test Example 1-2.

TABLE 129

| Compound No | P2X3 IC50 (μM) |
|---|---|
| I-001 | 0.011 |
| I-002 | 0.281 |
| I-003 | 0.102 |
| I-004 | 0.151 |
| I-005 | 0.017 |
| I-006 | 0.005 |
| I-007 | 0.023 |
| I-008 | 0.038 |
| I-009 | 0.005 |
| I-010 | 0.004 |
| I-011 | 0.002 |
| I-012 | 0.002 |
| I-013 | 0.002 |
| I-014 | 0.146 |
| I-015 | 0.160 |
| I-016 | 0.150 |
| I-017 | 0.401 |
| I-018 | 0.013 |
| I-019 | 0.135 |
| I-020 | 0.050 |
| I-021 | 0.020 |
| I-022 | 0.094 |

TABLE 129-continued

| Compound No | P2X3 IC50 (μM) |
|---|---|
| I-023 | 0.003 |
| I-024 | 0.014 |
| I-025 | 0.006 |
| I-026 | 0.003 |
| I-027 | 0.004 |
| I-028 | 0.001 |
| I-029 | 0.236 |
| I-030 | 0.005 |
| I-031 | 0.054 |
| I-032 | 0.034 |
| I-033 | 0.001 |
| I-034 | 0.014 |
| I-035 | 0.190 |
| I-036 | 0.022 |
| I-037 | 0.034 |
| I-038 | 0.002 |
| I-039 | <0.004 |
| I-040 | 0.003 |
| I-041 | 0.003 |

TABLE 130

| Compound No | P2X3 IC50 (μM) |
|---|---|
| I-042 | 0.014 |
| I-043 | 0.007 |
| I-044 | 0.103 |
| I-045 | 0.226 |
| I-046 | 0.278 |
| I-047 | 0.018 |
| I-048 | 0.022 |
| I-049 | 0.225 |
| I-050 | 0.067 |
| I-051 | 0.027 |
| I-052 | 0.021 |
| I-053 | 0.020 |
| I-054 | 0.043 |
| I-055 | 0.002 |
| I-056 | 0.013 |
| I-057 | 0.269 |
| I-058 | 0.223 |
| I-059 | 0.006 |
| I-060 | 0.160 |
| I-061 | 0.065 |
| I-062 | 0.049 |
| I-063 | 0.422 |
| I-064 | 0.036 |
| I-065 | 0.099 |
| I-066 | 0.081 |
| I-067 | 0.034 |
| I-069 | 0.068 |
| I-070 | 0.028 |
| I-071 | 0.171 |
| I-072 | 0.228 |
| I-073 | 0.140 |
| I-074 | 0.828 |
| I-076 | 0.432 |
| I-077 | 0.191 |
| I-078 | 0.020 |
| I-079 | 0.058 |
| I-080 | 0.020 |
| I-082 | 0.009 |
| I-083 | 0.168 |
| I-084 | 0.103 |
| I-086 | 0.002 |
| I-087 | 0.029 |
| I-088 | 0.049 |
| I-089 | 0.017 |
| I-090 | 0.011 |
| I-091 | 0.003 |
| I-092 | 0.019 |
| I-093 | 0.009 |
| I-094 | 0.010 |
| I-095 | 0.008 |
| I-096 | 0.064 |

TABLE 130-continued

| Compound No | P2X3 IC50 (μM) |
|---|---|
| I-097 | 0.005 |
| I-098 | 0.011 |
| I-099 | 0.534 |
| I-100 | 0.032 |
| I-101 | 0.071 |
| I-102 | 0.267 |
| I-103 | 0.144 |
| I-104 | 0.003 |
| I-105 | 0.005 |
| I-106 | 0.007 |
| I-107 | 0.029 |
| I-108 | 0.440 |
| I-109 | 0.034 |
| I-110 | 0.027 |
| I-111 | 0.022 |
| I-112 | 0.024 |
| I-113 | 0.187 |
| I-114 | 0.017 |
| I-115 | 0.009 |
| I-116 | 0.006 |
| I-117 | 0.026 |
| I-118 | 0.017 |
| I-119 | 0.008 |
| I-120 | 0.006 |
| I-121 | 0.026 |
| I-122 | 0.003 |
| I-123 | 0.024 |
| I-124 | 0.019 |
| I-125 | 0.023 |
| I-126 | 0.003 |
| I-127 | 0.003 |
| I-128 | 0.035 |
| I-129 | 0.061 |
| I-130 | 0.032 |
| I-131 | 0.002 |
| I-132 | 0.002 |
| I-133 | 0.001 |
| I-134 | 0.002 |
| I-135 | 0.002 |
| I-136 | 0.002 |
| I-137 | 0.001 |
| I-138 | 0.004 |
| I-139 | 0.016 |
| I-140 | 0.099 |
| I-141 | 0.467 |
| I-142 | 0.026 |
| I-143 | 0.002 |
| I-144 | 0.035 |
| I-145 | 0.040 |
| I-146 | 0.026 |
| I-147 | 0.112 |
| I-148 | 0.059 |
| I-151 | 0.031 |
| I-152 | 0.291 |
| I-153 | 0.021 |
| I-154 | 0.317 |
| I-155 | 0.017 |
| I-156 | 0.006 |
| I-157 | 0.011 |
| I-158 | 0.011 |
| I-159 | 0.007 |
| I-160 | 0.026 |
| I-161 | 0.022 |
| I-162 | 0.003 |
| I-163 | 0.021 |
| I-164 | 0.010 |
| I-165 | 0.003 |
| I-166 | 0.169 |
| I-167 | 0.035 |
| I-168 | 0.159 |
| I-169 | 0.011 |
| I-170 | 0.054 |
| I-171 | 0.021 |
| I-172 | 0.016 |
| I-173 | 0.004 |
| I-174 | 0.036 |
| I-175 | 0.037 |
| I-177 | 0.014 |

TABLE 130-continued

| Compound No | P2X3 IC50 (μM) |
|---|---|
| I-178 | 0.014 |
| I-179 | 0.359 |
| I-180 | 0.021 |
| I-181 | 0.131 |
| I-182 | 0.052 |
| I-183 | 0.006 |
| I-184 | 0.014 |
| I-185 | 0.158 |
| I-186 | 0.072 |
| I-187 | 0.004 |
| I-188 | 0.006 |

TABLE 131

| Compound No | P2X3 IC50 (μM) |
|---|---|
| I-189 | 0.012 |
| I-190 | 0.006 |
| I-192 | 0.006 |
| I-193 | 0.006 |
| I-194 | 0.658 |
| I-195 | 0.070 |
| I-196 | 0.037 |
| I-197 | 0.045 |
| I-198 | 0.012 |
| I-199 | 0.008 |
| I-200 | 0.010 |
| I-201 | 0.096 |
| I-203 | 0.336 |
| I-204 | 0.198 |
| I-205 | 0.153 |
| I-206 | 0.048 |
| I-207 | 0.252 |
| I-208 | 0.031 |
| I-209 | 0.102 |
| I-210 | 0.017 |
| I-211 | 0.015 |
| I-212 | 0.011 |
| I-213 | 0.027 |
| I-214 | 0.013 |
| I-215 | 0.004 |
| I-216 | 0.006 |
| I-217 | 0.005 |
| I-218 | 0.017 |
| I-219 | 0.014 |
| I-220 | 0.178 |
| I-221 | 0.065 |
| I-222 | 0.047 |
| I-223 | 0.078 |
| I-225 | 0.006 |
| I-226 | 0.208 |
| I-227 | 0.006 |
| I-228 | 0.010 |
| I-229 | 0.007 |
| I-230 | 0.009 |
| I-231 | 0.388 |
| I-233 | 0.236 |
| I-235 | 0.225 |
| I-237 | 0.219 |
| I-238 | 0.990 |
| I-239 | 0.005 |
| I-240 | 0.006 |
| I-241 | 0.008 |
| I-242 | 0.006 |
| I-243 | 0.557 |
| I-244 | 0.646 |
| I-245 | 0.058 |
| I-246 | 0.071 |
| I-247 | 0.096 |
| I-248 | 0.006 |
| I-249 | 0.006 |
| I-251 | 0.118 |
| I-253 | 0.061 |
| I-254 | 0.868 |
| I-255 | 0.147 |

TABLE 131-continued

| Compound No | P2X3 IC50 (μM) |
|---|---|
| I-256 | 0.014 |
| I-257 | 0.041 |
| I-258 | 0.027 |
| I-259 | 0.016 |
| I-260 | 0.036 |
| I-261 | 0.498 |
| I-262 | 0.098 |
| I-264 | 0.015 |
| I-265 | 0.048 |
| I-266 | 0.068 |
| I-267 | 0.045 |
| I-268 | 0.085 |
| I-269 | 0.016 |
| I-270 | 0.175 |
| I-272 | 0.211 |
| I-273 | 0.201 |
| I-274 | 0.356 |
| I-275 | 0.051 |
| I-276 | 0.165 |
| I-277 | 0.172 |
| I-278 | 0.020 |
| I-280 | 0.139 |
| I-281 | 0.041 |
| I-282 | 0.006 |
| I-283 | 0.226 |
| I-284 | 0.042 |
| I-287 | 0.356 |
| I-288 | 0.015 |
| I-289 | 0.024 |
| I-290 | 0.004 |
| I-294 | 0.084 |
| I-295 | 0.618 |
| I-297 | 0.021 |
| I-298 | 0.023 |
| I-299 | 0.018 |
| I-300 | 0.015 |
| I-301 | 0.163 |
| I-303 | 0.109 |
| I-304 | 0.012 |
| I-305 | 0.005 |
| I-306 | 0.019 |
| I-307 | 0.021 |
| I-308 | 0.005 |
| I-309 | 0.009 |
| I-310 | 0.016 |
| I-311 | 0.031 |
| I-312 | 0.007 |
| I-313 | 0.005 |
| I-314 | 0.010 |
| I-315 | 0.010 |
| I-316 | 0.013 |
| I-317 | 0.013 |
| I-318 | 0.027 |
| I-319 | 0.019 |
| I-320 | 0.019 |
| I-321 | 0.150 |
| I-322 | 0.005 |
| I-323 | 0.026 |
| I-324 | 0.014 |
| I-325 | 0.011 |
| I-326 | 0.328 |
| I-327 | 0.034 |
| I-328 | 0.011 |
| I-329 | 0.020 |
| I-330 | 0.366 |
| I-331 | 0.309 |
| I-332 | 0.179 |
| I-333 | 0.149 |
| I-334 | 0.838 |
| I-335 | 0.227 |
| I-336 | 0.041 |
| I-337 | 0.076 |
| I-338 | 0.009 |
| I-339 | 0.009 |
| I-340 | 0.008 |
| I-341 | 0.010 |
| I-342 | 0.010 |
| I-343 | 0.084 |

TABLE 131-continued

| Compound No | P2X3 IC50 (μM) |
|---|---|
| I-344 | 0.004 |
| I-345 | 0.038 |
| I-346 | 0.346 |
| I-347 | 0.152 |

TABLE 132

| Compound No | P2X3 IC50 (μM) |
|---|---|
| I-348 | 0.076 |
| I-349 | 0.073 |
| I-350 | 0.405 |
| I-351 | 0.098 |
| I-352 | 0.369 |
| I-353 | 0.006 |
| I-354 | 0.007 |
| I-355 | 0.053 |
| I-356 | 0.212 |
| I-357 | 0.781 |
| I-358 | 0.023 |
| I-359 | 0.057 |
| I-360 | 0.006 |
| I-361 | 0.032 |
| I-362 | 0.007 |
| I-363 | 0.008 |
| I-364 | 0.004 |
| I-365 | 0.005 |
| I-366 | 0.091 |
| I-367 | 0.471 |
| I-369 | 0.120 |
| I-370 | 0.384 |
| I-371 | 0.080 |
| I-372 | 0.051 |
| I-373 | 0.136 |
| I-374 | 0.046 |
| I-375 | 0.004 |
| I-376 | 0.040 |
| I-377 | 0.037 |
| I-378 | 0.020 |
| I-379 | 0.096 |
| I-380 | 0.004 |
| I-381 | 0.004 |
| I-382 | 0.009 |
| I-383 | 0.013 |
| I-384 | 0.060 |
| I-385 | 0.016 |
| I-386 | 0.015 |
| I-387 | 0.014 |
| I-388 | 0.029 |
| I-389 | 0.010 |
| I-390 | 0.059 |
| I-391 | 0.030 |
| I-392 | 0.128 |
| I-393 | 0.110 |
| I-394 | 0.011 |
| I-395 | 0.022 |
| I-396 | 0.025 |
| I-397 | 0.056 |
| I-398 | 0.022 |
| I-399 | 0.036 |
| I-400 | 0.016 |
| I-401 | 0.012 |
| I-402 | 0.009 |
| I-403 | 0.243 |
| I-404 | 0.102 |
| I-405 | 0.005 |
| I-406 | 0.008 |
| I-407 | 0.068 |
| I-408 | 0.407 |
| I-409 | 0.024 |
| I-410 | 0.626 |
| I-411 | 0.010 |
| I-412 | 0.009 |
| I-413 | 0.897 |
| I-414 | 0.392 |

TABLE 132-continued

| Compound No | P2X3 IC50 (μM) |
| --- | --- |
| I-416 | 0.406 |
| I-418 | 0.045 |
| I-419 | 0.055 |
| I-420 | 0.088 |
| I-421 | 0.017 |
| I-422 | 0.003 |
| I-423 | 0.081 |
| I-425 | 0.021 |
| I-426 | 0.015 |
| I-427 | 0.005 |
| I-428 | 0.289 |
| I-429 | 0.441 |
| I-430 | 0.083 |
| I-431 | 0.044 |
| I-432 | 0.012 |
| I-433 | 0.099 |
| I-434 | 0.193 |
| I-435 | 0.003 |
| I-436 | 0.013 |
| I-437 | 0.124 |
| I-438 | 0.109 |
| I-439 | 0.047 |
| I-440 | 0.015 |
| I-441 | 0.069 |
| I-442 | 0.08 |
| I-443 | 0.036 |
| I-444 | 0.009 |
| I-445 | 0.007 |
| I-446 | 0.047 |
| I-449 | 0.179 |
| I-450 | 0.021 |
| I-451 | 0.104 |
| I-452 | 0.098 |
| I-454 | 0.160 |
| I-456 | 0.009 |
| I-457 | 0.009 |
| I-458 | 0.015 |
| I-463 | 0.026 |
| I-466 | 0.597 |
| I-471 | 0.683 |
| I-472 | 0.015 |
| I-473 | 0.029 |
| I-474 | 0.005 |
| I-476 | 0.066 |
| I-477 | 0.005 |
| I-478 | 0.005 |
| I-480 | 0.007 |
| I-482 | 0.251 |
| I-483 | 0.017 |

The $IC_{50}$ values of the following compounds are also less than 30 μM:
The compounds I-447, I-448, I-455, I-461, I-464, I-465, I-467, I-468, I-470, I-479, and I-481.

The compounds of the present invention effects on $P2X_3$ subtype.

Furthermore, the compounds are considered to exhibit inhibitory activity against $P2X_{2/3}$ receptor also containing $P2X_3$ subtype.

Test Example 2

Evaluation of Rat $P2X_3$ Receptor Inhibitory Activity

Rat $P2X_3$ receptor gene (GenBank accession number NM_031075) is expressed in C6BU-1 cell. The C6BU-1 cells are seeded in a 96-well microtiter plate at a concentration of 2500 cells/well and culture in the medium (7.0% fetal bovine serum, 7.0% horse serum, and 1% antibiotic and antifungal in DMEM) for one day at 37° C. under 5% carbon dioxide atmosphere. The plasmid is transfected into the cells using transfection reagent FuGENE6 (Roche). The transfected cells are cultured in the medium for one day at 37° C. under 5% carbon dioxide atmosphere. The medium is replaced with 4 μM Fluo-3-AM solution (pH17.5) containing 20 mM HEPES, 137 mM NaCl, 5.27 mM KCl, 0.9 mM $MgCl_2$, 1.26 mM $CaCl_2$, 5.6 mM D-glucose, 2.5 mM probenecid, 1% BSA, and 0.08% Pluronic F-127, and incubates at 37° C. under 5% dioxide carbon atmosphere for one hour. The plate is washed with washing buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, pH7.5), and each well is added with 40 μL of this buffer. The plate is placed in High-Throughput Screening System FDSS 3000 (Hamamatsu Photonics K.K.). Measurement of fluorescence intensity by FDSS 3000 is started, and 40 μL of DMSO solutions containing different concentrations of the test compound as prepared by dilution with dilution buffer (20 mM HEPES, 1.37 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH7.5) are dispensed to each well through the built-in automatic dispenser. Five minutes after, 50 nM ATP solution (50 μL) prepared by dilution with the dilution buffer is dispensed through the built-in automatic dispenser, and the measurement of fluorescence intensity is continued for 4 min. For each well, the specific maximum fluorescence intensity is calculated as the ratio of the maximum fluorescence intensity after addition of the ATP solution to the fluorescence intensity at the starting of the measurement. The 50% inhibitory concentration ($IC_{50}$) is calculated under the assumption that the specific maximum fluorescence intensity without test compound is 0% inhibition and that the specific maximum fluorescence intensity when the dilution buffer is added in place of ATP solution is 100% inhibition, to evaluate the inhibitory activity of the test compound. FDSS software (Hamamatsu Photonics K.K.) is used for calculation of the specific maximum fluorescence intensity. $IC_{50}$ is calculated using Microsoft Excel (Microsoft Corporation) and XLfit (idbs Ltd.).

Test Example 3-1

Evaluation of Rat $P2X_3$ Receptor Inhibitory Activity in the Presence of Rat Serum Albumin (RSA)

Rat $P2X_3$ receptor gene (GenBank accession number NM_031075) is expressed in C6BU-1 cell. The C6BU-1 cells are seeded in a 96-well microtiter plate at a concentration of 2500 cells/well and culture in the medium (8.3% fetal bovine serum, 8.3% horse serum, and 1% antibiotic and antifungal in DMEM) for one day at 37° C. under 5% carbon dioxide atmosphere. The plasmid is transfected into the cells using transfection reagent FuGENE6 (Roche). The transfected cells are cultured in the medium for one day at 37° C. under 5% carbon dioxide atmosphere. The medium is replaced with 4 μM Fluo-3-AM solution (pH7.5) containing 20 mM HEPES, 137 mM NaCl, 5.27 mM KCl, 0.9 mM $MgCl_2$, 1.26 mM $CaCl_2$, 5.6 mM D-glucose, 2.5 mM probenecid, 10% BSA, and 0.08% Pluronic F-127, and incubates at 37° C. under 5% dioxide carbon atmosphere for one hour. The plate is washed with washing buffer (20 mM HEPES, 1.37 mM NaCl, 5.27 mM KCl, 0.9 mM $MgCl_2$, 1.26 mM $CaCl_2$, 5.6 mM D-glucose, 2.5 mM probenecid, pH7.5), and each well is added with 40 μL of this buffer. The plate is placed in High-Throughput Screening System FDSS 3000 (Hamamatsu Photonics K.K.). Measurement of fluorescence intensity by FDSS 3000 is started, and 40 μL of DMSO solutions containing 1% RSA (final concentrations)

and different concentrations of the test compound as prepared by dilution with dilution buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH7.5) are dispensed to each well through the built-in automatic dispenser. Five minutes after, 50 nM ATP solution (50 µL) prepared by dilution with the dilution buffer is dispensed through the built-in automatic dispenser, and the measurement of fluorescence intensity is continued for 4 min. For each well, the specific maximum fluorescence intensity is calculated as the ratio of the maximum fluorescence intensity after addition of the ATP solution to the fluorescence intensity at the starting of the measurement. The 50% inhibitory concentration ($IC_{50}$) is calculated under the assumption that the specific maximum fluorescence intensity without test compound is 0% inhibition and that the specific maximum fluorescence intensity when the dilution buffer is added in place of ATP solution is 100% inhibition, to evaluate the inhibitory activity of the test compound. FDSS software (Hamamatsu Photonics K.K.) is used for calculation of the specific maximum fluorescence intensity. $IC_{50}$ is calculated using Microsoft Excel (Microsoft Corporation) and XLfit (idbs Ltd.).

Test Example 3-2

Evaluation of Rat $P2X_3$ Receptor Inhibitory Activity in the Presence of Rat Serum Albumin (RSA)

Rat $P2X_3$ receptor gene (GenBank accession number NM_031075) was expressed in C6BU-1 cell. The C6BU-1 cells were seeded in a 96-well microtiter plate at a concentration of 2500 cells/well and cultured in the medium (7.0% fetal bovine serum, 7.0% horse serum, and 1% antibiotic and antifungal in DMEM) for one day at 37° C. under 5% carbon dioxide atmosphere. The plasmid was transfected into the cells using transfection reagent FuGENEG (Roche). The transfected cells were cultured in the medium for one day at 37° C. under 5% carbon dioxide atmosphere. The medium was replaced with 4 µM Fluo-3-AM solution (pH7.5) containing 20 mM HEPES, 1.37 mM NaCl, 5.27 mM KCl, 0.9 mM $MgCl_2$, 1.26 mM $CaCl_2$, 5.6 mM D-glucose, 2.5 mM probenecid, 1% BSA, and 0.08% Pluronic F-127, and incubated at 37° C. under 5% dioxide carbon atmosphere for one hour. The plate was washed with washing buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, pH7.5), and each well was added with 40 µL of this buffer. The plate was placed in High-Throughput Screening System FDSS 3000 (Hamamatsu Photonics K.K.). Measurement of fluorescence intensity by FDSS 3000 was started, and 40 µL of DMSO solutions containing 1% RSA (final concentrations) and different concentrations of the test compound as prepared by dilution with dilution buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH7.5) were dispensed to each well through the built-in automatic dispenser. Five minutes after, 50 nM ATP solution (50 µL) prepared by dilution with the dilution buffer was dispensed through the built-in automatic dispenser, and the measurement of fluorescence intensity was continued for 4 min. For each well, the specific maximum fluorescence intensity was calculated as the ratio of the maximum fluorescence intensity after addition of the ATP solution to the fluorescence intensity at the starting of the measurement. The 50% inhibitory concentration ($IC_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. $IC_{50}$ was calculated using Microsoft Excel (Microsoft Corporation) and XLfit (idbs Ltd.).

The data by the method of Test Example 3-2 are as shown in the following table.

TABLE 133

| Compound No | P2X3 IC50 (µM) |
|---|---|
| I-159 | 0.023 |
| I-162 | 0.013 |
| I-165 | 0.017 |
| I-215 | 0.005 |
| I-230 | 0.010 |
| I-304 | 0.012 |
| I-308 | 0.005 |
| I-309 | 0.022 |
| I-313 | 0.024 |
| I-339 | 0.012 |
| I-354 | 0.014 |

Test Example 4

Evaluation of the Urinary Function in a Rat Model of Cystitis Surgery for Cystometry A rat is fixed in the supine position after being given anesthesia through the inhalation of 2% isoflurane (Anesthetic background; Nitrous oxide: Oxygen=7:3). A midline incision is made in its abdomen to expose the bladder. A cannula (made by processing a polyethylene tube (PE-50: Becton Dickinson)) is inserted through a small incision on top of the bladder and fixed to create a bladder fistula. The other end of the cannula is led through the hypodermal tissue to the back, and the muscular coat and skin are sutured. The cannula, which is led to the back, is protected with a stainless spring in the middle and connected to the cannula swivel.

Acetic Acid Infusion

Two days after the surgery, 0.3% acetic acid is infused into the bladder through the indwelled cannula at a rate of 4 mL/hr for 30 minutes to induce cystitis. The animals, where acetic acid is not infused, are used as normal animals.

Cystometry Measurement

Two or three days after the acetic acid infusion, the other end of the cannula inserted into the bladder is connected to a T shape stopcock and then the intravesical pressure is recorded continuously using a pressure amplifier while infusing warmed normal saline solution at a rate of 3.0 mL/hr from one side and through a pressure transducer on the other side. The baseline of the intravesical pressure is measured (for approximately 40 minutes) after a measurement for stable duration (for approximately 20 minutes). After that, a vehicle, positive control compound or test compound are administered, and the value after administration is measured for approximately 120 minutes. A compound of the present invention is crushed with a mortar and pestle so as to be 0.1-2 mg/mL/kg solution or suspension using 0.5% methylcellulose solution, and administered to an animal orally with an oral sonde. At the same time, the voided urine is received on scales under the cage to measure the variation in weight simultaneously.

Data Adoption Criteria

Based on the voiding interval, normal animals whose voiding interval is 10 minutes or longer were adopted and those whose voiding interval is shorter than that were excluded. In the case of the animals into which acetic acid is infused, those whose voiding interval is less than half the average value of the normal animals are adopted as animals with cystitis and those whose voiding interval is longer than that were excluded.

Collection of Residual Urine

After the completion of the measurement, the infusion of normal saline solution is stopped immediately after urination to collect the residual urine under pentobarbital sodium anesthesia. The collected residual urine is transferred to the voided urine receiver and recorded on the chart.

Analysis Items

Intravesical pressure one to two hours after the start of the measurement (pressure during rest and pressure during urination), voiding interval, voided volume per urination, and residual urine volume The following value is used as an indicator of the effect on the voiding interval:

> Improvement rate of the urinary function=(Voiding interval of an animal with cystitis after drug treatment−Voiding interval of an animal with cystitis before drug treatment)/(Mean voiding interval of normal animals before drug treatment−Voiding interval of an animal with cystitis before drug treatment)

The following value is used as an indicator of the effect on the voided volume per urination:

> Improvement rate of the voided volume per urination=(Voided volume per urination of a rat with cystitis after drug treatment−Voided volume per urination of an animal with cystitis before drug treatment)/(Mean voided volume per urination of normal animals before drug treatment−Voided volume per urination of an animal with cystitis before drug treatment)

Test Example 5

Analgesic Effect in a Seltzer Model

Preparation of Partial Sciatic Nerve Ligation Model in Rats

Rats were anaesthetized using isoflurane/O2 inhalation anaesthesia. After induction of anesthesia, the left thigh was shaved. An incision was made in the skin just below the hip bone. The muscle was bluntly dissected to expose the sciatic nerve. One third (⅓) to one half (½) of the sciatic nerve thickness was tightly ligated and the wound was closed. The right thigh is used as a sham-operated control. The right thigh undergoes an identical procedure with the left hind limb, however, the sciatic nerve is not manipulated or ligated.

Evaluation (1)

Two weeks after nerve ligation, the effect on mechanical allodynia is assessed using a series of von Frey filaments. For habituation, the rats are placed into a plastic cage on a wire mesh bottom. The mechanical sensitivity (mechanical threshold) of the hind paws is estimated with a series of von Frey filaments (0.4-26 g). The measurement of mechanical sensitivity of the right and left hind paws is performed to obtain predose mechanical sensitivity. The rats showing the threshold change from 0.6 to 2 g (in nerve ligated side) and 8 to 15 g (in sham operated side) are used in the experiments.

On the day before the experiment, the rats are evaluated with a series of von Frey filaments to familiarize them with the test procedure. The adopted animal is administrated with the test compounds. The test compounds are homogenized with mortar and pestle and suspended or diluted in 0.5% Methyl Cellulose to prepare 0.03-30 mg/2 mL/kg suspension and orally administered to rat using a syringe attached with a sonde. Post-dose mechanical sensitivities of the right and left hind paws are measured at approximately 1 to 5 hours after drug administration. Percent reversal of mechanical allodynia for each rat is calculated using the following formula. The analgesic effects of the compounds are compared.

$$\% \text{ Reversal} = 100 \times \frac{\text{Log}_{10}(\text{Postdose mechanical sensitivity in nerve ligated side}) - \text{Log}_{10}(\text{Predose mechanical sensitivity in nerve ligated side})}{\text{Log}_{10}(\text{Predose mechanical sensitivity in sham operated side}) - \text{Log}_{10}(\text{Predose mechanical sensitivity in nerve ligated side})}$$

Evaluation (2)

Mechanical hyperalgesia is evaluated using an analgesy meter. Two weeks after nerve ligation, the paw pressure test is performed using an analgesy meter (stimulus pressure increased 16 g per second) to obtain paw withdrawal thresholds (PWT). Measurements are made on both sides of the hind paw and to obtain pre-dose PWT. The rats showing the threshold change from 60 to 90 g (in nerve ligated side) and 100 to 175 g (in sham operated side) are used in the experiments. On the day before the experiment, the rats have their hind paws set on the apparatus to familiarize them with the test procedure. The adopted animal is administrated with the test compounds. The test compounds are homogenized with mortar and pestle and suspended or diluted in 0.5% Methyl Cellulose to prepare 0.03-100 mg/2 mL/kg suspension and orally administered to rat using a syringe attached with a sonde. Post-dose PWT of the right and left hind paws are measured at approximately 1 to 5 hours after drug administration. Percent reversal of mechanical hyperalgesia for each rat is calculated using the following formula. The analgesic effects of the compounds are compared.

$$\% \text{ Reversal} = 100 \times \frac{\text{Postdose } PWT \text{ in nerve ligated side} - \text{Predose } PWT \text{ in nerve ligated side}}{\text{Predose } PWT \text{ in sham operated side} - \text{Predose } PWT \text{ in nerve ligated side}}$$

Test Example 6

CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (BFC) is debenzylated by the CYP3A4 enzyme to produce a metabolite, 7-hydroxytrifluoromethylchmarin (HFC) emitting fluorescent light.

The reaction conditions are as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 1.5625, 3.125, 6.25, 12.5, 25, 50 µmol/L (six points).

An enzyme in a K-Pi buffer (pH 7.4) and a test drug solution as a pre-reaction solution are added to a 96-well plate at the composition of the pre-reaction, a part of it was transferred to another 96-well plate so that it is ⅒ diluted by a substrate in a K-Pi buffer, NADPH as a co-factor is added to initiate a reaction as an index (without preincubation) and, after a predetermined time of a reaction, acetonitrile: 0.5 mol/L Tris(trishydroxyaminomethane)=4:1 was added to stop the reaction. In addition, NADPH is added to a remaining preincubation solution to initiate a preincubation (with preincubation) and, after a predetermined time of a preincubation, a part is transferred to another plate so that it was ⅒ diluted with a substrate and a K-Pi buffer to initiate a reaction as an index. After a predetermined time of a reaction, acetonitrile:0.5 mol/L Tris(trishydroxyaminomethane)=4:1 is added to stop the reaction. For the plate on which each index reaction have been performed, a fluorescent value of 7-HFC which is a metabolite is measured with a fluorescent plate reader. (Ex=420 nm, Em=535 nm).

Addition of only DMSO which is a solvent dissolving a drug to a reaction system is adopted as a control (100%), remaining activity (%) is calculated at each concentration of a test drug added as the solution, and $IC_{50}$ is calculated by reverse-presumption by a logistic model using a concentration and an inhibition rate. When a difference between $IC_{50}$ values is 5 µM or more, this is defined as (+) and, when the difference is 3 µM or less, this is defined as (−).

Test Example 7

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound is assessed.

The reaction conditions are as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1.0, 5.0, 10, 20 µmol/L (four points).

Each five kinds of substrates, human hepatic microsome, or a test drug in 50 mmol/L Hepes buffer as a reaction solution is added to a 96-well plate at the composition as described above, NADPH, as a cofactor is added to initiate metabolism reactions as markers and, after the incubation at 37° C. for 15 minutes, a methanol/acetonitrile=1/1 (v/v) solution is added to stop the reaction. After the centrifugation at 3000 rpm for 15 minutes, resorufin (CYP1A2 metabolite) in the supernatant is quantified by a fluorescent multilabel counter and tributamide hydroxide (CYP2CP metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system is adopted as a control (100%), remaining activity (%) is calculated at each concentration of a test drug added as the solution and $IC_{50}$ is calculated by reverse presumption by a logistic model using a concentration and an inhibition rate.

Test Example 8

FAT Test

20 µL of freezing-stored rat typhoid *bacillus* (*Salmonella typhimurium* TA98 strain, TA100 strain) is inoculated on 10 mL of a liquid nutrient medium (2.5% Oxoid nutrient broth No. 2), and this is cultured before shaking at 37° C. for 10 hours. 9 mL of a bacterial solution of the TA98 strain is centrifuged (2000×g, 10 minutes) to remove a culturing solution, the bacteria is suspended in 9 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), the suspension is added to 110 mL of an Exposure medium (Micro F buffer containing Biotin: 8 g/mL, histidine: 0.2 µg/mL, glucose: 8 mg/mL), and the TA100 strain is added to 120 mL of the Exposure medium relative to 3.16 mL of the bacterial solution to prepare a test bacterial solution. Each 1.2 µL of a test substance DMSO solution (8 stage dilution from maximum dose 50 µg/mL at 2-fold ratio), DMSO as a negative control, 50 µg/mL of 4-nitroquinoline-1-oxide DMSO solution for the TA98 strain, 0.25 µg/mL of 2-(furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µl of the test bacterial solution and 90 µL of S9 mix under the metabolism activating condition) are mixed, and this is shaking-cultured at 37° C. for 90 minutes. 460 µL of the bacterial solution exposed to the test substance is mixed with 2300 µL of an Indicator medium (Micro F buffer containing biotin: 8 µg/mL, histidine: 0.2 µg/mL, glucose: 8 mg/mL, Bromo Cresol Purple: 37.5 µg/mL), each 50 L is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group.

Test Example 9

Solubility Test

The solubility of a compound is determined under a condition in which 1% DMSO was added. 10 mmol/L compound solution is prepared using DMSO, and then 6 µL of the compound solution is added to 594 µL of artificial intestinal juice in pH 6.8 (to 250 mL of 0.2 mol/L potassium dihydrogen phosphate reagent solution is added 118 mL of 0.2 mol/L NaOH reagent solution and water to provide a final volume of 1000 mL). After standing at 25 degrees Celsius for 16 hours, the mixed solution is filtrated with suction. The filtrate is diluted twice with methanol/water (1/1), and then a concentration in the filtration is measured with HPLC or LC/MS/MS by the absolute calibration method.

Test Example 10

Metabolism Stability Test

Using commercially available pooled human hepatic microsomes, a test compound is reacted for a constant time, a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L tris-HCl pH 7.4, 150 mmol/L potassium chloride, 10 mmol/L magnesium chloride) containing 0.5 mg protein/mL of human liver microsomes. After the reaction, 50 μL of the reaction solution is added to 100 μL of a methanol/acetonitrile=1/1 (v/v), mixed and centrifuged at 3000 rpm for 15 minutes. The test compound in the supernatant is quantified by LC/MS/MS, and a remaining amount of the test compound after the reaction is calculated, letting a compound amount at 0 minute reaction time to be100%.

Test Example 11 hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, is studied using CHO cells expressing human ether-a-go-go related gene (hERG) channel.

After a cell is retained at a membrane potential of −80 mV by whole cell patch clamp method using an automated patch clamp system (PatchXpress 7000A, Axon Instruments Inc.), $I_{Kr}$ induced by depolarization pulse stimulation at +50 mV for 2 seconds and, further, repolarization pulse stimulation at −50 mV for 2 seconds is recorded. After the generated current is stabilized, extracellular solution (NaCl: 135 mmol/L, KCl: 5.4 mmol/L, NaH$_2$PO$_4$: 0.3 mmol/L, CaCl$_2$.2H$_2$O: 1.8 mmol/L, MgCl$_2$.6H$_2$O: 1 mmol/L, glucose: 10 mmol/L, HEPES (4-(2-hydroxyethyl)-1-piperazineethanesulfonic acid): 10 mmol/L, pH=7.4) in which the test compound have been dissolved at an objective concentration (1.0 μmol/L) is applied to the cell under the room temperature condition for 10 minutes. From the recording $I_{Kr}$, an absolute value of the tail peak current is measured based on the current value at the resting membrane potential using an analysis software (DataXpress ver. 2, Molecular Devices Corporation). Further, the % inhibition relative to the tail peak current before application of the test substance is calculated, and compared with the vehicle-applied group (0.1% dimethyl sulfoxide solution) to assess influence of the test substance on $I_{Kr}$.

Test Example 12

Metabolism Stability Test

The test compound is reacted for a given period of time using cryopreserved rat hepatocytes that are prepared and the residual ratio is calculated based on the comparison between reacted and unreacted samples to evaluate the degree of hepatic metabolism.

The compound is reacted in the Williams E medium containing 1.0×10$^6$ cells/mL of cryopreserved rat hepatocytes at a temperature of 37° C. for 0, 1 or 2 hours. After reaction, 50 μL of reaction solution is added to and mixed with 100 μL of a solution containing methanol and acetonitrile in the proportion of one to one (v/v) and the mixture is centrifuged at 3000 rpm for 15 minutes. The test compound contained in the centrifugal supernatant is quantitated using a LC/MS/MS system and the residual ratio of the test compound after reaction is calculated regarding the amount of compound after the reaction for 0 minute as 100%.

Test Example 13

Protein Binding Test

The unbound fraction of the present compound in serum is measured using serum of various species.

The reactive conditions are as follows: Evaluation method, Equilibrium dialysis; Reaction time, 24 hours; Reaction temperature, 37° C.; Concentration of the present compound, 2 μg/mL The test solution is added to each serum and the mixture is agitated to prepare the serum samples at the concentration mentioned above. Each serum sample is added into one side of the cell and phosphate buffered saline (PBS) is added into the other side to perform equilibrium dialysis at 37° C. for 24 hours. Then, the concentration of the compounds in the samples that are obtained from both sides is measured by LC/MS/MS.

Test Example 14

Bioavailability (BA) Test

Materials and Methods for Experiment of BA
(1) Animals: Mice or SD rats are used
(2) Breeding conditions: Mice or SD rats are allowed to freely take solid food and sterilized tap water.
(3) Dose and grouping: orally or intravenously administered at a predetermined dose; grouping is as follows (Dose depends on the compound)
　　Oral administration: 1 mg/kg (n=2)
　　Intravenous administration: 0.5 mg/kg (n=2)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood is collected over time, and the plasma concentration of drug is measured by LC/MS/MS
(7) Statistical analysis: regarding the transition of the plasma concentration of the present compound, the area under the plasma concentration-time curve (AUC) is calculated by non-linear least squares program WinNonlin (Registered trade name), and the bioavailability (BA) is calculated from the AUCs of the oral administration group and intravenous administration group.

Test Example 15

Powder Solubility Test

Appropriate quantity of the compound of the present invention is put in a suitable container and 200 μL of JP-1 solution (water was added to 2.0 g of sodium chloride and 7.0 mL of hydrochloric acid to reach 1000 mL), JP-2 solution (500 mL of water is added to 500 mL of phosphate buffer with a pH of 6.8) or 20 mmol/L sodium taurocholate (TCA)/JP-2 solution (JP-2 solution was added to 1.08 g of TCA to each 100 mL) is independently added to each container. When total amount is dissolved after adding the test reagent, the compound of the present invention is added appropriately. After sealing and shaking at 37° C. for 1 hour, solution is filtrated and 100 μL of methanol was added to 100 μL of each filtrate to dilute two-fold. The dilution rate is changed as necessary. After checking that there is no bubble and deposit, the container is sealed and shaken. The compound of the present invention is measured using HPLC by absolute calibration curve method.

PREPARATION EXAMPLE

The following Formulation Examples are only exemplified and not intended to limit the scope of the invention.

Formulation Example 1

Tablet

| Compound of the present invention | 15 mg |
| Lactose | 15 mg |
| Calcium Stearate | 3 mg |

The above ingredients other than Calcium Stearate are uniformly mixed, crushed, granule, dried to prepare granules of suitable size. After addition of Calcium Stearate, the mixture is compressed to prepare tables.

Formulation Example 2

Capsules

| Compound of the present invention | 10 mg |
| Magnecium Stearate | 10 mg |
| Lactose | 80 mg |

The above ingredients are uniformly mixed to prepare powdered medicine as powder or fine particles, which are put into capsule containers to prepare capsules.

Formulation Example 3

Granules

| Compound of the present invention | 30 g |
| Lactose | 265 g |
| Magnecium Stearate | 5 g |

The above ingredients are fully mixed, compressed, crushed, selected the size to prepare granules of suitable size.

INDUSTRIAL APPLICABILITY

The compounds represented by Formula (I) and Formula (II) have an antagonistic activity on $P2X_3$ and/or $P2X_{2/3}$ receptor and are useful in the treatment of diseases or conditions associated with a $P2X_3$ and/or $P2X_{2/3}$ receptor, such as chronic pain, urination disorder, respiratory disease, and the like.

The invention claimed is:
1. A compound of Formula (I):

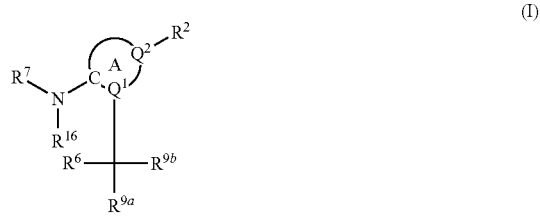

wherein
Formula (I) is a group represented by the formula:

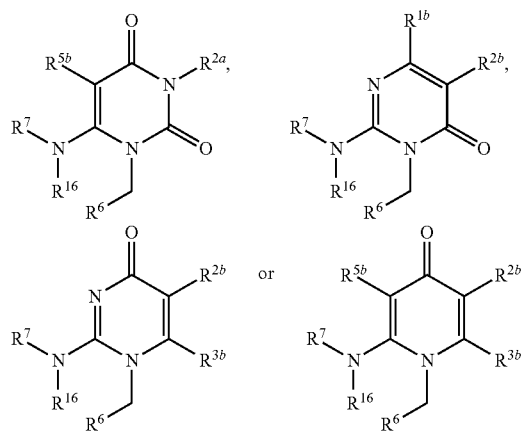

$R^{1b}$ is a hydrogen atom, carboxy, hydroxy, halogen, cyano, nitro, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, substituted or unsubstituted imino, or substituted or unsubstituted amino;

$R^{2b}$, $R^{3b}$, and $R^{5b}$ are each independently a hydrogen atom, carboxy, hydroxy, halogen, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, substituted or unsubstituted imino, or substituted or unsubstituted amino;

$R^6$ is a group represented by the formula:

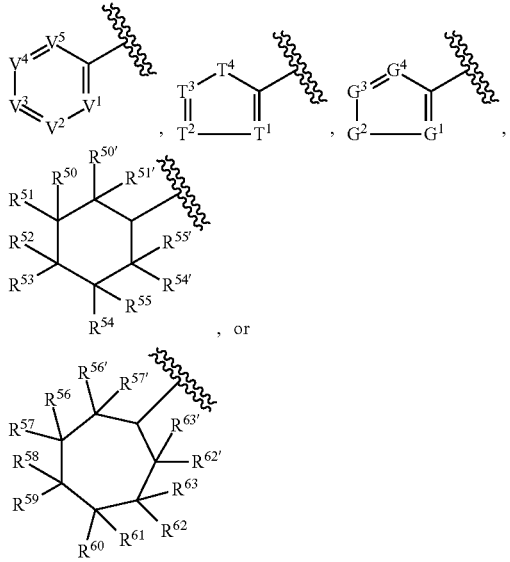

wherein $=V^1-V^2=V^3-V^4=V^5-$ is a group selected from the following (i)-(p) and (p'):

(i): $=C(R^{A'})-C(R^A)=C(R^B)-C(R^C)=C(R^{C'})-$;
(j): $=N-C(R^A)=C(R^B)-C(R^C)=C(R^{C'})-$;
(k): $=C(R^{A'})-N=C(R^B)-C(R^C)=C(R^{C'})-$;
(l): $=C(R^{A'})-C(R^A)=N-C(R^C)=C(R^{C'})-$;
(m): $=C(R^{A'})-N=N-C(R^C)=C(R^{C'})-$;
(n): $=N-C(R^A)=C(R^B)-C(R^C)=N-$;
(o): $=N-N=C(R^B)-C(R^C)=C(R^{C'})-$;
(p): $=C(R^{A'})-N=C(R^B)-N=C(R^{C'})-$; and
(p'): $=N-C(R^A)=C(R^B)-N=C(R^{C'})-$;

$R^A$, $R^{A'}$, $R^B$, R and $R^{C'}$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;

wherein $=T^1-T^2=T^3-T^4-$ is a group selected from the following (q)-(t):

(q): $=C(R^{D'})-C(R^D)=C(R^E)-S-$;
(r): $=C(R^{D'})-C(R^D)=C(R^E)-O-$;
(s): $=N-C(R^D)=C(R^E)-S-$; and
(t): $=N-C(R^D)=C(R^E)-O-$;

$R^D$, $R^{D'}$ and $R^E$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;

wherein $=G^1-G^2-G^3=G^4-$ is a group selected from the following (u)-(x):

(u): $=C(R^{F'})-S-C(R^F)-C(R^{F''})-$;
(v): $=C(R^{F'})-O-C(R^F)-C(R^{F''})-$;
(w): $=C(R^{F'})-S-C(R^F)=N-$; and
(x): $=C(R^{F'})-O-C(R^F)=N-$;

$R^F$, $R^{F'}$ and $R^{F''}$ are each independently a hydrogen atom, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;

$R^{50}$, $R^{50'}$, $R^{51}$, $R^{51'}$, $R^{52}$, $R^{53}$, $R^{54}$, $R^{54'}$, $R^{55}$, $R^{55'}$, $R^{56}$, $R^{56'}$, $R^{57}$, $R^{57'}$, $R^{58}$, $R^{59}$, $R^{60}$, $R^{61}$, $R^{62}$, $R^{62'}$, $R^{63}$ and $R^{63'}$ are each independently a hydrogen atom, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

$R^{16}$ is a hydrogen atom, substituted or unsubstituted alkyl, substituted or unsubstituted alkenyl, substituted or unsubstituted alkynyl or substituted or unsubstituted acyl;

$R^7$ is a group represented by the formula:

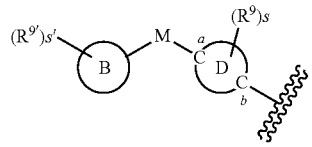

wherein
ring D is benzene, pyridine, pyrimidine, pyrazine or pyridazine;
carbon atom a and carbon atom b are carbon atoms which constitute ring D;
-M- is —O—, —S—, —N($R^{10}$)—, or —C($R^{10a}$)($R^{10b}$)—;
$R^{10}$ is a hydrogen atom, substituted or unsubstituted alkyl, substituted or unsubstituted alkenyl, substituted or unsubstituted alkynyl or substituted or unsubstituted acyl;
$R^{10a}$ and $R^{10b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy;
ring B is an aromatic carbocyclic ring, a non-aromatic carbocyclic ring, an aromatic heterocyclic ring or a non-aromatic heterocyclic ring;
s and s' are each independently integers of 0 to 3;

$R^9$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy;

$R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, provided that
(i) a compound represented by Formula (I) wherein a group represented by the formula:

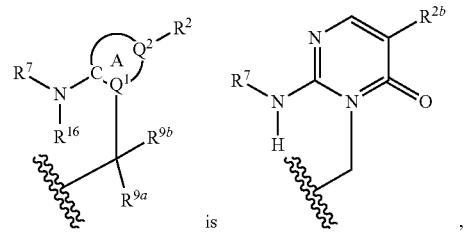

$R^7$ is 4-(6-methyl-3-pyridyl)oxy-phenyl, 4-(5-fluoro-3-pyridyl)oxy-phenyl or 4-(5-fluoro-6-methyl-3-pyridyl)oxy-phenyl, and $R^{2b}$ is substituted or unsubstituted amino;

(viii) the following compounds:
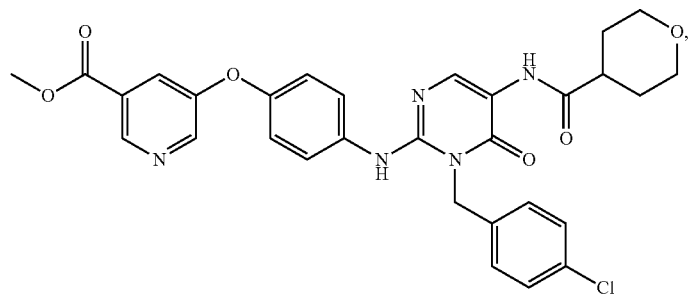
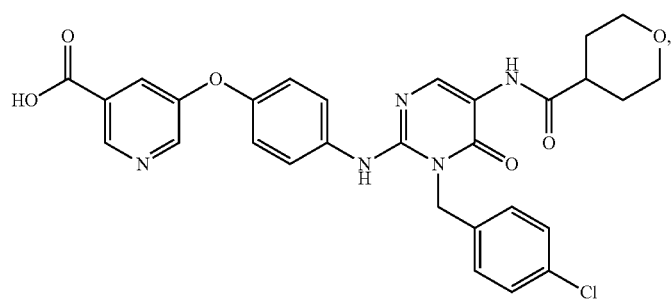
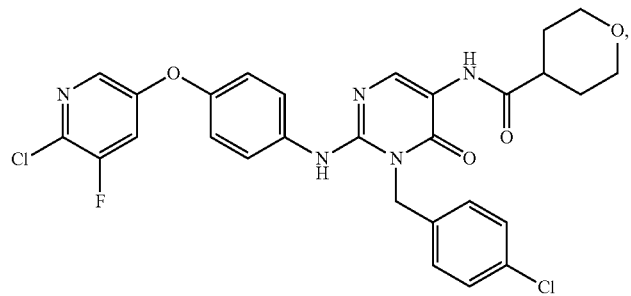
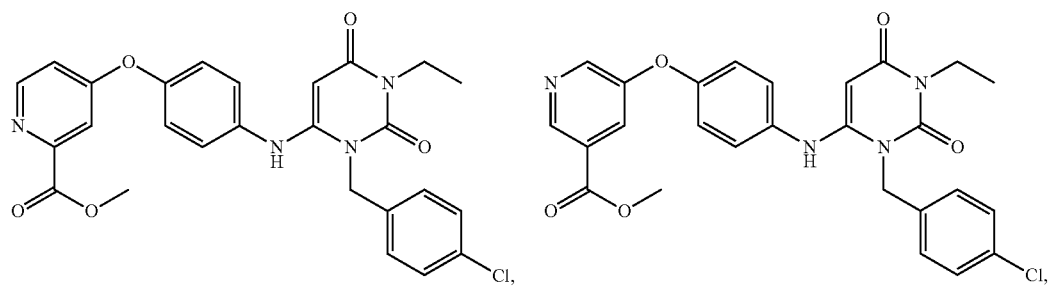
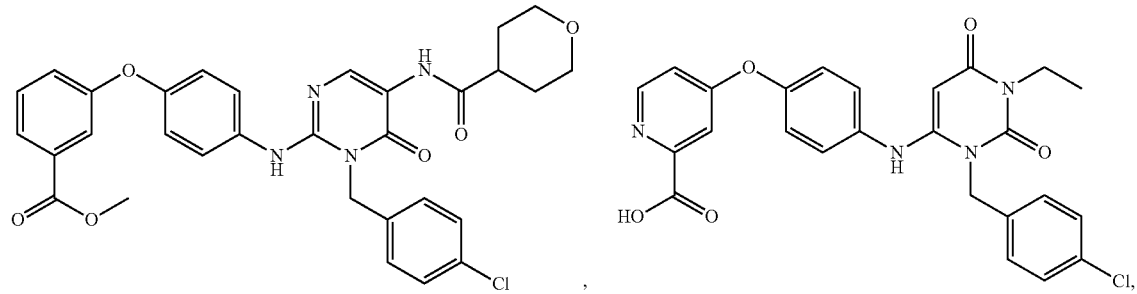

489
490
-continued
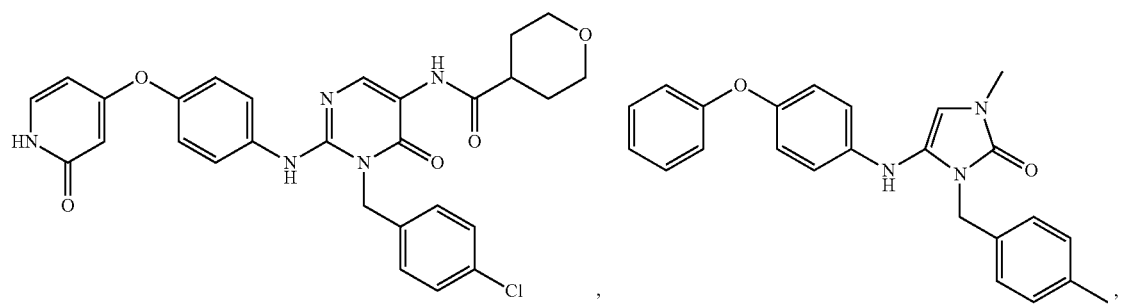
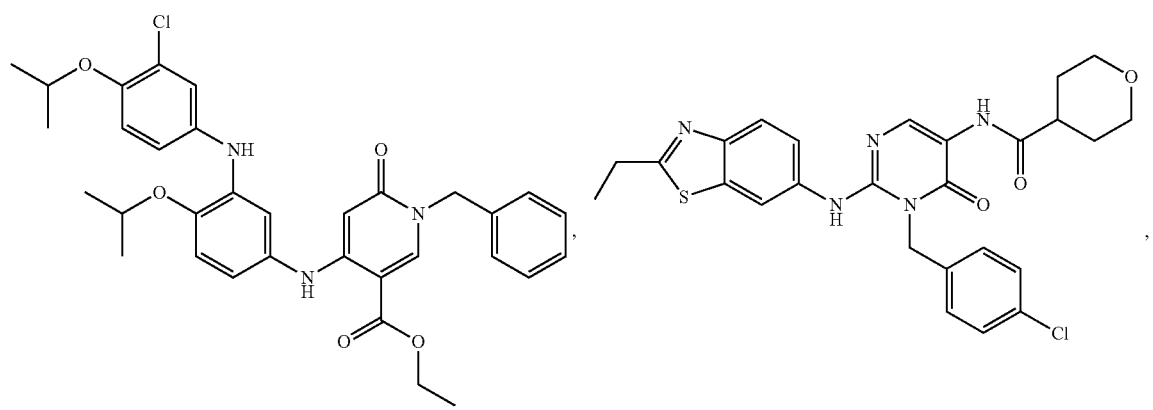
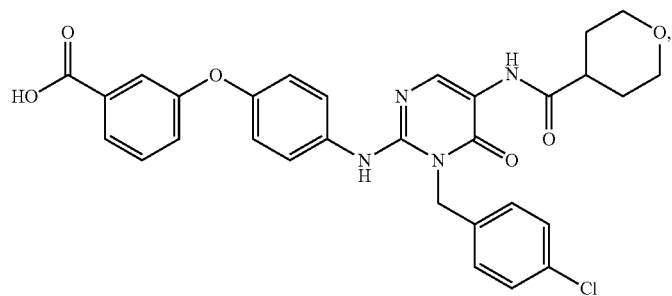
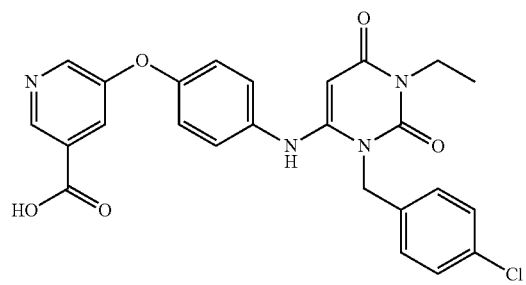

wherein "Me" is methyl, "Et" is ethyl, "Ph" is phenyl, and "Ac" is acetyl, are excluded,
or its pharmaceutically acceptable salt.

2. The compound according to claim 1, wherein Formula (I) is a group represented by the formula:

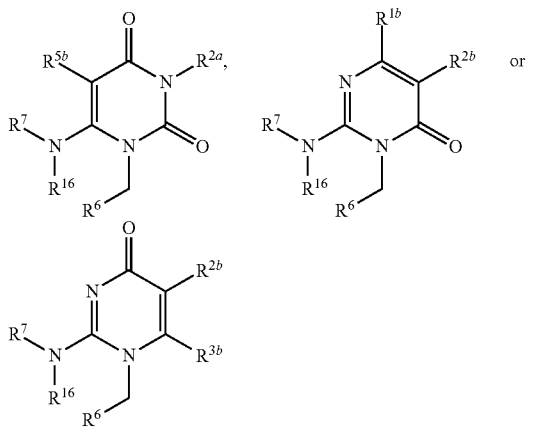

or its pharmaceutically acceptable salt.

3. The compound according to claim 1, wherein Formula (I) is a group represented by the formula:

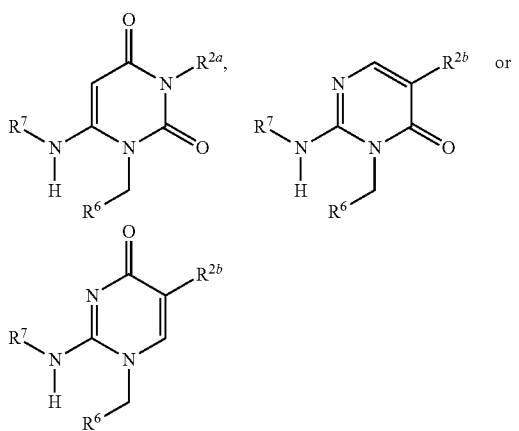

or its pharmaceutically acceptable salt.

4. The compound according to claim 1, wherein $-R^2$, $-R^{2a}$, $-R^{2b}$ or $-R^{2b}$ is the formula: $-(C(R^{11c})(R^{11d}))m'-COOR$
   wherein $R^{11c}$ are each independently a hydrogen atom, substituted or unsubstituted alkyl, substituted or unsubstituted alkenyl, or substituted or unsubstituted alkynyl;
   $R^{11d}$ are each independently a hydrogen atom, substituted or unsubstituted alkyl, substituted or unsubstituted alkenyl, or substituted or unsubstituted alkynyl; or
   $R^{11c}$ and $R^{11d}$ attached to the same carbon atom are taken together to form substituted or unsubstituted cycloalkane, substituted or unsubstituted cycloalkane or a substituted or unsubstituted non-aromatic heterocyclic ring;
   R is hydrogen or substituted or unsubstituted alkyl;
   m' is an integer of 1 to 4,
   or its pharmaceutically acceptable salt.

5. The compound according to claim 1, wherein $R^2$, $R^{2a}$, $R^{2b}$ or $R^{2b2}$ is unsubstituted alkyl, or its pharmaceutically acceptable salt.

6. The compound according to claim 1,
wherein
$-R^2$, $-R^{2b}$ or $-R^{2b2}$ is the formula: $-NH-C(=O)-(C(R^{8a})(R^{8b}))n-R^{13}$
wherein n is an integer of 0 to 4;
$R^{8a}$ are each independently a hydrogen atom, halogen, hydroxy, or substituted or unsubstituted alkyl;
$R^{8b}$ are each independently a hydrogen atom, halogen, hydroxy, or substituted or unsubstituted alkyl;
$R^{13}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl;
the formula: $-C(=O)-NH-(C(R^{8a'})(R^{8b'}))n'-R^{13'}$
wherein n' is an integer of 0 to 4;
$R^{8a'}$ are each independently a hydrogen atom, halogen, hydroxy, or substituted or unsubstituted alkyl;
$R^{8b'}$ are each independently a hydrogen atom, halogen, hydroxy, or substituted or unsubstituted alkyl;
$R^{13'}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl; or
the formula: $-(C(R^{8a''})(R^{8b''}))n''-R^{13''}$
wherein n" is an integer of 0 to 4;
$R^{8a''}$ are each independently a hydrogen atom, halogen, hydroxy, or substituted or unsubstituted alkyl;
$R^{8b''}$ are each independently a hydrogen atom, halogen, hydroxy, or substituted or unsubstituted alkyl;
$R^{13''}$ is a hydrogen atom, substituted or unsubstituted alkyl, substituted or unsubstituted alkenyl, substituted or unsubstituted alkynyl, hydroxy, carboxy, sulfo, cyano, substituted or unsubstituted cycloalkyl, a substituted or unsubstituted non-aromatic heterocyclic group, substituted or unsubstituted aryl, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or its pharmaceutically acceptable salt.

7. The compound according to claim 1, wherein $R^6$ is a group represented by the formula:

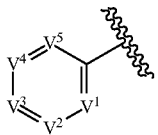

wherein $=V^1-V^2=V^3-V^4=V^5-$ is a group selected from the following (i)-(p) and (p'):
(i): $=C(R^{A'})-C(R^A)=C(R^B)-C(R^C)=C(R^{C'})-$;
(j): $=N-C(R^A)=C(R^B)-C(R^C)=C(R^{C'})-$;
(k): $=C(R^{A'})-N=C(R^B)-C(R^C)=C(R^{C'})-$;
(l): $=C(R^{A'})-C(R^A)=N-C(R^C)=C(R^{C'})-$;
(m): $=C(R^{A'})-N=N-C(R^C)=C(R^{C'})-$;
(n): $=N-C(R^A)=C(R^B)-C(R^C)=N-$;
(o): $=N-N=C(R^B)-C(R^C)=C(R^{C'})-$;
(p): $=C(R^{A'})-N=C(R^B)-N=C(R^{C'})-$; and
(p'): $=N-C(R^A)=C(R^B)-N=C(R^{C'})-$;
or its pharmaceutically acceptable salt.

8. The compound according to claim 1, wherein $R^6$ is a group represented by the formula:

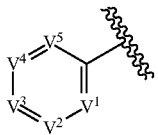

wherein $=V^1-V^2=V^3-V^4=V^5-$ is (i): $=C(R^{A'})-C(R^A)=C(R^B)-C(R^C)=C(R^{C'})-$,
wherein $R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl,
or its pharmaceutically acceptable salt.

9. The compound according to claim 1, wherein $R^{16}$ is a hydrogen atom, or its pharmaceutically acceptable salt.

10. The compound according to claim 1, wherein s' is an integer of 1 to 2, and at least one of $R^{9'}$ is halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl, or its pharmaceutically acceptable salt.

11. The compound according to claim 1, wherein s' is 1, and $R^{9'}$ is halogen, carboxy, substituted or unsubstituted alkyl or substituted or unsubstituted carbamoyl, or its pharmaceutically acceptable salt.

12. The compound according to claim 1, wherein s' is 0, or its pharmaceutically acceptable salt.

13. The compound according to claim 1, wherein ring B is an aromatic heterocyclic ring, or its pharmaceutically acceptable salt.

14. The compound according to claim 1, wherein ring B is thiazole, isothiazole, oxazole, isoxazole, pyrazole, imidazole, triazole, furan, thiophene, thiadiazole, oxadiazole, pyridine, pyrimidine, pyrazine, pyridazine, triazine or benzoxazole, or its pharmaceutically acceptable salt.

15. The compound according to claim 1, wherein ring B is thiazole, isothiazole, oxazole, isoxazole, thiadiazole, oxadiazole, pyridine, pyrimidine, pyrazine or pyridazine, or its pharmaceutically acceptable salt.

16. The compound according to claim 1, wherein -M- is —O—, or its pharmaceutically acceptable salt.

17. The compound according to claim 1, wherein ring D is benzene, or its pharmaceutically acceptable salt.

18. The compound according to claim 1, wherein carbon atom a is positioned on ring D in a (1,4) relationship with respect to carbon atom b, or its pharmaceutically acceptable salt.

19. The compound according to claim 1, wherein s is 1 or 2, and at least one of $R^9$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyl or substituted or unsubstituted cycloalkenyl, or its pharmaceutically acceptable salt.

20. The compound according to claim 1, wherein s is 0, or its pharmaceutically acceptable salt.

21. The compound according to claim 1, wherein a group represented by the formula:

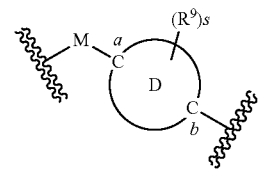

is a group represented by the formula:

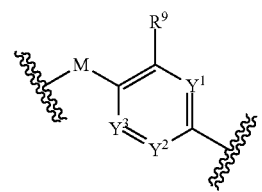

wherein -M- is as defined in claim 1;
$R^9$ is halogen or substituted or unsubstituted alkyl;
$Y^1$, $Y^2$ and $Y^3$ are each independently CH or N;
provided that $Y^1$, $Y^2$ and $Y^3$ are not N at the same time, or its pharmaceutically acceptable salt.

22. The compound according to claim 1, represented by the formula:

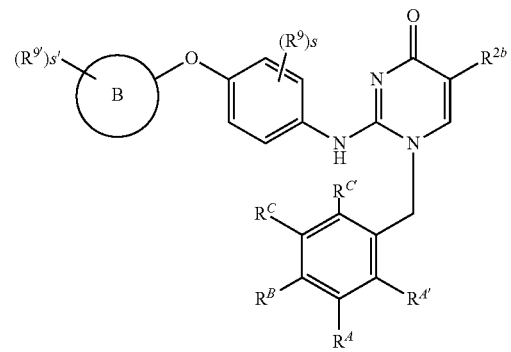

wherein

R$^{2b}$ is substituted or unsubstituted alkyl, substituted or unsubstituted alkyloxy, substituted or unsubstituted cycloalkyl, a substituted or unsubstituted non-aromatic heterocyclic group, substituted or unsubstituted aryl, substituted or unsubstituted heteroaryl, substituted or unsubstituted amino or substituted or unsubstituted carbamoyl;

R$^A$, R$^{A'}$, R$^B$, R$^C$ and R$^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;

ring B is thiazole, isothiazole, oxazole, isoxazole, thiadiazole, oxadiazole, pyridine, pyrimidine, pyrazine or pyridazine;

s and s' are each independently integers of 0 to 3;

R$^9$ are each independently halogen, hydroxy, cyano, substituted or unsubstituted alkyl or substituted or unsubstituted alkyloxy;

R$^{9'}$ are each independently halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl, or its pharmaceutically acceptable salt.

23. The compound according to claim 1, represented by the formula:

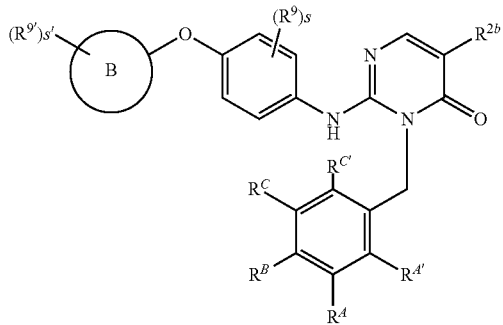

wherein

R$^{2b}$ is substituted or unsubstituted alkyl, substituted or unsubstituted alkyloxy, substituted or unsubstituted cycloalkyl, a substituted or unsubstituted non-aromatic heterocyclic group, substituted or unsubstituted aryl, substituted or unsubstituted heteroaryl, substituted or unsubstituted amino or substituted or unsubstituted carbamoyl;

R$^A$, R$^{A'}$, R$^B$, R$^C$ and R$^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;

ring B is thiazole, isothiazole, oxazole, isoxazole, thiadiazole, oxadiazole, pyridine, pyrimidine, pyrazine or pyridazine;

provided that ring B is not pyridine when R$^{2b}$ is amino or amino substituted with optionally substituted acyl;

s and s' are each independently integers of 0 to 3;

R$^9$ are each independently halogen, hydroxy, cyano, substituted or unsubstituted alkyl or substituted or unsubstituted alkyloxy;

R$^{9'}$ are each independently halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl, or its pharmaceutically acceptable salt.

24. The compound according to claim 1, represented by the formula:

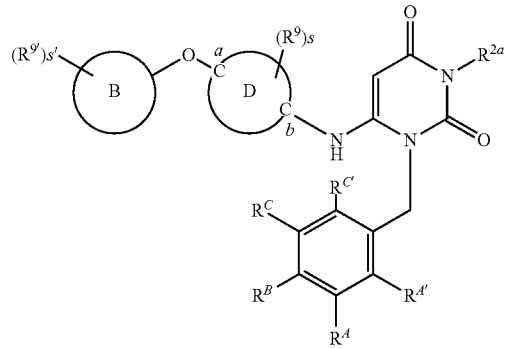

wherein ring D is benzene or pyridine;

carbon atom a and carbon atom b are carbon atoms which constitute ring D;

R$^{2a}$ is substituted or unsubstituted alkyl, substituted or unsubstituted cycloalkyl, a substituted or unsubstituted non-aromatic heterocyclic group, substituted or unsubstituted aryl, substituted or unsubstituted heteroaryl or substituted or unsubstituted carbamoyl;

R$^A$, R$^{A'}$, R$^B$, R$^C$ and R$^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;

ring B is thiazole, isothiazole, oxazole, isoxazole, thiadiazole, oxadiazole, pyridine, pyrimidine, pyrazine or pyridazine;

provided that

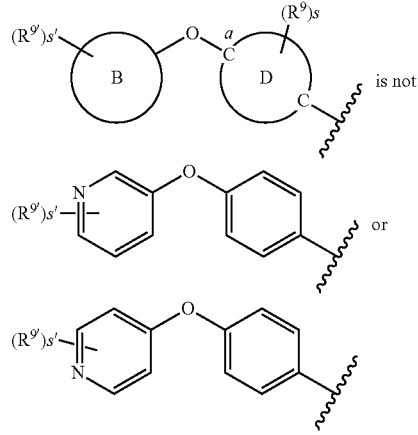

when R$^{2a}$ is unsubstituted alkyl;

s and s' are each independently integers of 0 to 3;

R$^9$ are each independently halogen, hydroxy, cyano, substituted or unsubstituted alkyl or substituted or unsubstituted alkyloxy;

R$^{9'}$ are each independently halogen, hydroxy, carboxy, cyano, substituted or unsubstituted alkyl, substituted or unsubstituted carbamoyl, substituted or unsubstituted amino, substituted or unsubstituted sulfamoyl, substituted sulfonyl, substituted sulfinyl or substituted or unsubstituted alkyloxycarbonyl,
or its pharmaceutically acceptable salt.

25. A pharmaceutical composition comprising the compound according to claim 1, or its pharmaceutically acceptable salt.

26. A method for treating pain comprising administering the compound according to claim 1, or its pharmaceutically acceptable salt.

27. The compound according to claim 1, wherein Formula (I) is a group represented by the formula:

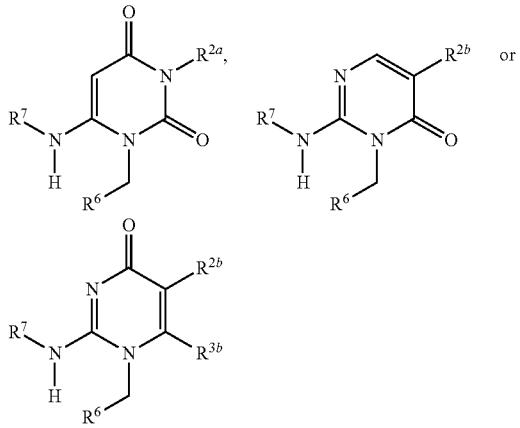

$R^6$ is a group represented by the formula:

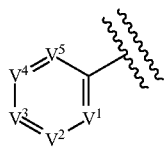

wherein $=V^1-V^2=V^3-V^4=V^5-$ is a group selected from the following (i)-(p) and (p'):

(i): $=C(R^{A'})-C(R^A)=C(R^B)-C(R^C)=C(R^{C'})-$;
(j): $=N-C(R^A)=C(R^B)-C(R^C)=C(R^{C'})=(R^{C'})-$;
(k): $=C(R^{A'})-N=C(R^B)-C(R^C)=C(R^{C'})-$;
(l): $=C(R^{A'})-C(R^A)=N-C(R^C)=C(R^{C'})-$;
(m): $=C(R^{A'})-C(R^A)=N-N=C(R^C)=C(R^{C'})-$;
(n): $=N-C(R^A)=C(R^B)-C(R^C)=N-$;
(o): $=N-N=C(R^B)-C(R^C)=C(R^{C'})-$;
(p): $=C(R^{A'})-N=C(R^B)-N=C(R^{C'})-$; and
(p'): $=N-C(R^A)=C(R^B)-N=C(R^{C'})-$;

$R^7$ is a group represented by the formula:

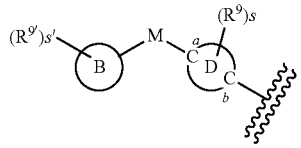

wherein
ring D is benzene or pyridine;
-M- is —O—;
or its pharmaceutically acceptable salt.

28. The compound according to claim 27, wherein $R^6$ is a group represented by the formula:

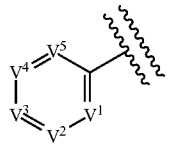

wherein $=V^1-V^2=V^3-V^4=V^5-$ is (i): $=C(R^{A'})-C(R^A)=C(R^B)-C(R^C)=C(R^{C'})-$,
wherein $R^A$, $R^{A'}$, $R^B$, $R^C$ and $R^{C'}$ are each independently a hydrogen atom, halogen, alkyl, alkenyl, alkynyl, alkyloxy, alkenyloxy, alkynyloxy, cycloalkyl, cycloalkenyl, cycloalkynyl, or alkylsilylalkynyl;
or its pharmaceutically acceptable salt.

29. The method of claim 26 wherein the pain is associated with mechanical allodynia.

* * * * *